US009931327B2

(12) United States Patent
Armani et al.

(10) Patent No.: US 9,931,327 B2
(45) Date of Patent: Apr. 3, 2018

(54) DERIVATIVES OF 1-PHENYL-2-PYRIDINYL ALKYL ALCOHOLS AS PHOSPHODIESTERASE INHIBITORS

(71) Applicant: Chiesi Farmaceutici S.p.A., Parma (IT)

(72) Inventors: Elisabetta Armani, Parma (IT); Gabriele Amari, Parma (IT); Laura Carzaniga, Parma (IT); Carmelida Capaldi, Parma (IT); Oriana Esposito, Parma (IT); Gino Villetti, Parma (IT); Renato De Fanti, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

(21) Appl. No.: 14/863,915

(22) Filed: Sep. 24, 2015

(65) Prior Publication Data

US 2016/0008338 A1 Jan. 14, 2016

Related U.S. Application Data

(63) Continuation of application No. 14/048,651, filed on Oct. 8, 2013, now abandoned, which is a continuation of application No. 13/488,818, filed on Jun. 5, 2012, now abandoned.

(30) Foreign Application Priority Data

Jun. 6, 2011 (EP) .................................... 11168853

(51) Int. Cl.

| | |
|---|---|
| *A61K 31/4425* | (2006.01) |
| *C07D 213/89* | (2006.01) |
| *C07D 401/12* | (2006.01) |
| *C07D 401/14* | (2006.01) |
| *C07D 405/14* | (2006.01) |
| *C07D 413/12* | (2006.01) |
| *C07D 417/12* | (2006.01) |
| *C07D 417/14* | (2006.01) |
| *A61K 45/06* | (2006.01) |
| *A61K 31/4439* | (2006.01) |
| *A61K 31/444* | (2006.01) |
| *A61K 31/4545* | (2006.01) |
| *A61K 31/496* | (2006.01) |
| *A61K 31/5377* | (2006.01) |
| *A61K 31/538* | (2006.01) |
| *A61K 31/541* | (2006.01) |
| *C07D 213/30* | (2006.01) |
| *A61K 31/517* | (2006.01) |
| *A61K 31/635* | (2006.01) |
| *C07D 471/04* | (2006.01) |
| *C07D 498/04* | (2006.01) |

(52) U.S. Cl.

CPC ........ *A61K 31/4425* (2013.01); *A61K 31/444* (2013.01); *A61K 31/4439* (2013.01); *A61K 31/4545* (2013.01); *A61K 31/496* (2013.01); *A61K 31/517* (2013.01); *A61K 31/538* (2013.01); *A61K 31/5377* (2013.01); *A61K 31/541* (2013.01); *A61K 31/635* (2013.01); *A61K 45/06* (2013.01); *C07D 213/30* (2013.01); *C07D 213/89* (2013.01); *C07D 401/12* (2013.01); *C07D 401/14* (2013.01); *C07D 405/14* (2013.01); *C07D 413/12* (2013.01); *C07D 417/12* (2013.01); *C07D 417/14* (2013.01); *C07D 471/04* (2013.01); *C07D 498/04* (2013.01)

(58) Field of Classification Search

None

See application file for complete search history.

(56) References Cited

U.S. PATENT DOCUMENTS

| | | | | |
|---|---|---|---|---|
| 7,671,066 | B2 | 3/2010 | Amari et al. | |
| 7,820,698 | B2 | 10/2010 | Rizzi et al. | |
| 7,923,565 | B2 | 4/2011 | Delcanale et al. | |
| 7,968,724 | B2 | 6/2011 | Armani et al. | |
| 8,203,000 | B2 | 6/2012 | Delcanale et al. | |
| 8,383,826 | B2 | 2/2013 | Delcanale et al. | |
| 8,440,834 | B2 | 5/2013 | Amari et al. | |
| 8,648,204 | B2 | 2/2014 | Amari et al. | |
| 8,859,778 | B2 | 10/2014 | Amari et al. | |
| 9,000,177 | B2 | 4/2015 | Delcanale et al. | |
| 9,024,027 | B2 * | 5/2015 | Armani ................ | C07D 401/14 546/139 |
| 9,056,176 | B2 | 6/2015 | Amari et al. | |
| 9,102,619 | B2 | 8/2015 | Delcanale et al. | |
| 9,132,121 | B2 | 9/2015 | Cocconi et al. | |
| 9,169,245 | B2 * | 10/2015 | Armani ................ | C07D 453/02 |
| 9,440,954 | B2 * | 9/2016 | Armani ................ | C07D 401/12 |

(Continued)

FOREIGN PATENT DOCUMENTS

| | | |
|---|---|---|
| CN | 101123971 A | 2/2008 |
| WO | 2001/032163 A1 | 5/2001 |

(Continued)

OTHER PUBLICATIONS

European Search Report in Application No. 11168853.7, dated Sep. 29, 2011.

(Continued)

*Primary Examiner* — Taofiq A Solola

(74) *Attorney, Agent, or Firm* — Oblon, McClelland, Maier & Neustadt, L.L.P.

(57) ABSTRACT

Derivatives of 1-phenyl-2-pyridinyl alkyl alcohols are useful as inhibitors of the phosphodiesterase 4 (PDE4) enzyme and the treatment of certain conditions such as COPD.

19 Claims, No Drawings

(56) References Cited

U.S. PATENT DOCUMENTS

| | | | |
|---|---|---|---|
| 2009/0274676 | A1 | 11/2009 | Robinson et al. |
| 2010/0204256 | A1 | 8/2010 | Amari et al. |
| 2011/0144075 | A1 | 6/2011 | Delcanale et al. |
| 2012/0031403 | A1 | 2/2012 | Cocconi et al. |
| 2012/0034172 | A1 | 2/2012 | Bonelli et al. |
| 2012/0116091 | A1 | 5/2012 | Delcanale et al. |
| 2013/0012487 | A1 | 1/2013 | Amari et al. |
| 2013/0079313 | A1 | 3/2013 | Armani et al. |
| 2013/0137648 | A1 | 5/2013 | Delcanale et al. |
| 2013/0289010 | A1 | 10/2013 | Amari et al. |
| 2013/0324501 | A1 | 12/2013 | Armani et al. |
| 2014/0142074 | A1 | 5/2014 | Armani et al. |
| 2015/0342936 | A1 | 12/2015 | Cocconi et al. |

FOREIGN PATENT DOCUMENTS

| | | |
|---|---|---|
| WO | 2009/018909 | 2/2009 |
| WO | 2009/019909 A2 | 2/2009 |

OTHER PUBLICATIONS

Carey, FA, Organic Chemistry $6^{th}$ Ed. McGraw Hill, 2006, p. 664, first paragraph.

Steglich, W. et al, Esterification of Carboxylic Acids with Dicyclohexylcarbodiimide/4-dimethylaminopyridine: tert-butyl ethyl fumarate. Organic Syntheses, Coll. 1990, vol. 7, p. 93.

Carey, FA. Organic Chemistry $6^{th}$ Ed. McGraw Hill, 2006, chapter 1, p. 9.

Steglich, W. et al. Esterification of Carboxylic Acids with Dicyclohexylcarbodiimide/4-dimethylaminopyridine: tert-butyl ethyl fumarate. Organic Syntheses, Coll. 1990, vol. 7, p. 93.

U.S. Appl. No. 14/164,527, filed Jan. 27, 2014, US 2014/0142074 A1, Armani, et al.

U.S. Appl. No. 13/032,288, filed Feb. 22, 2011, US 2011/0144075 A1, Delcanale, et al.

U.S. Appl. No. 13/747,812, filed Jan. 23, 2013, US 2013/0137648 A1, Delcanale, et al.

U.S. Appl. No. 13/618,346, filed Sep. 14, 2012, US 2013/0012487 A1, Amari, et al.

U.S. Appl. No. 13/195,903, filed Aug. 2, 2011, US 2012/0034172 A1, Bonelli, et al.

U.S. Appl. No. 14/820,939, filed Aug. 7, 2015, US 2015/034936 A1, Cocconi, et al.

International Search Report issued in PCT/EP20121060579 dated Jun. 6, 2011, with Written Opinion.

Chinese Office Action in Application No. 201280025202.0 dated Apr. 3, 2015 with English Translation.

* cited by examiner

DERIVATIVES OF 1-PHENYL-2-PYRIDINYL ALKYL ALCOHOLS AS PHOSPHODIESTERASE INHIBITORS

CROSS REFERENCES TO RELATED APPLICATIONS

This application claims priority to European Patent Application No. 11168853.7, filed on Jun. 6, 2011, which is incorporated herein by reference in its entirety.

BACKGROUND OF THE INVENTION

Field of the Invention

The present invention relates to inhibitors of the phosphodiesterase 4 (PDE4) enzyme. More particularly, the present invention relates to compounds that are derivatives of 1-phenyl-2-pyridinyl alkyl alcohols, methods of preparing such compounds, compositions containing them, and therapeutic uses of such compounds and compositions.

Discussion of the Background

Airway obstruction characterizes a number of severe respiratory diseases including asthma and chronic obstructive pulmonary disease (COPD). Events leading to airway obstruction include edema of airway walls, increased mucous production and inflammation.

Drugs for treating respiratory diseases such as asthma and COPD are currently administered through inhalation. One of the advantages of the inhalatory route over the systemic one is the possibility of delivering the drug directly at site of action, reducing systemic side-effects, thus resulting in a more rapid clinical response and a higher therapeutic ratio.

Inhaled corticosteroids are the current maintenance therapy of choice for asthma and together with bronchodilator $beta_2$-agonists for acute symptom relief, they form the mainstay of current therapy for the disease. The current management of COPD is largely symptomatic by means of bronchodilating therapy with inhaled anticholinergics and inhaled $beta_2$-adrenoceptor agonists. However, corticosteroids do not reduce the inflammatory response in COPD as they do in asthma.

Another class of therapeutic agents which has been widely investigated in view of its anti-inflammatory effects for the treatment of inflammatory respiratory diseases such as asthma and COPD is represented by the inhibitors of the enzymes phosphodiesterases (PDEs), in particular of the phosphodiesterase type 4 (hereinafter referred to as PDE4).

Various compounds acting as PDE4 inhibitors have been disclosed in the prior art. However, the usefulness of several PDE4 inhibitors of the first-generation such as rolipram and piclamilast has been limited due to their undesirable side effects. Said effects include nausea and emesis due to their action on PDE4 in the central nervous system and gastric acid secretion due to the action on PDE4 in parietal cells in the gut.

The cause of said side effects has been widely investigated. It has been found that PDE4 exists in two distinct forms representing different conformations, that were designated as high affinity rolipram binding site or HPDE4, especially present in the central nervous system and in parietal cells, and low affinity rolipram binding site or LPDE4 (see Jacobitz, S et al., *Mol. Pharmacol.,* 1996, 50, 891-899, which is incorporated herein by reference in its entirety), which is found in the immune and inflammatory cells. While both forms appear to exhibit catalytic activity, they differ with respect to their sensitivity to inhibitors. In particular compounds with higher affinity for LPDE4 appear less prone to induce side-effects such as nausea, emesis and increased gastric secretion.

The effort of targeting LPDE4 has resulted in a slight improvement in the selectivity for the second-generation PDE4 inhibitors such as roflumilast. Nonetheless, roflumilast is under dosed in order to achieve an acceptable side effect profile.

Other classes of compounds acting as PDE4 inhibitors have also been disclosed. For example, EP 1 634 606 discloses, among others, ketone derivatives like benzofuran or 1,3-benzodioxole derivatives.

WO 94/02465 discloses, among others, ketone derivatives of general formula

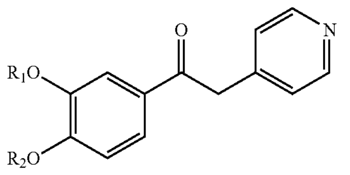

wherein $R_1$ is lower alkyl and $R_2$ may be alkyl, alkenyl, cycloalkyl, cycloalkyl, cycloalkenyl, cyclothioalkyl or cyclothioalkenyl.

WO 95/35281 in the name of Celltech Therapeutics relates to tri-substituted phenyl derivatives.

WO 2009/018909 discloses derivatives of 1-phenyl-2-pyridinyl alkyl alcohols which have general formula below reported

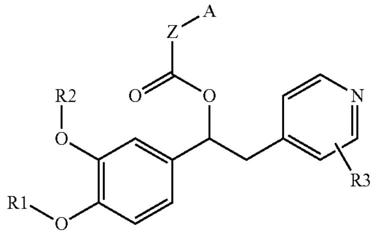

as inhibitors of phosphodiesterase 4 (PDE4) enzyme.

WO 2009/077068 discloses further derivatives of 1-phenyl-2-pyridinyl alkyl alcohols which have general formula below reported

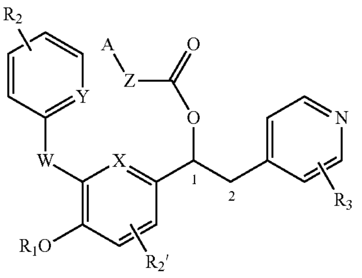

as inhibitors of phosphodiesterase 4 (PDE4) enzyme.

WO 2010/089107 discloses further derivatives of 1-phenyl-2-pyridinyl alkyl alcohols which have general formula below reported

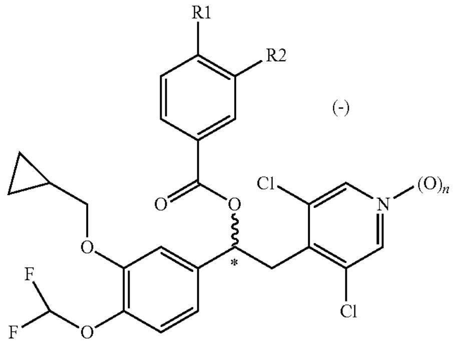

as inhibitors of phosphodiesterase 4 (PDE4) enzyme.

Although several PDE4 inhibitors have been disclosed so far as above reported, there is still a need for further PDE4 inhibitors. Particularly, there is still a need for further PDE4 inhibitors endowed with a high affinity for PDE4 enzyme. Particularly advantageous would also be the identification of further PDE4 inhibitors endowed with a high affinity for PDE4 enzyme and which would show an appropriate developability profile as an inhalation treatment for example in terms of reduced side effects.

Such reduction of side effects may be achieved, by way of example, through a low systemic exposure of the drug; an appropriate profile in terms of some pharmacokinetic characteristics, especially metabolic clearance, may be thus key to this goal.

SUMMARY OF THE INVENTION

Accordingly, it is one object of the present invention to provide novel PDE4 inhibitors endowed with a high affinity for PDE4 enzyme.

It is another object of the present invention to provide novel PDE4 inhibitors endowed with a high affinity for PDE4 enzyme and which show an appropriate developability profile as an inhalation treatment for example in terms of reduced side effects.

It is another object of the present invention to provide novel pharmaceutical compositions which contain such PDE4 inhibitor.

It is another object of the present invention to provide novel combinations of such a PDE4 inhibitor and one or more other active agents.

It is another object of the present invention to provide novel methods of treating a condition such as COPD by administering such a PDE4 inhibitor.

These and other objects, which will become apparent during the following detailed description, have been achieved by the inventors' discovery of certain new PDE4 inhibitors. Thus, the present invention addresses the above mentioned object by providing the compounds of the invention.

Thus, the present invention is directed to compounds acting as inhibitors of the phosphodiesterase 4 (PDE4) enzyme, methods of preparing said compounds, compositions containing them and therapeutic use thereof.

In particular, the present invention is directed to derivatives of 1-phenyl-2-pyridinyl alkyl alcohols of general formula (I):

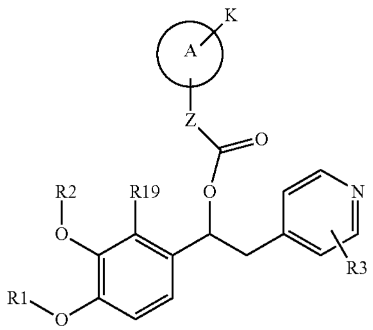

(I)

wherein:

$R_1$ is selected from the group consisting of:

- H;
- $(C_3-C_7)$ cycloalkylcarbonyl;
- $(C_1-C_6)$ alkyl, optionally substituted by one or more substituents selected from $(C_3-C_7)$ cycloalkyl or $(C_5-C_7)$ cycloalkenyl;
- $(C_1-C_6)$ haloalkyl;
- $(C_3-C_7)$ cycloalkyl;
- $(C_5-C_7)$ cycloalkenyl;
- $(C_2-C_6)$ alkenyl; and
- $(C_2-C_6)$ alkynyl;

$R_2$ is selected from the group consisting of:

- H;
- $(C_3-C_7)$ cycloalkylcarbonyl;
- $(C_1-C_6)$ alkyl, optionally substituted by one or more substituents selected from $(C_3-C_7)$ cycloalkyl or $(C_5-C_7)$ cycloalkenyl;
- $(C_1-C_6)$ haloalkyl;
- $(C_3-C_7)$ cycloalkyl;
- $(C_5-C_7)$ cycloalkenyl;
- $(C_2-C_6)$ alkenyl; and
- $(C_2-C_6)$ alkynyl;

or, when $R_{19}$ is different from hydrogen, $R_2$ forms together with $R_{19}$ a group of formula (x) as below defined;

or $R_1$ and $R_2$, together with the interconnecting atoms, form a 2,2-difluoro-1,3-dioxolane ring of formula (q) fused to the phenyl moiety which bears groups —$OR_1$ and —$OR_2$, wherein asterisks indicate carbon atoms shared with such phenyl ring:

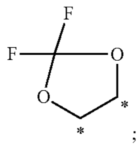

(q)

;

$R_{19}$ is hydrogen or, if different from hydrogen, it forms together with $R_2$ a group of formula (x) wherein bonds labeled with (1) and (2) indicate the points of attachment for group (x) to atoms bearing groups $R_{19}$ and $R_2$ respectively (x)

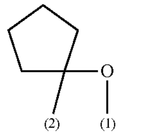

in such a way that $R_2$ and $R_{19}$ together with the interconnecting atoms form a ring of formula (w) which is fused to phenyl ring which bears groups —$OR_2$ and $R_{19}$, wherein asterisks indicate carbon atoms shared with such phenyl ring:

(w)

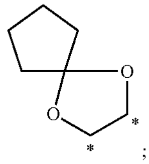

;

$R_3$ is one or more substituents independently selected from the group consisting of H, CN, $NO_2$, $CF_3$ and a halogen atom;

Z is a group —$(CH_2)_n$— wherein n is 0 or 1;

A is a saturated and monocyclic ($C_3$-$C_7$) heterocycloalkylene group;

K is selected from the group consisting of:

- —$(CH_2)_mC(O)R_4$ wherein m may be 0 or 1;
- —$C(O)(CH_2)_jR_4$, wherein j may be 1 or 2;
- —$SO_2(CH_2)_pR_4$ wherein p may be zero, 1 or 2;
- —$(CH_2)_ySO_2R_4$ wherein y may be 1 or 2;
- —$(CH_2)_zR_4$ wherein z may be 1 or 2; and
- —$C(O)(CH_2)_2SO_2R_4$;

$R_4$ is a ring system, that is a mono- or bicyclic ring which may be saturated, partially unsaturated or fully unsaturated, such as aryl, ($C_3$-$C_8$) cycloalkyl, ($C_3$-$C_7$) heterocycloalkyl or heteroaryl, such ring being optionally substituted by one or more groups $R_5$ which may be the same or different, and which are independently selected from the group consisting of:

- ($C_1$-$C_6$) alkyl optionally substituted by one or more groups independently selected in the list consisting of: ($C_3$-$C_7$) cycloalkyl, —OH and a group —$NR_{18}C(O)$($C_1$-$C_4$) alkyl, wherein $R_{18}$ is hydrogen or ($C_1$-$C_4$) alkyl;
- ($C_3$-$C_7$) heterocycloalkyl;
- 5 or 6-membered heteroaryl which is optionally substituted by one or two groups ($C_1$-$C_4$) alkyl;
- ($C_1$-$C_6$) haloalkyl;
- ($C_3$-$C_7$) heterocycloalkyl($C_1$-$C_4$) alkyl;
- a group —$OR_6$ wherein $R_6$ is selected from the group consisting of
  - H:
  - ($C_1$-$C_6$) haloalkyl;
  - a group —$SO_2R_7$, wherein $R_7$ is ($C_1$-$C_4$) alkyl;
  - a group —$C(O)R_7$ wherein $R_7$ is ($C_1$-$C_4$) alkyl;
  - ($C_1$-$C_{10}$) alkyl optionally substituted by one or more ($C_3$-$C_7$) cycloalkyl or by a group —$NR_8R_9$ as below defined; and
  - ($C_3$-$C_7$) cycloalkyl;
- a group —$SR_{20}$ wherein $R_{20}$ is selected from the group consisting of
  - H:
  - ($C_1$-$C_6$) haloalkyl;
  - a group —$C(O)R_7$ wherein $R_7$ is ($C_1$-$C_4$) alkyl; ($C_1$-$C_{10}$) alkyl optionally substituted by one or more ($C_3$-$C_7$) cycloalkyl or by a group —$NR_8R_9$; and
  - ($C_3$-$C_7$) cycloalkyl;
- halogen atoms;
- CN;
- $NO_2$;
- $NR_8R_9$ wherein $R_8$ and $R_9$ are different or the same and are independently selected from the group consisting of:
  - H;
  - ($C_1$-$C_4$) alkylene-$NR_{13}R_{14}$ wherein $R_{13}$ and $R_{14}$ are different or the same and are independently selected from the group consisting of: H and ($C_1$-$C_6$) alkyl, which is optionally substituted with ($C_3$-$C_7$) cycloalkyl or ($C_3$-$C_7$) heterocycloalkyl; or they form with the nitrogen atom to which they are linked a saturated or partially saturated ($C_3$-$C_7$) heterocyclic ring;
  - ($C_1$-$C_6$) alkyl, optionally substituted with ($C_3$-$C_7$) cycloalkyl, ($C_3$-$C_7$) heterocycloalkyl, a group —OH or ($C_1$-$C_6$) alkoxyl;
  - a group —$SO_2R_{15}$, wherein $R_{15}$ is selected in the group consisting of: ($C_1$-$C_4$) alkyl optionally substituted by ($C_3$-$C_7$) cycloalkyl or ($C_3$-$C_7$) heterocycloalkyl; ($C_3$-$C_7$) heterocycloalkyl; and phenyl optionally substituted by one or more ($C_1$-$C_6$) alkyl, halogen or a group —OH;
  - a group —$C(O)R_{16}$, wherein $R_{16}$ is selected in the group consisting of: ($C_1$-$C_6$) alkyl optionally substituted by ($C_3$-$C_7$) cycloalkyl or ($C_3$-$C_7$) heterocycloalkyl; ($C_3$-$C_7$) heterocycloalkyl; phenyl optionally substituted by one or more ($C_1$-$C_6$) alkyl, halogen or —OH; and a group —$NH_2$;
  - a group —$C(O)OR_{17}$, wherein $R_{17}$ is selected in the group consisting of: ($C_1$-$C_6$) alkyl optionally substituted by ($C_3$-$C_7$) cycloalkyl or ($C_3$-$C_7$) heterocycloalkyl; ($C_3$-$C_7$) heterocycloalkyl; phenyl optionally substituted by one or more ($C_1$-$C_6$) alkyl, halogen or —OH; and a group —$NH_2$;
  - or they form with the nitrogen atom to which they are linked a saturated or partially saturated heterocyclic ring, which is optionally substituted by one or more ($C_1$-$C_6$) alkyl or oxo groups;
- ($C_1$-$C_4$) alkylene-$NR_8R_9$ as above defined;
- $COR_{10}$ wherein $R_{10}$ is phenyl or ($C_1$-$C_6$) alkyl;
- oxo;
- —$SO_2R_{11}$ wherein $R_{11}$ is ($C_1$-$C_4$) alkyl, OH or $NR_8R_9$ wherein $R_8$ and $R_9$ are as defined above;
- —$COOR_{12}$ wherein $R_{12}$ is H, ($C_1$-$C_4$) alkyl or ($C_1$-$C_4$) alkylene-$NR_8R_9$ wherein $R_8$ and $R_9$ are as defined above; and
- —$CONR_8R_9$ wherein $R_8$ and $R_9$ are as defined above;

wherein groups $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$ and $R_{20}$ may assume the same or different meanings at each occurrence, if present in more than one group;

their N-oxides on the pyridine ring, and pharmaceutically acceptable salts, or solvates thereof.

In a preferred embodiment, the invention is directed to derivatives of 1-phenyl-2-pyridinyl alkyl alcohols of general formula (IG):

(IG)

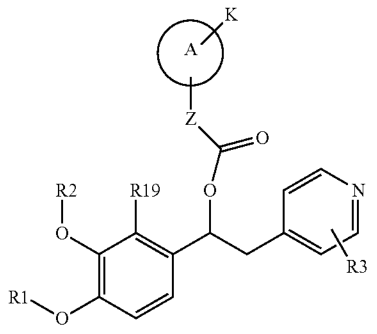

wherein:

$R_1$ is selected from the group consisting of:

H;

($C_3$-$C_7$) cycloalkylcarbonyl;

($C_1$-$C_6$) alkyl, optionally substituted by one or more substituents selected from ($C_3$-$C_7$) cycloalkyl or ($C_5$-$C_7$) cycloalkenyl;

($C_1$-$C_6$) haloalkyl;

($C_3$-$C_7$) cycloalkyl;

($C_5$-$C_7$) cycloalkenyl;

($C_2$-$C_6$) alkenyl; and ($C_2$-$C_6$) alkynyl;

$R_2$ is selected from the group consisting of:

H;

($C_3$-$C_7$) cycloalkylcarbonyl;

($C_1$-$C_6$) alkyl, optionally substituted by one or more substituents selected from ($C_3$-$C_7$) cycloalkyl or ($C_5$-$C_7$) cycloalkenyl;

($C_1$-$C_6$) haloalkyl;

($C_3$-$C_7$) cycloalkyl;

($C_5$-$C_7$) cycloalkenyl;

($C_2$-$C_6$) alkenyl; and ($C_2$-$C_6$) alkynyl;

or $R_1$ and $R_2$, together with the interconnecting atoms, form a 2,2-difluoro-1,3-dioxolane ring of formula (q) fused to the phenyl moiety which bears groups —$OR_1$ and —$OR_2$, wherein asterisks indicate carbon atoms shared with such phenyl ring:

(q)

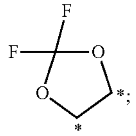

$R_{19}$ is hydrogen;

$R_3$ is one or more substituents independently selected from the group consisting of H, CN, $NO_2$, $CF_3$ and a halogen atom;

Z is a group —$(CH_2)_n$— wherein n is 0 or 1;

A is a saturated and monocyclic ($C_3$-$C_7$) heterocycloalkylene group;

K is selected from the group consisting of:

—$(CH_2)_m C(O)R_4$ wherein m may be 0 or 1;

—$C(O)(CH_2)R_4$, wherein j may be 1 or 2;

—$SO_2(CH_2)_p R_4$ wherein p may be zero, 1 or 2;

—$(CH_2)_y SO_2R_4$ wherein y may be 1 or 2;

—$(CH_2)_z R_4$ wherein z may be 1 or 2; and

—$C(O)(CH_2)_2SO_2R_4$;

$R_4$ is a ring system, that is a mono- or bicyclic ring which may be saturated, partially unsaturated or fully unsaturated, such as aryl, ($C_3$-$C_8$) cycloalkyl, ($C_3$-$C_7$) heterocycloalkyl or heteroaryl, such ring being optionally substituted by one or more groups $R_5$ which may be the same or different, and which are independently selected from the group consisting of:

($C_1$-$C_6$) alkyl optionally substituted by one or more groups independently selected in the list consisting of: ($C_3$-$C_7$) cycloalkyl, —OH and a group —$NR_{18}C(O)$($C_1$-$C_4$) alkyl, wherein $R_{18}$ is hydrogen or ($C_1$-$C_4$) alkyl;

($C_3$-$C_7$) heterocycloalkyl;

5 or 6-membered heteroaryl which is optionally substituted by one or two groups ($C_1$-$C_4$) alkyl;

($C_1$-$C_6$) haloalkyl;

($C_3$-$C_7$)heterocycloalkyl($C_1$-$C_4$) alkyl;

a group —$OR_6$ wherein $R_6$ is selected from the group consisting of

H:

($C_1$-$C_6$) haloalkyl;

a group —$SO_2R_7$, wherein $R_7$ is ($C_1$-$C_4$) alkyl;

a group —$C(O)R_7$ wherein $R_7$ is ($C_1$-$C_4$) alkyl;

($C_1$-$C_{10}$) alkyl optionally substituted by one or more ($C_3$-$C_7$) cycloalkyl or by a group —$NR_8R_9$; and ($C_3$-$C_7$) cycloalkyl;

a group —$SR_{20}$ wherein $R_{20}$ is selected from the group consisting of

H:

($C_1$-$C_6$) haloalkyl;

a group —$C(O)R_7$ wherein $R_7$ is ($C_1$-$C_4$) alkyl;

($C_1$-$C_{10}$) alkyl optionally substituted by one or more ($C_3$-$C_7$) cycloalkyl or by a group —$NR_8R_9$ as below defined; and ($C_3$-$C_7$) cycloalkyl;

halogen atoms;

CN;

$NO_2$;

$NR_8R_9$ wherein $R_8$ and $R_9$ are different or the same and are independently selected from the group consisting of:

H;

($C_1$-$C_4$) alkylene-$NR_{13}R_{14}$ wherein $R_{13}$ and $R_{14}$ are different or the same and are independently selected from the group consisting of: H and ($C_1$-$C_6$) alkyl, which is optionally substituted with ($C_3$-$C_7$) cycloalkyl or ($C_3$-$C_7$) heterocycloalkyl; or they form with the nitrogen atom to which they are linked a saturated or partially saturated ($C_3$-$C_7$) heterocyclic ring;

($C_1$-$C_6$) alkyl, optionally substituted with ($C_3$-$C_7$) cycloalkyl, ($C_3$-$C_7$) heterocycloalkyl, a group —OH or ($C_1$-$C_6$) alkoxyl;

a group —$SO_2R_{15}$, wherein $R_{15}$ is selected in the group consisting of: ($C_1$-$C_4$) alkyl optionally substituted by ($C_3$-$C_7$) cycloalkyl or ($C_3$-$C_7$) heterocycloalkyl; ($C_3$-$C_7$) heterocycloalkyl; and phenyl optionally substituted by one or more ($C_1$-$C_6$) alkyl, halogen or a group —OH;

a group —$C(O)R_{16}$, wherein $R_{16}$ is selected in the group consisting of: ($C_1$-$C_6$) alkyl optionally substituted by ($C_3$-$C_7$) cycloalkyl or ($C_3$-$C_7$) heterocycloalkyl; ($C_3$-$C_7$) heterocycloalkyl; phenyl optionally substituted by one or more ($C_1$-$C_6$) alkyl, halogen or —OH; and a group —$NH_2$;

a group —C(O)$OR_{17}$, wherein $R_{17}$ is selected in the group consisting of: ($C_1$-$C_6$) alkyl optionally substituted by ($C_3$-$C_7$) cycloalkyl or ($C_3$-$C_7$) heterocycloalkyl; ($C_3$-$C_7$) heterocycloalkyl; phenyl optionally substituted by one or more ($C_1$-$C_6$) alkyl, halogen or —OH; and a group —$NH_2$;

or they form with the nitrogen atom to which they are linked a saturated or partially saturated heterocyclic ring, which is optionally substituted by one or more ($C_1$-$C_6$) alkyl or oxo groups;

($C_1$-$C_4$) alkylene-$NR_8R_9$ as above defined;

$COR_{10}$ wherein $R_{10}$ is phenyl or ($C_1$-$C_6$) alkyl;

oxo;

$SO_2R_{11}$ wherein $R_{11}$ is ($C_1$-$C_4$) alkyl, OH or $NR_8R_9$ wherein $R_8$ and $R_9$ are as defined above;

$COOR_{12}$ wherein $R_{12}$ is H or ($C_1$-$C_4$) alkyl or ($C_1$-$C_4$) alkylene-$NR_8R_9$ wherein $R_8$ and $R_9$ are as defined above; and —$CONR_8R_9$ wherein $R_8$ and $R_9$ are as defined above;

wherein groups $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$ and $R_{20}$ may assume the same or different meanings at each occurrence, if present in more than one group;

their N-oxides on the pyridine ring, and pharmaceutically acceptable salts, or solvates thereof.

In another preferred embodiment, invention is directed to derivatives of 1-phenyl-2-pyridinyl alkyl alcohols of general formula (IL):

(IL)

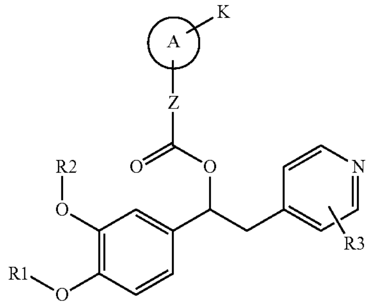

wherein:

$R_1$ and $R_2$ are different or the same and are independently selected from the group consisting of:

H;

($C_3$-$C_7$) cycloalkylcarbonyl;

($C_1$-$C_6$) alkyl, optionally substituted by one or more substituents selected from ($C_3$-$C_7$) cycloalkyl or ($C_5$-$C_7$) cycloalkenyl;

($C_1$-$C_6$) haloalkyl;

($C_3$-$C_7$) cycloalkyl;

($C_5$-$C_7$) cycloalkenyl;

($C_2$-$C_6$) alkenyl; and ($C_2$-$C_6$) alkynyl;

$R_3$ is one or more substituents independently selected from the group consisting of H, CN, $NO_2$, $CF_3$ and a halogen atom;

Z is a group —$(CH_2)_n$— wherein n is 0 or 1;

A is a saturated and monocyclic ($C_3$-$C_7$) heterocycloalkylene group;

K is selected from the group consisting of:

—$(CH_2)_m$C(O)$R_4$ wherein m may be 0 or 1;

—C(O)($CH_2$)$R_4$;

—$SO_2(CH_2)_pR_4$ wherein p may be zero or 1;

—$CH_2SO_2R_4$; and

—$CH_2R_4$;

$R_4$ is a ring system, that is a mono- or bicyclic ring which may be saturated, partially unsaturated or fully unsaturated, such as aryl, ($C_3$-$C_8$) cycloalkyl, ($C_3$-$C_7$) heterocycloalkyl or heteroaryl, such ring being optionally substituted by one or more groups $R_5$ which may be the same or different, and which are independently selected from the group consisting of:

($C_1$-$C_6$) alkyl optionally substituted by one or more ($C_3$-$C_7$) cycloalkyl;

($C_3$-$C_7$) heterocycloalkyl;

($C_3$-$C_7$) heterocycloalkyl($C_1$-$C_4$) alkyl;

a group —$OR_6$ wherein $R_6$ is selected from the group consisting of

H:

($C_1$-$C_6$) haloalkyl;

a group —$SO_2R_7$, wherein $R_7$ is ($C_1$-$C_4$) alkyl;

a group —C(O)$R_7$ wherein $R_7$ is ($C_1$-$C_4$) alkyl;

($C_1$-$C_{10}$) alkyl optionally substituted by one or more ($C_3$-$C_7$) cycloalkyl or by a group —$NR_8R_9$; and ($C_3$-$C_7$) cycloalkyl;

a group —$SR_{20}$ wherein $R_{20}$ is selected from the group consisting of

H:

($C_1$-$C_6$) haloalkyl;

a group —C(O)$R_7$ wherein $R_7$ is ($C_1$-$C_4$) alkyl;

($C_1$-$C_{10}$) alkyl optionally substituted by one or more ($C_3$-$C_7$) cycloalkyl or by a group —$NR_8R_9$ as below defined; and ($C_3$-$C_7$) cycloalkyl;

halogen atoms;

CN;

$NO_2$;

$NR_8R_9$ wherein $R_8$ and $R_9$ are different or the same and are independently selected from the group consisting of:

H;

($C_1$-$C_4$) alkylene-$NR_{13}R_{14}$ wherein $R_{13}$ and $R_{14}$ are different or the same and are independently selected from the group consisting of: H and ($C_1$-$C_6$) alkyl, which is optionally substituted with ($C_3$-$C_7$) cycloalkyl or ($C_3$-$C_7$) heterocycloalkyl; or they form with the nitrogen atom to which they are linked a saturated or partially saturated ($C_3$-$C_7$) heterocyclic ring;

($C_1$-$C_6$) alkyl, optionally substituted with ($C_3$-$C_7$) cycloalkyl, ($C_3$-$C_7$) heterocycloalkyl, a group —OH or ($C_1$-$C_6$) alkoxyl;

a group —$SO_2R_{15}$, wherein $R_{15}$ is selected in the group consisting of: ($C_1$-$C_4$) alkyl optionally substituted by ($C_3$-$C_7$) cycloalkyl or ($C_3$-$C_7$) heterocycloalkyl; ($C_3$-$C_7$) heterocycloalkyl; and phenyl optionally substituted by one or more ($C_1$-$C_6$) alkyl, halogen or a group —OH;

a group —C(O)$R_{16}$, wherein $R_{16}$ is selected in the group consisting of: ($C_1$-$C_6$) alkyl optionally substituted by ($C_3$-$C_7$) cycloalkyl or ($C_3$-$C_7$) heterocycloalkyl; ($C_3$-$C_7$) heterocycloalkyl; phenyl optionally substituted by one or more ($C_1$-$C_6$) alkyl, halogen or —OH; and a group —$NH_2$;

a group —C(O)$OR_{17}$, wherein $R_{17}$ is selected in the group consisting of: ($C_1$-$C_6$) alkyl optionally substituted by ($C_3$-$C_7$) cycloalkyl or ($C_3$-$C_7$) heterocycloalkyl; ($C_3$-$C_7$) heterocycloalkyl; phenyl optionally substituted by one or more ($C_1$-$C_6$) alkyl, halogen or —OH; and a group —$NH_2$;

or they form with the nitrogen atom to which they are linked a saturated or partially saturated heterocyclic ring, which is optionally substituted by one or more $(C_1-C_6)$ alkyl or oxo groups;

$(C_1-C_4)$ alkylene-$NR_8R_9$ as above defined;

$COR_{10}$ wherein $R_{10}$ is phenyl or $(C_1-C_6)$ alkyl;

oxo;

$SO_2R_{11}$ wherein $R_{11}$ is $(C_1-C_4)$ alkyl, OH or $NR_8R_9$ wherein $R_8$ and $R_9$ are as defined above;

—$COOR_{12}$ wherein $R_{12}$ is H or $(C_1-C_4)$ alkyl or $(C_1-C_4)$ alkylene-$NR_8R_9$ wherein $R_8$ and $R_9$ are as defined above; and —$CONR_8R_9$ wherein $R_8$ and $R_9$ are as defined above;

wherein groups $R_6$, $R_7$, $R_8$, $R_9$, $R_{10}$, $R_{11}$, $R_{12}$, $R_{13}$, $R_{14}$, $R_{15}$, $R_{16}$, $R_{17}$ and $R_{20}$ may assume the same or different meanings at each occurrence, if present in more than one group; their N-oxides on the pyridine ring, and pharmaceutically acceptable salts, or solvates thereof.

The present invention further provides the corresponding N-oxides on the pyridine ring of compounds of formula (I).

The present invention also provides the pharmaceutically acceptable salts and/or solvates thereof.

The term "pharmaceutically acceptable salts", as used herein, refers to derivatives of compounds of formula (I) or of their corresponding N-oxides on the pyridine ring wherein the parent compound is suitably modified by converting any of the free acid or basic groups, if present, into the corresponding addition salt with any base or acid conventionally intended as being pharmaceutically acceptable.

Suitable examples of said salts may thus include mineral or organic acid addition salts of basic residues such as amino groups, as well as mineral or organic acid residues such as carboxylic groups.

Cations of inorganic bases which can be suitably used to prepare salts within the invention comprise ions of alkali or alkaline earth metals such as potassium, sodium, calcium or magnesium.

Those obtained by reacting the main compound, functioning as a base, with an inorganic or organic acid to form a salt comprise, for example, salts of hydrochloric acid, sulfuric acid, phosphoric acid, methane sulfonic acid, camphor sulfonic acid, oxalic acid, maleic acid, succinic acid and citric acid.

Those skilled in the art of organic chemistry will appreciate that many organic compounds can form complexes with solvents in which they are reacted or from which they are precipitated or crystallized. These complexes are known as "solvates". Pharmaceutically acceptable solvates of compound of the invention are within the scope of the invention.

Included within the scope of the present invention are also polymorphs and crystalline forms of compounds of formula (I), of their N-oxides on the pyridine ring, or of pharmaceutically acceptable salts, or solvates thereof.

Hereinafter, compounds of formula (I), (IG), (IL), corresponding N— Oxides on the pyridine ring, embodiments, enantiomers, diastereoisomers thereof, their pharmaceutically acceptable salts and solvates, and polymorphs or crystalline forms thereof defined in any aspect of the invention (except intermediate compounds described in the chemical processes) are referred to as "compounds of the invention".

The present invention further provides a process for the preparation of compounds of the invention.

The present invention also provides pharmaceutical compositions of compounds of the invention either alone or in combination, in admixture with one or more pharmaceutically acceptable carriers.

In a further aspect the present invention provides the use of the compounds of the present invention as a medicament.

In another aspect the present invention provides the use of the compounds of the present invention for the manufacture of a medicament.

In particular, the present invention provides the use of the compounds of the present invention for the prevention and/or treatment of any disease characterized by phosphodiesterase 4 (PDE4) overactivity and/or wherein an inhibition of PDE4 activity is desirable.

In particular, the compounds of the present invention alone or combined with other active ingredients may be administered for the prevention and/or treatment of a disease the respiratory tract characterized by airway obstruction such as asthma and COPD.

In a further aspect, the present invention provides the use of compounds of the present invention for the preparation of a medicament for the prevention and/or treatment of any disease characterized by phosphodiesterase 4 (PDE4) overactivity and/or wherein an inhibition of PDE4 activity is desirable.

Moreover, the present invention provides methods for prevention and/or treatment of any disease wherein PDE4 inhibition is desirable, said method comprising administering to a patient in need of such treatment a therapeutically effective amount of a compound of the present invention.

DETAILED DESCRIPTION OF THE PREFERRED EMBODIMENTS

The term "halogen atoms" as used herein includes fluorine, chlorine, bromine, and iodine, preferably chlorine.

As used herein, the term "$(C_1-C_x)$ alkyl" where x is an integer greater than 1, refers to straight-chained and branched alkyl groups wherein the number of constituent carbon atoms is in the range 1 to x. Particular alkyl groups are methyl, ethyl, n-propyl, isopropyl, and t-butyl.

By analogy, the term "$(C_1-C_x)$alkylene", refers to a divalent $(C_1-C_x)$alkyl radical, wherein $(C_1-C_x)$alkyl is as above defined.

The term "$(C_1-C_x)$ alkoxyl" where x is an integer greater than 1, refers to straight-chained and branched alkoxy groups wherein the number of constituent carbon atoms is in the range 1 to x. Particular alkyl groups are methoxyl, ethoxyl, n-propoxyl, isopropoxyl, and t-butoxyl.

The expressions "$(C_1-C_x)$haloalkyl" refer to the above defined "$(C_1-C_x)$alkyl" groups wherein one or more hydrogen atoms are replaced by one or more halogen atoms, which can be the same or different from each other.

Examples of said $(C_1-C_6)$haloalkyl groups may thus include halogenated, poly-halogenated and fully halogenated alkyl groups wherein all of the hydrogen atoms are replaced by halogen atoms, e.g. trifluoromethyl or difluoro methyl groups.

The term "$(C_3-C_y)$ cycloalkyl", where y is an integer greater than or equal to 3, refers to saturated cyclic hydrocarbon groups containing from 3 to y ring carbon atoms. Examples include cyclopropyl, cyclobutyl, cyclopentyl, cyclohexyl, and cycloheptyl.

The derived expression "$(C_3-C_y)$heterocycloalkyl" refers to monocyclic $(C_3-C_y)$cycloalkyl groups, in which at least one ring carbon atom is replaced by a heteroatom (e.g. N, NH, S or O). Non-limiting examples of $(C_3-C_y)$heterocycloalkyl are represented by: pyrrolidinyl, thiazolidinyl, piperazinyl, piperidnyl, morpholinyl, thiomorpholinyl, and azetidinyl.

By analogy, the term "($C_3$-$C_y$)heterocycloalkyl-ene", refers to a divalent ($C_3$-$C_y$)heterocycloalkyl radical, wherein ($C_3$-$C_y$)heterocycloalkyl is as above defined.

The expression "($C_3$-$C_y$)cycloalkylcarbonyl" refers to ($C_3$-$C_y$)cycloalkylCO— groups wherein the group "($C_3$-$C_y$) cycloalkyl" has the meaning above defined.

The term "($C_2$-$C_6$)alkenyl" refers to straight or branched, conjugated or non-conjugated, carbon chains with one or more double bonds, in cis or trans configuration, wherein the number atoms is in the range 2 to 6.

The term "($C_5$-$C_z$) cycloalkenyl", where z is an integer greater than or equal to 5, refers to cyclic hydrocarbon groups containing from 5 to z ring carbon atoms and one or more double bonds.

The term "($C_2$-$C_6$)alkynyl" refers to straight or branched carbon chains with one or more triple bonds wherein the number of atoms is in the range 2 to 6.

The term "($C_3$-$C_y$)heterocycloalkyl($C_1$-$C_x$) alkyl" refers to the above "($C_1$-$C_x$)alkyl" group wherein one or more hydrogen atoms are replaced by one or more "($C_3$-$C_y$) heterocycloalkyl" groups.

As used herein, the expression "ring system" refers to mono- or bicyclic ring systems which may be saturated, partially unsaturated or unsaturated, such as aryl, ($C_3$-$C_8$) cycloalkyl, ($C_3$-$C_7$) heterocycloalkyl or heteroaryl, having 5 to 11 ring atoms in which at least one ring atom is a heteroatom (e.g. N, S or O).

The expression "aryl" refers to mono or bi-ring systems which have 6 to 10 ring atoms, wherein at least one ring is aromatic.

The expression "heteroaryl" refers to mono or bi-ring systems with 5 to 11 ring atoms, in which at least one ring is aromatic and in which at least one ring atom is a heteroatom (e.g. N, NH, S or O).

Examples of suitable aryl or 5 or 6-membered heteroaryl monocyclic systems include, for instance, phenyl, thiophene (thiophenyl), benzene (phenyl), pyrrole (pyrrolyl), pyrazole (pyrazolyl), imidazole (imidazolyl), isoxazole (isoxazolyl), oxazole (oxazolyl), isothiazole (isothiazolyl), thiazole (thiazolyl), pyridine (pyridinyl), imidazolidine (imidazolidinyl), furan (furanyl) radicals and the like.

Examples of suitable aryl or heteroaryl bicyclic systems include naphthalene (naphthyl), biphenylene (biphenylenyl), purine (purinyl), pteridine (pteridinyl), benzotriazole (benzotriazolyl), quinoline (quinolinyl), isoquinoline (isoquinolinyl), indole (indolyl), isoindole (isoindolyl), benzothiophene (benzothiophenyl), dihydrobenzo dioxin, dihydrobenzo dioxepin, benzo oxazin radicals and the like.

Thus, the present invention is directed to a class of compounds acting as inhibitors of the phosphodiesterase 4 (PDE4) enzyme. Said class of compounds inhibits the conversion of cyclic nucleotides, in particular cyclic adenosine monophosphate (cAMP), into their inactive 5'-mononucleotide forms.

In the airways, the physiological responses to elevated intracellular levels of cyclic nucleotides, in particular of cAMP, lead to the suppression of the activity of immune and pro-inflammatory cells such as mast cells, macrophages, T lymphocytes, eosinophils and neutrophils, resulting in a decrease of the release of inflammatory mediators which include cytokines such as IL-1, IL-3 and tumor necrosis factor-alpha (TNF-α). It also leads to an airway smooth muscle relaxation and a decrease in oedema.

The present invention relates to derivatives of 1-phenyl-2-pyridinyl alkyl alcohols of general formula (I), N-oxides on the pyridine ring and pharmaceutically acceptable salts or solvates thereof:

(I)

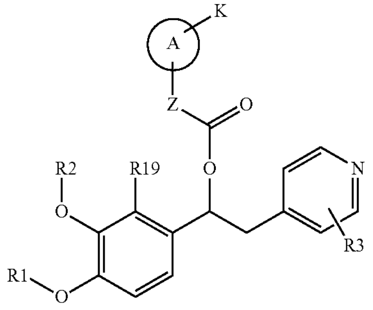

wherein $R_1$, $R_2$, $R_3$, $R_{19}$, Z, A and K are as above defined.

It will be apparent to those skilled in the art that compounds of general formula (I) contain at least one stereogenic center, namely represented by the carbon atom (1) with an asterisk below, and therefore exist as optical stereoisomers.

(I)

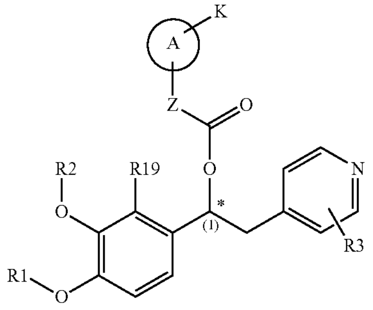

When the compounds according to the invention have at least one stereogenic center, they may accordingly exist as enantiomers. When the compounds according to the invention possess two or more stereogenic centers, they may additionally exist as diastereoisomers. It is to be understood that all such isomers and mixtures thereof in any proportion are encompassed within the scope of the present invention.

In a preferred embodiment, the present invention is directed to compounds of formula (I)', which are compounds of formula (I) as above defined where the absolute configuration of carbon (1) is that shown below:

(I)'

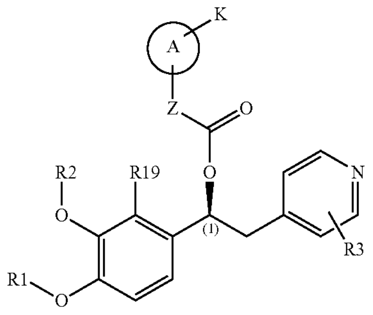

The absolute configuration for carbon (1) is assigned on the basis of Cahn-Ingold-Prelog nomenclature based on groups' priorities.

In one preferred embodiment, for compounds of formula (I), the absolute configuration at carbon (1) is (S).

When the compounds of formula (I) possess a second stereogenic center, namely at carbon (2) represented by another asterisk herebelow, they exist as at least four diastereoisomers:

(I)

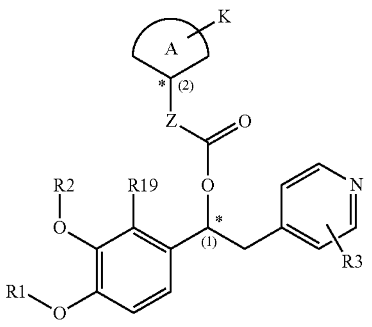

The four diastereoisomers thereof are represented below:

(I)''

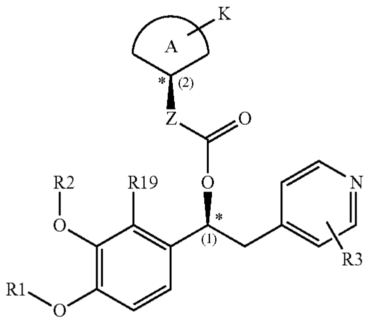

(I)'''

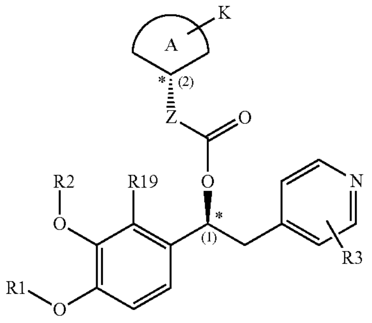

(I)''''

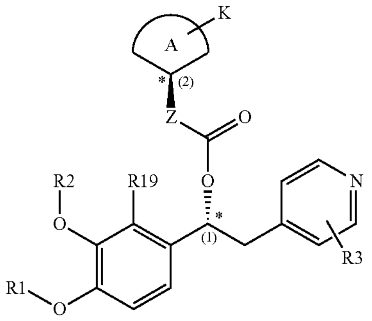

-continued (I)'''''

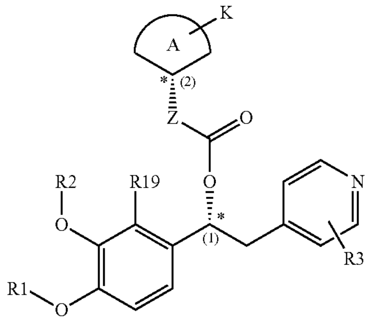

and are comprised within the scope of the present invention.

In a preferred embodiment, the present invention is directed to compounds of formula (I)", which are compounds of formula (I)' as above defined where the absolute configuration of carbon (2) is that shown below:

(I)''

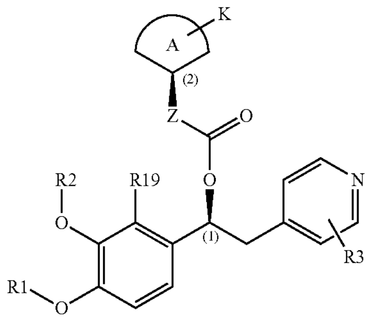

In another preferred embodiment, the present invention is directed to compounds of formula (I)'", which are compounds of formula (I)' as above defined where the absolute configuration of carbon (2) is that shown below:

(I)'''

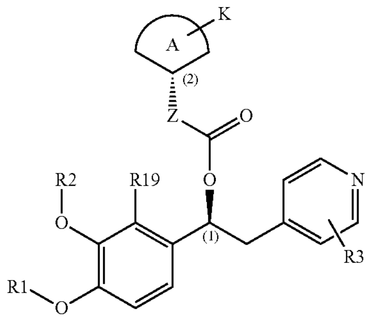

For compounds of formula (I)" and (I)'", the absolute configuration of carbon (1) and (2) is assigned on the basis of Cahn-Ingold-Prelog nomenclature based on groups' priorities.

It is to be understood that all preferred groups or embodiments described herebelow and hereabove for compounds of formula (I) may be combined among each other and apply to compounds of formula (IG), (IL), (I)', (I)", (I)'", (I)"" and (I)""' as well mutatis mutandis.

In a preferred embodiment, the invention provides compounds of formula (IH), which are N-oxides derivatives of the pyridine ring of compounds of formula (I), or pharmaceutically acceptable salts thereof:

(IH)

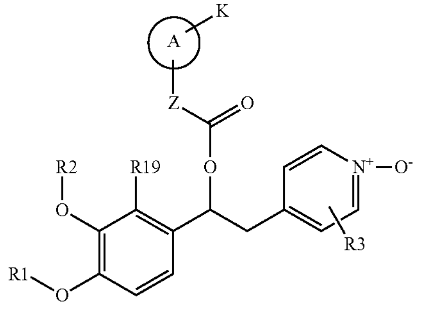

In a preferred embodiment, 2-pyridinyl ring has two $R_3$ substituents which are halogen atom. In a further preferred embodiment, such $R_3$ substituents are two chlorine atoms at positions 3 and 5 of the pyridine ring.

In one preferred embodiment, $R_1$ is ($C_1$-$C_6$) haloalkyl or ($C_1$-$C_6$) alkyl.

In one preferred embodiment, $R_2$ is ($C_1$-$C_6$) alkyl which optionally is substituted by ($C_3$-$C_7$) cycloalkyl or is a ($C_3$-$C_7$) cycloalkyl.

In another preferred embodiment, $R_1$ and $R_2$, together with the interconnecting atoms, form a 2,2-difluoro-1,3-dioxolane ring of formula (q) fused to the phenyl moiety which bears groups —$OR_1$ and —$OR_2$, wherein asterisks indicate carbon atoms shared with such phenyl ring:

(q)

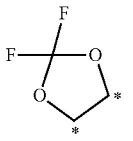

In a further preferred embodiment, $R_1$ is ($C_1$-$C_6$) haloalkyl and $R_2$ is ($C_1$-$C_6$) alkyl which is substituted by ($C_3$-$C_7$) cycloalkyl.

In another preferred embodiment, $R_1$ is ($C_1$-$C_6$)alkyl and $R_2$ is ($C_1$-$C_6$) alkyl.

In a preferred embodiment, $R_{19}$ is hydrogen.

In a further preferred embodiment, $R_{19}$ is hydrogen, $R_1$ is ($C_1$-$C_6$) haloalkyl and $R_2$ is ($C_1$-$C_6$) alkyl which is substituted by ($C_3$-$C_7$) cycloalkyl.

In another preferred embodiment, $R_{19}$, if different from hydrogen, forms together with $R_2$ a group of formula (x) wherein bonds labeled with (1) and (2) indicate the points of attachment for group (x) to atoms bearing groups $R_{19}$ and $R_2$ respectively (x)

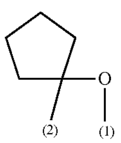

in such a way that $R_2$ and $R_{19}$ together with the interconnecting atoms form a ring of formula (w) which is fused to phenyl ring which bears groups —$OR_2$ and $R_{19}$, wherein asterisks indicate carbon atoms shared with such phenyl ring:

(w)

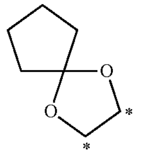

A preferred group of compounds of general formula (I) is that wherein the 2-pyridinyl ring is substituted in positions 3 and 5 with two atoms of chlorine, according to the general formula (IA):

IA)

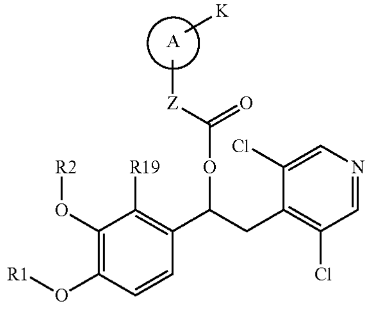

wherein $R_1$, $R_2$, $R_{19}$, K, z, and A are as defined above for compounds of formula (I); and the corresponding N-oxide on the pyridine ring, or pharmaceutically acceptable salts thereof.

Another preferred group of compounds of formula (I) is that shown below according to general formula (IB):

(IB)

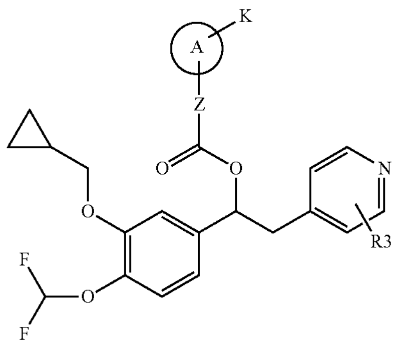

wherein $R_3$, K, Z and A are as defined above for compounds of formula (I); and the corresponding N-oxide on the pyridine ring, or pharmaceutically acceptable salts thereof.

A further preferred group of compounds of formula (I) is that shown below according to general formula (IC):

(IC)

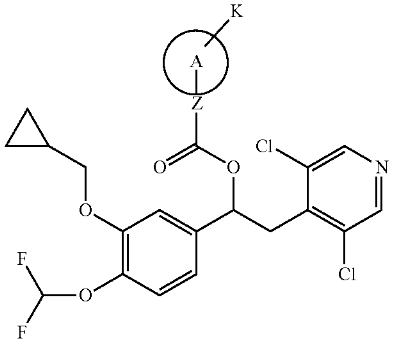

wherein K, Z and A are as defined above for compounds of formula (I); and the corresponding N-oxide on the pyridine ring, or pharmaceutically acceptable salts thereof.

In one preferred embodiment, A is a ($C_3$-$C_7$) heterocycloalkyl-ene group comprising a nitrogen atom which represents the connecting point to group K as below represented:

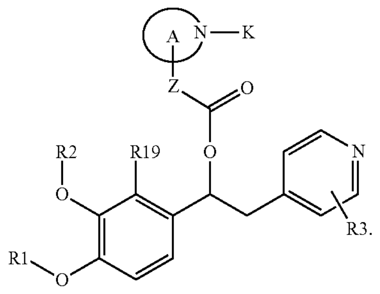

In another preferred embodiment, A is selected in the list of di-radicals below reported:

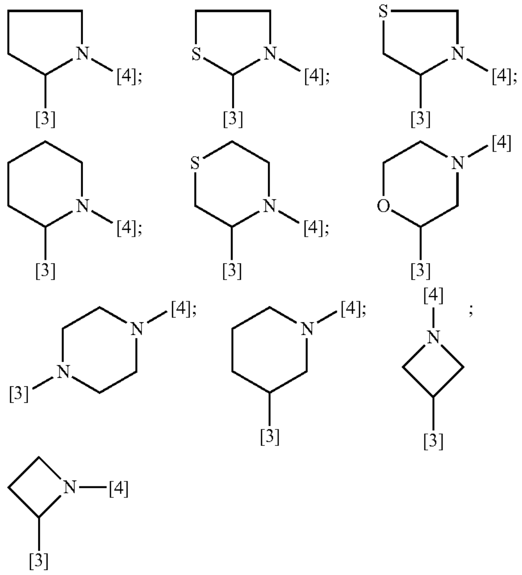

wherein the symbols [3] and [4] indicate the points of connection for group A with, respectively, groups Z and K.

In a further preferred embodiment, A is selected in the list of di-radicals below reported:

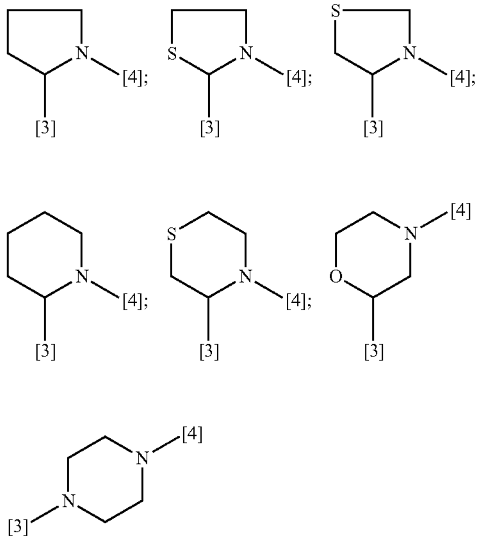

wherein the symbols [3] and [4] indicate the points of connection for group A with, respectively, groups Z and K.

In an additional preferred embodiment, A is a group

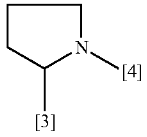 or 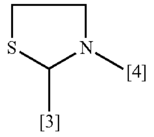

wherein the symbols [3] and [4] indicate the points of connection for group A with, respectively, groups Z and K.

In a preferred embodiment, Z is a group $-(CH_2)_n-$ in which n is zero.

Another preferred group of compounds of formula (I) is that shown below according to general formula (ID):

(ID)

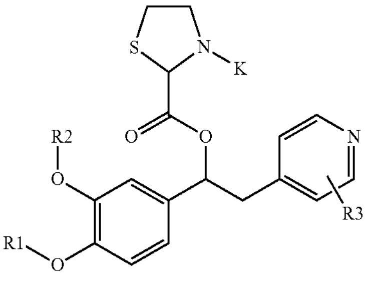

wherein $R_1$, $R_2$, $R_3$ and K are as defined above for compounds of formula (I), $R_{19}$ is hydrogen, Z is a bond (i.e., n is zero), and A is a thiazolidine divalent radical group as above represented; and the corresponding N-oxide on the pyridine ring, or pharmaceutically acceptable salts thereof.

Another preferred group of compounds of formula (I) is that shown below according to general formula (ID'''):

(ID'')

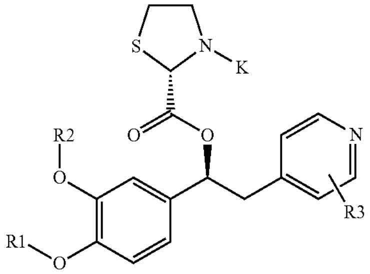

wherein $R_1$, $R_2$, $R_3$ and K are as defined above for compounds of formula (I), $R_{19}$ is hydrogen, Z is a bond (i.e. n is zero), A is a thiazolidine divalent radical group and stereogenic center have absolute configuration as above represented; and the corresponding N-oxide on the pyridine ring, or pharmaceutically acceptable salts thereof.

In one embodiment, for compounds of formula (ID) or (ID'''), $R_1$ is $(C_1-C_6)$ haloalkyl, $R_2$ is $(C_1-C_6)$ alkyl which is substituted by $(C_3-C_7)$ cycloalkyl, 2-pyridinyl ring is substituted in positions 3 and 5 with two chlorine $R_3$ groups, and K is a group

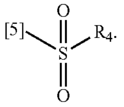

Another preferred group of compounds of formula (I) is that shown below according to general formula (IE):

(IE)

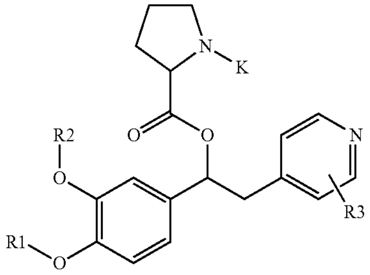

wherein $R_1$, $R_2$, $R_3$ and K are as defined above for compounds of formula (I), Z is a bond (i.e. n is zero), R19 is hydrogen and A is a pyrrolidine divalent radical group as above represented; and the corresponding N-oxide on the pyridine ring, or pharmaceutically acceptable salts thereof.

Another preferred group of compounds of formula (I) is that shown below according to general formula (IE'''):

(IE''')

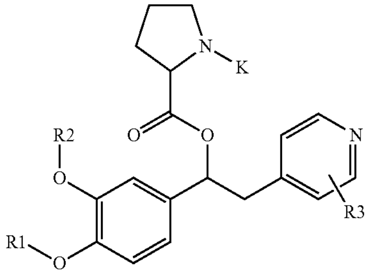

wherein $R_1$, $R_2$, $R_3$ and K are as defined above for compounds of formula (I), Z is a bond (i.e. n is zero), R19 is hydrogen, A is a pyrrolidine divalent radical group, and the stereogenic centers have the absolute configuration as above represented; and the corresponding N-oxide on the pyridine ring, or pharmaceutically acceptable salts thereof.

In one embodiment, for compounds of formula (IE) or (IE'''), $R_1$ is $(C_1-C_6)$ haloalkyl, $R_2$ is $(C_1-C_6)$ alkyl which is substituted by $(C_3-C_7)$ cycloalkyl, 2-pyridinyl ring is substituted in 3 and 5 with two chlorine $R_3$ groups, and K is a group

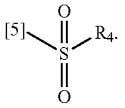

In one preferred embodiment, K is selected in the list of groups below reported:

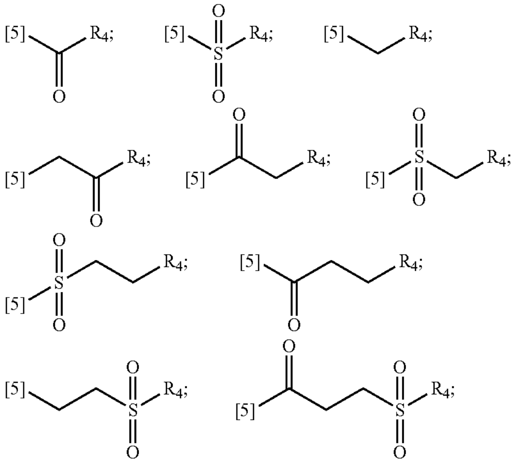

wherein the symbol [5] indicates the point of connection for group K with group A.

In another preferred embodiment, K is selected in the list of groups below reported:

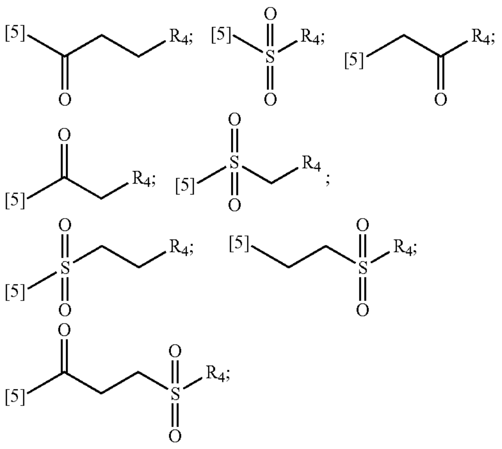

wherein the symbol [5] indicates the point of connection for group K with group A.

In yet another preferred embodiment, K is selected in the list of groups below reported:

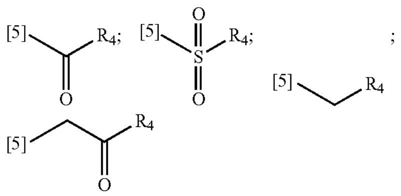

wherein the symbol [5] indicates the point of connection for group K with group A.

In further preferred embodiment, K is a group

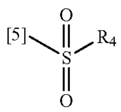

wherein the symbol [5] indicates the point of connection for group K with group A.

In a preferred embodiment, $R_4$ is selected in the group consisting of: a group phenyl, a 5 or 6-membered heteroaryl group, a monocyclic $(C_3\text{-}C_7)$heterocycloalkyl and a bicyclic ring system; and each of which is optionally substituted by one or more groups $R_5$.

In one preferred embodiment, $R_4$ is a group phenyl or a 5 or 6-membered heteroaryl group, each of which is optionally substituted by one or more groups $R_5$.

In a further preferred embodiment, $R_4$ is a group phenyl which is optionally substituted by one or more groups $R_5$.

In a still preferred embodiment, $R_4$ is a 5 or 6-membered heteroaryl group which is optionally substituted by one or more groups $R_5$.

In another preferred embodiment, $R_4$ is a monocyclic $(C_3\text{-}C_7)$heterocycloalkyl optionally substituted by one or more groups $R_5$.

In a still preferred embodiment, $R_4$ is a bicyclic ring system optionally substituted by one or more groups $R_5$.

In one preferred embodiment, the number of substituents $R_5$ is zero, 1, or 2. In a further preferred embodiment, such number is 1.

In one preferred embodiment, $R_5$ is independently selected in the group consisting of:

- $(C_1\text{-}C_6)$ alkyl optionally substituted by one or more groups independently selected in the list consisting of: $(C_3\text{-}C_7)$ cycloalkyl, —OH and a group $—NR_{18}C(O)(C_1\text{-}C_4)$ alkyl, wherein $R_{18}$ is hydrogen or $(C_1\text{-}C_4)$ alkyl-$(C_3\text{-}C_7)$ heterocycloalkyl;
- 5 or 6-membered heteroaryl which is optionally substituted by one or two groups $(C_1\text{-}C_4)$ alkyl;
- $(C_1\text{-}C_6)$ haloalkyl;
- $(C_3\text{-}C_7)$ heterocycloalkyl$(C_1\text{-}C_4)$ alkyl;
- a group $—OR_6$ wherein $R_6$ is selected from the group consisting of:
  - $(C_1\text{-}C_6)$ haloalkyl;
  - $(C_1\text{-}C_{10})$ alkyl optionally substituted by one or more $(C_3\text{-}C_7)$ cycloalkyl;
- a group $—SO_2R_7$, wherein $R_7$ is $(C_1\text{-}C_4)$ alkyl;
- halogen atoms;
- cyano;
- $NR_8R_9$ wherein $R_8$ and $R_9$ are different or the same and are independently selected from the group consisting of:
  - H;
  - $(C_1\text{-}C_6)$ alkyl, optionally substituted with $(C_3\text{-}C_7)$ cycloalkyl, $(C_3\text{-}C_7)$ heterocycloalkyl;
  - a group $—SO_2R_{15}$, wherein $R_{15}$ is $(C_1\text{-}C_4)$ alkyl;
  - or they form with the nitrogen atom to which they are linked a saturated or partially saturated heterocyclic ring, which is optionally substituted by one or more $(C_1\text{-}C_6)$ alkyl or oxo groups;
- $(C_1\text{-}C_4)$ alkylene-$NR_8R_9$;
- $COR_{10}$ wherein $R_{10}$ is phenyl or $(C_1\text{-}C_6)$ alkyl;
- oxo;
- $SO_2R_{11}$ wherein $R_{11}$ is $NR_8R_9$ wherein $R_8$ and $R_9$ are as defined above;
- $—COOR_{12}$ wherein $R_{12}$ is H or $(C_1\text{-}C_4)$ alkyl or $(C_1\text{-}C_4)$ alkylene-$NR_8R_9$ wherein $R_8$ and $R_9$ are as defined above; and
- $—CONR_8R_9$ wherein $R_8$ and $R_9$ are as defined above.

In another preferred embodiment, $R_5$ is independently selected in the group consisting of:

- $(C_1\text{-}C_6)$ alkyl;
- $(C_3\text{-}C_7)$ heterocycloalkyl;
- $(C_3\text{-}C_7)$ heterocycloalkyl$(C_1\text{-}C_4)$ alkyl;
- a group $—OR_6$ wherein $R_6$ is selected from the group consisting of:
  - $(C_1\text{-}C_6)$ haloalkyl;
  - $(C_1\text{-}C_{10})$ alkyl optionally substituted by one or more $(C_3\text{-}C_7)$ cycloalkyl;
- a group $—SO_2R_7$, wherein $R_7$ is $(C_1\text{-}C_4)$ alkyl;
- halogen atoms;
- $NR_8R_9$ wherein $R_8$ and $R_9$ are different or the same and are independently selected from the group consisting of:
  - H;
  - $(C_1\text{-}C_6)$ alkyl, optionally substituted with $(C_3\text{-}C_7)$ cycloalkyl, $(C_3\text{-}C_7)$ heterocycloalkyl;
  - a group $—SO_2R_{15}$, wherein $R_{15}$ is $(C_1\text{-}C_4)$ alkyl;
  - or they form with the nitrogen atom to which they are linked a saturated or partially saturated heterocyclic ring, which is optionally substituted by one or more $(C_1\text{-}C_6)$ alkyl or oxo groups;
- $(C_1\text{-}C_4)$ alkylene-$NR_8R_9$;
- $COR_{10}$ wherein $R_{10}$ is phenyl or $(C_1\text{-}C_6)$ alkyl;
- oxo;
- $—SO_2R_{11}$ wherein $R_{11}$ is $NR_8R_9$ wherein $R_8$ and $R_9$ are as defined above;
- $—COOR_{12}$ wherein $R_{12}$ is H or $(C_1\text{-}C_4)$ alkyl or $(C_1\text{-}C_4)$ alkylene-$NR_8R_9$ wherein $R_8$ and $R_9$ are as defined above; and
- $CONR_8R_9$ wherein $R_8$ and $R_9$ are as defined above.

In another preferred embodiment, $R_5$ is independently selected in the group consisting of:

- $(C_1\text{-}C_6)$ alkyl;
- $(C_3\text{-}C_7)$ heterocycloalkyl$(C_1\text{-}C_4)$ alkyl;
- a group $—OR_6$ wherein $R_6$ is $(C_1\text{-}C_{10})$ alkyl optionally substituted by one or more $(C_3\text{-}C_7)$ cycloalkyl;
- halogen atoms;
- $NR_8R_9$ wherein $R_8$ and $R_9$ are different or the same and are independently selected from the group consisting of:
  - H;
  - $(C_1\text{-}C_6)$ alkyl, optionally substituted with $(C_3\text{-}C_7)$ cycloalkyl, $(C_3\text{-}C_7)$ heterocycloalkyl;
  - a group $—SO_2R_{15}$, wherein $R_{15}$ is $(C_1\text{-}C_4)$ alkyl;
  - or they form with the nitrogen atom to which they are linked a saturated or partially saturated heterocyclic ring, which is optionally substituted by $(C_1\text{-}C_6)$ alkyl or oxo;

—$COOR_{12}$ wherein $R_{12}$ is H or $(C_1$-$C_4)$ alkyl or $(C_1$-$C_4)$ alkylene-$NR_8R_9$ wherein $R_8$ and $R_9$ are as defined above; and $CONR_8R_9$ wherein $R_8$ and $R_9$ are as defined above.

In a further preferred embodiment, $R_5$ is selected in the group consisting of:

—$(C_1$-$C_6)$ alkyl;

—$NR_8R_9$ wherein $R_8$ and $R_9$ are different or the same and are independently selected from the group consisting of:

H;

$(C_1$-$C_6)$ alkyl; and $CONR_8R_9$ wherein $R_8$ and $R_9$ are as defined above.

A further preferred group of compounds of formula (I) is that shown below according to general formula (IF):

(IF)

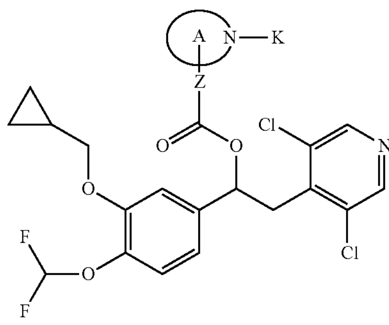

wherein Z is a bond, $R_{19}$ is hydrogen, A is a $(C_3$-$C_7)$ heterocycloalkyl-ene group comprising a nitrogen atom which represents the connecting point to group K, K is selected in the list of groups consisting of:

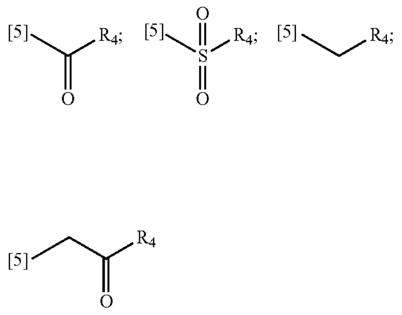

$R_4$ is a group phenyl or a 5 or 6-membered heteroaryl group, each of which is optionally substituted by one or more groups $R_5$: and the corresponding N-oxide on the pyridine ring, or pharmaceutically acceptable salts thereof.

According to a preferred embodiment, the present invention provides the compounds reported below:

| Compound | Chemical Name |
|---|---|
| 19 | 3,5-dichloro-4-((S)-2-(3-(cyclopropylmethoxy)-4-(difluoromethoxy)phenyl)-2-((S)-1-(3-(cyclopropylmethoxy)-4-(methylsulfonamido)benzoyl)pyrrolidine-2-carbonyloxy)ethyl)pyridine 1-oxide |
| 30 | 3,5-dichloro-4-((S)-2-(3-(cyclopropylmethoxy)-4-(difluoromethoxy)phenyl)-2-((S)-1-(4-methoxy-3-(methylsulfonyloxy)benzoyl)pyrrolidine-2-carbonyloxy)ethyl)pyridine 1-oxide |
| 53 | 3,5-dichloro-4-((S)-2-(3-(cyclopropylmethoxy)-4-(difluoromethoxy)phenyl)-2-((S)-1-(3,4-dimethoxyphenylsulfonyl)pyrrolidine-2-carbonyloxy)ethyl)pyridine 1-oxide |
| 135 | 4-((2S)-2-(3-(4-aminophenylsulfonyl)thiazolidine-2-carbonyloxy)-2-(3-(cyclopropylmethoxy)-4-(difluoromethoxy)phenyl)ethyl)-3,5-dichloropyridine 1-oxide |
| 142 | 3,5-dichloro-4-((2S)-2-(3-(cyclopropylmethoxy)-4-(difluoromethoxy)phenyl)-2-(3-(4-(methylsulfonamido)phenylsulfonyl)thiazolidine-2-carbonyloxy)ethyl)pyridine 1-oxide |
| 143 | 3,5-dichloro-4-((2S)-2-(3-(cyclopropylmethoxy)-4-(difluoromethoxy)phenyl)-2-(3-(4-(N-(2-morpholinoethyl)methylsulfonamido)phenylsulfonyl)thiazolidine-2-carbonyloxy)ethyl)pyridine 1-oxide |
| 151 | 4-((S)-2-((R)-3-(4-aminophenylsulfonyl)thiazolidine-2-carbonyloxy)-2-(3-(cyclopropylmethoxy)-4-(difluoromethoxy)phenyl)ethyl)-3,5-dichloropyridine 1-oxide |
| 150 | 4-((S)-2-((S)-3-(4-aminophenylsulfonyl)thiazolidine-2-carbonyloxy)-2-(3-(cyclopropylmethoxy)-4-(difluoromethoxy)phenyl)ethyl)-3,5-dichloropyridine 1-oxide |
| 136 | 4-((S)-2-((S)-1-(4-aminophenylsulfonyl)pyrrolidine-2-carbonyloxy)-2-(3-(cyclopropylmethoxy)-4-(difluoromethoxy)phenyl)ethyl)-3,5-dichloropyridine 1-oxide |
| 15 | 3,5-dichloro-4-((2S)-2-(3-(cyclopropylmethoxy)-4-(difluoromethoxy)phenyl)-2-(1-((4-(methoxycarbonyl)-5-methylfuran-2-yl)methyl)pyrrolidine-2-carbonyloxy)ethyl)pyridine 1-oxide |
| 124 | 3,5-dichloro-4-((S)-2-(3-(cyclopropylmethoxy)-4-(difluoromethoxy)phenyl)-2-((S)-1-(3-(dimethylcarbamoyl)-4-methoxyphenylsulfonyl)pyrrolidine-2-carbonyloxy)ethyl)pyridine 1-oxide |

-continued

| Compound | Chemical Name |
|---|---|
| 77 | 3,5-dichloro-4-((S)-2-(3-(cyclopropylmethoxy)-4-(difluoromethoxy)phenyl)-2-((R)-4-(3-sulfamoylphenylsulfonyl)morpholine-2-carbonyloxy)ethyl)pyridine 1-oxide or 3,5-dichloro-4-((S)-2-(3-(cyclopropylmethoxy)-4-(difluoromethoxy)phenyl)-2-((S)-4-(3-sulfamoylphenylsulfonyl)morpholine-2-carbonyloxy)ethyl)pyridine 1-oxide |
| 144 | 3,5-dichloro-4-((2S)-2-(3-(cyclopropylmethoxy)-4-(difluoromethoxy)phenyl)-2-(3-(2-oxo-2-(thiophen-2-yl)ethyl)thiazolidine-2-carbonyloxy)ethyl)pyridine 1-oxide |
| 16 | 3,5-dichloro-4-((S)-2-(3-(cyclopropylmethoxy)-4-(difluoromethoxy)phenyl)-2-((S)-3-(4-(dimethylcarbamoyl)benzyl)thiazolidine-2-carbonyloxy)ethyl)pyridine 1-oxide or 3,5-dichloro-4-((S)-2-(3-(cyclopropylmethoxy)-4-(difluoromethoxy)phenyl)-2-((R)-3-(4-(dimethylcarbamoyl)benzyl)thiazolidine-2-carbonyloxy)ethyl)pyridine 1-oxide |
| 17 | 3,5-dichloro-4-((S)-2-(3-(cyclopropylmethoxy)-4-(difluoromethoxy)phenyl)-2-((S)-3-(4-(dimethylcarbamoyl)benzyl)thiazolidine-2-carbonyloxy)ethyl)pyridine 1-oxide or 3,5-dichloro-4-((S)-2-(3-(cyclopropylmethoxy)-4-(difluoromethoxy)phenyl)-2-((R)-3-(4-(dimethylcarbamoyl)benzyl)thiazolidine-2-carbonyloxy)ethyl)pyridine 1-oxide |
| 26 | 4-((2S)-2-(3-(4-aminobenzoyl)thiazolidine-2-carbonyloxy)-2-(3-(cyclopropylmethoxy)-4-(difluoromethoxy)phenyl)ethyl)-3,5-dichloropyridine 1-oxide |
| 56 | 3,5-dichloro-4-((2S)-2-(3-(cyclopropylmethoxy)-4-(difluoromethoxy)phenyl)-2-(3-(3-(dimethylcarbamoyl)phenylsulfonyl)thiazolidine-2-carbonyloxy)ethyl)pyridine 1-oxide |
| 80 | 3,5-dichloro-4-((2S)-2-(3-(cyclopropylmethoxy)-4-(difluoromethoxy)phenyl)-2-(4-(3-(dimethylcarbamoyl)phenylsulfonyl)thiomorpholine-3-carbonyloxy)ethyl)pyridine 1-oxide |
| 81 | 3,5-dichloro-4-((2S)-2-(3-(cyclopropylmethoxy)-4-(difluoromethoxy)phenyl)-2-(4-(4-(N-methylsulfamoyl)phenylsulfonyl)thiomorpholine-3-carbonyloxy)ethyl)pyridine 1-oxide |
| 137 | 4-((2S)-2-(3-(3-amino-4-methoxyphenylsulfonyl)thiazolidine-2-carbonyloxy)-2-(3-(cyclopropylmethoxy)-4-(difluoromethoxy)phenyl)ethyl)-3,5-dichloropyridine 1-oxide |
| 57 | 3,5-dichloro-4-((2S)-2-(3-(cyclopropylmethoxy)-4-(difluoromethoxy)phenyl)-2-(3-(phenylsulfonyl)thiazolidine-2-carbonyloxy)ethyl)pyridine 1-oxide |
| 138 | 4-((S)-2-((R)-3-(4-aminophenylsulfonyl)thiazolidine-4-carbonyloxy)-2-(3-(cyclopropylmethoxy)-4-(difluoromethoxy)phenyl)ethyl)-3,5-dichloropyridine 1-oxide |
| 139 | 4-((2S)-2-(4-(4-aminophenylsulfonyl)morpholine-2-carbonyloxy)-2-(3-(cyclopropylmethoxy)-4-(difluoromethoxy)phenyl)ethyl)-3,5-dichloropyridine 1-oxide |
| 54 | 3,5-dichloro-4-((S)-2-(3-(cyclopropylmethoxy)-4-(difluoromethoxy)phenyl)-2-((S)-1-(3-(dimethylcarbamoyl)phenylsulfonyl)pyrrolidine-2-carbonyloxy)ethyl)pyridine 1-oxide |
| 78 | 3,5-dichloro-4-((2S)-2-(3-(cyclopropylmethoxy)-4-(difluoromethoxy)phenyl)-2-(4-(3-(dimethylcarbamoyl)phenylsulfonyl)morpholine-2-carbonyloxy)ethyl)pyridine 1-oxide |
| 84 | 3,5-dichloro-4-((S)-2-(3-(cyclopropylmethoxy)-4-(difluoromethoxy)phenyl)-2-((R)-3-(3-(dimethylcarbamoyl)phenylsulfonyl)thiazolidine-4-carbonyloxy)ethyl)pyridine 1-oxide |
| 58 | 3,5-dichloro-4-((2S)-2-(3-(cyclopropylmethoxy)-4-(difluoromethoxy)phenyl)-2-(3-(1,3-dioxoisoindolin-5-ylsulfonyl)thiazolidine-2-carbonyloxy)ethyl)pyridine 1-oxide |
| 125 | 3,5-dichloro-4-((2S)-2-(3-(cyclopropylmethoxy)-4-(difluoromethoxy)phenyl)-2-(3-(4-(dimethylcarbamoyl)phenylsulfonyl)thiazolidine-2-carbonyloxy)ethyl)pyridine 1-oxide |

-continued

| Compound | Chemical Name |
|---|---|
| 55 | 3,5-dichloro-4-((S)-2-(3-(cyclopropylmethoxy)-4-(difluoromethoxy)phenyl)-2-((R)-1-(3-(dimethylcarbamoyl)phenylsulfonyl)pyrrolidine-2-carbonyloxy)ethyl)pyridine 1-oxide |
| 59 | 3,5-dichloro-4-((2S)-2-(3-(cyclopropylmethoxy)-4-(difluoromethoxy)phenyl)-2-(3-(3-sulfamoylphenylsulfonyl)thiazolidine-2-carbonyloxy)ethyl)pyridine 1-oxide |
| 122 | 4-((2S)-2-(3-(3-carboxy-4-methoxyphenylsulfonyl)thiazolidine-2-carbonyloxy)-2-(3-(cyclopropylmethoxy)-4-(difluoromethoxy)phenyl)ethyl)-3,5-dichloropyridine 1-oxide |
| 60 | 3,5-dichloro-4-((2S)-2-(3-(cyclopropylmethoxy)-4-(difluoromethoxy)phenyl)-2-(3-(3-fluorophenylsulfonyl)thiazolidine-2-carbonyloxy)ethyl)pyridine 1-oxide |
| 61 | 3,5-dichloro-4-((2S)-2-(3-(cyclopropylmethoxy)-4-(difluoromethoxy)phenyl)-2-(3-(2,4-dimethylphenylsulfonyl)thiazolidine-2-carbonyloxy)ethyl)pyridine 1-oxide |
| 62 | 3,5-dichloro-4-((2S)-2-(3-(cyclopropylmethoxy)-4-(difluoromethoxy)phenyl)-2-(3-(thiophen-2-ylsulfonyl)thiazolidine-2-carbonyloxy)ethyl)pyridine 1-oxide |
| 123 | 3,5-dichloro-4-((2S)-2-(3-(cyclopropylmethoxy)-4-(difluoromethoxy)phenyl)-2-(3-(3-(dimethylcarbamoyl)-4-methoxyphenylsulfonyl)thiazolidine-2-carbonyloxy)ethyl)pyridine 1-oxide |
| 121 | (S)-3,5-dichloro-4-(2-(3-(cyclopropylmethoxy)-4-(difluoromethoxy)phenyl)-2-(2-(4-(3-(dimethylcarbamoyl)phenylsulfonyl)piperazin-1-yl)acetoxy)ethyl)pyridine 1-oxide |
| 126 | 3,5-dichloro-4-((2S)-2-(3-(cyclopropylmethoxy)-4-(difluoromethoxy)phenyl)-2-(3-(4-(4-methylpiperazine-1-carbonyl)phenylsulfonyl)thiazolidine-2-carbonyloxy)ethyl)pyridine 1-oxide |
| 63 | 3,5-dichloro-4-((2S)-2-(3-(3-chlorophenylsulfonyl)thiazolidine-2-carbonyloxy)-2-(3-(cyclopropylmethoxy)-4-(difluoromethoxy)phenyl)ethyl)pyridine 1-oxide |
| 64 | 3,5-dichloro-4-((2S)-2-(3-(cyclopropylmethoxy)-4-(difluoromethoxy)phenyl)-2-(3-(1-methyl-1H-imidazol-2-ylsulfonyl)thiazolidine-2-carbonyloxy)ethyl)pyridine 1-oxide |
| 65 | 3,5-dichloro-4-((2S)-2-(3-(cyclopropylmethoxy)-4-(difluoromethoxy)phenyl)-2-(3-(cyclopropylmethylsulfonyl)thiazolidine-2-carbonyloxy)ethyl)pyridine 1-oxide |
| 66 | 3,5-dichloro-4-((2S)-2-(3-(cyclopropylmethoxy)-4-(difluoromethoxy)phenyl)-2-(3-(pyridin-3-ylsulfonyl)thiazolidine-2-carbonyloxy)ethyl)pyridine 1-oxide |
| 67 | 3,5-dichloro-4-((2S)-2-(3-(cyclopropylmethoxy)-4-(difluoromethoxy)phenyl)-2-(3-(2,4-difluorophenylsulfonyl)thiazolidine-2-carbonyloxy)ethyl)pyridine 1-oxide |
| 68 | 3,5-dichloro-4-((2S)-2-(3-(2-chloro-4-fluorophenylsulfonyl)thiazolidine-2-carbonyloxy)-2-(3-(cyclopropylmethoxy)-4-(difluoromethoxy)phenyl)ethyl)pyridine 1-oxide |
| 69 | 3,5-dichloro-4-((2S)-2-(3-(cyclopropylmethoxy)-4-(difluoromethoxy)phenyl)-2-(3-(4-fluoro-2-methylphenylsulfonyl)thiazolidine-2-carbonyloxy)ethyl)pyridine 1-oxide |
| 70 | 3,5-dichloro-4-((2S)-2-(3-(2-chlorophenylsulfonyl)thiazolidine-2-carbonyloxy)-2-(3-(cyclopropylmethoxy)-4-(difluoromethoxy)phenyl)ethyl)pyridine 1-oxide |
| 71 | 3,5-dichloro-4-((2S)-2-(3-(cyclohexylsulfonyl)thiazolidine-2-carbonyloxy)-2-(3-(cyclopropylmethoxy)-4-(difluoromethoxy)phenyl)ethyl)pyridine 1-oxide |
| 72 | 3,5-dichloro-4-((2S)-2-(3-(cyclopropylmethoxy)-4-(difluoromethoxy)phenyl)-2-(3-(2,4-dioxo-1,2,3,4-tetrahydroquinazolin-6-ylsulfonyl)thiazolidine-2-carbonyloxy)ethyl)pyridine 1-oxide |
| 85 | 3,5-dichloro-4-((2S)-2-(3-(cyclopropylmethoxy)-4-(difluoromethoxy)phenyl)-2-(3-(thiophen-3-ylsulfonyl)thiazolidine-2-carbonyloxy)ethyl)pyridine 1-oxide |
| 52 | 3,5-dichloro-4-((S)-2-(3-(cyclopropylmethoxy)-4-(difluoromethoxy)phenyl)-2-((S)-3-(3-(dimethylcarbamoyl)phenylsulfonyl)thiazolidine-2-carbonyloxy)ethyl)pyridine 1-oxide |
| 82 | 3,5-dichloro-4-((S)-2-(3-(cyclopropylmethoxy)-4-(difluoromethoxy)phenyl)-2-((S)-1-(3-(dimethylcarbamoyl)phenylsulfonyl)piperidine-2-carbonyloxy)ethyl)pyridine 1-oxide |
| 83 | 3,5-dichloro-4-((S)-2-(3-(cyclopropylmethoxy)-4-(difluoromethoxy)phenyl)-2-((R)-1-(3-(dimethylcarbamoyl)phenylsulfonyl)piperidine-2-carbonyloxy)ethyl)pyridine 1-oxide |
| 49 | 3,5-dichloro-4-((2S)-2-(3-(cyclopropylmethoxy)-4-(difluoromethoxy)phenyl)-2-(3-(3-(cyclopropylmethoxy)-5-(N-(2- |

-continued

| Compound | Chemical Name |
|---|---|
| | morpholinoethyl)methylsulfonamido)benzoyl)thiazolidine-2-carbonyloxy)ethyl)pyridine 1-oxide |
| 73 | 3,5-dichloro-4-((2S)-2-(3-(cyclopropylmethoxy)-4-(difluoromethoxy)phenyl)-2-(3-(3,4-dimethoxyphenylsulfonyl)thiazolidine-2-carbonyloxy)ethyl)pyridine 1-oxide |
| 141 | (S)-4-(2-(2-(4-(4-aminophenylsulfonyl)piperazin-1-yl)acetoxy)-2-(3-(cyclopropylmethoxy)-4-(difluoromethoxy)phenyl)ethyl)-3,5-dichloropyridine 1-oxide |
| 129 | 3,5-dichloro-4-((S)-2-(3-(cyclopropylmethoxy)-4-(difluoromethoxy)phenyl)-2-((S)-1-(3-(dimethylcarbamoyl)-4-methoxyphenylsulfonyl)piperidine-2-carbonyloxy)ethyl)pyridine 1-oxide |
| 74 | 3,5-dichloro-4-((2S)-2-(3-(cyclopropylmethoxy)-4-(difluoromethoxy)phenyl)-2-(3-(6-morpholinopyridin-3-ylsulfonyl)thiazolidine-2-carbonyloxy)ethyl)pyridine 1-oxide |
| 127 | 3,5-dichloro-4-((2S)-2-(3-(cyclopropylmethoxy)-4-(difluoromethoxy)phenyl)-2-(3-(4-methoxy-3-(4-methylpiperazine-1-carbonyl)phenylsulfonyl)thiazolidine-2-carbonyloxy)ethyl)pyridine 1-oxide |
| 128 | 3,5-dichloro-4-((2S)-2-(3-(cyclopropylmethoxy)-4-(difluoromethoxy)phenyl)-2-(3-(4-methoxy-3-(morpholine-4-carbonyl)phenylsulfonyl)thiazolidine-2-carbonyloxy)ethyl)pyridine 1-oxide |
| 31 | 3,5-dichloro-4-((S)-2-(3-(cyclopropylmethoxy)-4-(difluoromethoxy)phenyl)-2-((S)-3-(4-methoxy-3-(morpholinomethyl)benzoyl)thiazolidine-2-carbonyloxy)ethyl)pyridine 1-oxide<br>or<br>3,5-dichloro-4-((S)-2-(3-(cyclopropylmethoxy)-4-(difluoromethoxy)phenyl)-2-((R)-3-(4-methoxy-3-(morpholinomethyl)benzoyl)thiazolidine-2-carbonyloxy)ethyl)pyridine 1-oxide |
| 32 | 3,5-dichloro-4-((2S)-2-(3-(cyclopropylmethoxy)-4-(difluoromethoxy)phenyl)-2-(3-(3-(N,N-dimethylsulfamoyl)-4-methoxybenzoyl)thiazolidine-2-carbonyloxy)ethyl)pyridine 1-oxide |
| 75 | 4-((S)-2-((S)-3-(3-carboxyphenylsulfonyl)thiazolidine-2-carbonyloxy)-2-(3-(cyclopropylmethoxy)-4-(difluoromethoxy)phenyl)ethyl)-3,5-dichloropyridine 1-oxide<br>or<br>4-((S)-2-((R)-3-(3-carboxyphenylsulfonyl)thiazolidine-2-carbonyloxy)-2-(3-(cyclopropylmethoxy)-4-(difluoromethoxy)phenyl)ethyl)-3,5-dichloropyridine 1-oxide |
| 33 | 3,5-dichloro-4-((2S)-2-(3-(cyclopropylmethoxy)-4-(difluoromethoxy)phenyl)-2-(3-(4-(morpholinomethyl)benzoyl)thiazolidine-2-carbonyloxy)ethyl)pyridine 1-oxide |
| 79 | 3,5-dichloro-4-((2S)-2-(3-(cyclopropylmethoxy)-4-(difluoromethoxy)phenyl)-2-(4-(phenylsulfonyl)morpholine-2-carbonyloxy)ethyl)pyridine 1-oxide |
| 76 | 3,5-dichloro-4-((2S)-2-(3-(cyclopropylmethoxy)-4-(difluoromethoxy)phenyl)-2-(3-(3,5-dimethylisoxazol-4-ylsulfonyl)thiazolidine-2-carbonyloxy)ethyl)pyridine 1-oxide |
| 38 | 3,5-dichloro-4-((2S)-2-(3-(cyclopropylmethoxy)-4-(difluoromethoxy)phenyl)-2-(3-(thiazole-5-carbonyl)thiazolidine-2-carbonyloxy)ethyl)pyridine 1-oxide |
| 34 | 3,5-dichloro-4-((2S)-2-(3-(cyclopropylmethoxy)-4-(difluoromethoxy)phenyl)-2-(3-(3-((dimethylamino)methyl)benzoyl)thiazolidine-2-carbonyloxy)ethyl)pyridine 1-oxide |
| 35 | 3,5-dichloro-4-((2S)-2-(3-(cyclopropylmethoxy)-4-(difluoromethoxy)phenyl)-2-(3-(oxazole-5-carbonyl)thiazolidine-2-carbonyloxy)ethyl)pyridine 1-oxide |
| 130 | 3,5-dichloro-4-((2S)-2-(3-(cyclopropylmethoxy)-4-(difluoromethoxy)phenyl)-2-(3-(3-(4-methylpiperazine-1-carbonyl)phenylsulfonyl)thiazolidine-2-carbonyloxy)ethyl)pyridine 1-oxide |
| 155 | 3,5-dichloro-4-((S)-2-(3-(cyclopropylmethoxy)-4-(difluoromethoxy)phenyl)-2-((S)-1-(1-methyl-1H-imidazol-2-ylsulfonyl)pyrrolidine-2-carbonyloxy)ethyl)pyridine 1-oxide |
| 86 | 3,5-dichloro-4-((S)-2-(3-(cyclopropylmethoxy)-4-(difluoromethoxy)phenyl)-2-((S)-1-(phenylsulfonyl)pyrrolidine-2-carbonyloxy)ethyl)pyridine 1-oxide |
| 87 | 3,5-dichloro-4-((2S)-2-(3-(cyclopropylmethoxy)-4-(difluoromethoxy)phenyl)-2-(3-(5-(methoxycarbonyl)thiophen-2-ylsulfonyl)thiazolidine-2-carbonyloxy)ethyl)pyridine 1-oxide |

-continued

| Compound | Chemical Name |
|---|---|
| 88 | 3,5-dichloro-4-((S)-2-(3-(cyclopropylmethoxy)-4-(difluoromethoxy)phenyl)-2-((S)-3-(pyridin-3-ylsulfonyl)thiazolidine-2-carbonyloxy)ethyl)pyridine 1-oxide |
| 131 | 3,5-dichloro-4-((S)-2-(3-(cyclopropylmethoxy)-4-(difluoromethoxy)phenyl)-2-((S)-3-(3-(dimethylcarbamoyl)-4-methoxyphenylsulfonyl)thiazolidine-2-carbonyloxy)ethyl)pyridine 1-oxide |
| 89 | 3,5-dichloro-4-((S)-2-(3-(cyclopropylmethoxy)-4-(difluoromethoxy)phenyl)-2-((S)-3-(phenylsulfonyl)thiazolidine-2-carbonyloxy)ethyl)pyridine 1-oxide |
| 90 | 3,5-dichloro-4-((S)-2-(3-(cyclopropylmethoxy)-4-(difluoromethoxy)phenyl)-2-((S)-3-(1-methyl-1H-imidazol-2-ylsulfonyl)thiazolidine-2-carbonyloxy)ethyl)pyridine 1-oxide |
| 91 | 3,5-dichloro-4-((S)-2-(3-(cyclopropylmethoxy)-4-(difluoromethoxy)phenyl)-2-((S)-3-(3-sulfamoylphenylsulfonyl)thiazolidine-2-carbonyloxy)ethyl)pyridine 1-oxide |
| 92 | 3,5-dichloro-4-((2S)-2-(3-(cyclopropylmethoxy)-4-(difluoromethoxy)phenyl)-2-(3-(4-(methylsulfonyl)phenylsulfonyl)thiazolidine-2-carbonyloxy)ethyl)pyridine 1-oxide |
| 93 | 3,5-dichloro-4-((S)-2-(3-(cyclopropylmethoxy)-4-(difluoromethoxy)phenyl)-2-((S)-3-(3,4-dimethoxyphenylsulfonyl)thiazolidine-2-carbonyloxy)ethyl)pyridine 1-oxide |
| 51 | 3,5-dichloro-4-((2S)-2-(3-(cyclopropylmethoxy)-4-(difluoromethoxy)phenyl)-2-(3-(5-((dimethylamino)methyl)thiophene-2-carbonyl)thiazolidine-2-carbonyloxy)ethyl)pyridine 1-oxide |
| 22 | 4-((2S)-2-(3-(4-(2-aminoethyl)benzoyl)thiazolidine-2-carbonyloxy)-2-(3-(cyclopropylmethoxy)-4-(difluoromethoxy)phenyl)ethyl)-3,5-dichloropyridine 1-oxide |
| 94 | 3,5-dichloro-4-((S)-2-(3-(cyclopropylmethoxy)-4-(difluoromethoxy)phenyl)-2-((S)-3-(4-(N-methylsulfamoyl)phenylsulfonyl)thiazolidine-2-carbonyloxy)ethyl)pyridine 1-oxide |
| 95 | 3,5-dichloro-4-((S)-2-(3-(cyclopropylmethoxy)-4-(difluoromethoxy)phenyl)-2-((S)-3-(furan-2-ylsulfonyl)thiazolidine-2-carbonyloxy)ethyl)pyridine 1-oxide |
| 96 | 3,5-dichloro-4-((S)-2-(3-(cyclopropylmethoxy)-4-(difluoromethoxy)phenyl)-2-((S)-3-(furan-3-ylsulfonyl)thiazolidine-2-carbonyloxy)ethyl)pyridine 1-oxide |
| 97 | 3,5-dichloro-4-((S)-2-(3-(cyclopropylmethoxy)-4-(difluoromethoxy)phenyl)-2-((S)-3-(3-(N,N-dimethylsulfamoyl)phenylsulfonyl)thiazolidine-2-carbonyloxy)ethyl)pyridine 1-oxide |
| 98 | 3,5-dichloro-4-((S)-2-(3-(cyclopropylmethoxy)-4-(difluoromethoxy)phenyl)-2-((S)-1-(3,4-dimethoxyphenylsulfonyl)piperidine-2-carbonyloxy)ethyl)pyridine 1-oxide |
| 99 | 3,5-dichloro-4-((S)-2-(3-(cyclopropylmethoxy)-4-(difluoromethoxy)phenyl)-2-((S)-1-(pyridin-3-ylsulfonyl)piperidine-2-carbonyloxy)ethyl)pyridine 1-oxide |
| 100 | 3,5-dichloro-4-((S)-2-(3-(cyclopropylmethoxy)-4-(difluoromethoxy)phenyl)-2-((S)-3-(4-(methoxycarbonyl)phenylsulfonyl)thiazolidine-2-carbonyloxy)ethyl)pyridine 1-oxide |
| 101 | 3,5-dichloro-4-((S)-2-(3-(cyclopropylmethoxy)-4-(difluoromethoxy)phenyl)-2-((S)-3-(2-(methoxycarbonyl)phenylsulfonyl)thiazolidine-2-carbonyloxy)ethyl)pyridine 1-oxide |
| 102 | 3,5-dichloro-4-((S)-2-(3-(cyclopropylmethoxy)-4-(difluoromethoxy)phenyl)-2-((S)-3-(3-(dimethylcarbamoyl)phenylsulfonyl)thiazolidine-4-carbonyloxy)ethyl)pyridine 1-oxide |
| 103 | 3,5-dichloro-4-((S)-2-(3-(cyclopropylmethoxy)-4-(difluoromethoxy)phenyl)-2-((S)-3-(3-methoxyphenylsulfonyl)thiazolidine-2-carbonyloxy)ethyl)pyridine 1-oxide |
| 104 | 3,5-dichloro-4-((S)-2-(3-(cyclopropylmethoxy)-4-(difluoromethoxy)phenyl)-2-((S)-3-(3-(trifluoromethoxy)phenylsulfonyl)thiazolidine-2-carbonyloxy)ethyl)pyridine 1-oxide |
| 36 | 3,5-dichloro-4-((S)-2-(3-(cyclopropylmethoxy)-4-(difluoromethoxy)phenyl)-2-((S)-3-(4-(1,1-dioxothiomorpholinobenzoyl)thiazolidine-2-carbonyloxy)ethyl)pyridine 1-oxide |

-continued

| Compound | Chemical Name |
|---|---|
| 37 | 4-((S)-2-((S)-3-(4-carbamoylbenzoyl)thiazolidine-2-carbonyloxy)-2-(3-(cyclopropylmethoxy)-4-(difluoromethoxy)phenyl)ethyl)-3,5-dichloropyridine 1-oxide |
| 105 | 3,5-dichloro-4-((S)-2-(3-(cyclopropylmethoxy)-4-(difluoromethoxy)phenyl)-2-((S)-3-(6-morpholinopyridin-3-ylsulfonyl)thiazolidine-2-carbonyloxy)ethyl)pyridine 1-oxide |
| 20 | 4-((S)-2-((S)-3-(4-(aminomethyl)picolinoyl)thiazolidine-2-carbonyloxy)-2-(3-(cyclopropylmethoxy)-4-(difluoromethoxy)phenyl)ethyl)-3,5-dichloropyridine 1-oxide or 4-((S)-2-((R)-3-(4-(aminomethyl)picolinoyl)thiazolidine-2-carbonyloxy)-2-(3-(cyclopropylmethoxy)-4-(difluoromethoxy)phenyl)ethyl)-3,5-dichloropyridine 1-oxide |
| 106 | 3,5-dichloro-4-((S)-2-(3-(cyclopropylmethoxy)-4-(difluoromethoxy)phenyl)-2-((S)-3-(2-methoxy-4-methylphenylsulfonyl)thiazolidine-2-carbonyloxy)ethyl)pyridine 1-oxide |
| 107 | 3,5-dichloro-4-((S)-2-(3-(cyclopropylmethoxy)-4-(difluoromethoxy)phenyl)-2-((S)-3-(2,4-dimethylthiazol-5-ylsulfonyl)thiazolidine-2-carbonyloxy)ethyl)pyridine 1-oxide |
| 108 | 3,5-dichloro-4-((S)-2-(3-(cyclopropylmethoxy)-4-(difluoromethoxy)phenyl)-2-((S)-3-(4-methyl-3,4-dihydro-2H-benzo[b][1,4]oxazin-6-ylsulfonyl)thiazolidine-2-carbonyloxy)ethyl)pyridine 1-oxide |
| 42 | 3,5-dichloro-4-((2S)-2-(3-(cyclopropylmethoxy)-4-(difluoromethoxy)phenyl)-2-(3-picolinoylthiazolidine-2-carbonyloxy)ethyl)pyridine 1-oxide |
| 133 | 3,5-dichloro-4-((S)-2-(3-(cyclopropylmethoxy)-4-(difluoromethoxy)phenyl)-2-((S)-3-(3-((2-morpholinoethoxy)carbonyl)phenylsulfonyl)thiazolidine-2-carbonyloxy)ethyl)pyridine 1-oxide or 3,5-dichloro-4-((S)-2-(3-(cyclopropylmethoxy)-4-(difluoromethoxy)phenyl)-2-((R)-3-(3-((2-morpholinoethoxy)carbonyl)phenylsulfonyl)thiazolidine-2-carbonyloxy)ethyl)pyridine 1-oxide |
| 110 | 3,5-dichloro-4-((S)-2-(3-(cyclopropylmethoxy)-4-(difluoromethoxy)phenyl)-2-((S)-3-(4-methoxyphenylsulfonyl)thiazolidine-2-carbonyloxy)ethyl)pyridine 1-oxide |
| 111 | 3,5-dichloro-4-((S)-2-(3-(cyclopropylmethoxy)-4-(difluoromethoxy)phenyl)-2-((S)-1-(6-morpholinopyridin-3-ylsulfonyl)piperidine-2-carbonyloxy)ethyl)pyridine 1-oxide |
| 112 | 3,5-dichloro-4-((S)-2-(3-(cyclopropylmethoxy)-4-(difluoromethoxy)phenyl)-2-((S)-1-(4-nitrophenylsulfonyl)piperidine-2-carbonyloxy)ethyl)pyridine 1-oxide |
| 113 | 3,5-dichloro-4-((S)-2-(3-(cyclopropylmethoxy)-4-(difluoromethoxy)phenyl)-2-((S)-1-(3-(N,N-dimethylsulfamoyl)phenylsulfonyl)piperidine-2-carbonyloxy)ethyl)pyridine 1-oxide |
| 114 | 3,5-dichloro-4-((S)-2-(3-(cyclopropylmethoxy)-4-(difluoromethoxy)phenyl)-2-((S)-1-(phenylsulfonyl)piperidine-2-carbonyloxy)ethyl)pyridine 1-oxide |
| 115 | 3,5-dichloro-4-((S)-2-(3-(cyclopropylmethoxy)-4-(difluoromethoxy)phenyl)-2-((S)-3-(2,5-dimethoxyphenylsulfonyl)thiazolidine-2-carbonyloxy)ethyl)pyridine 1-oxide |
| 116 | 3,5-dichloro-4-((S)-2-(3-(cyclopropylmethoxy)-4-(difluoromethoxy)phenyl)-2-((S)-1-(1-methyl-1H-imidazol-2-ylsulfonyl)piperidine-2-carbonyloxy)ethyl)pyridine 1-oxide |
| 117 | 4-((S)-2-((S)-3-(3-acetylphenylsulfonyl)thiazolidine-2-carbonyloxy)-2-(3-(cyclopropylmethoxy)-4-(difluoromethoxy)phenyl)ethyl)-3,5-dichloropyridine 1-oxide |
| 39 | 3,5-dichloro-4-((S)-2-(3-(cyclopropylmethoxy)-4-(difluoromethoxy)phenyl)-2-((S)-3-(4-(morpholinomethyl)benzoyl)thiazolidine-2-carbonyloxy)ethyl)pyridine 1-oxide |
| 40 | 3,5-dichloro-4-((S)-2-(3-(cyclopropylmethoxy)-4-(difluoromethoxy)phenyl)-2-((S)-3-(4-(1,1-dioxo thiomorpholinomethyl)benzoyl)thiazolidine-2-carbonyloxy)ethyl)pyridine 1-oxide |
| 21 | 4-((S)-2-((S)-3-(3-(aminomethyl)benzoyl)thiazolidine-2-carbonyloxy)-2-(3-(cyclopropylmethoxy)-4-(difluoromethoxy)phenyl)ethyl)-3,5-dichloropyridine 1-oxide |
| 41 | 3,5-dichloro-4-((S)-2-(3-(cyclopropylmethoxy)-4-(difluoromethoxy)phenyl)-2-((S)-3-(3-(oxazol-5-yl)benzoyl)thiazolidine-2-carbonyloxy)ethyl)pyridine 1-oxide |

-continued

| Compound | Chemical Name |
|---|---|
| 140 | 4-((S)-2-((S)-3-(3-aminophenylsulfonyl)thiazolidine-2-carbonyloxy)-2-(3-(cyclopropylmethoxy)-4-(difluoromethoxy)phenyl)ethyl)-3,5-dichloropyridine 1-oxide |
| 109 | 3,5-dichloro-4-((S)-2-(3-(cyclopropylmethoxy)-4-(difluoromethoxy)phenyl)-2-((S)-3-(4-(methylsulfonyl)phenylsulfonyl)thiazolidine-2-carbonyloxy)ethyl)pyridine 1-oxide |
| 132 | 3,5-dichloro-4-((S)-2-(3-(cyclopropylmethoxy)-4-(difluoromethoxy)phenyl)-2-((S)-3-(3-(4-methylpiperazine-1-carbonyl)phenylsulfonyl)thiazolidine-2-carbonyloxy)ethyl)pyridine 1-oxide |
| 118 | 3,5-dichloro-4-((2S)-2-(3-(cyclopropylmethoxy)-4-(difluoromethoxy)phenyl)-2-(3-(3-(N-methylsulfamoyl)phenylsulfonyl)thiazolidine-2-carbonyloxy)ethyl)pyridine 1-oxide |
| 119 | 3,5-dichloro-4-((S)-2-(3-(cyclopropylmethoxy)-4-(difluoromethoxy)phenyl)-2-((S)-3-(1-methyl-1H-imidazol-4-ylsulfonyl)thiazolidine-2-carbonyloxy)ethyl)pyridine 1-oxide |
| 188 | 3,5-dichloro-4-((S)-2-(3-(cyclopropylmethoxy)-4-(difluoromethoxy)phenyl)-2-((S)-3-(2-phenylacetyl)thiazolidine-2-carbonyloxy)ethyl)pyridine 1-oxide |
| 189 | 3,5-dichloro-4-((S)-2-((S)-3-(2-cyclopropylacetyl)thiazolidine-2-carbonyloxy)-2-(3-(cyclopropylmethoxy)-4-(difluoromethoxy)phenyl)ethyl)pyridine 1-oxide |
| 190 | 3,5-dichloro-4-((S)-2-(3-(cyclopropylmethoxy)-4-(difluoromethoxy)phenyl)-2-((S)-3-(3-(phenylsulfonyl)propanoyl)thiazolidine-2-carbonyloxy)ethyl)pyridine 1-oxide |
| 191 | 3,5-dichloro-4-((S)-2-(3-(cyclopropylmethoxy)-4-(difluoromethoxy)phenyl)-2-((S)-3-(3-morpholinopropanoyl)thiazolidine-2-carbonyloxy)ethyl)pyridine 1-oxide |
| 192 | 3,5-dichloro-4-((S)-2-(3-(cyclopropylmethoxy)-4-(difluoromethoxy)phenyl)-2-((S)-3-(3-(4-methylpiperazin-1-yl)propanoyl)thiazolidine-2-carbonyloxy)ethyl)pyridine 1-oxide |
| 193 | 3,5-dichloro-4-((S)-2-(3-(cyclopropylmethoxy)-4-(difluoromethoxy)phenyl)-2-((S)-1-(3-(dimethylcarbamoyl)benzoyl)pyrrolidine-2-carbonyloxy)ethyl)pyridine 1-oxide |
| 194 | 4-((S)-2-(2-((S)-1-benzoylpyrrolidin-2-yl)acetoxy)-2-(3-(cyclopropylmethoxy)-4-(difluoromethoxy)phenyl)ethyl)-3,5-dichloropyridine 1-oxide |
| 195 | 3,5-dichloro-4-((S)-2-(3-(cyclopropylmethoxy)-4-(difluoromethoxy)phenyl)-2-(2-((S)-1-(3-(dimethylcarbamoyl)benzoyl)pyrrolidin-2-yl)acetoxy)ethyl)pyridine 1-oxide |
| 198 | 3,5-dichloro-4-((S)-2-(3-(cyclopropylmethoxy)-4-(difluoromethoxy)phenyl)-2-((S)-3-(2-(3-(dimethylcarbamoyl)phenyl)acetyl)thiazolidine-2-carbonyloxy)ethyl)pyridine 1-oxide |
| 199 | 3,5-dichloro-4-((S)-2-(3-(cyclopropylmethoxy)-4-(difluoromethoxy)phenyl)-2-((S)-1-(2-(3-(dimethylcarbamoyl)phenyl)acetyl)pyrrolidine-2-carbonyloxy)ethyl)pyridine 1-oxide |
| 200 | 3,5-dichloro-4-((S)-2-((S)-3-(2-cyanophenylsulfonyl)thiazolidine-2-carbonyloxy)-2-(3-(cyclopropylmethoxy)-4-(difluoromethoxy)phenyl)ethyl)pyridine 1-oxide |
| 201 | 3,5-dichloro-4-((S)-2-(3-(cyclopropylmethoxy)-4-(difluoromethoxy)phenyl)-2-((S)-3-(2,3-dihydrobenzo[b][1,4]dioxin-6-ylsulfonyl)thiazolidine-2-carbonyloxy)ethyl)pyridine 1-oxide |
| 202 | 3,5-dichloro-4-((S)-2-((S)-3-(2-cyano-5-methylphenylsulfonyl)thiazolidine-2-carbonyloxy)-2-(3-(cyclopropylmethoxy)-4-(difluoromethoxy)phenyl)ethyl)pyridine 1-oxide |
| 203 | 3,5-dichloro-4-((S)-2-(3-(cyclopropylmethoxy)-4-(difluoromethoxy)phenyl)-2-((S)-3-(2,5-dimethylthiophen-3-ylsulfonyl)thiazolidine-2-carbonyloxy)ethyl)pyridine 1-oxide |
| 204 | 4-((S)-2-((S)-3-(4-bromo-2-fluoro-5-methylphenylsulfonyl)thiazolidine-2-carbonyloxy)-2-(3-(cyclopropylmethoxy)-4-(difluoromethoxy)phenyl)ethyl)-3,5-dichloropyridine 1-oxide |
| 205 | 4-((S)-2-((S)-3-(3-bromo-4-methylphenylsulfonyl)thiazolidine-2-carbonyloxy)-2-(3-(cyclopropylmethoxy)-4-(difluoromethoxy)phenyl)ethyl)-3,5-dichloropyridine 1-oxide |
| 206 | 3,5-dichloro-4-((S)-2-((S)-3-(4-cyanophenylsulfonyl)thiazolidine-2-carbonyloxy)-2-(3-(cyclopropylmethoxy)-4-(difluoromethoxy)phenyl)ethyl)pyridine 1-oxide |
| 207 | 3,5-dichloro-4-((S)-2-((S)-3-(3-cyanophenylsulfonyl)thiazolidine-2-carbonyloxy)-2-(3-(cyclopropylmethoxy)-4-(difluoromethoxy)phenyl)ethyl)pyridine 1-oxide |

-continued

| Compound | Chemical Name |
|---|---|
| 208 | 4-((S)-2-((S)-3-(4-(1H-pyrazol-1-yl)phenylsulfonyl)thiazolidine-2-carbonyloxy)-2-(3-(cyclopropylmethoxy)-4-(difluoromethoxy)phenyl)ethyl)-3,5-dichloropyridine 1-oxide |
| 209 | 3,5-dichloro-4-((S)-2-((S)-3-(3-cyano-4-fluorophenylsulfonyl)thiazolidine-2-carbonyloxy)-2-(3-(cyclopropylmethoxy)-4-(difluoromethoxy)phenyl)ethyl)pyridine 1-oxide |
| 210 | 3,5-dichloro-4-((S)-2-(3-(cyclopropylmethoxy)-4-(difluoromethoxy)phenyl)-2-((S)-3-(1-methyl-2-oxoindolin-5-ylsulfonyl)thiazolidine-2-carbonyloxy)ethyl)pyridine 1-oxide |
| 211 | 3,5-dichloro-4-((S)-2-((S)-3-(2-chloro-5-cyanophenylsulfonyl)thiazolidine-2-carbonyloxy)-2-(3-(cyclopropylmethoxy)-4-(difluoromethoxy)phenyl)ethyl)pyridine 1-oxide |
| 212 | 3,5-dichloro-4-((S)-2-(3-(cyclopropylmethoxy)-4-(difluoromethoxy)phenyl)-2-((S)-3-(5-methylbenzo[b]thiophen-2-ylsulfonyl)thiazolidine-2-carbonyloxy)ethyl)pyridine 1-oxide |
| 213 | 3,5-dichloro-4-((S)-2-(3-(cyclopropylmethoxy)-4-(difluoromethoxy)phenyl)-2-((S)-3-(4-(1-methyl-1H-pyrazol-3-yl)phenylsulfonyl)thiazolidine-2-carbonyloxy)ethyl)pyridine 1-oxide |
| 214 | 3,5-dichloro-4-((S)-2-(3-(cyclopropylmethoxy)-4-(difluoromethoxy)phenyl)-2-((S)-3-(4-(difluoromethoxy)phenylsulfonyl)thiazolidine-2-carbonyloxy)ethyl)pyridine 1-oxide |
| 215 | 3,5-dichloro-4-((S)-2-((S)-3-(4-chloro-2-(trifluoromethyl)phenylsulfonyl)thiazolidine-2-carbonyloxy)-2-(3-(cyclopropylmethoxy)-4-(difluoromethoxy)phenyl)ethyl)pyridine 1-oxide |
| 216 | 3,5-dichloro-4-((S)-2-(3-(cyclopropylmethoxy)-4-(difluoromethoxy)phenyl)-2-((S)-3-(5-fluoro-2-methoxyphenylsulfonyl)thiazolidine-2-carbonyloxy)ethyl)pyridine 1-oxide |
| 217 | 4-((S)-2-((S)-3-(benzo[b]thiophen-2-ylsulfonyl)thiazolidine-2-carbonyloxy)-2-(3-(cyclopropylmethoxy)-4-(difluoromethoxy)phenyl)ethyl)-3,5-dichloropyridine 1-oxide |
| 218 | 3,5-dichloro-4-((S)-2-(3-(cyclopropylmethoxy)-4-(difluoromethoxy)phenyl)-2-((S)-3-(2-oxo-2,3-dihydrobenzo[d]oxazol-6-ylsulfonyl)thiazolidine-2-carbonyloxy)ethyl)pyridine 1-oxide |
| 219 | 3,5-dichloro-4-((S)-2-(3-(cyclopropylmethoxy)-4-(difluoromethoxy)phenyl)-2-((S)-3-(4-(2-oxopyrrolidin-1-yl)phenylsulfonyl)thiazolidine-2-carbonyloxy)ethyl)pyridine 1-oxide |
| 220 | 4-((S)-2-((S)-3-(1-acetyl-1,2,3,4-tetrahydroquinolin-6-ylsulfonyl)thiazolidine-2-carbonyloxy)-2-(3-(cyclopropylmethoxy)-4-(difluoromethoxy)phenyl)ethyl)-3,5-dichloropyridine 1-oxide |
| 221 | 4-((S)-2-((S)-3-(4-(2-acetamidoethyl)phenylsulfonyl)thiazolidine-2-carbonyloxy)-2-(3-(cyclopropylmethoxy)-4-(difluoromethoxy)phenyl)ethyl)-3,5-dichloropyridine 1-oxide |
| 222 | 3,5-dichloro-4-((S)-2-(3-(cyclopropylmethoxy)-4-(difluoromethoxy)phenyl)-2-((S)-3-(4-(2,2,2-trifluoroethoxy)phenylsulfonyl)thiazolidine-2-carbonyloxy)ethyl)pyridine 1-oxide |
| 223 | 4-(2-((S)-3-(benzylsulfonyl)thiazolidine-2-carbonyloxy)-2-(3-(cyclopropylmethoxy)-4-(difluoromethoxy)phenyl)ethyl)-3,5-dichloropyridine 1-oxide |
| 224 | 3,5-dichloro-4-((S)-2-(3-(cyclopropylmethoxy)-4-(difluoromethoxy)phenyl)-2-((S)-3-(phenethylsulfonyl)thiazolidine-2-carbonyloxy)ethyl)pyridine 1-oxide |
| 225 | 4-((S)-2-((S)-1-(benzylsulfonyl)pyrrolidine-2-carbonyloxy)-2-(3-(cyclopropylmethoxy)-4-(difluoromethoxy)phenyl)ethyl)-3,5-dichloropyridine 1-oxide |
| 226 | 3,5-dichloro-4-((S)-2-(3-(cyclopropylmethoxy)-4-(difluoromethoxy)phenyl)-2-(R)-3-(1-methyl-2-oxoindolin-5-ylsulfonyl)thiazolidine-4-carbonyloxy)ethyl)pyridine 1-oxide |
| 227 | 3,5-dichloro-4-((S)-2-(3-(cyclopropylmethoxy)-4-(difluoromethoxy)phenyl)-2-(R)-1-(phenylsulfonyl)piperidine-3-carbonyloxy)ethyl)pyridine 1-oxide |
| 228 | 3,5-dichloro-4-((S)-2-(3-(cyclopropylmethoxy)-4-(difluoromethoxy)phenyl)-2-(R)-1-(3-(dimethylcarbamoyl)phenylsulfonyl)piperidine-3-carbonyloxy)ethyl)pyridine 1-oxide |
| 229 | 3,5-dichloro-4-((S)-2-(3-(cyclopropylmethoxy)-4-(difluoromethoxy)phenyl)-2-((S)-1-(phenylsulfonyl)piperidine-3-carbonyloxy)ethyl)pyridine 1-oxide |
| 230 | 3,5-dichloro-4-((S)-2-(3-(cyclopropylmethoxy)-4-(difluoromethoxy)phenyl)-2-((S)-1-(3-(dimethylcarbamoyl)phenylsulfonyl)piperidine-3-carbonyloxy)ethyl)pyridine 1-oxide |
| 231 | 3,5-dichloro-4-((S)-2-(3-(cyclopropylmethoxy)-4-(difluoromethoxy)phenyl)-2-(R)-4-(phenylsulfonyl)morpholine-2-carbonyloxy)ethyl)pyridine 1-oxide |

-continued

| Compound | Chemical Name |
|---|---|
| 232 | 3,5-dichloro-4-((S)-2-(3-(cyclopropylmethoxy)-4-(difluoromethoxy)phenyl)-2-(R)-4-(3-(dimethylcarbamoyl)phenylsulfonyl)morpholine-2-carbonyloxy)ethyl)pyridine 1-oxide |
| 233 | 3,5-dichloro-4-((S)-2-(3-(cyclopropylmethoxy)-4-(difluoromethoxy)phenyl)-2-((S)-4-(phenylsulfonyl)morpholine-2-carbonyloxy)ethyl)pyridine 1-oxide |
| 234 | 3,5-dichloro-4-((S)-2-(3-(cyclopropylmethoxy)-4-(difluoromethoxy)phenyl)-2-((S)-4-(3-(dimethylcarbamoyl)phenylsulfonyl)morpholine-2-carbonyloxy)ethyl)pyridine 1-oxide |
| 235 | 3,5-dichloro-4-((S)-2-(3-(cyclopropylmethoxy)-4-(difluoromethoxy)phenyl)-2-(2-((S)-1-(phenylsulfonyl)pyrrolidin-2-yl)acetoxy)ethyl)pyridine 1-oxide |
| 236 | 3,5-dichloro-4-((S)-2-(3-(cyclopropylmethoxy)-4-(difluoromethoxy)phenyl)-2-(2-((S)-1-(3-(dimethylcarbamoyl)phenylsulfonyl)pyrrolidin-2-yl)acetoxy)ethyl)pyridine 1-oxide |
| 237 | 4-((S)-2-(2-((S)-1-(benzylsulfonyl)pyrrolidin-2-yl)acetoxy)-2-(3-(cyclopropylmethoxy)-4-(difluoromethoxy)phenyl)ethyl)-3,5-dichloropyridine 1-oxide |
| 255 | 3,5-dichloro-4-((S)-2-(3-(cyclopropylmethoxy)-4-(difluoromethoxy)phenyl)-2-((S)-3-(2-oxo-2-phenylethyl)thiazolidine-2-carbonyloxy)ethyl)pyridine 1-oxide |
| 256 | 3,5-dichloro-4-((S)-2-(3-(cyclopropylmethoxy)-4-(difluoromethoxy)phenyl)-2-((S)-1-(2-oxo-2-phenylethyl)pyrrolidine-2-carbonyloxy)ethyl)pyridine 1-oxide |
| 257 | 4-((S)-2-((S)-1-benzylpyrrolidine-2-carbonyloxy)-2-(3-(cyclopropylmethoxy)-4-(difluoromethoxy)phenyl)ethyl)-3,5-dichloropyridine 1-oxide |
| 258 | 3,5-dichloro-4-((S)-2-(3-(cyclopropylmethoxy)-4-(difluoromethoxy)phenyl)-2-((S)-1-(3-(dimethylcarbamoyl)benzyl)pyrrolidine-2-carbonyloxy)ethyl)pyridine 1-oxide |
| 261 | 3,5-dichloro-4-((S)-2-(3-(cyclopropylmethoxy)-4-(difluoromethoxy)phenyl)-2-((S)-3-(2-(3-(dimethylcarbamoyl)phenyl)-2-oxoethyl)thiazolidine-2-carbonyloxy)ethyl)pyridine 1-oxide |
| 262 | 3,5-dichloro-4-((S)-2-(3-(cyclopropylmethoxy)-4-(difluoromethoxy)phenyl)-2-((S)-1-(2-(3-(dimethylcarbamoyl)phenyl)-2-oxoethyl)pyrrolidine-2-carbonyloxy)ethyl)pyridine 1-oxide |
| 264 | 3,5-dichloro-4-((S)-2-(3-(cyclopropylmethoxy)-4-(difluoromethoxy)phenyl)-2-((S)-3-(cyclopropylmethyl)thiazolidine-2-carbonyloxy)ethyl)pyridine 1-oxide |
| 265 | 4-((S)-2-((S)-3-benzylthiazolidine-2-carbonyloxy)-2-(3-(cyclopropylmethoxy)-4-(difluoromethoxy)phenyl)ethyl)-3,5-dichloropyridine 1-oxide |
| 266 | 3,5-dichloro-4-((S)-2-(3-(cyclopropylmethoxy)-4-(difluoromethoxy)phenyl)-2-((S)-3-(3-(dimethylcarbamoyl)benzyl)thiazolidine-2-carbonyloxy)ethyl)pyridine 1-oxide |
| 267 | 3,5-dichloro-4-((S)-2-(3-(cyclopropylmethoxy)-4-(difluoromethoxy)phenyl)-2-((S)-3-phenethylthiazolidine-2-carbonyloxy)ethyl)pyridine 1-oxide |
| 268 | 3,5-dichloro-4-((S)-2-(3-(cyclopropylmethoxy)-4-(difluoromethoxy)phenyl)-2-(2-((S)-1-(3-(dimethylcarbamoyl)benzyl)pyrrolidin-2-yl)acetoxy)ethyl)pyridine 1-oxide |
| 269 | 3,5-dichloro-4-((S)-2-(3-(cyclopropylmethoxy)-4-(difluoromethoxy)phenyl)-2-((S)-3-(3-ureidophenylsulfonyl)thiazolidine-2-carbonyloxy)ethyl)pyridine 1-oxide |
| 271 | 3,5-dichloro-4-((S)-2-(3-(cyclopropylmethoxy)-4-(difluoromethoxy)phenyl)-2-((S)-3-(3-(hydroxymethyl)phenylsulfonyl)thiazolidine-2-carbonyloxy)ethyl)pyridine 1-oxide |
| 274 | 4-((2S)-2-(2-(3-benzoylthiazolidin-2-yl)acetoxy)-2-(3-(cyclopropylmethoxy)-4-(difluoromethoxy)phenyl)ethyl)-3,5-dichloropyridine 1-oxide |
| 275 | 3,5-dichloro-4-((2S)-2-(3-(cyclopropylmethoxy)-4-(difluoromethoxy)phenyl)-2-(2-(3-(3-(dimethylcarbamoyl)benzoyl)thiazolidin-2-yl)acetoxy)ethyl)pyridine 1-oxide |
| 278 | 3,5-dichloro-4-((2S)-2-(3-(cyclopropylmethoxy)-4-(difluoromethoxy)phenyl)-2-(2-(3-(phenylsulfonyl)thiazolidin-2-yl)acetoxy)ethyl)pyridine 1-oxide |
| 279 | 3,5-dichloro-4-((2S)-2-(3-(cyclopropylmethoxy)-4-(difluoromethoxy)phenyl)-2-(2-(3-(3-(dimethylcarbamoyl)phenylsulfonyl)thiazolidin-2-yl)acetoxy)ethyl)pyridine 1-oxide |

-continued

| Compound | Chemical Name |
|---|---|
| 281 | (S)-3,5-dichloro-4-(2-(3-(cyclopropylmethoxy)-4-(difluoromethoxy)phenyl)-2-(1-(3-(dimethylcarbamoyl)phenylsulfonyl)azetidine-3-carbonyloxy)ethyl)pyridine 1-oxide |
| 282 | (S)-3,5-dichloro-4-(2-(3-(cyclopropylmethoxy)-4-(difluoromethoxy)phenyl)-2-(1-(phenylsulfonyl)azetidine-3-carbonyloxy)ethyl)pyridine 1-oxide |
| 283 | 3,5-dichloro-4-((S)-2-(3-(cyclopropylmethoxy)-4-(difluoromethoxy)phenyl)-2-((S)-1-(3-(dimethylcarbamoyl)phenylsulfonyl)azetidine-2-carbonyloxy)ethyl)pyridine 1-oxide |
| 284 | 3,5-dichloro-4-((S)-2-(3-(cyclopropylmethoxy)-4-(difluoromethoxy)phenyl)-2-((S)-1-(phenylsulfonyl)azetidine-2-carbonyloxy)ethyl)pyridine 1-oxide |
| 285 | 3,5-dichloro-4-((S)-2-(3-(cyclopropylmethoxy)-4-(difluoromethoxy)phenyl)-2-((S)-1-(1-methyl-2-oxoindolin-5-ylsulfonyl)pyrrolidine-2-carbonyloxy)ethyl)pyridine 1-oxide |
| 287 | 3,5-dichloro-4-((S)-2-(3-(cyclopropylmethoxy)-4-(difluoromethoxy)phenyl)-2-((S)-3-(2-morpholinoethylsulfonyl)thiazolidine-2-carbonyloxy)ethyl)pyridine 1-oxide |
| 288 | 3,5-dichloro-4-((S)-2-(3-(cyclopropylmethoxy)-4-(difluoromethoxy)phenyl)-2-((S)-3-(2-(4-methylpiperazin-1-yl)ethylsulfonyl)thiazolidine-2-carbonyloxy)ethyl)pyridine 1-oxide |
| 291 | 3,5-dichloro-4-((S)-2-(3-(cyclopropylmethoxy)-4-(difluoromethoxy)phenyl)-2-((S)-1-(2-(phenylsulfonyl)ethyl)pyrrolidine-2-carbonyloxy)ethyl)pyridine 1-oxide |
| 292 | 3,5-dichloro-4-((S)-2-(3-(cyclopropylmethoxy)-4-(difluoromethoxy)phenyl)-2-((S)-1-(2-phenylacetyl)pyrrolidine-2-carbonyloxy)ethyl)pyridine 1-oxide |
| 295 | 3,5-dichloro-4-((S)-2-(3-(cyclopropylmethoxy)-4-(difluoromethoxy)phenyl)-2-((S)-3-(3-(dimethylcarbamoyl)benzylsulfonyl)thiazolidine-2-carbonyloxy)ethyl)pyridine 1-oxide |
| 296 | 3,5-dichloro-4-((S)-2-(3-(cyclopropylmethoxy)-4-(difluoromethoxy)phenyl)-2-((S)-1-(3-(dimethylcarbamoyl)benzylsulfonyl)pyrrolidine-2-carbonyloxy)ethyl)pyridine 1-oxide |
| 299 | 3,5-dichloro-4-((S)-2-(4-(difluoromethoxy)-3-methoxyphenyl)-2-((S)-3-(3-(dimethylcarbamoyl)phenylsulfonyl)thiazolidine-2-carbonyloxy)ethyl)pyridine 1-oxide |
| 300 | 3,5-dichloro-4-((S)-2-(4-(difluoromethoxy)-3-methoxyphenyl)-2-((S)-3-(phenylsulfonyl)thiazolidine-2-carbonyloxy)ethyl)pyridine 1-oxide |
| 301 | 3,5-dichloro-4-((S)-2-(3-(cyclopentyloxy)-4-(difluoromethoxy)phenyl)-2-((S)-3-(phenylsulfonyl)thiazolidine-2-carbonyloxy)ethyl)pyridine 1-oxide |
| 302 | 3,5-dichloro-4-((S)-2-(3-(cyclopentyloxy)-4-(difluoromethoxy)phenyl)-2-((S)-3-(3-(dimethylcarbamoyl)phenylsulfonyl)thiazolidine-2-carbonyloxy)ethyl)pyridine 1-oxide |
| 303 | 3,5-dichloro-4-((S)-2-(2,2-difluorobenzo[d][1,3]dioxol-5-yl)-2-((S)-3-(3-(dimethylcarbamoyl)phenylsulfonyl)thiazolidine-2-carbonyloxy)ethyl)pyridine 1-oxide OR 3,5-dichloro-4-((R)-2-(2,2-difluorobenzo[d][1,3]dioxol-5-yl)-2-((S)-3-(3-(dimethylcarbamoyl)phenylsulfonyl)thiazolidine-2-carbonyloxy)ethyl)pyridine 1-oxide |
| 305 | 3,5-dichloro-4-((S)-2-(4-(difluoromethoxy)-3-methoxyphenyl)-2-((S)-1-(phenylsulfonyl)pyrrolidine-2-carbonyloxy)ethyl)pyridine 1-oxide |
| 306 | 3,5-dichloro-4-((S)-2-(4-(difluoromethoxy)-3-methoxyphenyl)-2-((S)-1-(3-(dimethylcarbamoyl)phenylsulfonyl)pyrrolidine-2-carbonyloxy)ethyl)pyridine 1-oxide |
| 307 | 3,5-dichloro-4-((S)-2-(3-(cyclopentyloxy)-4-(difluoromethoxy)phenyl)-2-((S)-1-(phenylsulfonyl)pyrrolidine-2-carbonyloxy)ethyl)pyridine 1-oxide |
| 308 | 3,5-dichloro-4-((S)-2-(3-(cyclopentyloxy)-4-(difluoromethoxy)phenyl)-2-((S)-1-(3-(dimethylcarbamoyl)phenylsulfonyl)pyrrolidine-2-carbonyloxy)ethyl)pyridine 1-oxide |
| 309 | 3,5-dichloro-4-((S)-2-(3,4-dimethoxyphenyl)-2-((S)-1-(phenylsulfonyl)pyrrolidine-2-carbonyloxy)ethyl)pyridine 1-oxide |
| 310 | 3,5-dichloro-4-((S)-2-(3,4-dimethoxyphenyl)-2-((S)-1-(3-(dimethylcarbamoyl)phenylsulfonyl)pyrrolidine-2-carbonyloxy)ethyl)pyridine 1-oxide |
| 311 | 3,5-dichloro-4-(2-(3-(cyclopentyloxy)-4-methoxyphenyl)-2-((S)-1-(phenylsulfonyl)pyrrolidine-2-carbonyloxy)ethyl)pyridine 1-oxide |
| 312 | 3,5-dichloro-4-(2-(3-(cyclopentyloxy)-4-methoxyphenyl)-2-((S)-1-(3-(dimethylcarbamoyl)phenylsulfonyl)pyrrolidine-2-carbonyloxy)ethyl)pyridine 1-oxide |

-continued

| Compound | Chemical Name |
|---|---|
| 313 | (S)-3,5-dichloro-4-(2-(3-(cyclopropylmethoxy)-4-methoxyphenyl)-2-(1-(phenylsulfonyl)pyrrolidine-2-carbonyloxy)ethyl)pyridine 1-oxide |
| 314 | (S)-3,5-dichloro-4-(2-(3-(cyclopropylmethoxy)-4-methoxyphenyl)-2-(1-(3-(dimethylcarbamoyl)phenylsulfonyl)pyrrolidine-2-carbonyloxy)ethyl)pyridine 1-oxide |
| 315 | 3,5-dichloro-4-((S)-2-(2,2-difluorobenzo[d][1,3]dioxol-5-yl)-2-((S)-1-(3-(dimethylcarbamoyl)phenylsulfonyl)pyrrolidine-2-carbonyloxy)ethyl)pyridine 1-oxide OR 3,5-dichloro-4-((R)-2-(2,2-difluorobenzo[d][1,3]dioxol-5-yl)-2-((S)-1-(3-(dimethylcarbamoyl)phenylsulfonyl)pyrrolidine-2-carbonyloxy)ethyl)pyridine 1-oxide |
| 316 | 3,5-dichloro-4-(2-(4-methoxyspiro[benzo[d][1,3]dioxole-2,1'-cyclopentane]-7-yl)-2-((S)-1-(phenylsulfonyl)pyrrolidine-2-carbonyloxy)ethyl)pyridine 1-oxide |
| 317 | 3,5-dichloro-4-(2-((S)-1-(3-(dimethylcarbamoyl)phenylsulfonyl)pyrrolidine-2-carbonyloxy)-2-(4-methoxyspiro[benzo[d][1,3]dioxole-2,1'-cyclopentane]-7-yl)ethyl)pyridine 1-oxide |
| 320 | 3,5-dichloro-4-(2-(3-(cyclopropylmethoxy)-4-methoxyphenyl)-2-((S)-3-(3-(dimethylcarbamoyl)phenylsulfonyl)thiazolidine-2-carbonyloxy)ethyl)pyridine 1-oxide |
| 321 | 3,5-dichloro-4-(2-(3-(cyclopropylmethoxy)-4-methoxyphenyl)-2-((S)-3-(phenylsulfonyl)thiazolidine-2-carbonyloxy)ethyl)pyridine 1-oxide |
| 322 | 3,5-dichloro-4-(2-(3-(cyclopentyloxy)-4-methoxyphenyl)-2-((S)-3-(phenylsulfonyl)thiazolidine-2-carbonyloxy)ethyl)pyridine 1-oxide |
| 323 | 3,5-dichloro-4-(2-(3-(cyclopentyloxy)-4-methoxyphenyl)-2-((S)-3-(3-(dimethylcarbamoyl)phenylsulfonyl)thiazolidine-2-carbonyloxy)ethyl)pyridine 1-oxide |
| 324 | 3,5-dichloro-4-((S)-2-(3,4-dimethoxyphenyl)-2-((S)-3-(phenylsulfonyl)thiazolidine-2-carbonyloxy)ethyl)pyridine 1-oxide |
| 325 | 3,5-dichloro-4-((S)-2-(3,4-dimethoxyphenyl)-2-((S)-3-(3-(dimethylcarbamoyl)phenylsulfonyl)thiazolidine-2-carbonyloxy)ethyl)pyridine 1-oxide |
| 326 | 3,5-dichloro-4-(2-(4-methoxyspiro[benzo[d][1,3]dioxole-2,1'-cyclopentane]-7-yl)-2-((S)-3-(phenylsulfonyl)thiazolidine-2-carbonyloxy)ethyl)pyridine 1-oxide |
| 327 | 3,5-dichloro-4-(2-((S)-3-(3-(dimethylcarbamoyl)phenylsulfonyl)thiazolidine-2-carbonyloxy)-2-(4-methoxyspiro[benzo[d][1,3]dioxole-2,1'-cyclopentane]-7-yl)ethyl)pyridine 1-oxide |
| 238 | 3,5-dichloro-4-((S)-2-(3-(cyclopropylmethoxy)-4-(difluoromethoxy)phenyl)-2-((S)-1-(3-(N,N-dimethylsulfamoyl)phenylsulfonyl)pyrrolidine-2-carbonyloxy)ethyl)pyridine 1-oxide |
| 239 | 3,5-dichloro-4-((S)-2-(3-(cyclopropylmethoxy)-4-(difluoromethoxy)phenyl)-2-((S)-3-(3-methylisoxazolo[5,4-b]pyridin-5-ylsulfonyl)thiazolidine-2-carbonyloxy)ethyl)pyridine 1-oxide |
| 240 | 3,5-dichloro-4-((S)-2-(3-(cyclopropylmethoxy)-4-(difluoromethoxy)phenyl)-2-((S)-3-(1,3-dimethyl-1H-pyrazolo[3,4-b]pyridin-5-ylsulfonyl)thiazolidine-2-carbonyloxy)ethyl)pyridine 1-oxide |
| 241 | 3,5-dichloro-4-((S)-2-(3-(cyclopropylmethoxy)-4-(difluoromethoxy)phenyl)-2-((S)-3-(1-methyl-5-(methylcarbamoyl)-1H-pyrrol-3-ylsulfonyl)thiazolidine-2-carbonyloxy)ethyl)pyridine 1-oxide |
| 242 | 3,5-dichloro-4-((S)-2-(3-(cyclopropylmethoxy)-4-(difluoromethoxy)phenyl)-2-((S)-3-(5-(pyrrolidine-1-carbonyl)-1H-pyrrol-3-ylsulfonyl)thiazolidine-2-carbonyloxy)ethyl)pyridine 1-oxide |
| 243 | (S)-((S)-1-(3-(cyclopropylmethoxy)-4-(difluoromethoxy)phenyl)-2-(3,5-dichloropyridin-4-yl)ethyl) 3-(1-methyl-1H-imidazol-2-ylsulfonyl)thiazolidine-2-carboxylate |
| 328 | 4-((S)-2-((S)-3-(1H-1,2,4-triazol-5-ylsulfonyl)thiazolidine-2-carbonyloxy)-2-(3-(cyclopropylmethoxy)-4-(difluoromethoxy)phenyl)ethyl)-3,5-dichloropyridine 1-oxide |
| 186 | 4-((S)-2-((S)-3-benzoylthiazolidine-2-carbonyloxy)-2-(3-(cyclopropylmethoxy)-4-(difluoromethoxy)phenyl)ethyl)-3,5-dichloropyridine 1-oxide |
| 187 | 3,5-dichloro-4-((S)-2-(3-(cyclopropylmethoxy)-4-(difluoromethoxy)phenyl)-2-((S)-3-(3-(dimethylcarbamoyl)benzoyl)thiazolidine-2-carbonyloxy)ethyl)pyridine 1-oxide |
| 244 | 3,5-dichloro-4-((S)-2-(3-(cyclopropylmethoxy)-4-(difluoromethoxy)phenyl)-2-((R)-1-(phenylsulfonyl)pyrrolidine-2-carbonyloxy)ethyl)pyridine 1-oxide |
| 184 | 4-((S)-2-((R)-1-benzoylpyrrolidine-2-carbonyloxy)-2-(3-(cyclopropylmethoxy)-4-(difluoromethoxy)phenyl)ethyl)-3,5-dichloropyridine 1-oxide |

-continued

| Compound | Chemical Name |
|---|---|
| 185 | 3,5-dichloro-4-((S)-2-(3-(cyclopropylmethoxy)-4-(difluoromethoxy)phenyl)-2-((R)-1-(3-(dimethylcarbamoyl)benzoyl)pyrrolidine-2-carbonyloxy)ethyl)pyridine 1-oxide |
| 245 | 3,5-dichloro-4-((R)-2-(3-(cyclopropylmethoxy)-4-(difluoromethoxy)phenyl)-2-((R)-1-(3-(dimethylcarbamoyl)phenylsulfonyl)pyrrolidine-2-carbonyloxy)ethyl)pyridine 1-oxide |
| 246 | 3,5-dichloro-4-((R)-2-(3-(cyclopropylmethoxy)-4-(difluoromethoxy)phenyl)-2-((S)-1-(3-(dimethylcarbamoyl)phenylsulfonyl)pyrrolidine-2-carbonyloxy)ethyl)pyridine 1-oxide |
| 247 | (S)-((S)-1-(3-(cyclopropylmethoxy)-4-(difluoromethoxy)phenyl)-2-(3,5-dichloropyridin-4-yl)ethyl) 3-(3-(dimethylcarbamoyl)phenylsulfonyl)thiazolidine-2-carboxylate |
| 248 | 3,5-dichloro-4-((R)-2-(3-(cyclopropylmethoxy)-4-(difluoromethoxy)phenyl)-2-((R)-3-(3-(dimethylcarbamoyl)phenylsulfonyl)thiazolidine-2-carbonyloxy)ethyl)pyridine 1-oxide |
| 249 | 3,5-dichloro-4-((R)-2-(3-(cyclopropylmethoxy)-4-(difluoromethoxy)phenyl)-2-((S)-3-(3-(dimethylcarbamoyl)phenylsulfonyl)thiazolidine-2-carbonyloxy)ethyl)pyridine 1-oxide |
| 263 | 3,5-dichloro-4-((S)-2-(4-(difluoromethoxy)-3-hydroxyphenyl)-2-((S)-3-(3-(dimethylcarbamoyl)phenylsulfonyl)thiazolidine-2-carbonyloxy)ethyl)pyridine 1-oxide |
| 250 | 3,5-dichloro-4-((S)-2-(3-(cyclopropylmethoxy)-4-(difluoromethoxy)phenyl)-2-((S)-1-(4-methyl-3,4-dihydro-2H-benzo[b][1,4]oxazin-6-ylsulfonyl)pyrrolidine-2-carbonyloxy)ethyl)pyridine 1-oxide |
| 251 | 3,5-dichloro-4-((S)-2-(3-(cyclopropylmethoxy)-4-(difluoromethoxy)phenyl)-2-((S)-1-(3-methylisoxazolo[5,4-b]pyridin-5-ylsulfonyl)pyrrolidine-2-carbonyloxy)ethyl)pyridine 1-oxide |
| 252 | 3,5-dichloro-4-((S)-2-(3-(cyclopropylmethoxy)-4-(difluoromethoxy)phenyl)-2-((R)-3-(4-methyl-3,4-dihydro-2H-benzo[b][1,4]oxazin-6-ylsulfonyl)thiazolidine-4-carbonyloxy)ethyl)pyridine 1-oxide |
| 253 | 3,5-dichloro-4-((S)-2-(3-(cyclopropylmethoxy)-4-(difluoromethoxy)phenyl)-2-((R)-3-(3-methylisoxazolo[5,4-b]pyridin-5-ylsulfonyl)thiazolidine-4-carbonyloxy)ethyl)pyridine 1-oxide |
| 254 | 3,5-dichloro-4-((S)-2-(3-(cyclopropylmethoxy)-4-(difluoromethoxy)phenyl)-2-((S)-3-(3-(methylcarbamoyl)phenylsulfonyl)thiazolidine-2-carbonyloxy)ethyl)pyridine 1-oxide |

or pharmaceutically acceptable salts or solvates thereof.

In another preferred embodiment, the compounds of the invention are selected in the group consisting of:

4-((S)-2-((S)-3-(4-aminophenylsulfonyl)thiazolidine-2-carbonyloxy)-2-(3-(cyclopropylmethoxy)-4-(difluoromethoxy)phenyl)ethyl)-3,5-dichloropyridine 1-oxide;

3,5-dichloro-4-((S)-2-(3-(cyclopropylmethoxy)-4-(difluoromethoxy)phenyl)-2-((S)-1-(3-(dimethylcarbamoyl)phenylsulfonyl)pyrrolidine-2-carbonyloxy)ethyl)pyridine 1-oxide;

3,5-dichloro-4-((S)-2-(3-(cyclopropylmethoxy)-4-(difluoromethoxy)phenyl)-2-((R)-3-(3-(dimethylcarbamoyl)phenylsulfonyl)thiazolidine-4-carbonyloxy)ethyl)pyridine 1-oxide;

3,5-dichloro-4-((S)-2-(3-(cyclopropylmethoxy)-4-(difluoromethoxy)phenyl)-2-((S)-3-(3-(dimethylcarbamoyl)phenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-1-(3-(dimethylcarbamoyl)phenylsulfonyl)piperidine-2-carbonyloxy)ethyl)pyridine 1-oxide;

3,5-dichloro-4-((S)-2-(3-(cyclopropylmethoxy)-4-(difluoromethoxy)phenyl)-2-((S)-1-(3-(dimethylcarbamoyl)-4-methoxyphenylsulfonyl)piperidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(3-(4-methylpiperazine-1-carbonyl)phenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(pyridin-3-ylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(3-(dimethylcarbamoyl)-4-methoxyphenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(phenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(1-methyl-1H-imidazol-2-ylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(3-sulfamoylphenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(4-(methylsulfonyl)phenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(3,4-dimethoxyphenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(3-(N,N-dimethylsulfamoyl)phenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(4-methoxyphenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(5-(pyrrolidine-1-carbonyl)-1H-pyrrol-3-ylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(1-methyl-5-(methylcarbamoyl)-1H-pyrrol-3-ylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(1,3-dimethyl-1H-pyrazolo[3,4-b]pyridin-5-ylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(3-methylisoxazolo[5,4-b]pyridin-5-ylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(3-(hydroxymethyl)phenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(3-ureidophenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(1-methyl-2-oxoindolin-5-ylsulfonyl)thiazolidine-2-carbonyloxy)ethyl)pyridine 1-oxide;

3,5-dichloro-4-((S)-2-((S)-3-(4-cyanophenylsulfonyl)thiazolidine-2-carbonyloxy)-2-(3-(cyclopropylmethoxy)-4-(difluoromethoxy)phenyl)ethyl)pyridine 1-oxide;

and pharmaceutically acceptable salts or solvates thereof.

In one aspect of the present invention, a process for the preparation of compounds of the invention is provided, according to general synthetic routes reported in Scheme 1 below, where reference is made to specific synthetic schemes which are better detailed in the following paragraphs.

The processes which can be used and are described below and reported in Schemes, should not be viewed as limiting the scope of the synthetic methods available for the preparation of the compounds of the invention.

Scheme 1.

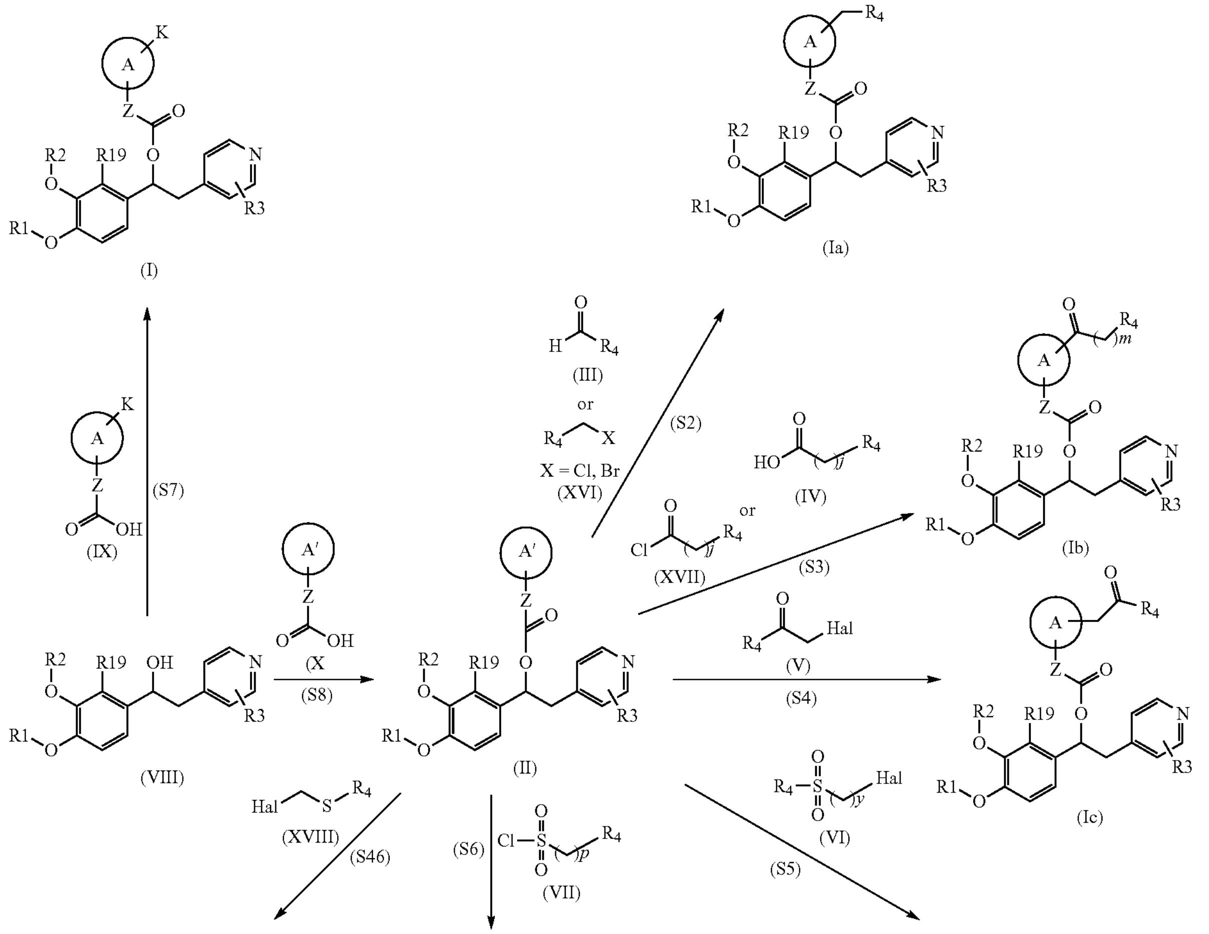

-continued

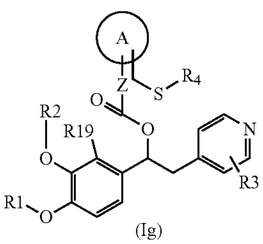

(Ig)

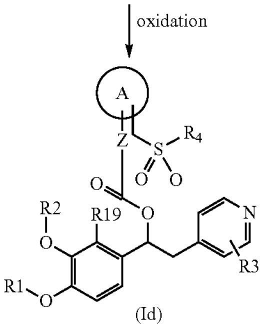

(Id)

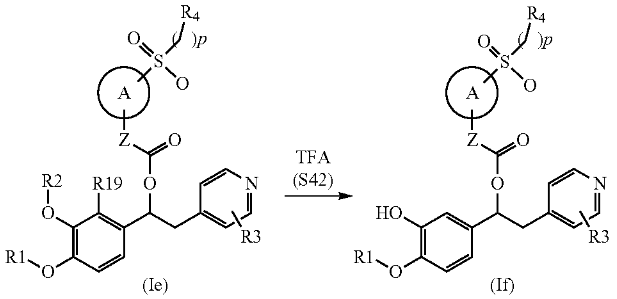

(Ie) (If)

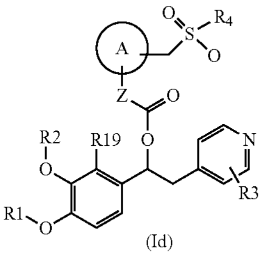

(Id)

In the following Schemes, for compounds of formula (II) to (XIX), unless otherwise indicated, groups $R_1$ to $R_{20}$, Z, A, and K have the same meanings as described for compounds of formula (I) above.

Compounds of formula (Ia), i.e. compounds of formula (I) wherein K is a group —$(CH_2)R_4$, may be prepared according to Scheme 2a below by reaction of a compound of formula (II) wherein A' is $(C_3$-$C_7)$ heterocycloalkyl-ene group comprising a group —NH—, with an appropriate compound of formula (III).

Scheme 2 (S2a).

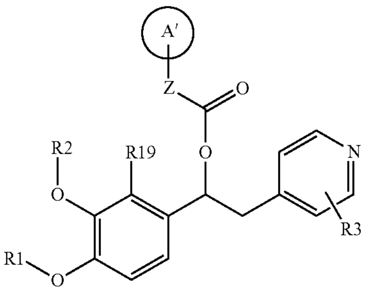

(II)

+

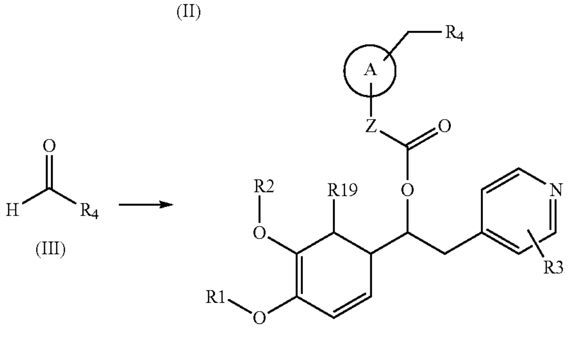

(III) (Ia)

Typical reaction conditions comprise reacting a compound of formula (II) with a compound of formula (III) in a suitable dipolar solvent, such as THF, methanol, ethanol or DCM, in the presence of an appropriate reducing agent, such as sodium triacetoxy borohydride, sodium cyano borohydride or sodium borohydride, and of an appropriate acid, such as acetic acid, HCl in methanol or ammonium acetate. It could be useful to preform the imine before adding the reducing agent. The reaction proceeds smoothly at room temperature (RT) over 1 to 12 hours.

Alternatively compounds of formula (Ia), i.e. compounds of formula (I) wherein K is a group —$(CH_2)R_4$, may be prepared according to Scheme 2b below by reaction of a compound of formula (II) wherein A' is $(C_3$-$C_7)$ heterocycloalkyl-ene group comprising a group —NH—, with an appropriate compound of formula (XVI).

Scheme 2b (S2b).

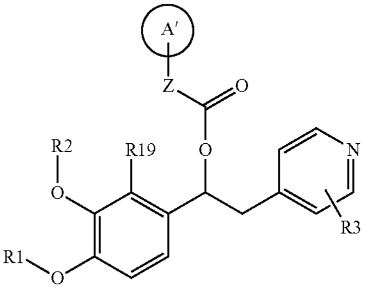

(II)

+

-continued

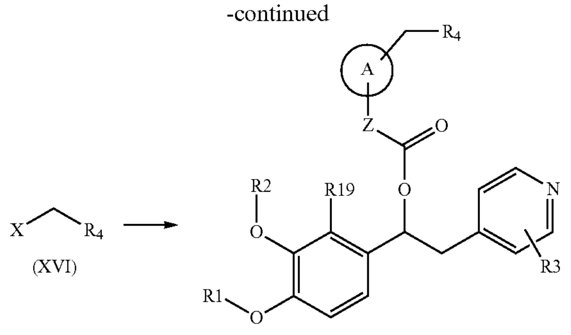

(XVI)

(Ia)

Typical reaction conditions comprise reacting a compound of formula (XVI), where X is a leaving group such as Cl or Br, with a compound of formula (II) in a suitable polar aprotic solvent, such as acetonitrile or DMF, in the presence of an appropriate base such as $K_2CO_3$, alkaline bicarbonate, TEA or DIPEA, at a temperature ranging from RT 10 to 70° C.

Compounds of formula (Ib), i.e. compounds of formula (I) wherein K is a group —$C(O)(CH_2)_jR_4$, may be prepared according to Scheme 3a below by reaction of a compound of formula (II) as above defined, with an appropriate compound of formula (IV).

Scheme 3 (S3a).

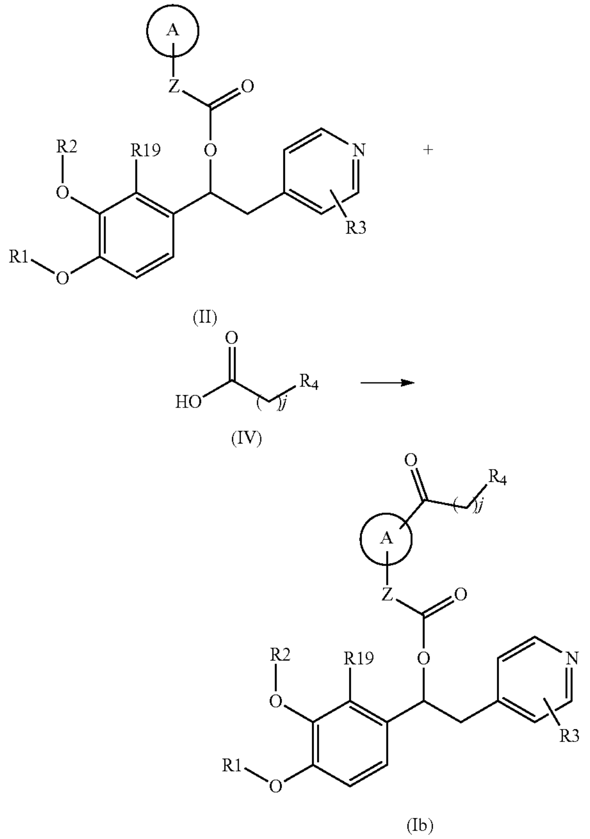

(II)

(IV)

(Ib)

Typical reaction conditions comprise reacting a compound of formula (II) with a compound of formula (IV) in a suitable dipolar aprotic solvent, such as DMF, chloroform or DCM, in the presence of an appropriate condensing agent such as EDC, DCC, HOBT, HOAT, or CDI, and, if necessary, of an appropriate agent, such as DMAP, HOBT, 4-pyrrolidinopyridine (4-PPY) or other 4-alkylamino pyridine, at room temperature.

Alternatively compounds of formula (Ib), i.e. compounds of formula (I) wherein K is a group —$C(O)(CH_2)_jR_4$, may be prepared according to Scheme 3b below by reaction of a compound of formula (II) as above defined, with an appropriate compound of formula (XVII).

Scheme 3b (S3b).

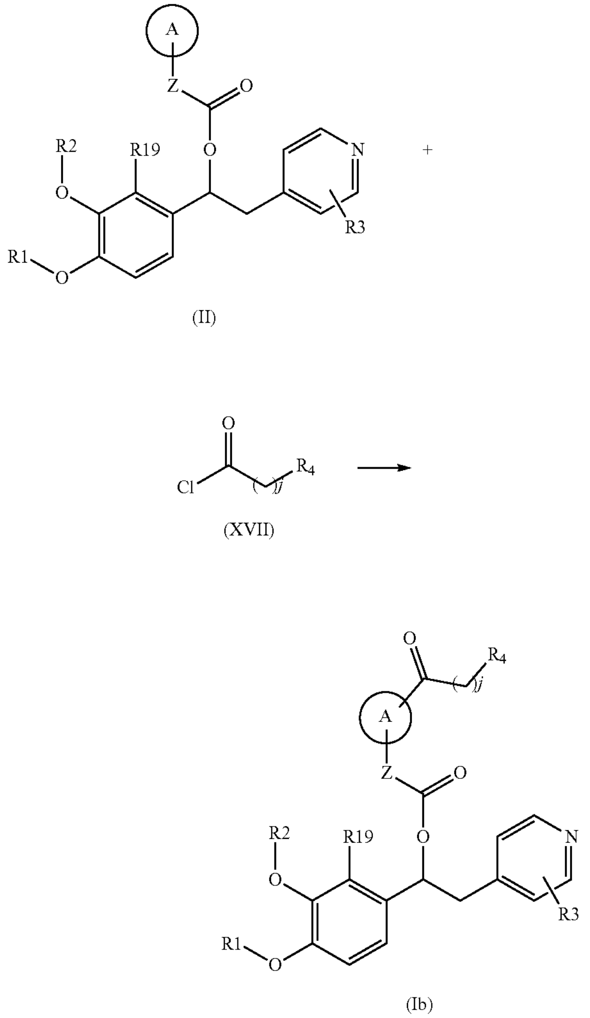

(II)

(XVII)

(Ib)

Typical reaction conditions comprise reacting a compound of formula (II) with a compound of formula (XVII) in a suitable solvent such as pyridine or DCM, and in the presence, if necessary, of an appropriate base such as TEA, DIPEA, DBU, or another organic base at a temperature ranging from 0° C. to room temperature.

Compounds of formula (Ic), i.e. compounds of formula (I) wherein K is a group —$(CH_2)_mC(O)R_4$, may be prepared according to Scheme 4 below by reaction of a compound of formula (II) as above defined, with an appropriate compound of formula (V), where Hal represents a suitable halogen leaving group.

Scheme 4 (S4).

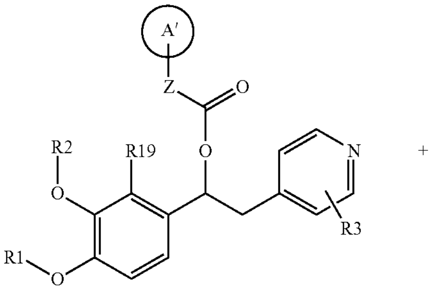

(II)

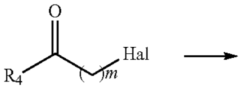

(V)

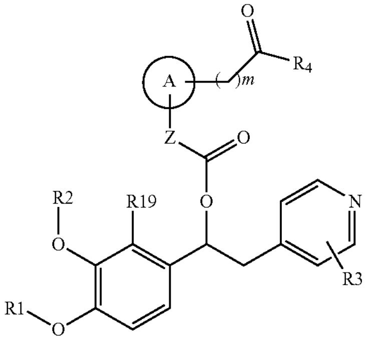

(Ic)

Typical reaction conditions comprise reacting a compound of formula (II) with a compound of formula (V) in a suitable polar aprotic solvent, such as DMF or acetonitrile, in the presence of an appropriate base such as $K_2CO_3$, alkaline bicarbonate, TEA or DIPEA, at a temperature ranging from RT to 50° C.

Compounds of formula (Id), i.e. compounds of formula (I) wherein K is a group —$(CH_2)_ySO_2R_4$, may be prepared according to Scheme 5 below by reaction of a compound of formula (II) as above defined, with an appropriate compound of formula (VI), where Hal represents a suitable halogen leaving group.

Scheme 5 (S5).

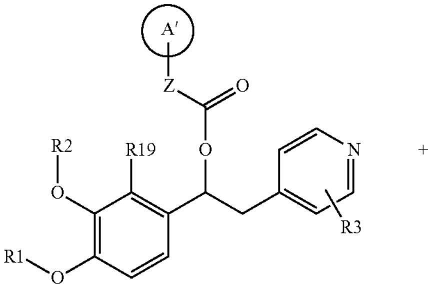

(II)

-continued

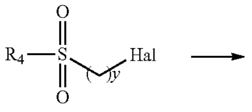

(VI)

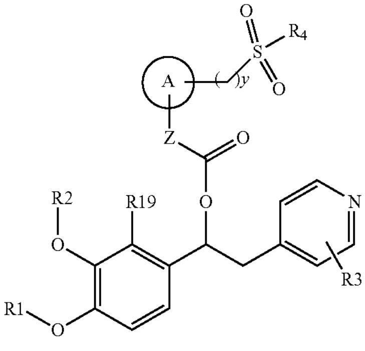

(Id)

Typical reaction conditions comprise reacting a compound of formula (II) with a compound of formula (VI) in a suitable polar aprotic solvent such as DMF or acetonitrile, in the presence of an appropriate base such as $K_2CO_3$, alkaline bicarbonate, TEA, or DIPEA, at a temperature ranging from RT to 50° C.

Compounds of formula (Id), i.e. compounds of formula (I) wherein K is a group —$(CH_2)_ySO_2R_4$ and y is 1, may also be prepared according to Scheme 46 below by reaction of a compound of formula (II) as above defined, with an appropriate compound of formula (XVIII), where Hal represents a suitable halogen leaving group.

Scheme 46 (S46).

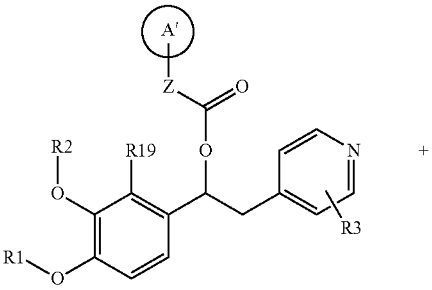

(II)

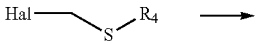

(XVIII)

-continued

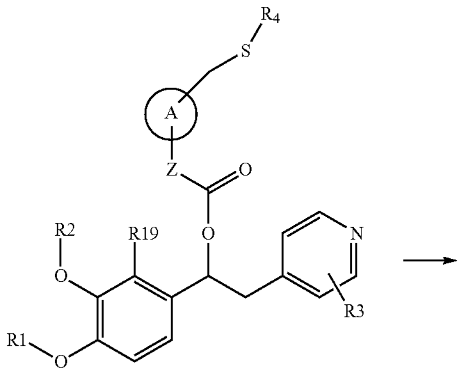

(XIX)

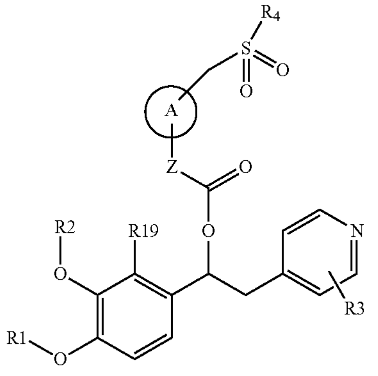

(Id)

Typical reaction conditions comprise reacting a compound of formula (II) with a compound of formula (XVIII) in a suitable polar aprotic solvent, such as DMF or acetonitrile, in the presence of an appropriate base such as $K_2CO_3$, alkaline bicarbonate, TEA, or DIPEA, at a temperature ranging from RT to 50° C. Compound (XIX) thus obtained is successively reacted with a suitable oxidizing agent, such as MCPBA or hydrogen peroxide, in a suitable polar solvent, such as DCM, chloroform, EtOH or MeOH, at a temperature ranging from room temperature to 60° C.

Compounds of formula (Ie), i.e. compounds of formula (I) wherein K is a group $—SO_2(CH_2)_pR_4$, may be prepared according to Scheme 6 below reported by reaction of a compound of formula (II) as above defined, with an appropriate compound of formula (VII).

Scheme 6 (S6).

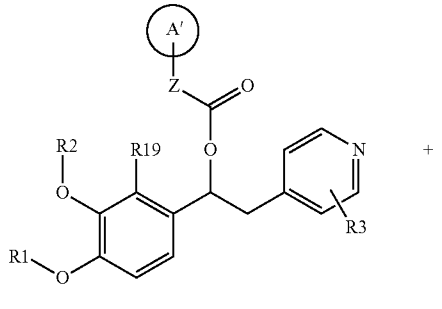

(II)

-continued

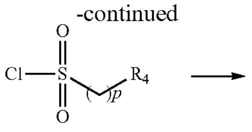

(VI)

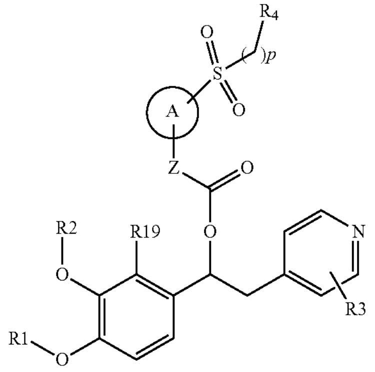

(Ie)

Typical reaction conditions comprise reacting a compound of formula (II) with a compound of formula (VII) in a suitable solvent such as pyridine or DCM, and in the presence, if necessary, of an appropriate base such as TEA, DIPEA, DBU, or another organic base at a temperature ranging from 0° C. to room temperature.

Alternatively, compounds of formula (I), may be prepared according to Scheme 7 below by reaction of a compound of formula (VIII), with an appropriate compound of formula (IX).

Scheme 7 (S7).

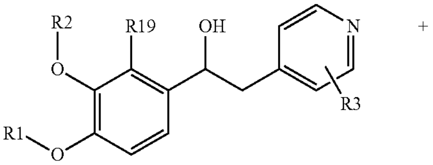

(VIII)

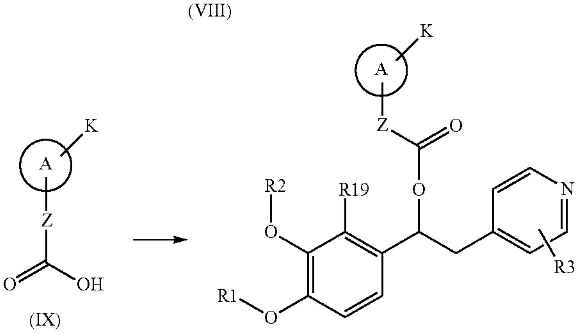

(IX)

(I)

Typical reaction conditions comprise reacting a compound of formula (VIII) with a compound of formula (IX) in a suitable polar aprotic solvent, such as DMF, THF, chloroform, or DCM, in the presence of an appropriate condensing agent such as EDC, DCC, or CDI and of an appropriate agent, such as DMAP, HOBT, 4-pyrrolidinopyridine (4-PPY) or other 4-alkylamino pyridine at room temperature; removal of possibly present protecting group is performed under conditions known to the person skilled in the art or as described in 'Protection Groups in Organic Synthesis' by T. W. Green and P. Wutz, (Wiley-Interscience publication, 1999, which is incorporated herein by reference in its entirety).

Compounds of formula (II), as above defined, may be prepared according to Scheme 8 below by reaction of a compound of formula (X), wherein A" is ($C_3$-$C_7$) heterocycloalkyl-ene group comprising a group —N— which is protected with a suitable protecting group, with an appropriate compound of formula (XI), followed by removal of N-protecting group under appropriate conditions.

Scheme 8 (S8).

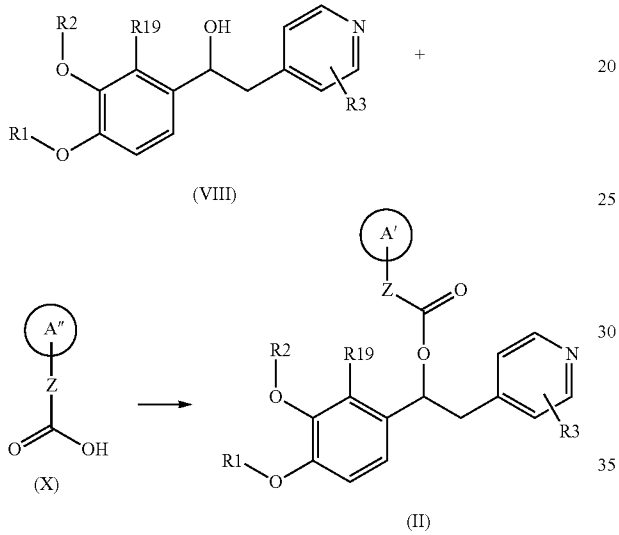

Typical coupling reaction conditions comprise reacting a compound of formula (VIII) with a compound of formula (X) in a suitable polar aprotic solvent, such as DMF, THF, chloroform, or DCM, in the presence of an appropriate (coupling) condensing agent such as EDC, DCC, or CDI and of an appropriate agent such as DMAP, HOBT, 4-pyrrolidinopyridine (4-PPY) or other 4-alkylamino pyridine at room temperature; removal of protecting group is performed under conditions known to the person skilled in the art or as described in 'Protection Groups in Organic Synthesis' by T. W. Green and P. Wutz (Wiley-Interscience publication, 1999, which is incorporated herein by reference in its entirety), for example when the protecting group is represented by a t-butoxycarbonyl group then deprotection may be conveniently performed under acidic conditions (such as HCl in dioxane or in AcOEt or TFA in $CH_2Cl_2$).

Alternatively the corresponding acyl chloride can be preformed, by reacting compound (X) with oxalyl chloride or thionyl chloride or other reagents well known to those skilled in the art, in a suitable aprotic solvent such as DCM at 0 degrees, in presence, if necessary, of a catalytic amount of DMF, and successively adding compound (VIII) and an appropriate base such as TEA or DIPEA.

Compounds of formula (If), i.e. compounds of formula (I) wherein K is a group —$SO_2(CH_2)_pR_4$ and $R_2$ is hydrogen, may be prepared according to Scheme 42 below by reaction of a compound of formula (Ie) as above defined, wherein $R_2$ is ($C_1$-$C_6$) alkyl, optionally substituted by one ($C_3$-$C_7$) cycloalkyl under appropriate conditions.

Scheme 42 (S42).

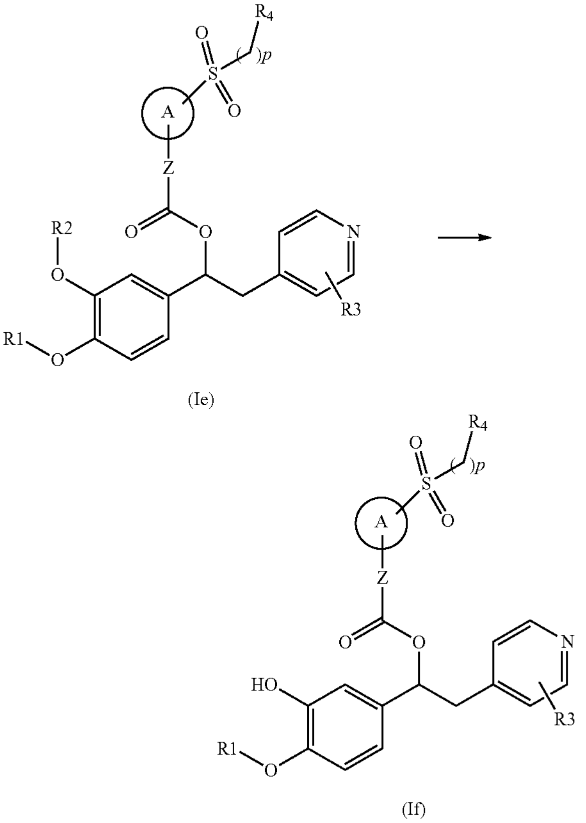

Typical reaction conditions comprise reacting a compound of formula (Ie) as above defined with a suitable acid, such as TFA or $BBr_3$ or $BCl_3$, at a temperature ranging from room temperature to 40 degrees.

The N-oxides on the 2-pyridinyl ring of the compounds of general formula (I) and embodiments thereof may be prepared according to methods available in the literature and well known to the skilled person. For instance, they may be prepared by dissolving the compound of general formula (I) or embodiments thereof in $CH_2Cl_2$ or $CHCl_3$, then adding an oxidizing agent such as m-chloro perbenzoic acid (mCPBA) to the resulting solution. Other oxidizing agents which may be used are hydrogen peroxide, perbenzoic acid, and peracetic acid.

Alternatively, in particular for those compounds in which A or A' is a ring substituted with a functional group sensitive to oxidation, the corresponding N-oxides are prepared by carrying out the oxidation step before further functional groups are introduced, for example on compounds of formula (II) or (VIII).

In a preferred embodiment, the process for preparation of compounds of formula (I) or embodiments thereof is performed starting from N-oxide on the pyridine ring of compound of formula (VIII), thus allowing the preparation of compound of formula (I) or embodiments thereof in the form of N-oxides on the pyridine ring.

Compounds of general formula (III), (IV), (V), (VI), (VII), (VIII), (IX), (XVI), (XVII), (XVIII), (XIX), and (X) may be commercially available, their preparation may be specifically described in the literature or they may be prepared according to methods available in the literature and known to the person skilled in the art.

In particular, compounds of formula (VIII) and corresponding N-oxides on the pyridine ring may also be prepared as described in International Patent Application Nos. WO 2009/018909 or WO 2010/089107.

In one embodiment, a preferred process for the preparation of compounds of formula (IDa), i.e. N-oxide derivatives on pyridine ring of compounds of formula (ID) wherein $R_9$ is hydrogen, K is a group $—SO_2(CH2)_pR_4$ and wherein absolute configuration at the stereogenic centers is as below represented, is provided according to Scheme 43 below reported.

Scheme 43 (S43).

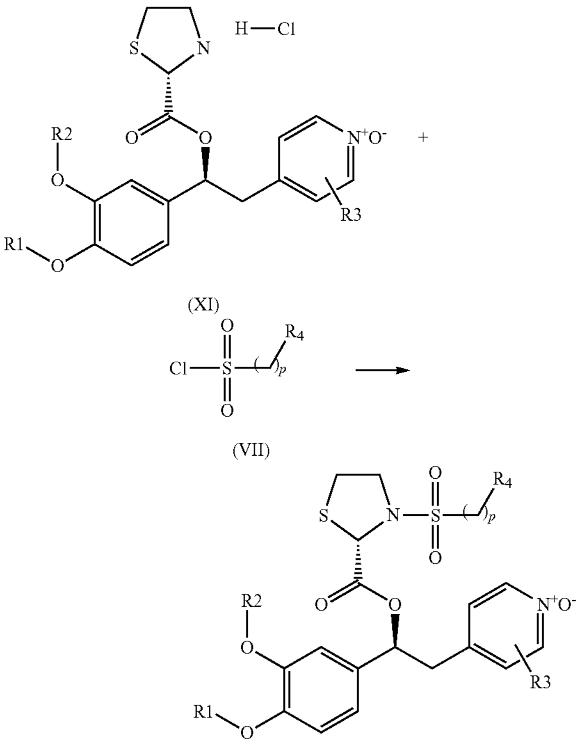

(XI)

(VII)

(IDa)

Typical reaction conditions for the process described in Scheme 43 comprise: a) adding a solution of a compound of formula (VII) in pyridine (3-30 vol. preferably 8 vol.) to a refrigerated solution of a compound of formula (XI), in pyridine (3-30 vol. preferably 8 vol.) stirring the resulting solution at room temperature; c) pouring the solution into aqueous HCl in excess; d) filtering the precipitated material and washing it with water, or d') extracting the aqueous phase with AcOEt, washing with aqueous HCl 1M, brine and evaporating the resulting organic phase; and optionally e) dissolving the solid obtained from step d) or d') in AcOEt, charging it on a silica gel pad, eluting with AcOEt/MeOH [100:0 to (90:10)] and evaporating under vacuum the resulting solution, or e') purifying the product by flash chromatography eluting with DCM/i-PrOH.

In a more preferred embodiment, compounds of formula (IDa) obtained as above reported according to Scheme 43 are crystallized by a process comprising: f) dissolving the compounds in EtOH (8 vol); g) vigorously stirring overnight at room temperature; h) filtering the solid formed; and, optionally, i) washing the solid obtained from step h) with EtOH (2 vol) and 1) drying the solid under vacuum.

In a further preferred embodiment, step 1) of Scheme 43 is conducted by drying first the solid under vacuum at room temperature, followed by drying under vacuum at 60° C.

In one embodiment, a preferred process is provided for the preparation of compounds of formula (XI) as above defined, according to Scheme 44 below reported:

Scheme 44 (S44).

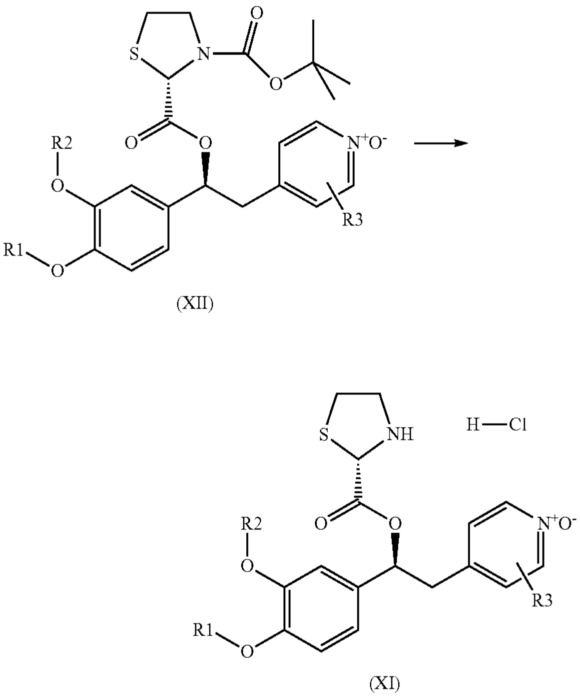

(XII)

(XI)

Typical reaction conditions for the process described in Scheme 44 comprise: a) adding under stirring a solution of conc. HCl (about 5M; large excess) in dry AcOEt (9 vol.) to a solution of a compound of formula (XII) in AcOEt (6 vol.) at room temperature; b) stirring; c) filtering the precipitated solid; optionally d) washing the obtained solid with AcOEt; and optionally e) drying the solid obtained under vacuum at room temperature.

In one embodiment, a preferred process is provided for the preparation of compounds of formula (XII) as above defined, according to Scheme 45 below reported:

Scheme 45 (S45).

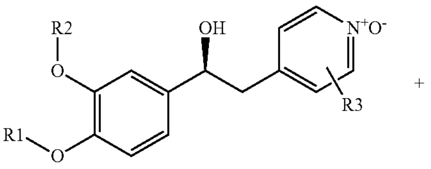

(XV)

-continued

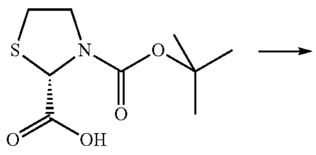

(XIV)

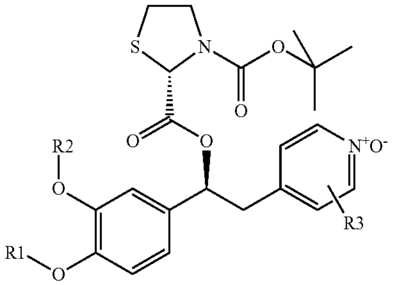

(XII)

Typical reaction conditions for the process described in Scheme 45 comprise: a) adding a compound of formula (XIV), DMAP, and EDC to a solution of a compound of formula (XV) in DMF; b) stirring the mixture, preferably overnight; c) pouring the mixture into cold water; d) filtering the precipitate; optionally e) dissolving the precipitate in DCM, washing the solution with water, drying and evaporating the solvent; and optionally f) dissolving the solid obtained from step d) or e) in boiling MTBE (3.5 vol.) adding petroleum ether (4 vol.) under stirring, stirring at room temperature, filtering the solid obtained and drying it at room temperature under vacuum.

In a preferred embodiment, processes according to schemes 43, 44, and 45 are sequentially performed to obtain crystalline compounds of formula (IDa).

In a preferred embodiment, a process is provided for the preparation of compounds of formula (IDaa), i.e. a compound of formula (IDa) wherein $R_1$ is ($C_1$-$C_6$) haloalkyl, $R_2$ is ($C_1$-$C_6$) alkyl which is substituted by ($C_3$-$C_7$) cycloalkyl, 2-pyridinyl ring is substituted in 3 and 5 with two chlorine $R_3$ groups, K is a group

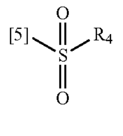

and $R_4$ is a phenyl group which is optionally substituted by one or more groups $R_5$; which process comprises sequentially performing reactions as provided in Schemes 43, 44, and above described.

In one aspect of the present invention, compounds of formula (II), their N-oxides on the pyridine ring, or salts thereof are provided as intermediates in the process for the preparation of compounds of formula (I)

(II)

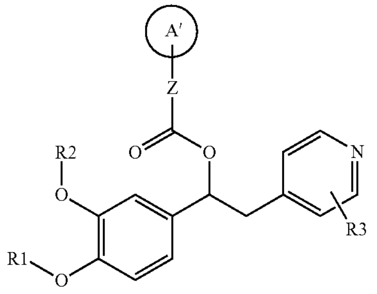

wherein A' is ($C_3$-$C_7$) heterocycloalkyl-ene group comprising a group —NH—.

In one embodiment, compounds of formula (XI) as above defined are provided as intermediates in the process of preparation of compounds of formula (IDa). In a further preferred embodiment, for compounds of formula (XI), $R_1$ is ($C_1$-$C_6$) haloalkyl and $R_2$ is ($C_1$-$C_6$) alkyl which is substituted by ($C_3$-$C_7$) cycloalkyl, and the pyridine ring is substituted by two groups $R_3$ placed at position 3 and 5.

In another aspect of the present invention, compounds of formula (II) as above defined are provided which act as inhibitors of the phosphodiesterase 4 (PDE4) enzyme, thus solving the above mentioned need of identifying further PDE4 inhibitors endowed with a high affinity for PDE4 enzyme, and possibly showing an appropriate developability profile as an inhalation treatment for example in terms of reduced side effects.

Also provided by the present invention are compositions containing compounds of formula (II) and therapeutic uses thereof.

Where applicable, preferred embodiments and groups described above for compounds of formula (I), apply to compounds of formula (II) as well mutatis mutandis.

The process described is particularly advantageous as it is susceptible of being properly modulated, through any proper variant known to the skilled person, so as to obtain any of the desired compounds of the invention. Such variants are comprised within the scope of the present invention.

From all of the above, it should be clear to the skilled person that any of the described groups may be present as such or in any properly protected form. In particular, functional groups present in the compounds of formula (II), (III), (IV), (V), (VI), (VII), (VIII), (IX), (X), (XI), (XII), (XIII), (XIV), (XV), (XVI), (XVII), (XVIII), and (XIX) and which could generate unwanted side reaction and by-products, need to be properly protected before the alkylation, acylation, coupling, oxidation, or sulfonylation takes place. Likewise, subsequent deprotection of those same protected groups may follow upon completion of the said reactions.

In the present invention, unless otherwise indicated, the term "protecting group" designates a protective group adapted to preserve the function of the group it is bound to. Typically, protective groups are used to preserve amino, hydroxyl, or carboxyl functions. Appropriate protecting groups may thus include, for example, benzyl, benzyloxycarbonyl, t-butoxycarbonyl, alkyl, or benzyl esters or the like, which are well known to those skilled in the art (see, for a general reference, T. W. Green; Protective Groups in Organic Synthesis (Wiley, N.Y. 1999) which is incorporated herein by reference in its entirety). Likewise, selective protection and deprotection of any of the said groups, for instance including carbonyl, hydroxyl, or amino groups, may be accomplished according to very well known methods commonly employed in organic synthetic chemistry.

Optional salification of the compounds of formula (I) or N-oxides on the pyridine ring thereof may be carried out by properly converting any of the free acidic or amino groups into the corresponding pharmaceutically acceptable salts. In this case too, the operative conditions being employed for the optional salification of the compounds of the invention are all within the ordinary knowledge of the skilled person.

From all of the above, it should be clear to the skilled person that the above processes, comprehensive of any variant thereof for the preparation of suitable compounds of the invention, may be conveniently modified so that to adapt the reaction conditions to the specific needs, for instance by choosing appropriate condensing agents, solvents and protective groups, as the case may be.

The present invention also provides pharmaceutical compositions of compounds of the invention or of compounds of formula (II) in admixture with one or more pharmaceutically acceptable carriers, for example those described in Remington's Pharmaceutical Sciences Handbook, XVII Ed., Mack Pub., N.Y., U.S.A., which is incorporated herein by reference in its entirety.

Administration of the compounds of the present invention or of compounds of formula (II) may be accomplished according to patient needs, for example, orally, nasally, parenterally (subcutaneously, intravenously, intramuscularly, intrasternally, and by infusion), by inhalation, rectally, vaginally, topically, locally, transdermally, and by ocular administration. Various solid oral dosage forms may be used for administering compounds of the present invention including such solid forms as tablets, gelcaps, capsules, caplets, granules, lozenges, and bulk powders. The compounds of the present invention or compounds of formula (II) may be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants, and the like. Time release capsules, tablets, and gels are also advantageous in administering the compounds of the present invention or compounds of formula (II).

Various liquid oral dosage forms may also be used for administering compounds of the present invention or compounds of formula (II), including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention or compounds of formula (II). The compounds of the present invention or compounds of formula (II) may be injected, for example, intravenously, in the form of an isotonic sterile solution. Other preparations are also possible.

Suppositories for rectal administration of the compounds of the present invention or of compounds of formula (II) may be prepared by mixing the compound with a suitable excipient such as cocoa butter, salicylates, and polyethylene glycols.

Formulations for vaginal administration may be in the form of cream, gel, paste, foam, or spray formula containing, in addition to the active ingredient, such suitable carriers as are known in the art.

For topical administration the pharmaceutical composition may be in the form of creams, ointments, liniments, lotions, emulsions, suspensions, gels, solutions, pastes, powders, sprays, and drops suitable for administration to the skin, eye, ear, or nose. Topical administration may also involve transdermal administration via means such as transdermal patches.

For the treatment of the diseases of the respiratory tract, the compounds according to the present invention or compounds of formula (II) are preferably administered by inhalation. Inhalable preparations include inhalable powders, propellant-containing metering aerosols, and propellant-free inhalable formulations.

For administration as a dry powder, single- or multi-dose inhalers known from the prior art may be utilized. In that case the powder may be filled in gelatine, plastic, or other capsules, cartridges, or blister packs or in a reservoir.

A diluent or carrier, generally non-toxic and chemically inert to the compounds of the invention, e.g. lactose or any other additive suitable for improving the respirable fraction may be added to the powdered compounds of the invention or compounds of formula (II).

Inhalation aerosols containing propellant gas such as hydrofluoroalkanes may contain the compounds of the invention or compounds of formula (II) either in solution or in dispersed form. The propellant-driven formulations may also contain other ingredients such as co-solvents, stabilizers, and optionally other excipients.

The propellant-free inhalable formulations comprising the compounds of the present invention or compounds of formula (II) may be in form of solutions or suspensions in an aqueous, alcoholic, or hydroalcoholic medium and they may be delivered by jet or ultrasonic nebulizers known from the prior art or by soft-mist nebulizers such as Respimat®.

The compounds of the present invention or compounds of formula (II) may be administered as the sole active agent or in combination with other pharmaceutical active ingredients including those currently used in the treatment of respiratory disorders, e.g. beta2-agonists, antimuscarinic agents, corticosteroids, mitogen-activated protein kinases (P38 MAP kinase) inhibitors, nuclear factor kappa-B kinase subunit beta (IKK2) inhibitors, human neutrophil elastase (HNE) inhibitors, phosphodiesterase 4 (PDE4) inhibitors, leukotriene modulators, non-steroidal anti-inflammatory agents (NSAIDs), and mucus regulators.

The present invention also provides combinations of a compound of the present invention or of compounds of formula (II), with a β32-agonist selected from the group consisting of carmoterol, GSK-642444, indacaterol, milveterol, arformoterol, formoterol, salbutamol, levalbuterol, terbutaline, AZD-3199, BI-1744-CL, LAS-100977, bambuterol, isoproterenol, procaterol, clenbuterol, reproterol, fenoterol and ASF-1020, and salts thereof.

The present invention also provides combinations of a compound of the present invention or of a compound of formula (II), with a corticosteroid selected from the group consisting of fluticasone propionate, fluticasone furoate, mometasone furoate, beclometasone dipropionate, ciclesonide, budesonide, GSK 685698, and GSK 870086.

The present invention also provides combinations of a compound of the present invention or of a compound of formula (II), with an antimuscarinic agent selected from the group consisting of aclidinium, tiotropium, ipratropium, trospium, glycopyrronium, and oxitropium salts.

The present invention also provides combinations of a compound of the present invention or of a compound of formula (II), with a PDE4 inhibitor selected from the group consisting of AN-2728, AN-2898, CBS-3595, apremilast, ELB-353, KF-66490, K-34, LAS-37779, IBFB-211913, AWD-12-281, cipamfylline, cilomilast, roflumilast, BAY19-8004 and SCH-351591, AN-6415, indus-82010, TPI-PD3, ELB-353, CC-11050, GSK-256066, oglemilast, OX-914, tetomilast, MEM-1414, and RPL-554.

The present invention also provides combinations of a compound of the present invention or of a compound of formula (II), with a P38 MAP kinase inhibitor selected from the group consisting of semapimod, talmapimod, pirfenidone, PH-797804, GSK-725, minokine, and losmapimod and salts thereof.

In a preferred embodiment, the present invention provides combinations of a compound of the present invention or of a compound of formula (II) with an IKK2 inhibitor.

The present invention also provides combinations of a compound of the present invention or of a compound of formula (II), with a HNE inhibitor selected from the group consisting of AAT, ADC-7828, Aeriva, TAPI, AE-3763, KRP-109, AX-9657, POL-6014, AER-002, AGTC-0106, respriva, AZD-9668, zemaira, AAT IV, PGX-100, elafin, SPHD-400, prolastin C, and prolastin inhaled.

The present invention also provides combinations of a compound of the present invention or of a compound of formula (II), with a leukotriene modulator selected from the group consisting of montelukast, zafirlukast, and pranlukast.

The present invention also provides combinations of a compound of the present invention or of a compound of formula (II), with a NSAID selected from the group consisting of ibuprofen and ketoprofen.

The present invention also provides combinations of a compound of the present invention or of a compound of formula (II), with a mucus regulator selected from the group consisting of INS-37217, diquafosol, sibenadet, CS-003, talnetant, DNK-333, MSI-1956, and gefitinib.

The dosages of the compounds of the present invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of the present invention or compounds of formula (II) may be administered for example, at a dosage comprised between 0.001 and 1000 mg/day, preferably between 0.1 and 500 mg/day.

When they are administered by inhalation route, the dosage of the compounds of the present invention or of compounds of formula (II) is advantageously comprised between 0.01 and 20 mg/day, preferably between 0.1 and 10 mg/day.

Preferably, the compounds of the present invention or compounds of formula (II) alone or combined with other active ingredients may be administered for the prevention and/or treatment of any obstructive respiratory disease such as asthma, chronic bronchitis, and chronic obstructive pulmonary disease (COPD).

However the compounds of the present invention or compounds of formula (II) may be administered for the prevention and/or treatment of any disease wherein PDE4 inhibition is required. Said disease include: allergic disease states such as atopic dermatitis, urticaria, allergic rhinitis, allergic conjunctivitis, vernal conjunctivitis, eosinophilic granuloma, psoriasis, inflammatory arthritis, rheumatoid arthritis, septic shock, ulcerative colitis, Crohn's disease, reperfusion injury of the myocardium and brain, chronic glomerulonephritis, endotoxic shock, cystic fibrosis, arterial restenosis, artherosclerosis, keratosis, rheumatoid spondylitis, osteoarthritis, pyresis, diabetes mellitus, pneumoconiosis, toxic and allergic contact eczema, atopic eczema, seborrheic eczema, lichen simplex, sunburn, pruritus in the anogenital area, alopecia areata, hypertrophic scars, discoid lupus erythematosus, systemic lupus erythematosus, follicular and wide-area pyodermias, endogenous and exogenous acne, acne rosacea, Beghet's disease, anaphylactoid purpura nephritis, inflammatory bowel disease, leukemia, multiple sclerosis, gastrointestinal diseases, autoimmune diseases and the like.

Such diseases also include neurological and psychiatric disorders such as Alzheimer's disease, multiple sclerosis, amylolaterosclerosis (ALS), multiple systems atrophy (MSA), schizophrenia, Parkinson's disease, Huntington's disease, Pick's disease, depression, stroke, and spinal cord injury.

Other features of the invention will become apparent in the course of the following descriptions of exemplary embodiments which are given for illustration of the invention and are not intended to be limiting thereof.

EXAMPLES

Chemical names of the compounds were generated with Structure To Name Enterprise 10.0 Cambridge Software.

Abbreviations

EDC=1-ethyl-3-(3-dimethylaminopropyl) carbodiimide) hydrochloride; DMAP=4-dimethylaminopyridine; DMF=dimethylformamide; EtOAc or AcOEt=Ethyl acetate; RT=room temperature; THF=tetrahydrofurane; DCM=dichloromethane; $Et_2O$=diethyl ether; MeOH=methylic alcohol; n-BuOH=n-butylic alcohol; EtOH=ethyl alcohol; IprOH or IPA=isopropyl alcohol; $(Ipr)_2O$=diisopropylether; MIK=methyl isobutyl ketone; MEK=methyl ethyl ketone; MTBE=methyl tert-butyl ether; AcOH=acetic acid; vv=volumes; v/w=ratio volume/weight; and w/w=ratio weight/weight.

General Experimental Details.

NMR Characterization:

$^1$H-NMR spectra were recorded on a 400 MHz Varian AS400 spectrometer. Chemical shift are reported as δ values in ppm relative to trimethyl silane (TMS) as an internal standard. Coupling constants (J values) are given in hertz (Hz) and multiplicities are reported using the following abbreviation (s=singlet, d=doublet, t=triplet, q=quartet, m=multiplet, b r=broad, nd=not determined).

or

1H-NMR spectra were recorded on a Bruker ARX300 Spectrometer at 300.13 MHz (1H) using deuterated solvents, such as deuterated dimethylsulfoxide (DMSO-d6) or deuterated chloroform (CDCl3). The instrument was equipped with a multinuclear inverse probe and temperature controller. Chemical shifts are expressed in parts per million (ppm) downfield of tetramethylsilane (d units). Multiplicity is indicated as follow: (s) singlet, (d) doublet, (dd) double doublet, (ddd) triple doublet, (t) triplet, (dt) double triplet, (q) quartet, (m) multiplet, (br s) broad signal. Coupling constants J are expressed in units of hertz (Hz).

LC/UV/MS Analytical Methods

LC/MS retention times are estimated to be affected by an experimental error of ±0.5 min.

LC/UV/MS—Method 1

LC instrument: HPLC Alliance Waters (or equivalent)

Column: Kinetex 2.6 u C18 100 A 100×4.6 mm (Phenomenex)

Column Temperature (° C.): 50.0

Mobile phases: HCOONH4 0.025M pH3 (A); Acetonitrile (B)
Flow (ml/min): 2.0 (split in MS 1:10)
Stop Time (mins): 17.0
Gradient:

| Time (min) | % A | % B |
|---|---|---|
| 0.00 | 80.0 | 20.0 |
| 10.00 | 20.0 | 80.0 |
| 12.00 | 20.0 | 80.0 |
| 14.00 | 80.0 | 20.0 |
| 17.00 | 80.0 | 20.0 |

UV detection: channel 1 245 nm; channel 2 254 nm
Injection Volume (ul): 5.00
Sample Solvent: Acetonitrile
MS instrument: Waters Quattro Micro API (or equivalent)

| Polarity ES+ | |
|---|---|
| Capillary (kV) | 3.20 |
| Cone (V) | 20.00 |
| Extractor (V) | 2.00 |
| RF Lens (V) | 0.3 |
| Polarity ES− | |
| Capillary (kV) | 3.20 |
| Cone (V) | 20.00 |
| Extractor (V) | 3.00 |
| RF Lens (V) | 0.3 |
| Source Temperature (° C.) | 110 |
| Desolvation Temperature (° C.) | 210 |
| Cone Gas Flow (L/Hr) | 150 |
| Desolvation Gas Flow (L/Hr) | 650 |
| Scan duration (secs): | 1.00 |
| Interscan delay (secs): | 0.10 |
| Mass range: | 125 to 1000 |

LC/UV/MS—Method 2
LC instrument: Acquity Waters UPLC (or equivalent)
Column: Kinetex 1.7 u XB-C18 100 A 100×2.1 mm (Phenomenex)
Column Temperature (° C.) 50.0
Mobile phases: $HCOONH_4$ 0.025 M pH3 (A); Acetonitrile+0.1% Formic Acid (B)
Flow (ml/min) 0.65 (split in MS 1:3)
Stop Time (mins) 10.0
Gradient:

| Time (min) | % A | % B |
|---|---|---|
| 0.00 | 80.0 | 20.0 |
| 5.50 | 20.0 | 80.0 |
| 7.50 | 20.0 | 80.0 |
| 8.00 | 80.0 | 20.0 |
| 10.00 | 80.0 | 20.0 |

UV detection: wavelength 254 nm
Injection Volume (ul)—2.00
Sample solvents: Acetonitrile
MS instrument: Waters ZQ (or equivalent)

| Polarity ES+ | |
|---|---|
| Capillary (kV) | 3.00 |
| Cone (V) | 20.00 |
| Extractor (V) | 3.00 |
| RF Lens (V) | 1.0 |
| Polarity ES− | |
| Capillary (kV) | 3.00 |
| Cone (V) | 20.00 |
| Extractor (V) | 3.00 |
| RF Lens (V) | 1.0 |
| Source Temperature (° C.) | 110 |
| Desolvation Temperature (° C.) | 210 |
| Cone Gas Flow (L/Hr) | 150 |
| Desolvation Gas Flow (L/Hr) | 650 |
| Mass range: | 100 to 950 |
| Scan time (sec): | 0.32 |

LC/UV/MS—Method 3
LC instrument: Acquity Waters UPLC (or equivalent) interfaced with 2996 PDA detector
Column: Acquity UPLC BEH C18 1.7 um 50×2.1 mm
Column Temperature (° C.) 40.0
Mobile phases: 95:5 H2O:ACN+(0.1% TFA) (A); 5:95 H2O:ACN+(0.1% TFA) (B)
Flow (ml/min) 0.6 (split in MS 1:6)
Stop Time (mins) 8.5
Gradient:

| Time (min) | % A | % B |
|---|---|---|
| 0.00 | 95.0 | 5.0 |
| 0.50 | 95.0 | 5.0 |
| 6.00 | 0.0 | 100.0 |
| 7.00 | 0.0 | 100.0 |
| 7.10 | 95.0 | 5.0 |
| 8.50 | 95.0 | 5.0 |

UV detection: BPI Detection (Start Wavelength nm 210, End Wavelength nm 400,
Sampling Rate spectra/sec=20)
Injection Volume (ul)—1.00
Sample solvents: DMSO:MeOH:ACN ratio 1:3:3
MS instrument: Waters ZQ (or equivalent)

| Polarity ES+ | |
|---|---|
| Capillary (kV) | 3.20 |
| Cone (V) | 25.00 |
| Extractor (V) | 3.00 |
| RF Lens (V) | 0.1 |
| Polarity ES− | |
| Capillary (kV) | 3.00 |
| Cone (V) | 20.00 |
| Extractor (V) | 3.00 |
| RF Lens (V) | 0.3 |
| Source Temperature (° C.) | 150 |
| Desolvation Temperature (° C.) | 350 |
| Cone Gas Flow (L/Hr) | 110 |
| Desolvation Gas Flow (L/Hr) | 800 |
| Mass range: | 60 to 1200 |
| Scan time (sec): | 0.4 |

LC/UV/MS—Method 4
LC instrument: Acquity Waters UPLC (or equivalent) interfaced with 2996 PDA detector
Column: Kinetex C18 1.7 um 50×2.1 mm (Phenomenex)
Column Temperature (° C.): 40.0
Mobile phases: 95:5 H2O:ACN+(0.1% TFA) (A); 5:95 H2O:ACN+(0.1% TFA) (B)
Flow (ml/min): 0.5 (no split in MS)
Stop Time (mins): 4.40

Gradient:

| Time (min) | % A | % B |
|---|---|---|
| 0.00 | 95.0 | 5.0 |
| 0.30 | 95.0 | 5.0 |
| 3.30 | 0.0 | 100.0 |
| 3.90 | 0.0 | 100.0 |
| 4.40 | 95.0 | 5.0 |

UV detection: BPI Detection (Start Wavelength nm 200, End Wavelength nm 400,

Sampling Rate points/sec=20)

Injection Volume (ul): 4.00

Sample Solvent: Acetonitrile

MS instrument: ZQ (or equivalent)

| Polarity ES+ | |
|---|---|
| Capillary (kV) | 3.25 |
| Cone (V) | 27.00 |
| Extractor (V) | 3.00 |
| RF Lens (V) | 0.4 |
| Source Temperature (° C.) | 120 |
| Desolvation Temperature (° C.) | 400 |
| Cone Gas Flow (L/Hr) | 100 |
| Desolvation Gas Flow (L/Hr) | 800 |
| Scan time (sec): | 0.42 |
| Mass range: | 100 to 800 |

Preparative Reverse-Phase HPLC Conditions

Preparative HPLC—Method 1

Waters Micromass ZQ/Sample manager 2767

Photodiode array detector 2996;

Column: XTerra Prep MS C18 Column (5 μm, 19×150 mm, Waters)

Flow rate: 20 ml/min with MS detection

UV wavelength: 254 nm.

Mobile phase: Solvent A (water:MeCN:HCOOH 95:5:0.05); Solvent B (water:MeCN:HCOOH 5:95:0.05)

Gradient:

| Time (min) | % A | % B |
|---|---|---|
| 0.00 | 100.0 | 0.00 |
| 1.00 | 100 | 0.00 |
| 10.00 | 0.00 | 100.0 |
| 11.00 | 0.00 | 100.0 |
| 12.00 | 100.0 | 0.00 |

Preparative HPLC—Method 2

Column: Waters Symmetry Prep C18 17 um 19×300

Flow: 20 ml/min

Mobile phase: 90% $H_2O$, 10% acetonitrile, 0.05% TFA (A); 10% $H_2O$, 90% acetonitrile, 0.05% TFA (B)

Gradient:

| Time (min) | % A | % B |
|---|---|---|
| 0.00 | 95 | 5 |
| 2.5 | 95 | 5 |
| 22 | 0 | 100 |
| 30 | 0 | 100 |

-continued

Preparative HPLC—Method 3

Waters Micromass ZQ/sample manager 2767

Photodiode array detector: 2996

Column: XTERRA Prep MS C18 10 um 19×300

Flow: 20 ml/min

Mobile phases: $H_2O$, 0.1% TFA (A); acetonitrile, 0.1% TFA (B)

Gradient:

| Time (min) | % A | % B |
|---|---|---|
| 0.00 | 90 | 10 |
| 2 | 90 | 10 |
| 23 | 0 | 100 |
| 30 | 0 | 100 |

Conditioning:

| Time (min) | % A | % B |
|---|---|---|
| 30.5 | 90 | 10 |
| 32 | 90 | 10 |

Chiral HLPC:

The enantiomeric purity was determined on Hewlett Packard 1050 HPLC system using Chiracel OD column (5μ 4.6×250 mm), eluting using isocratic mixture of hexane and isopropanol in different ratios as indicated in each specific example.

Flow=0.8 ml/min

UV detection=230 nm.

Optical Rotation (Activity) Determination

Specific rotations of compounds were measured with a Polarimeter Perkin Elmer model 241 or 341.

| | |
|---|---|
| Temperature (° C.) | 25 |
| Path Length (dm) | 1 |
| Wavelength | Sodium D-line (589 nm) |

Experiments requiring microwave heating were performed using a Biotage Initiator Sixty instrument.

Procedures for Salt Formation

Unless otherwise stated, salts described in the experimental section were obtained according to one of the procedures herebelow described:

Formate Salts: when stated in the Salt Name column, compounds containing one or more basic centres and purified by reverse-phase HPLC (Method 1) were obtained as formic acid salts, once clean fractions collected form chromatography were evaporated under reduced pressure without any further basic treatment.

Trifluoroacetate Salts: when stated in the Salt Name column, compounds containing one or more basic centres and purified by reverse-phase HPLC (Method 2 or 3) were obtained as 2,2,2-trifluoroacetic acid salts, once clean fractions collected from chromatography were evaporated under reduced pressure without any further basic treatment.

Hydrochloride Salts: when stated in the Salt Name column, Compounds containing one or more basic centres which underwent Boc deprotection under acidic condition without any further basic work-up, were obtained as hydrochloride salts.

Any other salt was obtained treating the base with a solution of the corresponding acid under conditions know to the skilled person.

The salt stoichiometry was determined, if required, by NMR.

In the procedures that follow, after each starting material, reference to a compound number is typically provided. This is provided merely for assistance to the skilled chemist. The starting material may not necessarily have been prepared from the batch referred to.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

Stereogenic centers which are indicated by an undefined line bond, represent those in compounds which were obtained as single diastereisomers or enantiomers but whose absolute configuration was anyway not determined.

Many of the Compounds described in the following Examples have been prepared from sterochemically pure starting materials, for example 95% ee.

The stereochemistry of the compounds in the Examples, where indicated, has been assigned on the assumption that the absolute configuration at resolved stereogenic centers of staring materials is maintained throughout any subsequent reaction conditions. The absolute configuration for some of the Compounds described has been confirmed as correct by X-ray or VCD (Vibrational Circular Dichroism) analysis of crystalline material.

Diastereoisomeric ratio by LC/UV/MS, when indicated, is estimated to be affected by an experimental error of +1%. Alternatively diastereoisomeric ratio is determined by $^1$H NMR and it is estimated to be >95:5 when a single diastereoisomer was detected using NMR analysis.

Detailed synthetic pathways and procedures for specific examples are outlined in Schemes 9-41 and 46 herebelow. The synthesis of alcohol intermediates listed in Table 12 is described in the listed patent applications, all of which are incorporated herein by reference in their entireties.

TABLE 12

| Entry | Structure | Preparation |
|---|---|---|
| 1 | 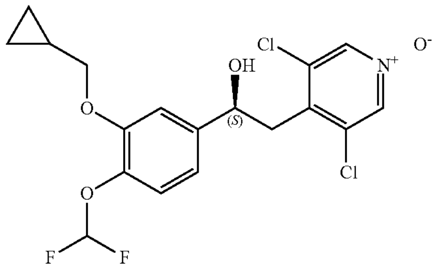 | Prepared as described in patent WO 2010/089107 |
| 156 | 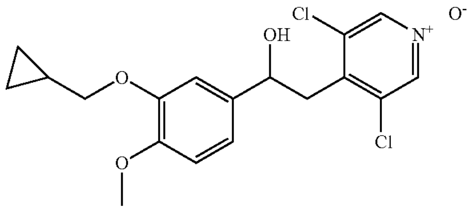 | Prepared as described in patent WO 2009/018909 |
| 157 | 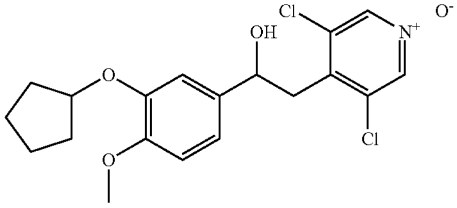 | Prepared as described in patent WO 2009/018909 |
| 158 | 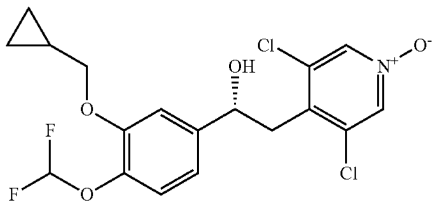 [SMILES: [O-][n+]1cc(Cl)c(C[C@@H](O)c2ccc(OC(F)F)c(OCC3CC3)c2)c(Cl)c1] | Prepared as described in patent WO 2010/089107 |

TABLE 12-continued

| Entry | Structure | Preparation |
|---|---|---|
| 159 | 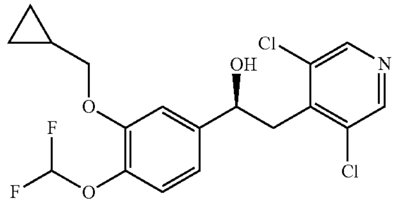 [SMILES: O[C@@H](Cc1c(Cl)cncc1Cl)c1ccc(OC(F)F)c(OCC2CC2)c1] | Prepared as described in patent WO 2010/089107 |
| 160 | 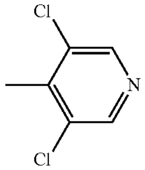 | Prepared as described in patent WO 2009/018909 |

The intermediates used in the procedures described below are commercially available, obtainable by the skilled person through synthetic approaches well known in the art, or obtainable following the synthetic procedures described in the Examples below.

Example 17. (S)-3,5-dichloro-4-(2-(4-(difluoromethoxy)-3-methoxyphenyl)-2-hydroxyethyl)pyridine 1-oxide 164)

Scheme 23.

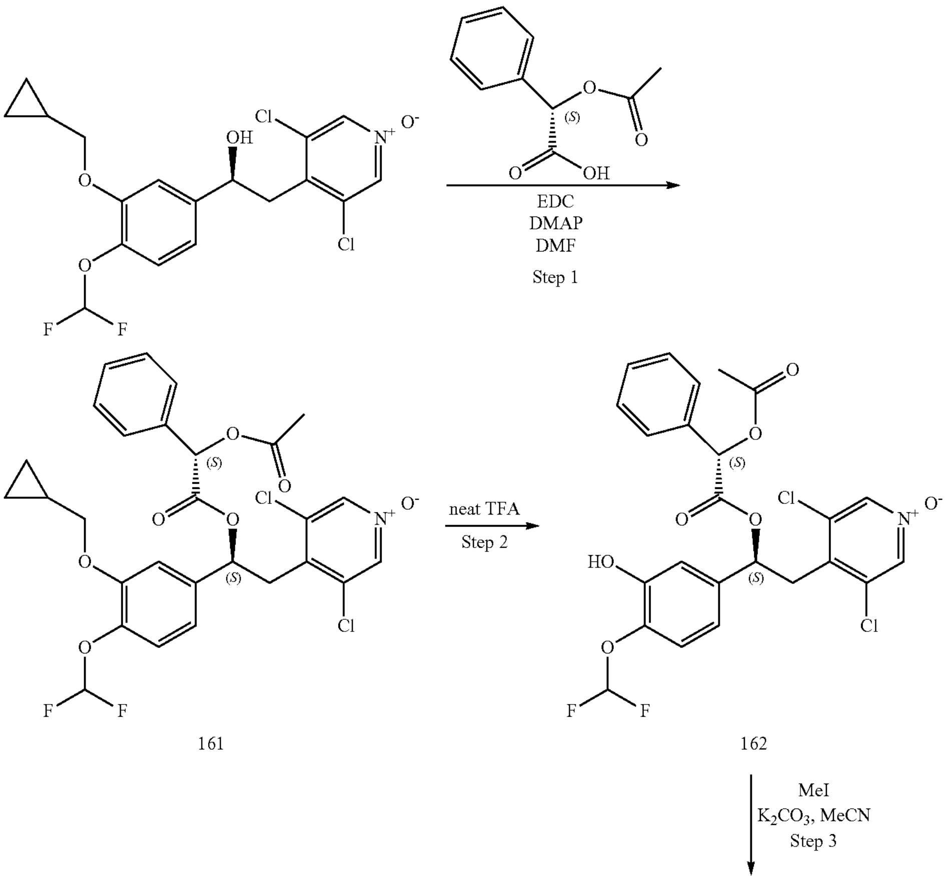

161

162

-continued

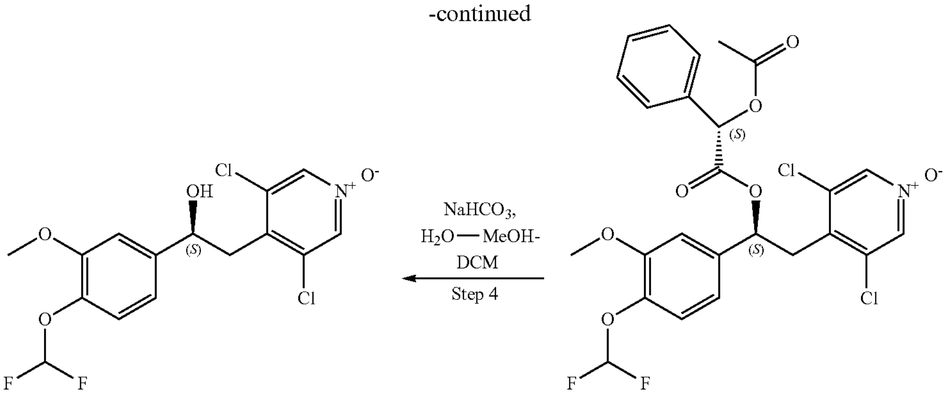

164 163

Step 1: 4-((S)-2-((S)-2-acetoxy-2-phenylacetoxy)-2-(3-(cyclopropyl-methoxy)-4-(difluoromethoxy)phenyl)ethyl)-3,5-dichloropyridine 1-oxide (161)

A mixture of (S)-2-acetoxy-2-phenylacetic acid (0.924 g, 4.76 mmol), (S)-3,5-dichloro-4-(2-(3-(cyclopropyl-methoxy)-4-(difluoromethoxy)phenyl)-2-hydroxyethyl) pyridine 1-oxide (1.0 g, 2.380 mmol), EDC (0.684 g, 3.57 mmol), and DMAP (0.436 g, 3.57 mmol) in DCM (150 ml) was stirred at RT for 24 hours. More (S)-2-acetoxy-2-phenylacetic acid (0.350 g, 1.802 mmol), EDC (0.456 g, 2.380 mmol), and DMAP (0.300 g, 2.456 mmol) were added and the stirring was continued for 3 hours to complete conversion. The reaction mixture was washed twice with aqueous 1N HCl and then with aqueous 1M $K_2CO_3$; the organic layer was dried over $Na_2SO_4$ and evaporated to dryness. The residue was triturated with iPrOH (30 ml) and filtered to afford the desired product (1.27 g, 2.129 mmol, 89% yield). MS/ESI$^+$ 596.18 [MH]$^+$ Step 2: 4-((S)-2-((S)-2-acetoxy-2-phenylacetoxy)-2-(4-(difluoromethoxy)-3-hydroxyphenyl)ethyl)-3,5-dichloropyridine 1-oxide (162)

4-((S)-2-((S)-2-acetoxy-2-phenylacetoxy)-2-(3-(cyclopropylmethoxy)-4-(difluoromethoxy)phenyl)ethyl)-3,5-dichloropyridine 1-oxide (1.27 g, 2.129 mmol) was treated with trifluoroacetic acid (15 ml, 195 mmol), and the resulting solution was stirred at RT for 20 hours. The reaction mixture was diluted with DCM and washed twice with water; the organic layer was dried over $Na_2SO_4$ and evaporated to dryness. The residue was purified by chromatography on silica gel (DCM/EtOAc=3:2 to 1:1). The mixed fractions were combined and triturated with a mixture of $iPr_2O/Et_2O$ (10:1). The collected solid was then combined to pure fractions from chromatography to afford the desired compound (1.08 g, 1.991 mmol, 94% yield); MS/ESI$^+$ 542.11 [MH]$^+$ $^1$H NMR (300 MHz, DMSO-d6) δ ppm 8.56 (s, 2H), 7.27-7.50 (m, 5H), 6.98 (d, 1H), 6.81 (d, 1H), 7.00 (t, 1H), 6.54 (dd, 1H), 5.89 (dd, 1H), 5.84 (s, 1H), 3.40 (dd, 1H), 3.18 (dd, 1H), 2.13 (s, 3H)

Step 3: 4-((S)-2-((S)-2-acetoxy-2-phenylacetoxy)-2-(4-(difluoromethoxy)-3-methoxyphenyl)ethyl)-3,5-dichloropyridine 1-oxide (163)

A suspension of 4-((S)-2-((S)-2-acetoxy-2-phenylacetoxy)-2-(4-(difluoromethoxy)-3-hydroxyphenyl)ethyl)-3,5-dichloropyridine 1-oxide (1.080 g, 1.991 mmol), methyl iodide (0.162 ml, 2.59 mmol), and potassium carbonate (0.550 g, 3.98 mmol) in $CH_3CN$ (40 ml) was vigorously stirred at RT for 20 hours. The reaction mixture was partitioned between DCM and water and the organic layer was dried over $Na_2SO_4$. The solvent was removed under vacuum to afford the desired compound (0.984 g, 1.769 mmol, 89% yield). MS/ESI$^+$ 556.17 [MH]$^+$. The raw compound was used without further purification.

Step 4: (S)-3,5-dichloro-4-(2-(4-(difluoromethoxy)-3-methoxyphenyl)-2-hydroxyethyl)pyridine 1-oxide (164)

4-((S)-2-((S)-2-acetoxy-2-phenylacetoxy)-2-(4-(difluoromethoxy)-3-methoxyphenyl)ethyl)-3,5-dichloropyridine 1-oxide (984 mg, 1.769 mmol) was dissolved in a mixture of MeOH (50 ml) and DCM (10 ml). Aqueous sat. $NaHCO_3$ solution (10 ml, 11.00 mmol) was added, and the resulting suspension was stirred at RT for 2 hours. The reaction mixture was partitioned between water and DCM; the organic layer was dried over $Na_2SO_4$ and evaporated to dryness to afford the desired compound (650 mg, 1.71 mmol, 97% yield). MS/ESI$^+$ 380.03 [MH]$^+$.

The compound listed in Table 13 was prepared with an analogous procedure to that described in Scheme 23, by using suitable alkylation reagent and performing Step 3 at 65° C.

TABLE 13

| Entry | Structure | MS/ESI$^+$ [MH] |
|---|---|---|
| 165 | 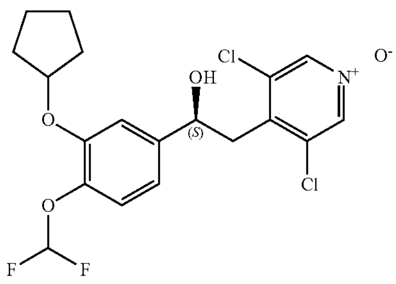 | 610.24 |

Example 18. Synthesis of (S)-3,5-dichloro-4-(2-(3,4-dimethoxyphenyl)-2-hydroxyethyl)pyridine 1-oxide (170)
Scheme 24
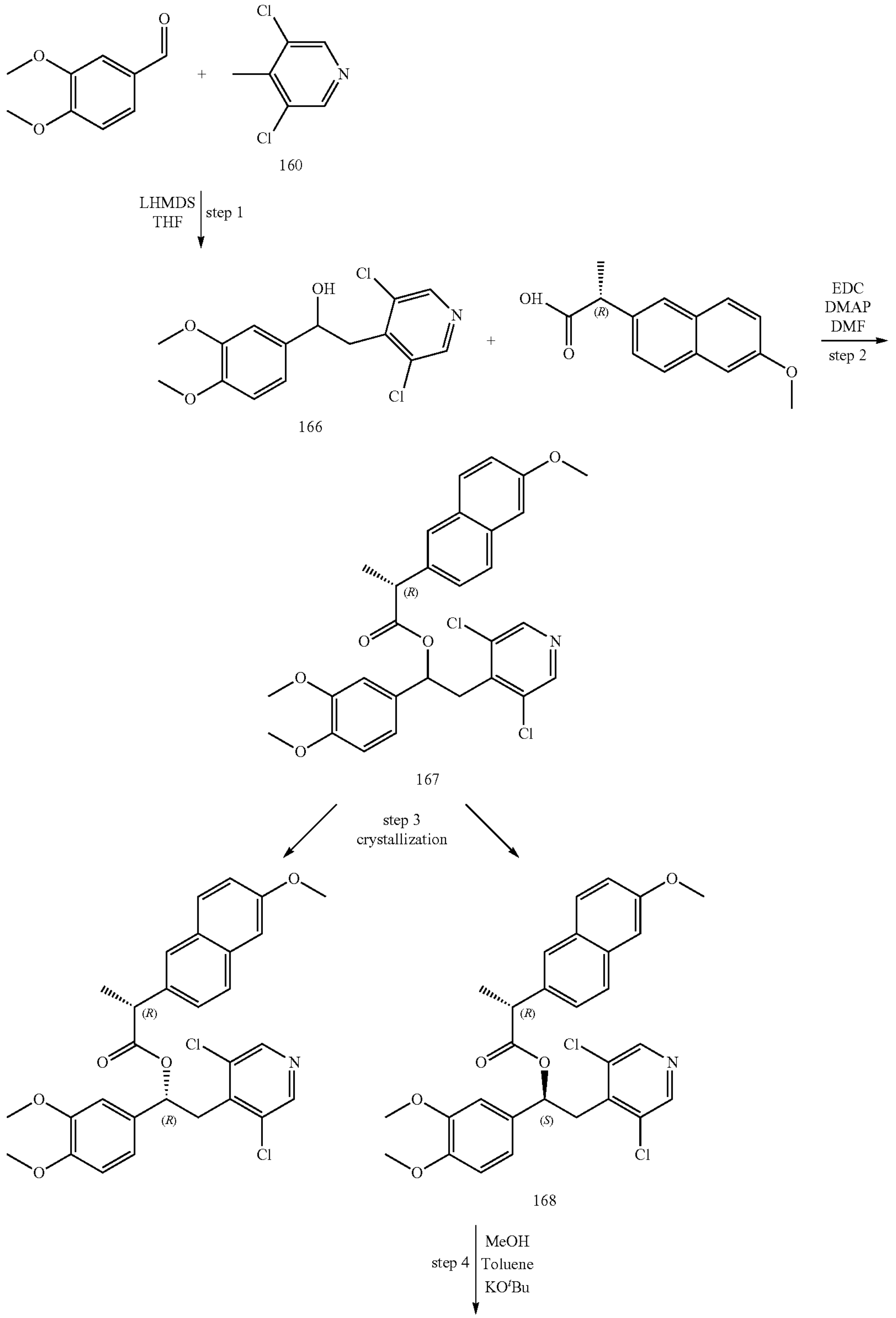

-continued

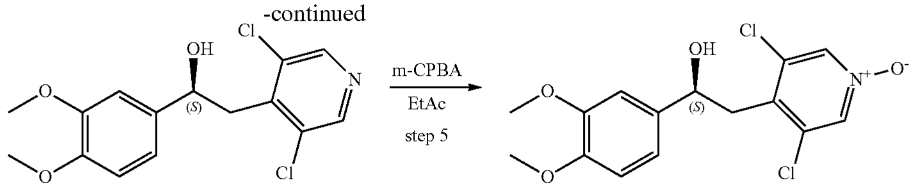

169 170

Step 1: Synthesis of 2-(3,5-dichloropyridin-4-yl)-1-(3,4-dimethoxyphenyl)ethanol (166)

3,5-dichloro-4-methylpyridine (160) (54 g, 331 mmol) was dissolved in dry THF (480 mL) under anargon atmosphere and it was cooled at −78° C. in dry-ice/acetone bath. LHMDS 1N THF solution (331 ml, 331 mmol) was added drop-wise by keeping the temperature at −78°. The mixture was stirred at −78° for 1 hour. After that, a solution of 3,4-dimethoxybenzaldehyde (50 g, 301 mmol) in dry THF (120 ml) was added drop-wise by keeping the temperature at −78° C. When the addition was completed, the mixture was allowed to warm at RT.

The reaction was poured in ice and water (1 L), and the mixture was stirred until a copious precipitate formed. The solid was filtered, and dissolved in ethyl acetate (500 ml), dried over $Na_2SO_4$ and the solvent evaporated under vacuum. The crude was crystallized in $CHCl_3$/hexane. The precipitate was filtered, washed with hexane and dried under vacuum at 40° C. for 8 hours to give 55 g (yield 45%). The mother liquor solution was evaporated under vacuum at 40° C., dissolved in ethyl acetate (200 ml) and extracted with 200 ml of water. The organic solution was dried over $Na_2SO_4$ and the solvent evaporated under vacuum at 40° C. The crude was crystallized in $CHCl_3$/hexane, and additional 15 g of the desired product (166) were obtained (overall yield 70%).

Step 2: Synthesis of ((R)-2-(3,5-dichloropyridin-4-yl)-1-(3,4-dimethoxyphenyl)ethyl)2-(6-methoxynaphthalen-2-yl)propanoate (167)

Intermediate 166 (50 g, 152 mmol), (R)-2-(6-methoxynaphthalen-2-yl)propanoic acid (38.6 g, 168 mmol), DMAP (20.5 g, 168 mmol), and EDC (43.8 g, 229 mmol) were dissolved in DMF (300 ml), and the reaction mixture was stirred at RT for 2 hours. After that time water (500 ml) was added, and the solution stirred upon precipitation occurs. The solid was filtered and dissolved in DCM (500 ml). The organic solution was washed with aqueous HCl 1N (2×500 ml), saturated aqueous $NaHCO_3$ solution (500 ml) and dried over $Na_2SO_4$. The solvent was evaporated under vacuum and the solid residue sonicated in EtOH (300 ml) and triturated for 1 hour. The resulting precipitate was collected by filtration and dried under vacuum at 40° C. for 4 hours to give 79 g (yield 99%) of compound 167, as diastereoisomeric mixture.

Step 3: Synthesis of (R)—((S)-2-(3,5-dichloropyridin-4-yl)-1-(3,4-dimethoxyphenyl)ethyl)2-(6-methoxynaphthalen-2-yl)propanoate (168)

Intermediate 167 (79 g, 146 mmol) was dissolved in $CHCl_3$ (100 ml), and MeOH (30 ml) was slowly added up to persistent opalescence and the mixture left at RT for 2 hours. The solid formed was collected by filtration and re-crystallized by $CHCl_3$/MeOH (70 ml/20 ml) solvent system to obtain 35 g of compound 168 (yield 88%, ee 98%). Chiral HPLC analysis $R_t$=42.33 min (fast isomer); eluent: hexane: isopropanol 97:3

$^1H$ NMR (600 MHz, CHLOROFORM-d) δ ppm 8.04 (s, 2H), 7.67 (d, J=8.79 Hz, 1H), 7.58 (d, J=8.52 Hz, 1H), 7.53 (m, 1H), 7.12-7.20 (m, 3H), 6.95 (dd, J=8.24, 1.92 Hz, 1H), 6.78-6.88 (m, 2H), 6.14 (dd, J=10.44, 4.12 Hz, 1H), 3.95 (s, 3H), 3.88 (s, 3H), 3.78-3.81 (m, 4H), 3.55 (dd, J=13.73, 10.44 Hz, 1H), 3.14 (dd, J=13.60, 4.26 Hz, 1H), 1.44 (d, J=7.14 Hz, 3H).

Step 4: Synthesis of (S)-2-(3,5-dichloropyridin-4-yl)-1-(3,4-dimethoxyphenyl)ethanol (169)

Intermediate 168 (30 g, 56 mmol) was dissolved in MeOH, and toluene was slowly added. Potassium terbutoxide was slowly added to the suspension. The mixture was stirred for 24 hours at RT. The reaction was diluted with water (500 ml), and the aqueous mixture was extracted with $CHCl_3$ (500 ml). The organic layer was dried over $Na_2SO_4$ and the solvent was evaporated under vacuum. The residue was crystallized from $CHCl_3$ (100 ml) and hexane (20 ml, till persistent opalescence). The mother liquor was concentrated and recrystallized in the same way giving a second crop of desired compound. Totally 16 g of compound 169 (yield 87%) were obtained.

Chiral HPLC analysis $R_t$=58.03 min; eluent: hexane: isopropanol 95:5. $[\alpha]_D^{20}$=+10.21 (c=0.506, methanol)

$^1H$ NMR (400 MHz, acetone) δ ppm 8.47 (s, 2H), 6.96-7.15 (m, 1H), 6.87 (m, 2H), 4.93-5.21 (m, 1H), 4.50 (d, J=3.97 Hz, 1H), 3.78 (s, 6H), 3.44 (dd, J=12.79, 8.38 Hz, 1H), 3.22 (dd, J=13.01, 5.51 Hz, 1H).

MS/ESI$^+$ $[MH]^+$: 328.19

Step 5: Synthesis of (S)-3,5-dichloro-4-(2-(3,4-dimethoxyphenyl)-2-hydroxyethyl)pyridine 1-oxide (170)

Compound 169 (4 g, 12 mmol) was dissolved in ethyl acetate, and m-CPB acid was added to the solution. The mixture was stirred at RT for 5 hours. The formed solid was collected by filtration, washed with ethyl acetate and dried under vacuum to give 1.72 g of title compound (yield 41%). Chiral HPLC analysis $R_t$=22.16 min; eluent: hexane:isopropanol 6:4. $[\alpha]_D^{20}$=+68.91 (c=0.253, Methanol/$CHCl_3$ 1:1). MS/ESI$^+$ $[MH]^+$: 344.19

$^1H$ NMR (400 MHz, CHLOROFORM-d) δ ppm 8.15 (s, 2H), 6.99 (m, 1H), 6.79-6.88 (m, 2H), 5.03 (dd, J=8.50, 5.32 Hz, 1H), 3.75-3.98 (m, 6H), 3.42 (dd, J=13.57, 8.56 Hz, 1H), 3.19 (dd, J=13.51, 5.32 Hz, 1H), 2.06-2.15 (m, 1H).

Example 36. Synthesis of 3,5-dichloro-4-(2-(2,2-dimethylbenzo[d][1,3]dioxol-5-yl)-2-hydroxyethyl) pyridine 1-oxide (172)

Scheme 25

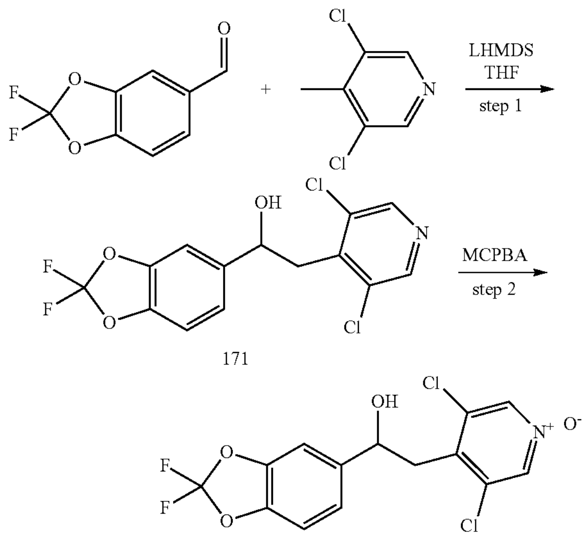

171

172

Step 1: Synthesis of 2-(3,5-dichloropyridin-4-yl)-1-(2,2-difluorobenzo[d][1,3]dioxol-5-yl)ethanol (171)

3,5-dichloro-4-methylpyridine (166)(4.37 g, 0.016 mol) was dissolved in dry THF (40 mL) under an argon atmosphere and it was cooled at −78° C. in dry-ice/acetone bath. LHMDS 1N THF solution (28 ml, 28 mmol) was added drop-wise by keeping the temperature at −78°. The mixture was stirred at −78° for 1 hour. After that, a solution of 2,3-difluoro-3,4-benzodioxolocarboxaldheyde (5 g, 0.026 mol) in dry THF (10 ml) was added drop-wise by keeping the temperature at −78° C. When the addition was completed, the mixture was allowed to warm at RT. The reaction was poured in ice and water, and the aqueous phase extracted with ethyl acetate (3×). The combined organic phases were dried over $Na_2SO_4$ and the solvent evaporated under vacuum. The crude was crystallized in petroleum ether/hexane 1/1. The precipitate was filtered, washed with hexane and dried under vacuum at 40° C. for 8 h to give 6.4 g (yield 45%).

MS/ESI$^+$ 349.14 [MH]$^+$; $^1$H NMR (200 MHz, CHLOROFORM-d) δ ppm 8.71 (s, 2H), 7.48-7.68 (m, 2H), 6.85-7.07 (m, 1H), 4.61 (m, 1H), 4.11-4.44 (m, 2H).

Step 2: Synthesis of 3,5-dichloro-4-(2-(2,2-dimethylbenzo[d][1,3]dioxol-5-yl)-2-hydroxyethyl)pyridine 1-oxide (172)

2-(3,5-dichloropyridin-4-yl)-1-(2,2-difluorobenzo[d][1,3]dioxol-5-yl)ethanol (2 g, 5.74 mmol) was dissolved in EtOAc (40 ml), and the solution was cooled to 0° C. m-CPBA (5.29 g, 22.98 mmol) was added, and the resulting mixture was stirred at RT for 24 hours. The reaction mixture was cooled to 0° C., and the white solid precipitate was filtered and washed twice with cold DCM to afford the desired product (1.738 g, 4.77 mmol, 83%); MS/ESI$^+$ 364.03 [MH]$^+$ Example 19. Synthesis of 3,5-dichloro-4-(2-hydroxy-2-(4-methoxyspiro[benzo[d][1,3]dioxole-2,1'-cyclopentane]-7-yl)ethyl)pyridine 1-oxide (174)

Scheme 26

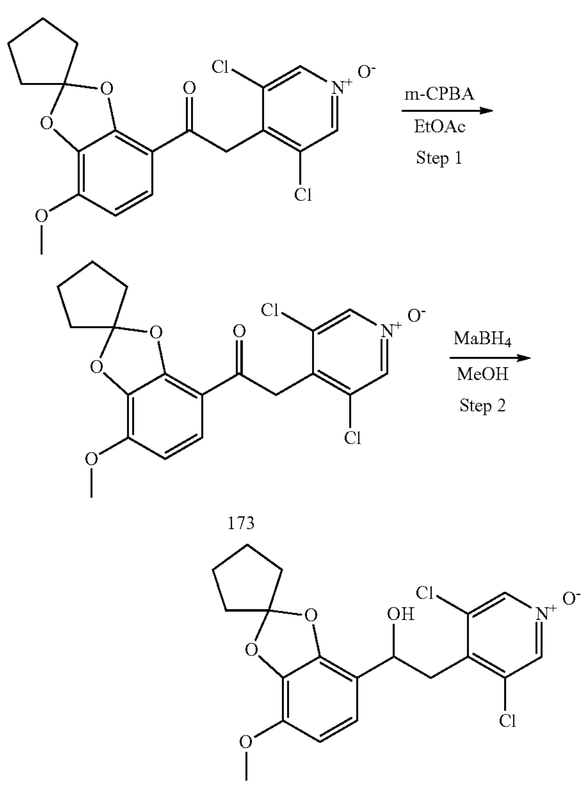

173

174

Step 1: 3,5-dichloro-4-(2-(4-methoxyspiro[benzo[dd][1,3]dioxole-2,1'-cyclopentane]-7-yl)-2-oxoethyl)pyridine 1-oxide (173)

To a solution of 2-(3,5-dichloropyridin-4-yl)-1-(4-methoxyspiro[benzo[d][1,3]dioxole-2,1'-cyclopentane]-7-yl)ethanone, (prepared as described in EP 1 535 920, which is incorporated herein by reference in its entirety, 4.75 g, 12.05 mmol) in EtOAc (125 ml) cooled at 0° C., m-CPBA (11.09 g, 48.2 mmol) was added and the reaction mixture was stirred at RT for 24 hours. More m-CPBA (5.54 g, 24.10 mmol) was added, and the stirring was continued for additional 24 hours. The mixture was washed several times with aqueous 1M $K_2CO_3$ and the organic layer was dried over $Na_2SO_4$ and evaporated to dryness. The residue was purified by chromatography on silica gel, (DCM/EtOAc=3/1 to 1/2) to afford 3,5-dichloro-4-(2-(4-methoxyspiro[benzo[d][1,3]dioxole-2,1'-cyclopentane]-7-yl)-2-oxoethyl)pyridine 1-oxide (2.14 g, 5.22 mmol, 43.3% yield); MS/ESI$^+$ 410.10 [MH]$^+$.

Step 2: 3,5-dichloro-4-(2-hydroxy-2-(4-methoxyspiro[benzo[d][1,3]dioxole-2,1'-cyclopentane]-7-yl)ethyl)pyridine 1-oxide (174)

To a solution of 3,5-dichloro-4-(2-(4-methoxyspiro[benzo[d][1,3]dioxole-2,1'-cyclopentane]-7-yl)-2-oxoethyl)pyridine 1-oxide (2.14 g, 5.22 mmol) in MeOH (100 ml), solid sodium borohydride (0.197 g, 5.22 mmol) was added portion-wise, and the mixture was stirred at RT overnight. Additional sodium borohydride (0.394 g, 10.44 mmol) was added and over 2 hours, and the stirring was continued for further 12 hours. The mixture was concentrated under vacuum, diluted with EtOAc, and washed twice with aqueous 1N NaOH. The organic layer was dried over $Na_2SO_4$, the solvent was removed under reduced pressure, and the residue was purified by chromatography on silica gel (EtOAc) to afford 3,5-dichloro-4-(2-hydroxy-2-(4-methoxyspiro[benzo[d][1,3]dioxole-2,1'-cyclopentane]-7-yl)ethyl)pyridine 1-oxide (650 mg, 1.577 mmol, 30.2% yield); MS/ESI$^+$ 412.10 [MH]$^+$.

Example 1. Synthesis of 3,5-dichloro-4-((S)-2-(3-(cyclopropylmethoxy)-4-(difluoromethoxy)phenyl)-2-((S)-pyrrolidine-2 carbonyloxy)ethyl)pyridine 1-oxide hydrochloride (3)

Scheme 9

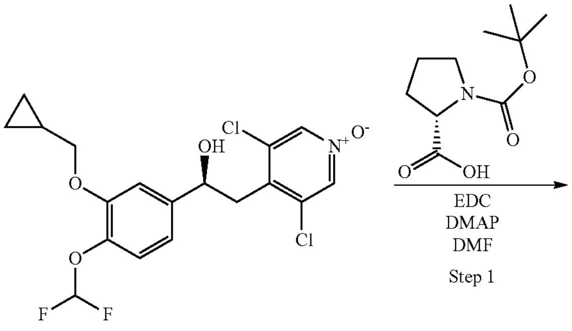

1

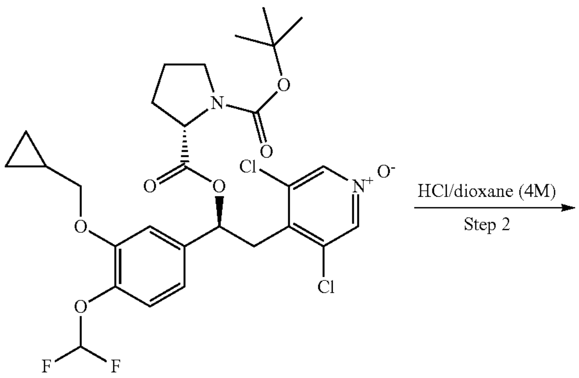

2

-continued

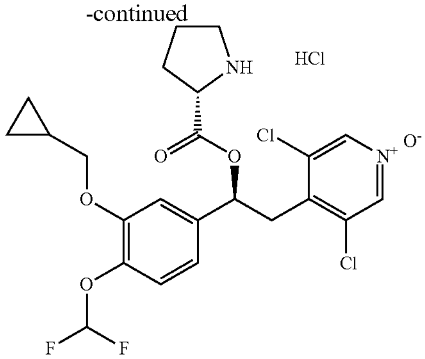

3

Step 1: 4-((S)-2-((S)-1-(tert-butoxycarbonyl)pyrrolidine-2-carbonyloxy)-2-(3-(cyclopropylmethoxy)-4-(difluoromethoxy)phenyl)ethyl)-3,5-dichloropyridine 1-oxide (2)

(S)-3,5-dichloro-4-(2-(3-(cyclopropylmethoxy)-4-(difluoromethoxy)phenyl)-2-hydroxyethyl)pyridine 1-oxide (1) (550 mg, 1.309 mmol), (S)-1-(tert-butoxycarbonyl)pyrrolidine-2-carboxylic acid (282 mg, 1.309 mmol), EDC (251 mg, 1.309 mmol), and DMAP (160 mg, 1.309 mmol) were dissolved in DMF (5 ml). The reaction was stirred at RT for 48 hours to achieve completion. After that time, the reaction was quenched with HCl 1M and extracted with EtOAc. The organic extract was washed with HCl 1M (x3) and with $K_2CO_3$ 5% (x3) before being dried over $Na_2SO_4$ and concentrated under vacuum to yield 800 mg of desired product (yield 99%). MS/ESI$^+$ 617.16 [MH]$^+$ Step 2: 3,5-dichloro-4-((S)-2-(3-(cyclopropylmethoxy)-4-(difluoromethoxy)phenyl)-2-((S)-pyrrolidine-2-carbonyloxy)ethyl)pyridine 1-oxide hydrochloride (3)

4-((S)-2-((S)-1-(tert-butoxycarbonyl)pyrrolidine-2-carbonyloxy)-2-(3-(cyclopropylmethoxy)-4-(difluoromethoxy)phenyl)ethyl)-3,5-dichloropyridine 1-oxide (2) (300 mg, 0.486 mmol) was dissolved in Dioxane/HCl (4M, 2 ml) and stirred at RT for 8 hours. After that time, the solvent was removed on a rotavapour under reduced pressure and dried in a vacuum oven overnight to yield the wanted product as an hydrochloride salt (200 mg; yield 80%).

MS/ESI$^+$ 517.2 [MH]$^+$; $t_R$/min (Methods 1)=3.75; Diastereomeric Ratio=>99:1; $[\alpha_D]$=−32.80 (c=0.25; $CHCl_3$)

$^1$H NMR (400 MHz, METHANOL-$d_4$) δ ppm 8.49 (s, 2H), 7.18 (d, J=7.94 Hz, 1H), 7.11 (d, J=1.76 Hz, 1H), 7.04 (d, J=1.76 Hz, 1H), 6.78 (t, J=75.00 Hz, 1H), 6.10-6.17 (m, 1H), 4.38-4.51 (m, 1H), 3.85-3.99 (m, 2H), 3.66 (m, 2H), 3.39-3.51 (m, 1H), 2.40-2.60 (m, 1H), 1.89-2.17 (m, 4H), 1.15-1.36 (m, 1H), 0.64 (dd, J=7.94, 1.32 Hz, 2H), 0.33-0.47 (m, 2H).

The compounds listed in Table 2 were prepared with an analogous procedure to that described in Example 1, by using suitable starting materials.

Compounds obtained as free bases underwent a basic work-up in place of removal of the solvent under reduced pressure described above (Ex: $NaHCO_3$ saturated solution), followed by extraction with polar organic solvent (Ex:

AcOEt) in order to remove the salification with HCl, which spontaneously occurs performing Step 2 (Scheme 9).

Compound 6, 7, 181, and 183 were obtained by reacting its appropriate Boc-protected precursor with AcOEt/HCl (5M), followed by filtration at room temperature of the hydrochloride salt, which spontaneously precipitates from the reaction mixture.

Compounds 177, 178, and 179 were obtained by performing Step 2 with HCl in EtOAc and removing the solvent without heating.

TABLE 1

| | | | HPLC-MS characterization | | | | |
|---|---|---|---|---|---|---|---|
| Entry | Structure | SALT NAME | MS/ESI$^+$ [MH]$^+$ | $t_R$/min Methods 1 or 2 | Diastereomeric Ratio | $^1$H NMR | $[\alpha]_D$ |
| 4 | 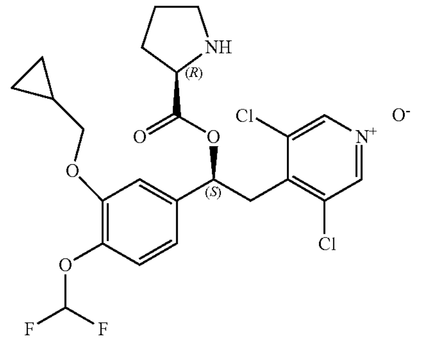 | Free base | 517.2 | | | | |
| 5 | 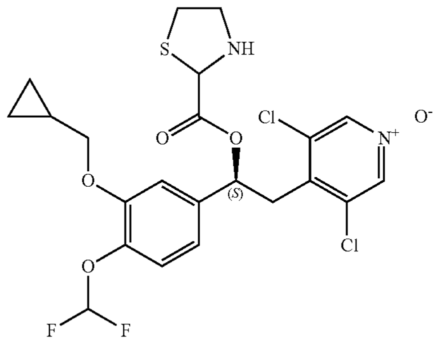 | Free base | 535.2 | 3.19; 3.26 (2) | 40:60 | | |
| 6 | 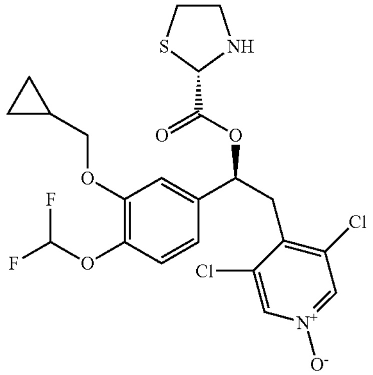 [SMILES: O=C(O[C@@H](Cc1c(Cl)c[n+]([O-])cc1Cl)c1ccc(OC(F)F)c(OCC2CC2)c1)[C@H]1NCCS1] | hydrochloride | 535.2 | 3.26 (2) | 99:1 | $^1$H NMR (400 MHz, DMSO-$d_6$) δ ppm 8.57 (s, 2 H), 7.19 (d, J = 7.94 Hz, 1 H), 7.12 (d, J = 1.76 Hz, 1 H), 7.08 (t, J = 75.00 Hz, 1 H), 6.93-7.00 (m, 1 H), 5.89=-5.98 (m, 1 H), 5.12 (s, 1 H), 3.91 (d, J = 7.06 Hz, 2 H), 3.37-3.47 (m, 1 H), 3.10-3.31 (m, 3 H), 2.77-2.93 (m, 2 H), 1.05-1.36 (m, 1 H), 0.51-0.63 (m, 2 H), 0.34 (d, J = 4.85 Hz, 2 H). | |

TABLE 1-continued
| | | | HPLC-MS characterization | | | | |
|---|---|---|---|---|---|---|---|
| Entry | Structure | SALT NAME | MS/ESI$^+$ $[MH]^+$ | $t_R$/min Methods 1 or 2 | Diastereo-meric Ratio | $^1$H NMR | $[\alpha]_D$ |
| 7 | 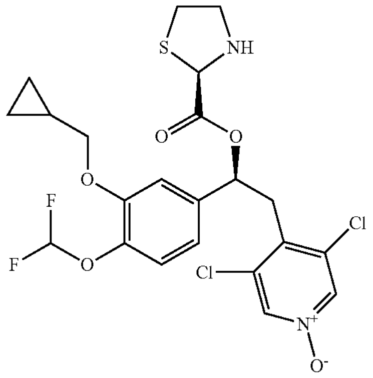 [SMILES: O=C(O[C@@H](Cc1c(Cl)c[n+]([O-])cc1Cl)c1ccc(OC(F)F)c(OCC2CC2)c1)[C@@H]1NCCS1] | Hydro-chloride | 535.2 | | | | |
| 8 | 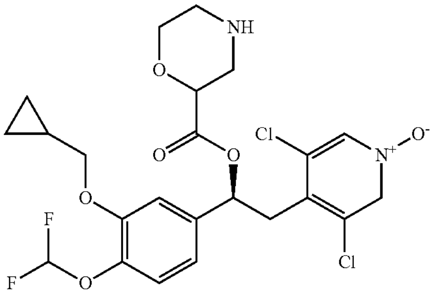 [SMILES: O=C(O[C@@H](CC1=C(Cl)C[NH+]([O-])C=C1Cl)c1ccc(OC(F)F)c(OCC2CC2)c1)C1CNCCO1] | Free base | 533.2 | 1.86; 1.90 (2) | 64:36 | | |
| 9 | 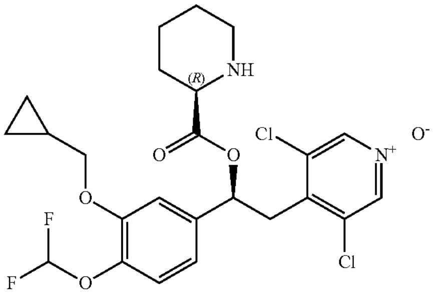 | hydro-chloride | 531.2 | 2.03 (2) | 97:3 | $^1$H NMR (400 MHz, DMSO-$d_6$) δ ppm 8.96-9.18 (bs, 1 H), 8.80-8.96 (bs, 1 H), 8.62 (s, 2 H), 7.22 (d, J = 8.38 Hz, 1 H), 7.18 (d, J = 1.76 Hz, 1 H), 7.02-7.10 (m, 2 H), 6.12 (dd, J = 9.48, 4.63 Hz, 1 H), 4.16 (m, 1 H), 3.94 (dd, J = 7.06, 1.32 Hz, 2 H), 3.49-3.62 (m, 1 H), 3.17-3.34 (m, 3 H), 2.76-2.95 (m, 1 H), 2.04-2.17 (m, 1 H), 1.69 (d, J = 4.85 Hz, 2 H), 1.38-1.60 (m, 2 H), 1.23 (d, J = 3.53 Hz, 1 H), 0.51-0.66 (m, 2 H), 0.31-0.45 (m, 2 H). | −10.83 (c = 0.48; $CHCl_3$) |
| 10 | 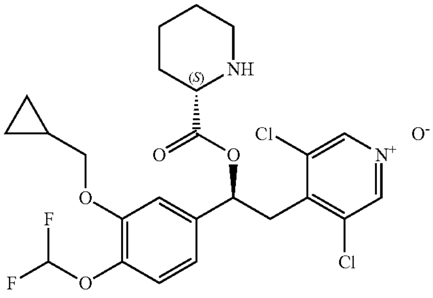 | hydro-chloride | 531.2 | | | | |

TABLE 1-continued
| Entry | Structure | SALT NAME | HPLC-MS characterization MS/ESI+ [MH]+ | $t_R$/min Methods 1 or 2 | Diastereo-meric Ratio | $^1H$ NMR | $[\alpha]_D$ |
|---|---|---|---|---|---|---|---|
| 11 | 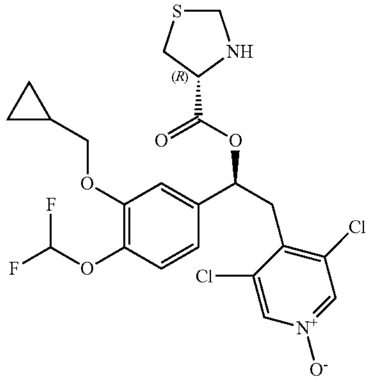 | Free base | 535.2 | 3.19 (2) | 99:1 | $^1H$ NMR (400 MHz, DMSO-$d_6$) δ ppm 8.56 (s, 2 H), 7.18 (d, J = 7.94 Hz, 1 H), 7.04-7.13 (m, 2 H), 6.97 (dd, J = 8.16, 1.54 Hz, 1 H), 5.88-6.03 (m, 1 H), 3.97-4.15 (m, 3 H), 3.90 (d, J = 7.06 Hz, 2 H), 3.43 (dd, J = 14.11, 9.26 Hz, 1 H), 3.24 (dd, J = 14.11, 4.85 Hz, 1 H), 3.08 (dd, J = 10.14, 7.06 Hz, 1 H), 2.80 (dd, J = 10.14, 5.73 Hz, 1 H), 1.14-1.28 (m, 1 H), 0.48-0.67 (m, 2 H), 0.26-0.46 (m, 2 H). | −45.77 (c = 0.48; $CHCl_3$ |
| 12 | 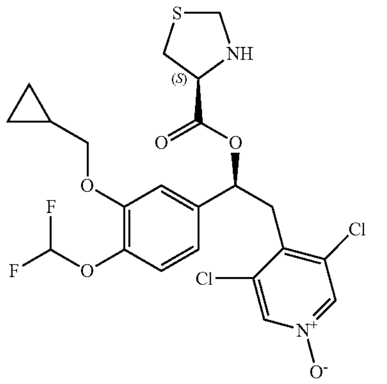 | hydro-chloride | 535.2 | | | | |
| 13 | 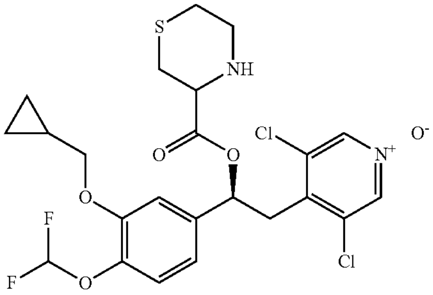 | Free base | 548.6 | | | | |

TABLE 1-continued

| Entry | Structure | SALT NAME | HPLC-MS characterization MS/ESI⁺ [MH]⁺ | $t_R$/min Methods 1 or 2 | Diastereo-meric Ratio | $^1$H NMR | [α]$_D$ |
|---|---|---|---|---|---|---|---|
| 14 | 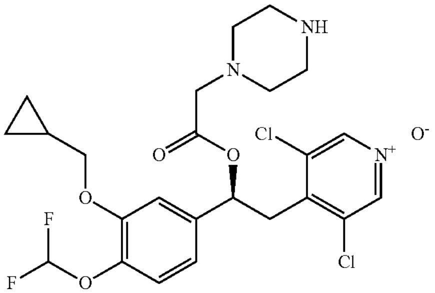 | Bis hydro-chloride | 545.1 | | | 1H NMR (400 MHz, DMSO-$d_6$) δ ppm 8.89 (bs, 3 H), 8.58 (s, 2 H), 7.19 (d, J = 7.94 Hz, 1 H), 7.07-7.14 (m, 2 H), 6.98 (dd, J = 8.38, 1.76 Hz, 1 H), 6.00 (dd, J = 9.04, 4.63 Hz, 1 H), 3.90-3.92 (d, 2H), 3.45 (dd, J = 14.11, 9.26 Hz, 1 H), 3.34 (s, 2H), 3.25 (dd, J = 14.11, 4.85 Hz, 1 H), 3.09 (m, 4 H), 2.80 (m, 4 H), 1.12-1.32 (m, 1 H), 0.52-0.66 (m, 2 H), 0.27-0.44 (m, 2 H) | |
| 175 | 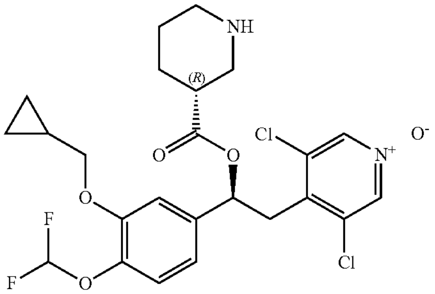 | hydro-chloride | 531.2 | 1.86 (Method 4) | >95:5 $^1$H NMR | $^1$H NMR (300 MHz, DMSO-$d_6$) δ ppm 8.87 (br. s., 2 H), 8.56 (s, 2 H), 7.19 (d, 1 H), 7.09 (d, 1 H), 6.97 (dd, 1 H), 7.07 (t, 1 H), 5.94 (dd, 1 H), 3.91 (d, 2 H), 3.46 (dd, 1 H), 3.28-3.38 (m, 1 H), 3.23 (dd, 1 H), 3.09-3.19 (m, 1 H), 2.69-3.00 (m, 3 H), 1.90-2.11 (m, 1 H), 1.41-1.84 (m, 3 H), 1.09-1.30 (m, 1 H), 0.49-0.65 (m, 2 H), 0.30-0.42 (m, 2 H) | |
| 176 | 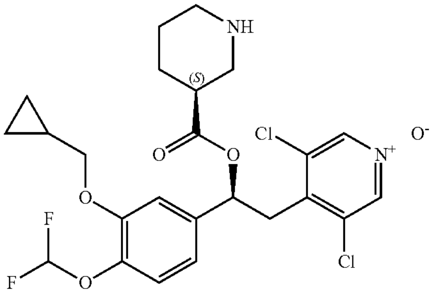 | hydro-chloride | 531.2 | 1.84 (Method 4) | >95:5 $^1$H NMR | $^1$H NMR (300 MHz, DMSO-$d_6$) δ ppm 8.97-9.15 (m, 1 H), 8.82-8.97 (m, 1 H), 8.57 (s, 2 H), 7.20 (d, 1 H), 7.11 (d, 1 H), 7.00 (dd, 1 H), 7.08 (t, 1 H), 5.99 (dd, 1 H), 3.93 (d, 2 H), 3.49 (dd, 1 H), 3.28-3.37 (m, 1 H), 3.22 (dd, 1 H), 3.07-3.18 (m, 1 H), 2.69-3.00 (m, 3 H), 1.85-2.06 (m, 1 H), 1.60-1.85 (m, 2 H), 1.37-1.60 (m, 1 H), 1.01-1.32 (m, 1 H), 0.47-0.74 (m, 2 H), 0.19-0.47 (m, 2 H) | |

TABLE 1-continued

| Entry | Structure | SALT NAME | HPLC-MS characterization MS/ESI+ [MH]+ | $t_R$/min Methods 1 or 2 | Diastereo-meric Ratio | $^1$H NMR | [α]$_D$ |
|---|---|---|---|---|---|---|---|
| 177 | 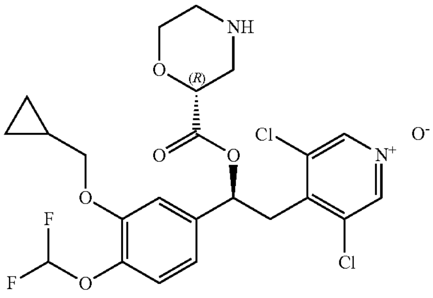 | hydro-chloride | 533.1 | 1.78 (Method 4) | >95:5 $^1$H NMR | $^1$H NMR (300 MHz, DMSO-$d_6$) δ ppm 9.45 (br. s., 1 H), 9.35 (br. s., 1 H), 8.55 (s, 2 H), 7.19 (d, 1 H), 7.10 (d, 1 H), 6.98 (dd, 1 H), 7.08 (t, 1 H), 5.99 (dd, 1 H), 4.52 (dd, 1 H), 3.98 (ddd, 1 H), 3.91 (d, 2 H), 3.79 (ddd, 1 H), 3.50 (dd, 1 H), 3.35-3.44 (m, 1 H), 3.25 (dd, 1 H), 2.88-3.21 (m, 3 H), 1.07-1.31 (m, 1 H), 0.47-0.77 (m, 2 H), 0.15-0.45 (m, 2 H) | |
| 178 | 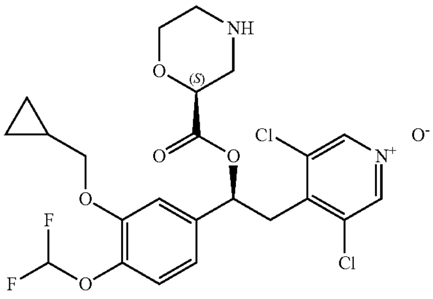 | hydro-chloride | 533.0 | 1.78 (Method 4) | >95:5 $^1$H NMR | $^1$H NMR (300 MHz, DMSO-$d_6$) δ ppm 9.65-10.08 (m, 1 H), 9.36-9.65 (m, 1 H), 8.55 (s, 2 H), 7.19 (d, 1 H), 7.11 (d, 1 H), 6.98 (dd, 1 H), 7.08 (t, 1 H), 5.98 (dd, 1 H), 4.53 (dd, 1 H), 3.96-4.07 (m, 1 H), 3.92 (d, 2 H), 3.82 (ddd, 1 H), 3.49 (dd, 1 H), 3.38-3.47 (m, 1 H), 3.26 (dd, 1 H), 3.10-3.21 (m, 1 H), 2.87-3.11 (m, 2 H), 1.12-1.32 (m, 1 H), 0.49-0.68 (m, 2 H), 0.15-0.49 (m, 2 H) | |
| 179 | 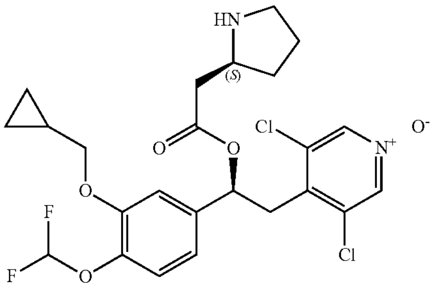 | hydro-chloride | 531.11 | | | | |
| 180 | 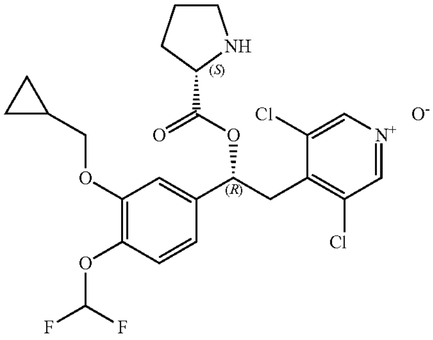 | Free base | 517.2 | 1.91 (2) | 98:2 | | |

TABLE 1-continued
| Entry | Structure | SALT NAME | HPLC-MS characterization MS/ESI⁺ [MH]⁺ | $t_R$/min Methods 1 or 2 | Diastereo-meric Ratio | $^1$H NMR | $[\alpha]_D$ |
|---|---|---|---|---|---|---|---|
| 181 | 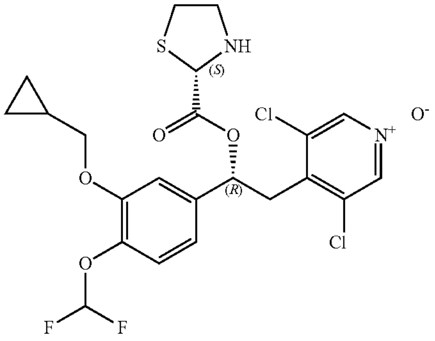 | Hydro-chloride salt | 535.2 | | | | |
| 182 | 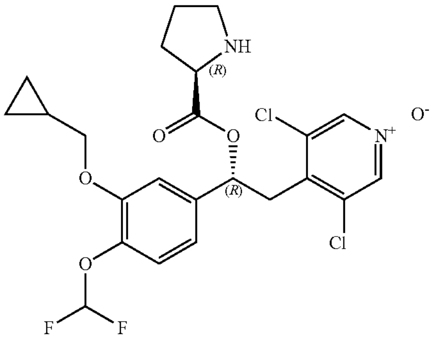 | Free base | 517.2 | 1.99 (2) | 98:2 | | |
| 183 | 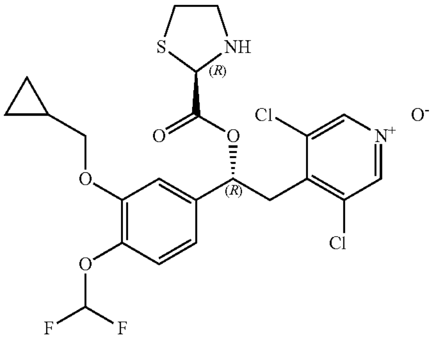 | Hydro-chloride salt | 535.2 | | | | |

Example 2. Synthesis of 3,5-dichloro-4-((2S)-2-(3-(cyclopropylmethoxy)-4-(difluoromethoxy)phenyl)-2-(1-((4-(methoxycarbonyl)-5-methylfuran-2-yl)methyl)pyrrolidine-2-carbonyloxy)ethyl)pyridine 1-oxide (15)

Scheme 10

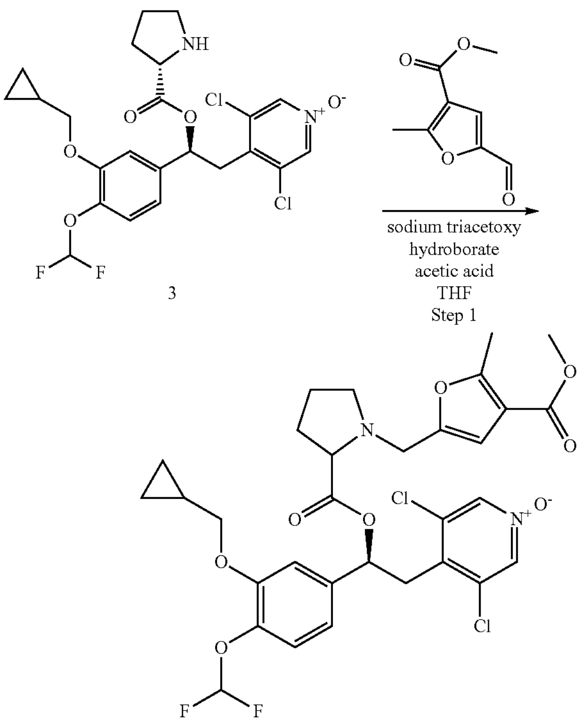

3

15

3,5-dichloro-4-((S)-2-(3-(cyclopropylmethoxy)-4-(difluoromethoxy)phenyl)-2-((S)-pyrrolidine-2-carbonyloxy)ethyl)pyridine 1-oxide (3) (40 mg, 0.077 mmol) was dissolved in THF (1 ml), and methyl 5-formyl-2-methylfuran-3-carboxylate (13.00 mg, 0.077 mmol) and acetic acid (4.64 mg, 0.077 mmol) were added to it. The reaction was stirred at RT for 30 minutes before adding sodium triacetoxyhydroborate (16.39 mg, 0.077 mmol). After that time, the reaction was stirred for further 2 hours to get to completion. The solvent was removed, and the residue was partitioned between EtOAc and aq HCl 1M. The organic layer was then washed with aq $K_2CO_3$ 5% and dried over $Na_2SO_4$. The solvent was removed under vacuum to obtain a transparent oil (35 mg; yield 68%) that was purified by preparative HPLC to yield 18 mg of diasteromeric mixture (47.5:52.5) of the desired product as transparent oil (yield 36%). MS/ESI$^+$ 668.9 [MH]$^+$; $t_R$=5.97; 6.15 min (Method1); Diastereomeric Ratio=47:53.

The compounds listed in Table 3 were prepared with an analogous procedure to that described in Step 1; Scheme 10, and by reacting the precursor (5) with suitable reagents.

A diastereomeric mixture was obtained from (5) which was were separated by means of preparative HPLC instrument (Method 1 General Experimental Details section) to give the two diastereomers, (16) and (17) identified as fast and slow isomer, respectively, according to their observed retention times under the chromatographic conditions described in the General Experimental Details section (Method 1).

TABLE 3

| Entry | Structure | SALT NAME | HPLC-MS characterization: MS/ESI$^+$ [MH]$^+$ | HPLC-MS characterization: $t_R$/min Methods 1 or 2 | HPLC-MS characterization: Diastereomeric ratio | $^1$H NMR | $[\alpha]_D$ | Precursor |
|---|---|---|---|---|---|---|---|---|
| 16 | 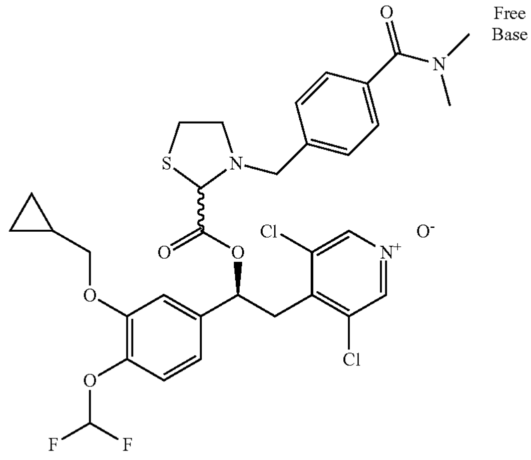 | Free Base | 696.0 | 6.52 (1) | >99:1 | $^1$H NMR (400 MHz, DMSO-$d_6$) δ ppm 8.55 (s, 2 H), 7.32-7.43 (m, 4 H), 7.17 (m, 1 H), 7.05-7.11 (m, 2 H), 6.92-6.97 (m, 1 H), 5.83-5.96 (m, 1 H), 4.74 (s, 1 H), 3.90 (d, J = 7.06 Hz, 2 H), 3.56 (d, J = 8.38 Hz, 2 H), 3.36 (m, 4 H), 3.07-3.26 (m, 2 H), 2.84 and 3.04 (2s, 6 H), 1.16-1.30 (m, 1 H), 0.58 (m, 2 H), 0.34 (d, J = 3.97 Hz, 2 H). | | 5 |

TABLE 3-continued

| En-try | Structure | SALT NAME | HPLC-MS characterization MS/ ESI$^+$ [MH]$^+$ | $t_R$/min Methods 1 or 2 | Diastereo-meric ratio | $^1$H NMR | $[\alpha]_D$ | Pre-cursor |
|---|---|---|---|---|---|---|---|---|
| 17 | 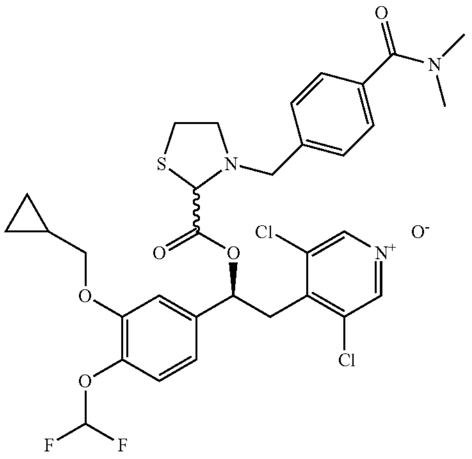 | Free Base | 695.9 | 6.87 (1) | >99:1 | $^1$H NMR (400 MHz, DMSO-$d_6$) δ ppm 8.56-8.67 (m, 2 H), 7.29-7.37 (m, 4 H), 7.20 (d, J = 7.94 Hz, 1 H), 7.05-7.11 (m, 2 H), 6.88-6.95 (m, 1 H), 5.88 (dd, J = 10.14, 4.41 Hz, 1 H), 4.85 (s, 1 H), 3.76-3.96 (m, 2 H), 3.50-3.69 (m, 2 H), 3.07-3.46 (m, 6 H), 2.83 and 3.02 (2s, 6 H), 1.18-1.30 (m, 1 H), 0.47-0.66 (m, 2 H), 0.22-0.42 (m, 2 H). | | 5 |

Example 3. Synthesis of 3,5-dichloro-4-((S)-2-((S)-1-(4-(cyclopropylmethoxy)-3-(methylsulfonamido)benzoyl)pyrrolidine-2-carbonyloxy)-2-(3-(cyclopropylmethoxy)-4-(difluoromethoxy)phenyl)ethyl)pyridine 1-oxide (19)

Scheme 11

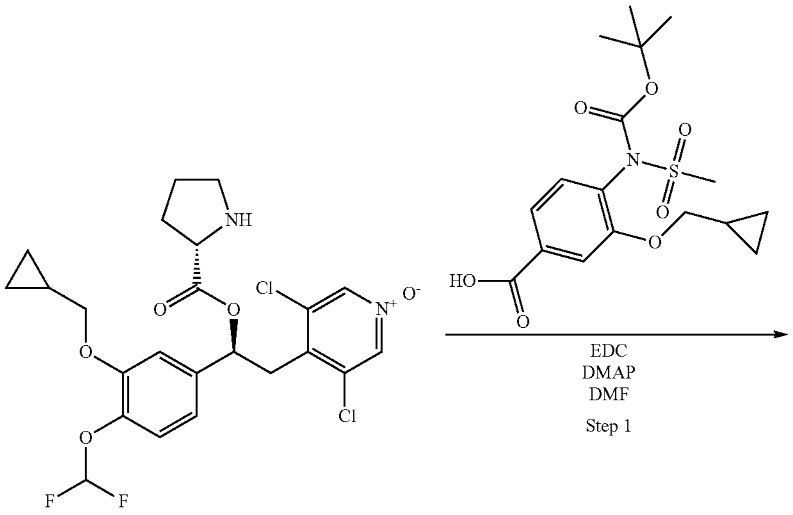

3

-continued

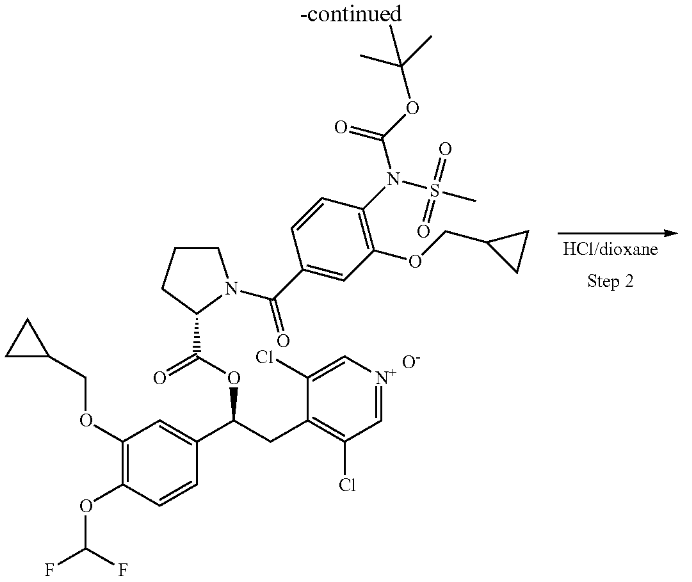

18

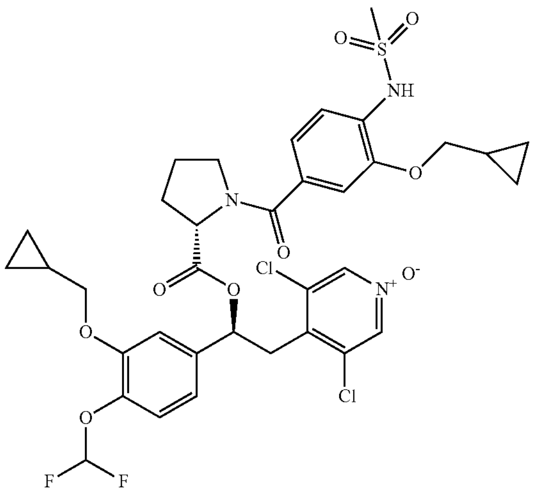

19

Step 1: 4-((S)-2-((S)-1-(3-(N-(tert-butoxycarbonyl) methylsulfonamido)-4-(cyclopropylmethoxy)benzoyl)pyrrolidine-2-carbonyloxy)-2-(3-(cyclopropylmethoxy)-4-(difluoromethoxy)phenyl)ethyl)-3,5-dichloropyridine 1-oxide (18)

3,5-dichloro-4-((S)-2-(3-(cyclopropylmethoxy)-4-(difluoromethoxy)phenyl)-2-((S)-pyrrolidine-2-carbonyloxy) ethyl)pyridine 1-oxide (3) (40 mg; 0.077 mmol) was placed in a 50 ml round bottom flask and dissolved in DMF (2 ml). 3-(N-(tert-butoxycarbonyl)methylsulfonamido)-4-(cyclopropylmethoxy)benzoic acid (40 mg, 0.104 mmol, obtainable as described in WO 2010/089107, which is incorporated herein by reference in its entirety), was added to the reaction solution followed by EDC (20.0 mg, 0.104 mmol) and DMAP (15.0 mg, 0.123 mmol). The reaction was stirred at RT for 6 hours to get to completion and quenched by adding 20 ml of aq HCl 1M. The aqueous layer was extracted with EtOAc and washed with HCl 1M (x3) and with aq $K_2CO_3$ 5% (x3). The resulting organic extract was dried with $Na_2SO_4$, filtered on a filter paper, and the solvent removed on a rotary evaporator under reduced pressure. The oil residue was purified by preparative HPLC (Method 1) to yield 30 mg of desired product (yield 44%).

MS/ESI$^+$ 884.1 [MH]$^+$ $^1$H NMR (400 MHz, acetone) δ ppm 8.28 (s, 2H), 7.33 (d, J=7.94 Hz, 1H), 7.14-7.23 (m, 4H), 6.68-7.13 (m, 2H), 6.16 (dd, J=9.92, 4.19 Hz, 1H), 4.52 (dd, J=7.94, 6.17 Hz, 1H), 3.88-4.12 (m, 6H), 3.56-3.74 (m, 3H), 3.53 (s, 3H), 3.34 (dd, J=14.11, 4.41 Hz, 1H), 1.74-1.93 (m, 2H), 1.47 (s, 9H), 1.25-1.35 (m, 2H), 0.51-0.69 (m, 4H), 0.27-0.48 (m, 4H).

Step 2: 3,5-dichloro-4-((S)-2-((S)-1-(4-(cyclopropylmethoxy)-3-(methylsulfonamido)benzoyl)pyrrolidine-2-carbonyloxy)-2-(3-(cyclopropylmethoxy)-4-(difluoromethoxy)phenyl)ethyl)pyridine 1-oxide (19)

4-((S)-2-((S)-1-(3-(N-(tert-butoxycarbonyl)methylsulfonamido)-4-(cyclopropylmethoxy)benzo yl)pyrrolidine-2-carbonyloxy)-2-(3-(cyclopropylmethoxy)-4-(difluoromethoxy)phenyl)ethyl)-3,5-dichloropyridine 1-oxide (18)

(30 mg, 0.034 mmol) was dissolved in HC/EOAc (4M; 2 ml) and stirred for 10 hours at RT to achieve completion. The reaction was quenched by adding $K_2CO_3$ 5% and extracted with EtOAc. The resulting organic extract was dried over $Na_2SO_4$, filtered on a filter paper, and the solvent removed on a rotary evaporator under reduced pressure. The residue was recrystallised from EtOH:hexane (1:3) to yield a white solid (18 mg; yield 68%) of the title compound. MS/ESI$^+$ 784.1 [MH]$^+$; $t_R$=5.72 (Method 1); $[\alpha_D]$=−48.92 (c=3.7; DCM); Diastereomeric Ratio >99:1.

$^1$H NMR (400 MHz, CHLOROFORM-d) δ ppm 8.16 (br. s., 2H), 7.53 (m, 1H), 7.09-7.20 (m, 3H), 7.05 (m, 1H), 6.96

(m, 2H), 6.41-6.63-6.84 (t, 1H, $CHF_2$), 6.08-6.17 (m, 1H), 4.53-4.66 (m, 1H), 3.81-3.98 (m, 4H), 3.61 (m, 3H), 3.22-3.39 (m, 1H), 3.02 (s, 3H), 2.20-2.34 (m, 1H), 1.78-2.02 (m, 3H), 1.27 (m, 2H), 0.59-0.75 (m, 4H), 0.28-0.42 (m, 4H).

The compounds listed in Table 4 were prepared with an analogous procedure to that described above in Example 3, Scheme 11, by reacting the appropriate precursors listed with suitable reagents, followed by a purification step as indicated in the table below in place of recrystallization above described.

TABLE 4

| | | | HPLC-MS characterization | | | | | |
|---|---|---|---|---|---|---|---|---|
| Entry | Structure | SALT NAME | MS/ESI$^+$ [MH]$^+$ | $t_R$/min Methods 1 or 2 | Diastereomeric ratio | $^1$H NMR | Precursor | Purification method |
| 20 | 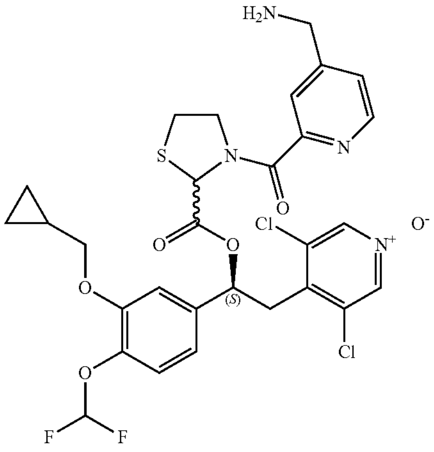 | formate | 669.3 | 3.07 (2) | 99:1 | | 5 | Preparative HPLC |
| 21 | 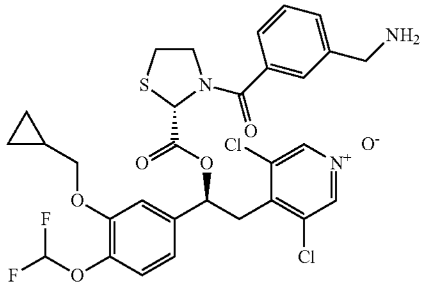 | hydrochloride | 668.3 | 2.57 (2) | >99:1 | $^1$H NMR (400 MHz, DMSO-$d_6$) δ ppm 9.54 (bs, 1H), 8.57 (s, 2 H), 7.40-7.65 (m, 4 H), 7.20 (d, J = 7.94 Hz, 1 H), 7.10 (m, 2 H), 6.95-7.04 (m, 1 H), 5.91-6.13 (m, 1 H), 5.51 (s, 1 H), 4.04-4.21 (m, 3 H), 3.83-4.03 (m, 2 H), 3.67-3.82 (m, 1 H), 3.25-3.37 (m, 2 H), 3.19 (m, 4 H), 1.09-1.32 (m, 1 H), 0.56 (d, J = 7.94 Hz, 2 H), 0.32 (d, J = 4.41 Hz, 2 H) | 6 | Filtration of the hydrochloride salt from reaction mixture |
| 22 | 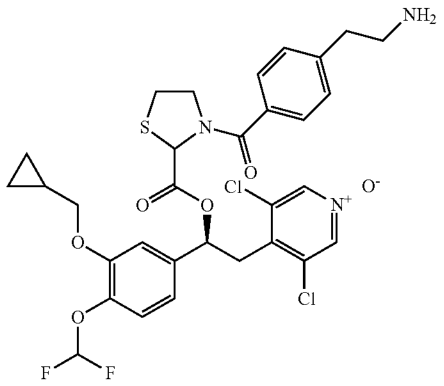 | formate | 682.3 | 2.69; 2.82 (2) | 14:86 | | 5 | Preparative HPLC |

Example 4. Synthesis of 4-((2S)-2-(3-(4-aminobenzoyl)thiazolidine-2-carbonyloxy)-2-(3-(cyclopropylmethoxy)-4-(difluoromethoxy)phenyl)ethyl)-3,5-dichloropyridine 1-oxide (26)

Scheme 12

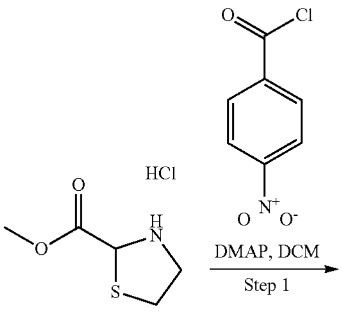

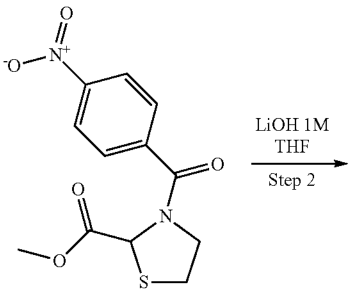

23

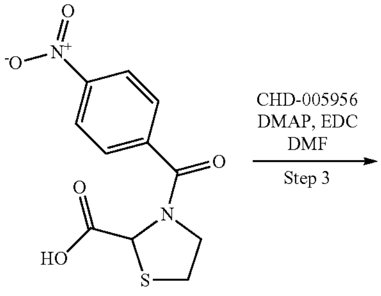

24

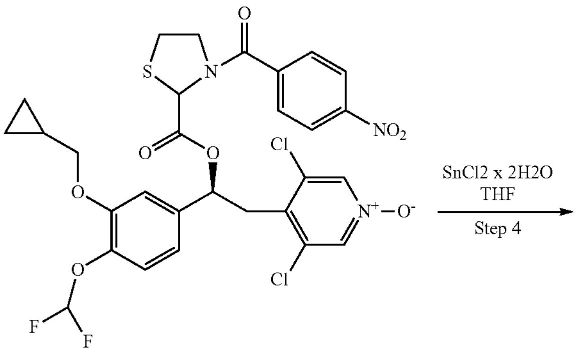

25

-continued

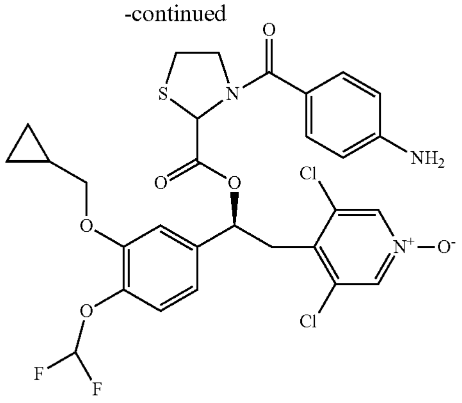

26

Step 1: methyl 3-(4-nitrobenzoyl)thiazolidine-2-carboxylate (23)

Methyl thiazolidine-2-carboxylate hydrochloride (200 mg, 1.089 mmol) was dissolved in DCM (2 ml). DMAP (173 mg, 1.416 mmol) and 4-nitrobenzoyl chloride (263 mg, 1.416 mmol) were added, and the reaction was stirred at RT for 2 hours to achieve completion. The reaction mixture was diluted with DMC and extracted with aq HCl 1M. The organic phase was washed with HCl 1N and brine, dried over $Na_2SO_4$ and concentrated under vacuum to give methyl 3-(4-nitrobenzoyl)thiazolidine-2-carboxylate (220 mg, 0.742 mmol, 68% yield). MS/ESI$^+$ 297.05 [MH]$^+$

Step 2: 3-(4-nitrobenzoyl)thiazolidine-2-carboxylic acid (24)

Methyl 3-(4-nitrobenzoyl)thiazolidine-2-carboxylate (220 mg, 0.742 mmol) was dissolved in THF (2 ml). LiOH 1M (1 ml, 1.000 mmol) was added, and the reaction was stirred at RT for 6 hours to achieve completion. The reaction mixture was diluted with HCl 1N and extracted with EtOAc. The organic phase was dried over $Na_2SO_4$ and concentrated under vacuum to give 3-(4-nitrobenzoyl)thiazolidine-2-carboxylic acid (180 mg, 0.638 mmol, 86% yield). MS/ESI$^+$ 283.03 [MH]$^+$

Step 3: 3,5-dichloro-4-((2S)-2-(3-(cyclopropylmethoxy)-4-(difluoromethoxy)phenyl)-2-(3-(4-nitrobenzoyl)thiazolidine-2-carbonyloxy)ethyl)pyridine 1-oxide (25)

(S)-3,5-dichloro-4-(2-(3-(cyclopropylmethoxy)-4-(difluoromethoxy)phenyl)-2-hydroxyethyl)pyridine 1-oxide (100 mg, 0.238 mmol), 3-(4-nitrobenzoyl)thiazolidine-2-carboxylic acid (134 mg, 0.476 mmol), DMAP (34.9 mg, 0.286 mmol), and EDC (137 mg, 0.714 mmol) were dissolved in DMF (1.5 ml). The reaction was stirred at RT for 2 hours to achieve completion. The reaction mixture was diluted with water, and the precipitate was washed with water, dissolved in EtOAc and extracted with HCl 1N, $Na_2CO_3$ sat. sol. and brine. The organic phase was dried over $Na_2SO_4$ and concentrated under vacuum to give 3,5-dichloro-4-((2S)-2-(3-(cyclopropylmethoxy)-4-(difluoromethoxy)phenyl)-2-(3-(4-nitrobenzoyl)thiazolidine-2-carbonyloxy)ethyl)pyridine 1-oxide (130 mg, 0.190 mmol, 80% yield).

MS/ESI$^+$ 684.07 [MH]$^+$

Step 4: 4-((2S)-2-(3-(4-aminobenzoyl)thiazolidine-2-carbonyloxy)-2-(3-(cyclopropylmethoxy)-4-(difluoromethoxy)phenyl)ethyl)-3,5-dichloropyridine 1-oxide (26)

3,5-dichloro-4-((2S)-2-(3-(cyclopropylmethoxy)-4-(difluoromethoxy)phenyl)-2-(3-(4-nitrobenzoyl)thiazolidine-2-carbonyloxy)ethyl)pyridine 1-oxide (130 mg, 0.190 mmol) was dissolved in THF (3 ml). Tin(II) chloride dihydrate (257 mg, 1.140 mmol) was added, and the mixture was stirred at RT for 4 days. The solvent was removed under vacuum, and the crude product was dissolved in EtOAc and diluted with $Na_2CO_3$ sat. sol. Diatomaceus earth was added to the two phases, and the mixture was filtered on a Diatomaceus earth pad. The organic phase was washed with $Na_2CO_3$ sat. sol., brine, dried over $Na_2SO_4$ and concentrated under vacuum. The crude product was triturated in $Et_2O$ to give 4-((2S)-2-(3-(4-aminobenzoyl)thiazolidine-2-carbonyloxy)-2-(3-(cyclopropylmethoxy)-4-(difluoromethoxy)phenyl)ethyl)-3,5-dichloropyridine 1-oxide (30 mg, 0.046 mmol, 24% yield). MS/ESI$^+$ 653.8 $[MH]^+$; $t_R$=5.80; 6.00 (Method 1); Diastereomeric Ratio 30:70.

Example 5. Synthesis of 3,5-dichloro-4-((S)-2-(3-(cyclopropylmethoxy)-4-(difluoromethoxy)phenyl)-2-((S)-1-(4-methoxy-3-(methylsulfonyloxy)benzoyl)pyrrolidine-2-carbonyloxy)ethyl)pyridine 1-(30)

Scheme 13

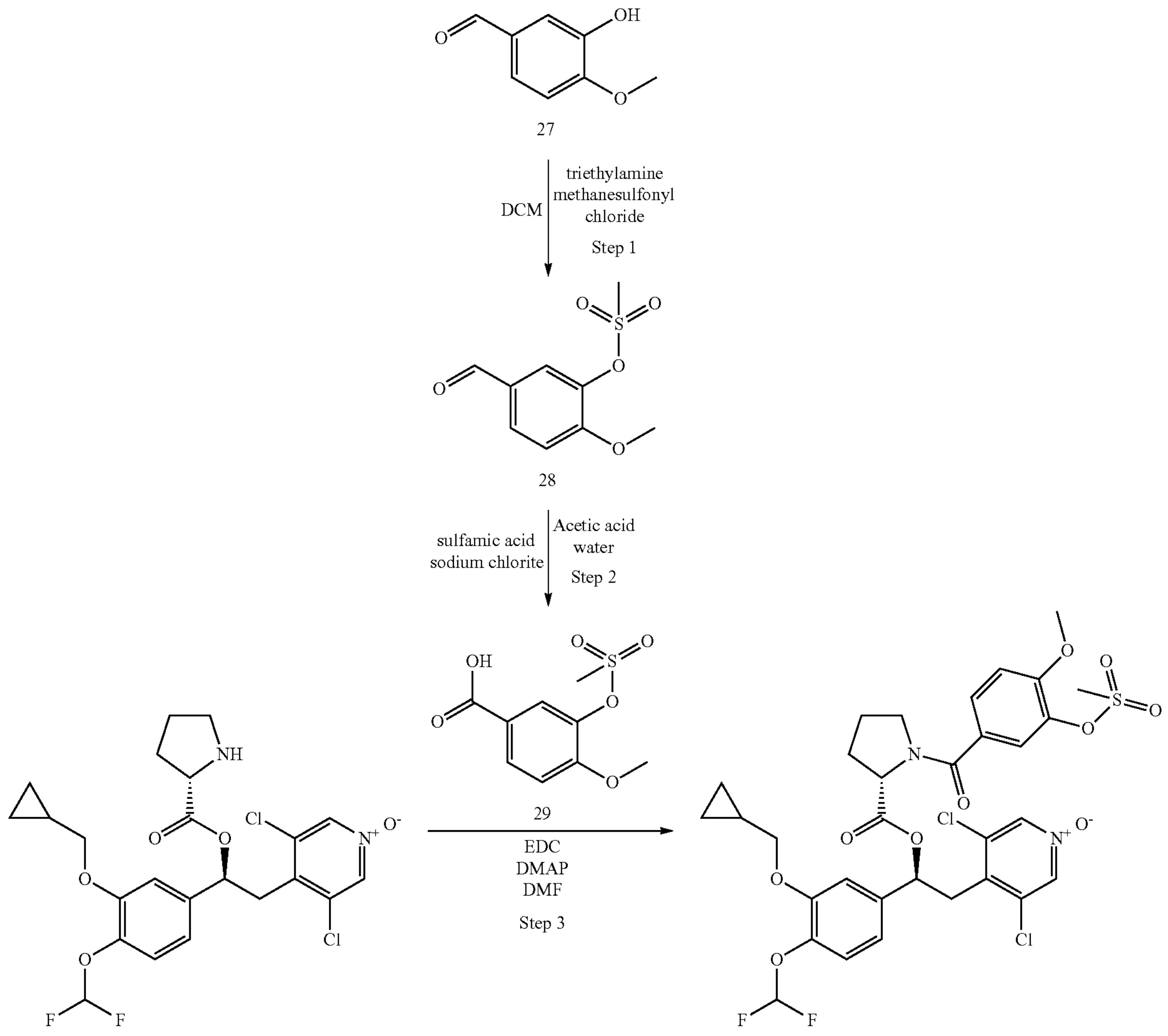

27

28

29

3

30

Step 1: 5-formyl-2-methoxyphenyl methanesulfonate (28)

3-hydroxy-4-methoxybenzaldehyde (27) (0.5 g, 3.291 mmol) was dissolved in DCM, and methanesulfonyl chloride (0.376 g, 3.29 mmol) followed by triethylamine (0.499 g, 4.931 mmol) were added. The reaction solution was stirred at RT for 2 hours, after that time, it was quenched with aq HCl 1M and extracted with EtOAc. The organic extract was then washed with aq $K_2CO_3$ 5%, dried over $Na_2SO_4$ and the solvent removed on a rotary evaporator. The desired product was obtained as a white powder (0.750 g, yield 99%). MS/ESI$^+$ 231.02 [MH]$^+$ Step 2: 4-methoxy-3-(methylsulfonyloxy)benzoic acid (29)

5-formyl-2-methoxyphenyl methanesulfonate (28) (0.750 g, 3.261 mmol) and sulfamic acid (0.316 g, 3.261 mmol) were dissolved in acetic acid (10 ml) and cooled down by ice bath. Sodium chlorite (0.589 g, 6.521 mmol) was dissolved in water (4 ml) and slowly added to the cold reaction solution. The reaction mixture was allowed to warm at RT and stirred for about 2 hours. After that time, full conversion was observed by UPLC-MS analysis. Addition of water (15 ml) caused precipitation of a white solid, which was filtered and washed several times with water (0.700 g, yield 87%). MS/ESI$^+$ 247.02 [MH]$^+$ Step 3: 3,5-dichloro-4-((S)-2-(3-(cyclopropylmethoxy)-4-(difluoro methoxy)phenyl)-2-((S)-1-(4-methoxy-3-(methylsulfonyloxy)benzoyl)pyrrolidine-2-carbonyloxy)ethyl)pyridine 1-oxide (30)

3,5-dichloro-4-((S)-2-(3-(cyclopropylmethoxy)-4-(difluoromethoxy)phenyl)-2-((S)-1-(4-methoxy-3-(methylsulfonyloxy)benzoyl)pyrrolidine-2-carbonyloxy)ethyl)pyridine-1-oxide (30) was prepared by following an analogous procedure to that described in Step 1 (Example 3). MS/ESI$^+$ 745.0 [MH]$^+$; $[\alpha_D]$=31.30 (c=0.34; $CHCl_3$), $t_R$=5.57 (Method 1); Diastereomeric Ratio >99:1. $^1$H NMR (400 MHz, CHLOROFORM-d) δ ppm 8.17 (s, 2H), 7.56 (m, 2H), 7.13 (m, 4H), 6.60 (t, J=75.00 Hz, 1H), 6.04-6.21 (m, 1H), 4.46-4.75 (m, 1H), 3.95 (s, 3H), 3.85 (m, 2H), 3.50-3.70 (m, 3H), 3.25-3.31 (m, 1H), 3.22 (s, 3H), 2.19-2.41 (m, 1H), 1.74-2.03 (m, 3H), 1.14-1.34 (m, 1H), 0.64 (d, J=7.09 Hz, 2H), 0.34 (d, J=4.16 Hz, 2H).

The compounds listed in Table 5 were prepared according to an analogous procedure to that described in Step 3 (Scheme 13) and by reacting the appropriate precursors listed with suitable commercial reagents, followed by an appropriate purification step in place of preparative HPLC as below indicated.

TABLE 5

| | | | HPLC-MS characterization | | | | | |
|---|---|---|---|---|---|---|---|---|
| Entry | Structure | SALT NAME | MS/ESI$^+$ [MH]$^+$ | $t_R$/min Methods 1 or 2 | Diastereomeric ratio | $^1$H NMR | Precursor | Purification Method |
| 31 | 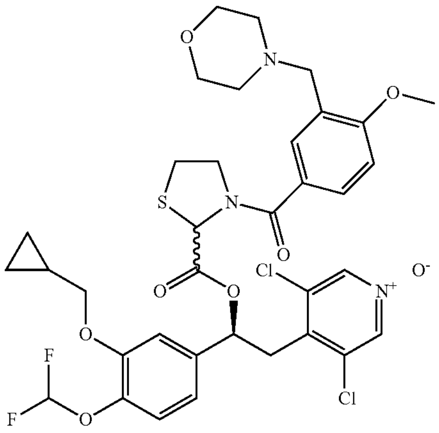 | Free Base | 768.65 | 2.65; 2.82 (2) | 6:94 | $^1$H NMR (400 MHz, DMSO-$d_6$) δ ppm 8.56 (s, 1 H), 7.36-7.55 (m, 2 H), 7.16-7.21 (m, 1 H), 7.01-7.11 (m, 3 H), 6.92-6.99 (m, 1 H), 5.93-6.05 (m, 1 H), 5.52 (s, 1 H), 3.92-4.12 (m, 1 H), 3.84 (m, 6 H), 3.52-3.64 (m, 4 H), 3.47 (m, 3 H), 3.25-3.29 (m, 1 H), 3.06-3.18 (m, 1 H), 2.89-3.03 (m, 1 H), 2.38 (m, 4 H), 1.09-1.20 (m, 1 H), 0.46-0.61 (m, 2 H), 0.19-0.29 (m, 2 H). | 5 | Filtration of the precipitate obtained after water addition, and trituration with MeOH |

TABLE 5-continued
| Entry | Structure | SALT NAME | HPLC-MS characterization MS/ESI+ [MH]+ | tR/min Methods 1 or 2 | Diastereomeric ratio | 1H NMR | Precursor | Purification Method |
|---|---|---|---|---|---|---|---|---|
| 32 | 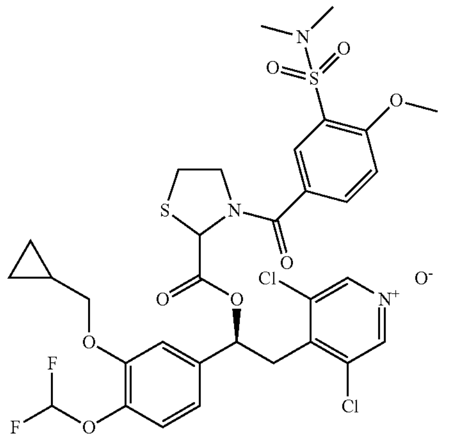 | Free Base | 776.65 | 3.77; 3.81 (2) | 38:62 | | 5 | Preparative HPLC |
| 33 | 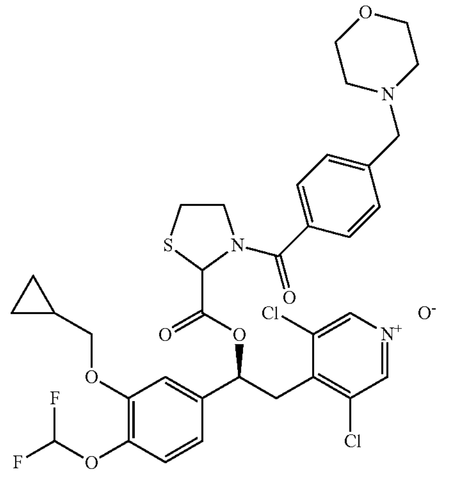 | Free Base | 738.62 | 2.56; 2.69 (2) | 38:62 | | 5 | Preparative HPLC |
| 34 | 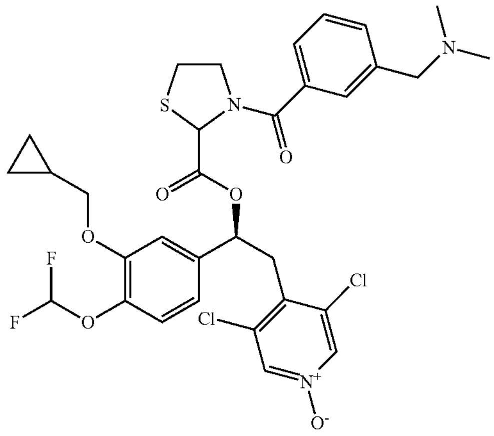 [SMILES: CN(C)Cc1cccc(C(=O)N2CCSC2C(=O)O[C@@H](Cc2c(Cl)c[n+]([O-])cc2Cl)c2ccc(OC(F)F)c(OCC3CC3)c2)c1] | Free Base | 696.3 | 2.49; 2.67 (2) | 16:84 | | 5 | Preparative HPLC |

TABLE 5-continued

| En-try | Structure | SALT NAME | HPLC-MS characterization MS/ ESI+ [MH]+ | tR/min Methods 1 or 2 | Diastereo-meric ratio | 1H NMR | Pre-cursor | Purifica-tion Method |
|---|---|---|---|---|---|---|---|---|
| 35 | 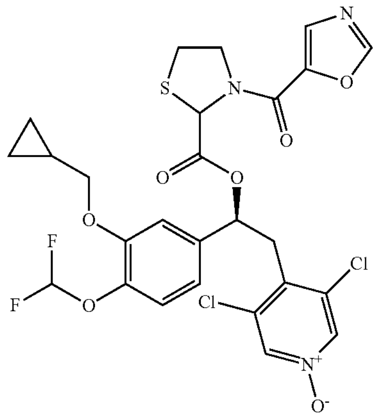 [SMILES: O=C(O[C@@H](Cc1c(Cl)c[n+]([O-])cc1Cl)c1ccc(OC(F)F)c(OCC2CC2)c1)C1SCCN1C(=O)c1cnco1] | Free Base | 630.2 | 3.19; 3.29 (2) | 24:76 | | 5 | No purification of the crude performed |
| 36 | 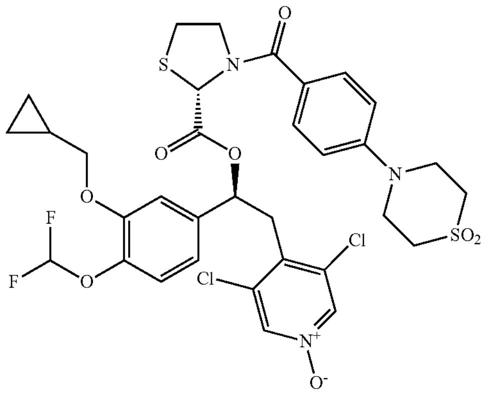 [SMILES: O=C(O[C@@H](Cc1c(Cl)c[n+]([O-])cc1Cl)c1ccc(OC(F)F)c(OCC2CC2)c1)[C@@H]1SCCN1C(=O)c1ccc(N2CCS(=O)(=O)CC2)cc1] | Free Base | 772.2 | 4.14 (2) | >99:1 | $^1$H NMR (400 MHz, DMSO-$d_6$) δ ppm 8.55 (s, 2 H), 7.36-7.45 (m, 2 H), 7.15-7.22 (m, 1 H), 7.01-7.12 (m, 4 H), 6.92-7.00 (m, 1 H), 5.94-6.06 (m, 1 H), 5.50 (s, 1 H), 3.97-4.11 (m, 1 H), 3.84 (m, 7 H), 3.39-3.50 (m, 1 H), 3.26 (d, J = 5.73 Hz, 1 H), 3.12 (m, 5 H), 2.91-3.04 (m, 1 H), 1.12-1.30 (m, 1 H), 0.45-0.61 (m, 2 H), 0.24-0.32 (m, 2 H). | 6 | Trituration with MeOH |
| 37 | 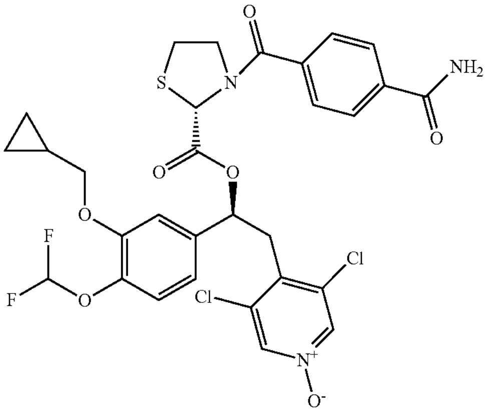 [SMILES: NC(=O)c1ccc(C(=O)N2CCS[C@H]2C(=O)O[C@@H](Cc2c(Cl)c[n+]([O-])cc2Cl)c2ccc(OC(F)F)c(OCC3CC3)c2)cc1] | Free Base | 682.2 | 3.75 (2) | 96:4 | $^1$H NMR (400 MHz, DMSO-$d_6$) δ ppm 8.47-8.73 (m, 2 H), 8.07-8.20 (m, 1 H), 7.91-8.04 (m, 2 H), 7.49-7.65 (m, 2 H), 7.16-7.22 (m, 1 H), 7.07-7.14 (m, 1 H), 6.93-7.03 (m, 1 H), 5.96-6.12 (m, 1 H), 5.53 (s, 1 H), 3.68-4.00 (m, 5 H), 3.39-3.54 (m, 1 H), 3.06-3.21 (m, 1 H), 2.89-3.05 (m, 1 H), 1.06-1.32 (m, 1 H), 0.42-0.64 (m, 2 H), 0.12-0.36 (m, 2 H). | 6 | Trituration with MeOH |

TABLE 5-continued

| Entry | Structure | SALT NAME | HPLC-MS characterization MS/ESI+ [MH]+ | tR/min Methods 1 or 2 | Diastereomeric ratio | 1H NMR | Precursor | Purification Method |
|---|---|---|---|---|---|---|---|---|
| 38 | 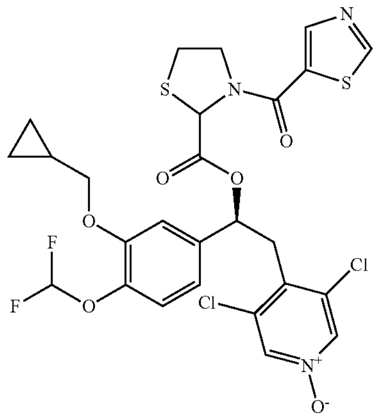 [SMILES: O=C(O[C@@H](Cc1c(Cl)c[n+]([O-])cc1Cl)c1ccc(OC(F)F)c(OCC2CC2)c1)C1SCCN1C(=O)c1cncs1] | Free Base | 646.2 | 3.32; 3.40 (2) | 11:89 | | 5 | Trituration with MeOH |
| 39 | 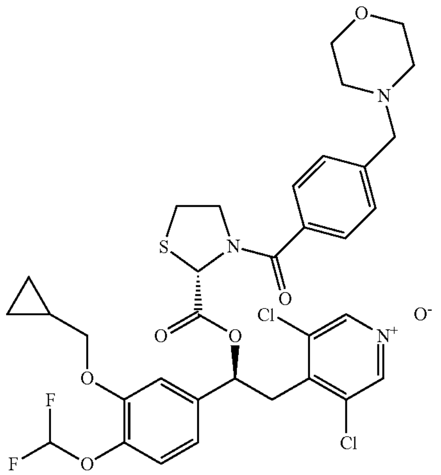 | formate | 738.3 | 2.67 (2) | 98:2 | $^{1}$H NMR (400 MHz, DMSO-d6) δ ppm 8.56 (s, 2 H), 7.31-7.52 (m, 4 H), 7.14-7.22 (m, 1 H), 7.05-7.12 (m, 2 H), 6.93-7.00 (m, 1 H), 5.93-6.14 (m, 1 H), 5.50 (s, 1 H), 3.89-3.97 (m, 1 H), 3.82-3.88 (m, 2 H), 3.70-3.81 (m, 1 H), 3.58 (m, 4 H), 3.52 (s, 2 H), 3.41-3.48 (m, 1 H), 3.20-3.25 (m, 1 H), 3.06-3.18 (m, 1 H), 2.93-3.03 (m, 1 H), 2.28-2.41 (m, 4 H), 1.13-1.21 (m, 1 H), 0.45-0.64 (m, 2 H), 0.19-0.33 (m, 2 H) | 6 | No purification of the crude performed |
| 40 | 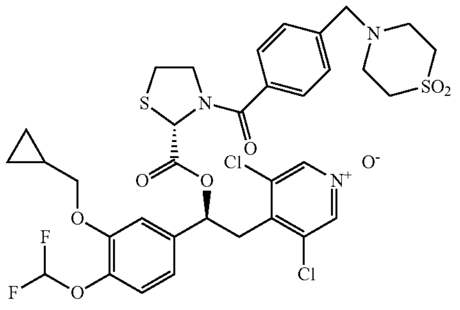 | Free Base | 786.2 | 3.58 (2) | 97:3 | $^{1}$H NMR (400 MHz, DMSO-d6) δ ppm 8.56 (s, 2 H), 7.33-7.50 (m, 4 H), 7.15-7.22 (m, 1 H), 7.06-7.12 (m, 2 H), 6.93-7.00 (m, 1 H), 5.93-6.10 (m, 1 H), 5.50 (s, 1 H), 3.90-4.00 (m, 1 H), 3.83-3.88 (m, 2 H), 3.73 (m, 3 H), 3.37-3.52 (m, 2 H), 3.05-3.21 (m, 5 H), 2.94-3.04 (m, 1 H), 2.82-2.92 (m, 4 H), 1.11-1.28 (m, 1 H), 0.46-0.61 (m, 2 H), 0.17-0.41 (m, 2 H). | 6 | Trituration with EtOH |

TABLE 5-continued
| En-try | Structure | SALT NAME | HPLC-MS characterization MS/ ESI+ [MH]+ | tR/min Methods 1 or 2 | Diastereo-meric ratio | 1H NMR | Pre-cursor | Purifica-tion Method |
|---|---|---|---|---|---|---|---|---|
| 41 | 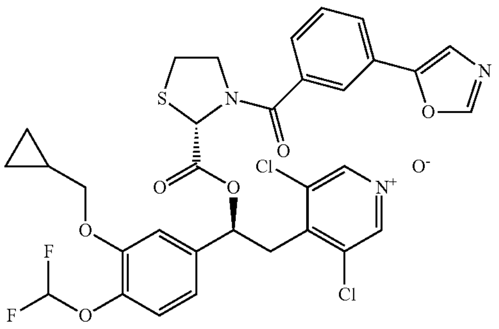 | Free Base | 706.2 | 3.73 (2) | >99:1 | $^1$H NMR (400 MHz, DMSO-d6) δ ppm 8.53-8.64 (s, 1 H), 8.43-8.51 (s, 2 H), 7.73-7.93 (m, 3 H), 7.37-7.67 (m, 2 H), 7.14-7.22 (m, 1 H), 7.05-7.13 (m, 2 H), 6.96-7.04 (m, 1 H), 5.98-6.12 (m, 1 H), 5.53 (s, 1 H), 3.74-3.99 (m, 4 H), 3.41-3.57 (m, 1 H), 3.07-3.20 (m, 2 H), 2.92-3.06 (m, 1 H), 1.06-1.29 (m, 1 H), 0.47-0.62 (m, 2 H), 0.13-0.37 (m, 2 H) | 6 | No purifica-tion of the crude perform-ed |
| 42 | 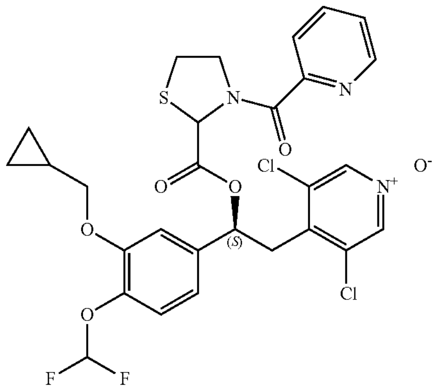 | formate | 640.3 | 4.05; 4.15 (2) | 38:62 | | 5 | Prepara-tive HPLC |
| 184 | 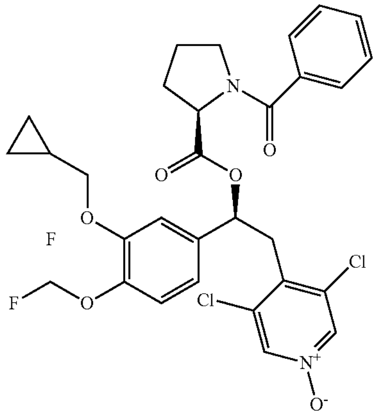 | Free Base | 621.3 | | 80:20 ($^1$H NMR) | | | |

TABLE 5-continued

| | | | HPLC-MS characterization | | | | | |
|---|---|---|---|---|---|---|---|---|
| Entry | Structure | SALT NAME | MS/ ESI$^+$ [MH]$^+$ | $t_R$/min Methods 1 or 2 | Diastereomeric ratio | $^1$H NMR | Precursor | Purification Method |
| 185 | 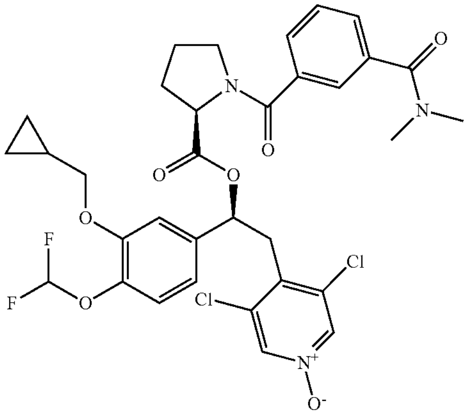 [SMILES: CN(C)C(=O)c1cccc(C(=O)N2CCC[C@@H]2C(=O)O[C@@H](Cc2c(Cl)c[n+]([O-])cc2Cl)c2ccc(OC(F)F)c(OCC3CC3)c2)c1] | Free Base | 692.2 | 3.14 (2) | 98/2 | $^1$H NMR (400 MHz, DMSO-$d_6$) δ ppm 8.56 (s, 2 H), 7.47-7.65 (m, 4 H), 7.11-7.25 (m, 2 H), 7.07 (t, J = 75.00 Hz, 1 H), 7.04 (d, J = 1.76 Hz, 1 H), 5.98-6.10 (m, 1 H), 4.49 (s, 1 H), 3.89-4.02 (m, 2 H), 3.34-3.64 (m, 4 H), 2.82-3.03 (m, 6 H), 2.14-2.29 (m, 1 H), 1.85 (t, J = 6.62 Hz, 2 H), 1.55-1.67 (m, 1 H), 1.12-1.30 (m, 1 H), 0.54 (dd, J = 8.16, 1.54 Hz, 3 H), 0.30 (d, J = 4.41 Hz, 2 H). | | |
| 186 | 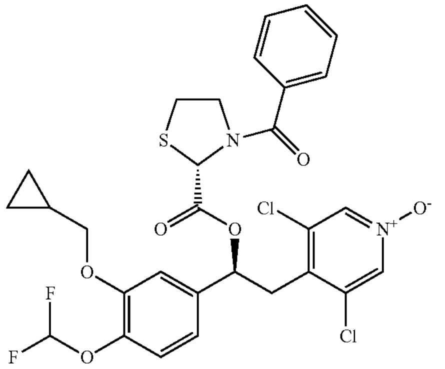 [SMILES: O=C(O[C@@H](Cc1c(Cl)c[n+]([O-])cc1Cl)c1ccc(OC(F)F)c(OCC2CC2)c1)[C@@H]1SCCN1C(=O)c1ccccc1] | Free Base | 639.1 | 3.92 | >99:1 | $^1$H NMR (400 MHz, DMSO-$d_6$) δ ppm 8.55 (s, 2 H), 7.34-7.59 (m, 5 H), 7.13-7.21 (m, 1 H), 7.08 (s, 2 H), 6.93-7.01 (m, 1 H), 5.93-6.11 (m, 1 H), 5.40-5.59 (m, 1 H), 3.83-4.03 (m, 3 H), 3.69-3.82 (m, 1 H), 3.40-3.54 (m, 1 H), 3.05-3.18 (m, 1 H), 2.92-3.04 (m, 1 H), 1.14-1.28 (m, 1 H), 0.46-0.63 (m, 2 H), 0.22-0.40 (m, 2 H). | | |
| 187 | 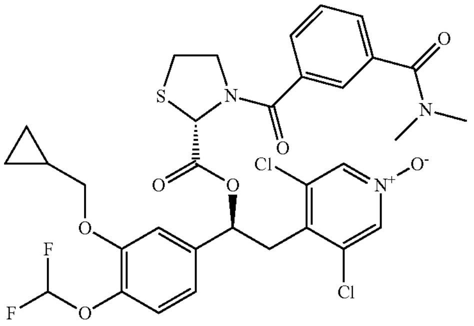 [SMILES: CN(C)C(=O)c1cccc(C(=O)N2CCS[C@H]2C(=O)O[C@@H](Cc2c(Cl)c[n+]([O-])cc2Cl)c2ccc(OC(F)F)c(OCC3CC3)c2)c1] | Free Base | 710.2 | 3.38 (2) | 3/97 | $^1$H NMR (400 MHz, DMSO-$d_6$) δ ppm 8.55 (s, 2 H), 7.40-7.65 (m, 4 H), 6.78-7.31 (m, 4 H), 5.85-6.14 (m, 1 H), 5.24 (s, 1 H), 3.69-4.02 (m, 4 H), 3.36-3.63 (m, 2 H), 3.09-3.21 (m, 1 H), 2.74-3.07 (m, 7 H), 1.12-1.28 (m, 1 H), 0.42-0.66 (m, 2 H), 0.18-0.39 (m, 2 H) | | |

The compounds listed in Table 14 were prepared according to an analogous procedure to that described in Step 3 (Scheme 13) and by reacting the appropriate precursors listed with suitable commercial reagents using DCM instead of DMF as the solvent, followed by an appropriate purification step as below indicated. Compounds 193, 194, and 195 were prepared starting from intermediate 3 or 179 obtained as free bases after a basic treatment of hydrochloride salts with aqueous 1M $NaHCO_3$ followed by extraction with DCM.

TABLE 14

| Entry | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 188 | 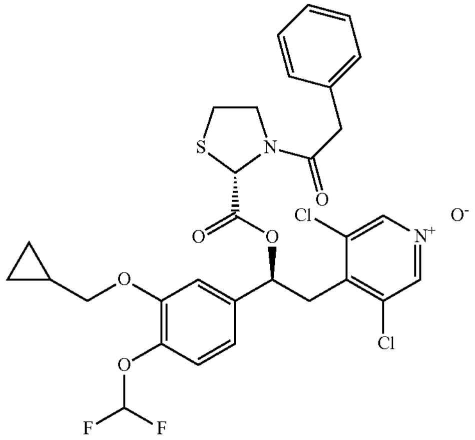 | Free Base | 653.24 | 4.03 (3) | >95:5 ($^1$H NMR) | $^1$H NMR (300 MHz, DMSO-$d_6$ 353 K) δ ppm 8.38 (s, 2 H), 7.18-7.36 (m, 5 H), 7.15 (d, 1 H), 7.08 (d, 1 H), 6.94 (dd, 1 H), 6.98 (t, 1 H), 6.01 (dd, 1 H), 5.50 (br. s., 1 H), 3.95-4.10 (m, 1 H), 3.92 (d, 2 H), 3.63-3.89 (m, 3 H), 3.47 (dd, 1 H), 3.31 (dd, 1 H), 3.06-3.23 (m, 2 H), 1.06-1.37 (m, 1 H), 0.47-0.69 (m, 2 H), 0.21-0.46 (m, 2 H) | −33.6 (c = 0.46, DCM) | 6 | Treatment with polymer supported isocyanate scavenger followed by preparative HPLC (Method 2) |
| 189 | 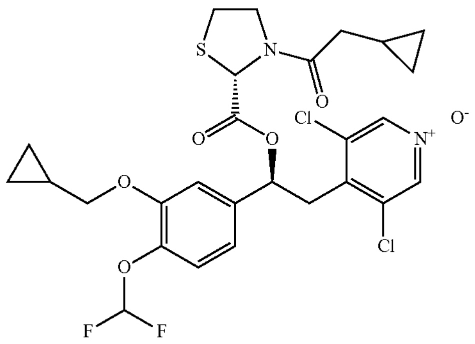 | Free Base | 617.08 | 3.78 (3) | >95:5 ($^1$H NMR) | $^1$H NMR (300 MHz, DMSO-$d_6$) δ ppm 8.54 (s, 2 H), 7.16 (d, 1 H), 7.04-7.10 (m, 1 H), 6.93 (dd, 1 H), 7.07 (t, 1 H), 5.95 (dd, 1 H), 5.37 and 5.64 (s, 1 H), 3.93 (d, 2 H), 3.84 (dd, 2 H), 3.42 (dd, 1 H), 3.28 (dd, 1 H), | −42.5 (c = 0.54, DCM) | 6 | Preparative HPLC (Method 2) |

TABLE 14-continued

| Entry | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| | | | | | | 3.16 (dt, 1 H), 2.93-3.07 (m, 1 H), 2.32 (d, 2 H), 1.10-1.36 (m, 1 H), 0.84-1.04 (m, 1 H), 0.51-0.67 (m, 2 H), 0.40-0.51 (m, 2 H), 0.26-0.39 (m, 2 H), -0.03-0.18 (m, 2 H) | | | |
| 190 | 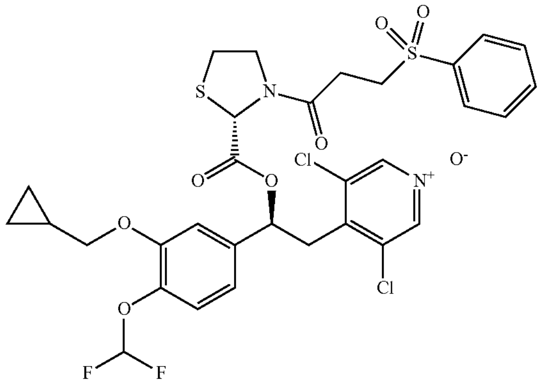 | Free Base | 731.3 | 3.85 (3) | >95:5 ($^1$H NMR) | $^1$H NMR (300 MHz, DMSO-$d_6$) δ ppm 8.52 (s, 2 H), 7.87-8.01 (m, 2 H), 7.73-7.84 (m, 1 H), 7.58-7.73 (m, 2 H), 7.16 (d, 1 H), 7.05 (d, 1 H), 6.92 (dd, 1 H), 7.07 (t, 1 H), 5.93 (dd, 1 H), 5.17 (s, 1 H), 3.91 (d, 2 H), 3.70-3.88 (m, 2 H), 3.35-3.63 (m, 4 H), 2.76-3.25 (m, 4 H), 1.08-1.31 (m, 1 H), 0.43-0.69 (m, 2 H), 0.20-0.43 (m, 2 H) | −27.4 (c = 0.3, DCM) | 6 | Flash chromatography on silica gel followed by preparative HPLC (Method 3) |

TABLE 14-continued

| Entry | Structure | SALT NAME | HPLC-MS characterization: MS/ESI$^+$ [MH]$^+$ | HPLC-MS characterization: $t_R$/min Method 1, 2 or 3 | Diastereomeric ratio | $^1$H NMR | $[\alpha]_D$ | Precursor | Purification Method |
|---|---|---|---|---|---|---|---|---|---|
| 191 | 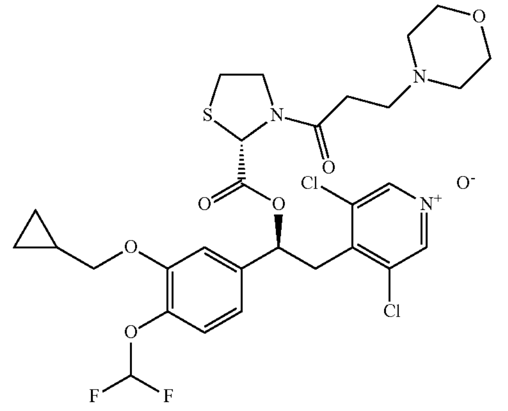 | trifluoroacetate | 676.01 | 3.19 (3) | >95:5 ($^1$H NMR) | $^1$H NMR (300 MHz, DMSO-$d_6$) δ ppm 9.41 (br. s., 1 H), 8.56 (s, 2 H), 7.22 (d, 1 H), 7.10 (d, 1 H), 6.98 (dd, 1 H), 7.09 (t, 1 H), 6.04 (dd, 1 H), 5.29 (s, 1 H), 3.96-4.15 (m, 2 H), 3.93 (d, 2 H), 3.62-3.90 (m, 4 H), 3.00-3.37 (m, 10 H), 2.90 (t, 2 H), 1.07-1.45 (m, 1 H), 0.51-0.68 (m, 2 H), 0.28-0.44 (m, 2 H) | −27.1 (c = 0.5, DCM) | 6 | Preparative HPLC (Method 3) |
| 192 | 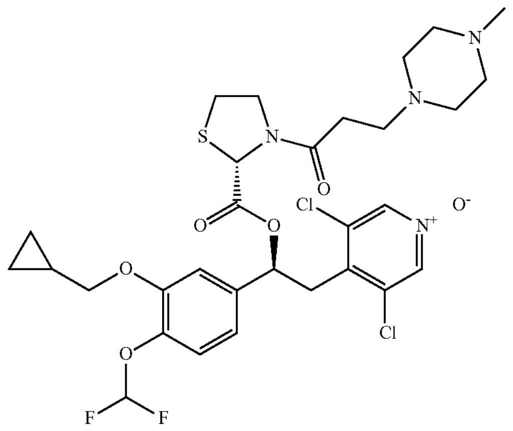 | trifluoroacetate mono salt | 689.44 | 2.92 (3) | >95:5 ($^1$H NMR) | $^1$H NMR (300 MHz, DMSO-$d_6$) δ ppm 8.55 (s, 2 H), 7.20 (d, 1 H), 7.08 (s, 1 H), 6.96 (dd, 1 H), 7.08 (t, 1 H), 6.00 (dd, 1 H), 5.30 (s, 1 H), 3.93 (d, 2 H), 2.75-3.84 (m, 18 H), 2.76 (s, 3 H), 1.11-1.40 (m, 1 H), 0.49-0.66 (m, 2 H), 0.24-0.44 (m, 2 H) | −32.4 (c = 0.3, DCM) | 6 | Preparative HPLC (Method 3) |

TABLE 14-continued
| Entry | Structure | SALT NAME | HPLC-MS characterization: MS/ESI$^+$ [MH]$^+$ | HPLC-MS characterization: $t_R$/min Method 1, 2 or 3 | Diastereomeric ratio | $^1$H NMR | $[\alpha]_D$ | Precursor | Purification Method |
|---|---|---|---|---|---|---|---|---|---|
| 193 | 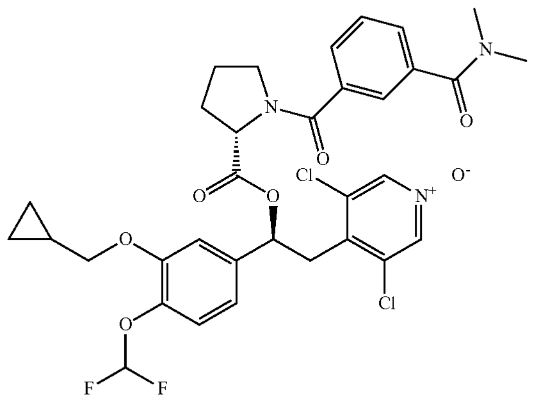 | Free Base | 692.43 | 3.39 (3) | >95:5 ($^1$H NMR) | $^1$H NMR (300 MHz, DMSO-$d_6$ 353 K) δ ppm 8.41 (s, 2 H), 7.37-7.61 (m, 4 H), 7.15 (d, 1 H), 7.07 (d, 1 H), 6.96 (dd, 1 H), 6.97 (t, 1 H), 6.01 (br. s., 1 H), 4.52 (dd, 1 H), 3.88 (d, 2 H), 3.50-3.64 (m, 2 H), 3.15-3.29 (m, 2 H), 2.97 (s, 6 H), 2.16-2.42 (m, 1 H), 1.52-2.03 (m, 3 H), 0.99-1.32 (m, 1 H), 0.42-0.73 (m, 2 H), 0.14-0.40 (m, 2 H) | −32.8 (c = 0.51, DCM) | Free base of 3 | Preparative HPLC (Method 2) |

TABLE 14-continued
| Entry | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 194 | 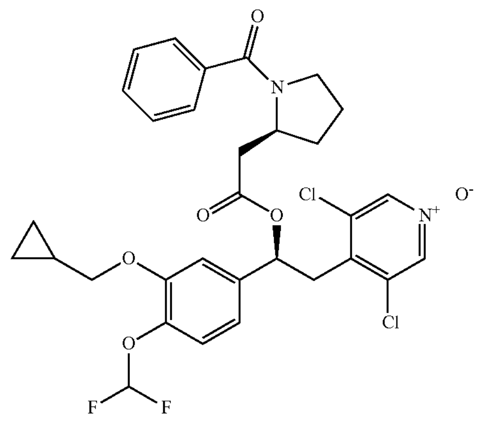 | Free Base | 635.34 | 3.88 (3) | >95:5 ($^1$H NMR) | $^1$H NMR (300 MHz, DMSO-$d_6$) δ ppm 8.55 (s, 2 H), 7.36-7.52 (m, 5 H), 7.19 (d, 1 H), 7.12 (br. s., 1 H), 6.99 (d, 1 H), 7.07 (t, 1 H), 5.87-6.14 (m, 1 H), 4.28 (br. s., 1 H), 3.91 (d, 2 H), 3.32-3.56 (m, 2 H), 3.13-3.32 (m, 2 H), 2.95 (dd, 1 H), 2.39-2.46 (m, 1 H), 1.91-2.10 (m, 1 H), 1.59-1.90 (m, 2 H), 1.35-1.59 (m, 1 H), 1.08-1.33 (m, 1 H), 0.45-0.71 (m, 2 H), 0.08-0.45 (m, 2 H) | −60.9 (c = 0.72, DCM) | Free Base of 179 | Preparative HPLC (Method 2) |

TABLE 14-continued
| Entry | Structure | SALT NAME | HPLC-MS characterization: MS/ESI$^+$ [MH]$^+$ | HPLC-MS characterization: $t_R$/min Method 1, 2 or 3 | Diastereomeric ratio | $^1$H NMR | $[\alpha]_D$ | Precursor | Purification Method |
|---|---|---|---|---|---|---|---|---|---|
| 195 | 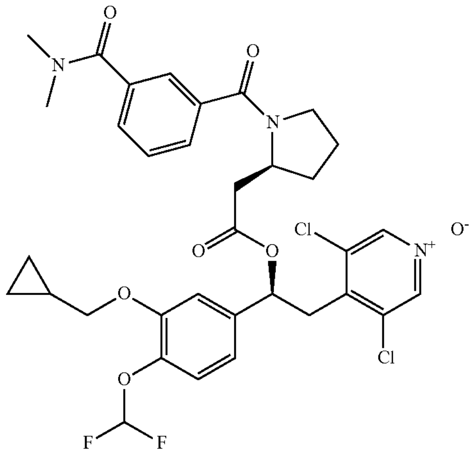 | Free Base | 706.38 | 3.42 (3) | >95:5 ($^1$H NMR) | $^1$H NMR (300 MHz, DMSO-$d_6$) δ ppm 8.55 (s, 2 H), 7.41-7.55 (m, 4 H), 7.18 (d, 1 H), 7.12 (s, 1 H), 6.99 (d, 1 H), 7.07 (t, 1 H), 6.00 (dd, 1 H), 4.18-4.45 (m, 1 H), 3.91 (d, 2 H), 3.77-4.01 (m, 2 H), 3.34-3.58 (m, 2 H), 3.15-3.34 (m, 2 H), 2.98 (br. s., 3 H), 2.91 (br. s., 3 H), 1.90-2.13 (m, 1 H), 1.60-1.90 (m, 2 H), 1.34-1.60 (m, 1 H), 1.02-1.32 (m, 1 H), 0.49-0.67 (m, 2 H), 0.24-0.42 (m, 2 H) | −60.1 (c = 0.48, DCM) | Free base of 179 | Preparative HPLC (Method 2) |

Example 20. Synthesis of 3,5-dichloro-4-((S)-2-(3-(cyclopropylmethoxy)-4-(difluoro-methoxy)phenyl)-2-((S)-3-(2-(3-(dimethylcarbamoyl)phenyl)acetyl)-thiazolidine-2-carbonyloxy)ethyl)pyridine 1-oxide (198)

Scheme 27

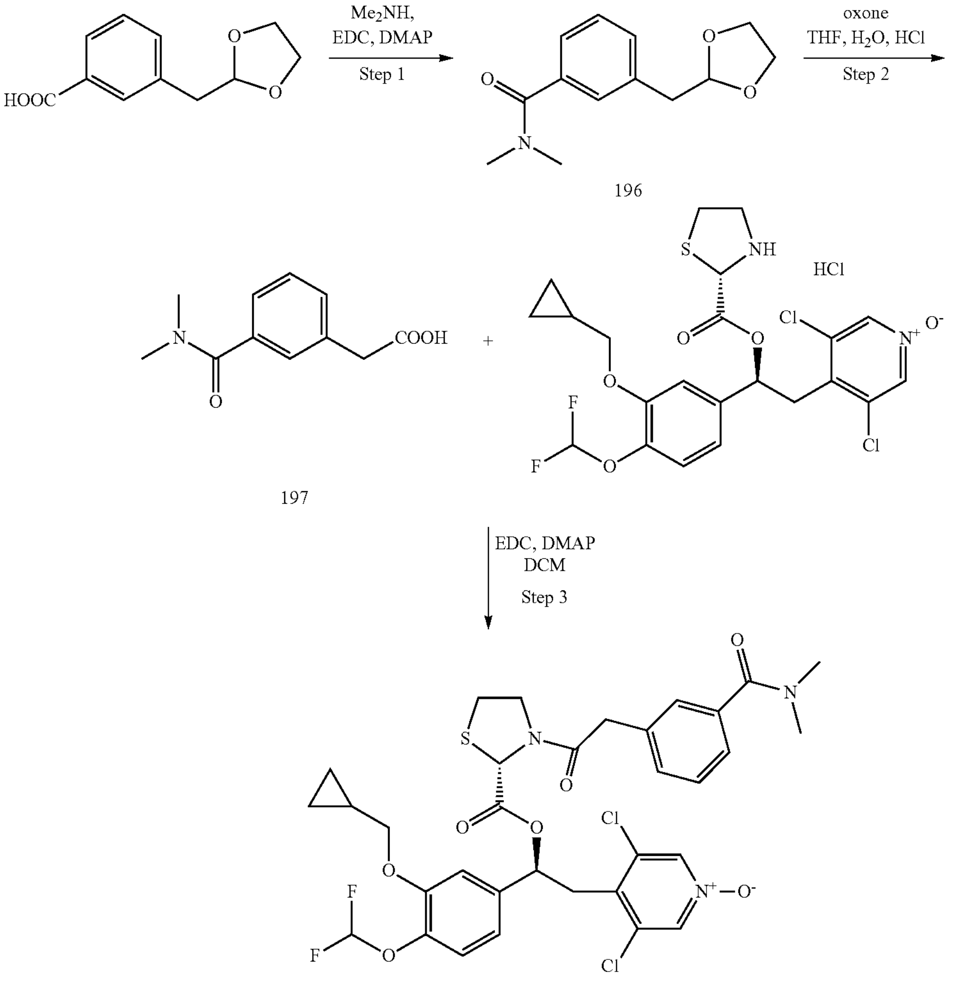

198

Step 1: 3-((1,3-dioxolan-2-yl)methyl)-N,N-dimethylbenzamide (196)

3-((1,3-dioxolan-2-yl)methyl)benzoic acid (250 mg, 1.201 mmol), dimethylamine hydrochloride (147 mg, 1.801 mmol), EDC (345 mg, 1.801 mmol), and DMAP (513 mg, 4.20 mmol) were dissolved in DCM (30 ml) and the solution was stirred at RT for 1 hour. The reaction mixture was washed twice with 1N HCl, and the organic layer was dried over $Na_2SO_4$. The solvent was removed under reduced pressure to give the desired product (244 mg, 1.037 mmol, 86% yield) MS/$ESI^+$ 236.18 $[MH]^+$.

Step 2: 2-(3-(dimethylcarbamoyl)phenyl)acetic acid (197)

To a solution of 3-((1,3-dioxolan-2-yl)methyl)-N,N-dimethylbenzamide (244 mg, 1.037 mmol) in THF (30 ml), water (20 ml), oxone (1913 mg, 3.11 mmol), and aqueous 37% HCl (2 ml, 23.92 mmol) were added, and the mixture was stirred at RT for 24 hours. Additional oxone (1.0 g, 1.627 mmol) and aqueous 37% HCl (1 ml, 11.96 mmol) were added, and the stirring was continued at RT for further 24 hours. The reaction mixture was diluted with water (100 ml) and extracted twice with DCM; (2×70 ml); the combined organic layers were dried over $Na_2SO_4$ and evaporated to dryness to afford the desired product (200 mg, 0.965 mmol, 93% yield) MS/$ESI^+$ 208.20 $[MH]^+$.

Step 3: 3,5-dichloro-4-((S)-2-(3-(cyclopropylmethoxy)-4-(difluoro-methoxy)phenyl)-2-((S)-3-(2-(3-(dimethylcarbamoyl)phenyl)acetyl)-thiazolidine-2-carbonyloxy)ethyl)pyridine 1-oxide (198)

3,5-dichloro-4-((S)-2-(3-(cyclopropylmethoxy)-4-(difluoro-methoxy)phenyl)-2-((S)-3-(2-(3-(dimethylcarbamoyl)

phenyl)acetyl)-thiazolidine-2-carbonyloxy)ethyl)pyridine 1-oxide was prepared according to an analogous procedure to that described in Step 3 (Scheme 13) Example 5, using DCM as the solvent. It was purified by treatment with polymer supported isocyanate followed by preparative HPLC (Method 2) (10% yield).

MS/ESI$^+$ 724.28 [MH]$^+$, $t_R$=3.82 min (Method 3); Diastereomeric Ratio >95:5 ($^1$H NMR);

$^1$H NMR (300 MHz, DMSO-d6) δ ppm 8.52 (s, 2H), 7.23-7.48 (m, 4H), 7.15 (d, 1H), 7.06 (d, 1H), 6.91 (dd, 1H), 6.79-7.43 (m, 1H), 5.93 (dd, 1H), 5.41 (s, 1H), 3.93 (dd, 2H), 3.88 (d, 2H), 3.82 (s, 2H), 3.41 (dd, 1H), 3.27 (dd, 1H), 3.00-3.22 (m, 2H), 2.96 (br. s., 3H), 2.90 (br. s., 3H), 1.06-1.39 (m, 1H), 0.46-0.63 (m, 2H), 0.06-0.41 (m, 2H)

The compound listed in Table 15 was prepared according to an analogous procedure to that described in Scheme 27 and by reacting the appropriate precursor listed (obtained as free base after basic treatment of hydrochloride salt with aqueous sat. $NaHCO_3$ followed by extraction with DCM), followed by an appropriate purification step as below indicated.

TABLE 15

| Entry | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 199 | 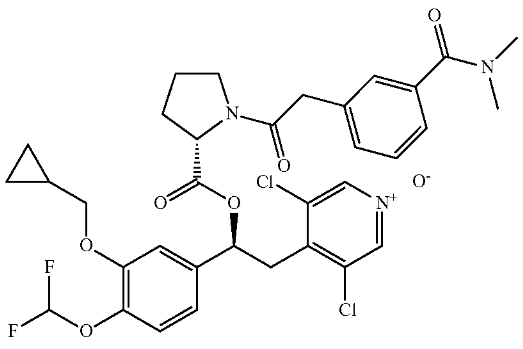 | Free Base | 706.36 | 3.50 (3) | >95:5 ($^1$H NMR B) | $^1$H NMR (300 MHz, DMSO-d6) δ ppm 8.56 (s, 2 H), 7.23-7.43 (m, 4 H), 7.13 (d, 1 H), 7.06 (d, 1 H), 6.90 (dd, 1 H), 7.05 (t, 1 H), 5.88 (dd, 1 H), 4.32 (dd, 1 H), 3.78-3.95 (m, 2 H), 3.73 (s, 2 H), 3.49-3.67 (m, 2 H), 3.39 (dd, 1 H), 3.22 (dd, 1 H), 2.94 (br. s., 3 H), 2.90 (br. s., 3 H), 2.05-2.24 (m, 1 H), 1.76-1.95 (m, 1 H), 1.47-1.76 (m, 2 H), 1.05-1.23 (m, 1 H), 0.46-0.62 (m, 2 H), 0.20-0.38 (m, 2 H) | −18.2 (c = 0.57, DCM). | Free base of 3 | Preparative HPLC (Method 2) followed by flash chromatography on silica gel |

Example 6. Synthesis of 3,5-dichloro-4-((2S)-2-(3-(cyclopropylmethoxy)-4-(difluoromethoxy)phenyl)-2-(3-(3-(cyclopropylmethoxy)-5-(N-(2-morpholinoethyl)methylsulfonamido)benzoyl)thiazolidine-2-carbonyloxy)ethyl)pyridine 1-oxide formate (49)
Scheme 14
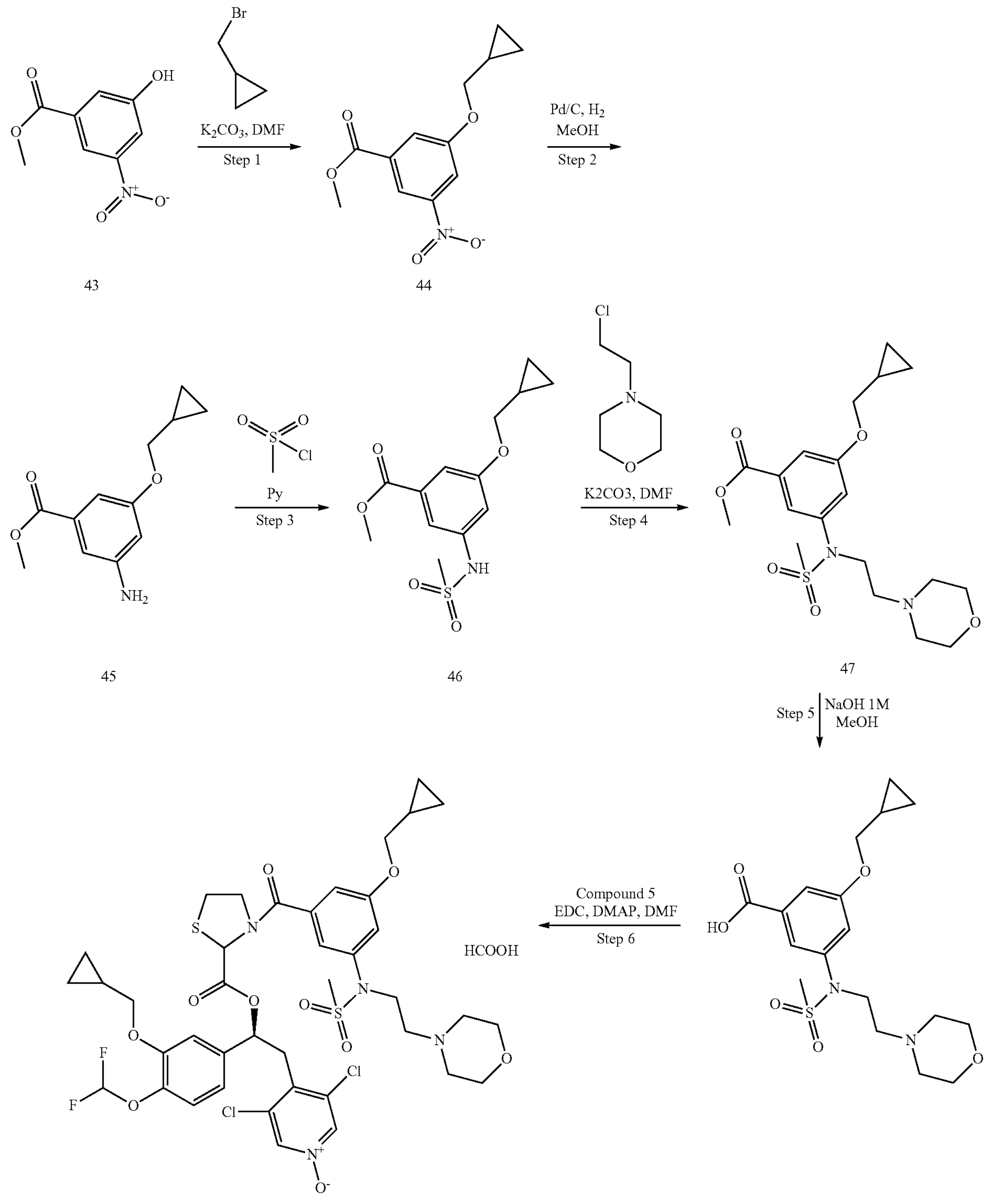
43 44 45 46 47 48 49

Step 1: methyl 3-(cyclopropylmethoxy)-5-nitrobenzoate (44)

Methyl 3-hydroxy-5-nitrobenzoate (43) (1.6 g, 8.1 mmol) was dissolved in DMF (15 ml). (Bromomethyl)cyclopropane (2.2 g, 16.2 mmol) and $K_2CO_3$ (1.7 g, 12.2 mmol) were added, and the mixture was stirred at 80° C. for 2 hours. The reaction was cooled at RT, diluted with water and filtered. The precipitate was dissolved in ethyl acetate, and the organic phase was dried over $Na_2SO_4$ and evaporated under vacuum to give 1.65 g of the desired product (yield 81%).

MS/ESI$^+$ 252.08 [MH]$^+$

Step 2: methyl 3-amino-5-(cyclopropylmethoxy)benzoate (45)

Methyl 3-(cyclopropylmethoxy)-5-nitrobenzoate (44) (4.9 g, 19.5 mmol) was dissolved in MeOH (200 ml), and Pd/C 5% (1.5 g, 0.7 mmol) was added. The solution was shaken under hydrogen atmosphere on a Parr apparatus at 40 psi for 1 hour. The catalyst was filtered on a Diatomaceus earth pad, and the solvent was evaporated under vacuum to give 3.67 g of the desired product (yield 85%).

MS/ESI$^+$ 222.11 [MH]$^+$

Step 3: methyl 3-(cyclopropylmethoxy)-5-(methylsulfonamido)benzoate (46)

Methyl 3-amino-5-(cyclopropylmethoxy)benzoate (45) (1.3 g, 5.9 mmol) was dissolved in pyridine (4 ml). Methanesulfonyl chloride (0.6 ml, 7.7 mmol) was added slowly at 0° C., and the mixture was stirred at RT for 2.5 hours. The reaction was diluted with aq HCl 1N, and the product was extracted with ethyl acetate. The organic phase was washed with HCl 1N, dried over $Na_2SO_4$ and evaporated under vacuum to give 1.7 g of the desired product (yield 97%). MS/ESI$^+$ 300.08 [MH]$^+$ Step 4: methyl 3-(cyclopropylmethoxy)-5-(N-(2-morpholinoethyl)methylsulfonamido)-benzoate (47)

Methyl 3-(cyclopropylmethoxy)-5-(methylsulfonamido) benzoate (46) (3 g, 10.02 mmol) was dissolved in DMF (25 ml). 4-(2-chloroethyl)morpholine (4.5 g, 30.1 mmol) and $K_2CO_3$ (2.1 g, 15.03 mmol) were added, and the mixture was stirred at 60° C. for 2 hours. The reaction was diluted with water and extracted with ethyl acetate. The organic phase was washed with water, dried over $Na_2SO_4$ and evaporated under vacuum to give 3 g of the desired product (yield 73%).

MS/ESI$^+$ 413.17 [MH]$^+$

Step 5: 3-(cyclopropylmethoxy)-5-(N-(2-morpholinoethyl)methylsulfonamido)benzoic acid (48)

Methyl 3-(cyclopropylmethoxy)-5-(N-(2-morpholinoethyl)methylsulfonamido)-benzoate (47) (3 g, 7.3 mmol) was dissolved in MeOH (45 ml). Aq. NaOH 1N (9 ml) was added, and the mixture was stirred at RT overnight. The reaction was diluted with aq. HCl 1N (9 ml), and the solvent was removed under vacuum to yield 3.7 g of the desired product (quantitative yield).

MS/ESI$^+$ 399.15 [MH]$^+$

Step 6: 3,5-dichloro-4-((2S)-2-(3-(cyclopropylmethoxy)-4-(difluoromethoxy)phenyl)-2-(3-(3-(cyclopropylmethoxy)-5-(N-(2-morpholinoethyl)methylsulfonamido)benzoyl)-thiazolidine-2-carbonyloxy)ethyl)pyridine 1-oxide formate (49)

Compound (49) was prepared according to an analogous procedure to that described in Example 3, step 1, starting from compound 5. The crude product was purified by preparative HPLC to obtain compound (49) as a formate salt.

MS/ESI$^+$ 915.3 [MH]$^+$; $t_R$=3.37; 3.43 (Method 2); Diastereomeric Ratio=47:53.

Example 7. Synthesis of 3,5-dichloro-4-((2S)-2-(3-(cyclopropylmethoxy)-4-(difluoromethoxy)phenyl)-2-(3-(5-((dimethylamino)methyl)thiophene-2-carbonyl)thiazolidine-2-carbonyloxy)ethyl)pyridine 1-oxide formate (51)

Scheme 15

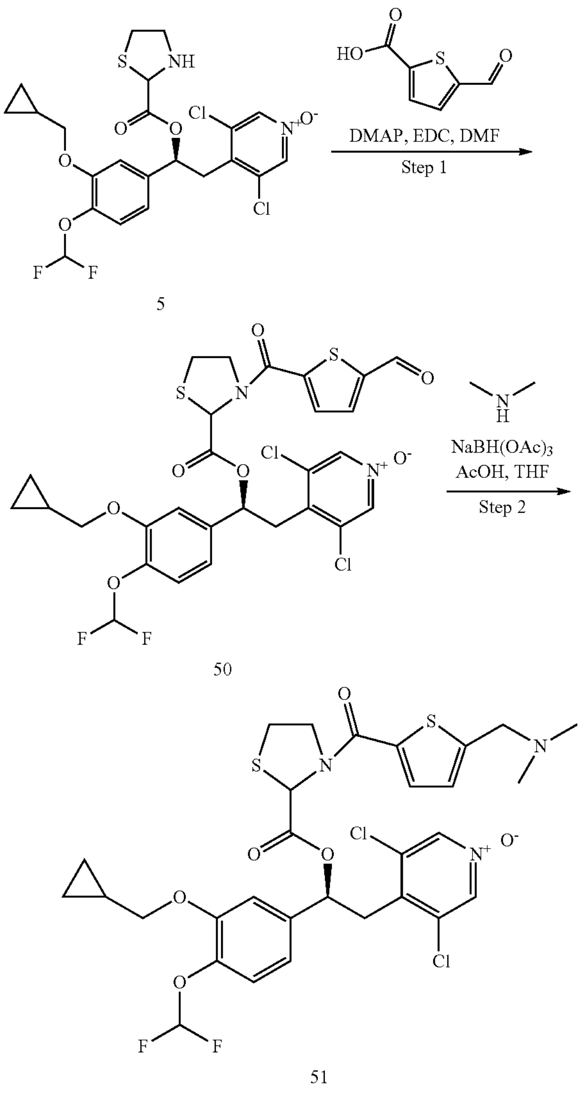

5

50

51

Step 1: 3,5-dichloro-4-((2S)-2-(3-(cyclopropylmethoxy)-4-(difluoromethoxy)phenyl)-2-(3-(5-formylthiophene-2-carbonyl)thiazolidine-2-carbonyloxy)ethyl)pyridine 1-oxide (50)

3,5-dichloro-4-((2S)-2-(3-(cyclopropylmethoxy)-4-(difluoromethoxy)phenyl)-2-(thiazolidine-2-carbonyloxy)ethyl)pyridine 1-oxide (5) (200 mg, 0.374 mmol), 5-formylthiophene-2-carboxylic acid (233 mg, 1.494 mmol), DMAP (100 mg, 0.822 mmol), and EDC (358 mg, 1.868 mmol) were dissolved in DMF (2 ml). The reaction was stirred at RT overnight, then it was diluted with water, and the precipitate was washed with water, dissolved in AcOEt and washed with aq. HCl 1N, aq. $Na_2CO_3$ sat. sol., and brine. The organic phase was dried over $Na_2SO_4$ and concentrated under vacuum to give 3,5-dichloro-4-((2S)-2-(3-(cyclopropylmethoxy)-4-(difluoromethoxy)phenyl)-2-(3-(5-formylthiophene-2-carbonyl)thiazolidine-2-carbonyloxy)ethyl)pyridine 1-oxide (150 mg, yield 60%). MS/ESI$^+$ 673.04 $[MH]^+$ Step 2: 3,5-dichloro-4-((2S)-2-(3-(cyclopropylmethoxy)-4-(difluoromethoxy)phenyl)-2-(3-(5-((dimethylamino)methyl)thiophene-2-carbonyl)thiazolidine-2-carbonyl oxy)ethyl)pyridine 1-oxide (51)

3,5-dichloro-4-((2S)-2-(3-(cyclopropylmethoxy)-4-(difluoromethoxy)phenyl)-2-(3-(3-formyl benzoyl)thiazolidine-2-carbonyloxy)ethyl)pyridine 1-oxide (50) (50 mg, 0.075 mmol) was dissolved in THF (1 ml). Acetic acid (8.58 μl, 0.150 mmol) and dimethylamine 2M in THF (7.95 μl, 0.150 mmol) were added, and the mixture was stirred at RT for 30 minutes. Sodium triacetoxyborohydride (32 mg, 0.150 mmol) was added, and the mixture was stirred at RT for 3 hours to achieve completion. The reaction mixture was diluted with water and extracted with AcOEt. The organic phase was dried over $Na_2SO_4$ and concentrated under vacuum. The crude product was purified by semi-preparative HPLC (Method 1) to give the wanted product as formate salt (16 mg, yield 31%). MS/ESI$^+$ 702.2 $[MH]^+$; $t_R$ (Method 2)=2.54; 2.68 min; Diastereomeric Ratio=21:79

Example 8. Synthesis of 3,5-dichloro-4-((S)-2-(3-(cyclopropylmethoxy)-4-(difluoromethoxy)phenyl)-2-((S)-3-(3-(dimethylcarbamoyl)phenylsulfonyl)thiazolidine-2-carbonyloxy)ethyl)pyridine 1-oxide (52)

Scheme 16

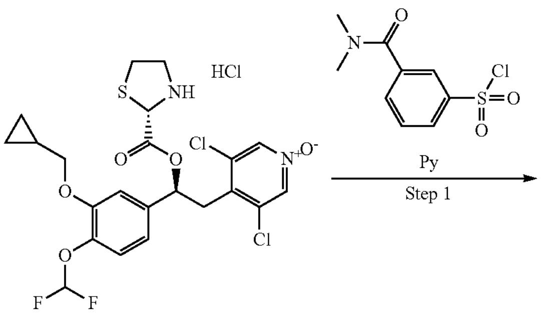

6

-continued

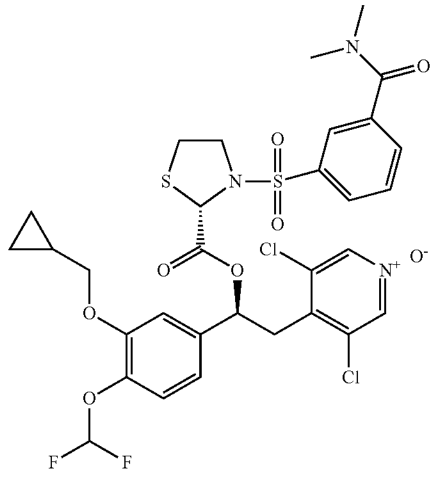

52

3,5-dichloro-4-((S)-2-(3-(cyclopropylmethoxy)-4-(difluoromethoxy)phenyl)-2-((S)-thiazolidine-2-carbonyloxy)ethyl)pyridine 1-oxide hydrochloride (6) (300 mg, 0.525 mmol) was dissolved in Py (3 ml, 37.1 mmol). 3-(dimethylcarbamoyl)benzene-1-sulfonyl chloride (156 mg, 0.630 mmol) was added, and the reaction was stirred at RT for 4 hours to achieve completion. The reaction mixture was diluted with aqueous HCl 1N, and extracted with ethyl acetate. The organic phase was washed with aqueous HCl 1N and brine, dried over $Na_2SO_4$ and concentrated under vacuum. The crude product was purified by flash chromatography (DCM/IsoPrOH 98/2) to give 3,5-dichloro-4-((S)-2-(3-(cyclopropylmethoxy)-4-(difluoromethoxy)phenyl)-2-((S)-3-(3-(dimethylcarbamoyl)phenylsulfonyl)thiazolidine-2-carbonyloxy)ethyl)pyridine 1-oxide (250 mg, 0.335 mmol, 63.8% yield).

MS/ESI$^+$ 746.2 $[MH]^+$; $[\alpha_D]$=−43.30 (c=0.51; $CHCl_3$), $t_R$=3.66 (Method 1); Diastereomeric Ratio=>99/1; $^1H$ NMR (400 MHz, DMSO-$d_6$) δ ppm 8.58 (s, 2H), 7.88-7.97 (m, 1H), 7.75-7.82 (m, 1H), 7.68-7.74 (m, 1H), 7.14-7.21 (m, 1H), 7.09-7.13 (m, 1H), 7.08 (t, J=75.00 Hz, 1H), 6.92-6.99 (m, 1H), 5.91-6.10 (m, 1H), 5.54 (s, 1H), 3.79-3.94 (m, 3H), 3.60-3.71 (m, 1H), 3.41-3.51 (m, 1H), 3.26-3.32 (m, 1H), 3.02 (s, 3H), 2.92-3.00 (m, 1H), 2.89 (s, 3H), 2.56-2.70 (m, 1H), 1.20-1.27 (m, 1H), 0.53-0.60 (m, 1H), 0.29-0.36 (m, 1H).

The compounds listed in Table 6 were prepared according to an analogous procedure to that described for Scheme 16 by reacting the appropriate precursors listed with commercial suitable reagents, followed by appropriate purification step as below reported, if needed. Heating under MW irradiation (50° C., 30 minutes) was used for the synthesis of compound 224.

TABLE 6

| En-try | Structure | SALT NAME | HPLC-MS characterization MS/ESI+ [MH]+ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 53 | 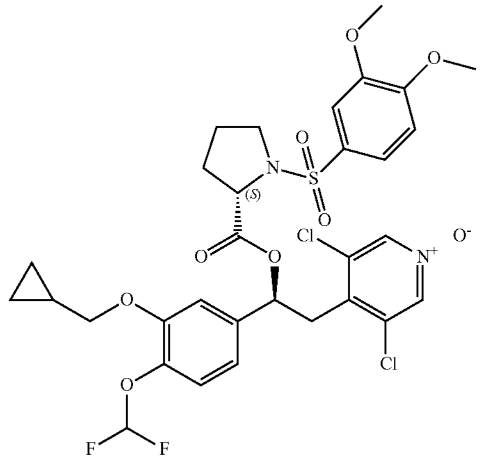 | Free Base | 717.2 | 6.97 (1) | >99:1 | 1H NMR (400 MHz, acetone) δ ppm 8.30 (s, 2 H), 7.39-7.48 (m, 1 H), 7.25-7.35 (m, 2 H), 7.17 (dd, J = 14.77, 8.16 Hz, 2 H), 7.03-7.10 (m, 1 H), 6.93 (t, J = 75.00 Hz, 1 H), 6.10-6.19 (m, 1 H), 4.21-4.31 (m, 1 H), 4.00 (d, J = 7.06 Hz, 2 H), 3.91 and 3.92 (2s, 2CH3, 6 H), 3.54-3.65 (m, 1 H), 3.40-3.50 (m, 1 H), 3.22-3.38 (m, 2 H), 1.70-1.86 (m, 2 H), 1.55-1.71 (m, 1 H), 1.29 (m, 2 H), 0.53-0.66 (m, 2 H), 0.32-0.46 (m, 2 H). | | 3 | Preparative HPLC (Method 1) |
| 54 | 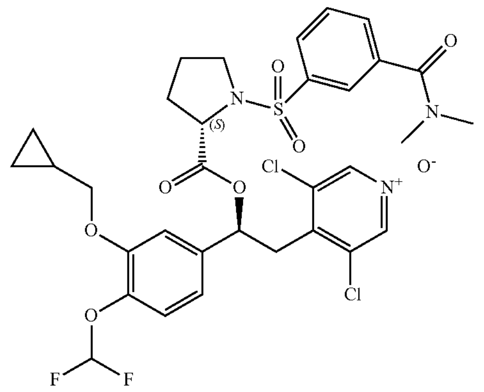 | Free Base | 728.1 | 6.12 (1) | >99:1 | $^1$H NMR (400 MHz, DMSO-$d_6$) δ ppm 8.60 (s, 2 H), 7.80-7.87 (m, 1 H), 7.68-7.80 (m, 3 H), 7.19 (d, J = 7.94 Hz, 1 H), 7.14 (d, J = 1.76 Hz, 1 H), 7.09 (t, J = 75.00 Hz, 1 H), 6.98 (dd, J = 8.38, 1.76 Hz, 1 H), 6.01 (dd, J = 9.70, 4.41 Hz, 1 H), 4.18 (dd, J = 8.60, 4.19 Hz, 1 H), 3.91 (d, J = 7.06 Hz, 2 H), 3.47 (dd, J = 14.33, 9.92 Hz, 1 H), 3.35-3.41 (m, 1 H), 3.26 (dd, J = 14.11, 4.41 Hz, 1 H), 3.18 (dt, J = 9.70, 6.84 Hz, 1 H), 3.02 (s, 3 H), 2.89 (s, 3 H), 1.88-2.02 (m, 1 H), 1.60-1.73 (m, 2 H), 1.47-1.60 (m, 1 H), 1.13-1.28 (m, 1 H), 0.51-0.60 (m, 2 H), 0.26-0.49 (m, 2 H). | | 3 | Flash Cromatography |

TABLE 6-continued

| En-try | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 55 | 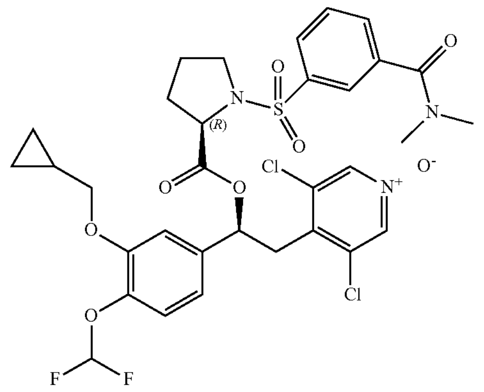 | Free Base | 728.1 | 6.20 (1) | >99:1 | $^1$H NMR (400 MHz, DMSO-$d_6$) δ ppm 8.54 (s, 2 H), 7.79-7.87 (m, 1 H), 7.70-7.76 (m, 2 H), 7.67 (d, J = 7.50 Hz, 1 H), 7.21 (d, J = 8.38 Hz, 1 H), 7.13 (d, J = 1.76 Hz, 1 H), 7.10 (t, J = 75.00 Hz, 1 H), 6.96-7.03 (m, 1 H), 5.94-6.01 (m, 1 H), 4.13-4.25 (m, 1 H), 3.85-3.97 (m, 2 H), 3.34-3.53 (m, 2 H), 3.23-3.30 (m, 1 H), 3.12-3.22 (m, 1 H), 3.00 (s, 3 H), 2.87 (s, 3 H), 1.86-2.01 (m, 1 H), 1.64-1.83 (m, 2 H), 1.52-1.63 (m, 1 H), 1.13-1.29 (m, 1 H), 0.56 (dd, J = 7.94, 1.32 Hz, 2 H), 0.25-0.41 (m, 2 H). | +39.02 (c = 0.51; $CHCl_3$) | 4 | Preparative HPLC (Method 1) |
| 56 | 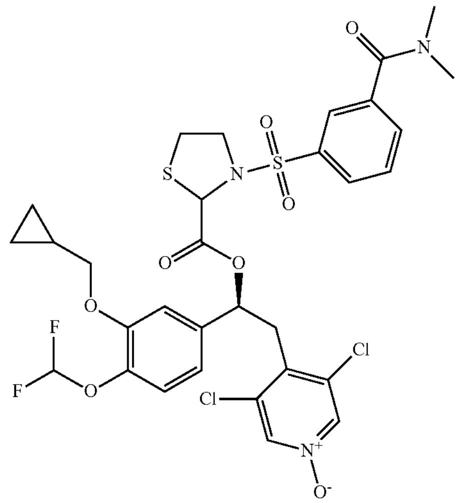 [SMILES: CN(C)C(=O)c1cccc(S(=O)(=O)N2CCSC2C(=O)O[C@@H](Cc2c(Cl)c[n+]([O-])cc2Cl)c2ccc(OC(F)F)c(OCC3CC3)c2)c1] | Free Base | 745.8 | 6.20; 6.30 (1) | 41:59 | | | 5 | Preparative HPLC (Method 1) |

TABLE 6-continued
| En-try | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 57 | 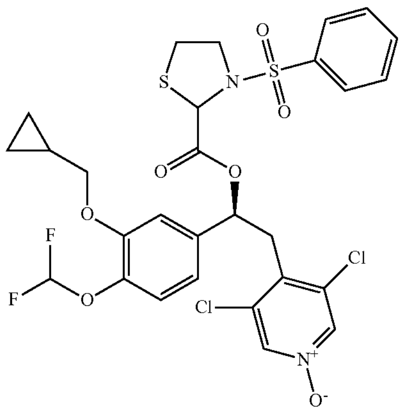 [SMILES: O=C(O[C@@H](Cc1c(Cl)c[n+]([O-])cc1Cl)c1ccc(OC(F)F)c(OCC2CC2)c1)C1SCCN1S(=O)(=O)c1ccccc1] | Free Base | 674.1 | 7.15; 7.27 (1) | 40:60 | | | 5 | Preparative HPLC (Method 1) |
| 58 | 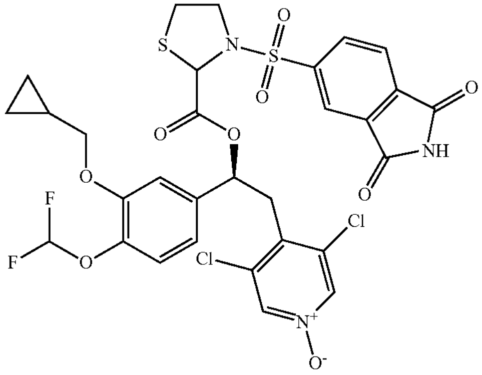 [SMILES: O=C1NC(=O)c2cc(S(=O)(=O)N3CCSC3C(=O)O[C@@H](Cc3c(Cl)c[n+]([O-])cc3Cl)c3ccc(OC(F)F)c(OCC4CC4)c3)ccc21] | Free Base | 744.0 | 6.44; 6.35 (1) | 40:60 | | | 5 | Triturated with Et2O |

TABLE 6-continued
| En-try | Structure | SALT NAME | HPLC-MS characterization MS/ESI+ [MH]+ | tR/min Method 1, 2 or 3 | Diastereomeric ratio | 1H NMR | [α]D | Precursor | Purification Method |
|---|---|---|---|---|---|---|---|---|---|
| 59 | 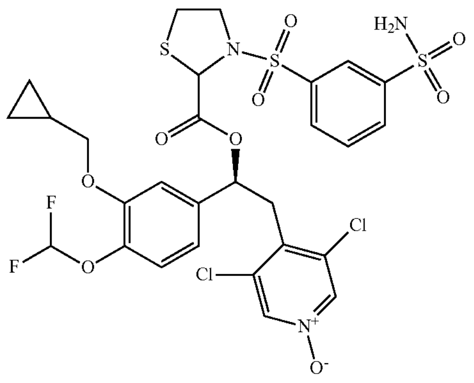 [SMILES: NS(=O)(=O)c1cccc(S(=O)(=O)N2CCSC2C(=O)O[C@@H](Cc2c(Cl)c[n+]([O-])cc2Cl)c2ccc(OC(F)F)c(OCC3CC3)c2)c1] | Free Base | 753.9 | 6.02; 6.22 (1) | 36:64 | | | 5 | Preparative HPLC (Method 1) |
| 60 | 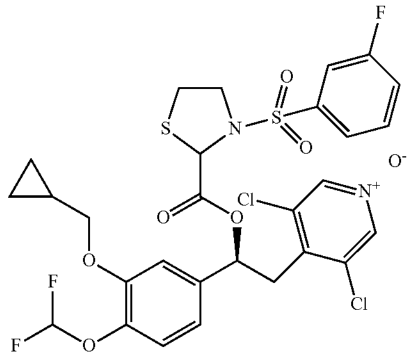 | Free Base | 693.0 | 7.52; 7.62 (1) | 38:62 | | | 5 | Preparative HPLC (Method 1) |

TABLE 6-continued
| En-try | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 61 | 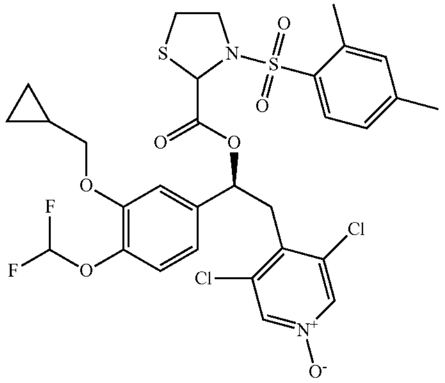 [SMILES: Cc1ccc(S(=O)(=O)N2CCSC2C(=O)O[C@@H](Cc2c(Cl)c[n+]([O-])cc2Cl)c2ccc(OC(F)F)c(OCC3CC3)c2)c(C)c1] | Free Base | 703.1 | 8.23; 8.32 (1) | 37:63 | | | 5 | Preparative HPLC (Method 1) |
| 62 | 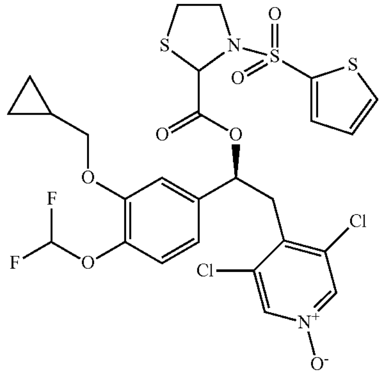 [SMILES: O=C(O[C@@H](Cc1c(Cl)c[n+]([O-])cc1Cl)c1ccc(OC(F)F)c(OCC2CC2)c1)C1SCCN1S(=O)(=O)c1cccs1] | Free Base | 681.0 | 7.17; 7.27 (1) | 42:58 | | | 5 | Preparative HPLC (Method 1) |

TABLE 6-continued
| En-try | Structure | SALT NAME | HPLC-MS characterization MS/ESI+ [MH]+ | tR/min Method 1, 2 or 3 | Diastereomeric ratio | $^1$H NMR | $[\alpha]_D$ | Precursor | Purification Method |
|---|---|---|---|---|---|---|---|---|---|
| 63 | 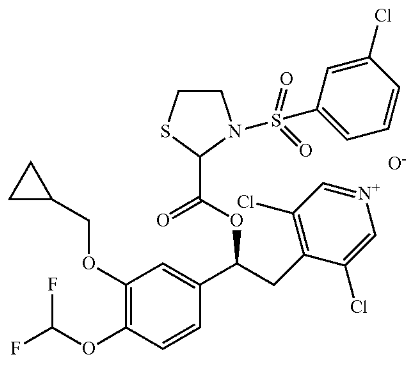 | Free Base | 708.8 | 7.92; 8.02 (1) | 38:62 | | | 5 | Preparative HPLC (Method 1) |
| 64 | 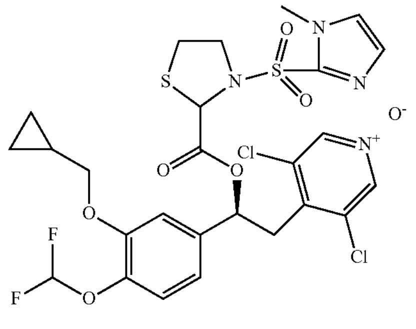 | Free Base | 678.9 | 6.35; 6.44 (1) | 41:59 | | | 5 | Preparative HPLC (Method 1) |

TABLE 6-continued
| En-try | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 65 | 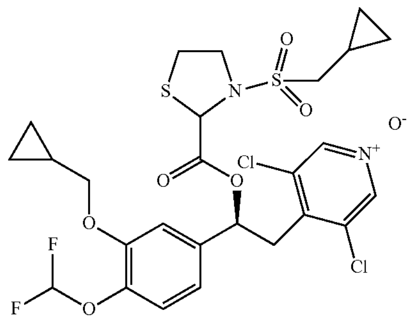 | Free Base | 652.8 | 6.97; 7.12 (1) | 51:49 | | | 5 | Preparative HPLC (Method 1) |
| 66 | 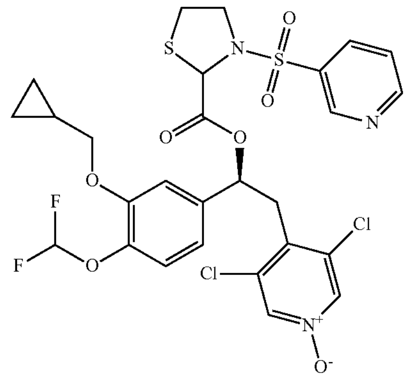 [SMILES: O=C(O[C@@H](Cc1c(Cl)c[n+]([O-])cc1Cl)c1ccc(OC(F)F)c(OCC2CC2)c1)C1SCCN1S(=O)(=O)c1cccnc1] | hydro-chloride | 675.7 | 6.40; 6.48 (1) | 38:62 | | | 5 | Preparative HPLC (Method 1) |

TABLE 6-continued
| En-try | Structure | SALT NAME | HPLC-MS characterization MS/ESI$^+$ [MH]$^+$ | t$_R$/min Method 1, 2 or 3 | Diastereomeric ratio | $^1$H NMR | $[\alpha]_D$ | Precursor | Purification Method |
|---|---|---|---|---|---|---|---|---|---|
| 67 | 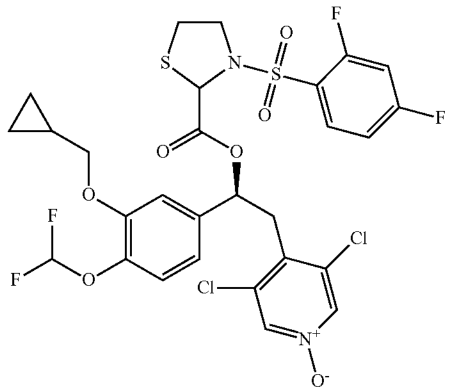 [SMILES: O=C(O[C@@H](Cc1c(Cl)c[n+]([O-])cc1Cl)c1ccc(OC(F)F)c(OCC2CC2)c1)C1SCCN1S(=O)(=O)c1ccc(F)cc1F] | Free Base | 710.9 | 7.63; 7.73 (1) | 41:59 | | | 5 | Preparative HPLC (Method 1) |
| 68 | 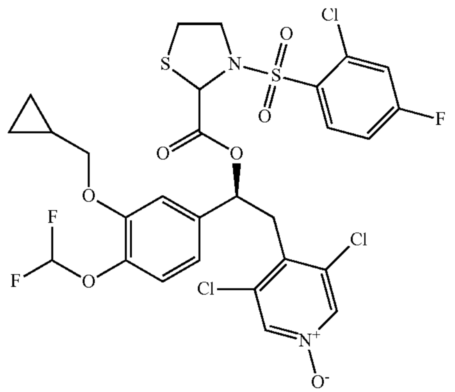 [SMILES: O=C(O[C@@H](Cc1c(Cl)c[n+]([O-])cc1Cl)c1ccc(OC(F)F)c(OCC2CC2)c1)C1SCCN1S(=O)(=O)c1ccc(F)cc1Cl] | Free Base | 726.9 | 7.90; 7.98 (1) | 40:60 | | | 5 | Preparative HPLC (Method 1) |

TABLE 6-continued
| | | | HPLC-MS characterization | | | | | | |
|---|---|---|---|---|---|---|---|---|---|
| En-try | Structure | SALT NAME | MS/ESI$^+$ [MH]$^+$ | $t_R$/min Method 1, 2 or 3 | Diastereomeric ratio | $^1$H NMR | $[\alpha]_D$ | Precursor | Purification Method |
| 69 | 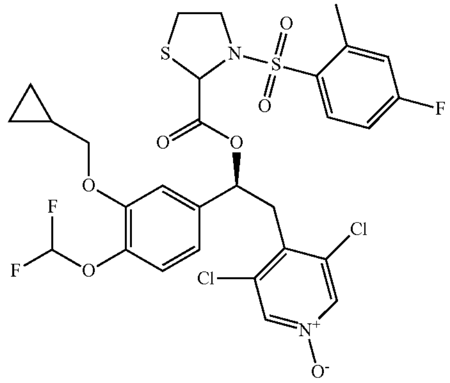 [SMILES: Cc1cc(F)ccc1S(=O)(=O)N1CCSC1C(=O)O[C@@H](Cc1c(Cl)c[n+]([O-])cc1Cl)c1ccc(OC(F)F)c(OCC2CC2)c1] | Free Base | 706.7 | 7.95; 8.05 (1) | 45:55 | | | 5 | Preparative HPLC (Method 1) |
| 70 | 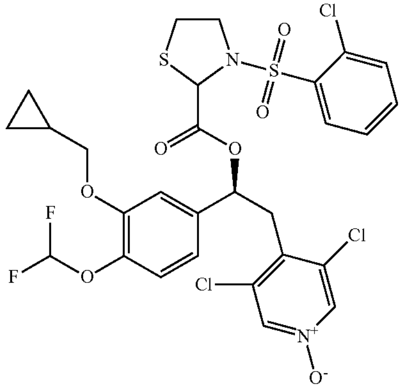 [SMILES: O=C(O[C@@H](Cc1c(Cl)c[n+]([O-])cc1Cl)c1ccc(OC(F)F)c(OCC2CC2)c1)C1SCCN1S(=O)(=O)c1ccccc1Cl] | Free Base | 708.8 | 7.72; 7.80 (1) | 39:61 | | | 5 | Preparative HPLC (Method 1) |

TABLE 6-continued
| En-try | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 71 | 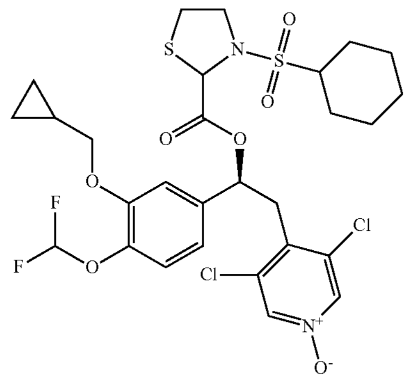 [SMILES: O=C(O[C@@H](Cc1c(Cl)c[n+]([O-])cc1Cl)c1ccc(OC(F)F)c(OCC2CC2)c1)C1SCCN1S(=O)(=O)C1CCCCC1] | Free Base | 680.9 | 7.87; 7.97 (1) | 32:68 | | | 5 | Preparative HPLC (Method 1) |
| 72 | 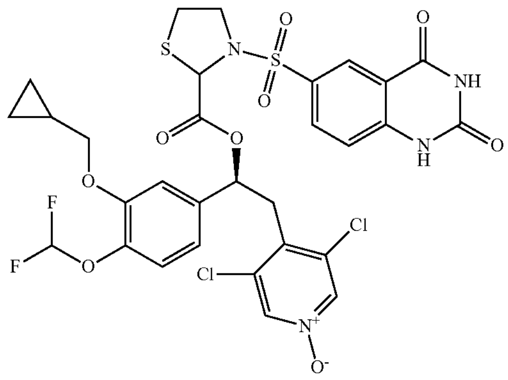 [SMILES: O=C(O[C@@H](Cc1c(Cl)c[n+]([O-])cc1Cl)c1ccc(OC(F)F)c(OCC2CC2)c1)C1SCCN1S(=O)(=O)c1ccc2[nH]c(=O)[nH]c(=O)c2c1] | Free Base | 758.8 | 5.53; 5.63 (1) | 37:63 | | | 5 | Trituration with ethyl ether |

TABLE 6-continued
| Entry | Structure | SALT NAME | HPLC-MS characterization MS/ESI+ $[MH]^+$ | $t_R$/min Method 1, 2 or 3 | Diastereomeric ratio | $^1H$ NMR | $[\alpha]_D$ | Precursor | Purification Method |
|---|---|---|---|---|---|---|---|---|---|
| 73 | 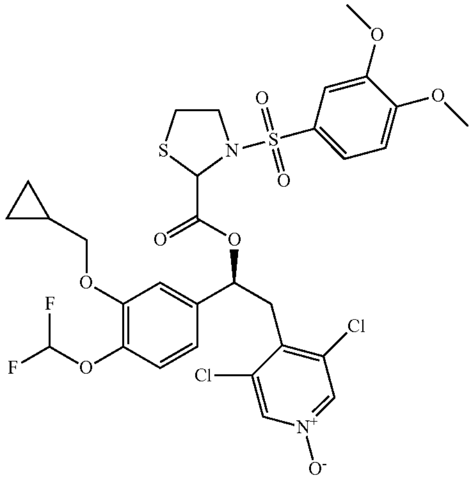 [SMILES: COc1ccc(S(=O)(=O)N2CCSC2C(=O)O[C@@H](Cc2c(Cl)c[n+]([O-])cc2Cl)c2ccc(OC(F)F)c(OCC3CC3)c2)cc1OC] | Free Base | 735.2 | 4.03; 4.09 (2) | 60:40 | | | 5 | Preparative HPLC (Method 1) |
| 74 | 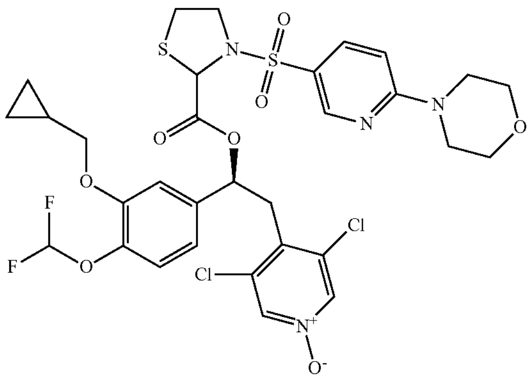 [SMILES: O=C(O[C@@H](Cc1c(Cl)c[n+]([O-])cc1Cl)c1ccc(OC(F)F)c(OCC2CC2)c1)C1SCCN1S(=O)(=O)c1ccc(N2CCOCC2)nc1] | formate | 761.2 | 3.97; 4.02 (2) | 35:65 | | | 5 | Preparative HPLC (Method 1) |

TABLE 6-continued
| En-try | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 75 | 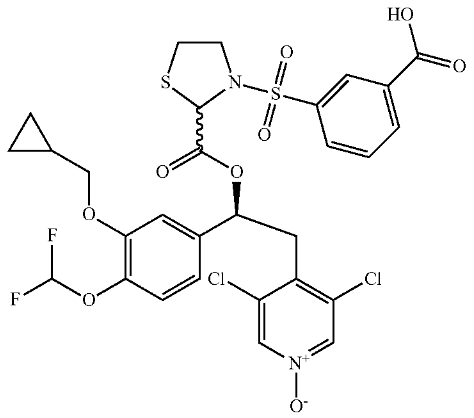 [SMILES: O=C(O)c1cccc(S(=O)(=O)N2CCSC2C(=O)O[C@@H](Cc2c(Cl)c[n+]([O-])cc2Cl)c2ccc(OC(F)F)c(OCC3CC3)c2)c1] | Free Base | 719.1 | 3.60 (2) | 96:4 | $^1$H NMR (400 MHz, DMSO-$d_6$) δ ppm 13.23-13.92 (bs, 1 H), 8.58 (s, 2 H), 8.20-8.41 (m, 2 H), 8.00-8.17 (m, 1 H), 7.78 (m, 1 H), 7.17 (d, J = 8.38 Hz, 1 H), 7.04-7.14 (m, 2 H), 6.96 (d, J = 1.76 Hz, 1 H), 5.94-6.13 (m, 1 H), 5.46 (s, 1 H), 3.90 (d, J = 6.62 Hz, 2 H), 3.69 (m, 2 H), 3.42-3.54 (m, 1 H), 3.25-3.30 (m, 1 H), 2.89-3.03 (m, 1 H), 2.64-2.73 (m, 1 H), 1.11-1.31 (m, 1 H), 0.56 (dd, J = 7.94, 1.76 Hz, 2 H), 0.33 (d, J = 4.85 Hz, 2 H). | | 5 | Triturated with Et2O |
| 76 | 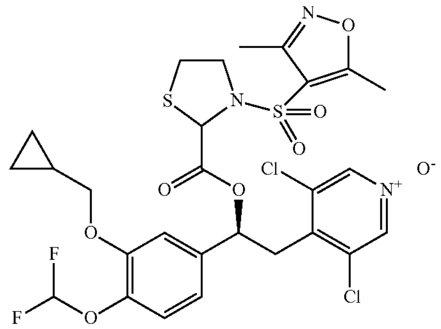 | Free Base | 694.2 | 4.09; 4.13 (2) | 33:67 | | | 5 | Preparative HPLC (Method 1) |

TABLE 6-continued
| En-try | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 77 | 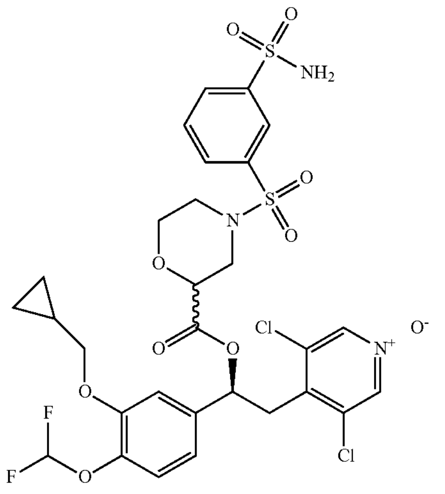 | Free Base | 751.8 | 5.62 (1) | >99:1 | $^1$H NMR (400 MHz, DMSO-$d_6$) δ ppm 8.55 (s, 2 H), 8.15 (m, 2 H), 7.96-8.02 (m, 1 H), 7.91 (m, 1 H), 7.65 (s, 2 H), 7.17 (m, 1 H), 7.05-7.13 (m, 2 H), 6.94-7.04 (m, 1 H), 5.65-6.06 (m, 1 H), 4.37-4.50 (m, 1 H), 3.92 (d, J = 7.06 Hz, 2 H), 3.72-3.82 (m, 1 H), 3.57-3.68 (m, 1 H), 3.41-3.53 (m, 1 H), 3.19-3.27 (m, 2 H), 3.09-3.18 (m, 1 H), 2.91-3.02 (m, 1 H), 2.78-2.89 (m, 1 H), 1.20-1.26 (m, 1 H), 0.49-0.65 (m, 2 H), 0.35 (d, J = 5.73 Hz, 2 H). | | 8 | Preparative HPLC (Method 1) |
| 78 | 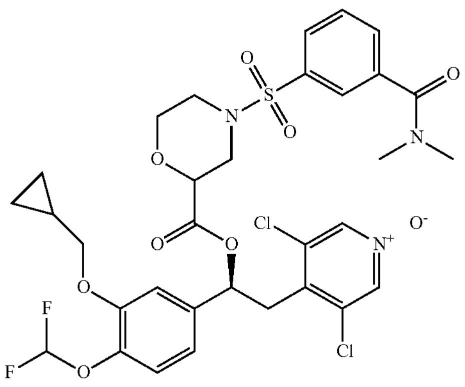 | Free Base | 744.0 | 5.84; 6.00 (1) | 64:36 | | | 8 | Preparative HPLC (Method 1) |

TABLE 6-continued
| En-try | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 79 | 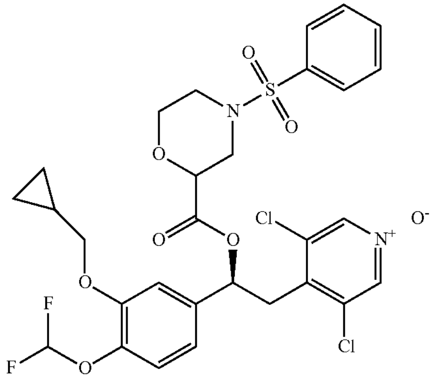 | Free Base | 673.2 | 3.92; 3.93 (2) | 67:33 | | | 8 | Triturated with MeOH |
| 80 | 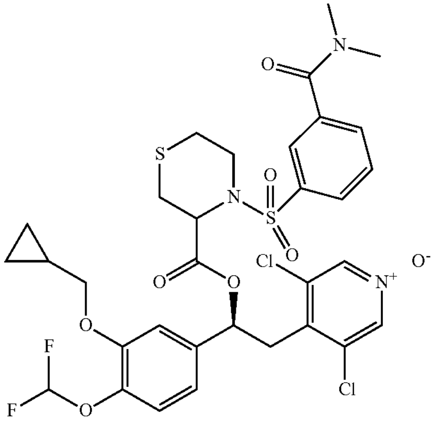 | Free Base | 759.8 | 6.27; 6.45 (1) | 47:53 | | | 13 | Preparative HPLC (Method 1) |

TABLE 6-continued
| Entry | Structure | SALT NAME | HPLC-MS characterization: MS/ESI$^+$ [MH]$^+$ | HPLC-MS characterization: $t_R$/min Method 1, 2 or 3 | Diastereomeric ratio | $^1$H NMR | $[\alpha]_D$ | Precursor | Purification Method |
|---|---|---|---|---|---|---|---|---|---|
| 81 | 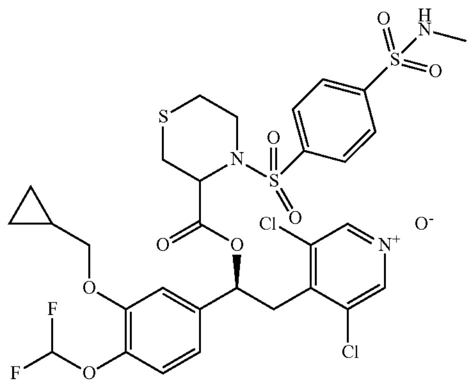 | Free Base | 781.8 | 6.52; 6.77 (1) | 39:61 | | | 13 | Preparative HPLC (Method 1) |
| 82 | 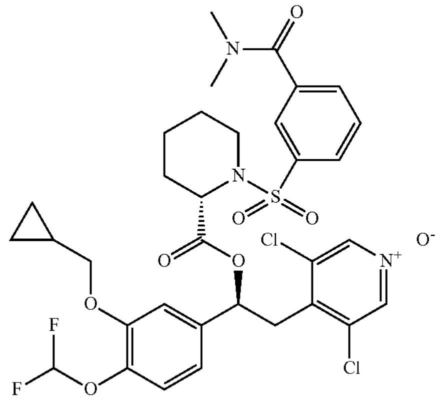 | Free Base | 742.2 | 3.85 (2) | >99:1 | $^1$H NMR (400 MHz, DMSO-$d_6$) δ ppm 8.50 (s, 2 H), 7.57-7.84 (m, 4 H), 7.08-7.17 (m, 1 H), 7.02-7.08 (m, 2 H), 6.83-6.93 (m, 1 H), 5.77-5.96 (m, 1 H), 4.56-4.73 (m, 1 H), 3.78-3.99 (m, 2 H), 3.56-3.74 (m, 1 H), 3.33-3.46 (m, 2 H), 3.17-3.26 (m, 1 H), 2.99 (s, 3 H), 2.86 (s, 3 H), 1.99-2.17 (m, 1 H), 1.43-1.69 (m, 3 H), 1.08-1.31 (m, 2 H), 0.71-0.99 (m, 1 H), 0.43-0.61 (m, 2 H), 0.25-0.38 (m, 2 H). | | 10 | Preparative HPLC (Method 1) |

TABLE 6-continued

| Entry | Structure | SALT NAME | HPLC-MS characterization MS/ESI+ [MH]+ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 83 | 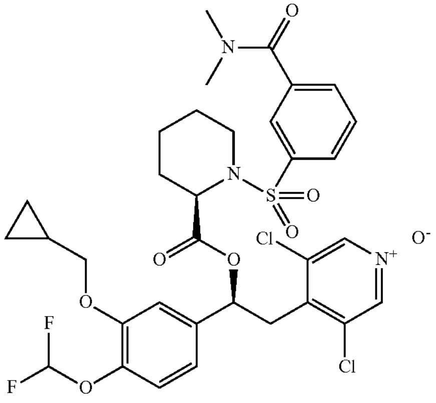 | Free Base | 742.3 | 3.74 (2) | 96:4 | $^1$H NMR (400 MHz, DMSO-$d_6$) δ ppm 8.58 (s, 2 H), 7.67-7.75 (m, 2 H), 7.56-7.64 (m, 1 H), 7.40-7.50 (m, 1 H), 7.18-7.24 (m, 1 H), 7.05-7.13 (m, 2 H), 6.89-6.95 (m, 1 H), 5.92-6.00 (m, 1 H), 4.68-4.80 (m, 1 H), 3.85-4.02 (m, 2 H), 3.54-3.66 (m, 1 H), 3.36-3.48 (m, 2 H), 3.16-3.26 (m, 1 H), 2.97 (s, 3 H), 2.81 (s, 3 H), 1.88-2.02 (m, 1 H), 1.38-1.64 (m, 4 H), 1.11-1.29 (m, 2 H), 0.65-0.80 (m, 1 H), 0.50-0.64 (m, 2 H), 0.29-0.42 (m, 2 H). | +16.33 (c = 0.24; CHCl3) | 9 | Preparative HPLC (Method 1) |
| 84 | 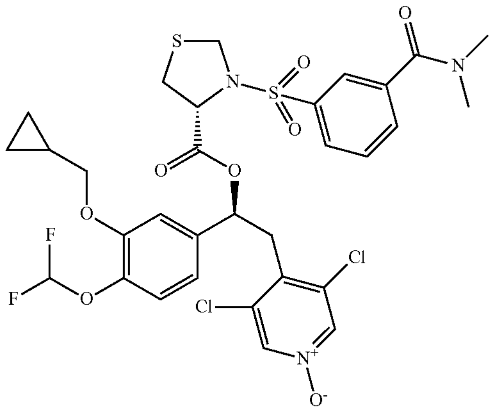 [SMILES: CN(C)C(=O)c1cccc(S(=O)(=O)N2CSC[C@H]2C(=O)O[C@@H](Cc2c(Cl)c[n+]([O-])cc2Cl)c2ccc(OC(F)F)c(OCC3CC3)c2)c1] | Free Base | 746.1 | 6.30 (1) | >99:1 | $^1$H NMR (400 MHz, DMSO-$d_6$) δ ppm 8.59 (s, 2 H), 7.85-7.99 (m, 2 H), 7.65-7.79 (m, 2 H), 7.13-7.22 (m, 2 H), 7.09 (t, J = 75.00 Hz, 1 H), 6.98 (dd, J = 8.38, 1.76 Hz, 1 H), 6.00 (dd, J = 9.26, 4.41 Hz, 1 H), 4.89 (dd, J = 7.28, 4.63 Hz, 1 H), 4.73 (d, J = 10.58 Hz, 1 H), 4.32 (d, J = 10.58 Hz, 1 H), 3.92 (d, J = 7.06 Hz, 2 H), 3.46 (dd, J = 14.11, 9.70 Hz, 1 H), 3.23-3.30 (m, 1 H), 2.93-3.08 (m, 5 H), 2.88 (s, 3 H), 1.23 (d, J = 7.06 Hz, 1 H), 0.49-0.64 (m, 2 H), 0.33 (q, J = 4.85 Hz, 2 H). | | 11 | Preparative HPLC (Method 1) |

TABLE 6-continued

| En-try | Structure | SALT NAME | HPLC-MS characterization MS/ESI+ [MH]+ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 85 | 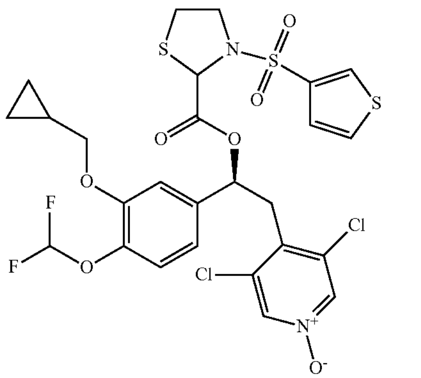 [SMILES: O=C(O[C@@H](Cc1c(Cl)c[n+]([O-])cc1Cl)c1ccc(OC(F)F)c(OCC2CC2)c1)C1SCCN1S(=O)(=O)c1ccsc1] | Free Base | 680.8 | 7.07; 7.18 (1) | 36:64 | | | 5 | Triturated with Et2O |
| 86 | 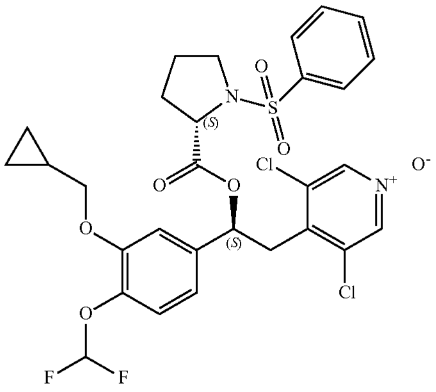 | Free Base | 657.3 | 4.09 (2) | 98:2 | $^1$H NMR (400 MHz, DMSO-$d_6$) δ ppm 8.61 (s, 2 H), 7.69-7.82 (m, 3 H), 7.60-7.68 (m, 2 H), 7.19 (d, J = 7.94 Hz, 1 H), 7.14 (d, J = 1.76 Hz, 1 H), 7.08 (t, J = 75.00 Hz, 1 H), 6.98 (dd, J = 8.38, 1.76 Hz, 1 H), 6.02 (dd, J = 9.70, 4.41 Hz, 1 H), 4.13 (dd, J = 8.60, 4.19 Hz, 1 H), 3.92 (d, J = 6.62 Hz, 2 H), 3.47 (dd, J = 14.11, 9.70 Hz, 1 H), 3.33-3.41 (m, 1 H), 3.26 (dd, J = 14.11, 4.41 Hz, 1 H), 3.16 (ddd, J = 9.81, 6.84, 6.73 Hz, 1 H), 1.83-1.98 (m, 1 H), 1.58-1.74 (m, 2 H), 1.41-1.57 (m, 1 H), 1.14-1.27 (m, 1 H), 0.48-0.63 (m, 2 H), 0.26-0.40 (m, 2 H) | | 3 | No purification |

TABLE 6-continued

| Entry | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 87 | 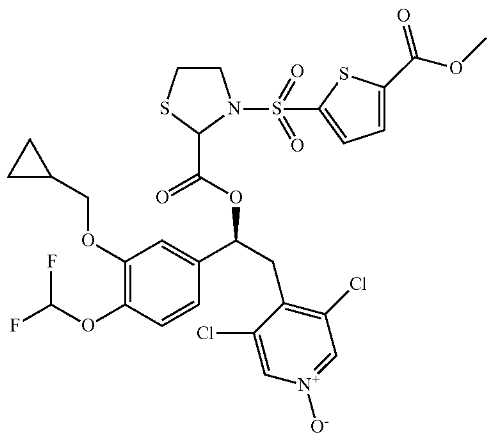 [SMILES: COC(=O)c1ccc(S(=O)(=O)N2CCSC2C(=O)O[C@@H](Cc2c(Cl)c[n+]([O-])cc2Cl)c2ccc(OC(F)F)c(OCC3CC3)c2)s1] | Free Base | 739.1 | 4.30; 4.25 (2) | 32:68 | | | 5 | Preparative HPLC (Method 1) |
| 88 | 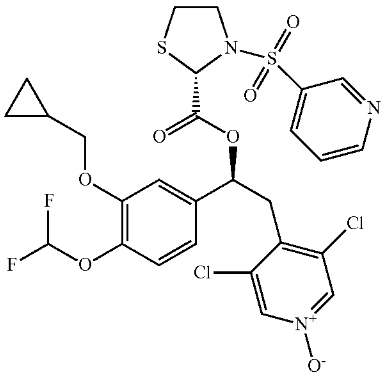 [SMILES: O=C(O[C@@H](Cc1c(Cl)c[n+]([O-])cc1Cl)c1ccc(OC(F)F)c(OCC2CC2)c1)[C@@H]1SCCN1S(=O)(=O)c1cccnc1] | Free Base | 676.2 | 3.62 (2) | 99:1 | $^1$H NMR (400 MHz, DMSO-$d_6$) δ ppm 9.05 (d, J = 2.20 Hz, 1 H), 8.91 (dd, J = 4.63, 1.54 Hz, 1 H), 8.58 (s, 2 H), 8.31 (ddd, J = 8.27, 1.87, 1.76 Hz, 1 H), 7.69 (dd, J = 8.38, 4.85 Hz, 1 H), 7.18 (d, J = 7.94 Hz, 1 H), 7.05-7.14 (m, 2 H), 6.95 (dd, J = 8.16, 1.54 Hz, 1 H), 6.01 (dd, J = 9.04, 5.07 Hz, 1 H), 5.63 (s, 1 H), 3.80-3.96 (m, 3 H), 3.61-3.72 (m, 1 H), 3.46 (dd, J = 14.11, 9.26 Hz, 1 H), 3.28-3.40 (m, 2 H), 2.91-3.04 (m, 1 H), 2.69 (ddd, J = 11.14, 6.39, 6.28 Hz, 1 H), 1.21 (ddd, J = 12.13, 7.50, 4.63 Hz, 1 H), 0.49-0.64 (m, 2 H), 0.26-0.41 (m, 2 H). | −43.74 (c = 0.53; $CHCl_3$) | 6 | Preparative HPLC (Method 1) |

TABLE 6-continued

| En-try | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 89 | 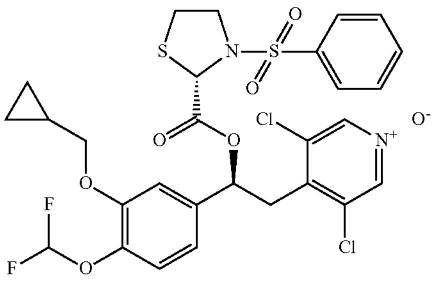 | Free Base | 675.2 | 4.20 (2) | 97:3 | $^1$H NMR (400 MHz, DMSO-$d_6$) δ ppm 8.60 (s, 2 H), 7.87 (d, J = 7.50 Hz, 2 H), 7.75 (d, J = 7.50 Hz, 1 H), 7.61-7.70 (m, 2 H), 7.18 (d, J = 7.94 Hz, 1 H), 7.05-7.14 (m, 2 H), 6.96 (dd, J = 8.38, 1.76 Hz, 1 H), 6.01 (dd, J = 9.26, 4.85 Hz, 1 H), 5.43 (s, 1 H), 3.90 (d, J = 7.06 Hz, 2 H), 3.75-3.85 (m, 1 H), 3.59-3.68 (m, 1 H), 3.44 (d, J = 9.26 Hz, 1 H), 3.29 (m, 1 H), 2.91-3.00 (m, 1 H), 2.64 (d, J = 11.03 Hz, 1 H), 1.18 (d, J = 7.06 Hz, 1 H), 0.56 (dd, J = 7.94, 1.76 Hz, 2 H), 0.26-0.40 (m, 2 H). | −37.96 (c = 0.56; $CHCl_3$) | 6 | Flash Cromatography |
| 90 | 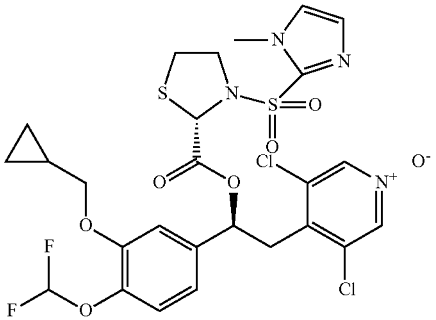 | Free Base | 679.2 | 3.61 (2) | 99:1 | $^1$H NMR (400 MHz, DMSO-$d_6$) δ ppm 8.54 (s, 2 H), 7.52 (m, 1 H), 7.18 (d, J = 8.38 Hz, 1 H), 7.10-7.16 (m, 2 H), 7.09 (t, J = 75.00 Hz, 1 H), 6.97 (dd, J = 8.38, 1.76 Hz, 1 H), 6.02 (dd, J = 9.26, 4.85 Hz, 1 H), 5.49 (s, 1 H), 3.86-3.99 (m, 6 H), 3.71-3.80 (m, 1 H), 3.43 (dd, J = 14.11, 9.70 Hz, 1 H), 3.25-3.31 (m, 1 H), 2.92-3.10 (m, 2 H), 1.15-1.30 (m, 1 H), 0.49-0.65 (m, 2 H), 0.29-0.42 (m, 2 H). | −43.30 (c = 0.48; $CHCl_3$) | 6 | Preparative HPLC (Method 1) |

TABLE 6-continued
| En-try | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 91 | 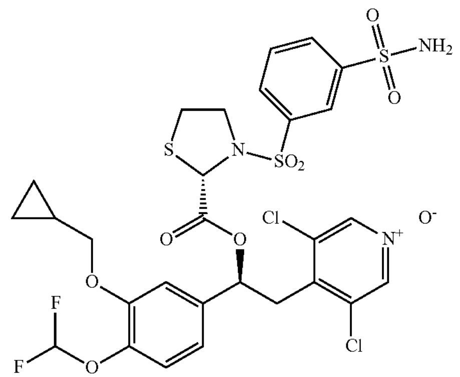 | Free Base | 754.1 | 3.58 (2) | >99:1 | $^1$H NMR (400 MHz, DMSO-$d_6$) δ ppm 8.59 (s, 2 H), 8.28 (m, 1 H), 8.14 (dd, J = 15.66, 8.16 Hz, 2 H), 7.87 (t, J = 7.94 Hz, 1 H), 7.56-7.72 (m, 2 H), 7.18 (d, J = 8.38 Hz, 1 H), 7.06-7.15 (m, 2 H), 6.96 (dd, J = 8.38, 1.76 Hz, 1 H), 6.03 (dd, J = 8.82, 5.29 Hz, 1 H), 5.50 (s, 1 H), 3.85-3.99 (m, 2 H), 3.65-3.82 (m, 2 H), 3.47 (dd, J = 14.11, 8.82 Hz, 1 H), 3.25-3.30 (m, 1 H), 2.94-3.05 (m, 1 H), 2.63-2.78 (m, 1 H), 1.13-1.32 (m, 1 H), 0.46-0.63 (m, 2 H), 0.26-0.43 (m, 2 H). | | 6 | Preparative HPLC (Method 1) |
| 92 | 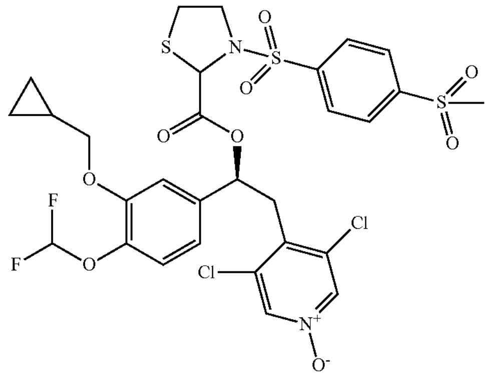 | Free Base | 753.1 | 3.70; 3.77 (2) | 27:73 | | | 5 | Preparative HPLC (Method 1) |

TABLE 6-continued

| Entry | Structure | SALT NAME | HPLC-MS characterization MS/ESI+ [MH]+ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 93 | 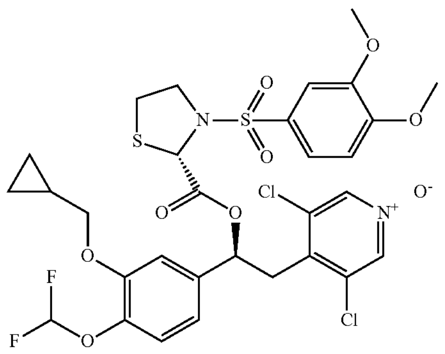 | Free Base | 735.2 | 4.12 (2) | 97:3 | $^1$H NMR (400 MHz, DMSO-$d_6$) δ ppm 8.59 (s, 2 H), 7.45 (dd, J = 8.38, 2.21 Hz, 1H), 7.32 (d, J = 1.76 Hz, 1 H), 7.15-7.21 (m, 2 H), 7.11 (d, J = 1.76 Hz, 1 H), 7.08 (t, J = 75.00 Hz, 1 H), 6.95 (dd, J = 8.38, 1.76 Hz, 1 H), 6.01 (dd, J = 9.26, 4.85 Hz, 1 H), 5.51 (s, 1 H), 3.77-3.95 (m, 9 H), 3.54-3.66 (m, 1 H), 3.45 (dd, J = 14.11, 9.26 Hz, 1 H), 3.25-3.28 (m, 1 H), 2.87-3.00 (m, 1 H), 2.52-2.64 (m, 1 H), 1.19-1.28 (m, 1 H), 0.45-0.65 (m, 2 H), 0.27-0.39 (m, 2 H). | | 6 | No purification |
| 94 | 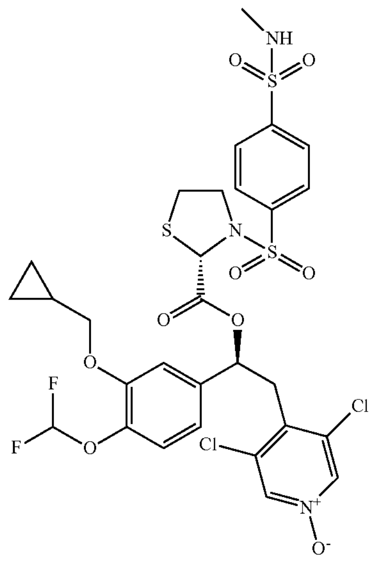 [SMILES: CNS(=O)(=O)c1ccc(S(=O)(=O)N2CCS[C@H]2C(=O)O[C@@H](Cc2c(Cl)c[n+]([O-])cc2Cl)c2ccc(OC(F)F)c(OCC3CC3)c2)cc1] | Free Base | 768.1 | 4.00 (2) | 99:1 | $^1$H NMR (400 MHz, DMSO-$d_6$) δ ppm 8.60 (s, 2 H), 8.07-8.16 (m, 2 H), 7.94-8.05 (m, 2 H), 7.71-7.84 (bs, 1 H), 7.14-7.21 (m, 1 H), 7.08 (m, 2 H), 6.91-6.99 (m, 1 H), 5.92-6.11 (m, 1 H), 5.51 (s, 1 H), 3.90 (d, J = 7.06 Hz, 2 H), 3.76-3.85 (m, 1 H), 3.63-3.74 (m, 1 H), 3.40-3.52 (m, 1 H), 3.25-3.35 (m, 1 H), 2.92-3.07 (m, 1 H), 2.63-2.80 (m, 1 H), 2.48 (s, 3H), 1.13-1.30 (m, 1 H), 0.49-0.63 (m, 2 H), 0.26-0.40 (m, 2 H). | | 6 | Preparative HPLC (Method 1) |

TABLE 6-continued

| En-try | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 95 | 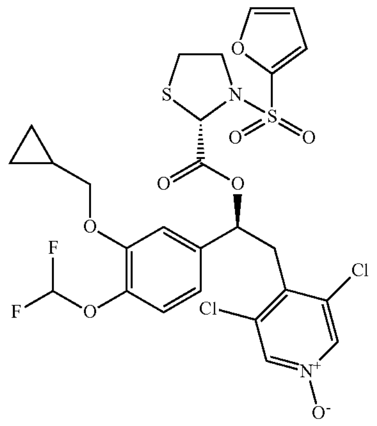 [SMILES: O=C(O[C@@H](Cc1c(Cl)c[n+]([O-])cc1Cl)c1ccc(OC(F)F)c(OCC2CC2)c1)[C@@H]1SCCN1S(=O)(=O)c1ccco1] | Free Base | 665.2 | 4.19 (2) | 99:1 | $^1$H NMR (400 MHz, DMSO-$d_6$) δ ppm 8.59 (s, 2 H), 8.06-8.11 (m, 1 H), 7.32-7.41 (m, 1 H), 7.15-7.22 (m, 1 H), 7.06-7.14 (m, 2 H), 6.94-7.01 (m, 1 H), 6.76-6.82 (m, 1 H), 5.95-6.07 (m, 1 H), 5.33 (s, 1 H), 3.84-3.98 (m, 2 H), 3.67-3.83 (m, 2 H), 3.39-3.53 (m, 1 H), 3.24-3.29 (m, 1 H), 2.98-3.09 (m, 1 H), 2.77-2.88 (m, 1 H), 1.16-1.29 (m, 1 H), 0.52-0.63 (m, 2 H), 0.29-0.40 (m, 2 H). | | 6 | Preparative HPLC (Method 1) |
| 96 | 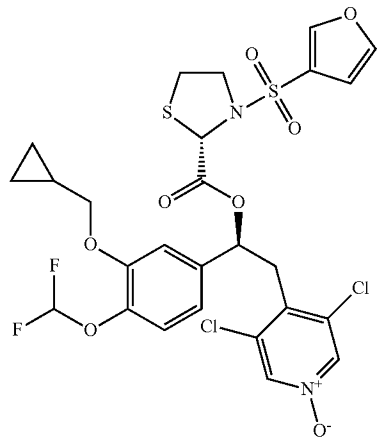 [SMILES: O=C(O[C@@H](Cc1c(Cl)c[n+]([O-])cc1Cl)c1ccc(OC(F)F)c(OCC2CC2)c1)[C@@H]1SCCN1S(=O)(=O)c1ccoc1] | Free Base | 665.2 | 4.13 (2) | >99:1 | $^1$H NMR (400 MHz, DMSO-$d_6$) δ ppm 8.58 (s, 2 H), 8.45-8.52 (m, 1 H), 7.89-8.00 (m, 1 H), 7.15-7.22 (m, 1 H), 7.05-7.14 (m, 2 H), 6.93-7.01 (m, 2 H), 5.92-6.09 (m, 1 H), 5.45 (s, 1 H), 3.84-3.96 (m, 2 H), 3.60-3.82 (m, 2 H), 3.37-3.52 (m, 2 H), 2.94-3.09 (m, 1 H), 2.79-2.89 (m, 1 H), 1.13-1.32 (m, 1 H), 0.48-0.65 (m, 2 H), 0.26-0.42 (m, 2 H). | | 6 | Preparative HPLC (Method 1) |

TABLE 6-continued

| En-try | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 97 | 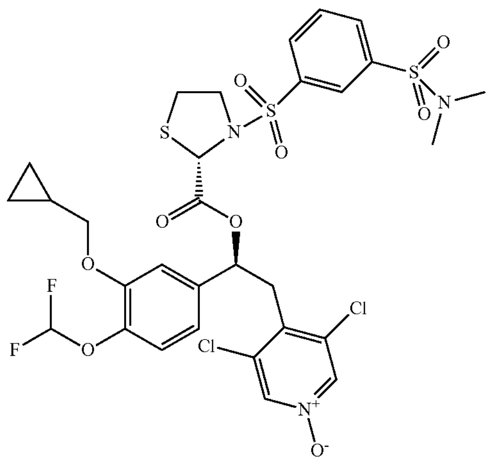 [SMILES: CN(C)S(=O)(=O)c1cccc(S(=O)(=O)N2CCS[C@H]2C(=O)O[C@@H](Cc2c(Cl)c[n+]([O-])cc2Cl)c2ccc(OC(F)F)c(OCC3CC3)c2)c1] | Free Base | 782.1 | 4.35 (2) | 98:2 | $^1$H NMR (400 MHz, DMSO-$d_6$) δ ppm 8.57 (s, 2 H), 8.23 (m, 1 H), 8.11 (m, 2 H), 7.95 (m, 1 H), 7.18 (d, J = 7.94 Hz, 1 H), 7.11 (d, J = 2.20 Hz, 1 H), 7.08 (t, J = 75.00 Hz, 1 H), 6.91-6.98 (m, 1 H), 5.95-6.06 (m, 1 H), 5.61 (s, 1 H), 3.90 (dd, J = 7.06, 1.32 Hz, 3 H), 3.61-3.72 (m, 1 H), 3.42-3.51 (m, 1 H), 3.26-3.31 (m, 1 H), 2.92-3.05 (m, 1 H), 2.62-2.75 (m, 7 H), 1.14-1.28 (m, 1 H), 0.56 (dd, J = 7.94, 1.76 Hz, 2 H), 0.33 (dd, J = 4.63, 1.10 Hz, 2 H). | | 6 | Preparative HPLC (Method 1) |
| 98 | 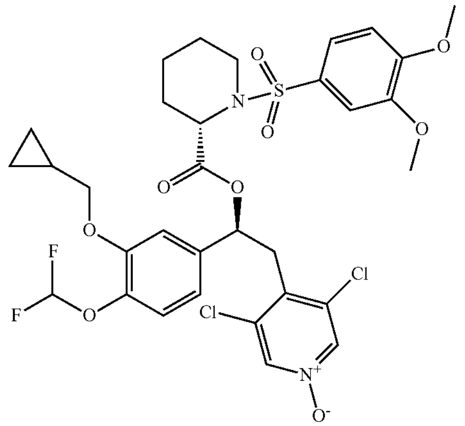 [SMILES: COc1ccc(S(=O)(=O)N2CCCC[C@H]2C(=O)O[C@@H](Cc2c(Cl)c[n+]([O-])cc2Cl)c2ccc(OC(F)F)c(OCC3CC3)c2)cc1OC] | Free Base | 731.2 | 4.52 (2) | 98:2 | $^1$H NMR (400 MHz, DMSO-$d_6$) δ ppm 8.62 (s, 2 H), 7.20 (m, 2 H), 7.12-7.17 (m, 1 H), 7.07 (d, J = 2.21 Hz, 3 H), 6.86-6.93 (m, 1 H), 5.81-5.96 (m, 1 H), 4.53-4.70 (m, 1 H), 3.85 (m, 5 H), 3.80 (s, 3 H), 3.51-3.65 (m, 1 H), 3.35-3.47 (m, 1 H), 3.17-3.28 (m, 1 H), 2.93-3.06 (m, 1 H), 1.97-2.10 (m, 1 H), 1.40-1.64 (m, 3 H), 1.12-1.29 (m, 2 H), 0.80-0.99 (m, 1 H), 0.50-0.62 (m, 2 H), 0.25-0.40 (m, 2 H). | | 10 | Preparative HPLC (Method 1) |

TABLE 6-continued

| En-try | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 99 | 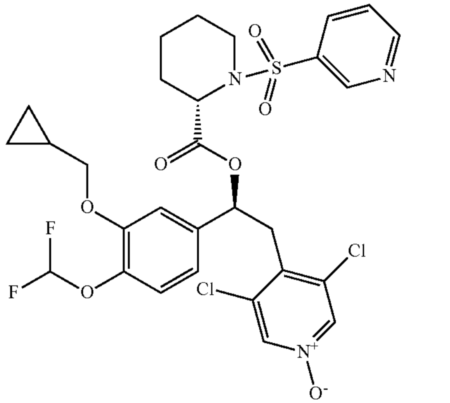 [SMILES: O=C(O[C@@H](Cc1c(Cl)c[n+]([O-])cc1Cl)c1ccc(OC(F)F)c(OCC2CC2)c1)[C@@H]1CCCCN1S(=O)(=O)c1cccnc1] | Free Base | 672.3 | 4.17 (2) | 98:2 | $^1$H NMR (400 MHz, DMSO-$d_6$) δ ppm 8.78-8.86 (m, 2 H), 8.66 (s, 2 H), 7.99-8.11 (m, 1 H), 7.55-7.65 (m, 1 H), 7.11-7.21 (m, 1 H), 7.02-7.10 (m, 2 H), 6.84-6.93 (m, 1 H), 5.83-5.92 (m, 1 H), 4.65-4.76 (m, 1 H), 3.79-3.96 (m, 2 H), 3.62-3.74 (m, 1 H), 3.35-3.47 (m, 1 H), 3.18-3.26 (m, 1 H), 2.86-3.05 (m, 1 H), 2.05-2.17 (m, 1 H), 1.46-1.74 (m, 3 H), 1.12-1.32 (m, 2 H), 0.80-0.98 (m, 1 H), 0.50-0.63 (m, 2 H), 0.26-0.41 (m, 2 H). | | 10 | Preparative HPLC (Method 1) |
| 100 | 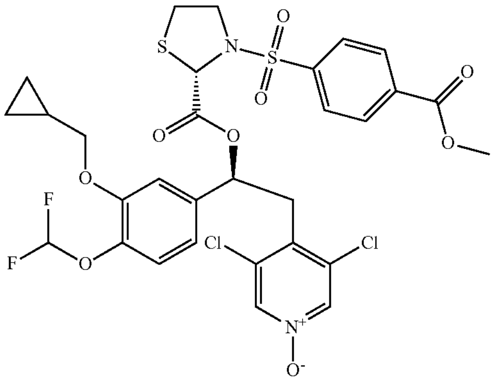 [SMILES: COC(=O)c1ccc(S(=O)(=O)N2CCS[C@H]2C(=O)O[C@@H](Cc2c(Cl)c[n+]([O-])cc2Cl)c2ccc(OC(F)F)c(OCC3CC3)c2)cc1] | Free Base | 733.1 | 4.54 (2) | >99:1 | $^1$H NMR (400 MHz, DMSO-$d_6$) δ ppm 8.60 (s, 2 H), 8.17 (d, J = 8.38 Hz, 2 H), 8.03 (m, 2 H), 7.15-7.20 (m, 1 H), 7.05-7.13 (m, 2 H), 6.92-6.98 (m, 1 H), 5.93-6.09 (m, 1 H), 5.49 (s, 1 H), 3.91 (m, 5 H), 3.77-3.86 (m, 1 H), 3.64-3.72 (m, 1 H), 3.41-3.51 (m, 1 H), 3.26-3.30 (m, 1 H), 2.91-3.03 (m, 1 H), 2.64-2.77 (m, 1 H), 1.14-1.29 (m, 1 H), 0.51-0.60 (m, 2 H), 0.28-0.37 (m, 2 H). | | 6 | Preparative HPLC (Method 1) |

TABLE 6-continued

| En-try | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 101 | 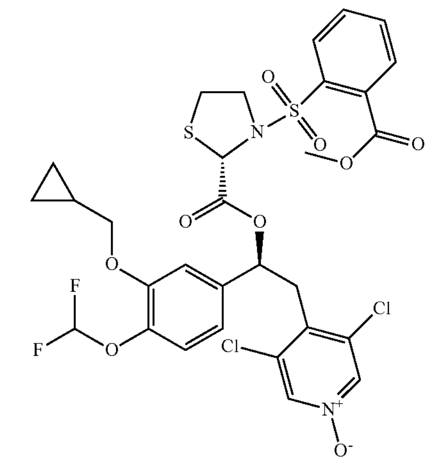 [SMILES: COC(=O)c1ccccc1S(=O)(=O)N1CCS[C@H]1C(=O)O[C@@H](Cc1c(Cl)c[n+]([O-])cc1Cl)c1ccc(OC(F)F)c(OCC2CC2)c1] | Free Base | 733.1 | 4.44 (2) | 96:4 | $^1$H NMR (400 MHz, DMSO-$d_6$) δ ppm 8.57 (s, 2 H), 7.96-8.04 (m, 1 H), 7.71-7.84 (m, 2 H), 7.62-7.69 (m, 1 H), 7.13-7.20 (m, 1 H), 7.05-7.12 (m, 2 H), 6.91-6.98 (m, 1 H), 5.92-6.02 (m, 1 H), 5.68 (s, 1 H), 3.96-4.06 (m, 1 H), 3.86-3.92 (m, 2 H), 3.84 (s, 3 H), 3.56-3.67 (m, 1 H), 3.39-3.51 (m, 1 H), 3.24-3.29 (m, 1 H), 2.95-3.06 (m, 1 H), 2.74-2.84 (m, 1 H), 1.16-1.27 (m, 1 H), 0.51-0.63 (m, 2 H), 0.29-0.37 (m, 2 H). | | 6 | Preparative HPLC (Method 1) |
| 102 | 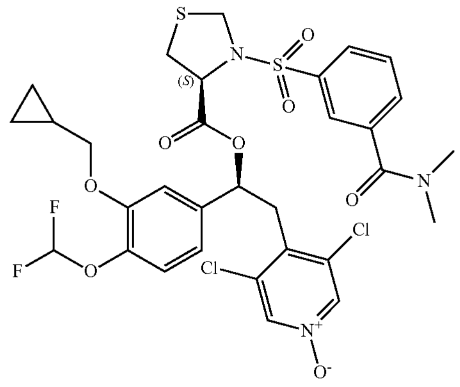 | Free Base | 746.2 | 4.12 (2) | 99:1 | $^1$H NMR (400 MHz, DMSO-$d_6$) δ ppm 8.54 (s, 2 H), 7.92-7.98 (m, 1 H), 7.84-7.91 (m, 1 H), 7.63-7.77 (m, 2 H), 7.18-7.25 (m, 1 H), 7.12-7.17 (m, 1 H), 7.09 (t, J = 75.00 Hz, 1 H), 6.96-7.03 (m, 1 H), 5.95-6.02 (m, 1 H), 4.92-5.04 (m, 1 H), 4.67-4.78 (m, 1 H), 4.25-4.34 (m, 1 H), 3.86-4.00 (m, 2 H), 3.42-3.56 (m, 1 H), 3.21-3.29 (m, 1 H), 3.00 (m, 4 H), 2.86 (m, 4 H), 1.14-1.29 (m, 1 H), 0.50-0.63 (m, 2 H), 0.28-0.39 (m, 2 H). | | 12 | Preparative HPLC (Method 1) |

TABLE 6-continued

| En-try | Structure | SALT NAME | HPLC-MS characterization MS/ESI+ [MH]+ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 103 | 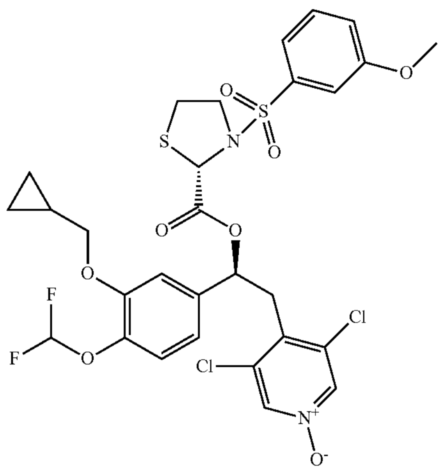 [SMILES: COc1cccc(S(=O)(=O)N2CCS[C@H]2C(=O)O[C@@H](Cc2c(Cl)c[n+]([O-])cc2Cl)c2ccc(OC(F)F)c(OCC3CC3)c2)c1] | Free Base | 705.2 | 4.80 (2) | 97:3 | $^1$H NMR (400 MHz, DMSO-$d_6$) δ ppm 8.58 (s, 2 H), 7.53-7.60 (m, 1 H), 7.40-7.46 (m, 1 H), 7.29-7.37 (m, 2 H), 7.16-7.20 (m, 1 H), 7.09-7.12 (m, 1 H), 7.08 (t, J = 75.00 Hz, 1 H), 6.93-6.98 (m, 1 H), 5.96-6.07 (m, 1 H), 5.50 (s, 1 H), 3.88-3.94 (m, 2 H), 3.87 (s, 3 H), 3.77-3.85 (m, 1 H), 3.59-3.67 (m, 1 H), 3.40-3.50 (m, 1 H), 3.25-3.30 (m, 1 H), 2.91-3.02 (m, 1 H), 2.61-2.70 (m, 1 H), 1.15-1.29 (m, 1 H), 0.53-0.61 (m, 2 H), 0.29-0.38 (m, 2 H) | | 6 | Trituration with Et2O |
| 104 | 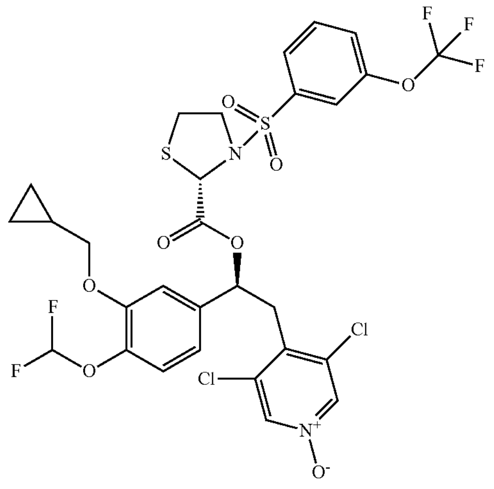 [SMILES: O=C(O[C@@H](Cc1c(Cl)c[n+]([O-])cc1Cl)c1ccc(OC(F)F)c(OCC2CC2)c1)[C@@H]1SCCN1S(=O)(=O)c1cccc(OC(F)(F)F)c1] | Free Base | 759.1 | 5.20 (2) | 98:2 | $^1$H NMR (400 MHz, DMSO-$d_6$) δ ppm 8.57 (s, 2 H), 7.89-7.98 (m, 2 H), 7.80 (d, J = 5.29 Hz, 2 H), 7.18 (d, J = 8.38 Hz, 1 H), 7.07-7.13 (m, 2 H), 6.95 (dd, J = 8.38, 1.76 Hz, 1 H), 6.01 (dd, J = 8.82, 5.29 Hz, 1 H), 5.62 (s, 1 H), 3.79-3.97 (m, 3 H), 3.58-3.73 (m, 1 H), 3.41-3.53 (m, 1 H), 3.29 (d, J = 4.85 Hz, 1 H), 2.90-3.03 (m, 1 H), 2.62-2.74 (m, 1 H), 1.14-1.31 (m, 1 H), 0.48-0.65 (m, 2 H), 0.26-0.41 (m, 2 H). | | 6 | No purification |

TABLE 6-continued

| En-try | Structure | SALT NAME | HPLC-MS characterization MS/ESI+ [MH]+ | tR/min Method 1, 2 or 3 | Diastereomeric ratio | $^1$H NMR | $[\alpha]_D$ | Precursor | Purification Method |
|---|---|---|---|---|---|---|---|---|---|
| 105 | 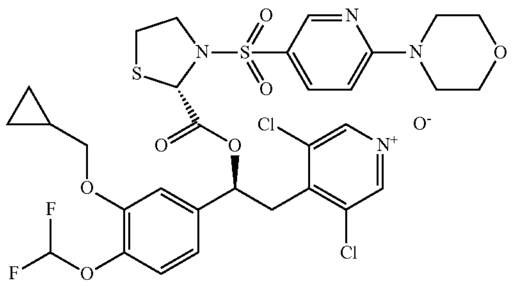 | Free Base | 761.2 | 4.74 (2) | >99:1 | $^1$H NMR (400 MHz, DMSO-$d_6$) δ ppm 8.57 (s, 2 H), 8.45-8.50 (m, 1 H), 7.83-7.93 (m, 1 H), 7.14-7.21 (m, 1 H), 7.04-7.12 (m, 2 H), 6.89-6.99 (m, 2 H), 5.92-6.05 (m, 1 H), 5.46 (s, 1 H), 3.85-3.94 (m, 2 H), 3.75-3.84 (m, 1 H), 3.66 (d, J = 9.26 Hz, 9 H), 3.39-3.49 (m, 1 H), 3.18-3.28 (m, 1 H), 2.90-3.03 (m, 1 H), 2.59-2.74 (m, 1 H), 1.13-1.30 (m, 1 H), 0.48-0.60 (m, 2 H), 0.26-0.38 (m, 2 H). | | 6 | Preparative HPLC (Method 1) |
| 106 | 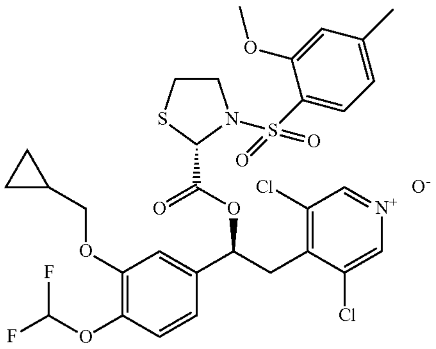 | Free Base | 719.2 | 5.12 (2) | 97:3 | $^1$H NMR (400 MHz, DMSO-$d_6$) δ ppm 8.59 (s, 2 H), 7.64 (d, J = 7.94 Hz, 1 H), 7.17 (d, J = 8.38 Hz, 1 H), 7.10 (dd, J = 6.39, 2.43 Hz, 3 H), 6.95 (m, 2 H), 5.89-6.09 (m, 1 H), 5.51 (s, 1 H), 3.83-4.00 (m, 5 H), 3.62-3.79 (m, 1 H), 3.51-3.62 (m, 1 H), 3.36-3.48 (m, 1 H), 3.22-3.31 (m, 1 H), 2.93-3.04 (m, 1 H), 2.63-2.81 (m, 1 H), 2.39 (s, 3 H), 1.15-1.31 (m, 1 H), 0.51-0.65 (m, 2 H), 0.33 (d, J = 4.85 Hz, 2 H). | | 6 | Preparative HPLC (Method 1) |
| 107 | 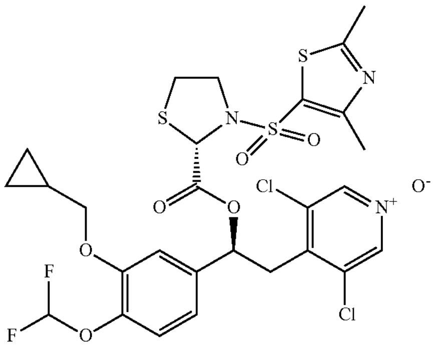 | Free Base | 710.1 | 4.79 (2) | 98:2 | $^1$H NMR (400 MHz, DMSO-$d_6$) δ ppm 8.58 (s, 2 H), 7.16-7.23 (m, 1 H), 7.07-7.14 (m, 2 H), 6.94-7.00 (m, 1 H), 5.87-6.14 (m, 1 H), 5.31 (s, 1 H), 3.84-3.97 (m, 2 H), 3.73 (m, 2 H), 3.40-3.58 (m, 1 H), 3.19-3.28 (m, 1 H), 2.88-3.15 (m, 2 H), 2.69 (s, 3 H), 2.55 (s, 3 H), 1.14-1.31 (m, 1 H), 0.51-0.64 (m, 2 H), 0.26-0.42 (m, 2 H). | | 6 | Preparative HPLC (Method 1) |

TABLE 6-continued

| En-try | Structure | SALT NAME | HPLC-MS characterization MS/ESI+ [MH]+ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 108 | 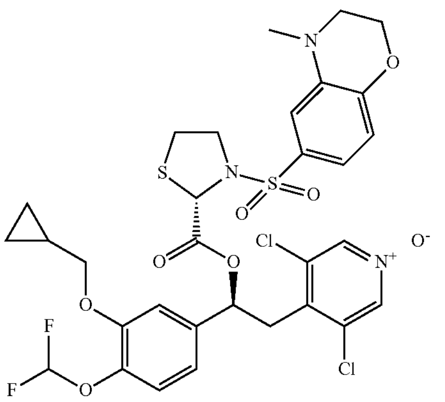 | Free Base | 746.2 | 5.13 (2) | 98:2 | $^1$H NMR (400 MHz, DMSO-$d_6$) δ ppm 8.58 (s, 2 H), 7.18 (d, J = 8.38 Hz, 1 H), 7.11 (d, J = 1.76 Hz, 1 H), 7.08 (t, J = 75.00 Hz, 1 H), 7.03 (m, 1 H), 7.00 (d, J = 2.21 Hz, 1 H), 6.93-6.98 (m, 1 H), 6.86 (d, J = 8.38 Hz, 1 H), 5.92-6.09 (m, 1 H), 5.42 (s, 1 H), 4.32 (m, 2 H), 3.90 (d, J = 6.17 Hz, 2 H), 3.69-3.84 (m, 1 H), 3.56-3.66 (m, 1 H), 3.33-3.53 (m, 3 H), 3.24-3.29 (m, 1 H), 2.91 (m, 4 H), 2.59-2.68 (m, 1 H), 1.15-1.27 (m, 1 H), 0.56 (dd, J = 7.94, 1.76 Hz, 2 H), 0.33 (d, J = 5.73 Hz, 2 H). | | 6 | Preparative HPLC (Method 1) |
| 109 | 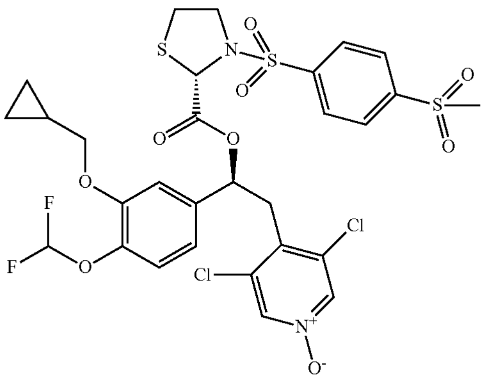 [SMILES: CS(=O)(=O)c1ccc(S(=O)(=O)N2CCS[C@H]2C(=O)O[C@@H](Cc2c(Cl)c[n+]([O-])cc2Cl)c2ccc(OC(F)F)c(OCC3CC3)c2)cc1] | Free Base | 753.1 | 5.40 (2) | >99:1 | $^1$H NMR (400 MHz, DMSO-d6) δ ppm 8.60 (s, 2 H), 8.17 (d, J = 10.58 Hz, 4 H), 7.15-7.21 (m, 1 H), 7.05-7.14 (m, 2 H), 6.93-7.00 (m, 1 H), 5.96-6.08 (m, 1 H), 5.54 (s, 1 H), 3.86-3.97 (m, 2 H), 3.76-3.84 (m, 1 H), 3.62-3.74 (m, 1 H), 3.39-3.53 (m, 1 H), 3.35 (s, 3 H), 3.24-3.31 (m, 1 H), 2.91-3.05 (m, 1 H), 2.69-2.82 (m, 1 H), 1.13-1.27 (m, 1 H), 0.47-0.65 (m, 2 H), 0.25-0.44 (m, 2 H). | | 6 | Crystallized from EtOH/iprOH |

TABLE 6-continued

| En-try | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 110 | 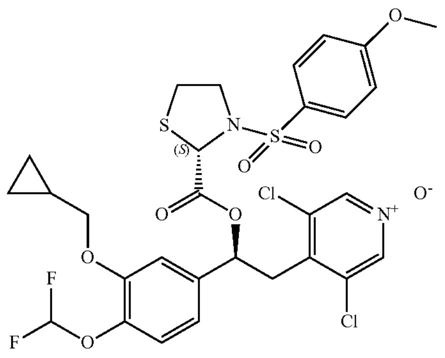 | Free Base | 705.1 | 4.41 (2) | 97:3 | $^1$H NMR (400 MHz, DMSO-d6) δ ppm 8.60 (s, 2 H), 7.80 (d, J = 9.26 Hz, 2 H), 7.13-7.22 (m, 3 H), 7.11 (d, J = 1.76 Hz, 1 H), 7.08 (t, J = 75.00 Hz, 1 H), 6.93-6.99 (m, 1 H), 5.95-6.07 (m, 1 H), 5.39 (s, 1 H), 3.84-3.94 (m, 5 H), 3.72-3.82 (m, 1 H), 3.54-3.65 (m, 1 H), 3.40-3.50 (m, 1 H), 3.20-3.29 (m, 1 H), 2.89-2.99 (m, 1 H), 2.57-2.70 (m, 1 H), 1.14-1.27 (m, 1 H), 0.56 (dd, J = 7.94, 1.76 Hz, 2 H), 0.33 (dd, J = 4.63, 1.54 Hz, 2 H). | | 6 | Flash Cromatography |
| 111 | 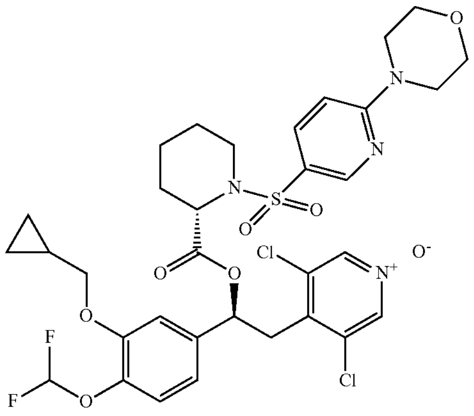 | Free Base | 752.2 | 4.36 (2) | 98:2 | $^1$H NMR (400 MHz, DMSO-d6) δ ppm 8.63 (s, 2 H), 8.24 (d, J = 2.65 Hz, 1 H), 7.64 (dd, J = 9.26, 2.65 Hz, 1 H), 7.16 (d, J = 8.38 Hz, 1 H), 7.04-7.09 (m, 2 H), 6.80-6.95 (m, 2 H), 5.89 (dd, J = 8.82, 4.85 Hz, 1 H), 4.61 (d, J = 3.97 Hz, 1 H), 3.88 (t, J = 6.62 Hz, 2 H), 3.67-3.75 (m, 4 H), 3.59-3.65 (m, 4 H), 3.50-3.58 (m, 1 H), 3.35-3.46 (m, 1 H), 3.22 (dd, J = 14.11, 5.29 Hz, 1 H), 2.96 (d, J = 2.65 Hz, 1 H), 2.07 (m, 1 H), 1.57-1.70 (m, 1 H), 1.51 (d, J = 11.03 Hz, 2 H), 1.15-1.35 (m, 2 H), 0.80-0.96 (m, 1 H), 0.49-0.62 (m, 2 H), 0.28-0.41 (m, 2 H). | | 10 | Preparative HPLC (Method 1) |

TABLE 6-continued

| En-try | Structure | SALT NAME | HPLC-MS characterization MS/ESI+ [MH]+ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 112 | 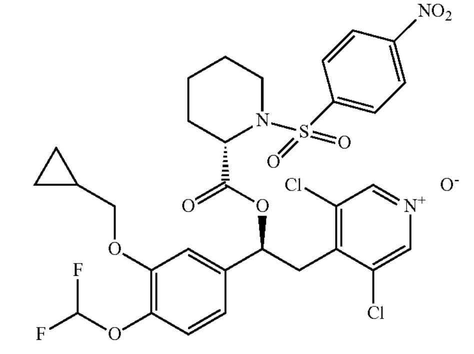 | Free Base | 716.1 | 4.66 (2) | 98:2 | $^1$H NMR (400 MHz, DMSO-d6) δ ppm 8.62 (s, 2 H), 8.37 (d, J = 8.82 Hz, 2 H), 7.97 (d, J = 8.82 Hz, 2 H), 7.14 (m, 1 H), 7.06 (m, 2 H), 6.83-6.92 (m, 1 H), 5.84-5.96 (m, 1 H), 4.64-4.75 (m, 1 H), 3.86 (m, 2 H), 3.64-3.75 (m, 1 H), 3.35-3.47 (m, 1 H), 3.16-3.27 (m, 1 H), 2.90-3.05 (m, 1 H), 2.08-2.17 (m, 1 H), 1.49-1.70 (m, 3 H), 1.13-1.31 (m, 2 H), 0.78-0.98 (m, 1 H), 0.48-0.66 (m, 2 H), 0.32 (m, 2 H). | | 10 | Preparative HPLC (Method 1) |
| 113 | 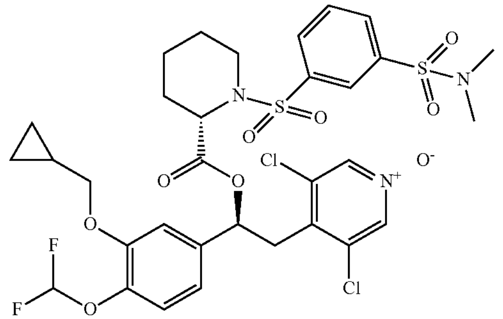 | Free Base | 778.2 | 4.45 (2) | 98:2 | $^1$H NMR (400 MHz, DMSO-d6) δ ppm 8.60 (s, 2 H), 7.99-8.06 (m, 2 H), 7.97 (d, J = 1.76 Hz, 1 H), 7.80-7.90 (m, 1 H), 7.14 (d, J = 8.38 Hz, 1 H), 7.07 (t, J = 75.00 Hz, 1 H), 7.04 (d, J = 1.76 Hz, 1 H), 6.83-6.90 (m, 1 H), 5.85 (dd, J = 8.38, 5.29 Hz, 1 H), 4.73 (d, J = 4.41 Hz, 1 H), 3.86 (t, J = 7.50 Hz, 2 H), 3.63-3.74 (m, 1 H), 3.36-3.46 (m, 1 H), 3.18-3.26 (m, 1 H), 2.94 (m, 1 H), 2.65 (s, 6 H), 2.09-2.19 (m, 1 H), 1.54 (d, J = 15.88 Hz, 3 H), 1.19 (d, J = 4.85 Hz, 2 H), 0.78-0.98 (m, 1 H), 0.48-0.63 (m, 2 H), 0.26-0.40 (m, 2 H). | | 10 | Preparative HPLC (Method 1) |

TABLE 6-continued

| En-try | Structure | SALT NAME | HPLC-MS characterization MS/ESI+ [MH]+ | $t_R$/min Method 1, 2 or 3 | Diastereomeric ratio | ¹H NMR | $[\alpha]_D$ | Precursor | Purification Method |
|---|---|---|---|---|---|---|---|---|---|
| 114 | 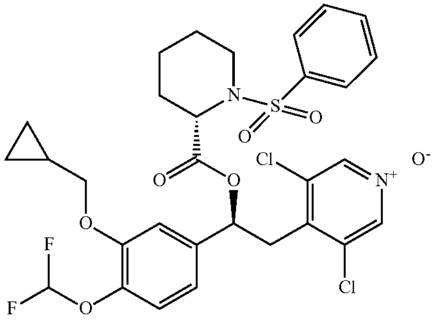 | Free Base | 671.2 | 4.44 (2) | 99:1 | ¹H NMR (400 MHz, DMSO-d6) δ ppm 8.64 (s, 2 H), 7.62-7.70 (m, 3 H), 7.57 (d, J = 7.50 Hz, 2 H), 7.15 (m, 1 H), 7.02-7.10 (m, 2 H), 6.89 (m, 1 H), 5.84-5.91 (m, 1 H), 4.56-4.66 (m, 1 H), 3.87 (m, 2 H), 3.57-3.67 (m, 1 H), 3.36-3.48 (m, 1 H), 3.16-3.27 (m, 1 H), 2.90-3.08 (m, 1 H), 1.98-2.12 (m, 1 H), 1.41-1.66 (m, 3 H), 1.10-1.30 (m, 2 H), 0.78-0.98 (m, 1 H), 0.57 (m, 2 H), 0.57 (m, 2 H), 0.33 (dd, J = 4.85, 1.32 Hz, 2 H). | | 10 | Preparative HPLC (Method 1) |
| 115 | 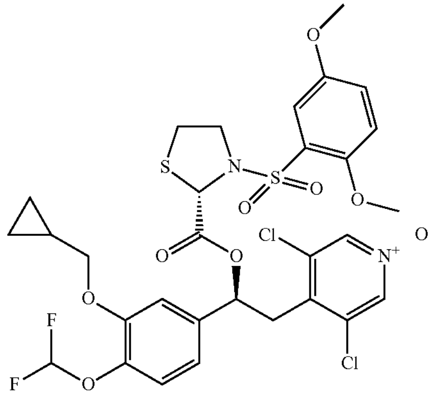 [SMILES: COc1ccc(OC)c(S(=O)(=O)N2CCS[C@H]2C(=O)O[C@@H](Cc2c(Cl)c[nH+]cc2Cl)c2ccc(OC(F)F)c(OCC3CC3)c2)c1 ; O] | Free Base | 735.1 | 4.30 (2) | 98:2 | ¹H NMR (400 MHz, DMSO-d6) δ ppm 8.56 (s, 2 H), 7.15-7.33 (m, 4 H), 7.11 (m, 1 H), 7.09 (t, J = 75.00 Hz, 1 H), 6.92-6.99 (m, 1 H), 5.95-6.11 (m, 1 H), 5.59 (s, 1 H), 3.87-3.97 (m, 2 H), 3.85 (s, 3 H), 3.78 (m, 4 H), 3.52-3.63 (m, 1 H), 3.37-3.50 (m, 1 H), 3.28 (m, 1 H), 2.94-3.04 (m, 1 H), 2.67-2.80 (m, 1 H), 1.15-1.30 (m, 1 H), 0.52-0.60 (m, 2 H), 0.28-0.41 (m, 2 H). | | 6 | Preparative HPLC (Method 1) |

TABLE 6-continued

| En-try | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 116 | 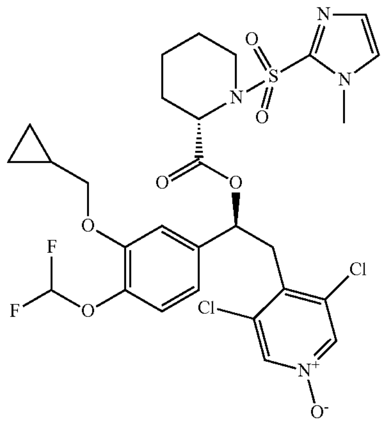 [SMILES: Cn1ccnc1S(=O)(=O)N1CCCC[C@H]1C(=O)O[C@@H](Cc1c(Cl)c[n+]([O-])cc1Cl)c1ccc(OC(F)F)c(OCC2CC2)c1] | Free Base | 675.3 | 3.79 (2) | 98:2 | $^1$H NMR (400 MHz, DMSO-d6) δ ppm 8.55 (s, 2 H), 7.42 (m, 1 H), 7.12-7.20 (m, 1 H), 7.07 (d, J = 1.32 Hz, 2 H), 6.99 (d, J = 0.88 Hz, 1 H), 6.84-6.95 (m, 1 H), 5.86-5.96 (m, 1 H), 4.56-4.65 (m, 1 H), 3.87 (m, 2 H), 3.78 (s, 3 H), 3.60-3.69 (m, 1 H), 3.36-3.47 (m, 1 H), 3.17-3.26 (m, 1 H), 3.00-3.14 (m, 1 H), 2.03-2.13 (m, 1 H), 1.68-1.86 (m, 1 H), 1.43-1.64 (m, 2 H), 1.25-1.43 (m, 1 H), 1.11-1.24 (m, 1 H), 0.84-1.01 (m, 1 H), 0.47-0.62 (m, 2 H), 0.28-0.40 (m, 2 H). | | 10 | No purification |
| 117 | 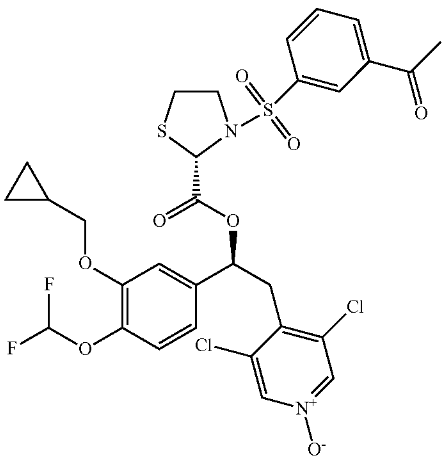 [SMILES: CC(=O)c1cccc(S(=O)(=O)N2CCS[C@H]2C(=O)O[C@@H](Cc2c(Cl)c[n+]([O-])cc2Cl)c2ccc(OC(F)F)c(OCC3CC3)c2)c1] | Free Base | 717.1 | 4.06 (2) | >99:1 | $^1$H NMR (400 MHz, DMSO-d6) δ ppm 8.58 (s, 2 H), 8.26-8.36 (m, 2 H), 8.10-8.16 (m, 1 H), 7.77-7.86 (m, 1 H), 7.15-7.21 (m, 1 H), 7.10-7.14 (m, 1 H), 7.08 (t, J = 75.00 Hz, 1 H), 6.92-6.98 (m, 1 H), 5.97-6.06 (m, 1 H), 5.56 (s, 1 H), 3.87-3.94 (m, 2 H), 3.75-3.86 (m, 1 H), 3.63-3.72 (m, 1 H), 3.42-3.51 (m, 1 H), 3.38 (d, J = 7.06 Hz, 1 H), 2.91-3.03 (m, 1 H), 2.68 (m, 4 H), 1.15-1.33 (m, 1 H), 0.50-0.62 (m, 2 H), 0.27-0.41 (m, 2 H). | | 6 | No purification |

TABLE 6-continued
| En-try | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 118 | 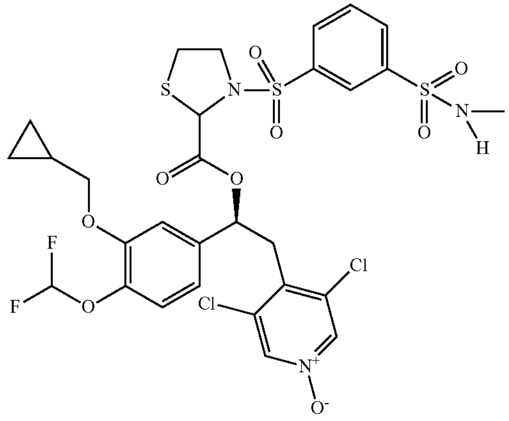 [SMILES: CNS(=O)(=O)c1cccc(S(=O)(=O)N2CCSC2C(=O)O[C@@H](Cc2c(Cl)c[n+]([O-])cc2Cl)c2ccc(OC(F)F)c(OCC3CC3)c2)c1] | Free Base | 768.1 | 3.75; 3.84 (2) | 22:78 | | | 6 | Preparative HPLC (Method 1) |
| 119 | 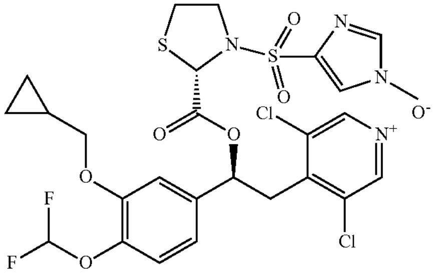 | Free Base | 679.2 | 3.28 (2) | >99:1 | $^1$H NMR (400 MHz, DMSO-d6) δ ppm 8.56 (s, 2 H), 7.93 (m, 1 H), 7.87 (m, 1 H), 7.17 (m, 1 H), 7.10 (d, J = 9.70 Hz, 2 H), 6.92-6.98 (m, 1 H), 5.94-6.11 (m, 1 H), 5.35 (s, 1 H), 3.91 (d, J = 7.06 Hz, 2 H), 3.73 (m, 4 H), 3.61-3.71 (m, 1 H), 3.40-3.49 (m, 1 H), 3.23-3.30 (m, 1 H), 2.94-3.04 (m, 1 H), 2.76-2.88 (m, 1 H), 1.16-1.28 (m, 1 H), 0.56 (d, J = 7.94 Hz, 2 H), 0.34 (d, J = 4.41 Hz, 2 H). | | 6 | Preparative HPLC (Method 1) |

TABLE 6-continued

| En-try | Structure | SALT NAME | HPLC-MS characterization MS/ESI+ [MH]+ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 121 | 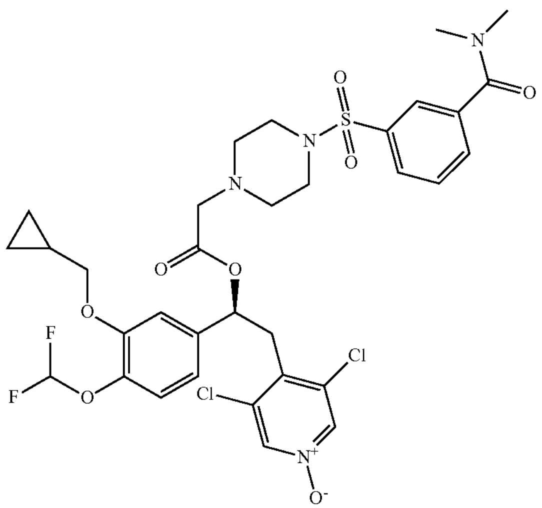 [SMILES: CN(C)C(=O)c1cccc(S(=O)(=O)N2CCN(CC(=O)O[C@@H](Cc3c(Cl)c[n+]([O-])cc3Cl)c3ccc(OC(F)F)c(OCC4CC4)c3)CC2)c1] | Free Base | 757.1 | | | $^1$H NMR (400 MHz, DMSO-$d_6$) δ ppm 8.56 (s, 2 H), 7.70-7.82 (m, 3 H), 7.66-7.70 (m, 1 H), 7.13-7.20 (m, 1 H), 7.06 (t, J = 75.00 Hz, 2 H), 6.92-6.99 (m, 1 H), 5.89-6.07 (m, 1 H), 3.83-3.93 (m, 2 H), 3.34-3.48 (m, 2 H), 3.16-3.24 (m, 2 H), 2.95-3.07 (m, 3 H), 2.89 (m, 7 H), 2.42-2.48 (m, 4 H), 1.13-1.26 (m, 1 H), 0.49-0.62 (m, 2 H), 0.28-0.38 (m, 2 H). | na | 14 | Preparative HPLC (Method 1) |
| 200 | 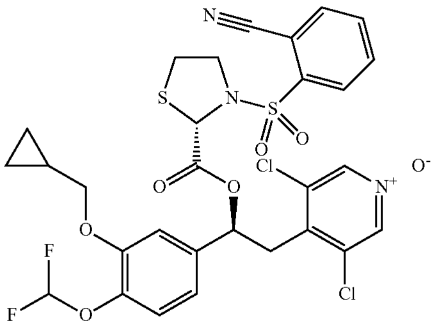 | Free Base | 699.98 | 4.03 (3) | 95:5 ($^1$H NMR) | $^1$H NMR (300 MHz, DMSO-d6) δ ppm 8.55 (s, 2 H), 8.12-8.21 (m, 1 H), 8.04-8.12 (m, 1 H), 7.96 (td, 1 H), 7.91 (td, 1 H), 7.17 (d, 1 H), 7.10 (d, 1 H), 6.94 (dd, 1 H), 7.08 (t, 1 H), 5.94 (dd, 1 H), 5.62 (s, 1 H), 3.93-4.00 (m, 1 H), 3.90 (d, 2 H), 3.67-3.73 (m, 1 H), 3.44 (dd, 1 H), 3.27 (dd, 1 H), 3.07 (ddd, 1 H), 2.90 (dt, 1 H), 1.12-1.29 (m, 1 H), 0.46-0.66 (m, 2 H), 0.18-0.42 (m, 2 H) | −56.05 (c = 0.4, DCM) | 6 | Preparative HPLC (Method 2) |

TABLE 6-continued

| En-try | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 201 | 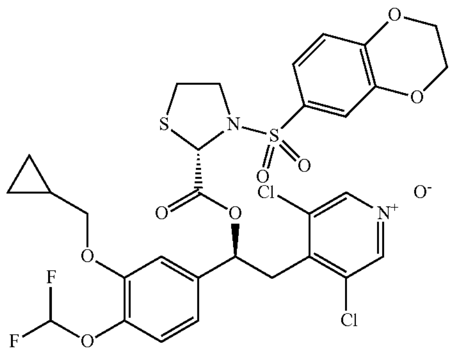 | Free Base | 732.96 | 4.12 (3) | >95:5 ($^1$H NMR) | $^1$H NMR (300 MHz, DMSO-d6) δ ppm 8.56 (s, 2 H), 7.29-7.36 (m, 2 H), 7.18 (d, 1 H), 7.07-7.14 (m, 2 H), 6.96 (dd, 1 H), 7.08 (t, 1 H), 6.02 (dd, 1 H), 5.41 (s, 1 H), 4.27-4.47 (m, 4 H), 3.91 (d, 2 H), 3.77 (dt, 1 H), 3.61 (dt, 1 H), 3.46 (dd, 1 H), 3.32-3.35 (m, 1 H), 2.97 (dt, 1 H), 2.69 (ddd, 1 H), 1.10-1.36 (m, 1 H), 0.48-0.68 (m, 2 H), 0.22-0.43 (m, 2 H) | −50.2 (c = 0.44, DCM) | 6 | Chromatogrphy on silica gel followed by treatment with polymer supported carbonate in DCM/$CH_3CN$, filtration and evaporation |
| 202 | 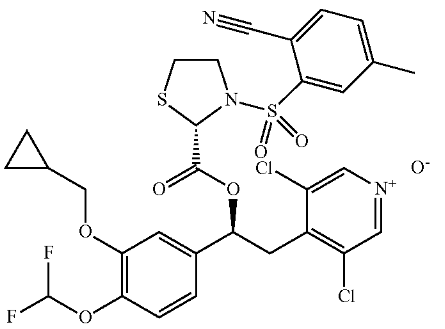 | Free Base | 714.01 | 4.18 (3) | >95:5 ($^1$H NMR B) | $^1$H NMR (300 MHz, DMSO-d6) δ ppm 8.53 (s, 2 H), 8.03 (d, 1 H), 7.96 (d, 1 H), 7.72 (dd, 1 H), 7.17 (d, 1 H), 7.10 (d, 1 H), 6.94 (dd, 1 H), 7.08 (t, 1 H), 5.98 (dd, 1 H), 5.67 (s, 1 H), 3.94 (ddd, 1 H), 3.83-3.92 (m, 2 H), 3.65 (dt, 1 H), 3.45 (dd, 1 H), 3.29 (dd, 1 H), 3.07 (ddd, 1 H), 2.86 (dt, 1 H), 2.50 (s, 3H), 1.11-1.30 (m, 1 H), 0.50-0.66 (m, 2 H), 0.27-0.40 (m, 2 H) | −81.2 (c = 0.7, DCM) | 6 | Chromatography on silica gel followed by preparative HPLC (Method 2) |

TABLE 6-continued

| En-try | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 203 | 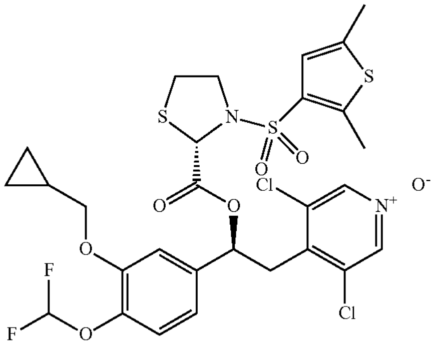 | Free Base | 709.02 | 4.41 (3) | >95:5 ($^1$H NMR) | $^1$H NMR (300 MHz, DMSO-$d_6$) δ ppm 8.56 (s, 2 H), 7.19 (d, 1 H), 7.12 (d, 1 H), 6.98 (s, 1 H), 6.97 (dd, 1 H), 7.08 (t, 1 H), 6.02 (dd, 1 H), 5.40 (s, 1 H), 3.91 (d, 2 H), 3.78 (dt, 1 H), 3.62 (dt, 1 H), 3.45 (dd, 1 H), 3.30 (dd, 1 H), 3.03 (dt, 1 H), 2.80 (dt, 1 H), 2.57 (s, 3 H), 2.40 (s, 3 H), 1.11-1.34 (m, 1 H), 0.45-0.70 (m, 2 H), 0.24-0.45 (m, 2 H) | −50.27 (c = 0.3, DCM) | 6 | Preparative HPLC (Method 2) |
| 204 | 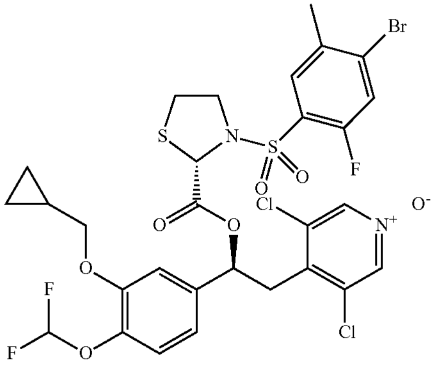 | Free Base | 786.87 | 4.68 (3) | >95:5 ($^1$H NMR) | $^1$H NMR (300 MHz, DMSO-$d_6$) δ ppm 8.57 (s, 2 H), 7.88 (d, 1 H), 7.83 (d, 1 H), 7.18 (d, 1 H), 7.11 (d, 1 H), 6.96 (dd, 1 H), 7.08 (t, 1 H), 6.01 (dd, 1 H), 5.46 (s, 1 H), 3.91 (d, 2 H), 3.80-3.88 (m, 1 H), 3.68 (dt, 1 H), 3.44 (dd, 1 H), 3.30 (dd, 1 H), 3.06 (dt, 1 H), 2.91 (dt, 1 H), 2.42 (s, 3 H), 1.05-1.32 (m, 1 H), 0.47-0.66 (m, 2 H), 0.21-0.47 (m, 2 H) | −74.95 (c = 0.4, DCM) | 6 | Preparative HPLC (Method 2) |

TABLE 6-continued

| Entry | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 205 | 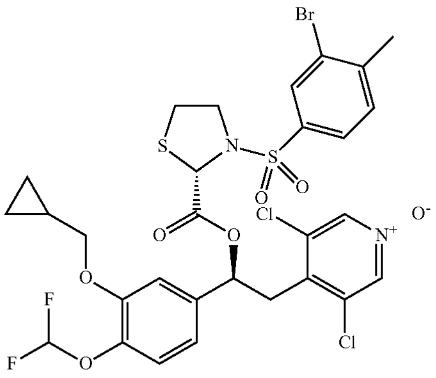 | Free Base | 766.98 | 4.57 (3) | >95:5 ($^1$H NMR) | $^1$H NMR (300 MHz, DMSO-$d_6$) δ ppm 8.56 (s, 2 H), 8.05 (d, 1 H), 7.79 (dd, 1 H), 7.63 (d, 1 H), 7.18 (d, 1 H), 7.11 (d, 1 H), 6.96 (dd, 1 H), 7.08 (t, 1 H), 6.02 (dd, 1 H), 5.56 (s, 1 H), 3.91 (d, 2 H), 3.82 (dt, 1 H), 3.59-3.69 (m, 1 H), 3.46 (dd, 1 H), 3.31 (dd, 1 H), 2.98 (dt, 1 H), 2.71 (dt, 1 H), 2.46 (s, 3 H), 1.07-1.34 (m, 1 H), 0.47-0.67 (m, 2 H), 0.24-0.47 (m, 2 H) | −58.39 (c = 1.5, DCM) | 6 | Preparative HPLC (Method 2) |
| 206 | 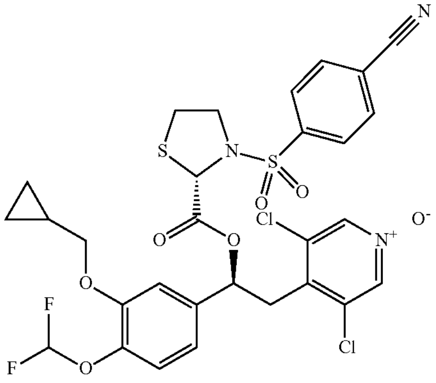 | Free Base | 700.06 | 4.05 (3) | >95:5 ($^1$H NMR) | $^1$H NMR (300 MHz, DMSO-$d_6$) δ ppm 8.59 (s, 2 H), 8.11-8.22 (m, 2 H), 7.98-8.11 (m, 2 H), 7.18 (d, 1 H), 7.11 (d, 1 H), 6.96 (dd, 1 H), 7.08 (t, 1 H), 6.02 (dd, 1 H), 5.56 (s, 1 H), 3.90 (d, 2 H), 3.84 (dt, 1 H), 3.67 (dt, 1 H), 3.46 (dd, 1 H), 3.31 (dd, 1 H), 2.99 (dt, 1 H), 2.75 (dt, 1 H), 1.00-1.34 (m, 1 H), 0.47-0.66 (m, 2 H), 0.26-0.42 (m, 2 H) | −52.16 (c = 0.5, DCM) | 6 | Preparative HPLC (Method 2) |

TABLE 6-continued

| En-try | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 207 | 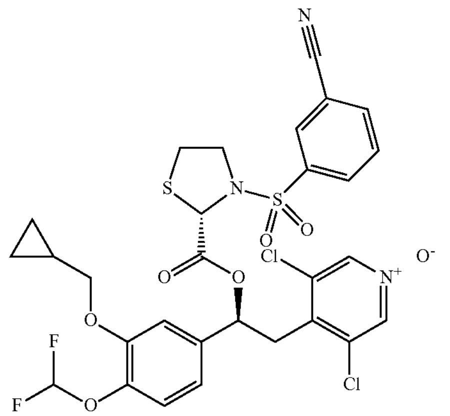 | Free Base | 700.1 | 4.02 (3) | >95:5 ($^1$H NMR) | $^1$H NMR (300 MHz, DMSO-$d_6$) δ ppm 8.57 (s, 2 H), 8.44 (t, 1 H), 8.08-8.29 (m, 2 H), 7.85 (t, 1 H), 7.18 (d, 1 H), 7.11 (d, 1 H), 6.96 (dd, 1 H), 7.08 (dd, 1 H), 6.03 (dd, 1 H), 5.70 (s, 1 H), 3.90 (d, 2 H), 3.85 (t, 1 H), 3.67 (dt, 1 H), 3.47 (dd, 1 H), 3.32 (dd, 1 H), 2.89-3.12 (m, 1 H), 2.59-2.79 (m, 1 H), 1.22 (m, 1 H), 0.46-0.77 (m, 2 H), 0.31-0.37 (m, 2 H) | −38.8 (c = 0.3, DCM) | 6 | Preparative HPLC (method 2) |
| 208 | 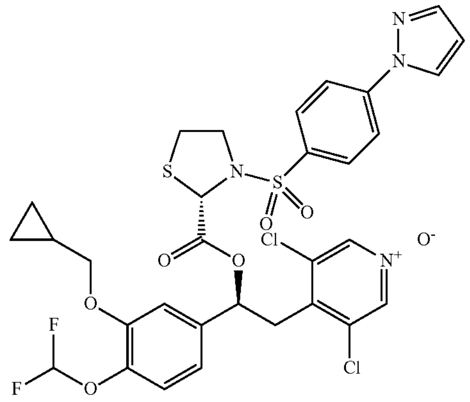 | Free Base | 741.07 | 5.99 (3) | >95:5 ($^1$H NMR) | $^1$H NMR (300 MHz, DMSO-$d_6$) δ ppm 8.70 (d, 1 H), 8.59 (s, 2 H), 8.07-8.20 (m, 2 H), 7.93-8.06 (m, 2 H), 7.87 (d, 1 H), 7.18 (d, 1 H), 7.12 (d, 1 H), 6.97 (dd, 1 H), 7.08 (t, 1 H), 6.65 (dd, 1 H), 6.03 (dd, 1 H), 5.51 (s, 1 H), 3.91 (d, 2 H), 3.86 (dt, 1 H), 3.66 (dt, 1 H), 3.47 (dd, 1 H), 3.32 (dd, 1 H), 2.98 (dt, 1 H), 2.70 (dt, 1 H), 1.05-1.41 (m, 1 H), 0.45-0.67 (m, 2 H), 0.23-0.45 (m, 2 H) | −50.75 (c = 0.4, DCM) | 6 | Preparative HPLC (Method 2) |

TABLE 6-continued

| En-try | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 209 | 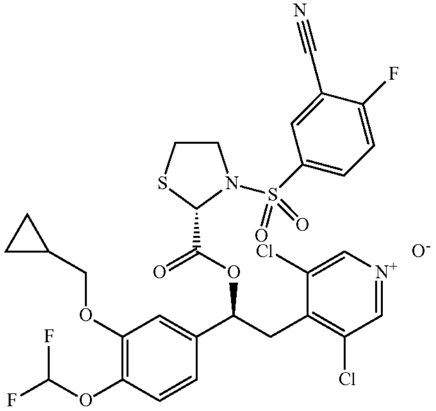 | Free Base | 718.08 | 4.16 (3) | >95:5 ($^1$H NMR) | $^1$H NMR (300 MHz, DMSO-$d_6$) δ ppm 8.57-8.63 (m, 0 H), 8.56 (s, 2 H), 8.18-8.36 (m, 0 H), 7.80 (t, 1 H), 7.18 (d, 1 H), 7.10 (d, 1 H), 6.95 (dd, 1 H), 7.08 (t, 1 H), 6.03 (dd, 1 H), 5.73 (s, 1 H), 3.90 (d, 2 H), 3.79-3.88 (m, 1 H), 3.59-3.74 (m, 1 H), 3.18-3.41 (m, 2 H), 2.91-3.05 (m, 1 H), 2.65-2.77 (m, 3 H), 1.01-1.34 (m, 1 H), 0.44-0.66 (m, 2 H), 0.21-0.44 (m, 2 H) | −108 (c = 0.7, DCM) | 6 | Preparative HPLC (Method 2) |
| 210 | 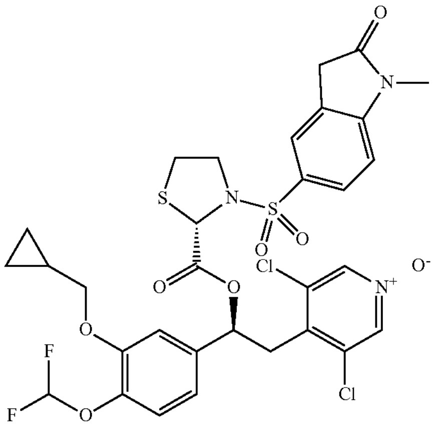 | Free Base | 744.15 | 3.79 (3) | >95:5 ($^1$H NMR) | $^1$H NMR (300 MHz, DMSO-$d_6$) δ ppm 8.58 (s, 2 H), 7.80 (dd, 1 H), 7.73 (d, 1 H), 7.19 (d, 1 H), 7.19 (d, 1 H), 7.11 (d, 1 H), 6.96 (dd, 1 H), 7.08 (t, 1 H), 6.03 (dd, 1 H), 5.40 (s, 1 H), 3.91 (d, 2 H), 3.78 (dt, 1 H), 3.69 (s, 2 H), 3.58-3.68 (m, 1 H), 3.46 (dd, 1 H), 3.31 (dd, 1 H), 3.18 (s, 3 H), 2.97 (dt, 1 H), 2.65-2.79 (m, 1 H), 1.02-1.37 (m, 1 H), 0.45-0.68 (m, 2 H), 0.27-0.45 (m, 2 H) | −61.80 (c = 0.4, DCM) | 6 | Preparative HPLC (Method 2) |

TABLE 6-continued

| En-try | Structure | SALT NAME | HPLC-MS characterization MS/ESI+ [MH]+ | tR/min Method 1, 2 or 3 | Diastereomeric ratio | $^1$H NMR | $[\alpha]_D$ | Precursor | Purification Method |
|---|---|---|---|---|---|---|---|---|---|
| 211 | 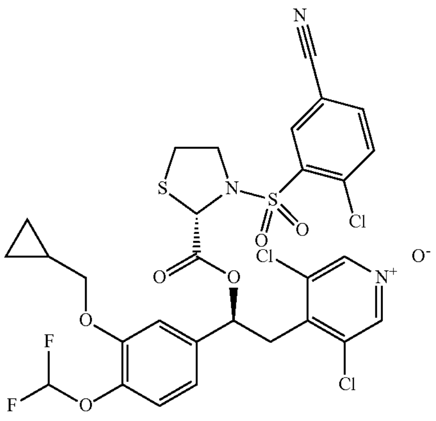 | Free Base | 734.04 | 4.27 (3) | >95:5 ($^1$H NMR) | $^1$H NMR (300 MHz, DMSO-$d_6$) δ ppm 8.52 (s, 2 H), 8.19 (d, 1 H), 8.14 (d, 1 H), 8.03 (dd, 1 H), 7.17 (d, 1 H), 7.10 (d, 1 H), 6.94 (dd, 1 H), 7.08 (t, 1 H), 5.97 (dd, 1 H), 5.77 (s, 1 H), 3.95-4.11 (m, 1 H), 3.76-3.95 (m, 2 H), 3.67 (dt, 1 H), 3.45 (dd, 1 H), 3.29 (dd, 1 H), 3.08 (ddd, 1 H), 2.95 (dt, 1 H), 1.05-1.33 (m, 1 H), 0.46-0.69 (m, 2 H), 0.22-0.46 (m, 2 H) | −40.70 (c = 0.4, DCM) | 6 | Preparative HPLC (Method 2) |
| 212 | 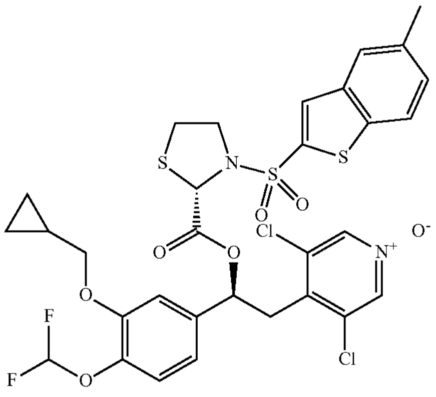 | Free Base | 745.17 | 4.79 (3) | >95:5 ($^1$H NMR) | $^1$H NMR (300 MHz, DMSO-$d_6$) δ ppm 8.60 (s, 2 H), 8.13 (s, 1 H), 8.04 (d, 1 H), 7.88 (s, 1 H), 7.45 (dd, 1 H), 7.18 (d, 1 H), 7.12 (d, 1 H), 6.97 (dd, 1 H), 7.08 (t, 1 H), 6.03 (dd, 1 H), 5.41 (s, 1 H), 3.91 (d, 2 H), 3.80 (t, 2 H), 3.47 (dd, 1 H), 3.32 (dd, 1 H), 3.04 (dt, 1 H), 2.89 (dt, 1 H), 2.47 (s, 3 H), 1.05-1.36 (m, 1 H), 0.46-0.81 (m, 2 H), 0.07-0.46 (m, 2 H) | −72.10 (c = 0.4, DCM) | 6 | Preparative HPLC (Method 2) |

TABLE 6-continued

| En-try | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 213 | 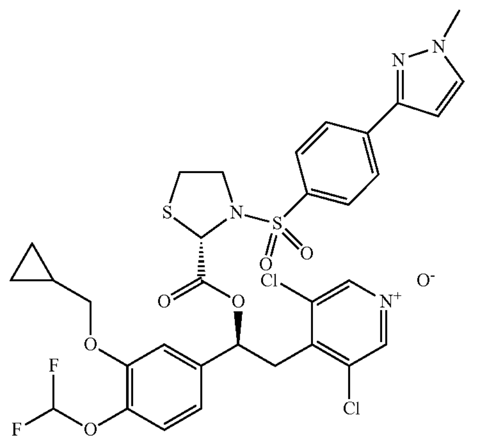 | Free Base | 755.21 | 4.15 (3) | >95:5 ($^1$H NMR) | $^1$H NMR (300 MHz, DMSO-$d_6$) δ ppm 8.60 (s, 2 H), 8.03 (m, 2 H), 7.87 (m, 2 H), 7.82 (d, 1 H), 7.18 (d, 1 H), 7.12 (d, 1 H), 6.96 (dd, 1 H), 6.88 (d, 1 H), 7.08 (t, 1 H), 6.02 (dd, 1 H), 5.45 (s, 1 H), 3.93 (s, 3 H), 3.91 (d, 2 H), 3.83 (dt, 1 H), 3.65 (dt, 1 H), 3.47 (dd, 1 H), 3.31 (dd, 1 H), 2.98 (dt, 1 H), 2.67 (dt, 1 H), 1.01-1.37 (m, 1 H), 0.46-0.69 (m, 2 H), 0.20-0.44 (m, 2 H) | −53.00 (c = 0.7, DCM) | 6 | Preparative HPLC (Method 2) |
| 214 | 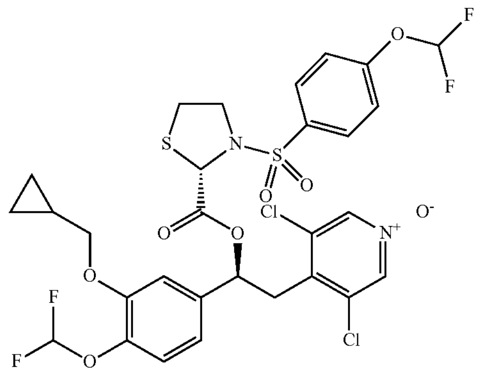 | Free Base | 741.19 | 4.36 (3) | >95:5 ($^1$H NMR) | $^1$H NMR (300 MHz, DMSO-$d_6$) δ ppm 8.59 (s, 2 H), 7.86-8.03 (m, 2 H), 7.37-7.44 (m, 2 H), 7.45 (t, 1 H), 7.19 (d, 1 H), 7.11 (d, 1 H), 6.96 (dd, 1 H), 7.08 (t, 1 H), 6.02 (dd, 1 H), 5.47 (s, 1 H), 3.91 (d, 2 H), 3.80 (dt, 1 H), 3.65 (dt, 1 H), 3.46 (dd, 1 H), 3.31 (dd, 1 H), 2.98 (dt, 1 H), 2.70 (dt, 1 H), 1.04-1.38 (m, 1 H), 0.46-0.68 (m, 2 H), 0.24-0.42 (m, 2 H) | −42.49 (c = 1.4, DCM) | 6 | Preparative HPLC (Method 2) |

TABLE 6-continued

| En-try | Structure | SALT NAME | HPLC-MS characterization MS/ESI⁺ [MH]⁺ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 215 | 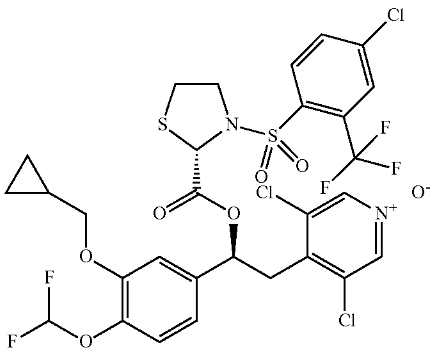 | Free Base | 777.16 | 4.68 (3) | >95:5 ($^1$H NMR) | $^1$H NMR (300 MHz, DMSO-$d_6$) δ ppm 8.53 (s, 2 H), 8.12 (d, 1 H), 8.08 (d, 1 H), 8.02 (dd, 1 H), 7.16 (d, 1 H), 7.09 (d, 1 H), 6.92 (dd, 1 H), 7.08 (t, 1 H), 5.94 (dd, 1 H), 5.61 (s, 1 H), 3.90-4.00 (m, 1 H), 3.90 (d, 2 H), 3.60-3.69 (m, 1 H), 3.43 (dd, 1 H), 3.26 (dd, 1 H), 3.02-3.19 (m, 2 H), 0.91-1.43 (m, 1 H), 0.44-0.85 (m, 2 H), 0.23-0.44 (m, 2 H) | −48.29 (c = 0.7, DCM) | 6 | Preparative HPLC (Method 2) |
| 216 | 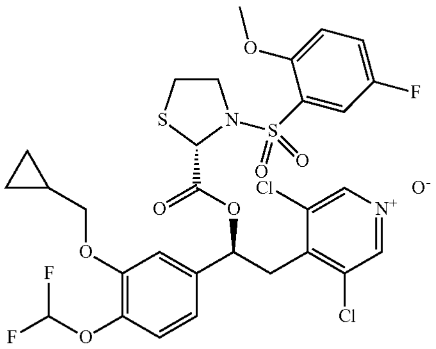 | Free Base | 723.15 | 54.25 (3) | >95:5 ($^1$H NMR) | $^1$H NMR (300 MHz, DMSO-$d_6$) δ ppm 8.55 (s, 2 H), 7.51-7.63 (m, 2 H), 7.31 (dd, 1 H), 7.18 (d, 1 H), 7.11 (d, 1 H), 6.96 (dd, 1 H), 7.08 (t, 1 H), 6.03 (dd, 1 H), 5.58 (s, 1 H), 3.91 (s, 3 H), 3.86-3.97 (m, 2 H), 3.71-3.84 (m, 1 H), 3.60 (dt, 1 H), 3.44 (dd, 1 H), 3.31 (dd, 1 H), 3.03 (ddd, 1 H), 2.78 (dt, 1 H), 1.04-1.35 (m, 1 H), 0.43-0.69 (m, 2 H), 0.24-0.43 (m, 2 H) | −26.09 (c = 1.6, DCM) | 6 | Preparative HPLC (Method 2) |

TABLE 6-continued

| En-try | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 217 | 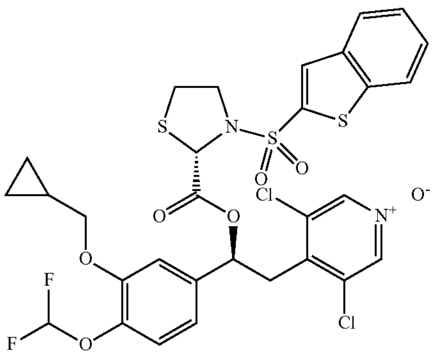 | Free Base | 731.18 | 4.58 (3) | >95:5 ($^1$H NMR) | $^1$H NMR (300 MHz, DMSO-$d_6$) δ ppm 8.60 (s, 2 H), 8.23 (s, 1 H), 8.14-8.20 (m, 1 H), 8.00-8.14 (m, 1 H), 7.50-7.68 (m, 2 H), 7.19 (d, 1 H), 7.12 (d, 1 H), 6.98 (dd, 1 H), 7.08 (t, 1 H), 6.04 (dd, 1 H), 5.43 (s, 1 H), 3.91 (d, 2 H), 3.81 (t, 2 H), 3.48 (dd, 1 H), 3.32 (dd, 1 H), 3.05 (dt, 1 H), 2.91 (dt, 1 H), 1.05-1.40 (m, 1 H), 0.45-0.66 (m, 2 H), 0.18-0.45 (m, 2 H) | −46.14 (c = 0.7, DCM) | 6 | Preparative HPLC (Method 2) |
| 218 | 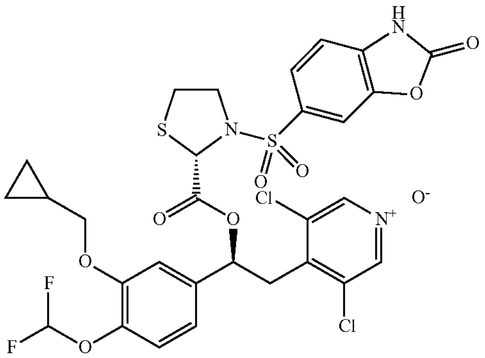 | Free Base | 732.18 | 3.66 (3) | >95:5 ($^1$H NMR) | $^1$H NMR (300 MHz, DMSO-$d_6$) δ ppm 8.57 (s, 2 H), 7.79 (d, 1 H), 7.64 (dd, 1 H), 7.26 (d, 1 H), 7.18 (d, 1 H), 7.11 (d, 1 H), 6.96 (dd, 1 H), 7.08 (t, 1 H), 6.02 (dd, 1 H), 5.49 (s, 1 H), 3.90 (d, 2 H), 3.75-3.88 (m, 1 H), 3.62 (dt, 1 H), 3.46 (dd, 1 H), 3.31 (dd, 1 H), 2.95 (dt, 1 H), 2.60-2.68 (m, 1 H), 0.97-1.37 (m, 1 H), 0.45-0.71 (m, 2 H), 0.18-0.45 (m, 2 H) | −32.95 (c = 0.4, DCM) | 6 | Preparative HPLC (Method 2) followed by flash chromatography on silica gel and further preparative HPLC (Method 2) |

TABLE 6-continued

| Entry | Structure | SALT NAME | HPLC-MS characterization: MS/ESI$^+$ [MH]$^+$ | HPLC-MS characterization: $t_R$/min Method 1, 2 or 3 | Diastereomeric ratio | $^1$H NMR | $[\alpha]_D$ | Precursor | Purification Method |
|---|---|---|---|---|---|---|---|---|---|
| 219 | 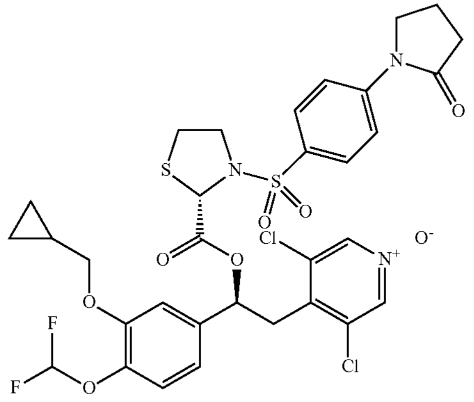 | Free Base | 758 | 3.92 (3) | >95:5 ($^1$H NMR) | $^1$H NMR (300 MHz, DMSO-$d_6$) δ ppm 8.58 (s, 2 H), 7.91-8.00 (m, 2 H), 7.80-7.91 (m, 2 H), 7.18 (d, 1 H), 7.11 (d, 1 H), 6.96 (dd, 1 H), 7.08 (t, 1 H), 6.02 (dd, 1 H), 5.42 (s, 1 H), 3.91 (d, 2 H), 3.90 (t, 2 H), 3.81 (dt, 1 H), 3.63 (dt, 1 H), 3.46 (dd, 1 H), 3.31 (dd, 1 H), 2.97 (dt, 1 H), 2.64 (dt, 1 H), 2.57 (t, 2 H), 2.10 (quin, 2 H), 1.07-1.38 (m, 1 H), 0.47-0.71 (m, 2 H), 0.22-0.41 (m, 2 H) | −65.83 (c = 1.8, DCM) | 6 | Preparative HPLC (Method 2) |
| 220 | 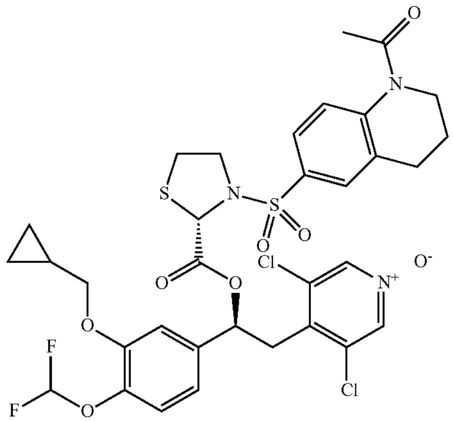 | Free Base | 772.09 | 3.93 (3) | >95:5 ($^1$H NMR) | $^1$H NMR (300 MHz, DMSO-$d_6$) δ ppm 8.58 (s, 2 H), 7.88 (d, 1 H), 7.69 (d, 1 H), 7.62 (dd, 1 H), 7.18 (d, 1 H), 7.12 (d, 1 H), 6.97 (dd, 1 H), 7.08 (t, 1 H), 6.03 (dd, 1 H), 5.43 (s, 1 H), 3.91 (d, 2 H), 3.77-3.84 (m, 1 H), 3.71-3.77 (m, 2 H), 3.64 (ddd, 1 H), 3.47 (dd, 1 H), 3.31 (dd, 1 H), 2.98 (dt, 1 H), 2.83 (t, 2 H), 2.68 (dt, 1 H), 2.25 (s, 3 H), 1.91 (quin, 2 H), 1.06-1.36 (m, 1 H), 0.45-0.68 (m, 2 H), 0.23-0.45 (m, 2 H) | −67.13 (c = 0.6, DCM) | 6 | Preparative HPLC (Method 2) |

TABLE 6-continued

| En-try | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 221 | 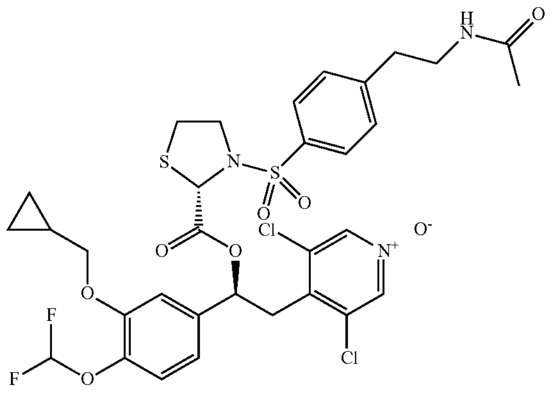 | Free Base | 760.15 | 3.61 (3) | >95:5 ($^1$H NMR) | $^1$H NMR (300 MHz, DMSO-$d_6$) δ ppm 8.58 (s, 2 H), 7.90 (t, 1 H), 7.70-7.85 (m, 2 H), 7.40-7.59 (m, 2 H), 7.18 (d, 1 H), 7.12 (d, 1 H), 6.96 (dd, 1 H), 7.08 (t, 1 H), 6.02 (dd, 1 H), 5.42 (s, 1 H), 3.91 (d, 2 H), 3.78 (dt, 1 H), 3.63 (dt, 1 H), 3.46 (dd, 1 H), 3.23-3.39 (m, 3 H), 2.96 (dt, 1 H), 2.83 (t, 2 H), 2.63 (dt, 1 H), 1.77 (s, 3 H), 1.05-1.48 (m, 1 H), 0.47-0.66 (m, 2 H), 0.25-0.47 (m, 2 H) | −51.61 (c = 1.6, DCM) | 6 | Preparative HPLC (Method 2) |
| 222 | 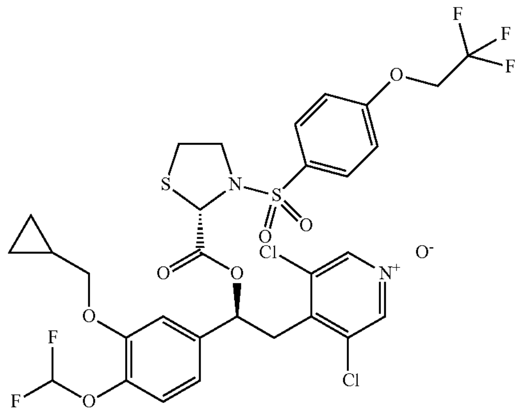 | Free Base | 773.19 | 4.46 (3) | >95:5 ($^1$H NMR) | $^1$H NMR (300 MHz, DMSO-$d_6$) δ ppm 8.59 (s, 2 H), 7.22-8.01 (m, 2 H), 7.25-7.32 (m, 2 H), 7.19 (d, 1 H), 7.11 (d, 1 H), 6.96 (dd, 1 H), 7.08 (t, 1 H), 6.02 (dd, 1 H), 5.44 (s, 1 H), 4.94 (q, 2 H), 3.91 (d, 2 H), 3.80 (dt, 1 H), 3.62 (dt, 1 H), 3.46 (dd, 1 H), 3.31 (dd, 1 H), 2.97 (dt, 1 H), 2.65 (dt, 1 H), 1.13-1.35 (m, 1 H), 0.47-0.71 (m, 2 H), 0.25-0.40 (m, 2 H) | −51.04 (c = 0.50, DCM) | 6 | Trituration with EtOH |

TABLE 6-continued

| En-try | Structure | SALT NAME | HPLC-MS characterization: MS/ESI$^+$ [MH]$^+$ | HPLC-MS characterization: $t_R$/min Method 1, 2 or 3 | Diastereomeric ratio | $^1$H NMR | $[\alpha]_D$ | Precursor | Purification Method |
|---|---|---|---|---|---|---|---|---|---|
| 223 | 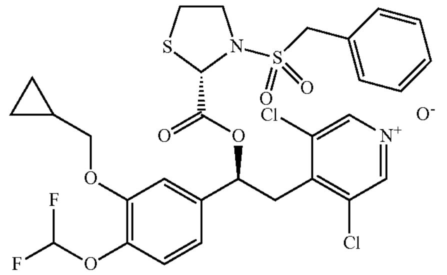 | Free Base | 689.17 | 4.26 (3) | >95:5 ($^1$H NMR) | $^1$H NMR (300 MHz, DMSO-$d_6$) δ ppm 8.53 (s, 2 H), 7.36-7.50 (m, 5 H), 7.17 (d, 1 H), 7.09 (d, 1 H), 6.94 (dd, 1 H), 7.07 (t, 1 H), 5.99 (dd, 1 H), 5.20 (s, 1 H), 4.61 (d, 1 H), 4.54 (d, 1 H), 3.86-3.96 (m, 2 H), 3.82 (dt, 1 H), 3.57 (dt, 1 H), 3.41 (dd, 1 H), 3.28 (dd, 1 H), 2.92-3.14 (m, 2 H), 1.05-1.37 (m, 1 H), 0.46-0.66 (m, 2 H), 0.18-0.44 (m, 2 H) | −18.6 (c = 0.9, DCM) | 6 | Treatment with polymer supported isocyanate followed by preparative HPLC (Method 2) |
| 224 | 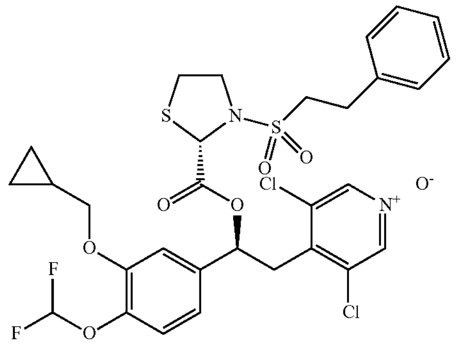 | Free Base | 703 | 4.33 (3) | >95:5 ($^1$H NMR) | $^1$H NMR (300 MHz, DMSO-$d_6$) δ ppm 8.52 (s, 2 H), 7.20-7.41 (m, 5 H), 7.16 (s, 1 H), 7.11 (d, 1 H), 6.96 (dd, 1 H), 7.07 (t, 1 H), 6.03 (dd, 1 H), 5.59 (s, 1 H), 3.94-4.13 (m, 1 H), 3.91 (d, 2 H), 3.39-3.67 (m, 4 H), 3.28 (d, 1 H), 3.02-3.19 (m, 2 H), 2.97 (t, 2 H), 1.08-1.36 (m, 1 H), 0.47-0.68 (m, 2 H), 0.23-0.42 (m, 2 H) | −58.4 (c = 0.4 DCM) | 6 | Preparative (Method 3) |
| 225 | 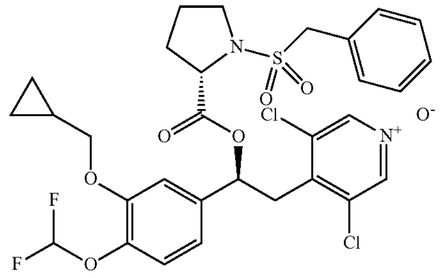 | Free Base | 671.24 | 4.06 (3) | >95:5 ($^1$H NMR) | $^1$H NMR (300 MHz, DMSO-$d_6$) δ ppm 8.54 (s, 2 H), 7.33-7.46 (m, 5 H), 7.16 (d, 1 H), 7.10 (d, 1 H), 6.95 (dd, 1 H), 7.06 (t, 1 H), 5.98 (dd, 1 H), 4.48 (d, 1 H), 4.39 (d, 1 H), 4.03 (dd, 1 H), 3.91 (dd, 1 H), 3.87 (dd, 1 H), 3.42 (dd, 1 H), 3.30-3.37 (m, 2 H), 3.23 (dd, 1 H), 1.97-2.22 (m, 1 H), 1.75-1.92 (m, 1 H), 1.59-1.75 (m, 2 H), 1.08-1.32 (m, 1 H), 0.46-0.70 (m, 2 H), 0.14-0.40 (m, 2 H) | -14.55 (c = 0.22, DCM) | 3 | Flash chromatography on silica gel followed by trituration with MeOH |

TABLE 6-continued

| En-try | Structure | SALT NAME | HPLC-MS characterization MS/ESI+ [MH]+ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 226 | 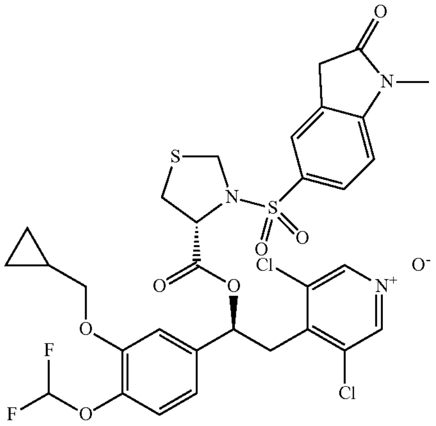 | Free Base | 744.11 | 3.72 (3) | >95:5 ($^1$H NMR) | $^1$H NMR (300MHz, DMSO-$d_6$) δ ppm 8.58 (s, 2 H), 7.81 (dd, 1 H), 7.73 (d, 1 H), 7.18 (d, 2 H), 7.15 (d, 1 H), 6.98 (dd, 1 H), 7.08 (t, 1 H), 6.03 (dd, 1 H), 4.80 (dd, 1 H), 4.63 (d, 1 H), 4.31 (d, 1 H), 3.93 (d, 2 H), 3.67 (s, 2 H), 3.47 (dd, 1 H), 3.27 (dd, 1 H), 3.18 (s, 3 H), 3.03 (dd, 1 H), 2.96 (dd, 1 H), 1.10-1.36 (m, 1 H), 0.49-0.69 (m, 2 H), 0.24-0.42 (m, 2 H) | −95.8 (c = 0.52, DCM) | 11 | Preparative HPLC (Method 2) |
| 227 | 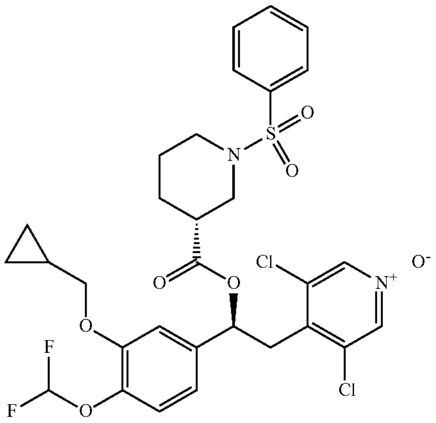 | Free Base | 671.12 | 4.19 (3) | >95:5 ($^1$H NMR) | $^1$H NMR (300 MHz, DMSO-$d_6$) δ ppm 8.56 (s, 2 H), 7.61-7.81 (m, 5 H), 7.18 (d, 1 H), 7.09 (d, 1 H), 6.96 (dd, 1 H), 7.07 (t, 1 H), 5.93 (dd, 1 H), 3.92 (d, 2 H), 3.45 (dd, 2 H), 3.31-3.37 (m, 1 H), 3.21 (dd, 1 H), 2.54-2.70 (m, 2 H), 2.30-2.46 (m, 1 H), 1.80 (m, 1 H), 1.58-1.74 (m, 1 H), 1.40-1.58 (m, 1 H), 1.27-1.40 (m, 1 H), 1.07-1.27 (m, 1 H), 0.46-0.71 (m, 2 H), 0.08-0.46 (m, 2 H) | +1.349 (c = 0.43, MeOH) | 15 | Flash chromatogrphy on silica gel |

TABLE 6-continued

| En-try | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 228 | 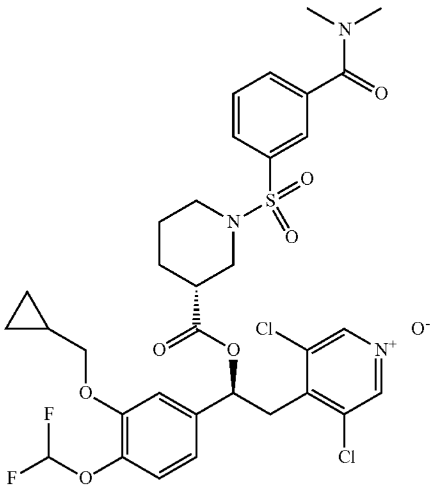 | Free Base | 742.12 | 3.78 (3) | >95:5 ($^1$H NMR) | $^1$H NMR (300 MHz, DMSO-$d_6$) δ ppm 8.55 (s, 2 H), 7.72-7.84 (m, 3 H), 7.70 (t, 1 H), 7.18 (d, 1 H), 7.10 (d, 1 H), 6.96 (dd, 1 H), 7.07 (t, 1 H), 5.94 (dd, 1 H), 3.92 (d, 2 H), 3.47-3.59 (m, 1 H), 3.45 (dd, 1 H), 3.32-3.39 (m, 1 H), 3.21 (dd, 1 H), 3.02 (br. s., 3 H), 2.90 (br. s., 3 H), 2.55-2.69 (m, 2 H), 1.03-1.96 (m, 6 H), 0.47-0.69 (m, 2 H), 0.20-0.47 (m, 2 H) | +2.018 (c = 0.565, MeOH) | 15 | Flash chromatogrphy on silica gel |
| 229 | 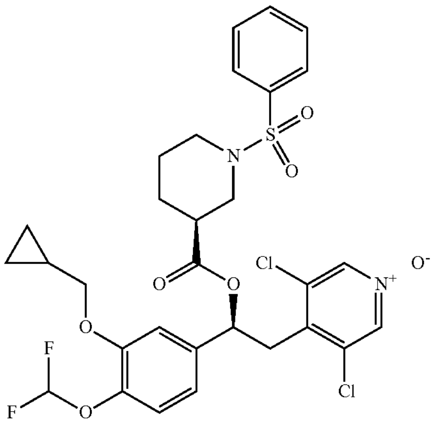 | Free Base | 671.17 | 4.22 (3) | >95:5 ($^1$H NMR) | $^1$H NMR (300 MHz, DMSO-$d_6$) δ ppm 8.56 (s, 2 H), 7.60-7.81 (m, 5 H), 7.18 (d, 1 H), 7.10 (d, 1 H), 7.00 (dd, 1 H), 7.08 (t, 1 H), 5.93 (dd, 1 H), 3.93 (d, 2 H), 3.44 (dd, 1 H), 3.33-3.39 (m, 1 H), 3.21 (dd, 1 H), 3.06-3.17 (m, 1 H), 2.55-2.86 (m, 3 H), 1.63-1.82 (m, 1 H), 1.29-1.63 (m, 3 H), 1.04-1.29 (m, 1 H), 0.47-0.72 (m, 2 H), 0.18-0.43 (m, 2 H) | −25.04 (c = 0.46, MeOH) | 16 | Flash chromatogrphy on silica gel |

TABLE 6-continued

| En-try | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 230 | 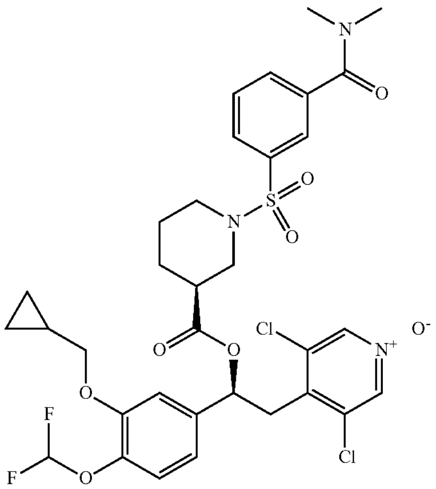 | Free Base | 742.23 | 3.83 (3) | >95:5 ($^1$H NMR) | $^1$H NMR (300 MHz, DMSO-$d_6$) δ ppm 8.56 (s, 2 H), 7.80 (dt, 1 H), 7.76 (dt, 1 H), 7.75 (t, 1 H), 7.70 (t, 1 H), 7.18 (d, 1 H), 7.10 (d, 1 H), 6.99 (dd, 1 H), 7.08 (t, 1 H), 5.93 (dd, 1 H), 3.93 (d, 2 H), 3.44 (dd, 1 H), 3.35-3.42 (m, 1 H), 3.21 (dd, 1 H), 3.09-3.17 (m, 1 H), 3.01 (br. s., 3 H), 2.89 (br. s., 3 H), 2.79-2.88 (m, 1 H), 2.55-2.71 (m, 2 H), 1.65-1.86 (m, 1 H), 1.31-1.65 (m, 3 H), 1.05-1.30 (m, 1 H), 0.49-0.66 (m, 2 H), 0.22-0.43 (m, 2 H) | −25.66 (c = 0.265, MeOH) | 16 | Flash chromatogrphy on silica gel |
| 231 | 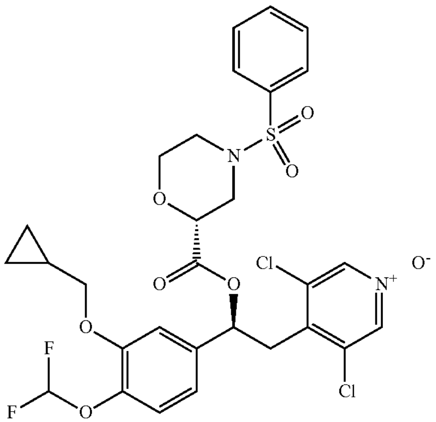 | Free Base | 673.15 | 3.96 (3) | >95:5 ($^1$H NMR) | $^1$H NMR (300 MHz, DMSO-$d_6$) δ ppm 8.58 (s, 2 H), 7.53-7.87 (m, 5 H), 7.19 (d, 1 H), 7.12 (d, 1 H), 6.99 (dd, 1 H), 7.07 (t, 1 H), 5.95 (dd, 1 H), 4.38 (dd, 1 H), 3.88 (dt, 1 H), 3.93 (d, 2 H), 3.46-3.69 (m, 3 H), 3.08-3.29 (m, 2 H), 2.54-2.61 (m, 2 H), 1.15-1.29 (m, 1 H), 0.49-0.71 (m, 2 H), 0.17-0.44 (m, 2 H) | +5.102 (c = 0.49, DCM) | 17 | Flash chromatogrphy on silica gel followed by preparative HPLC (Method 2) |

TABLE 6-continued

| En-try | Structure | SALT NAME | HPLC-MS characterization MS/ESI+ [MH]+ | tR/min Method 1, 2 or 3 | Diastereomeric ratio | 1H NMR | [α]D | Precursor | Purification Method |
|---|---|---|---|---|---|---|---|---|---|
| 232 | 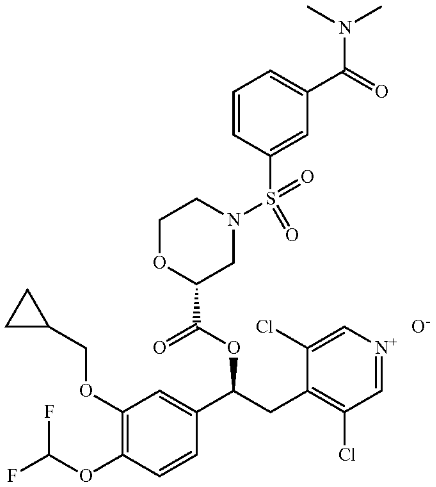 | Free Base | 744.18 | 3.58 (3) | >95:5 ($^1$H NMR) | $^1$H NMR (300 MHz, DMSO-$d_6$) δ ppm 8.56 (s, 2 H), 7.73-7.86 (m, 3 H), 7.67-7.73 (m, 1 H), 7.19 (d, 1 H), 7.12 (d, 1 H), 6.99 (dd, 1 H), 7.07 (t, 1 H), 5.96 (dd, 1 H), 4.39 (dd, 1 H), 3.93 (d, 2 H), 3.89 (dt, 1 H), 3.61 (ddd, 1 H), 3.50 (dd, 1 H), 3.38-3.48 (m, 1 H), 3.13-3.27 (m, 2 H), 3.03 (br. s., 3 H), 2.91 (br. s., 3 H), 2.55-2.70 (m, 2 H), 1.06-1.37 (m, 1 H), 0.51-0.65 (m, 2 H), 0.30-0.42 (m, 2 H) | −9.114 (c = 0.7, DCM) | 17 | Trituration with EtOH |
| 233 | 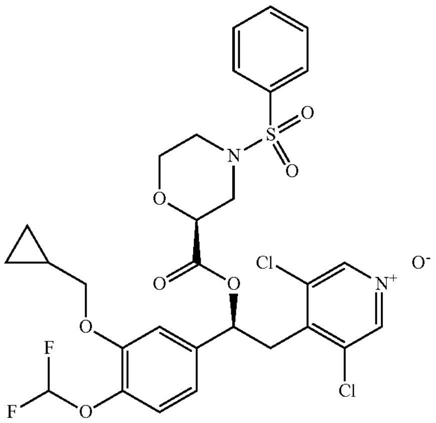 | Free Base | 673.29 | 3.97 (3) | >95:5 ($^1$H NMR) | $^1$H NMR (300 MHz, DMSO-$d_6$) δ ppm 8.54 (s, 2 H), 7.60-7.84 (m, 5 H), 7.19 (d, 1 H), 7.11 (d, 1 H), 7.01 (dd, 1 H), 7.09 (t, 1 H), 5.92 (dd, 1 H), 4.38 (dd, 1 H), 3.93 (d, 2 H), 3.77 (ddd, 1 H), 3.53-3.69 (m, 1 H), 3.45 (dd, 1 H), 3.17-3.29 (m, 2 H), 3.02 (dd, 1 H), 2.86-2.98 (m, 1 H), 2.69-2.83 (m, 1 H), 1.07-1.40 (m, 1 H), 0.47-0.66 (m, 2 H), 0.28-0.45 (m, 2 H) | −31.66 (c = 0.47, DCM) | 18 | Preparative HPLC (Method 2) |

TABLE 6-continued

| En-try | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 234 | 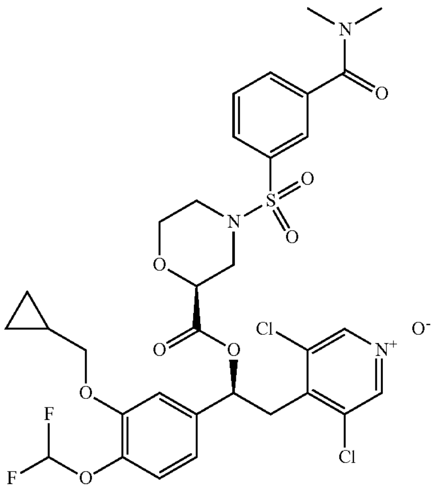 | Free Base | 744.4 | 3.59 (3) | >95:5 ($^1$H NMR) | $^1$H NMR (300 MHz, DMSO-$d_6$) δ ppm 8.54 (s, 2 H), 7.69-7.89 (m, 4 H), 7.19 (d, 1 H), 7.12 (d, 1 H), 7.00 (dd, 1 H), 7.09 (t, 1 H), 5.93 (dd, 1 H), 4.39 (dd, 1 H), 3.85-4.01 (m, 2 H), 3.72-3.85 (m, 1 H), 3.52-3.71 (m, 1 H), 3.45 (dd, 1 H), 3.17-3.27 (m, 2 H), 3.08 (dd, 1 H), 3.02 (br. s., 3 H), 2.93-2.99 (m, 1 H), 2.90 (br. s., 3 H), 2.75-2.85 (m, 1 H), 1.09-1.38 (m, 1 H), 0.48-0.66 (m, 2 H), 0.28-0.43 (m, 2 H) | −28.12 (c = 0.51, DCM) | 18 | Flash chromatography on silica gel |
| 235 | 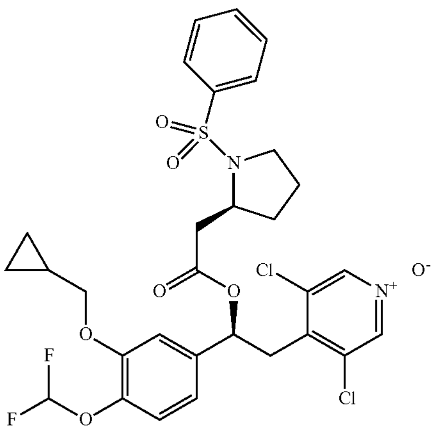 | Free Base | 671.34 | 4.09 (3) | >95:5 ($^1$H NMR) | $^1$H NMR (300 MHz, DMSO-$d_6$) δ ppm 8.56 (s, 2 H), 7.76-7.86 (m, 2 H), 7.69-7.76 (m, 1 H), 7.57-7.69 (m, 2 H), 7.19 (d, 1 H), 7.10 (d, 1 H), 6.98 (dd, 1 H), 7.07 (t, 1 H), 5.99 (dd, 1 H), 3.92 (dd, 1 H), 3.88 (dd, 1 H), 3.72-3.80 (m, 1 H), 3.47 (dd, 1 H), 3.28-3.37 (m, 1 H), 3.24 (dd, 1 H), 3.04-3.16 (m, 1 H), 2.83 (dd, 1 H), 2.55 (dd, 1 H), 1.62-1.91 (m, 1 H), 1.43-1.62 (m, 1 H), 1.29-1.45 (m, 2 H), 1.09-1.29 (m, 1 H), 0.44-0.67 (m, 2 H), 0.21-0.43 (m, 2 H) | −79 (c = 0.23 DCM) | 19 | Preparative HPLC (Method 2) |

TABLE 6-continued

| Entry | Structure | SALT NAME | HPLC-MS characterization MS/ESI+ [MH]+ | $t_R$/min Method 1, 2 or 3 | Diastereomeric ratio | $^1H$ NMR | $[\alpha]_D$ | Precursor | Purification Method |
|---|---|---|---|---|---|---|---|---|---|
| 236 | 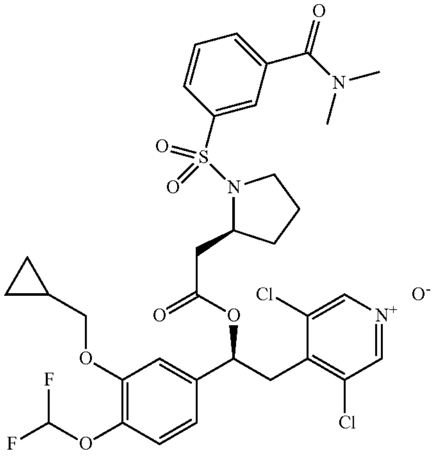 | Free Base | 742.43 | 3.74 (3) | >95:5 ($^1H$ NMR) | $^1H$ NMR (300 MHz, DMSO-$d_6$) δ ppm 8.56 (s, 2 H), 7.85 (dt, 1 H), 7.65-7.80 (m, 3 H), 7.19 (d, 1 H), 7.10 (d, 1 H), 6.98 (dd, 1 H), 7.07 (t, 1 H), 5.98 (dd, 1 H), 3.92 (dd, 1 H), 3.88 (dd, 1 H), 3.70-3.84 (m, 1 H), 3.46-3.54 (m, 2 H), 3.28-3.37 (m, 2 H), 3.24 (dd, 1 H), 3.07-3.19 (m, 1 H), 3.00 (br. s., 3 H), 2.88 (br. s., 3 H), 2.83 (dd, 1 H), 2.54-2.65 (m, 1 H), 1.63-1.91 (m, 0 H), 1.48-1.63 (m, 0 H), 1.29-1.48 (m, 2 H), 1.05-1.29 (m, 1 H), 0.46-0.62 (m, 2 H), 0.17-0.46 (m, 2 H) | | 19 | Preparative HPLC (Method 2) |
| 237 | 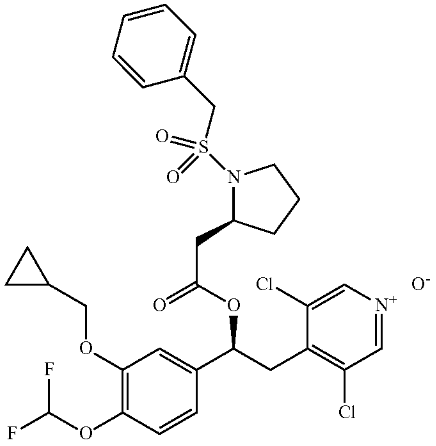 | Free Base | 685.41 | 4.11 (3) | >95:5 ($^1H$ NMR) | $^1H$ NMR (300 MHz, DMSO-$d_6$) δ ppm 8.56 (s, 2 H), 7.34-7.46 (m, 5 H), 7.19 (d, 1 H), 7.07 (d, 1 H), 6.93 (dd, 1 H), 7.07 (t, 1 H), 5.95 (dd, 1 H), 4.42 (s, 2 H), 3.91 (d, 2 H), 3.76-3.88 (m, 1 H), 3.35-3.43 (m, 2 H), 3.07-3.30 (m, 2 H), 2.61 (dd, 1 H), 2.34 (dd, 1 H), 1.64-1.99 (m, 3 H), 1.27-1.49 (m, 1 H), 1.09-1.28 (m, 1 H), 0.48-0.67 (m, 2 H), 0.24-0.43 (m, 2 H) | −23.8 (c = 0.18, DCM) | 19 | Preparative HPLC (Method 2) followed by chromatograohy on silica gel |

TABLE 6-continued

| En-try | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 238 | 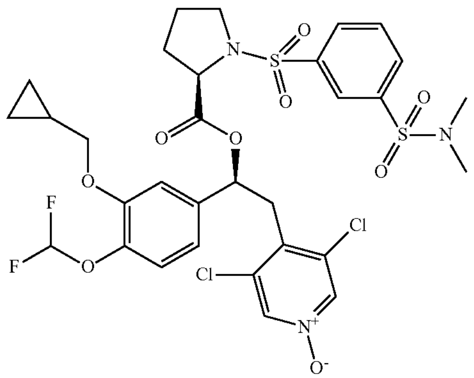 [SMILES: CN(C)S(=O)(=O)c1cccc(S(=O)(=O)N2CCC[C@@H]2C(=O)O[C@@H](Cc2c(Cl)c[n+]([O-])cc2Cl)c2ccc(OC(F)F)c(OCC3CC3)c2)c1] | Free Base | 764.1 | 4.06 (2) | >99:1 | $^1$H NMR (400 MHz, DMSO-$d_6$) δ ppm 8.58 (s, 2 H), 8.10 (m, 2 H), 8.01 (m, 1 H), 7.93 (m, 1 H), 7.15-7.21 (m, 1 H), 7.13 (m, 1 H), 7.08 (t, J = 75.00 Hz, 1 H), 6.94-7.03 (m, 1 H), 5.95-6.08 (m, 1 H), 4.18-4.28 (m, 1 H), 3.92 (d, J = 7.06 Hz, 2 H), 3.43-3.55 (m, 1 H), 3.36-3.43 (m, 1 H), 3.25-3.30 (m, 1 H), 3.16-3.23 (m, 1 H), 2.67 (s, 6 H), 1.94-2.05 (m, 1 H), 1.54-1.79 (m, 3 H), 1.14-1.29 (m, 1 H), 0.48-0.63 (m, 2 H), 0.33 (d, J = 4.85 Hz, 2 H). | | | |
| 239 | 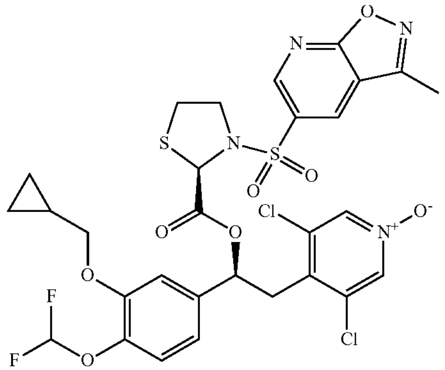 [SMILES: Cc1noc2ncc(S(=O)(=O)N3CCS[C@@H]3C(=O)O[C@@H](Cc3c(Cl)c[n+]([O-])cc3Cl)c3ccc(OC(F)F)c(OCC4CC4)c3)cc12] | hydro-chloride | 731.1 | 4.10 (2) | >99:1 | $^1$H NMR (400 MHz, DMSO-$d_6$) δ ppm 9.14 (d, J = 2.20 Hz, 1 H), 9.06 (d, J = 2.21 Hz, 1 H), 8.59 (s, 2 H), 7.16 (m, 1 H), 7.05-7.13 (m, 2 H), 6.92-6.99 (m, 1 H), 5.95-6.10 (m, 1 H), 5.78 (s, 1 H), 3.82-3.98 (m, 3 H), 3.65-3.79 (m, 1 H), 3.41-3.55 (m, 1 H), 3.34-3.38 (m, 1 H), 2.90-3.01 (m, 1 H), 2.67 (m, 4 H), 1.14-1.27 (m, 1 H), 0.56 (d, J = 7.94 Hz, 2 H), 0.33 (d, J = 4.85 Hz, 2 H). | | | |

TABLE 6-continued

| En-try | Structure | SALT NAME | HPLC-MS characterization MS/ESI+ [MH]+ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 240 | 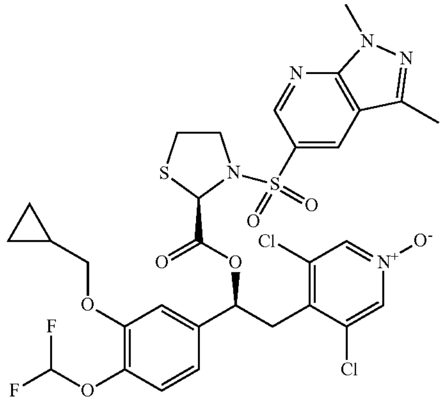 [SMILES: Cc1nn(C)c2ncc(S(=O)(=O)N3CCS[C@@H]3C(=O)O[C@@H](Cc3c(Cl)c[n+]([O-])cc3Cl)c3ccc(OC(F)F)c(OCC4CC4)c3)cc12] | hydro-chloride | 744.2 | 4.07 (2) | >99:1 | $^1$H NMR (400 MHz, DMSO-$d_6$) δ ppm 8.93-8.97 (m, 1 H), 8.85-8.90 (m, 1 H), 8.58 (s, 2 H), 7.14-7.19 (m, 1 H), 7.05-7.12 (m, 2 H), 6.91-6.97 (m, 1 H), 5.96-6.04 (m, 1 H), 5.70 (s, 1 H), 4.03 (s, 3 H), 3.80-3.97 (m, 4 H), 3.60-3.76 (m, 1 H), 3.39-3.53 (m, 1 H), 3.23-3.27 (m, 1 H), 2.88-2.98 (m, 1 H), 2.58 (m, 4 H), 1.12-1.33 (m, 1 H), 0.47-0.62 (m, 2 H), 0.20-0.41 (m, 2 H). | | | |
| 241 | 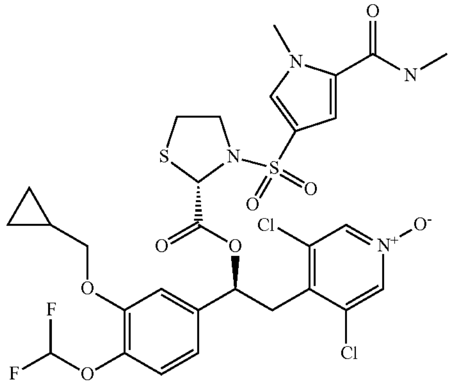 [SMILES: CNC(=O)c1cc(S(=O)(=O)N2CCS[C@H]2C(=O)O[C@@H](Cc2c(Cl)c[n+]([O-])cc2Cl)c2ccc(OC(F)F)c(OCC3CC3)c2)cn1C] | Free Base | 735.2 | 3.47 (2) | >99:1 | $^1$H NMR (400 MHz, DMSO-$d_6$) δ ppm 12.45-12.98 (bs, 1 H), 8.59 (s, 2 H), 8.27 (d, J = 4.85 Hz, 1 H), 7.67 (d, J = 1.76 Hz, 1 H), 7.18 (d, J = 8.38 Hz, 1 H), 7.06-7.13 (m, 3 H), 6.96 (dd, J = 8.38, 1.76 Hz, 1 H), 6.03 (dd, J = 9.26, 4.85 Hz, 1 H), 5.22 (s, 1 H), 3.84-3.96 (m, 5 H), 3.58-3.73 (m, 2 H), 3.45 (dd, J = 14.11, 9.26 Hz, 1 H), 3.28-3.30 (m, 1 H), 2.94-3.05 (m, 1 H), 2.75-2.84 (m, 1 H), 2.72 (d, J = 4.41 Hz, 3 H), 1.22 (d, J = 7.50 Hz, 1 H), 0.48-0.63 (m, 2 H), 0.33 (q, J = 4.85 Hz, 2 H) | | | |

TABLE 6-continued

| Entry | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 242 | 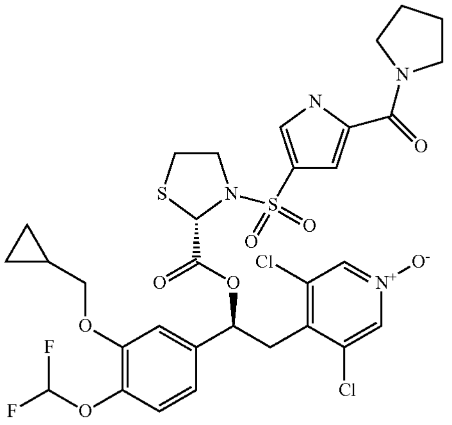 [SMILES: O=C(O[C@@H](Cc1c(Cl)c[n+]([O-])cc1Cl)c1ccc(OC(F)F)c(OCC2CC2)c1)[C@@H]1SCCN1S(=O)(=O)c1c[nH]c(C(=O)N2CCCC2)c1] | Free Base | 761.2 | 3.61 | >99:1 | $^1$H NMR (400 MHz, DMSO-$d_6$) δ ppm 12.46 (bs, 1 H), 8.57 (s, 2 H), 7.54 (dd, J = 3.53, 1.32 Hz, 1 H), 7.17 (d, J = 8.38 Hz, 1 H), 7.10 (d, J = 1.76 Hz, 1 H), 7.08 (t, J = 75.00 Hz, 1 H), 6.92-7.00 (m, 2 H), 6.01 (dd, J = 9.04, 5.07 Hz, 1 H), 5.46 (s, 1 H), 3.90 (dd, J = 7.06, 1.32 Hz, 2 H), 3.81 (ddd, J = 11.69, 6.17, 5.95 Hz, 1 H), 3.72 (t, J = 6.84 Hz, 2 H), 3.56-3.66 (m, 1 H), 3.39-3.55 (m, 3 H), 3.29 (d, J = 5.29 Hz, 1 H), 2.88-2.99 (m, 1 H), 2.64 (ddd, J = 10.81, 6.62, 6.39 Hz, 1 H), 1.91-2.02 (m, 2 H), 1.84 (q, J = 6.62 Hz, 2 H), 1.21 (ddd, J = 7.83, 4.52, 3.09 Hz, 1 H), 0.49-0.62 (m, 2 H), 0.28-0.40 (m, 2 H). | | | |
| 243 | 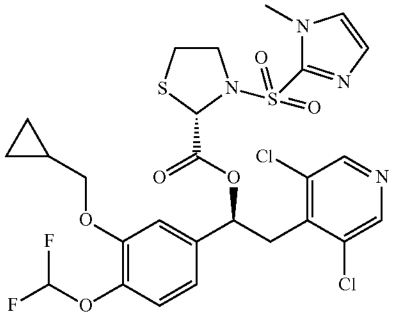 [SMILES: Cn1ccnc1S(=O)(=O)N1CCS[C@H]1C(=O)O[C@@H](Cc1c(Cl)cncc1Cl)c1ccc(OC(F)F)c(OCC2CC2)c1] | Free Base | 663.2 | 4.62 (2) | >99:1 | $^1$H NMR (400 MHz, DMSO-$d_6$) δ ppm 8.59 (s, 2 H), 7.52 (m, 1 H), 7.17 (m, 1 H), 7.08-7.12 (m, 2 H), 7.07 (t, J = 75.00 Hz, 1 H), 6.95 (m, 1 H), 6.02-6.10 (m, 1 H), 5.46 (s, 1 H), 3.77-3.95 (m, 6 H), 3.65-3.75 (m, 1 H), 3.47-3.59 (m, 1 H), 3.33-3.41 (m, 1 H), 2.96 (d, J = 15.88 Hz, 2 H), 1.09-1.30 (m, 1 H), 0.46-0.62 (m, 2 H), 0.21-0.39 (m, 2 H). | | | |

TABLE 6-continued
| Entry | Structure | SALT NAME | HPLC-MS characterization MS/ESI+ [MH]+ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 328 | 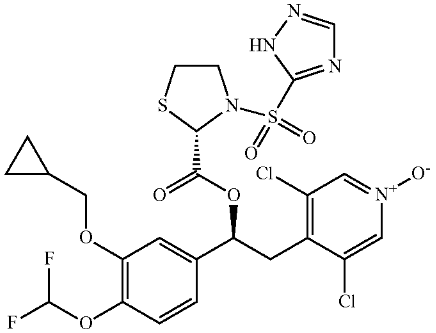 [SMILES: O=C(O[C@@H](Cc1c(Cl)c[n+]([O-])cc1Cl)c1ccc(OC(F)F)c(OCC2CC2)c1)[C@@H]1SCCN1S(=O)(=O)c1ncn[nH]1] | Free Base | 666.1 | 3.07; 3.11 (2) | 21:79 | | | | |
| 244 | 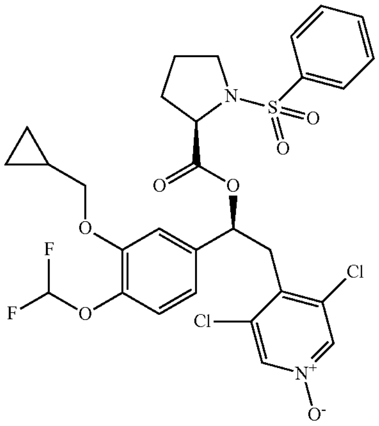 [SMILES: O=C(O[C@@H](Cc1c(Cl)c[n+]([O-])cc1Cl)c1ccc(OC(F)F)c(OCC2CC2)c1)[C@H]1CCCN1S(=O)(=O)c1ccccc1] | Free Base | 657.2 | 4.03; (2) | 97:3 | $^1$H NMR (400 MHz, DMSO-$d_6$) δ ppm 8.54 (s, 2 H), 77.4-7.83 (m, 2 H), 7.66-7.74 (m, 1 H), 7.57-7.65 (m, 2 H), 7.21 (d, J = 8.38 Hz, 1 H), 7.14 (d, J = 1.76 Hz, 1 H), 7.09 (t, J = 75.00 Hz, 1 H), 7.00 (dd, J = 8.38, 1.76 Hz, 1 H), 5.98 (dd, J = 9.48, 4.63 Hz, 1 H), 4.14 (dd, J = 8.60, 4.63 Hz, 1 H), 3.86-4.01 (m, 2 H), 3.37-3.50 (m, 2 H), 3.27 (dd, J = 14.11, 4.41 Hz, 1 H), 3.14 (ddd, J = 9.81, 7.06, 6.95 Hz, 1 H), 1.45-1.98 (m, 4 H), 1.14-1.30 (m, 1 H), 0.48-0.63 (m, 2 H), 0.25-0.39 (m, 2 H). | | | |

TABLE 6-continued
| En-try | Structure | SALT NAME | HPLC-MS characterization: MS/ESI$^+$ [MH]$^+$ | HPLC-MS characterization: $t_R$/min Method 1, 2 or 3 | Diastereomeric ratio | $^1$H NMR | $[\alpha]_D$ | Precursor | Purification Method |
|---|---|---|---|---|---|---|---|---|---|
| 245 | 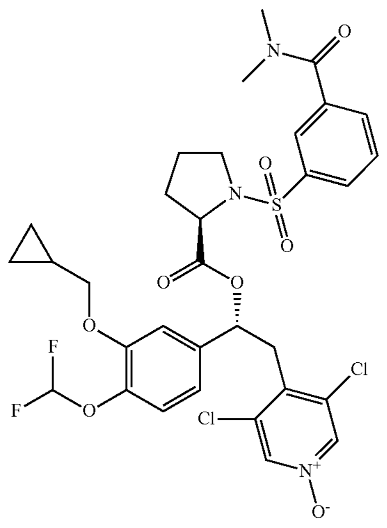 [SMILES: CN(C)C(=O)c1cccc(S(=O)(=O)N2CCC[C@@H]2C(=O)O[C@H](Cc2c(Cl)c[n+]([O-])cc2Cl)c2ccc(OC(F)F)c(OCC3CC3)c2)c1] | Free Base | 728.2 | 3.52 (2) | 1:99 | $^1$H NMR (400 MHz, DMSO-$d_6$) δ ppm 8.58 (s, 2 H), 7.65-7.87 (m, 4 H), 7.18 (d, J = 7.94 Hz, 1 H), 7.14 (d, J = 1.76 Hz, 1 H), 7.07 (t, J = 75.00 Hz, 1 H), 6.99 (m, 1 H), 5.96-6.08 (m, 1 H), 4.11-4.24 (m, 1 H), 3.91 (d, J = 7.06 Hz, 2 H), 3.33-3.51 (m, 2 H), 3.28 (m, 2 H), 2.83-3.06 (m, 6 H), 1.88-2.04 (m, 1 H), 1.45-1.76 (m, 3 H), 1.12-1.29 (m, 1 H), 0.55 (dd, J = 8.16, 1.54 Hz, 2 H), 0.25-0.38 (m, 2 H). | | | |

TABLE 6-continued
| Entry | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 246 | 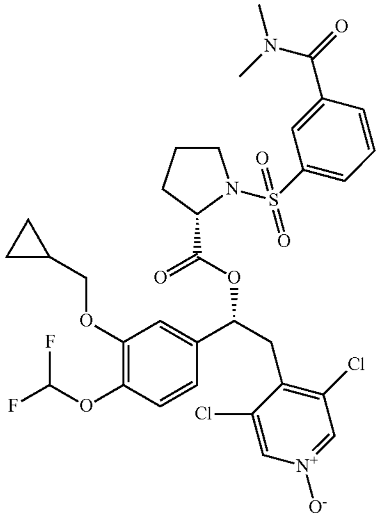 [SMILES: CN(C)C(=O)c1cccc(S(=O)(=O)N2CCC[C@H]2C(=O)O[C@H](Cc2c(Cl)c[n+]([O-])cc2Cl)c2ccc(OC(F)F)c(OCC3CC3)c2)c1] | Free Base | 728.2 | 3.47 (2) | 98:2 | $^1$H NMR (400 MHz, DMSO-$d_6$) δ ppm 8.58 (s, 2 H), 7.65-7.87 (m, 4 H), 7.18 (d, J = 7.94 Hz, 1 H), 7.14 (d, J = 1.76 Hz, 1 H), 7.07 (t, J = 75.00 Hz, 1 H), 6.99 (m, 1 H), 5.96-6.08 (m, 1 H), 4.11-4.24 (m, 1 H), 3.91 (d, J = 7.06 Hz, 2 H), 3.33-3.51 (m, 2 H), 3.28 (m, 2 H), 2.83-3.06 (m, 6 H), 1.88-2.04 (m, 1 H), 1.45-1.76 (m, 3 H), 1.12-1.29 (m, 1 H), 0.55 (dd, J = 8.16, 1.54 Hz, 2 H), 0.25-0.38 (m, 2 H). | | | |
| 247 | 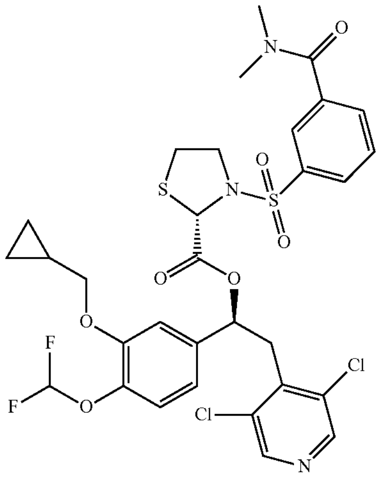 [SMILES: CN(C)C(=O)c1cccc(S(=O)(=O)N2CCS[C@H]2C(=O)O[C@@H](Cc2c(Cl)cncc2Cl)c2ccc(OC(F)F)c(OCC3CC3)c2)c1] | Free Base | 730.2 | | 65:35 ($^1$H NMR) | | | | |

TABLE 6-continued

| Entry | Structure | SALT NAME | HPLC-MS characterization MS/ESI+ [MH]+ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 248 | 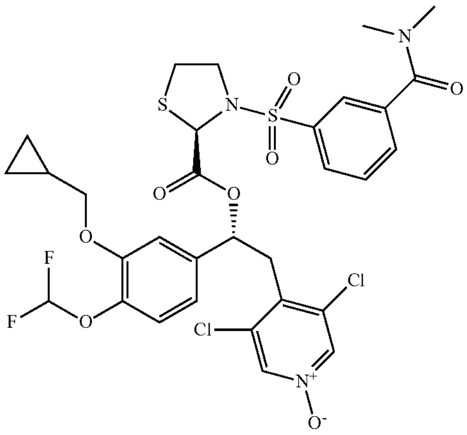 [SMILES: CN(C)C(=O)c1cccc(S(=O)(=O)N2CCS[C@@H]2C(=O)O[C@H](Cc2c(Cl)c[n+]([O-])cc2Cl)c2ccc(OC(F)F)c(OCC3CC3)c2)c1] | Free Base | 746.0 | 3.63 (2) | >99:1 | $^1$H NMR (400 MHz, DMSO-$d_6$) δ ppm 8.57 (s, 2 H), 7.86-8.00 (m, 2 H), 7.65-7.83 (m, 2 H), 7.18 (d, J = 7.94 Hz, 1 H), 7.11 (d, J = 1.32 Hz, 1 H), 7.08 (t, J = 75.00 Hz, 1 H), 6.86-6.96 (m, 1 H), 6.01 (dd, J = 9.04, 5.07 Hz, 1 H), 5.54 (s, 1 H), 3.80-3.98 (m, 3 H), 3.60-3.72 (m, 1 H), 3.46 (dd, J = 14.11, 9.26 Hz, 1 H), 3.30-3.35 (m, 1 H), 2.82-3.06 (m, 7 H), 2.63-2.73 (m, 1 H), 1.15-1.33 (m, 1 H), 0.47-0.65 (m, 2 H), 0.33 (q, J = 4.85 Hz, 2 H) | | | |
| 249 | 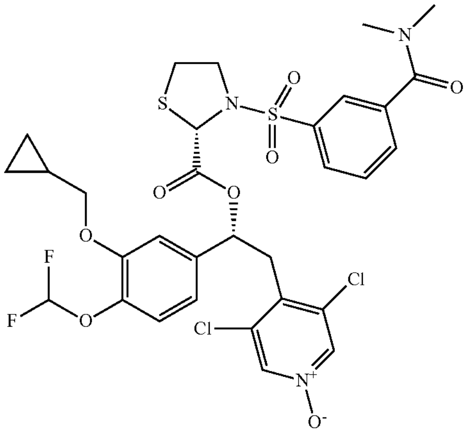 [SMILES: CN(C)C(=O)c1cccc(S(=O)(=O)N2CCS[C@H]2C(=O)O[C@H](Cc2c(Cl)c[n+]([O-])cc2Cl)c2ccc(OC(F)F)c(OCC3CC3)c2)c1] | Free Base | 746.0 | 3.57; 3.64 (2) | 84:16 | $^1$H NMR (400 MHz, DMSO-$d_6$) δ ppm 8.54 (s, 2 H), 7.89-7.98 (m, 2 H), 7.63-7.80 (m, 2 H), 7.22 (d, J = 7.94 Hz, 1 H), 7.06-7.15 (m, 2 H), 7.00 (dd, J = 8.38, 1.32 Hz, 1 H), 5.97 (dd, J = 9.70, 4.41 Hz, 1 H), 5.57 (s, 1 H), 3.89-4.02 (m, 2 H), 3.57-3.86 (m, 2 H), 3.47 (dd, J = 14.11, 9.70 Hz, 1 H), 3.26 (d, J = 4.85 Hz, 1 H), 2.80-3.10 (m, 7 H), 2.61-2.74 (m, 1 H), 1.15-1.31 (m, 1 H), 0.50-0.64 (m, 2 H), 0.34 (q, J = 4.85 Hz, 2 H) | | | |

TABLE 6-continued

| En-try | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 250 | 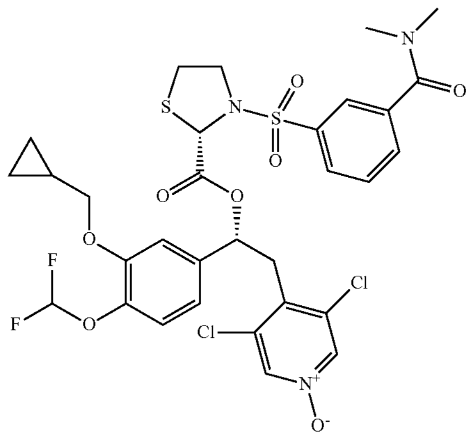 [SMILES: CN(C)C(=O)c1cccc(S(=O)(=O)N2CCS[C@H]2C(=O)O[C@H](Cc2c(Cl)c[n+]([O-])cc2Cl)c2ccc(OC(F)F)c(OCC3CC3)c2)c1] | Free Base | 728.1 | 4.26 (2) | 3:97 | $^1$H NMR (400 MHz, DMSO-$d_6$) δ ppm 8.48 (s, 2 H), 7.12-7.21 (m, 2 H), 7.08 (t, J = 75.00 Hz, 1 H), 6.95-7.02 (m, 2 H), 6.93 (d, J = 2.21 Hz, 1 H), 6.86 (d, J = 8.38 Hz, 1 H), 6.03 (dd, J = 9.70, 4.41 Hz, 1 H), 4.22-4.40 (m, 2 H), 4.11 (dd, J = 8.82, 3.97 Hz, 1 H), 3.92 (d, J = 7.06 Hz, 2 H), 3.45 (dd, J = 14.11, 9.70 Hz, 1 H), 3.08-3.27 (m, 5 H), 2.90 (s, 3 H), 1.83-2.01 (m, 1 H), 1.45-1.74 (m, 3 H), 1.13-1.28 (m, 1 H), 0.48-0.65 (m, 2 H), 0.33 (q, J = 4.85 Hz, 2 H). | | | |
| 251 | 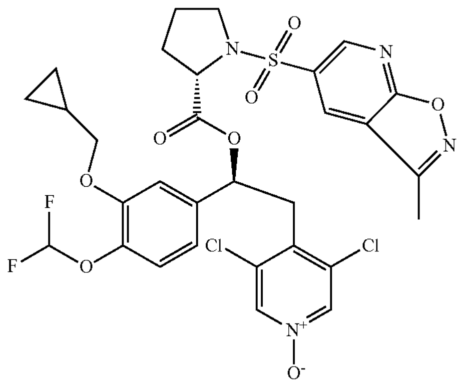 [SMILES: Cc1noc2ncc(S(=O)(=O)N3CCC[C@H]3C(=O)O[C@@H](Cc3c(Cl)c[n+]([O-])cc3Cl)c3ccc(OC(F)F)c(OCC4CC4)c3)cc12] | Free Base | 713.1 | 4.00 (2) | >99:1 | $^1$H NMR (400 MHz, DMSO-$d_6$) δ ppm 8.92-9.04 (m, 1 H), 8.86-8.92 (m, 1 H), 8.61 (s, 2 H), 7.12-7.23 (m, 2 H), 7.07 (t, J = 75.00 Hz, 1 H), 6.95-7.02 (m, 1 H), 5.97-6.09 (m, 1 H), 4.34-4.41 (m, 1 H), 3.85-3.96 (m, 2 H), 3.38-3.55 (m, 2 H), 3.19-3.29 (m, 2 H), 2.67 (s, 3 H), 1.89-2.06 (m, 1 H), 1.52-1.77 (m, 3 H), 1.10-1.31 (m, 1 H), 0.47-0.62 (m, 2 H), 0.27-0.41 (m, 2 H). | | | |

TABLE 6-continued

| En-try | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 252 | 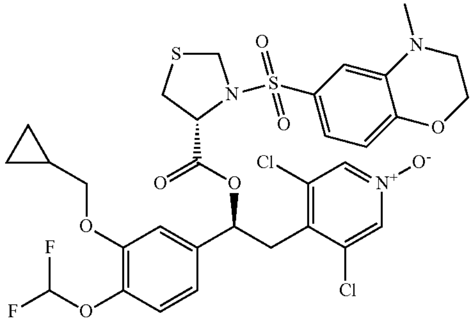 [SMILES: CN1CCOc2ccc(S(=O)(=O)N3CSC[C@H]3C(=O)O[C@@H](Cc3c(Cl)c[n+]([O-])cc3Cl)c3ccc(OC(F)F)c(OCC4CC4)c3)cc21] | Free Base | 746.1 | 4.35 (2) | >99:1 | $^1$H NMR (400 MHz, DMSO-$d_6$) δ ppm 8.57 (s, 2 H), 7.13-7.22 (m, 2 H), 6.94-7.10 (m, 4 H), 6.85 (d, J = 7.94 Hz, 1 H), 5.96-6.06 (m, 1 H), 4.85 (m, 1 H), 4.63 (d, J = 10.14 Hz, 1 H), 4.23-4.38 (m, 3 H), 3.92 (d, J = 7.06 Hz, 2 H), 3.40-3.52 (m, 1 H), 3.28 (m, 3 H), 2.96-3.08 (m, 1 H), 2.90 (m, 4 H), 1.13-1.29 (m, 1 H), 0.56 (dd, J = 8.38, 1.76 Hz, 2 H), 0.33 (d, J = 4.41 Hz, 2 H). | | | |
| 253 | 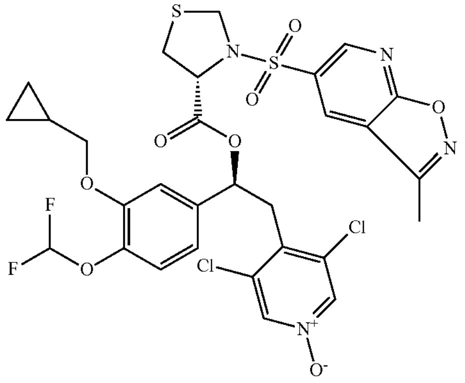 [SMILES: Cc1noc2ncc(S(=O)(=O)N3CSC[C@H]3C(=O)O[C@@H](Cc3c(Cl)c[n+]([O-])cc3Cl)c3ccc(OC(F)F)c(OCC4CC4)c3)cc12] | Free Base | 731.0 | 4.08 (2) | >99:1 | $^1$H NMR (400 MHz, DMSO-$d_6$) δ ppm 9.13 (d, J = 2.21 Hz, 1 H), 9.02 (d, J = 2.21 Hz, 1 H), 8.59 (s, 2 H), 7.14-7.22 (m, 2 H), 7.08 (t, J = 75.00 Hz, 1 H), 6.94-7.02 (m, 1 H), 5.93-6.10 (m, 1 H), 4.95-5.09 (m, 1 H), 4.73-4.86 (m, 1 H), 4.27-4.44 (m, 1 H), 3.82-4.01 (m, 2 H), 3.41-3.55 (m, 1 H), 3.22-3.28 (m, 1 H), 2.96-3.10 (m, 2 H), 2.66 (s, 3 H), 1.12-1.30 (m, 1 H), 0.50-0.64 (m, 2 H), 0.22-0.42 (m, 2 H). | | | |

TABLE 6-continued
| En-try | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method |
|---|---|---|---|---|---|---|---|---|---|
| 254 | 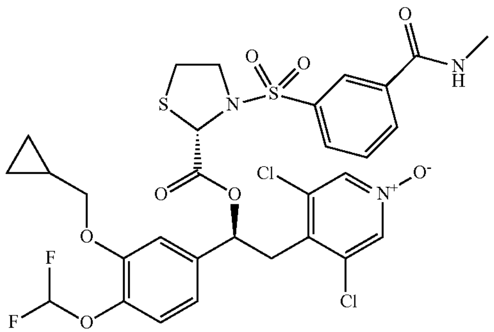 [SMILES: CNC(=O)c1cccc(S(=O)(=O)N2CCS[C@H]2C(=O)O[C@@H](Cc2c(Cl)c[n+]([O-])cc2Cl)c2ccc(OC(F)F)c(OCC3CC3)c2)c1] | Free Base | 731.9 | 3.52 (2) | 2:98 | $^1$H NMR (400 MHz, DMSO-$d_6$) δ ppm 8.77 (d, J = 4.41 Hz, 1 H), 8.60 (s, 2 H), 8.30 (m, 1 H), 8.13-8.22 (m, 1 H), 8.02 (d, J = 7.94 Hz, 1 H), 7.76 (t, J = 7.94 Hz, 1 H), 7.18 (d, J = 7.94 Hz, 1 H), 7.11 (d, J = 1.32 Hz, 1 H), 7.08 (t, J = 75.00 Hz, 1 H), 6.95 (dd, J = 8.38, 1.76 Hz, 1 H), 6.01 (dd, J = 8.82, 4.85 Hz, 1 H), 5.51 (s, 1 H), 3.87-3.97 (m, 2 H), 3.82 (ddd, J = 11.58, 5.95, 5.84 Hz, 1 H), 3.68 (ddd, J = 11.80, 6.39, 6.06 Hz, 1 H), 3.46 (dd, J = 14.11, 9.26 Hz, 1 H), 3.35 (m, 1 H), 2.90-3.03 (m, 1 H), 2.56-2.70 (m, 1 H), 1.13-1.31 (m, 1 H), 0.50-0.64 (m, 2 H), 0.27-0.43 (m, 2 H). | | | |

Some of the compounds described above in Table 6 were further crystallized under the conditions described below in Table 7 to obtain one or more crystalline forms. Where reference in Table 7 is made to crystallization conditions (A), (B), (C), (D), or (E), the following operating conditions were used:

Temperature Cycling Experiments—(A)

Slurries of the materials were prepared in each of the selected solvent systems. Approximately 10 mg of material was slurried in ca. 200 μl of solvent (if material dissolved the clear solution was used). The slurries were temperature cycled at 40° C. in 4 hour cycles for a period of 3 days (the cooling/heating rates after the 4 hour periods were up was ca. 1° C./minute). Any solids present were isolated and allowed to dry at ambient conditions prior to analysis.

Slow Cooling Experiments—(B)

This was carried out by placing saturated solutions of the material in each of the selected solvent systems in an environment of 2° C. for ca. 3 days. A saturated solution was created and this exposed to the relevant experimental condition. Any solid material was then recovered and allowed to dry at ambient conditions prior to analysis.

Rapid Cooling Experiments—(C)

This was carried out by placing saturated solutions of the material, in each of the selected solvent systems in environment of −18° C. for ca. 3 days. A saturated solution was created and this exposed to the relevant experimental condition. Any solid material was then recovered and allowed to dry at ambient conditions prior to analysis.

Evaporation Experiments—(D)

Evaporation experiments were conducted on saturated mixtures as above described. This was carried out by allowing the solvents to evaporate freely at ambient conditions. Any solid material was then recovered and analysed after the solvent had evaporated to dryness.

Anti-Solvent Addition Experiments—(E)

Anti-solvent addition experiments were conducted on saturated solutions of the material in each of the respective solvent systems and adding anti-solvent until precipitation occurred. Any solid material was then recovered and allowed to dry at ambient conditions prior to analysis.

TABLE 7

| Entry | Structure | Solvent systems | Crystallization conditions | Crystalline Form |
|---|---|---|---|---|
| 52a | 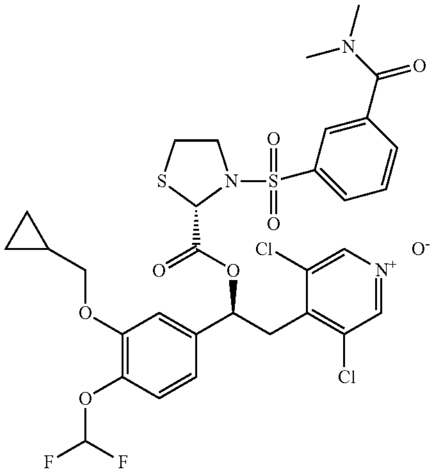 | EtOH | RT; 7.5 vv w/w | I |
| 52a | 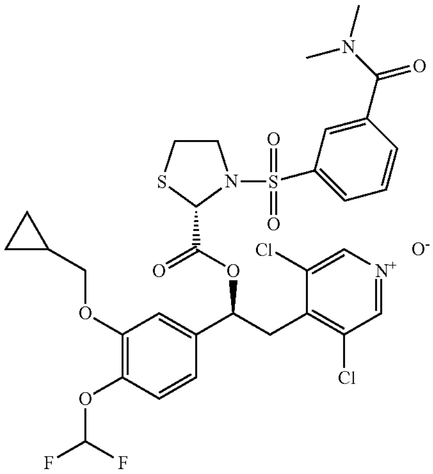 | AcOEt/Heptane | from 60 degrees to RT; 15 vv/12.5 vv w/w | I |

TABLE 7-continued
| Entry | Structure | Solvent systems | Crystallization conditions | Crystalline Form |
|---|---|---|---|---|
| 52a | 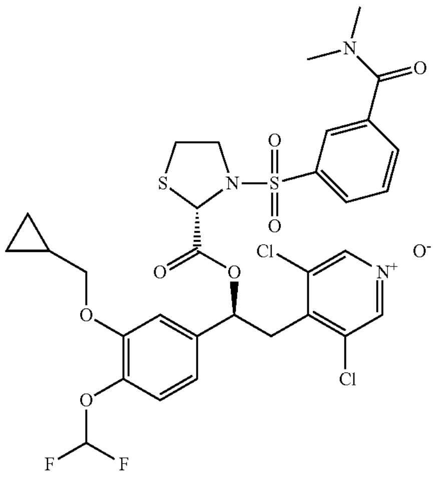 | IprOAc | from RT to −20 degrees; 5 vv w/w | I |
| 52a | 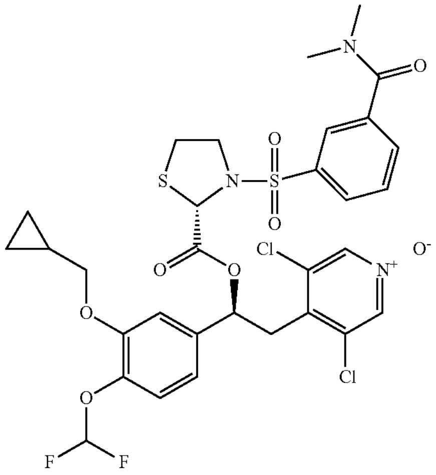 | MeOH | from 40 degrees to RT; 4 vv w/w | I |
| 52a | 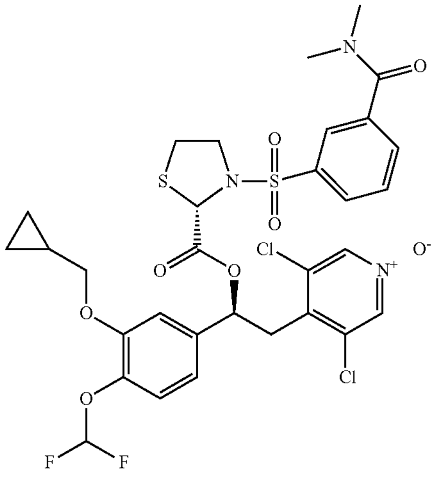 | nBuOH; IprOH; Toluene; MTBE; $(Irp)_2O$; EtOH | (A) or (B) or (C) or (D) | I |

TABLE 7-continued
| Entry | Structure | Solvent systems | Crystallization conditions | Crystalline Form |
|---|---|---|---|---|
| 90a | 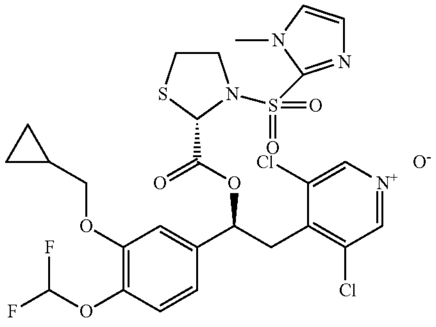 | MeOH | From 50 degrees to RT; 10 vv v/w | N/A |
| 90b | 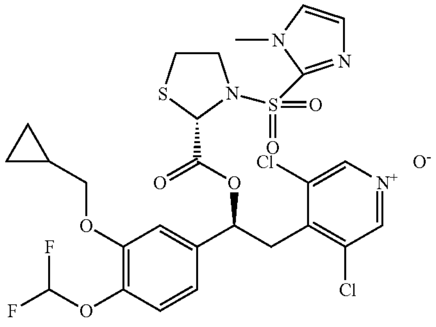 | nBuOH; MeOH; EtOH | (A) or (B) or (C) or (D) | I |
| 90b | 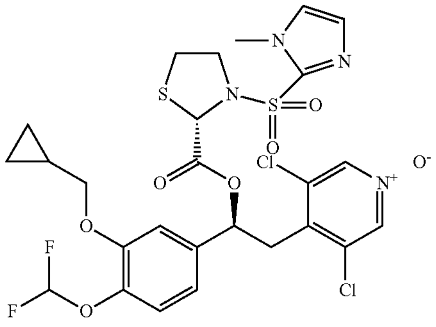 | Dioxane; MIK | (C) or (D) | I |
| 90b | 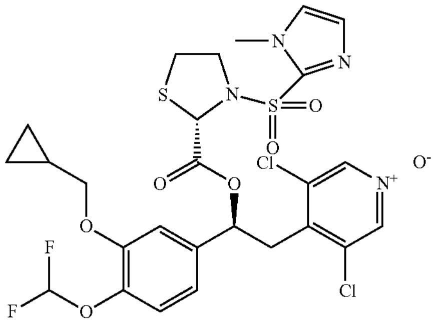 | Acetone; MEK | (D) | I |

TABLE 7-continued
| Entry | Structure | Solvent systems | Crystallization conditions | Crystalline Form |
|---|---|---|---|---|
| 90c | 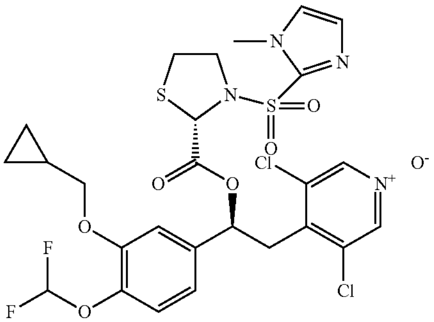 | $(Ipr)_2O$; IprOH; MTBE; Toluene | (A) or (B) or (C) or (D) | II |
| 88a | 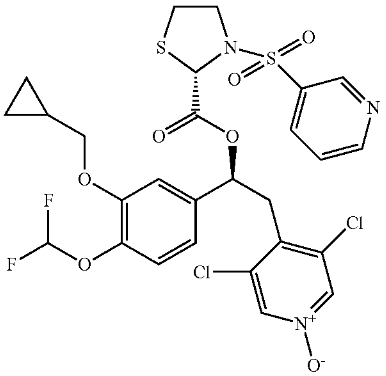 [SMILES: O=C(O[C@@H](Cc1c(Cl)c[n+]([O-])cc1Cl)c1ccc(OC(F)F)c(OCC2CC2)c1)[C@@H]1SCCN1S(=O)(=O)c1cccnc1] | Acetone $(Ipr)_2O$ | (A) | I |
| 88b | 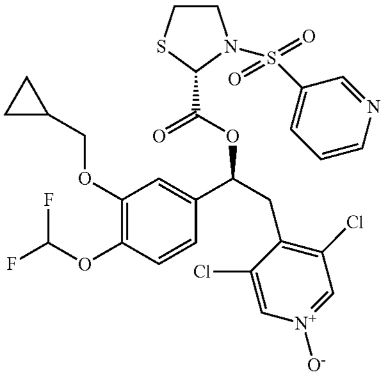 [SMILES: O=C(O[C@@H](Cc1c(Cl)c[n+]([O-])cc1Cl)c1ccc(OC(F)F)c(OCC2CC2)c1)[C@@H]1SCCN1S(=O)(=O)c1cccnc1] | EtOH; Methyl Isobutyl Ketone | (A) or (B) (with MIK) or (C) (with MIK) | III |
| 88c | 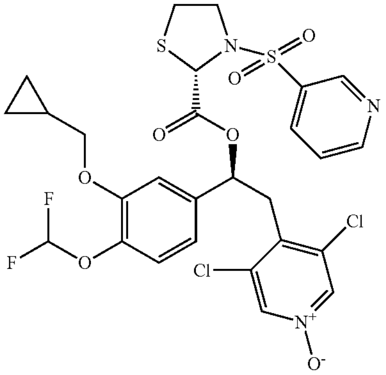 [SMILES: O=C(O[C@@H](Cc1c(Cl)c[n+]([O-])cc1Cl)c1ccc(OC(F)F)c(OCC2CC2)c1)[C@@H]1SCCN1S(=O)(=O)c1cccnc1] | MeOH | (A) or (B) or (C) | II |

TABLE 7-continued
| Entry | Structure | Solvent systems | Crystallization conditions | Crystalline Form |
|---|---|---|---|---|
| 89a | 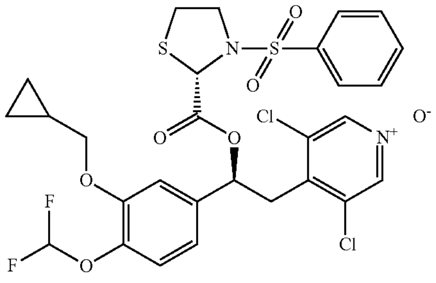 | n-BuOH; $(Ipr)_2O$; IprOH; MTBE; | (A) or (B) or (C) or (D) | I |
| 89b | 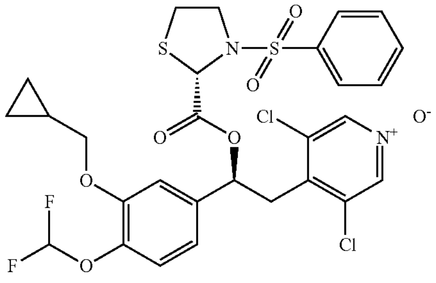 | EtOH; MeOH | (A) or (B) or (C) or (D) | II |
| 93a | 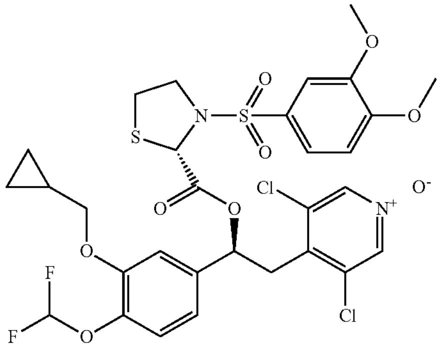 | EtOH; MeOH; IprOH | (A) or (B) or (C) or (D) | I |
| 93a | 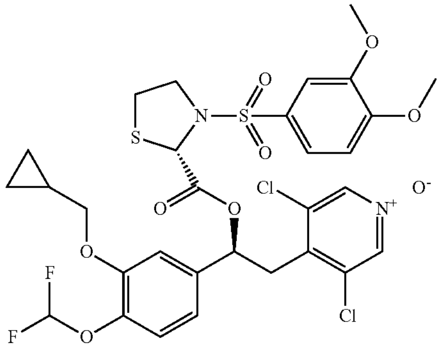 | Acetone | (D) | I |

TABLE 7-continued
| Entry | Structure | Solvent systems | Crystallization conditions | Crystalline Form |
|---|---|---|---|---|
| 93b | 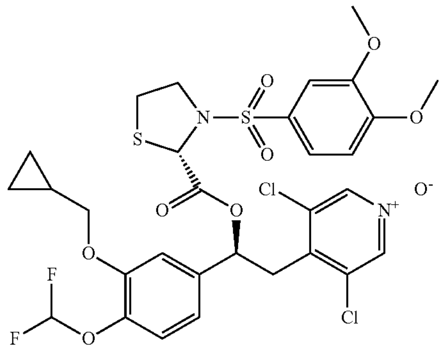 | n-BuOH | (B) or (C) or (D) | II |
| 91a | 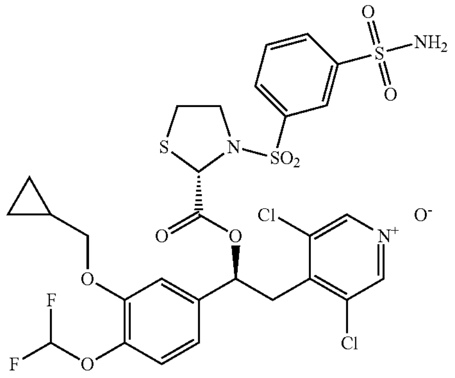 | Acetone/MeOH | From 50 degrees to RT; From 5/5 to 100% MeOH (acetone was evaporated) | I |
| 54a | 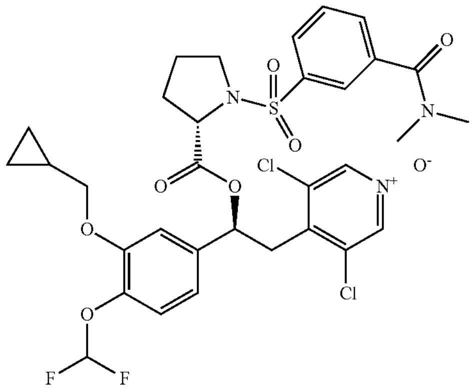 | EtOH | From 50 degrees to RT; 5 vvv/w | I |
| 110a | 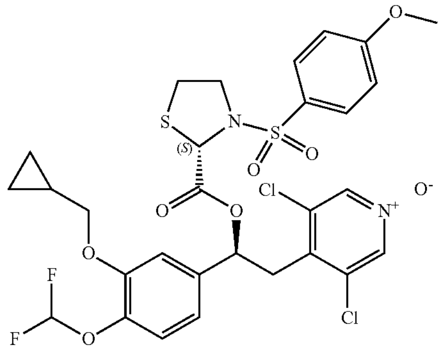 | MeOH | RT; 5 vv v/w | I |

TABLE 7-continued
| Entry | Structure | Solvent systems | Crystallization conditions | Crystalline Form |
|---|---|---|---|---|
| 150a | 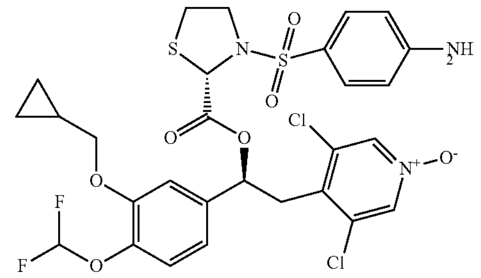 [SMILES: Nc1ccc(S(=O)(=O)N2CCS[C@H]2C(=O)O[C@@H](Cc2c(Cl)c[n+]([O-])cc2Cl)c2ccc(OC(F)F)c(OCC3CC3)c2)cc1] | EtOH | (A) or (B) or (C) or (D) | II |
| 150b | 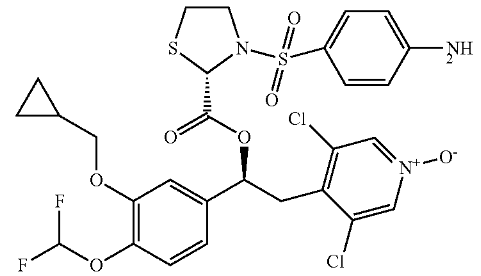 [SMILES: Nc1ccc(S(=O)(=O)N2CCS[C@H]2C(=O)O[C@@H](Cc2c(Cl)c[n+]([O-])cc2Cl)c2ccc(OC(F)F)c(OCC3CC3)c2)cc1] | nBuOH; MeOH | (B) or (C) or (D) | I |
| 84a | 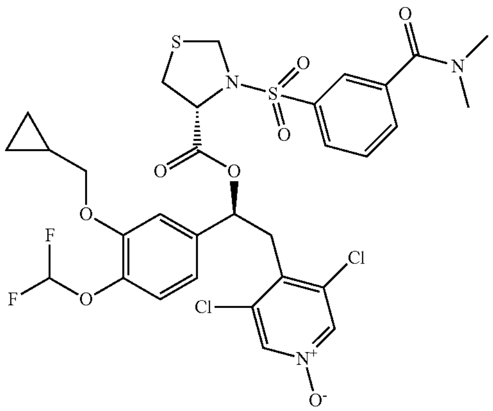 [SMILES: CN(C)C(=O)c1cccc(S(=O)(=O)N2CSC[C@H]2C(=O)O[C@@H](Cc2c(Cl)c[n+]([O-])cc2Cl)c2ccc(OC(F)F)c(OCC3CC3)c2)c1] | EtOH (anti-solvent Cyclohexane) | (A) or (B) or (C) or (D) or (E) | I |
| 84b | 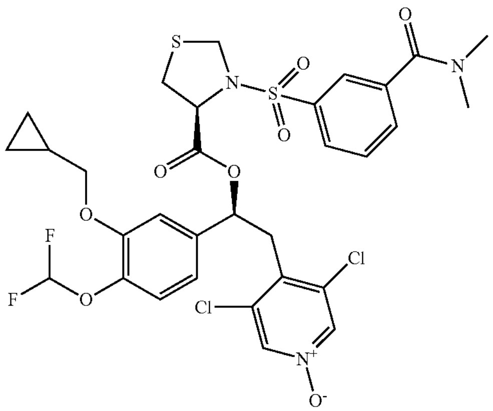 [SMILES: CN(C)C(=O)c1cccc(S(=O)(=O)N2CSC[C@@H]2C(=O)O[C@@H](Cc2c(Cl)c[n+]([O-])cc2Cl)c2ccc(OC(F)F)c(OCC3CC3)c2)c1] | IprOH (anti-solvent Cyclohexane) | (A) or (B) or (C) or (D) or (E) | II |

TABLE 7-continued
| Entry | Structure | Solvent systems | Crystallization conditions | Crystalline Form |
|---|---|---|---|---|
| 84b | 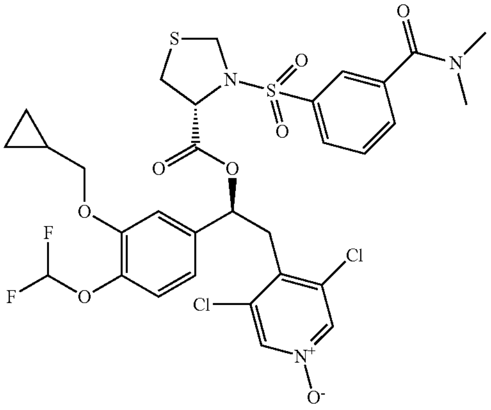 [SMILES: CN(C)C(=O)c1cccc(S(=O)(=O)N2CSC[C@H]2C(=O)O[C@@H](Cc2c(Cl)c[n+]([O-])cc2Cl)c2ccc(OC(F)F)c(OCC3CC3)c2)c1] | nBuOH (anti-solvent Cyclohexane) | (B) or (C) or (D) or (E) | II |
| 84c | 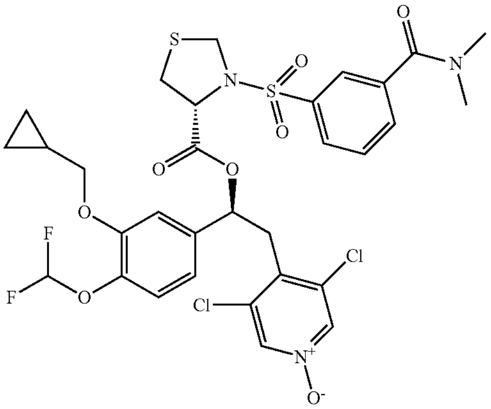 [SMILES: CN(C)C(=O)c1cccc(S(=O)(=O)N2CSC[C@H]2C(=O)O[C@@H](Cc2c(Cl)c[n+]([O-])cc2Cl)c2ccc(OC(F)F)c(OCC3CC3)c2)c1] | $(Ipr)_2O$ (anti-solvent Cyclohexane) | (B) or (C) or (D) or (E) | III |
| 131a | 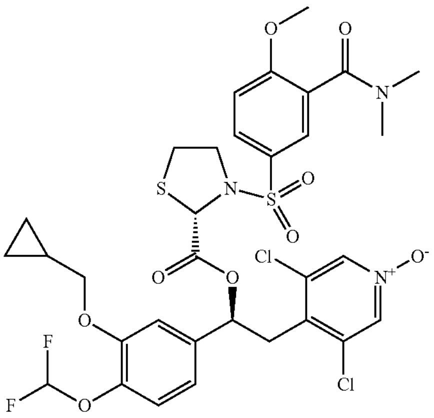 [SMILES: COc1ccc(S(=O)(=O)N2CCS[C@H]2C(=O)O[C@@H](Cc2c(Cl)c[n+]([O-])cc2Cl)c2ccc(OC(F)F)c(OCC3CC3)c2)cc1C(=O)N(C)C] | nBuOH (anti-solvent Diisopropyl Ether) | (C) or (D) or (E) | I |

TABLE 7-continued
| Entry | Structure | Solvent systems | Crystallization conditions | Crystalline Form |
|---|---|---|---|---|
| 97a | 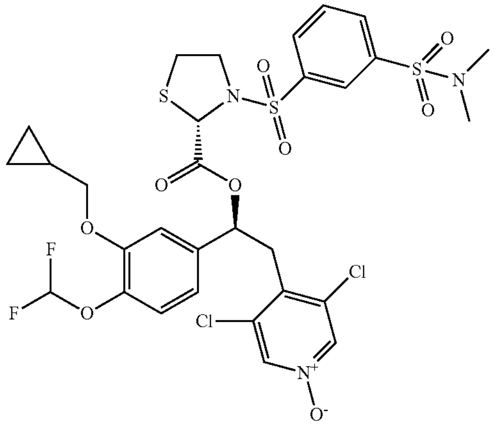 [SMILES: CN(C)S(=O)(=O)c1cccc(S(=O)(=O)N2CCS[C@H]2C(=O)O[C@@H](Cc2c(Cl)c[n+]([O-])cc2Cl)c2ccc(OC(F)F)c(OCC3CC3)c2)c1] | DCM; $(Ipr)_2O$; MTBE; Toluene; | (A) | I |
| 97b | 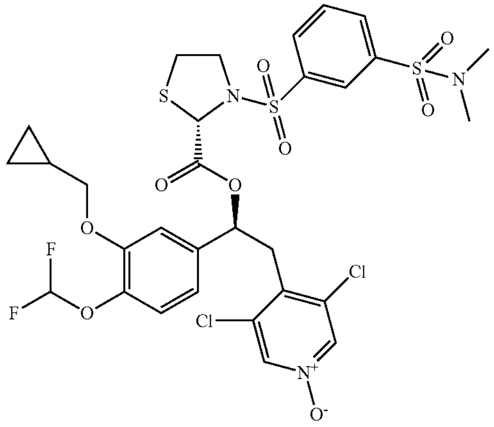 [SMILES: CN(C)S(=O)(=O)c1cccc(S(=O)(=O)N2CCS[C@H]2C(=O)O[C@@H](Cc2c(Cl)c[n+]([O-])cc2Cl)c2ccc(OC(F)F)c(OCC3CC3)c2)c1] | nBuOH; EtOH; Ethyl Acetate; MeOH; MEK; MIK; IprOH | (A) | II |
| 97a | 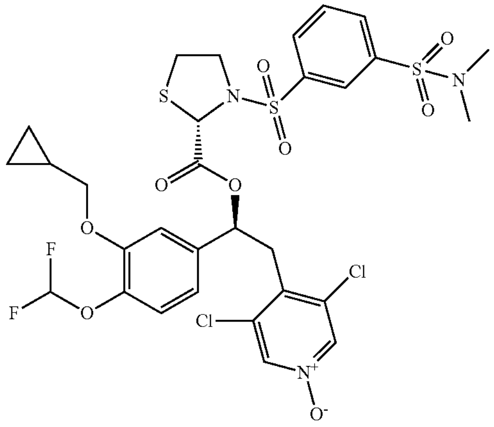 [SMILES: CN(C)S(=O)(=O)c1cccc(S(=O)(=O)N2CCS[C@H]2C(=O)O[C@@H](Cc2c(Cl)c[n+]([O-])cc2Cl)c2ccc(OC(F)F)c(OCC3CC3)c2)c1] | nBuOH; $(Ipr)_2O$; EtOH; IprOH; MTBE | (B) or (C) | I |

TABLE 7-continued
| Entry | Structure | Solvent systems | Crystallization conditions | Crystalline Form |
| --- | --- | --- | --- | --- |
| 97b | 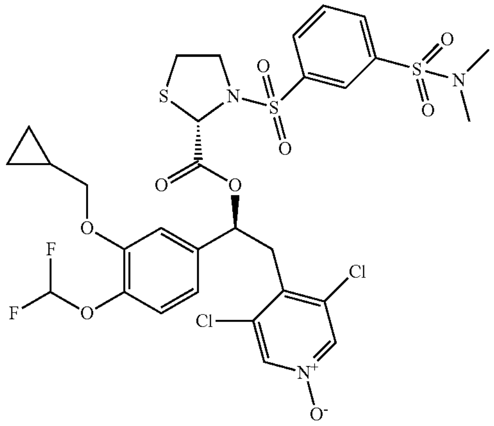 [SMILES: CN(C)S(=O)(=O)c1cccc(S(=O)(=O)N2CCS[C@H]2C(=O)O[C@@H](Cc2c(Cl)c[n+]([O-])cc2Cl)c2ccc(OC(F)F)c(OCC3CC3)c2)c1] | CH3CN; EtOAc; MeOH; MIK; Toluene | (B) or (C) | II |
| 109a | 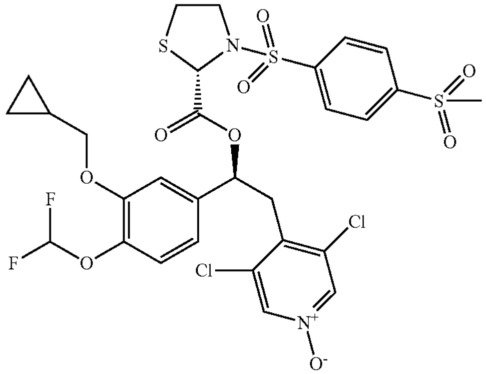 [SMILES: CS(=O)(=O)c1ccc(S(=O)(=O)N2CCS[C@H]2C(=O)O[C@@H](Cc2c(Cl)c[n+]([O-])cc2Cl)c2ccc(OC(F)F)c(OCC3CC3)c2)cc1] | Acetone; nBuOH; EtOH; Ethyl Acetate; MeOH; MIK; IprOH; Toluene | Temperature Cycling (or Slow Cooling, except for MeOH, IprOH and Acetone) | II |
| 109b | 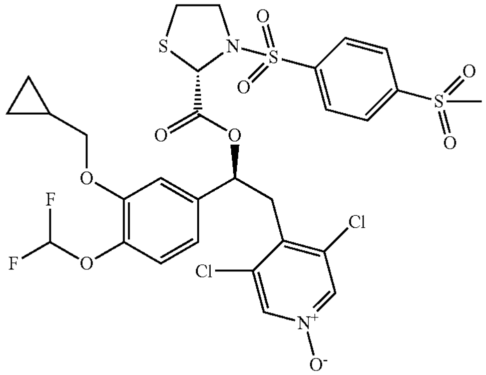 [SMILES: CS(=O)(=O)c1ccc(S(=O)(=O)N2CCS[C@H]2C(=O)O[C@@H](Cc2c(Cl)c[n+]([O-])cc2Cl)c2ccc(OC(F)F)c(OCC3CC3)c2)cc1] | MeOH; IprOH; | (B) | I |
| 109c | 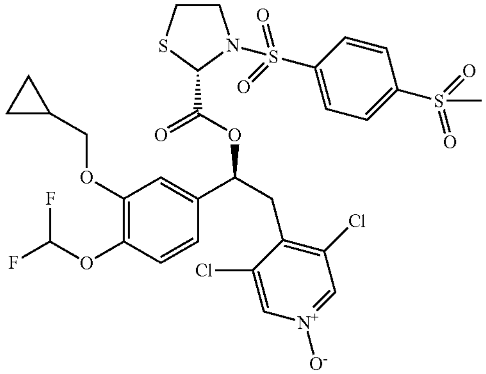 [SMILES: CS(=O)(=O)c1ccc(S(=O)(=O)N2CCS[C@H]2C(=O)O[C@@H](Cc2c(Cl)c[n+]([O-])cc2Cl)c2ccc(OC(F)F)c(OCC3CC3)c2)cc1] | $(Ipr)_2O$; MTBE | (A) or (B) | III |

Example 9. Synthesis of 3,5-dichloro-4-((2S)-2-(3-(cyclopropylmethoxy)-4-(difluoromethoxy)phenyl)-2-(3-(3-(dimethylcarbamoyl)-4-methoxyphenylsulfonyl)thiazolidine-2-carbonyloxy)ethyl)pyridine 1-oxide (123)

Scheme 17

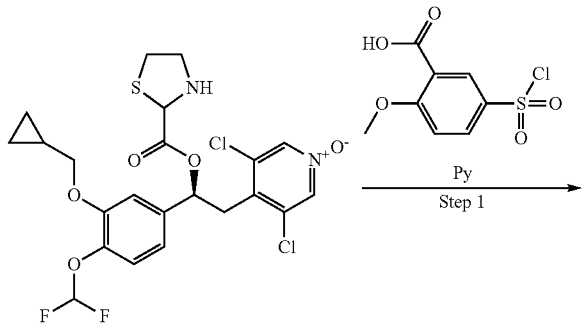

5

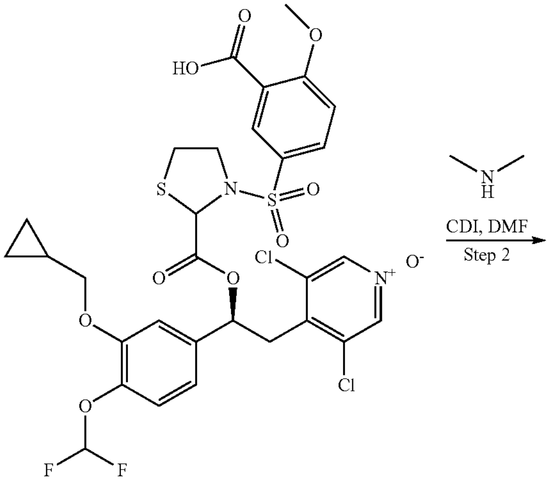

122

-continued

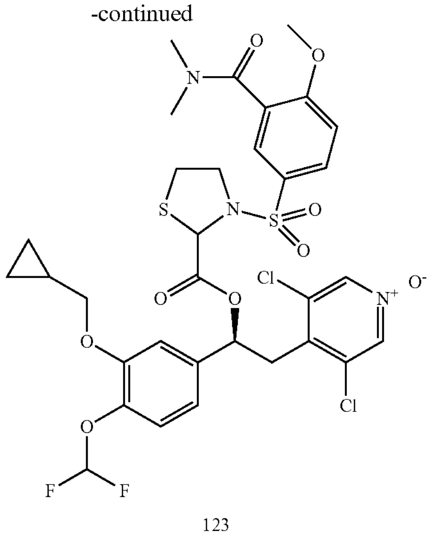

123

Step 1: 4-((2S)-2-(3-(3-carboxy-4-methoxyphenylsulfonyl)thiazolidine-2-carbonyloxy)-2-(3-(cyclopropylmethoxy)-4-(difluoromethoxy)phenyl)ethyl)-3,5-dichloropyridine 1-oxide, (122)

3,5-dichloro-4-((2S)-2-(3-(cyclopropylmethoxy)-4-(difluoromethoxy)phenyl)-2-(thiazolidine-2-carbonyloxy) ethyl)pyridine 1-oxide (5) (60 mg, 0.112 mmol) was dissolved in pyridine (1 ml), then 5-(chlorosulfonyl)-2-methoxybenzoic acid (56 ml, 0.224 mmol) was added at 0° C., and the mixture was stirred at RT for 2 hours. The reaction was quenched with HCl 1N, and the product was extracted with AcOEt. The organic phase was washed with HCl 1N (×2) and brine, then dried over $Na_2SO_4$. The solvent was removed to yield 70 mg of the desired compound (yield 83%). MS/ESI$^+$ 749.0 [MH]$^+$; $t_R$=5.94; 6.02 (Method 1); Diastereomeric Ratio=32:68.

Step 2: 3,5-dichloro-4-((2S)-2-(3-(cyclopropylmethoxy)-4-(difluoromethoxy)phenyl)-2-(3-(3-(dimethylcarbamoyl)-4-methoxyphenylsulfonyl)thiazolidine-2-carbonyloxy)ethyl)pyridine 1-oxide (123)

4-((2S)-2-(3-(3-carboxy-4-methoxyphenylsulfonyl)thiazolidine-2-carbonyloxy)-2-(3-(cyclopropylmethoxy)-4-(difluoromethoxy)phenyl)ethyl)-3,5-dichloropyridine 1-oxide (122) (70 mg, 0.093 mmol) was dissolved in DMF (1 ml). CDI (18 mg, 0.112 mmol) was added, and the mixture stirred for 30 minutes at RT. Then dimethylamine 2M in THF was added (300 μL, 0.600 mmol), and the mixture stirred at RT for 2 hours. The reaction was quenched with water, and the product was extracted with AcOEt. The organic layer was washed with water (2×) and NaCl saturated solution, dried over $Na_2SO_4$ and evaporated under vacuum. The crude product was purified by preparative HPLC (Method 1) condition to give 70 mg of the desired compound (yield 97%). MS/ESI$^+$ 776.1 [MH]$^+$; $t_R$ (Method 1)=6.40; 6.50 min; Diasteromeric Ratio=36:64.

The compounds listed in Table 8 were prepared according to analogous procedure as that described for Scheme 17 and by reacting the appropriate precursors listed with suitable reagents, followed by an appropriate purification procedure as below indicated.

TABLE 8

| Entry | Structure | SALT NAME | HPLC-MS characterization MS/ESI$^+$ [MH]$^+$ | $t_R$/min Methods 1 or 2 | Diastereomeric ratio | $^1$H NMR | $[\alpha]_D$ | Precursor | Purification Method | Amine |
|---|---|---|---|---|---|---|---|---|---|---|
| 124 | 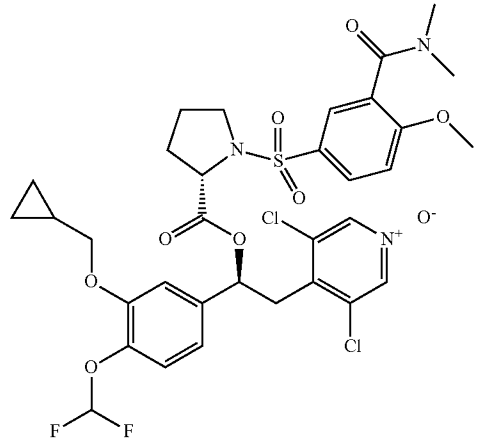 | Free Base | 757.09 | 3.56 (2) | >99:1 | $^1$H NMR (400 MHz, DMSO-$d_6$) δ ppm 8.54 (s, 2H), 7.80 (dd, J = 8.60, 2.43 Hz, 1 H), 7.56 (d, J = 2.65 Hz, 1 H), 7.32 (d, J = 8.82 Hz, 1 H), 7.10-7.21 (m, 2 H), 7.08 (t, J = 75.00 Hz, 1 H), 6.98 (dd, J = 8.38, 1.76 Hz, 1 H), 5.89-6.11 (m, 1 H), 4.04-4.20 (m, 1 H), 3.87-3.97 (m, 5 H), 3.46 (m, 1 H), 3.08-3.30 (m, 3 H), 2.99 (s, 3 H), 2.75 (s, 3 H), 1.60-1.75 (m, 2 H), 1.43-1.59 (m, 2 H), 0.85 (m, 1 H), 0.49-0.62 (m, 2 H), 0.33 (d, J = 4.41 Hz, 2 H). | −55.88 (c = 0.48; $CHCl_3$) | 3 | Preparative HPLC (Method 1) | 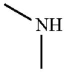 |
| 125 | 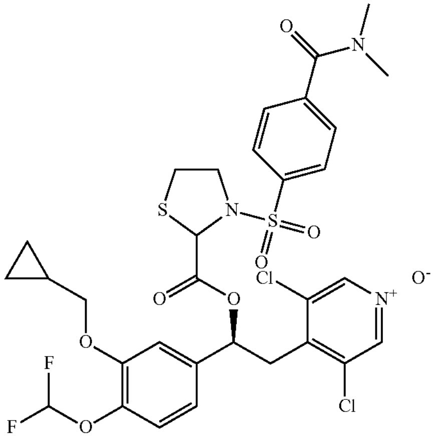 | Free Base | 747.0 | 6.37; 6.47 (1) | 38:62 | | | 5 | Preparative HPLC (Method 1) | 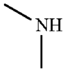 |

TABLE 8-continued
| Entry | Structure | SALT NAME | HPLC-MS characterization MS/ESI$^+$ [MH]$^+$ | $t_R$/min Methods 1 or 2 | Diastereomeric ratio | $^1$H NMR | $[\alpha]_D$ | Precursor | Purification Method | Amine |
|---|---|---|---|---|---|---|---|---|---|---|
| 126 | 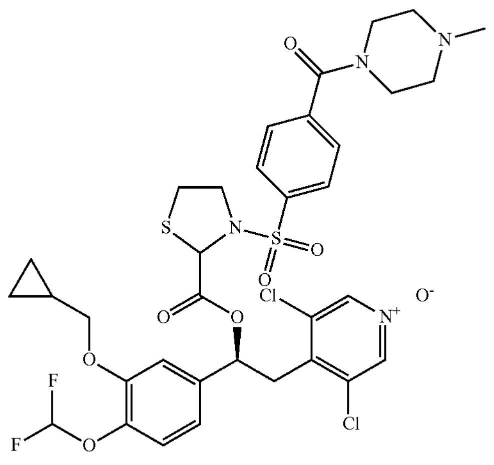 | formate | 801.1 | 4.78; 4.88 (1) | 38:62 | | | 5 | Preparative HPLC (Method 1) | 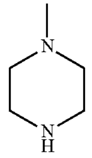 |
| 127 | 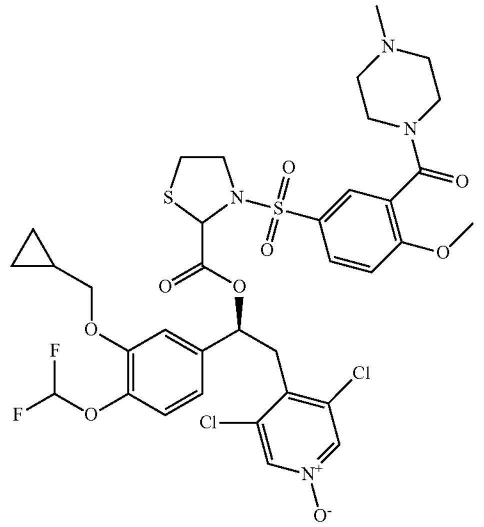 [SMILES: COc1ccc(S(=O)(=O)N2CCSC2C(=O)O[C@@H](Cc2c(Cl)c[n+]([O-])cc2Cl)c2ccc(OC(F)F)c(OCC3CC3)c2)cc1C(=O)N1CCN(C)CC1] | Free Base | 831.1 | 4.85; 4.92 (2) | 26:74 | | | 5 | No purification | 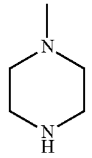 |

TABLE 8-continued
| Entry | Structure | SALT NAME | HPLC-MS characterization MS/ESI$^+$ [MH]$^+$ | $t_R$/min Methods 1 or 2 | Diastereomeric ratio | $^1$H NMR | $[\alpha]_D$ | Precursor | Purification Method | Amine |
|---|---|---|---|---|---|---|---|---|---|---|
| 128 | 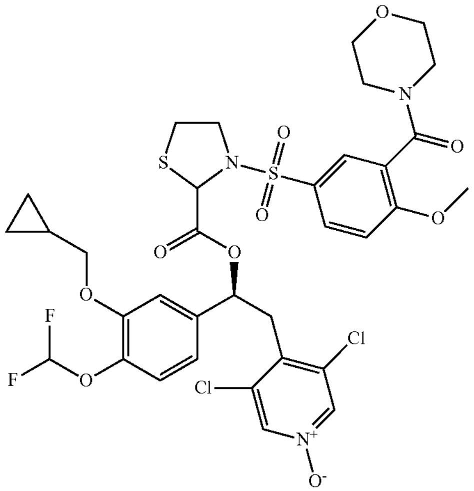 [SMILES: COc1ccc(S(=O)(=O)N2CCSC2C(=O)O[C@@H](Cc2c(Cl)c[n+]([O-])cc2Cl)c2ccc(OC(F)F)c(OCC3CC3)c2)cc1C(=O)N1CCOCC1] | Free Base | 818.0 | 6.32; 6.40 (2) | 33:67 | | | 5 | No purification | 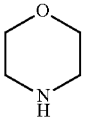 |
| 129 | 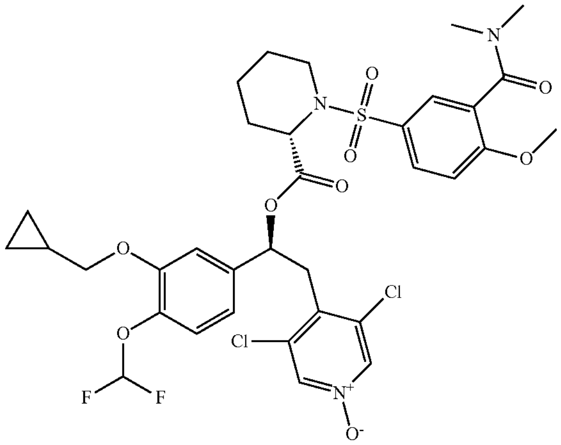 [SMILES: COc1ccc(S(=O)(=O)N2CCCC[C@H]2C(=O)O[C@@H](Cc2c(Cl)c[n+]([O-])cc2Cl)c2ccc(OC(F)F)c(OCC3CC3)c2)cc1C(=O)N(C)C] | Free Base | 772.3 | 3.84 (2) | >99:1 | $^1$H NMR (400 MHz, DMSO-$d_6$) δ ppm 8.62 (s, 2 H), 7.59-7.77 (m, 1 H), 7.45-7.56 (m, 1 H), 7.18-7.22 (m, 1 H), 7.13-7.17 (m, 1 H), 7.03-7.09 (m, 2 H), 6.79-6.95 (m, 1 H), 5.83-5.94 (m, 1 H), 4.53-4.72 (m, 1 H), 3.81-3.96 (m, 5 H), 3.60 (d, J = 11.91 Hz, 1 H), 3.40 (d, J = 10.58 Hz, 1 H), 3.28-3.29 (m, 1 H), 3.23 (dd, J = 14.11, 5.29 Hz, 1 H), 2.98 (s, 3 H), 2.74 (s, 3 H), 2.06 (d, J = 12.79 Hz, 1 H), 1.43-1.61 (m, 3 H), 1.12-1.31 (m, 2 H), | | 10 | Preparative HPLC (Method 1) | 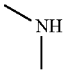 |

TABLE 8-continued
| Entry | Structure | SALT NAME | HPLC-MS characterization MS/ESI$^+$ [MH]$^+$ | $t_R$/min Methods 1 or 2 | Diastereomeric ratio | $^1$H NMR | $[\alpha]_D$ | Precursor | Purification Method | Amine |
|---|---|---|---|---|---|---|---|---|---|---|
| | | | | | | 0.88 (d, J = 12.79 Hz, 1 H), 0.52-0.61 (m, 2 H), 0.29-0.36 (m, 2 H). | | | | |
| 130 | 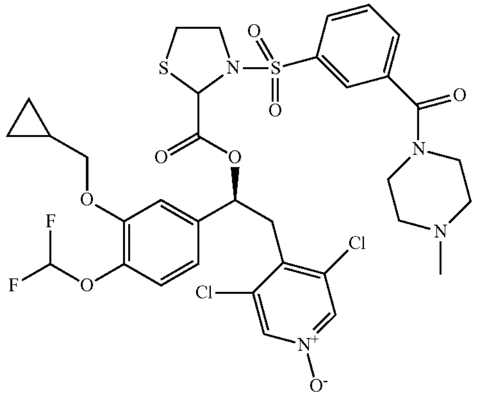 [SMILES: CN1CCN(C(=O)c2cccc(S(=O)(=O)N3CCSC3C(=O)O[C@@H](Cc3c(Cl)c[n+]([O-])cc3Cl)c3ccc(OC(F)F)c(OCC4CC4)c3)c2)CC1] | formate | 801.2 | 2.59; 2.64 (2) | 29:71 | | | 5 | Triturated with $Et_2O$ | 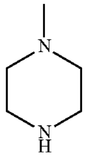 |
| 131 | 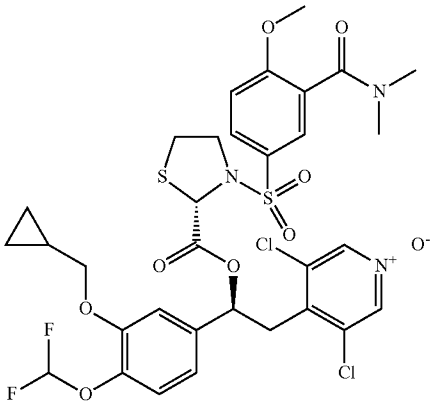 | Free Base | 776.2 | 3.64 (2) | 97:3 | $^1$H NMR (400 MHz, DMSO-$d_6$) δ ppm 8.57 (s, 2 H), 7.81-7.97 (m, 1 H), 7.68-7.76 (m, 1 H), 7.32 (m, 1 H), 7.18 (d, J = 7.94 Hz, 1 H), 7.05-7.13 (m, 2 H), 6.91-6.98 (m, 1 H), 5.92-6.07 (m, 1 H), 5.57 (s, 1 H), 3.75-4.06 (m, 6 H), 3.55-3.68 (m, 1 H), 3.37-3.49 (m, 1 H), 3.25-3.35 (m, 1 H), 2.99 (s, 4 H), 2.75 (s, 3 H), 2.54-2.65 (m, 1 H), 1.14-1.29 (m, 1 H), 0.56 (dd, J = 7.94, 1.76 Hz, 2 H), 0.33 (d, J = 5.29 Hz, 2 H). | | 6 | Preparative HPLC (Method 1) | 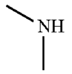 |

TABLE 8-continued
| Entry | Structure | SALT NAME | HPLC-MS characterization MS/ESI$^+$ [MH]$^+$ | $t_R$/min Methods 1 or 2 | Diastereomeric ratio | $^1$H NMR | $[\alpha]_D$ | Precursor | Purification Method | Amine |
|---|---|---|---|---|---|---|---|---|---|---|
| 132 | 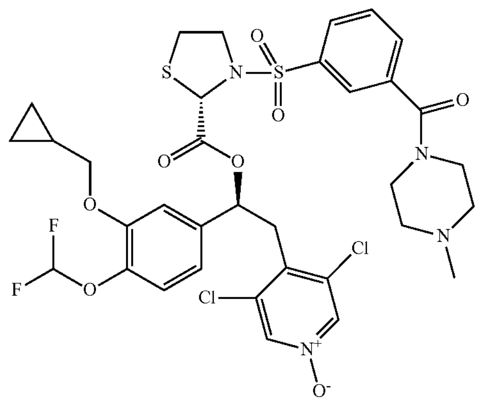 [SMILES: CN1CCN(C(=O)c2cccc(S(=O)(=O)N3CCS[C@H]3C(=O)O[C@@H](Cc3c(Cl)c[n+]([O-])cc3Cl)c3ccc(OC(F)F)c(OCC4CC4)c3)c2)CC1] | Free Base | 801.2 | 2.66 (2) | >99:1 | $^1$H NMR (400 MHz, DMSO-$d_6$) δ ppm 9.66-9.90 (bs, 1 H), 8.58 (s, 2 H), 7.95 (m, 2 H), 7.65-7.86 (m, 2 H), 7.19 (d, J = 8.38 Hz, 1 H), 7.10 (d, J = 9.26 Hz, 2 H), 6.97 (m, 1 H), 5.94-6.12 (m, 1 H), 5.53 (s, 1 H), 3.90 (m, 3 H), 3.60-3.77 (m, 2 H), 3.38 (m, 3 H), 3.25-3.30 (m, 3 H), 2.93-3.22 (m, 4 H), 2.81 (s, 3 H), 2.55-2.73 (m, 1 H), 2.29 (s, 3 H), 1.16-1.30 (m, 1 H), 0.57 (d, J = 7.94 Hz, 2 H), 0.33 (d, J = 4.41 Hz, 2 H). | | 6 | Preparative HPLC (Method 1) | 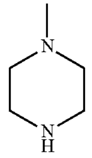 |

The compound listed in Table 9 was prepared under analogous conditions to those described in Scheme 17 by reacting the appropriate precursor listed with suitable reagents and using an alcohol nucleofile in step 2 in place of an amine, followed by a purification step as below indicated.

TABLE 9

| Entry | Structure | SALT NAME | HPLC-MS characterization: MS/ESI$^+$ [MH]$^+$ | HPLC-MS characterization: $t_R$/min Methods 1 or 2 | HPLC-MS characterization: Diastereomeric ratio | $^1$H NMR | Precursor | Purification Method | Alcohol |
|---|---|---|---|---|---|---|---|---|---|
| 133 | 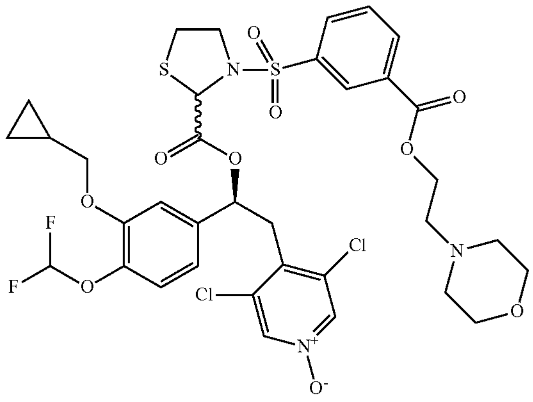 [SMILES: O=C(OCCN1CCOCC1)c1cccc(S(=O)(=O)N2CCSC2C(=O)O[C@@H](Cc2c(Cl)c[n+]([O-])cc2Cl)c2ccc(OC(F)F)c(OCC3CC3)c2)c1] | formate | 832.1 | 3.12 (2) | 97:3 | $^1$H NMR (400 MHz, DMSO-$d_6$) δ ppm 8.58 (s, 2 H), 8.23-8.35 (m, 2 H), 8.12-8.20 (m, 1 H), 7.84 (t, J = 7.94 Hz, 1 H), 7.18 (d, J = 8.38 Hz, 1 H), 7.05-7.15 (m, 2 H), 6.95 (dd, J = 8.38, 1.76 Hz, 1 H), 6.01 (dd, J = 9.04, 5.07 Hz, 1 H), 5.48 (s, 1 H), 4.45 (t, J = 5.51 Hz, 2 H), 3.89 (d, J = 6.62 Hz, 2 H), 3.74-3.82 (m, 1 H), 3.64-3.72 (m, 1 H), 3.50-3.60 (m, 4 H), 3.46 (dd, J = 14.11, 9.26 Hz, 1 H), 3.30 (dd, J = 14.11, 4.85 Hz, 1 H), 2.94-3.04 (m, 1 H), 2.66-2.78 (m, 3 H), 2.47 (d, J = 4.41 Hz, 4 H), 1.15-1.28 (m, 1 H), 0.51-0.60 (m, 2 H), 0.28-0.38 (m, 2 H). | 5 | No purification | 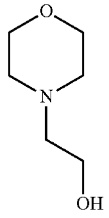 |

Example 10. Synthesis of 4-((2S)-2-(3-(4-aminophenylsulfonyl)thiazolidine-2-carbonyloxy)-2-(3-(cyclopropylmethoxy)-4-(difluoromethoxy)phenyl)ethyl)-3,5-dichloropyridine 1-oxide (135)

Scheme 11

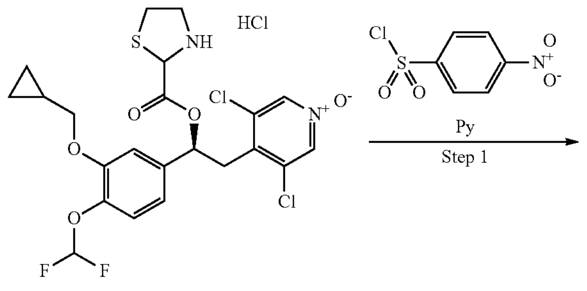

6

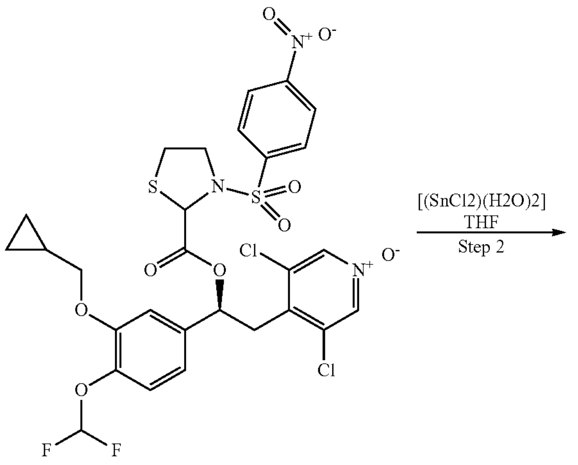

134

-continued

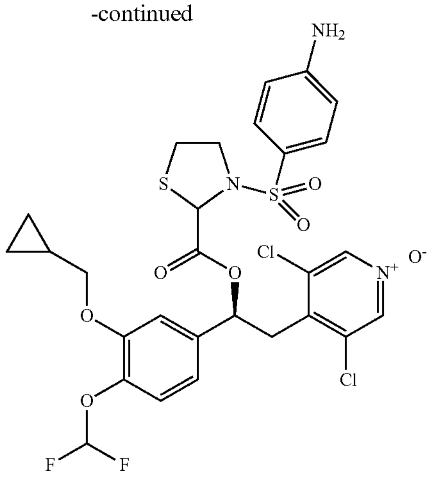

135

Step 1: 3,5-dichloro-4-((2S)-2-(3-(cyclopropylmethoxy)-4-(difluoromethoxy)phenyl)-2-(3-(4-nitrophenylsulfonyl)thiazolidine-2-carbonyloxy)ethyl)pyridine 1-oxide (134)

3,5-dichloro-4-((2S)-2-(3-(cyclopropylmethoxy)-4-(difluoromethoxy)phenyl)-2-(thiazolidine-2-carbonyloxy)ethyl)pyridine 1-oxide (6) (1.2 g, 2.24 mmol) was dissolved in pyridine (6 m), then 4-nitrobenzene-(II)-sulfonyl chloride (596 mg, 2.69 mmol) was added at 0° C., and the mixture was stirred at RT for 2 hours. The reaction was quenched with HC 391N, and the product was extracted with AcOEt. The organic phase was washed with HCl 1N (×2) and brine, then dried over $Na_2SO_4$. The solvent was removed to yield 1.5 g of the desired compound (yield 93%). MS/ESI$^+$ 720.04 $[MH]^+$ Step 2: 4-((2S)-2-(3-(4-aminophenylsulfonyl)thiazolidine-2-carbonyloxy)-2-(3-(cyclopropylmethoxy)-4-(difluoromethoxy)phenyl)ethyl)-3,5-dichloropyridine 1-oxide (135)

3,5-dichloro-4-((2S)-2-(3-(cyclopropylmethoxy)-4-(difluoromethoxy)phenyl)-2-(3-(4-nitrophenyl sulfonyl)thiazolidine-2-carbonyloxy)ethyl)pyridine 1-oxide (134) (1 g, 1.388 mmol), was dissolved in THF (10 ml). Tin(II) chloride dihydrate (3.13 g, 13.881 mmol) was added, and the mixture was stirred at RT for 2 days. The solvent was removed under vacuum, and the crude product was dissolved in AcOEt and diluted with HCl 1N. Diatomaceus earth was added to the emulsion, and the mixture was filtered on a Diatomaceus earth pad. The organic phase was washed with HCl 1N, brine, dried over $Na_2SO_4$ and concentrated under vacuum to give 1.5 g of crude, that was purified by Flash Chromatography (DCM/IPA 97:3) to obtain 780 mg of the final compound (1.130 mmol, yield 81%). MS/ESI$^+$ 689.9 $[MH]^+$; $t_R$=6.30; 6.40 (Method 1); Diastereomeric Ratio=38:62

The compounds listed in Table 10 were prepared according to analogous procedures as those described for Scheme 11 and by reacting the corresponding precursors listed with suitable reagents, followed by a purification step as below indicated.

TABLE 10
| Entry | Structure | SALT NAME | HPLC-MS characterization MS/ESI$^+$ [MH]$^+$ | $t_R$/min Methods 1 or 2 | Diastereomeric ratio | $^1$H NMR | $[\alpha]_D$ | Precursor | Purification Method | Sulfonyl chloride |
|---|---|---|---|---|---|---|---|---|---|---|
| 136 | 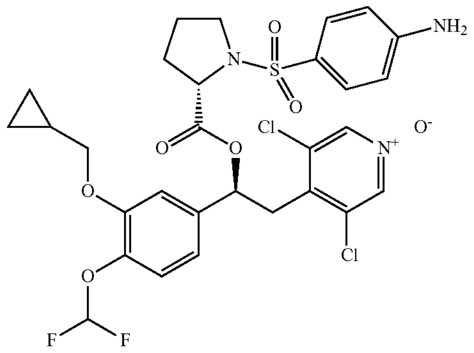 | Free Base | 671.9 | 6.14 (1) | >99:1 | $^1$H NMR (400 MHz, DMSO-$d_6$) δ ppm 8.59 (s, 2 H), 7.35-7.44 (m, 2 H), 7.12-7.22 (m, 2 H), 7.08 (t, J = 75.00 Hz, 1 H), 6.95-7.02 (m, 1 H), 6.53-6.71 (m, 2 H), 6.06-6.17 (bs, 2 H), 5.95-6.04 (m, 1 H), 3.95-4.01 (m, 1 H), 3.86-3.94 (m, 2 H), 3.43-3.53 (m, 1 H), 3.21-3.30 (m, 3 H), 2.99-3.13 (m, 1 H), 1.83-1.95 (m, 1 H), 1.55-1.68 (m, 2 H), 1.35-1.54 (m, 1 H), 1.18-1.29 (m, 1 H), 0.49-0.63 (m, 2 H), 0.26-0.39 (m, 2 H). | | 3 | Crystallization from AcOEt/Hexane | 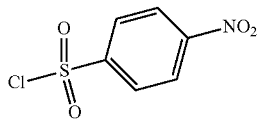 [SMILES: O=[N+]([O-])c1ccc(S(=O)(=O)Cl)cc1] |

TABLE 10-continued

| Entry | Structure | SALT NAME | HPLC-MS characterization MS/ESI$^+$ $[MH]^+$ | $t_R$/min Methods 1 or 2 | Diastereomeric ratio | $^1H$ NMR | $[\alpha]_D$ | Precursor | Purification Method | Sulfonyl chloride |
|---|---|---|---|---|---|---|---|---|---|---|
| 137 | 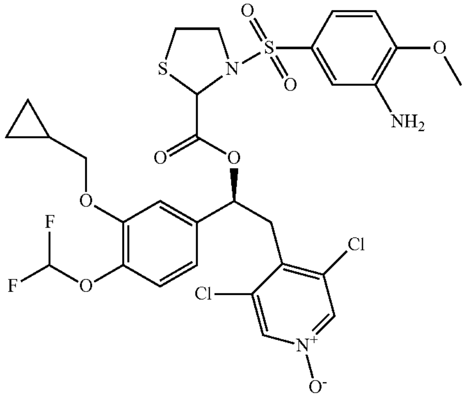 [SMILES: COc1ccc(S(=O)(=O)N2CCSC2C(=O)O[C@@H](Cc2c(Cl)c[n+]([O-])cc2Cl)c2ccc(OC(F)F)c(OCC3CC3)c2)cc1N] | Free Base | 719.8 | 6.67; 6.79 (1) | 41:59 | | +88.93 (c = 0.51; $CHCl_3$) | 5 | Preparative HPLC (Method 1) | 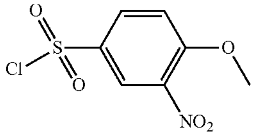 |
| 138 | 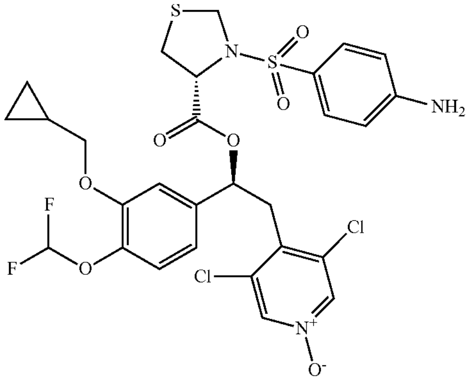 [SMILES: Nc1ccc(S(=O)(=O)N2CSC[C@H]2C(=O)O[C@@H](Cc2c(Cl)c[n+]([O-])cc2Cl)c2ccc(OC(F)F)c(OCC3CC3)c2)cc1] | Free Base | 690.0 | 6.34 (1) | >99:1 | $^1H$ NMR (400 MHz, DMSO-$d_6$) δ ppm 8.57 (s, 2 H), 7.46 (d, J = 8.82 Hz, 2 H), 7.15-7.20 (m, 1 H), 7.11-7.15 (m, 1 H), 7.08 (t, J = 75.00 Hz, 1 H), 6.93-6.99 (m, 1 H), 6.62 (d, J = 8.38 Hz, 2 H), 6.15 (s, 2 H), 5.96-6.05 (m, 1 H), 4.63-4.74 (m, 1 H), 4.50-4.59 (m, 1 H), 4.19-4.27 (m, 1 H), 3.91 (d, J = 6.62 Hz, 2 H), 3.39-3.50 (m, 1 H), 3.21-3.29 (m, 1 H), 2.93-3.02 (m, 1 H), 2.82-2.90 (m, 1 H), 1.16-1.27 (m, | | 11 | Preparative HPLC (Method 1) | 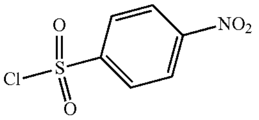 [SMILES: O=[N+]([O-])c1ccc(S(=O)(=O)Cl)cc1] |

TABLE 10-continued
| Entry | Structure | SALT NAME | HPLC-MS characterization MS/ESI⁺ [MH]⁺ | $t_R$/min Methods 1 or 2 | Diastereomeric ratio | $^1$H NMR | $[\alpha]_D$ | Precursor | Purification Method | Sulfonyl chloride |
|---|---|---|---|---|---|---|---|---|---|---|
| | | | | | | 1 H), 0.51-0.61 (m, 2 H), 0.28-0.39 (m, 2 H). | | | | |
| 139 | 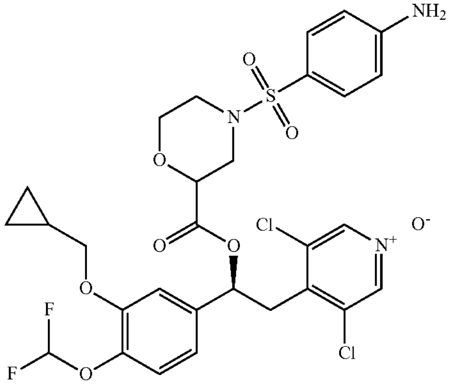 | Free Base | 688.0 | 5.80; 5.97 (1) | 63:37 | | | 8 | Preparative HPLC (Method 1) | 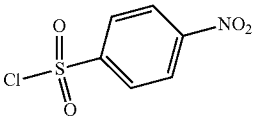 [SMILES: O=[N+]([O-])c1ccc(S(=O)(=O)Cl)cc1] |
| 140 | 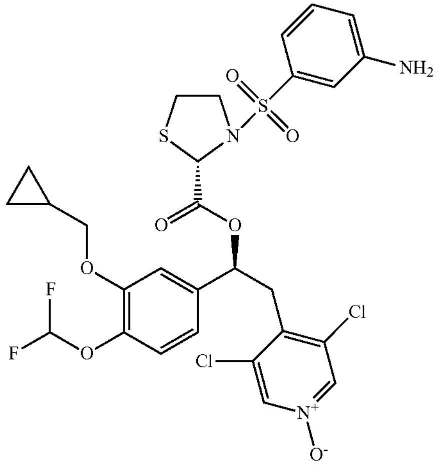 [SMILES: Nc1cccc(S(=O)(=O)N2CCS[C@H]2C(=O)O[C@@H](Cc2c(Cl)c[n+]([O-])cc2Cl)c2ccc(OC(F)F)c(OCC3CC3)c2)c1] | Free Base | 690.2 | 3.79 (2) | 99:1 | 1H NMR (400 MHz, DMSO-d6) δ ppm 8.59 (s, 2 H), 7.22-7.30 (m, 1 H), 7.15-7.21 (m, 1 H), 7.08 (m, 2 H), 6.93-7.03 (m, 2 H), 6.80-6.92 (m, 2 H), 5.92-6.07 (m, 1 H), 5.61-5.74 (bs, 2 H), 5.25 (s, 1 H), 3.90 (d, J = 7.06 Hz, 2 H), 3.59-3.79 (m, 2 H), 3.39-3.51 (m, 1 H), 3.14-3.24 (m, 1 H), 2.60-3.05 (m, 1 H), 2.62-2.75 (m, 1 H), | | 6 | Preparative HPLC (Method 1) | 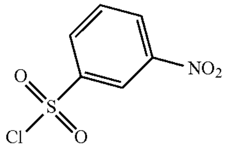 [SMILES: O=[N+]([O-])c1cccc(S(=O)(=O)Cl)c1] |

TABLE 10-continued
| Entry | Structure | SALT NAME | HPLC-MS characterization MS/ESI$^+$ [MH]$^+$ | $t_R$/min Methods 1 or 2 | Diastereomeric ratio | $^1$H NMR | $[\alpha]_D$ | Precursor | Purification Method | Sulfonyl chloride |
|---|---|---|---|---|---|---|---|---|---|---|
| | | | | | | 1.14-1.28 (m, 1 H), 0.51-0.60 (m, 1 H), 0.27-0.41 (m, 1 H). | | | | |
| 141 | 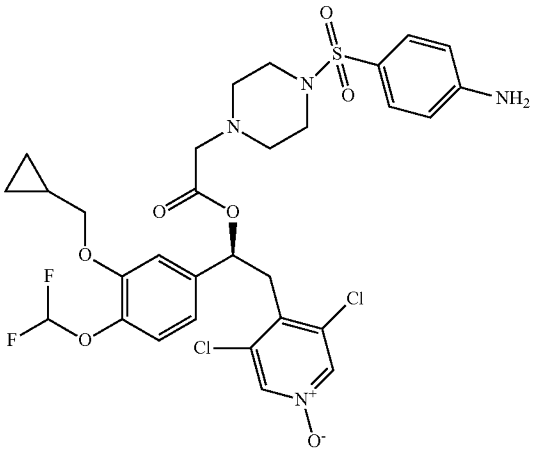 [SMILES: Nc1ccc(S(=O)(=O)N2CCN(CC(=O)O[C@@H](Cc3c(Cl)c[n+]([O-])cc3Cl)c3ccc(OC(F)F)c(OCC4CC4)c3)CC2)cc1] | Free Base | 701.3 | | | $^1$H NMR (400 MHz, DMSO-$d_6$) δ ppm 8.56 (s, 2 H), 7.32 (d, J = 8.82 Hz, 2 H), 7.14-7.20 (m, 1 H), 7.06 (m, 2 H), 6.91-6.98 (m, 1 H), 6.64 (d, J = 8.82 Hz, 2 H), 6.08 (bs, 2 H), 5.93-6.03 (m, 1 H), 3.79-4.05 (m, 2 H), 3.37-3.58 (m, 2 H), 3.21 (dd, J = 13.89, 4.63 Hz, 2 H), 2.68-2.83 (m, 4 H), 2.40-2.48 (m, 4 H), 1.09-1.28 (m, 1 H), 0.50-0.65 (m, 2 H), 0.23-0.44 (m, 2 H). | na | 14 | Preparative HPLC (Method 1) | 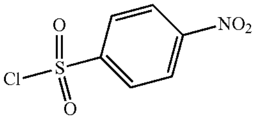 [SMILES: O=[N+]([O-])c1ccc(S(=O)(=O)Cl)cc1] |

Example 11. Synthesis of 3,5-dichloro-4-((2S)-2-(3-(cyclopropylmethoxy)-4-(difluoromethoxy)phenyl)-2-(3-(4-(N-(2-morpholinoethyl)methylsulfonamido)phenylsulfonyl)thiazolidine-2-carbonyloxy)ethyl)pyridine 1-oxide formate (143)

Scheme 19

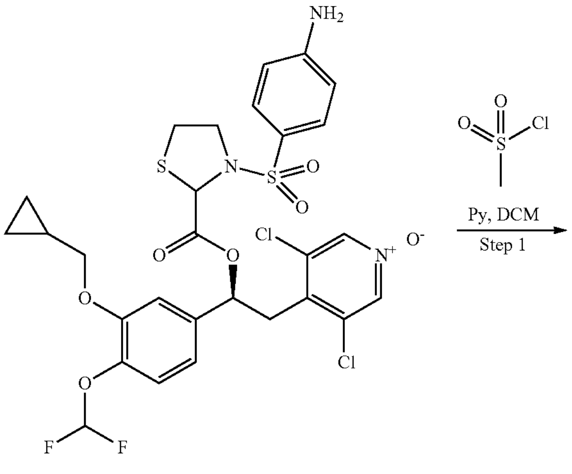

135

-continued

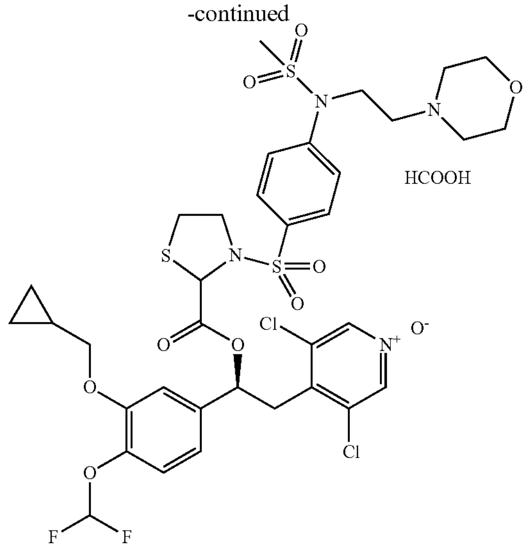

143

Step 1: 3,5-dichloro-4-((2S)-2-(3-(cyclopropylmethoxy)-4-(difluoromethoxy)phenyl)-2-(3-(4-(methylsulfonamido)phenylsulfonyl)thiazolidine-2-carbonyloxy)ethyl)pyridine 1-oxide (142)

4-((2S)-2-(3-(4-aminophenylsulfonyl)thiazolidine-2-carbonyloxy)-2-(3-(cyclopropylmethoxy)-4-(difluoromethoxy)phenyl)ethyl)-3,5-dichloropyridine 1-oxide (135) (128 mg, 0.185 mmol), obtained according to analogous procedure as that described in Example 9, was dissolved in DCM (1.5 ml). Pyridine (29.3 mg, 0.371 mmol) and methanesulfonyl chloride (36.1 mg, 0.315 mmol) were added, and the reaction was stirred at RT for 3 hours to achieve completion. The reaction mixture was diluted with DCM and extracted with HCl 1N. The organic phase was washed with HCl 1N and brine, dried over $Na_2SO_4$ and concentrated under vacuum. The crude product was purified by preparative HPLC (Method 1) to give 80 mg of the final compound (yield 56%). MS/ESI$^+$ 767.9 [MH]$^+$, $t_R$=6.25; 6.35 min (Method 1); Diastereomeric Ratio: 40:60.

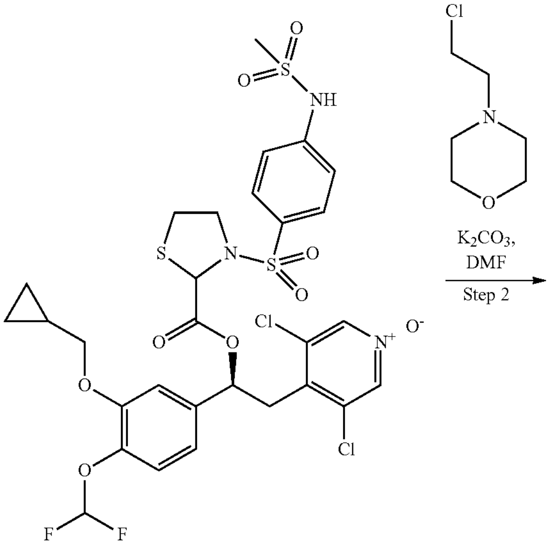

142

Step 2: 3,5-dichloro-4-((2S)-2-(3-(cyclopropylmethoxy)-4-(difluoromethoxy)phenyl)-2-(3-(4-(N-(2-morpholinoethyl)methylsulfonamido)phenylsulfonyl)thiazolidine-2-carbonyloxy)ethyl)pyridine 1-oxide formate (143)

3,5-dichloro-4-((2S)-2-(3-(cyclopropylmethoxy)-4-(difluoromethoxy)phenyl)-2-(3-(4-(methyl sulfonamido)phenylsulfonyl)thiazolidine-2-carbonyloxy)ethyl)pyridine 1-oxide, (142) (80 mg, 0.104 mmol) was dissolved in DMF (1.5 ml). 4-(2-chloroethyl)morpholine (78 mg, 0.520 mmol) and $K_2CO_3$ (17.26 mg, 0.125 mmol) were added, and the reaction is stirred at 45° C. for 6 hours to achieve completion. The reaction mixture was diluted with water and extracted with AcOEt. The organic phase was dried over $Na_2SO_4$ and concentrated under vacuum. The crude product was purified by preparative HPLC (Method 1) to give 40 mg of the final compound as formate salt (yield 44%).

MS/ESI$^+$ 880.9 [MH]$^+$; 5 $t_R$=5.15; 5.28 min (Method 1); Diastereomeric Ratio=37:63.

Example 12. Synthesis of 3,5-dichloro-4-((2S)-2-(3-(cyclopropylmethoxy)-4-(difluoromethoxy)phenyl)-2-(3-(2-oxo-2-(thiophen-2-yl)ethyl)thiazolidine-2-carbonyloxy)ethyl)pyridine 1-oxide (144)

-continued

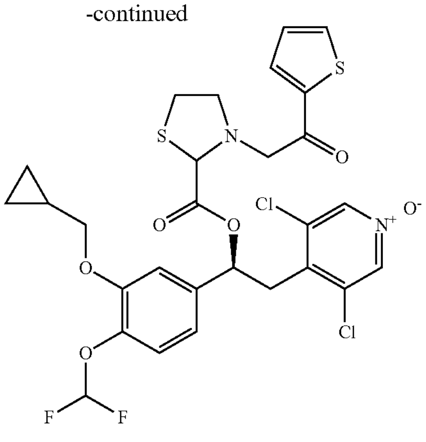

144

Scheme 20

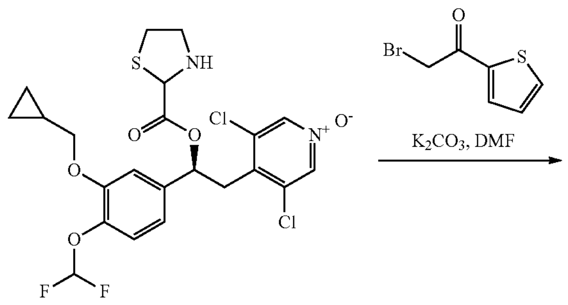

5

3,5-dichloro-4-((S)-2-(3-(cyclopropylmethoxy)-4-(difluoromethoxy)phenyl)-2-(thiazolidine-2-carbonyloxy)ethyl)pyridine 1-oxide (5) (70 mg, 0.131 mmol) was dissolved in DMF (1 ml). $K_2CO_3$ (22 mg, 0.157 mmol) and 2-bromo-1-(thiophen-2-yl)ethanone (80 mg, 0.392 mmol) were added, and the reaction is stirred at 45° C. for 3 hours to achieve completion. The reaction mixture was diluted with water and extracted with AcOEt. The organic phase was dried over $Na_2SO_4$ and concentrated under vacuum. The crude product was purified by preparative HPLC (Method 1) to give 50 mg of the final product, (yield 58%). MS/ESI$^+$ 658.9 [MH]$^+$; $t_R$ (Method 2)=7.10; 7.24 min; Diastereomeric Ratio=44:56

The compounds listed in Table 16 were prepared according to analogous procedure as that described for Scheme 20 and by reacting the appropriate precursors listed (obtained as free base after basic treatment of hydrochloride salt with aqueous sat. $NaHCO_3$ followed by extraction with DCM) with suitable commercial reagents, using $CH_3CN$ instead of DMF as the solvent and heating at 70° C., followed by an appropriate purification step as below indicated.

TABLE 16
| Entry | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method | Alkylation reagent |
|---|---|---|---|---|---|---|---|---|---|---|
| 255 | 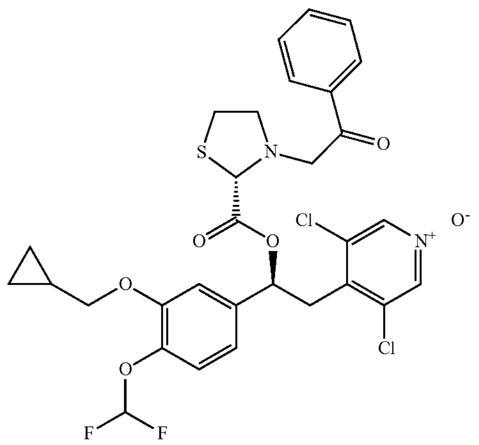 | Free Base | 653.19 | 4.21; 4.28 (3) | 5:95 ($^1$H NMR) | $^1$H NMR (300 MHz, DMSO-$d_6$) δ ppm 8.54 (s, 2 H), 7.87-8.02 (m, 2 H), 7.61-7.71 (m, 1 H), 7.47-7.61 (m, 2 H), 7.18 (d, 1 H), 7.13 (d, 1 H), 6.96 (dd, 1 H), 7.08 (t, 1 H), 5.98 (dd, 1 H), 4.89 (s, 1 H), 4.11 (d, 1 H), 3.99 (d, 1 H), 3.92 (d, 2 H), 3.41-3.56 (m, 2 H), 3.13-3.32 (m, 2 H), 2.83-3.08 (m, 2 H), 1.02-1.41 (m, 1 H), 0.50-0.65 (m, 2 H), 0.23-0.43 (m, 2 H) | −38.6 (c = 0.62, DCM) | Free Base of 6 | Preparative HPLC (Method 2) | 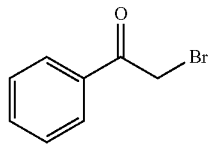 |

TABLE 16-continued

| Entry | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method | Alkylation reagent |
|---|---|---|---|---|---|---|---|---|---|---|
| 256 | 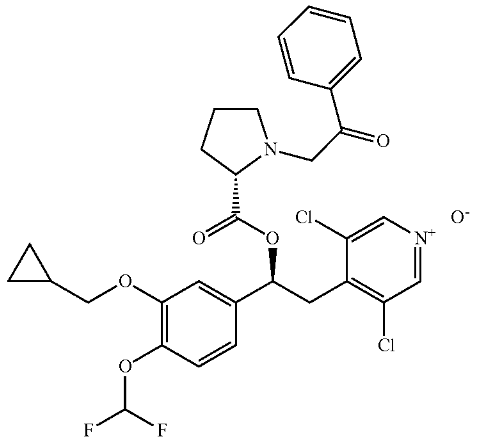 | Free Base | 635.28 | 3.16 (3) | >95:5 ($^1$H NMR) | $^1$H NMR (300 MHz, DMSO-$d_6$) δ ppm 8.50 (s, 2 H), 7.82-8.01 (m, 2 H), 7.56-7.69 (m, 1 H), 7.41-7.56 (m, 2 H), 7.16 (d, 1 H), 7.07 (d, 1 H), 6.96 (dd, 1 H), 7.05 (t, 1 H), 5.99 (dd, 1 H), 4.18 (d, 1 H), 3.82-3.93 (m, 2 H), 3.86 (d, 1 H), 3.51 (dd, 1 H), 3.44 (dd, 1 H), 3.23 (dd, 1 H), 2.87-3.05 (m, 1 H), 2.54-2.69 (m, 1 H), 2.02-2.22 (m, 1 H), 1.52-1.89 (m, 3 H), 1.02-1.34 (m, 1 H), 0.44-0.64 (m, 2 H), 0.15-0.44 (m, 2 H) | −52.52 (c = 0.23, MeOH) | Free Base of 3 | Flash chromatography on silica gel followed by trituration with $iPr_2O$ | 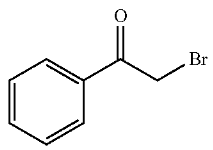 |

TABLE 16-continued

| Entry | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method | Alkylation reagent |
|---|---|---|---|---|---|---|---|---|---|---|
| 257 | 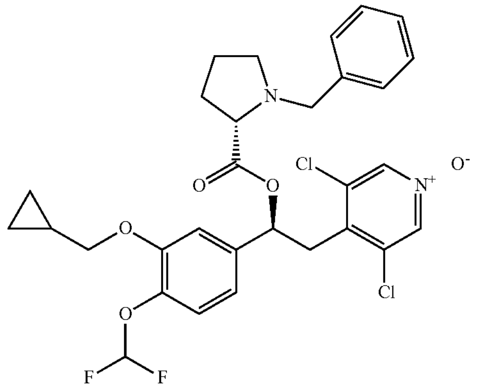 | trifluoroacetate | 607.28 | 3.02 (3) | >95:5 ($^1$H NMR) | $^1$H NMR (300 MHz, DMSO-$d_6$) δ ppm 10.04 (br. s., 1 H), 8.59 (s, 2 H), 7.40 (br. s., 5 H), 7.19 (d, 1 H), 7.08 (d, 1 H), 6.95 (dd, 1 H), 7.07 (t, 1 H), 5.50-5.96 (m, 1 H), 4.08-4.68 (m, 3 H), 3.89 (d, 2 H), 3.42 (dd, 1 H), 3.26-3.37 (m, 2 H), 3.21 (dd, 1 H), 2.31-2.47 (m, 1 H), 1.96-2.17 (m, 1 H), 1.60-1.93 (m, 2 H), 1.12-1.31 (m, 1 H), 0.47-0.73 (m, 2 H), 0.23-0.45 (m, 2 H) | −31.90 (c = 0.2, DCM) | Free Base of 3 | Flash chromatography on silica gel followed by preparative HPLC (Method 2) | 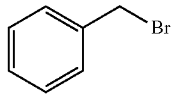 |

TABLE 16-continued

| Entry | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method | Alkylation reagent |
|---|---|---|---|---|---|---|---|---|---|---|
| 258 | 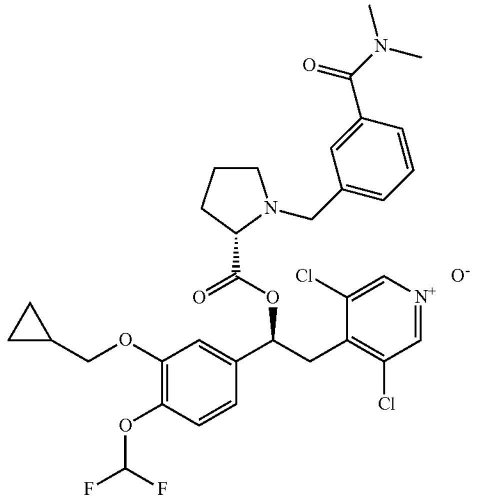 | hydrochloride | 678.43 | 2.86 (3) | >95:5 ($^1$H NMR) | $^1$H NMR (300 MHz, DMSO-$d_6$) δ ppm 10.30 (br. s., 1 H), 8.59 (s, 2 H), 7.37-7.60 (m, 4 H), 7.19 (d, 1 H), 7.09 (d, 1 H), 6.94 (dd, 1 H), 7.07 (t, 1 H), 5.80 (br. s., 1 H), 4.22-4.68 (m, 3 H), 3.89 (d, 2 H), 3.44 (dd, 1 H), 3.27-3.38 (m, 1 H), 3.23 (dd, 1 H), 2.99 (br. s., 3 H), 2.92-2.98 (m, 1 H), 2.90 (br. s., 3 H), 2.56-2.68 (m, 1 H), 1.67-2.23 (m, 3 H), 1.14-1.35 (m, 1 H), 0.48-0.75 (m, 2 H), 0.24-0.44 (m, 2 H) | −37.2 (c = 0.32, DCM) | Free Base of 3 | Preparative HPLC (method 2) followed by dissolution in DCM, treatment with 4M HCl in dioxane, evaporation and trituration with $Et_2O$ | 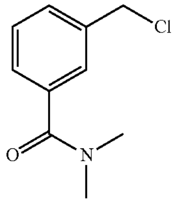 |

Example 21. Synthesis of 3,5-dichloro-4-((S)-2-(3-(cyclopropylmethoxy)-4-(difluoro-methoxy)phenyl)-2-((S)-3-(2-(3-(dimethylcarbamoyl)phenyl)-2-oxo-ethyl)-thiazolidine-2-carbonyloxy)ethyl)pyridine 1-oxide (261)

Scheme 28

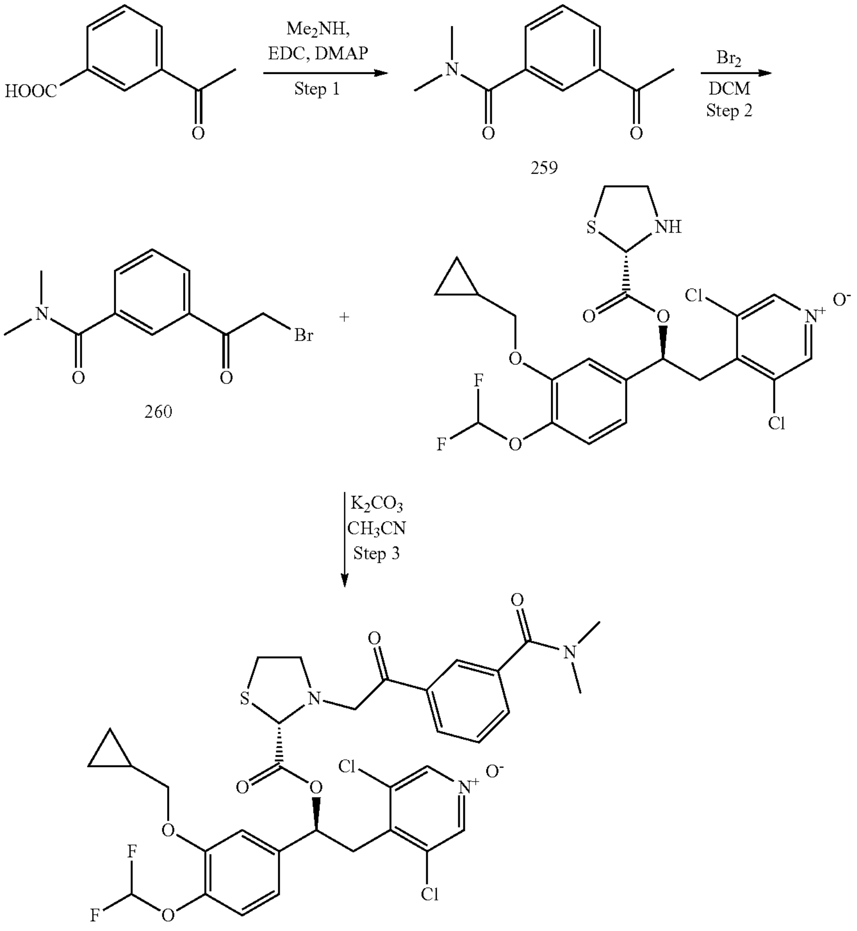

259

260

261

Step 1: Acetyl-N,N-dimethylbenzamide (259)

3-Acetylbenzoic acid (400 mg, 2.437 mmol), dimethylamine hydrochloride (238 mg, 2.92 mmol), EDC (701 mg, 3.66 mmol), and DMAP (447 mg, 3.66 mmol) were dissolved in DCM (80 ml), and the resulting solution was stirred at RT overnight. The reaction mixture was washed twice with aqueous 1N HCl and with brine; the organic phase was dried over $Na_2SO_4$, filtered and evaporated to give the desired product (450 mg, 2.353 mmol, 97% yield); MS/ESI$^+$ 192.12 [MH]$^+$.

Step 2: 3-(2-bromoacetyl)-N,N-dimethylbenzamide (260)

To a solution of 3-acetyl-N,N-dimethylbenzamide (450 mg, 2.353 mmol) in DCM (20 ml), bromine (0.121 ml, 2.353 mmol) was added drop-wise. The resulting dark solution was stirred at RT for 24 hours. More bromine (60 ml, 1164 mmol) was added, and the stirring was continued for 4 hours. The solution was washed twice with aqueous sat. $NaHCO_3$ solution, and the organic layer was dried over $Na_2SO_4$. The solvent was removed under vacuum to afford the desired product (526 mg, 1.947 mmol, 83% yield), which was employed in the next step without further purification. MS/ESI$^+$ 269.96 [MH]$^+$.

Step 3: 3,5-dichloro-4-((S)-2-(3-(cyclopropylmethoxy)-4-(difluoro-methoxy)phenyl)-2-((S)-3-(2-(3-(dimethylcarbamoyl)phenyl)-2-oxoethyl)-thiazolidine-2-carbonyloxy)ethyl)pyridine 1-oxide (261)

3,5-dichloro-4-((S)-2-(3-(cyclopropylmethoxy)-4-(difluoro-methoxy)phenyl)-2-((S)-3-(2-(3-(dimethylcarbamoyl)phenyl)-2-oxoethyl)-thiazolidine-2-carbonyloxy)ethyl)pyridine 1-oxide was prepared according to analogous procedure as that described for Scheme 20 (Example 12) starting from intermediate (6), obtained as free base after basic treatment of the hydrochloride salt with aqueous sat. $NaHCO_3$ followed by extraction with DCM, using $CH_3CN$ as the solvent and heating at 60° C. It was purified by preparative HPLC (Method 2) (41% yield); MS/ESI$^+$ 724.24 $[MH]^+$; $t_R$ (Method 3)=3.82 min; Diastereomeric Ratio >95:5 ($^1H$ NMR); □□$_D$]=−40.6 (c=0.38, DCM).

$^1H$ NMR (B) (300 MHz, DMSO-d6) δ ppm 8.54 (s, 2H), 8.00 (dt, 1H), 7.96 (t, 1H), 7.67 (dt, 1H), 7.60 (t, 1H), 7.18 (d, 1H), 7.13 (d, 1H), 6.96 (dd, 1H), 6.81-7.41 (m, 1H), 5.98 (dd, 1H), 4.90 (s, 1H), 4.13 (d, 1H), 4.02 (d, 1H), 3.92 (d, 2H), 3.45-3.55 (m, 1H), 3.40 (dd, 1H), 3.28 (m, 0H), 3.13-3.23 (m, 1H), 3.01 (br. s., 3H), 2.86-2.94 (m, 4H), 2.82-3.05 (m, 2H), 1.07-1.39 (m, 1H), 0.45-0.70 (m, 2H), 0.18-0.44 (m, 2H)

The compound listed in Table 17 was prepared according to analogous procedures as those described for Scheme 28 and by reacting the appropriate precursor listed (obtained as free base after basic treatment of the hydrochloride salt with aqueous sat. $NaHCO_3$ followed by extraction with DCM), heating at 70° C. in Step 3, followed by an appropriate purification step as below indicated.

TABLE 17

| Entry | Structure | SALT NAME | HPLC-MS characterization: MS/ESI$^+$ $[MH]^+$ | HPLC-MS characterization: $t_R$/min Method 1 or 2 | Diastereomeric ratio | $^1H$ NMR | $[\alpha]_D$ | Precursor | Purification Method |
|---|---|---|---|---|---|---|---|---|---|
| 262 | 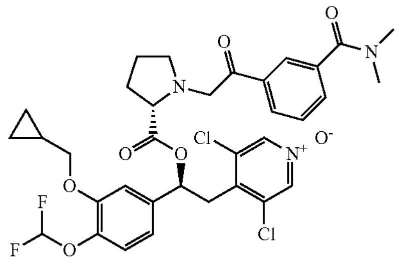 | trifluoroacetate | 706.25 | 2.98 (3) | >95:5 ($^1H$ NMR) | $^1H$ NMR (300 MHz, DMSO-d6) δ ppm 8.56 (s, 2 H), 8.01 (dt, 1 H), 7.97 (t, 1 H), 7.77 (dt, 1 H), 7.66 (t, 1 H), 7.21 (d, 1 H), 7.14 (d, 1 H), 7.00 (dd, 1 H), 7.08 (t, 1 H), 6.08 (dd, 1 H), 5.00 (br. s., 2 H), 4.38 (br s., 1 H), 3.91 (d, 2 H), 3.60 (br. s., 1 H), 3.53 (dd, 1 H), 3.30 (dd, 1 H), 3.19 (br. s., 1 H), 3.02 (br. s., 3 H), 2.92 (br. s., 3 H), 2.32-2.46 (m, 1 H), 1.68-2.18 (m, 3 H), 1.05-1.36 (m, 1 H), 0.51-0.72 (m, 2 H), 0.22-0.40 (m, 2 H) | −19.6 (c = 0.37, DCM). | Free Base of 3 | Preparative HPLC (Method 2) |

Example 13. Synthesis of 4-((S)-2-((S)-3-(4-aminophenylsulfonyl)thiazolidine-2-carbonyloxy)-2-(3-(cyclopropylmethoxy)-4-(difluoromethoxy)phenyl)ethyl)-3,5-dichloropyridine 1-oxide (150)

Scheme 21

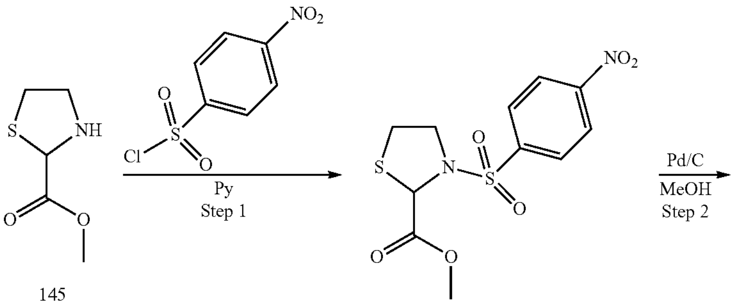

145

146

-continued

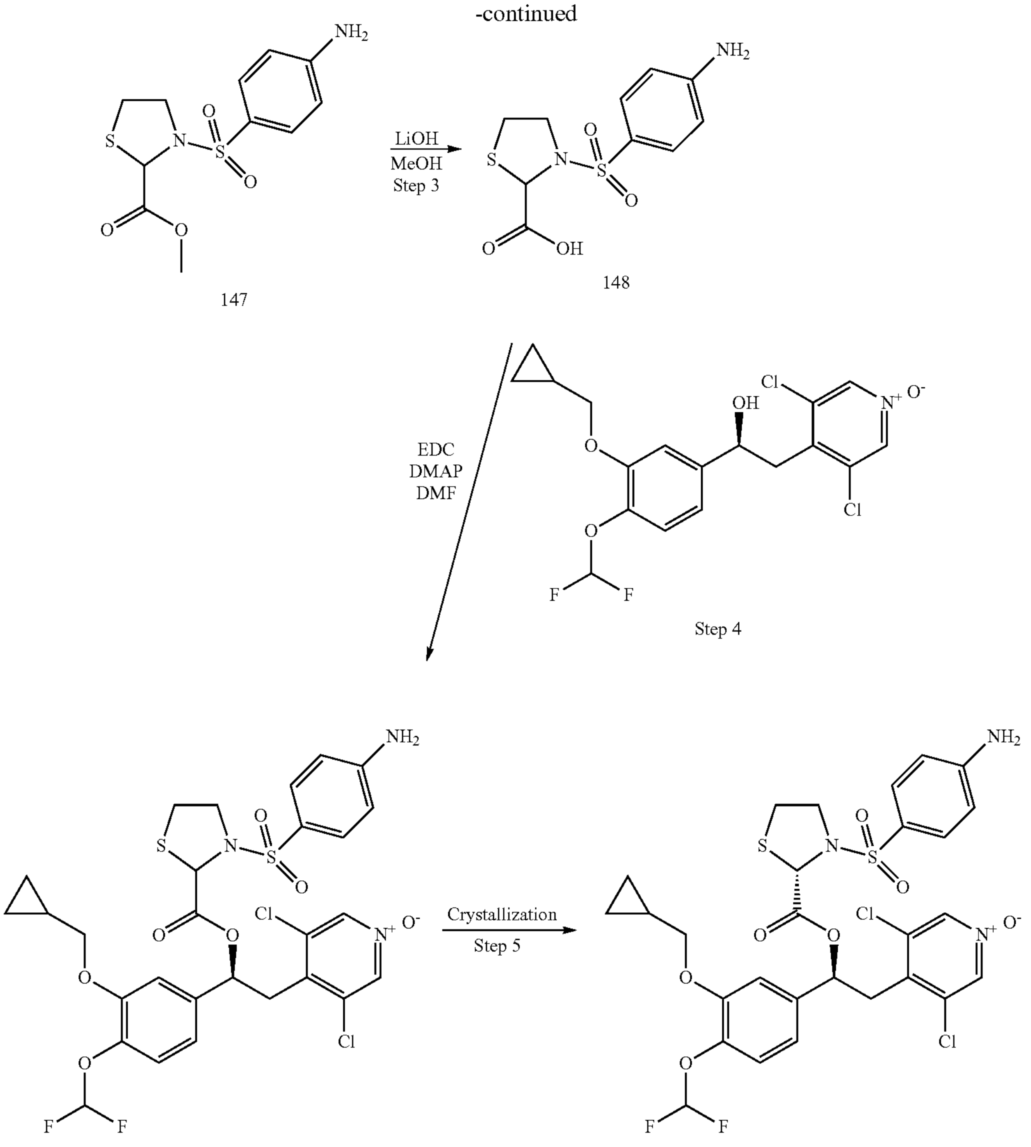

147 148 149 150

Step 1: methyl 3-(4-nitrophenylsulfonyl)thiazolidine-2-carboxylate (146)

Methyl thiazolidine-2-carboxylate hydrochloride (145) (20 g; 109 mmol) was dissolved in pyridine (100 ml), then 4-nitrobenzene-1-sulfonyl chloride (27 g, 124 mmol) was added at 0° C., and the mixture was stirred for 3 hours. After that time, the reaction was quenched with HCl 1N to precipitate a solid that was filtered on a frit and washed with water several times. The orange solid was triturated in acetone, washed with acetone (×2) and dried under vacuum to yield 27 g (76%).

MS/ESI$^+$ 333.01 [MH]$^+$

Step 2: methyl 3-(4-aminophenylsulfonyl)thiazolidine-2-carboxylate hydrochloride (147)

A mixture of methyl 3-(4-nitrophenylsulfonyl)thiazolidine-2-carboxylate (146) (5.74 g; 17.27 mmol) and 5% Pd/C (16 g; 7.547 mmol) in 600 ml of MeOH and 400 ml of HCl 1N was hydrogenated for 10 hrs at 50 psi. After that time, the reaction was filtered over Celite, washed with MeOH and the solution was concentrated under vacuum to yield the desired product (10.47 g; 72%). MS/ESI 312.04 [MH]$^+$ Step 3: 3-(4-aminophenylsulfonyl)thiazolidine-2-carboxylic acid (148)

To a solution of methyl 3-(4-aminophenylsulfonyl)thiazolidine-2-carboxylate hydrochloride (147) (7.43 g, 24.57 mmol) in MeOH (62 ml), LiOH 1M (62 ml) was added. The solution was stirred at room temperature for 1 hour, then the pH was adjusted to 6 with HCl 1M. MeOH was evaporated under reduced pressure, and HCl 1M was added until the pH=3 and the mixture cooled at 0 degrees for 3 hours, until complete precipitation. The solid was filtered, washed with water and dried in vacuo at 45 degrees to give 6.44 g of the desired product (yield 91%).

MS/ESI$^+$ 289.02 [MH]$^+$

Step 4: 4-((2S)-2-(3-(4-aminophenylsulfonyl)thiazolidine-2-carbonyloxy)-2-(3-(cyclopropylmethoxy)-4-(difluoromethoxy)phenyl)ethyl)-3,5-dichloropyridine 1-oxide (149)

To a solution of (S)-3,5-dichloro-4-(2-(3-(cyclopropylmethoxy)-4-(difluoromethoxy)phenyl)-2-hydroxyethyl) pyridine 1-oxide (1.55 g, 3.69 mmol) dissolved in DMF (20 ml), EDC (2.83 g, 14.77 mmol) and 3-(4-aminophenylsulfonyl)thiazolidine-2-carboxylic acid (148) (1.81 g, 6.28 mmol) were added. The mixture was cooled at 0 degrees, and DMAP (0.541 g. 4.43 mmol) was added. The mixture was stirred at −20 degrees for 20 minutes, then it was allowed to warm to room temperature and stirred for 3 hours. The reaction mixture was poured into water (500 ml), and the precipitate isolated by filtration. The filtered solid was washed with water (150 ml) and dried in vacuo at 45 degrees to afford 2.49 g of the desired product (yield 98%). MS/ESI$^+$ 689.8 $[MH]^+$ Step 5: 4-((S)-2-((S)-3-(4-aminophenylsulfonyl) thiazolidine-2-carbonyloxy)-2-(3-(cyclopropylmethoxy)-4-(difluoromethoxy)phenyl)ethyl)-3,5-dichloropyridine 1-oxide (150)

4-((2S)-2-(3-(4-aminophenylsulfonyl)thiazolidine-2-carbonyloxy)-2-(3-(cyclopropylmethoxy)-4-(difluoromethoxy) phenyl)ethyl)-3,5-dichloropyridine 1-oxide (149) (2.49 g, 3.61 mmol) was dissolved in EtOH (35 ml) at 50 degrees, and a solution of methansulfonic acid in EtOH 10% w/w was added (3.47 g, 3.61 mmol) to achieve salification. The methanesulfonate salt was filtered off and crystallized again from hot EtOH (25 ml). The salt was dissolved in $CH_2Cl_2$ (40 ml), and $NaHCO_3$ sat sol (30 ml) was added. The mixture was stirred for 30 minutes at RT, and then the two phases were separated. The organic phase was dried over $Na_2SO_4$ and evaporated under reduced pressure to afford a solid which was crystallized again from hot EtOH (25 ml) to yield 800 mg of the desired product. MS/ESI$^+$ 689.8 $[MH]^+$; $t_R$ (Method 1)=6.37 min; $[\alpha_D]$=+38.57 (c=0.49; CHCl3). $^1H$ NMR (400 MHz, DMSO-$d_6$) δ ppm 8.58 (s, 2H), 7.42-7.52 (m, 2H), 7.14-7.20 (m, 1H), 7.05-7.12 (m, 2H), 6.90-6.97 (m, 1H), 6.60-6.69 (m, 2H), 6.15-6.24 (s, 2H), 5.96-6.05 (m, 1H), 5.29 (s, 1H), 3.86-3.95 (m, 2H), 3.68-3.80 (m, 1H), 3.52 (d, J=47.63 Hz, 1H), 3.38-3.48 (m, 1H), 3.29 (m, 1H), 2.84-2.99 (m, 1H), 2.53-2.60 (m, 1H), 1.22-1.36 (m, 1H), 0.46-0.63 (m, 2H), 0.28-0.40 (m, 2H).

The compound listed in Table 11 was prepared according to analogous procedures as those described for Scheme 21 (Steps 1-4), followed by purification of compound (131), through Flash Chromatography eluting with DCM/n-Hexane/i-PrOH/EtOH=55/40/4/1.

TABLE 11

| Entry | Structure | SALT NAME | HPLC-MS characterization: MS/ESI$^+$ $[MH]^+$ | HPLC-MS characterization: $t_R$/min Methods 1 or 2 | Diastereomeric ratio | $^1H$ NMR | $[\alpha]_D$ |
|---|---|---|---|---|---|---|---|
| 151 | 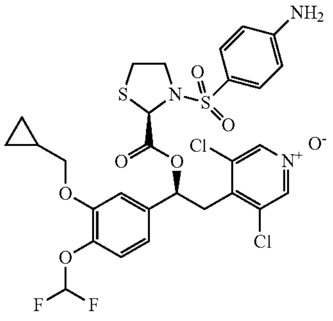 | Free Base | 689.8 | 6.28 (1) | >99:1 | $^1H$ NMR (400 MHz, DMSO-$d_6$) □ ppm 8.54 (s, 2 H), 7.44-7.50 (m, 2 H), 7.17-7.24 (m, 1 H), 7.07-7.14 (m, 2 H), 6.94-7.03 (m, 1 H), 6.57-6.64 (m, 2 H), 6.18 (s, 2 H), 5.84-6.01 (m, 1 H), 5.27 (s, 1 H), 3.86-3.99 (m, 2 H), 3.55-3.72 (m, 2 H), 3.38-3.51 (m, 1 H), 3.25 (m, 1 H), 2.94-3.06 (m, 1 H), 2.55-2.64 (m, 1 H), 1.24-1.31 (m, 1 H), 0.46-0.67 (m, 2 H), 0.27-0.42 (m, 2 H) | −41.36 (c = 0.51; $CHCl_3$) |

Example 14. Synthesis of 3,5-dichloro-4-((S)-2-(3-(cyclopropylmethoxy)-4-(difluoromethoxy)phenyl)-2-((S)-1-(1-methyl-1H-imidazol-2-ylsulfonyl)pyrrolidine-2-carbonyloxy)ethyl)pyridine 1-oxide (155)

Scheme 22

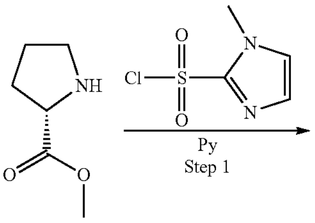

152

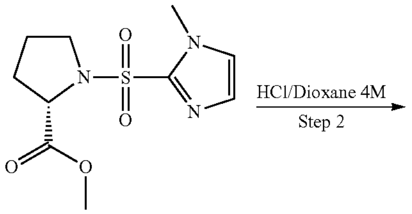

153

-continued

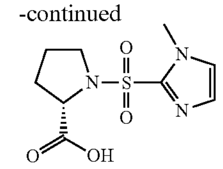

154

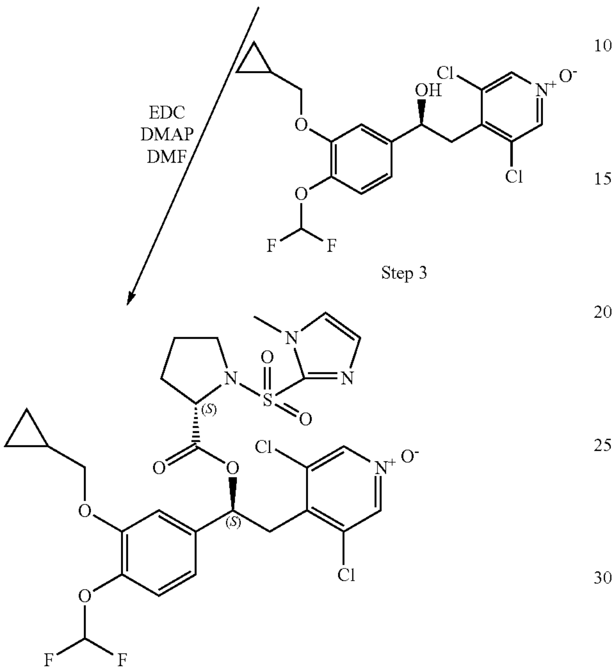

155

Step 1: (S)-methyl 1-(1-methyl-1H-imidazol-2-yl-sulfonyl)pyrrolidine-2-carboxylate (153)

(S)-methyl pyrrolidine-2-carboxylate (152) (50 mg; 0.387 mmol) was dissolved in pyridine (1 ml), then 1-methyl-1H-imidazole-2-sulfonyl chloride (70 mg, 0.387 mmol) was added at 0° C., and the mixture was stirred for 3 hours. After that time, the reaction was quenched with HCl 1N and extracted with AcOEt twice. The organic phase was dried over $Na_2SO_4$ and evaporated under vacuum to yield 50 mg (yield 47%).

MS/ESI$^+$ 274.08 [MH]$^+$

Step 2: (S)-1-(1-methyl-1H-imidazol-2-ylsulfonyl) pyrrolidine-2-carboxylic acid (154)

A solution of (S)-methyl 1-(1-methyl-1H-imidazol-2-yl-sulfonyl)pyrrolidine-2-carboxylate (153) (50 mg, 0.183 mmol) in HCl/Dioxane 4M (1 ml) was reacted under micro-wave irradiation at 100 degrees for 30 minutes. Then Dioxane was evaporated under reduced pressure to yield 40 mg of the desired compound (yield 84%).

MS/ESI$^+$ 260.06 [MH]$^+$

Step 3: 3,5-dichloro-4-((S)-2-(3-(cyclopropyl-methoxy)-4-(difluoromethoxy)phenyl)-2-((S)-1-(1-methyl-1H-imidazol-2-ylsulfonyl)pyrrolidine-2-carbonyloxy)ethyl)pyridine 1-oxide (155)

To a solution of (S)-3,5-dichloro-4-(2-(3-(cyclopropyl-methoxy)-4-(difluoromethoxy)phenyl)-2-hydroxyethyl) pyridine 1-oxide (20 mg, 0.048 mmol) dissolved in DMF (1 ml), EDC (9 mg, 0.048 mmol) and 3-(4-aminophenylsulfonyl)thiazolidine-2-carboxylic acid (154) (40 mg, 0.154 mmol) were added. The mixture was cooled at 0 degrees, and DMAP (6 mg. 0.048 mmol) was added. The mixture was stirred at −20 degrees for 20 minutes, and then it was allowed to warm to RT and stirred for 3 hours. The reaction mixture was poured into water and extracted with AcOEt (×3). The organic phase was dried over $Na_2SO_4$, evaporated in vacuo to afford 30 mg of the desired product (yield 95%). MS/ESI$^+$ 661.3 [MH]$^+$; $t_R$ (Method 2)=3.60 min; Diastereomeric Ratio=99:1; $^1$H NMR (400 MHz, DMSO-$d_6$) δ ppm 8.51 (s, 2H), 7.47 (m, 1H), 7.18 (d, J=7.94 Hz, 1H), 7.13 (d, J=1.76 Hz, 1H), 7.08 (d, J=4.41 Hz, 2H), 6.98 (dd, J=8.38, 1.76 Hz, 1H), 6.00 (dd, J=9.48, 4.63 Hz, 1H), 4.47 (dd, J=8.82, 4.41 Hz, 1H), 3.92 (dd, J=7.06, 1.76 Hz, 2H), 3.84 (s, 3H), 3.37-3.55 (m, 3H), 3.24 (dd, J=14.11, 4.41 Hz, 1H), 2.22-2.37 (m, 1H), 1.83-1.95 (m, 1H), 1.65-1.82 (m, 2H), 1.12-1.30 (m, 1H), 0.49-0.64 (m, 2H), 0.28-0.42 (m, 2H).

Example 22. Synthesis of 3,5-dichloro-4-((S)-2-(4-(difluoromethoxy)-3-hydroxyphenyl)-2-((S)-3-(3-(dimethylcarbamoyl)phenylsulfonyl)thiazolidine-2-carbonyloxy)ethyl)pyridine 1-oxide (263)

Scheme 47

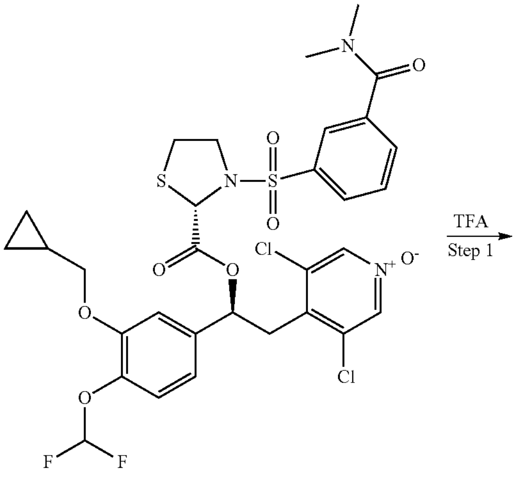

52

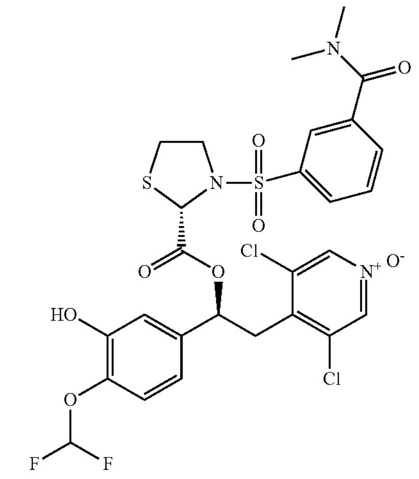

263

3,5-dichloro-4-((S)-2-(3-(cyclopropylmethoxy)-4-(difluoromethoxy)phenyl)-2-((S)-3-(3-(dimethylcarbamoyl)phenylsulfonyl)thiazolidine-2-carbonyloxy)ethyl)pyridine 1-oxide (Compound 52) (200 mg, 0.268 mmol) was dissolved in 2,2,2-trifluoroacetic acid (2 ml, 0.268 mmol), and the solution stirred overnight at RT. The reaction mixture was diluted with DCM and concentrated under vacuum (2×) to give a crude which was purified through preparative HPLC (method 1) to give 3,5-dichloro-4-((S)-2-(4-(difluoromethoxy)-3-hydroxyphenyl)-2-((S)-3-(3-(dimethylcarbamoyl)phenylsulfonyl)thiazolidine-2-carbonyloxy)ethyl)pyridine 1-oxide (90 mg, 0.130 mmol, 49% yield). MS/ESI$^+$ 661.3 [MH]$^+$; $t_R$ (Method 2)=2.49; Diastereomeric Ratio=99:1; $^1$H NMR (400 MHz, DMSO-$d_6$) δ ppm 10.05 (s, 1H), 8.58 (s, 2H), 7.85-7.97 (m, 2H), 7.67-7.80 (m, 2H), 7.11 (d, J=8.38 Hz, 1H), 7.04 (t, J=75.00 Hz, 1H), 6.94 (d, J=2.21 Hz, 1H), 6.83 (m, 1H), 5.86-6.02 (m, 1H), 5.47 (s, 1H), 3.78-3.92 (m, 1H), 3.56-3.68 (m, 1H), 3.37-3.49 (m, 1H), 3.20-3.28 (m, 1H), 2.93-3.09 (m, 4H), 2.89 (s, 3H), 2.66 (m 1H).

Example 23. Synthesis of 3,5-dichloro-4-((S)-2-(3-(cyclopropylmethoxy)-4-(difluoromethoxy)phenyl)-2-((S)-3-(cyclopropylmethyl)thiazolidine-2-carbonyloxy)ethyl)pyridine 1-oxide (264)

Scheme 30

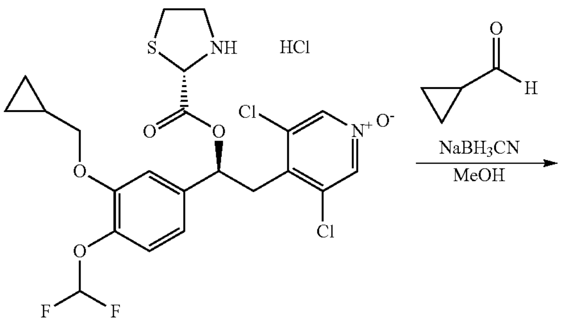

6

-continued

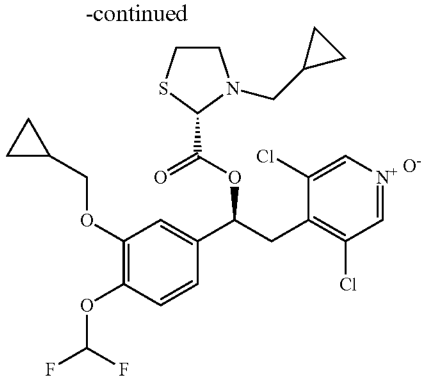

264

3,5-dichloro-4-((S)-2-(3-(cyclopropylmethoxy)-4-(difluoromethoxy)phenyl)-2-((S)-thiazolidine-2-carbonyloxy)ethyl)pyridine 1-oxide hydrochloride (6) (150 mg, 0.262 mmol) was dissolved in MeOH (10 ml), and cyclopropanecarbaldehyde (19.60 μl, 0.262 mmol) was added followed by sodium cyanoborohydride (33.0 mg, 0.525 mmol). The resulting mixture was stirred at RT for 2 hours. The volatiles were removed under reduced pressure, and the residue was purified by preparative HPLC (Method 2). A further purification by flash chromatography on silica gel (DCM/MeOH=99/1) was required to afford 3,5-dichloro-4-((S)-2-(3-(cyclopropylmethoxy)-4-(difluoromethoxy)phenyl)-2-((S)-3-(cyclopropylmethyl)thiazolidine-2-carbonyloxy)ethyl)pyridine 1-oxide (25 mg, 0.042 mmol, 16.17% yield). MS/ESI$^+$ 588.94 [MH]$^+$; $t_R$ (Method 3)=3.54; Diastereomeric Ratio=>95:5 ($^1$H NMR); $[\alpha_D]$=−30.1 (c=0.31, DCM); $^1$H NMR (B) (300 MHz, DMSO-$d_6$) δ ppm 8.58 (s, 2H), 7.19 (d, 1H), 7.13 (d, 1H), 6.97 (dd, 1H), 7.08 (t, 1H), 5.95 (dd, 1H), 4.96 (s, 1H), 3.93 (d, 2H), 3.38-3.56 (m, 1H), 3.40 (dd, 1H), 3.26 (dd, 1H), 2.98-3.17 (m, 1H), 2.76-2.95 (m, 2H), 2.31 (dd, 1H), 2.17 (dd, 1H), 1.14-1.35 (m, 1H), 0.72-0.98 (m, 1H), 0.53-0.66 (m, 2H), 0.43-0.53 (m, 2H), 0.26-0.42 (m, 2H), −0.03-0.19 (m, 2H)

The compounds listed in Table 18 were prepared according to analogous procedure as that described for Scheme 30 and by reacting the appropriate precursors listed with commercial suitable reagents, followed by appropriate purification step as below reported.

TABLE 18

| Entry | Structure | SALT NAME | MS/ESI+ [MH]+ (HPLC-MS characterization) | $t_R$/min Method 1, 2 or 3 (HPLC-MS characterization) | Diastereomeric ratio | $^1H$ NMR | $[\alpha]_D$ | Precursor | Purification Method | Starting aldehyde |
|---|---|---|---|---|---|---|---|---|---|---|
| 265 | 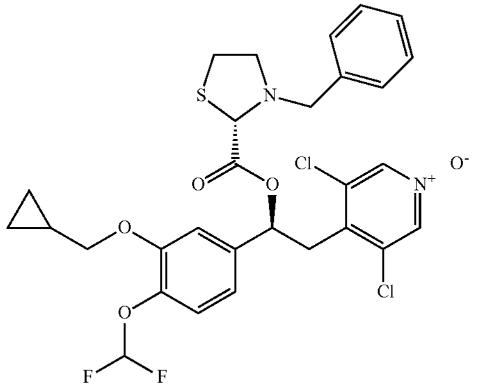 | Free Base | 625.11 | 4.36 (3) | >95:5 ($^1H$ NMR) | $^1H$ NMR (300 MHz, DMSO-$d_6$) δ ppm 8.46 (s, 2 H), 7.24-7.44 (m, 5 H), 7.18 (d, 1 H), 7.10 (d, 1 H), 6.95 (dd, 1 H), 7.08 (t, 1 H), 5.92 (dd, 1 H), 4.73 (s, 1 H), 3.91 (d, 2 H), 3.57 (d, 1 H), 3.51 (d, 1 H), 3.32-3.43 (m, 2 H), 3.21 (dd, 1 H), 3.05-3.17 (m, 1 H), 2.79-3.04 (m, 2 H), 1.05-1.38 (m, 1 H), 0.48-0.72 (m, 2 H), 0.21-0.43 (m, 2 H) | +1.3 (c = 0.51; DCM) | 6 | Preparative HPLC (Method 2) | 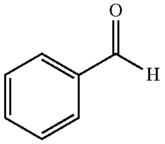 |
| 266 | 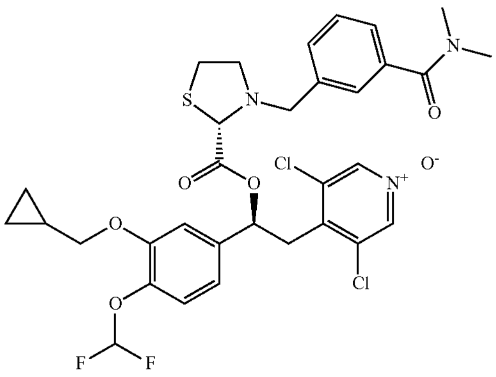 | Free Base | 696.27 | 3.79 (3) | >95:5 ($^1H$ NMR) | $^1H$ NMR (300 MHz, DMSO-$d_6$) δ ppm 8.50 (s, 2 H), 7.28-7.49 (m, 4 H), 7.18 (d, 1 H), 7.10 (d, 1 H), 6.94 (dd, 1 H), 7.07 (t, 1 H), 5.90 (dd, 1 H), 4.78 (s, 1 H), 3.91 (d, 2 H), 3.59 (s, 2 H), 3.32-3.44 (m, 2 H), 3.22 (dd, 1 H), 3.06-3.17 (m, 1 H), 2.81-3.05 (m, 8 H), 1.06-1.33 (m, 1 H), 0.45-0.71 (m, 2 H), 0.21-0.45 (m, 2 H) | +4.0 (c = 0.9, DCM) | 6 | Preparative HPLC (Method 2) | 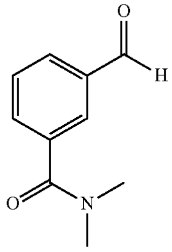 |

TABLE 18-continued

| Entry | Structure | SALT NAME | HPLC-MS characterization: MS/ESI+ [MH]+ | HPLC-MS characterization: $t_R$/min Method 1, 2 or 3 | Diastereomeric ratio | $^1$H NMR | $[\alpha]_D$ | Precursor | Purification Method | Starting aldehyde |
|---|---|---|---|---|---|---|---|---|---|---|
| 267 | 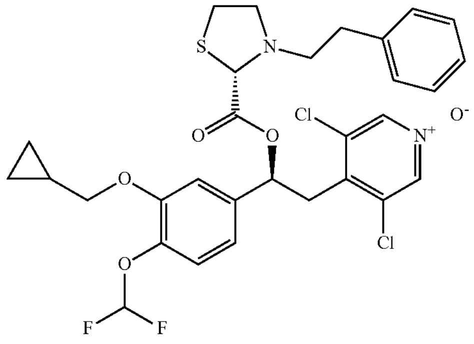 | Free Base | 639.37 | 4.25 (minor) 4.34 (major) (3) | 85:15 ($^1$H NMR) | $^1$H NMR (300 MHz, DMSO-$d_6$) δ ppm 8.56 (s, 2 H), 7.14-7.32 (m, 6 H), 7.11 (d, 1 H), 6.94 (dd, 1 H), 7.08 (t, 1 H), 5.93 (dd, 1 H), 4.93 (s, 1 H), 3.91 (d, 2 H), 3.45-3.52 (m, 1 H), 3.40 (dd, 1 H), 3.25 (dd, 1 H), 2.98-3.15 (m, 1 H), 2.69-2.90 (m, 4 H), 2.54-2.68 (m, 2 H), 1.02-1.34 (m, 1 H), 0.48-0.66 (m, 2 H), 0.16-0.42 (m, 2 H) | | 6 | Prepararive HPLC (Method 2) | 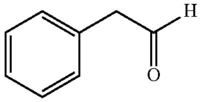 |
| 268 | 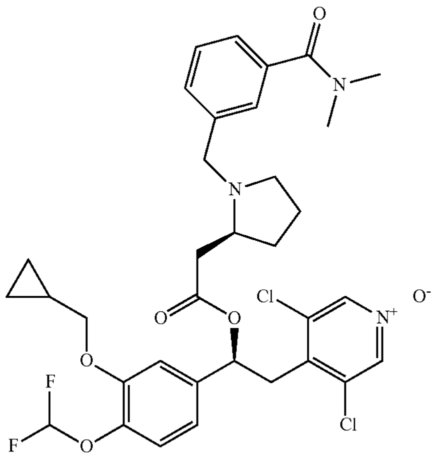 | Trifluoroacetate | 692.39 | 2.99 (3) | 90:10 ($^1$H NMR) | $^1$H NMR (300 MHz, DMSO-$d_6$) δ ppm 9.70 (br. s., 1 H), 8.59 (s, 2 H), 7.42-7.62 (m, 4 H), 7.22 (d, 1 H), 7.13 (d, 1 H), 7.01 (dd, 1 H), 7.07 (t, 1 H), 6.03 (dd, 1 H), 4.59 (d, 1 H), 4.08-4.37 (m, 1 H), 3.93 (d, 2 H), 3.69-3.84 (m, 1 H), 3.37-3.49 (m, 2 H), 3.10-3.33 (m, 2 H), 2.99 (br. s., 3 H), 2.89 (br. s., 3 H), 2.58-2.77 (m, 1 H), 2.54-2.61 (m, 1 H), 2.09-2.25 (m, 1 H), 1.71- | −7.7 (c = 0.25, DCM) | 179 | Preparative HPLC (Method 2) | 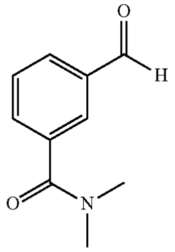 |

TABLE 18-continued

| Entry | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method | Starting aldehyde |
|---|---|---|---|---|---|---|---|---|---|---|
| | | | | | | 2.09 (m, 2 H), 1.42-1.64 (m, 1 H), 1.08-1.33 (m, 1 H), 0.47-0.70 (m, 2 H), 0.27-0.44 (m, 2 H) | | | | |

Example 24. Synthesis of 3,5-dichloro-4-((S)-2-(3-(cyclopropylmethoxy)-4-(difluoromethoxy)phenyl)-2-((S)-3-(3-ureidophenylsulfonyl)thiazolidine-2-carbonyloxy)ethyl)pyridine 1-oxide (269)

Scheme 31

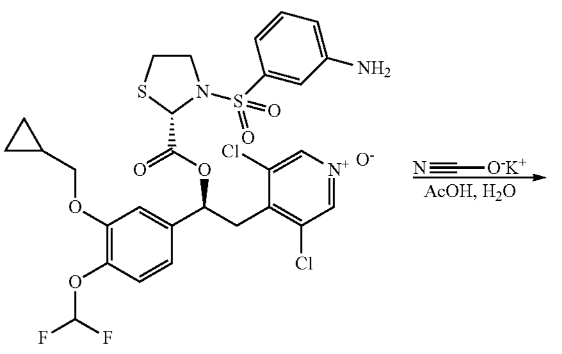

140

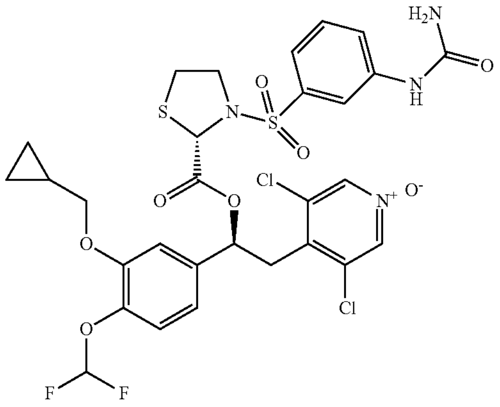

269

4-((S)-2-((S)-3-(3-aminophenylsulfonyl)thiazolidine-2-carbonyloxy)-2-(3-(cyclopropylmethoxy)-4-(difluoromethoxy)phenyl)ethyl)-3,5-dichloropyridine 1-oxide 140 (140, prepared as described in Example 10, 210 mg, 0.304 mmol), was dissolved in a mixture of AcOH (4 ml) and water (2 ml) at 10° C., and potassium cyanate (99 mg, 1.216 mmol) was immediately added. The reaction was stirred for 1 hour at 10° C. Water was added (30 ml), and the precipitate was collected by filtration and purified by preparative HPLC (Method 2) to afford 3,5-dichloro-4-((S)-2-(3-(cyclopropylmethoxy)-4-(difluoromethoxy)phenyl)-2-((S)-3-(3-ureidophenylsulfonyl)thiazolidine-2-carbonyloxy)ethyl)pyridine 1-oxide (136 mg, 0.185 mmol, 61.0% yield). MS/ESI$^+$ 733.05 $[MH]^+$; $t_R$ (Method 3)=5.39; Diastereomeric Ratio >95:5 ($^1H$ NMR); $[\alpha_D]$=−78.85 (c=0.4, DCM);

$^1H$ NMR (B) (300 MHz, DMSO-$d_6$) δ ppm 8.95 (s, 1H), 8.58 (s, 2H), 8.08 (t, 1H), 7.62 (ddd, 1H), 7.49 (t, 1H), 7.36 (dt, 1H), 7.18 (d, 1H), 7.12 (d, 1H), 6.96 (dd, 1H), 7.08 (t, 1H), 6.02 (dd, 1H), 6.01 (br. S., 2H), 5.30 (s, 1H), 3.91 (d, 2H), 3.61-3.82 (m, 2H), 3.49-3.54 (m, 1H), 3.31 (dd, 1H), 2.99 (dt, 1H), 2.73 (dt, 1H), 1.09-1.38 (m, 1H), 0.48-0.62 (m, 2H), 0.21-0.45 (m, 2H)

Example 25. Synthesis of 3,5-dichloro-4-((S)-2-(3-(cyclopropylmethoxy)-4-(difluoromethoxy)phenyl)-2-((S)-3-(3-(hydroxymethyl)phenylsulfonyl)thiazolidine-2-carbonyloxy)ethyl)pyridine 1-oxide (271)

Scheme 32

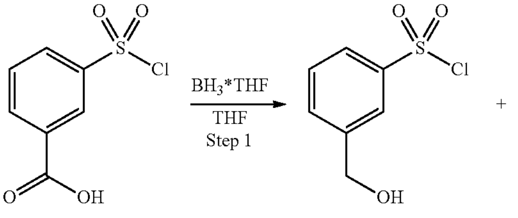

270

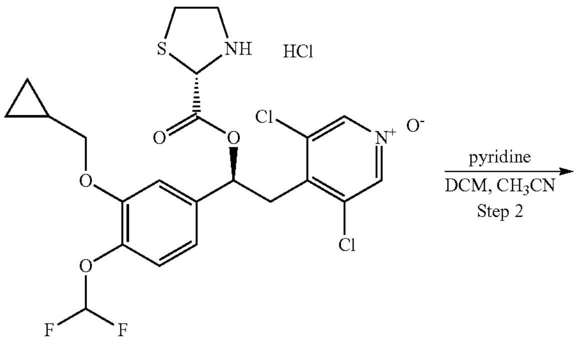

6

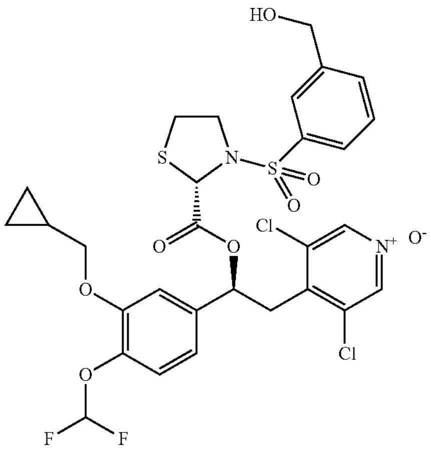

271

Step 1: 3-(hydroxymethyl)benzene-1-sulfonyl chloride (270)

To a solution of 3-(chlorosulfonyl)benzoic acid (0.300 g, 1.360 mmol) in dry THF (6 ml) cooled at 0° C., BH3*THF complex 1M in THF (5.44 ml, 5.44 mmol) was added. and the resulting mixture was left to warm to RT and stirred overnight. Additional BH3*THF complex 1M in THF (1.360 ml, 1.360 mmol) was added, and the stirring was continued for 3 days at RT. The mixture was carefully quenched with 2M HCl, diluted with brine and extracted twice with EtOAc. The combined organic layers were washed with brine and dried over sodium sulfate. The solvent was removed and the crude was purified by filtration through a silica gel cartridge (petroleum ether:EtOAc=70:30) affording 3-(hydroxymethyl)benzene-1-sulfonyl chloride (0.086 g, 0.416 mmol, 30.6% yield). MS/ESI not detectable $[MH]^+$.

Step 2: 3,5-dichloro-4-((S)-2-(3-(cyclopropylmethoxy)-4-(difluoromethoxy)phenyl)-2-((S)-3-(3-(hydroxymethyl)phenylsulfonyl)thiazolidine-2-carbonyloxy)ethyl)pyridine 1-oxide (271)

To a solution of 3,5-dichloro-4-((S)-2-(3-(cyclopropylmethoxy)-4-(difluoromethoxy)phenyl)-2-((S)-thiazolidine-2-carbonyloxy)ethyl)pyridine 1-oxide hydrochloride (6) (0.183 g, 0.320 mmol) in DCM (5 ml), $CH_3CN$ (2 ml), and pyridine (0.078 ml, 0.960 mmol) cooled at 0° C., a solution of 3-(hydroxymethyl)benzene-1-sulfonyl chloride (0.086 g, 0.416 mmol) in DCM (2 ml) was added, and the resulting mixture was warmed to RT and stirred. The volatiles were removed under vacuum; the residue was purified by preparative HPLC (Method 2 under neutral conditions, without TFA) and the collected fractions were frozen dry to afford 3,5-dichloro-4-((S)-2-(3-(cyclopropylmethoxy)-4-(difluoromethoxy)phenyl)-2-((S)-3-(3-(hydroxymethyl)phenylsulfonyl)thiazolidine-2-carbonyloxy)ethyl)pyridine 1-oxide (0.100 g, 0.142 mmol, 44.3% yield); MS/ESI$^+$ 705.14 $[MH]^+$; $t_R$ (Method 3)=3.78; Diastereomeric Ratio >95:5 ($^1$H NMR); $[\alpha_D]$=−65.67 (c=0.42; MeOH);

$^1$H NMR (B) (300 MHz, DMSO-$d_6$) δ ppm 8.58 (s, 2H), 7.83 (t, 1H), 7.73 (dt, 1H), 7.68 (dt, 1H), 7.61 (t, 1H), 7.19 (d, 1H), 7.12 (d, 1H), 6.97 (dd, 1H), 7.08 (t, 1H), 6.03 (dd, 1H), 5.44 (t, 1H), 5.38 (s, 1H), 4.62 (d, 2H), 3.91 (d, 2H), 3.76 (dt, 1H), 3.67 (dt, 1H), 3.47 (dd, 1H), 3.31 (dd, 1H), 2.98 (dt, 1H), 2.68 (dt, 1H), 1.03-1.38 (m, 1H), 0.49-0.67 (m, 2H), 0.15-0.45 (m, 2H).

Example 26. Synthesis of 4-((2S)-2-(2-(3-benzoylthiazolidin-2-yl)acetoxy)-2-(3-(cyclopropylmethoxy)-4-(difluoromethoxy)phenyl)ethyl)-3,5-dichloropyridine 1-oxide (274)

Scheme 33

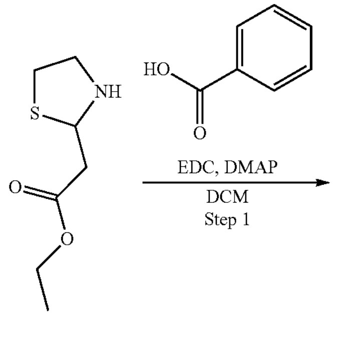

-continued

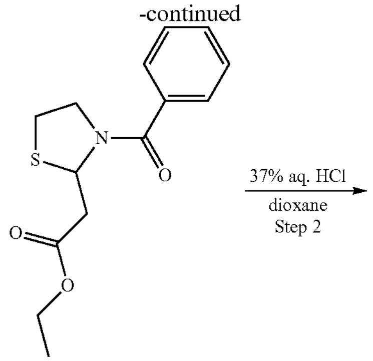

272

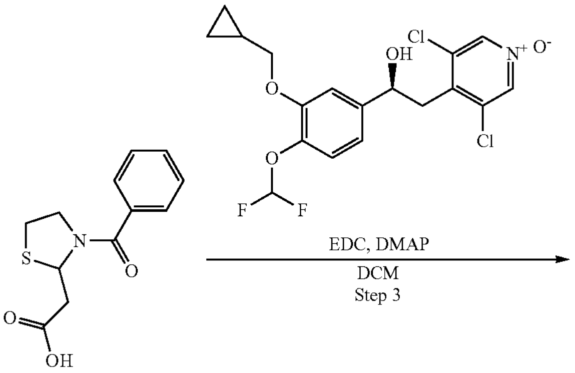

273

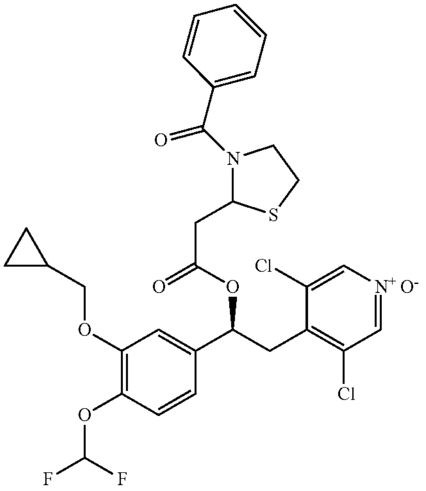

274

Step 1: ethyl 2-(3-benzoylthiazolidin-2-yl)acetate (272)

A mixture of ethyl 2-(thiazolidin-2-yl)acetate (0.100 g, 0.571 mmol) (prepared following the synthetic protocol described in J. Chem. Soc. Perkin Trans. I, 1987, 1845-1851, which is incorporated herein by reference in its entirety), benzoic acid (0.084 g, 0.685 mmol), EDC (0.219 g, 1.141 mmol), and DMAP (0.070 g, 0.571 mmol) in DCM (10 ml) was stirred at RT for 1 hour. The mixture was diluted with DCM and washed with aqueous 1N HCl, 1N $NaHCO_3$ and brine; the organic phase was dried over sodium sulfate and the solvent was removed. The residue was purified by flash chromatography on silica gel cartridge (petroleum ether: EtOAc=80:20 to 70:30) yielding ethyl 2-(3-benzoylthiazolidin-2-yl)acetate (0.085 g, 0.304 mmol, 53% yield). MS/ESI$^+$ 280.0 [MH]$^+$.

Step 2: 2-(3-benzoylthiazolidin-2-yl)acetic acid (273)

To a solution of ethyl 2-(3-benzoylthiazolidin-2-yl)acetate (0.083 g, 0.297 mmol) in dioxane (4 ml), aqueous 37% HCl (4 ml) was added, and the mixture was stirred at RT for 20 hours. The volatiles were removed under vacuum yielding crude 2-(3-benzoylthiazolidin-2-yl)acetic acid (0.074 g, 0.294 mmol, 99% yield) which was used without purification. MS/ESI$^+$ 251.9 [MH]$^+$.

Step 3: 4-((2S)-2-(2-(3-benzoylthiazolidin-2-yl)acetoxy)-2-(3-(cyclopropylmethoxy)-4-(difluoromethoxy)phenyl)ethyl)-3,5-dichloropyridine 1-oxide (274)

A mixture of 2-(3-benzoylthiazolidin-2-yl)acetic acid (0.074 g, 0.294 mmol), (S)-3,5-dichloro-4-(2-(3-(cyclopropylmethoxy)-4-(difluoromethoxy)phenyl)-2-hydroxyethyl) pyridine 1-oxide (0.103 g, 0.245 mmol), EDC (0.141 g, 0.736 mmol), and DMAP (0.030 g, 0.245 mmol) in DCM (10 ml) was stirred at RT for 2 hours. The mixture was diluted with DCM and washed with 1N HCl, 1N $NaHCO_3$ and brine; the organic phase was dried over sodium sulfate and the solvent was removed. The crude was purified by preparative HPLC (Method 2) followed by flash chromatography on silica gel cartridge (DCM:MeOH=99:1) yielding title compound as a distereomeric mixture (0.065 g, 0.099 mmol, 40.5% yield); MS/ESI$^+$ 653.19 [MH]$^+$; $t_R$ (Method 3)=3.92; Diastereomeric Ratio=1:1 ($^1$H NMR).

The compound listed in Table 19 was prepared according to analogous procedures as those described for Scheme 33 and using suitable reagents, followed by appropriate purification step as below reported.

TABLE 19

| Entry | Structure | SALT NAME | HPLC-MS characterization: MS/ESI$^+$ [MH]$^+$ | $t_R$/min Method 1, 2 or 3 | Diastereomeric ratio | Purification Method |
|---|---|---|---|---|---|---|
| 275 | 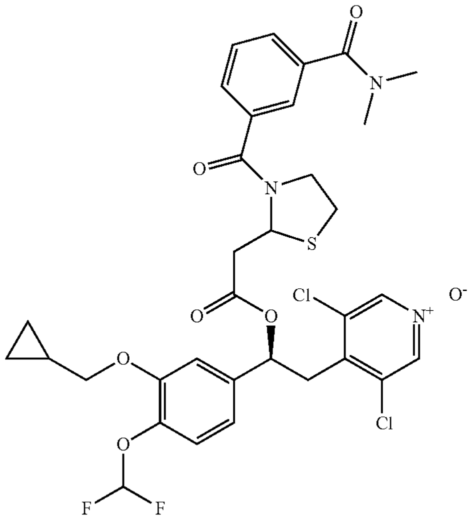 | Free Base | 724.39 | 3.53 (3) | 1:1 ($^1$H NMR) | Preparative HPLC (Method 2) |

Example 27. Synthesis of 3,5-dichloro-4-((2S)-2-(3-(cyclopropylmethoxy)-4-(difluoromethoxy)phenyl)-2-(2-(3-(phenylsulfonyl)thiazolidin-2-yl)acetoxy)ethyl)pyridine 1-oxide (278)

Scheme 42

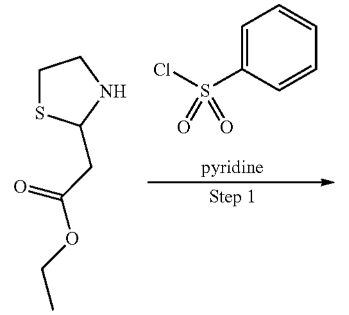

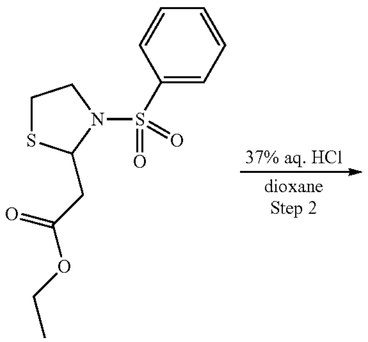

276

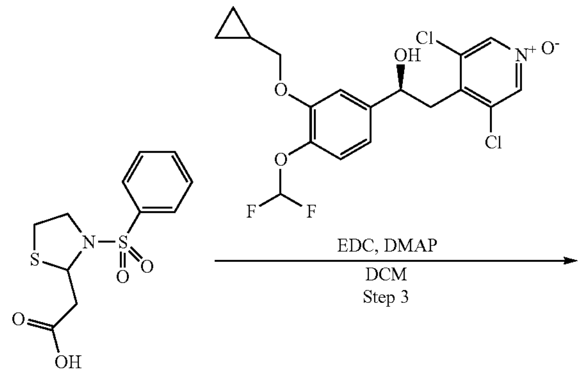

277

-continued

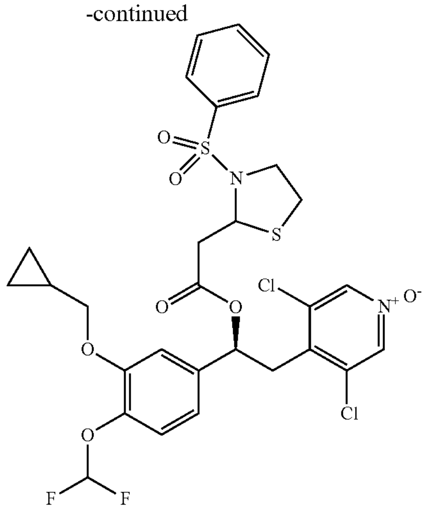

278

Step 1: ethyl 2-(3-(phenylsulfonyl)thiazolidin-2-yl)acetate (276)

To a solution of ethyl 2-(thiazolidin-2-yl)acetate (0.100 g, 0.571 mmol) (prepared following the synthetic protocol described in J. Chem. Soc. Perkin Trans. I, 1987, 1845-1851, which is incorporated herein by reference in its entirety) in pyridine (4 ml) cooled at 0° C., benzenesulfonyl chloride (0.088 ml, 0.685 mmol) was added, and the reaction was stirred for 2 hours at RT. The mixture was partitioned between EtOAc and 1N HCl; the organic phase was washed with 1N HCl and brine and dried over sodium sulfate. The solvent was removed and the crude was purified by flash chromatography on silica gel (petroleum ether:EtOAc=90:10 to 80:20) affording ethyl 2-(3-(phenylsulfonyl)thiazolidin-2-yl)acetate (0.096 g, 0.304 mmol, 53.3% yield). MS/ESI 316.0 $[MH]^+$.

Step 2: 2-(3-(phenylsulfonyl)thiazolidin-2-yl)acetic acid (277)

To a solution of ethyl 2-(3-(phenylsulfonyl)thiazolidin-2-yl)acetate (0.096 g, 0.304 mmol) in dioxane (5 ml), aqueous 37% HCl (5 ml) was added, and the mixture was stirred at RT for 25 hours. The volatiles were removed under vacuum to afford 2-(3-(phenylsulfonyl)thiazolidin-2-yl)acetic acid (0.083 g, 0.289 mmol, 95% yield) which was used without purification. $MS/ESI^+$ 310.0 $[Mna]^+$.

Step 3: 3,5-dichloro-4-((2S)-2-(3-(cyclopropylmethoxy)-4-(difluoromethoxy)phenyl)-2-(2-(3-(phenylsulfonyl)thiazolidin-2-yl)acetoxy)ethyl)pyridine 1-oxide (278)

A mixture of 2-(3-(phenylsulfonyl)thiazolidin-2-yl)acetic acid (0.083 g, 0.289 mmol), (S)-3,5-dichloro-4-(2-(3-(cyclopropylmethoxy)-4-(difluoromethoxy)phenyl)-2-hydroxyethyl)pyridine 1-oxide (0.101 g, 0.241 mmol), EDC (0.046 g, 0.241 mmol), and DMAP (0.029 g, 0.241 mmol) in DCM (10 ml) was stirred at RT for 1 hour. The mixture was diluted with DCM and washed with 1N HCl, 1N $NaHCO_3$ and brine; the organic phase was dried over sodium sulfate and the solvent was removed. The crude was purified by preparative HPLC (Method 2) affording 3,5-dichloro-4-((2S)-2-(3-(cyclopropylmethoxy)-4-(difluoromethoxy)phenyl)-2-(2-(3-(phenylsulfonyl)thiazolidin-2-yl)acetoxy)ethyl)pyridine 1-oxide (0.122 g, 0.177 mmol, 73.5% yield); $MS/ESI^+$ 689.14 $[MH]^+$; $t_R$ (Method 3)=4.09; Diastereomeric Ratio=1:1 ($^1H$ NMR).

The compound listed in Table 20 was prepared according to analogous procedures as those described for Scheme 42 and using suitable reagents, followed by appropriate purification step as below reported.

TABLE 20

| Entry | Structure | SALT NAME | HPLC-MS characterization MS/ESI+ [MH]+ | $t_R$/min Method 1, 2 or 3 | Diastereomeric ratio | Purification Method |
|---|---|---|---|---|---|---|
| 279 | 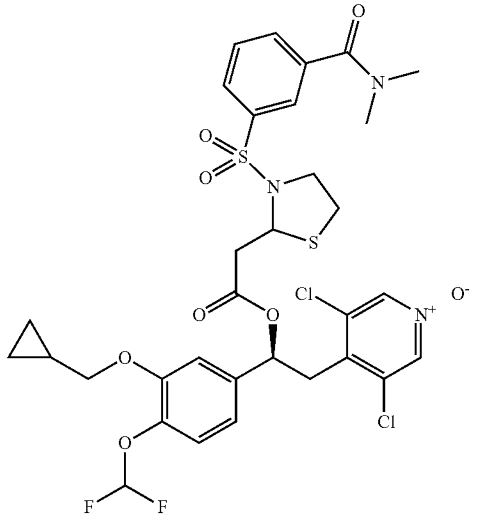 | Free Base | 760.23 | 3.67 (3) | 1:1 ($^1$H NMR) | Flash chromatography on silica gel |

Example 28. (S)-3,5-dichloro-4-(2-(3-(cyclopropylmethoxy)-4-(difluoromethoxy)phenyl)-2-(1-(3-(dimethylcarbamoyl)phenylsulfonyl)azetidine-3-carbonyloxy)ethyl)pyridine 1-oxide (281)

Scheme 34

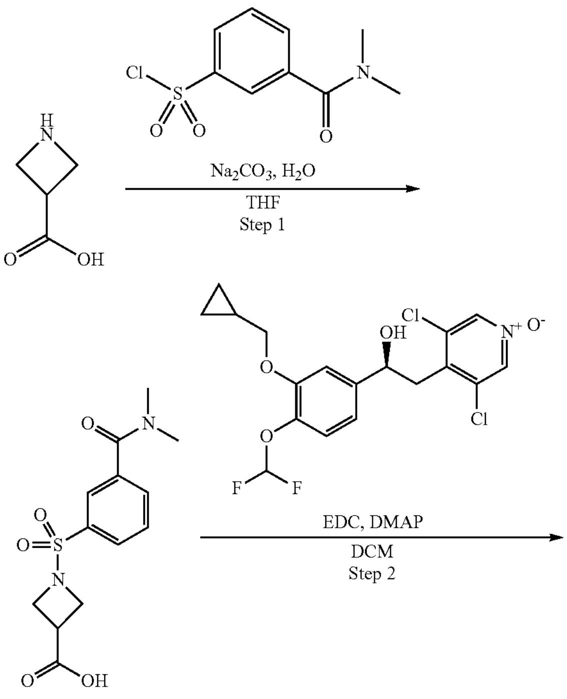

280

-continued

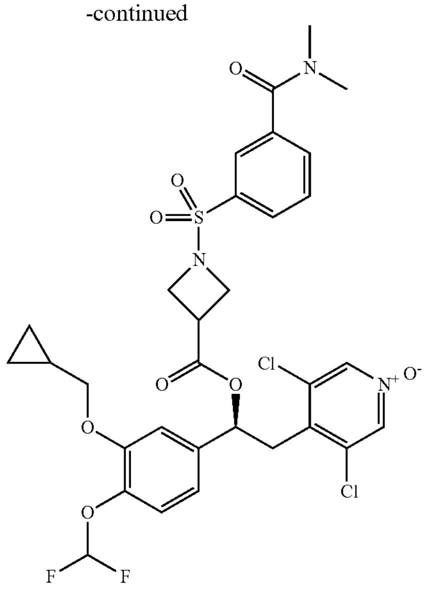

281

Step 1: 1-(3-(dimethylcarbamoyl)phenylsulfonyl)azetidine-3-carboxylic acid (280)

To a suspension of azetidine-3-carboxylic acid (100 mg, 0.989 mmol) in a mixture of THF (6 ml) and aqueous 1M $Na_2CO_3$ (6 ml, 6.00 mmol) cooled at 0° C., 3-(dimethylcarbamoyl)benzene-1-sulfonyl chloride (269 mg, 1.088 mmol) was added, and the reaction was stirred at 0° C. for 1 hour. The mixture was extracted with $Et_2O$, and the organic layer was discarded. The aqueous layer was carefully acidified by addition of solid $KHSO_4$ (pH=3) and extracted twice with EtOAc. The combined organic layers were dried over $Na_2SO_4$ and evaporated to dryness yielding crude 1-(3-

(dimethylcarbamoyl)phenylsulfonyl)azetidine-3-carboxylic acid (255 mg, 0.816 mmol, 83% yield) which was used without purification.

MS/ESI$^+$ 313.12 [MH]$^+$

Step 2: (S)-3,5-dichloro-4-(2-(3-(cyclopropylmethoxy)-4-(difluoromethoxy)phenyl)-2-(1-(3-(dimethylcarbamoyl)phenylsulfonyl)azetidine-3-carbonyloxy)ethyl)pyridine 1-oxide (281)

A solution of 1-(3-(dimethylcarbamoyl)phenylsulfonyl) azetidine-3-carboxylic acid (255 mg, 0.816 mmol), (S)-3,5-dichloro-4-(2-(3-(cyclopropylmethoxy)-4-(difluoromethoxy)phenyl)-2-hydroxyethyl)pyridine 1-oxide (175 mg, 0.416 mmol), EDC (96 mg, 0.500 mmol), and DMAP (61.0 mg, 0.500 mmol) in DCM (30 ml) was stirred at RT overnight. More EDC (80 mg, 0.416 mmol) and DMAP (61.0 mg, 0.500 mmol) were added, and the stirring was continued for further 2 hours. The reaction mixture was washed twice with aqueous 1N HCl then with aqueous 1M $Na_2CO_3$, the organic phase was dried over $Na_2SO_4$ and the solvent was removed under reduced pressure. The residue was purified by preparative HPLC (Method 2) to afford (S)-3,5-dichloro-4-(2-(3-(cyclopropylmethoxy)-4-(difluoromethoxy)phenyl)-2-(1-(3-(dimethylcarbamoyl)phenylsulfonyl)azetidine-3-carbonyloxy)ethyl)pyridine 1-oxide (192 mg, 0.269 mmol, 64.5% yield); MS/ESI$^+$ 714.16 [MH]$^+$; $[\alpha_D]$=−14.3 (c=0.37, DCM);

$^1$H NMR (B) (300 MHz, DMSO-$d_6$) δ ppm 8.56 (s, 2H), 7.68-7.90 (m, 4H), 7.16 (d, 1H), 7.02 (d, 1H), 6.85 (dd, 1H), 7.07 (t, 1H), 5.82 (dd, 1H), 3.85-4.06 (m, 2H), 3.89 (d, 2H), 3.71 (dd, 1H), 3.56 (dd, 1H), 3.42-3.49 (m, 2H), 3.14 (dd, 1H), 3.01 (br. S., 3H), 2.86 (br. S., 3H), 1.02-1.37 (m, 1H), 0.50-0.78 (m, 2H), 0.07-0.50 (m, 2H)

The compounds listed in Table 21 were prepared according to analogous procedures as those described for Scheme 34 and by reacting the appropriate amino acid precursor listed with commercial suitable reagents, followed by appropriate purification step as below reported, if needed. For the preparation of compound 283 and compound 284, Step 1 was accomplished using water as the solvent.

TABLE 21
| Entry | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method | Sulfonyl chloride |
|---|---|---|---|---|---|---|---|---|---|---|
| 282 | 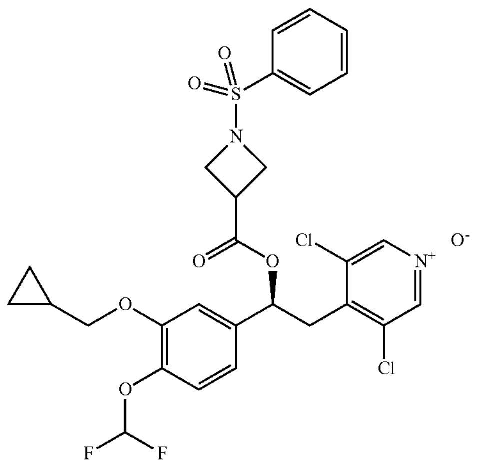 | Free Base | 643.14 | 3.93 (3) | | $^1$H NMR (300 MHz, DMSO-$d_6$) δ ppm 8.58 (s, 2 H), 7.60-7.85 (m, 5 H), 7.16 (d, 1 H), 7.02 (d, 1 H), 6.84 (dd, 1 H), 7.07 (t, 1 H), 5.82 (dd, 1 H), 3.89 (d, 2 H), 3.84-3.98 (m, 2 H), 3.69 (dd, 1 H), 3.51 (dd, 1 H), 3.36-3.47 (m, 2 H), 3.13 (dd, 1 H), 1.08-1.39 (m, 1 H), 0.47-0.67 (m, 2 H), 0.20-0.44 (m, 2 H) | −10.9 (c = 0.48, DCM) | 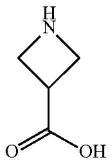 | Preparative HPLC (Method 2) | 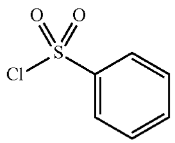 |

TABLE 21-continued

| Entry | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method | Sulfonyl chloride |
|---|---|---|---|---|---|---|---|---|---|---|
| 283 | 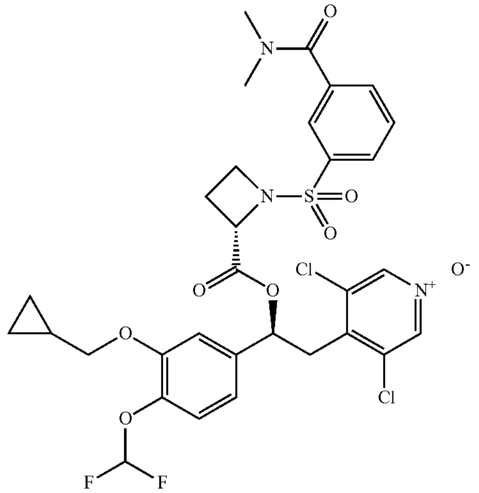 | Free Base | 714.14 | 6.74 (3) | >95:5 ($^1$H NMR) | $^1$H NMR (300 MHz, DMSO-$d_6$) δ ppm 8.57 (s, 2 H), 7.65-7.90 (m, 4 H), 7.18 (d, 1 H), 7.14 (d, 1 H), 6.96 (dd, 1 H), 7.07 (t, 1 H), 6.03 (dd, 1 H), 4.50 (dd, 1 H), 3.91 (d, 2 H), 3.68-3.80 (m, 1 H), 3.59-3.68 (m, 1 H), 3.47 (dd, 1 H), 3.20-3.27 (m, 1 H), 3.02 (br. S., 3 H), 2.92 (br. S., 3 H), 2.19-2.39 (m, 1 H), 2.02-2.19 (m, 1 H), 1.03-1.34 (m, 1 H), 0.47-0.64 (m, 2 H), 0.15-0.43 (m, 2 H) | −73.97 (c = 1.2, DCM) | 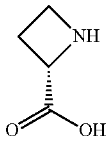 | Preparative HPLC (Method 2) | 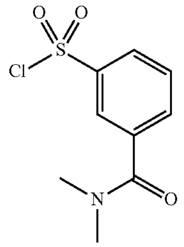 |
| 284 | 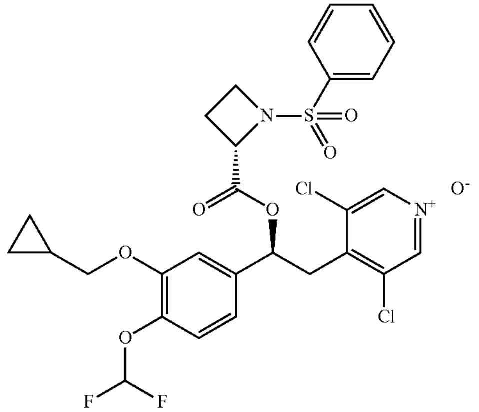 | Free Base | 643.23 | 3.93 (3) | >95:5 ($^1$H NMR) | $^1$H NMR (300 MHz, DMSO-$d_6$) δ ppm 8.59 (s, 2 H), 7.74-7.89 (m, 3 H), 7.61-7.74 (m, 2 H), 7.18 (d, 1 H), 7.14 (d, 1 H), 6.96 (dd, 1 H), 7.08 (t, 1 H), 6.03 (dd, 1 H), 4.42 (dd, 1 H), 3.91 (d, 2 H), 3.65-3.78 (m, 1 H), 3.55-3.67 (m, 1 H), 3.47 (dd, 1 H), 3.21-3.26 (m, 1 H), 2.13-2.26 (m, 1 H), 1.91-2.15 (m, 1 H), 1.05-1.34 (m, 1 H), 0.48-0.63 (m, 2 H), 0.24-0.41 (m, 2 H) | −85.36 (c = 0.53, DCM) | 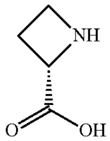 | Trituration with MeOH | 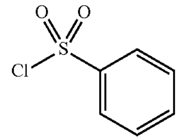 |

TABLE 21-continued
| Entry | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Precursor | Purification Method | Sulfonyl chloride |
|---|---|---|---|---|---|---|---|---|---|---|
| 285 | 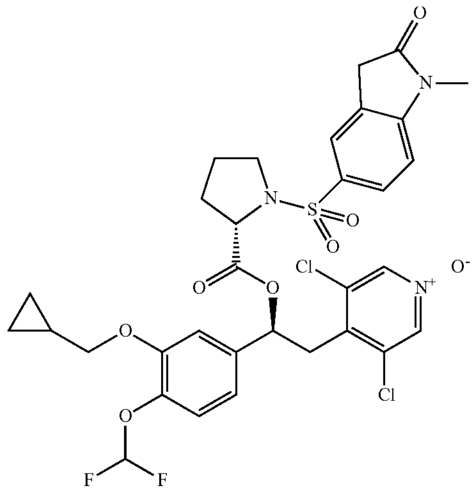 | Free Base | 726.1 | 3.66 (3) | >95:5 ($^1$H NMR) | $^1$H NMR (300 MHz, DMSO-$d_6$) δ ppm 8.60 (s, 2 H), 7.71 (dd, 1 H), 7.64 (d, 1 H), 7.19 (d, 1 H), 7.18 (d, 1 H), 7.14 (d, 1 H), 6.99 (dd, 1 H), 7.08 (t, 1 H), 6.04 (dd, 1 H), 4.10 (dd, 1 H), 3.93 (d, 2 H), 3.69 (s, 2 H), 3.32-3.58 (m, 3 H), 3.18 (s, 3 H), 2.99-3.26 (m, 1 H), 1.80-2.10 (m, 1 H), 1.60-1.80 (m, 2 H), 1.54 (d, 1 H), 0.93-1.32 (m, 1 H), 0.44-0.71 (m, 2 H), 0.05-0.44 (m, 2 H) | −48.1 (c = 0.46, DCM) | 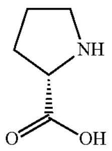 | Flash chromatography on silica gel | 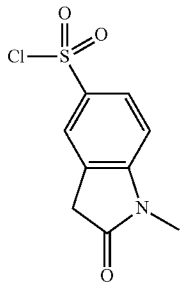 |

Example 29. Synthesis of 3,5-dichloro-4-((S)-2-(3-(cyclopropylmethoxy)-4-(difluoromethoxy)phenyl)-2-((S)-3-(2-morpholinoethylsulfonyl)thiazolidine-2-carbonyloxy)ethyl)pyridine 1-oxide (287)

Scheme 35

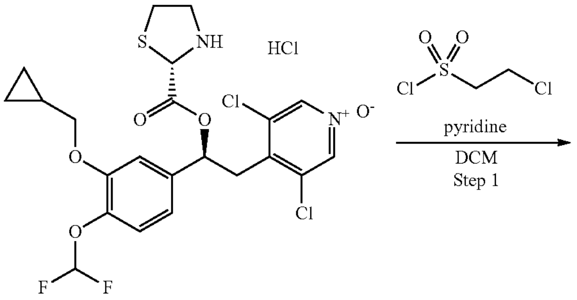

6

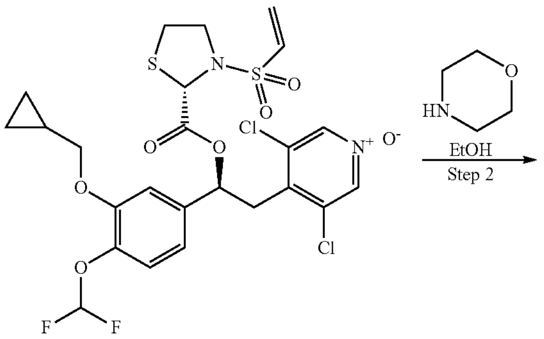

286

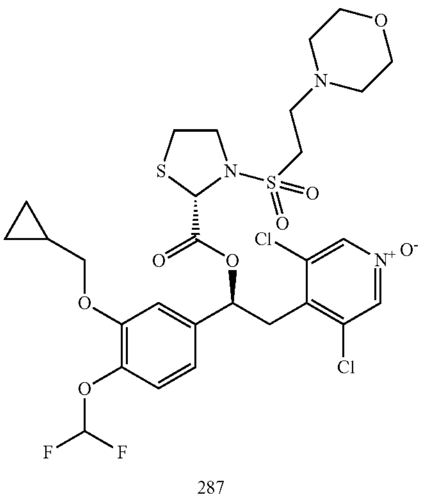

287

Step 1: 3,5-dichloro-4-((S)-2-(3-(cyclopropylmethoxy)-4-(difluoromethoxy)phenyl)-2-((S)-3-(vinylsulfonyl)thiazolidine-2-carbonyloxy)ethyl)pyridine 1-oxide (286)

To a solution of 3,5-dichloro-4-((S)-2-(3-(cyclopropylmethoxy)-4-(difluoromethoxy)phenyl)-2-((S)-thiazolidine-2-carbonyloxy)ethyl)pyridine 1-oxide hydrochloride (6) (500 mg, 0.874 mmol) in DCM (10 ml) cooled at 0° C., pyridine (212 µl, 2.62 mmol) and 2-chloroethanesulfonyl chloride (137 µl, 1.312 mmol) were added, and the mixture was left to warm to RT and stirred for 2 hours. Additional pyridine (707 µl, 8.74 mmol) and 2-chloroethanesulfonyl chloride (137 µl, 1.312 mmol) were added at 0° C., and the mixture reacted for 6 hours at RT. The mixture was diluted with DCM and washed with 1N HCl and brine; the organic layer was dried over $Na_2SO_4$ and the solvent was removed under vacuum. The resulting crude was purified by flash chromatography on silica gel (DCM/MeOH=98/2) yielding 3,5-dichloro-4-((S)-2-(3-(cyclopropylmethoxy)-4-(difluoromethoxy)phenyl)-2-((S)-3-(vinylsulfonyl)thiazolidine-2-carbonyloxy)ethyl)pyridine 1-oxide (360 mg, 0.576 mmol, 66% yield); MS/ESI$^+$ 624.9 $[MH]^+$ Step 2: 3,5-dichloro-4-((S)-2-(3-(cyclopropylmethoxy)-4-(difluoromethoxy)phenyl)-2-((S)-3-(2-morpholinoethylsulfonyl)thiazolidine-2-carbonyloxy)ethyl)pyridine 1-oxide (287)

To a solution of 3,5-dichloro-4-((S)-2-(3-(cyclopropylmethoxy)-4-(difluoromethoxy)phenyl)-2-((S)-3-(vinylsulfonyl)thiazolidine-2-carbonyloxy)ethyl)pyridine 1-oxide (110 mg, 0.176 mmol) in EtOH (5 ml), morpholine (35.2 µl, 0.352 mmol) was added and the mixture was reacted at RT for 1 hour. The solvent was removed under reduced pressure, and the crude was purified by preparative HPLC (Method 3) yielding 3,5-dichloro-4-((S)-2-(3-(cyclopropylmethoxy)-4-(difluoromethoxy)phenyl)-2-((S)-3-(vinylsulfonyl)thiazolidine-2-carbonyloxy)ethyl)pyridine 1-oxide as trifluoroacetate salt; MS/ESI$^+$ 712.14 $[MH]^+$; $t_R$ (Method 3)=3.16; Diastereomeric Ratio >95:5 ($^1H$ NMR); $[\alpha_D]$=−126.6 (c=0.23 DCM);

$^1H$ NMR (B) (300 MHz, DMSO-$d_6$) δ ppm 8.55 (s, 2H), 7.19 (d, 1H), 7.11 (d, 1H), 6.97 (dd, 1H), 7.08 (t, 1H), 6.03 (dd, 1H), 5.58 (s, 1H), 3.94-4.02 (m, 1H), 3.91 (d, 2H), 3.61-3.74 (m, 1H), 3.45 (dd, 1H), 3.31 (dd, 1H), 3.06-3.81 (m, 12H), 3.00-3.25 (m, 2H), 1.03-1.35 (m, 1H), 0.47-0.70 (m, 2H), 0.10-0.45 (m, 2H)

The compound listed in Table 22 was prepared according to analogous procedures as those described for Scheme 35 and by reacting the appropriate precursor listed with commercial suitable reagents, followed by appropriate purification step.

TABLE 22

| | | | HPLC-MS characterization | | | | | | | |
|---|---|---|---|---|---|---|---|---|---|---|
| Entry | Structure | SALT NAME | MS/ ESI+ [MH]+ | $t_R$/min Method 1, 2 or 3 | Diastereomeric ratio | $^1$H NMR | $[\alpha]_D$ | Precursor | Purification Method | Amine |
| 288 | 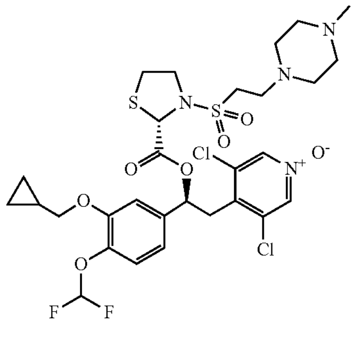 | Trifluoroacetate (mono salt) | 725.15 | 3.09 (3) | >95:5 ($^1$H NMR) | $^1$H NMR (300 MHz, DMSO-$d_6$) δ ppm 8.58 (s, 2 H), 7.60-7.85 (m, 5 H), 7.16 (d, 1 H), 7.02 (d, 1 H), 6.84 (dd, 1 H), 7.07 (t, 1 H), 5.82 (dd, 1 H), 3.89 (d, 2 H), 3.84-3.98 (m, 2 H), 3.69 (dd, 1 H), 3.51 (dd, 1 H), 3.36-3.47 (m, 2 H), 3.13 (dd, 1 H), 1.08-1.39 (m, 1 H), 0.47-0.67 (m, 2 H), 0.20-0.44 (m, 2 H) | −80.24 (c = 0.325, DCM) | 6 | Preparative HPLC (Method 3) | 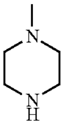 |

Example 30. 3,5-dichloro-4-((S)-2-(3-(cyclopropylmethoxy)-4-(difluoro-methoxy)phenyl)-2-((S)-1-(2-(phenylsulfonyl)ethyl)pyrrolidine-2-carbonyloxy)ethyl)pyridine 1-oxide (291)

Scheme 36

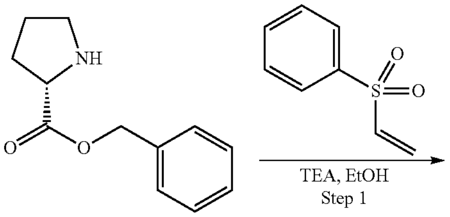

-continued

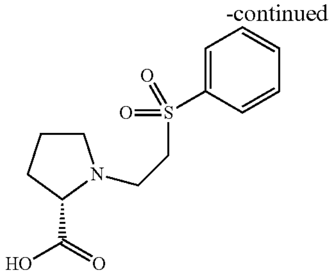

290

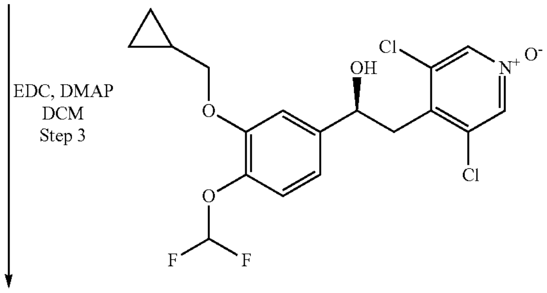

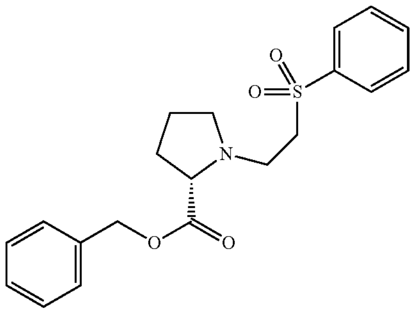

289

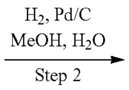

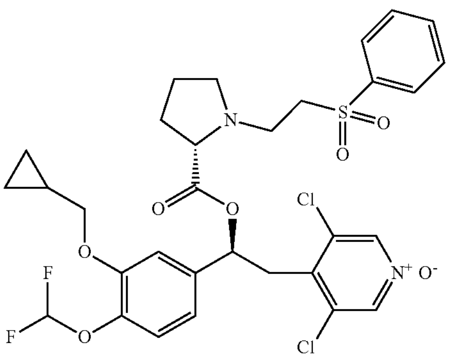

291

Step 1: (S)-benzyl 1-(2-(phenylsulfonyl)ethyl)pyrrolidine-2-carboxylate (289)

A solution of (S)-benzyl pyrrolidine-2-carboxylate hydrochloride (250 mg, 1.034 mmol), vinylsulfonylbenzene (261 mg, 1.551 mmol), and TEA (0.216 ml, 1.551 mmol) in EtOH (15 ml) was stirred at RT for 24 hours. The reaction mixture was then diluted with DCM (50 ml) and washed twice with aqueous sat. $NH_4Cl$. The organic layer was dried over $Na_2SO_4$ and the solvent was removed under vacuum. The residue was dissolved in DCM (15 ml) and EtOH (15 ml), and PS-trisamine (free —$NH_2$ group: 4.7 mmol/g, 0.5 g, 0.35 mmol) was added. The suspension was stirred at RT for 3 days. The resin was filtered off and the solution evaporated to dryness to afford the desired product (379 mg, 1.01 mmol, 98% yield). MS/ESI$^+$ 374.10 [MH]$^+$.

Step 2: (S)-1-(2-(phenylsulfonyl)ethyl)pyrrolidine-2-carboxylic acid (290)

A suspension of 10% Pd/C (10.80 mg, 0.101 mmol) in water (2 ml) was added to a solution of (S)-benzyl 1-(2-(phenylsulfonyl)ethyl)pyrrolidine-2-carboxylate (379 mg, 1.015 mmol) in MeOH (15 ml). The mixture was hydrogenated in a Parr apparatus at 30 psi for 1 hour at RT. The catalyst was filtered off and the resulting clear solution was evaporated to dryness to afford the desired product (272 mg, 0.860 mmol, 95% yield).

MS/ESI$^+$ 284.02 [MH]$^+$.

Step 3: 3,5-dichloro-4-((S)-2-(3-(cyclopropylmethoxy)-4-(difluoro-methoxy)phenyl)-2-((S)-1-(2-(phenylsulfonyl)ethyl)pyrrolidine-2-carbonyloxy) ethyl)pyridine 1-oxide (291)

A solution of (S)-3,5-dichloro-4-(2-(3-(cyclopropylmethoxy)-4-(difluoromethoxy)phenyl)-2-hydroxyethyl) pyridine 1-oxide (150 mg, 0.357 mmol), (S)-1-(2-(phenylsulfonyl)ethyl)pyrrolidine-2-carboxylic acid (152 mg, 0.535 mmol), EDC (103 mg, 0.535 mmol), and DMAP (21.80 mg, 0.178 mmol) in DCM (30 ml) was stirred at RT for 1 hour. The reaction mixture was washed twice with 1N HCl, dried over $Na_2SO_4$ and evaporated to dryness. The residue was purified by preparative HPLC (Method 2), and the collected fractions were evaporated to dryness, redissolved DCM and eluted through a PL-$HCO_3$ cartridge (200 mg, 0.36 mmoles). The eluted solution was evaporated to dryness affording title compound (110 mg, 0.160 mmol, 45% yield); [$\alpha_D$]=−33.8 (c=0.44, DCM); MS/ESI$^+$ 685.42 [MH]$^+$; $t_R$=3.15 min (Method 3); Diastereomeric Ratio >95:5 ($^1$H NMR);

$^1$H NMR (B) (300 MHz, DMSO-d6) δ ppm 8.55 (s, 2H), 7.83-7.98 (m, 2H), 7.69-7.82 (m, 1H), 7.53-7.69 (m, 2H), 7.17 (d, 1H), 7.06 (d, 1H), 6.93 (dd, 1H), 7.06 (t, 1H), 5.92 (dd, 1H), 3.80-4.04 (m, 2H), 3.43-3.58 (m, 1H), 3.41 (dd, 1H), 3.23 (dd, 1H), 2.61-3.09 (m, 5H), 2.25-2.44 (m, 1H), 1.84-2.08 (m, 1H), 1.37-1.78 (m, 3H), 1.09-1.33 (m, 1H), 0.48-0.73 (m, 2H), 0.25-0.43 (m, 2H)

Example 31. 3,5-dichloro-4-((S)-2-(3-(cyclopropylmethoxy)-4-(difluoromethoxy)phenyl)-2-((S)-1-(2-phenylacetyl)pyrrolidine-2-carbonyloxy)ethyl)pyridine 1-oxide (292)

Scheme 37

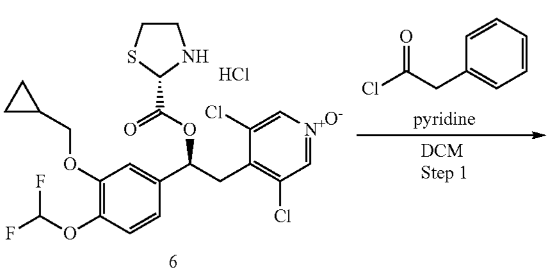

6

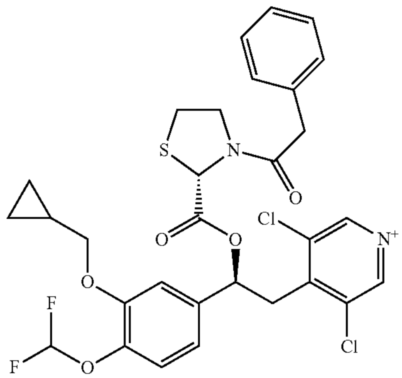

292

To a solution of 3,5-dichloro-4-((S)-2-(3-(cyclopropylmethoxy)-4-(difluoromethoxy)phenyl)-2-((S)-pyrrolidine-2-carbonyloxy)ethyl)pyridine 1-oxide hydrochloride (6) (200 mg, 0.361 mmol) and pyridine (292 μl, 3.61 mmol) in dry DCM (5 ml), a solution of phenyl-acetyl chloride (84 mg, 0.542 mmol) in dry DCM (1 ml) was added dropwise at 0° C. and the mixture was left to warm to RT and stirred for 2 hours. EtOAc (20 ml) was added, and the mixture was washed with aqueous 5% citric acid and brine; the organic phase was dried over $Na_2SO_4$, filtered and evaporated. The residue was purified by flash chromatography on silica gel (DCM/MeOH=95/5). A further purification by preparative HPLC (Method 2) was required to afford 3,5-dichloro-4-((S)-2-(3-(cyclopropylmethoxy)-4-(difluoromethoxy)phenyl)-2-((S)-1-(2-phenylacetyl)pyrrolidine-2-carbonyloxy) ethyl)pyridine 1-oxide (35 mg, 0.055 mmol, 15.25% yield); MS/ESI$^+$ 635.23 [MH]$^+$; $t_R$=3.91 min (Method 3); Diastereomeric Ratio >95:5 ($^1$H NMR); [$\alpha_D$]=−28.26 (c=0.23, MeOH);

$^1$H NMR (B) (300 MHz, DMSO-$d_6$ 353 K) 8 ppm 8.40 (s, 2H), 7.16-7.39 (m, 5H), 7.13 (d, 1H), 7.08 (d, 1H), 6.89-6.95 (m, 1H), 6.97 (t, 1H), 5.85-6.08 (m, 1H), 4.26-4.45 (m, 1H), 3.91 (d, 2H), 3.66 (br. S., 2H), 3.47-3.63 (m, 3H), 3.27 (dd, 1H), 2.01-2.25 (m, 1H), 1.83-1.99 (m, 1H), 1.49-1.83 (m, 2H), 1.07-1.26 (m, 1H), 0.44-0.69 (m, 2H), 0.19-0.40 (m, 2H)

Example 32. 3,5-dichloro-4-((S)-2-(3-(cyclopropylmethoxy)-4-(difluoro-methoxy)phenyl)-2-((S)-3-(3-(dimethylcarbamoyl)benzylsulfonyl)-thiazolidine-2-carbonyloxy)ethyl)pyridine 1-oxide (295)
Scheme 38
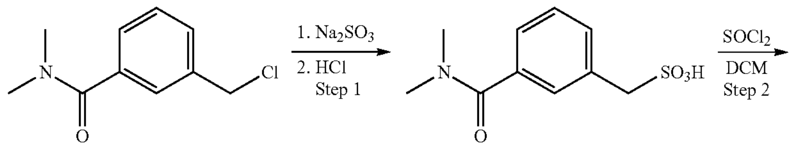
293
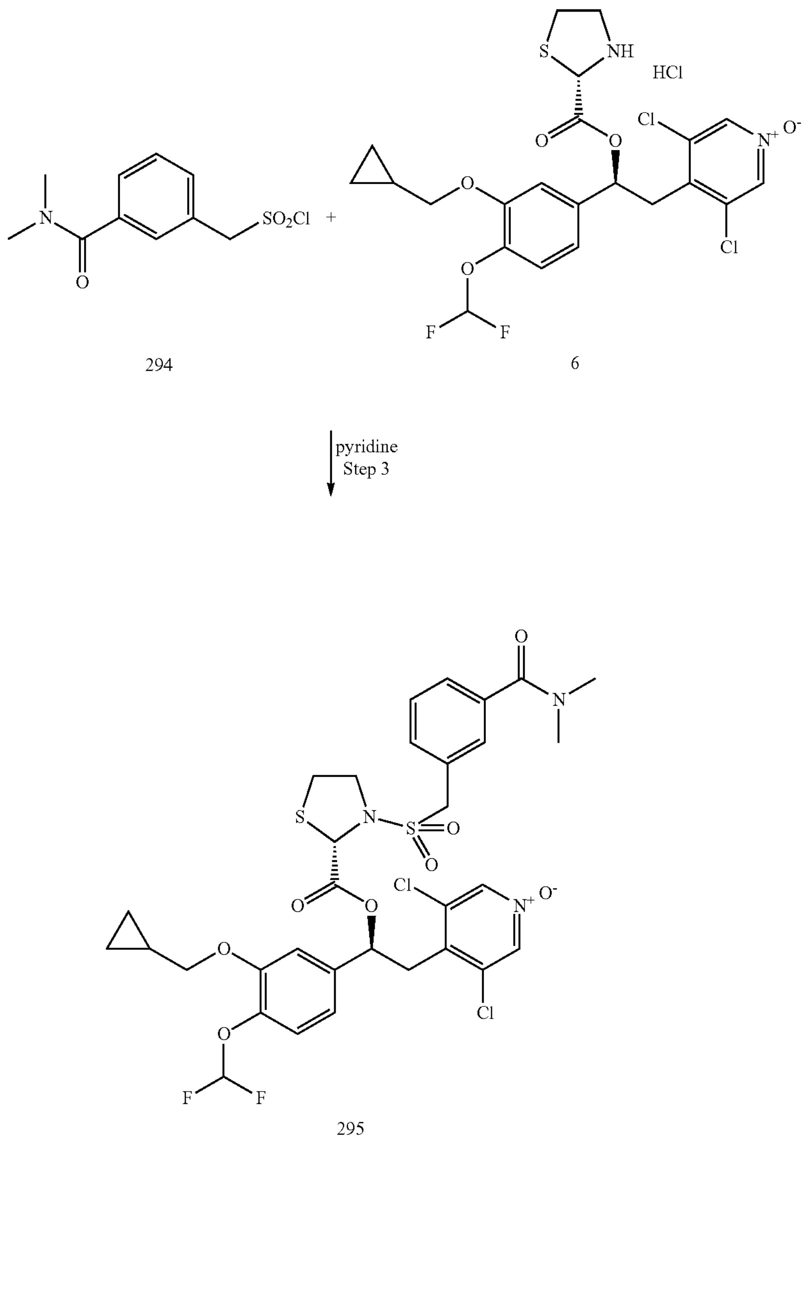
294
6
295

Step 1: (3-(dimethylcarbamoyl)phenyl)methanesulfonic acid (293)

To a suspension of 3-(chloromethyl)-N,N-dimethylbenzamide (1.15 g, 5.82 mmol) in water (30 ml), sodium sulfite (1.100 g, 8.73 mmol) was added, and the mixture was heated at 100° C. for 1 hour. The solvent was removed under vacuum, and the residue was suspended in MeOH (40 ml). HCl 4M in dioxane (5 ml) was added, and the insoluble inorganic salts were filtered off. The filtrate was evaporated to dryness and the residue was purified by several trituration with $CH_3CN$ affording (3-(dimethylcarbamoyl)phenyl) methanesulfonic acid (1.04 g, 4.27 mmol, 73.5% yield).

MS/ESI$^+$ 243.95 [MH]$^+$.

MS/ESI$^+$ 760.17 [MH]$^+$, $t_R$=3.78 min (Method 3); Diastereomeric Ratio >95:5 ($^1$H NMR); [$\alpha_D$]=−15.8 (c=3.0, DCM);

$^1$H NMR (B) (300 MHz, DMSO-d6) δ ppm 8.53 (s, 2H), 7.38-7.55 (m, 4H), 7.17 (d, 1H), 7.08 (d, 1H), 6.94 (dd, 1H), 7.07 (t, 1H), 6.00 (dd, 1H), 5.27 (s, 1H), 4.67 (d, 1H), 4.61 (d, 1H), 3.85-3.98 (m, 2H), 3.74-3.85 (m, 1H), 3.51-3.66 (m, 1H), 3.36-3.50 (m, 2H), 3.20-3.26 (m, 1H), 3.04-3.14 (m, 1H), 2.99 (br. S., 3H), 2.92 (br. S., 3H), 1.04-1.42 (m, 1H), 0.46-0.66 (m, 2H), 0.20-0.41 (m, 2H)

The compound listed in Table 23 was obtained according to analogous procedures as those described for Scheme 38, and by reacting the appropriate precursor, obtained as free base after basic treatment of hydrochloride salt with aqueous sat. $NaHCO_3$ followed by extraction with DCM. The purification step is described below.

TABLE 23

| | | | HPLC-MS characterization | | | | | | |
|---|---|---|---|---|---|---|---|---|---|
| Entry | Structure | SALT NAME | MS/ ESI$^+$ [MH]$^+$ | $t_R$/min Method 1, 2 or 3 | Diastereomeric ratio | $^1$H NMR | [α]$_D$ | Precursor | Purification Method |
| 296 | 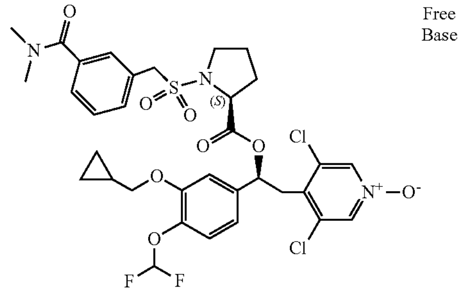 | Free Base | 742.30 | 3.61 (3) | >95:5 ($^1$H NMR B) | 11H NMR (300 MHz, DMSO-d6) δ ppm 8.54 (s, 2 H), 7.36-7.54 (m, 4 H), 7.16 (d, 1 H), 7.10 (d, 1 H), 6.94 (dd, 1 H), 7.06 (t, 1 H), 5.98 (dd, 1 H), 4.54 (d, 1 H), 4.46 (d, 1 H), 4.07 (dd, 1 H), 3.83-3.97 (m, 2 H), 3.42 (dd, 1 H), 3.27-3.36 (m, 2 H), 3.23 (dd, 1 H), 2.98 (br. S., 3 H), 2.91 (br. S., 3 H), 2.00-2.24 (m, 1 H), 1.57-1.95 (m, 3 H), 0.93-1.31 (m, 1 H), 0.45-0.64 (m, 2 H), 0.12-0.44 (m, 2 H) | −8.7 (c 0.33 in DCM) | Free Base of 3 | Preparative HPLC (Method 2) |

Step 2: (3-(dimethylcarbamoyl)phenyl)methanesulfonyl chloride (294)

To a suspension of (3-(dimethylcarbamoyl)phenyl)methanesulfonic acid (500 mg, 2.055 mmol) in DCM (40 ml), thionyl chloride (0.900 ml, 12.33 mmol) was added, and the resulting mixture was stirred at RT for 20 hours. The reaction mixture was poured into crushed ice and the organic phase was separated and dried over $Na_2SO4$. The solvent was removed under vacuum to afford desired product (357 mg, 1.364 mmol, 66% yield).

MS/ESI$^+$ 261.96 [MH]$^+$.

Step 3: 3,5-dichloro-4-((S)-2-(3-(cyclopropylmethoxy)-4-(difluoro-methoxy)phenyl)-2-((S)-3-(3-(dimethylcarbamoyl)benzylsulfonyl)-thiazolidine-2-carbonyloxy)ethyl)pyridine 1-oxide (295)

3,5-dichloro-4-((S)-2-(3-(cyclopropylmethoxy)-4-(difluoro-methoxy)phenyl)-2-((S)-3-(3-(dimethylcarbamoyl) benzylsulfonyl)-thiazolidine-2-carbonyloxy)ethyl)pyridine 1-oxide was obtained according to analogous procedure as that described for Scheme 16. (Example 8). It was purified by treatment with polymer supported isocyanate scavenger followed by preparative HPLC (Method 2) (20% yield);

Example 33. Synthesis of 3,5-dichloro-4-((S)-2-(4-(difluoromethoxy)-3-methoxyphenyl)-2-((S)-3-(3-(dimethylcarbamoyl)phenylsulfonyl)thiazolidine-2-carbonyloxy)ethyl)pyridine 1-oxide (299)

Scheme 39

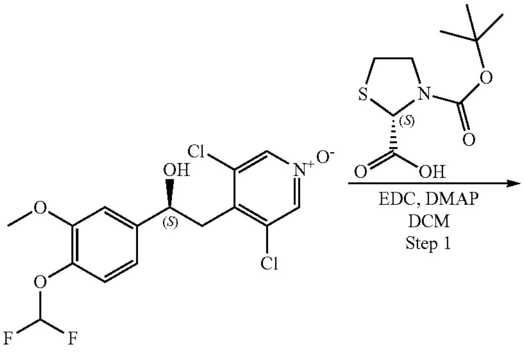

164

-continued

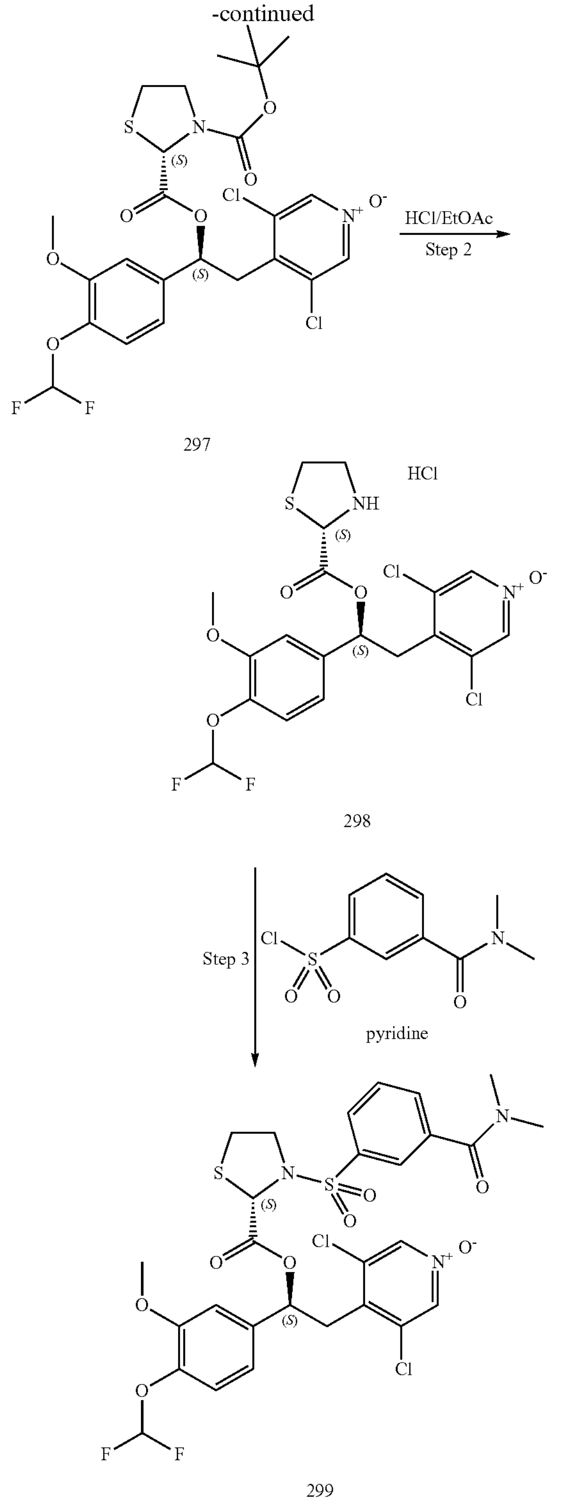

297

298

299

Step 1: 4-((S)-2-((S)-3-(tert-butoxycarbonyl)thiazolidine-2-carbonyloxy)-2-(4-(difluoromethoxy)-3-methoxyphenyl)ethyl)-3,5-dichloropyridine 1-oxide (297)

A solution of (S)-3-(tert-butoxycarbonyl)thiazolidine-2-carboxylic acid (479 mg, 2.052 mmol), (S)-3,5-dichloro-4-(2-(4-(difluoromethoxy)-3-methoxyphenyl)-2-hydroxyethyl)pyridine 1-oxide (164) (prepared according to analogous procedure as that described for Scheme 23), (650 mg, 1.710 mmol), EDC (492 mg, 2.56 mmol), and DMAP (313 mg, 2.56 mmol) in DCM (60 ml) was stirred at RT for 3 hours. The reaction mixture was diluted with DCM and washed twice with aqueous 1N HCl; the organic layer was dried over $Na_2SO_4$ and evaporated to dryness to afford the desired compound (quantitative yield). MS/ESI$^+$ 595.24 $[MH]^+$.

Step 2: 3,5-dichloro-4-((S)-2-(4-(difluoromethoxy)-3-methoxyphenyl)-2-((S)-thiazolidine-2-carbonyloxy)ethyl)pyridine 1-oxide hydrochloride (298)

To a solution of 4-((S)-2-((S)-3-(tert-butoxycarbonyl)thiazolidine-2-carbonyloxy)-2-(4-(difluoromethoxy)-3-methoxyphenyl)ethyl)-3,5-dichloropyridine 1-oxide (1.710 mmol) in EtOAc (10 ml) cooled at 0° C., HCl, 4M solution in EtOAc (10 ml, 40.0 mmol) was added, and the resulting mixture was stirred at RT for 2 hours. More HCl, 4M solution in EtOAc (10 ml, 40.0 mmol) was added, and the solution was stirred at 0° C. for additional 2 hours to reach complete conversion. The solution was concentrated to 10 ml under reduced pressure (bath temperature: 10° C.; partial pressure: 8 psi), then $iPr_2O$ (20 ml) was added and the product precipitated as a sticky gummy solid. After the solid was allowed to settle down, the solvent was removed by aspiration. The residue was dried in vacuo at RT to afford 3,5-dichloro-4-((S)-2-(4-(difluoromethoxy)-3-methoxyphenyl)-2-((S)-thiazolidine-2-carbonyloxy)ethyl)pyridine 1-oxide hydrochloride (0.890 g, 1.674 mmol, 97% yield), which was employed in the next step without any additional purification. MS/ESI$^+$ 494.97 [MH].

Step 3: 3,5-dichloro-4-((S)-2-(4-(difluoromethoxy)-3-methoxyphenyl)-2-((S)-3-(3-(dimethylcarbamoyl)phenylsulfonyl)thiazolidine-2-carbonyloxy)ethyl)pyridine 1-oxide (299)

To a solution of 3,5-dichloro-4-((S)-2-(4-(difluoromethoxy)-3-methoxyphenyl)-2-((S)-thiazolidine-2-carbonyloxy)ethyl)pyridine 1-oxide hydrochloride (350 mg, 0.658 mmol) in pyridine (6 ml) cooled at 0° C., a solution of 3-(dimethylcarbamoyl)benzene-1-sulfonyl chloride (245 mg, 0.987 mmol) in DCM (3 ml) was added drop-wise, and the reaction was stirred at 0° C. for 1 hour. The mixture was diluted with DCM (30 ml) and washed twice with aqueous 1N HCl; the organic layer was dried over $Na_2SO_4$ and the solvent was removed under vacuum. The residue was purified by preparative HPLC (Method 2) followed by flash chromatography on silica gel (DCM/MeOH=97/3) to afford 3,5-dichloro-4-((S)-2-(4-(difluoromethoxy)-3-methoxyphenyl)-2-((S)-3-(3-(dimethylcarbamoyl)phenylsulfonyl)thiazolidine-2-carbonyloxy)ethyl)pyridine 1-oxide (147 mg, 0.208 mmol, 31.6% yield); MS/ESI$^+$ 705.97 $[MH]^+$, $t_R$=3.28 min (Method 3); Diastereomeric Ratio=95:5 ($^1$H NMR); $[\alpha_D]$=−43.1 (c=0.57, DCM);

$^1$H NMR (300 MHz, DMSO-$d_6$) δ ppm 8.57 (s, 2H), 7.94 (dt, 1H), 7.90 (t, 1H), 7.77 (dt, 1H), 7.71 (t, 1H), 7.18 (d, 1H), 7.15 (d, 1H), 6.97 (dd, 1H), 7.07 (t, 1H), 6.04 (dd, 1H), 5.54 (s, 1H), 3.84 (s, 3H), 3.75-3.94 (m, 1H), 3.66 (dt, 1H), 3.48 (dd, 1H), 3.33 (dd, 1H), 3.02 (br. S., 3H), 2.98 (dd, 1H), 2.90 (br. S., 3H), 2.66 (dt, 1H)

The compounds listed in Table 24 were prepared according to analogous procedures as those described for Scheme 39 and by reacting the appropriate alcohol listed with commercial suitable reagents, followed by appropriate purification step as below reported. Compound 303 was obtained as second eluted diastereoisomer from a mixture of diastereoisomers

TABLE 24

| Entry | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Alcohol | Purification Method |
|---|---|---|---|---|---|---|---|---|---|
| 300 | 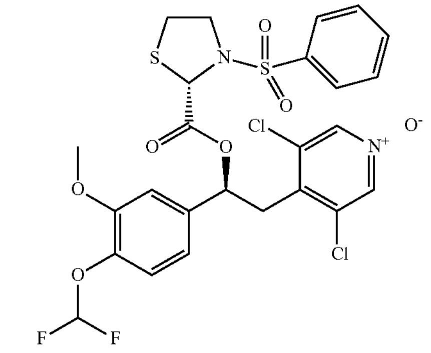 | Free Base | 653.03 | 3.69 (3) | >95:5 ($^1$H NMR) | $^1$H NMR (300 MHz, DMSO-d6) δ ppm 8.59 (s, 2H), 7.83-7.93 (m, 2 H), 7.71-7.81 (m, 0 H), 7.58-7.71 (m, 2 H), 7.19 (d, 1 H), 7.15 (d, 1 H), 6.97 (dd, 1 H), 7.08 (t, 1 H), 6.04 (dd, 1 H), 5.44 (s, 1 H), 3.85 (s, 3 H), 3.81 (dt, 1 H), 3.65 (dt, 1 H), 3.48 (dd, 1 H), 3.32 (dd, 1 H), 2.99 (dt, 1 H), 2.66 (dt, 1 H) | −51.1 (c = 0.52, DCM) | 164 | Preparative HPLC (Method 2) |
| 301 | 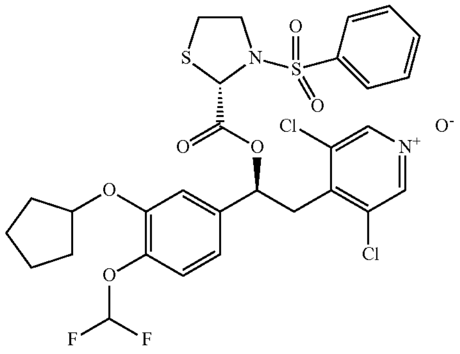 | Free Base | 689.13 | 4.37 (3) | >95:5 ($^1$H NMR) | $^1$H NMR (300 MHz, DMSO-d6) δ ppm 8.58 (s, 2 H), 7.84-7.97 (m, 2 H), 7.72-7.83 (m, 1 H), 7.59-7.70 (m, 2 H), 7.17 (d, 1 H), 7.08 (d, 1 H), 6.94 (dd, 1 H), 7.00 (t, 1 H), 6.02 (dd, 1 H), 5.46 (s, 1 H), 4.69-5.06 (m, 1 H), 3.82 (dt, 1 H), 3.64 (dt, 1 H), 3.46 (dd, 1 H), 3.31 (dd, 1 H), 2.98 (dt, 1 H), 2.65 (dt, 1 H), 1.42-2.03 (m, 8 H) | −43.0 (c = 0.53; DCM) | 165 | Preparative HPLC (Method 2) |

TABLE 24-continued

| Entry | Structure | SALT NAME | HPLC-MS characterization MS/ESI$^+$ [MH]$^+$ | $t_R$/min Method 1, 2 or 3 | Diastereomeric ratio | $^1$H NMR | $[\alpha]_D$ | Alcohol | Purification Method |
|---|---|---|---|---|---|---|---|---|---|
| 302 | 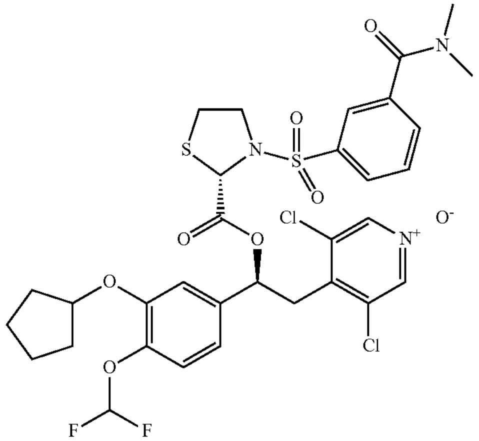 | Free Base | 760.17 | 3.98 (3) | >95:5 ($^1$H NMR) | $^1$H NMR (300 MHz, DMSO-d6) δ ppm 8.57 (s, 2 H), 7.95 (dt, 1 H), 7.91 (t, 1 H), 7.77 (dt, 1 H), 7.72 (td, 1 H), 7.16 (d, 1 H), 7.08 (d, 1 H), 6.94 (dd, 1 H), 6.99 (t, 1 H), 6.02 (dd, 1 H), 5.57 (s, 1 H), 4.82-5.00 (m, 1 H), 3.87 (dt, 1 H), 3.65 (dt, 1 H), 3.46 (dd, 1 H), 3.32 (dd, 1 H), 3.03 (br. S., 3 H), 2.93-3.01 (m, 1 H), 2.90 (br. S., 3 H), 2.65 (dt, 1 H), 1.38-2.04 (m, 8 H) | −42.7 (c = 0.50; DCM) | 165 | Preparative HPLC (Method 2) |
| 303 | 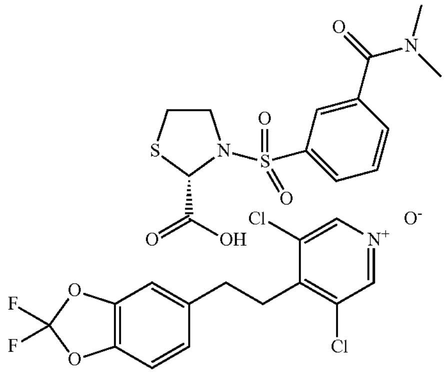 | Free Base | 689.97 | 3.59 (3) | 95:5 ($^1$H NMR) | $^1$H NMR (300 MHz, DMSO-$d_6$) δ ppm 8.56 (s, 2 H), 7.94 (dt, 1 H), 7.89 (t, 1 H), 7.77 (dt, 1 H), 7.71 (t, 1 H), 7.51 (d, 1 H), 7.43 (d, 1 H), 7.23 (dd, 1 H), 6.04 (dd, 1 H), 5.53 (s, 1 H), 3.83 (dt, 1 H), 3.65 (dt, 1 H), 3.48 (dd, 1 H), 3.31 (dd, 1 H), 3.02 (br. S., 3 H), 2.93-3.01 (m, 1 H), 2.90 (br. S., 3 H), 2.67 (dt, 1 H) | −48.68 (c = 0.49, DCM) | 172 | Preparative HPLC (Method 2) |

Example 34. Synthesis of 3,5-dichloro-4-((S)-2-(4-(difluoromethoxy)-3-methoxyphenyl)-2-((S)-1-(phenylsulfonyl)pyrrolidine-2-carbonyloxy)ethyl)pyridine 1-oxide (Compound 305)

Scheme 40

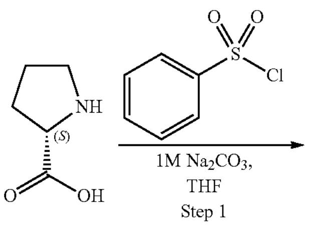

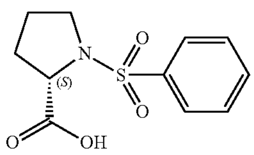

+

304

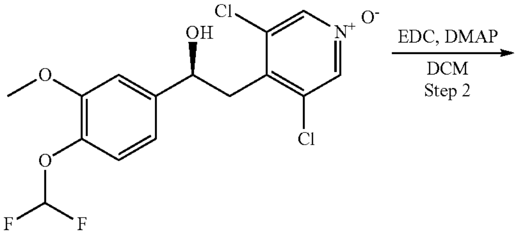

164

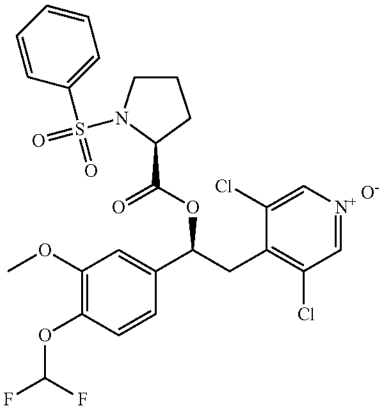

305

Step 1: (S)-1-(phenylsulfonyl)pyrrolidine-2-carboxylic acid (304)

Benzenesulfonyl chloride (4.03 ml, 31.3 mmol) was added to a cooled suspension (0° C.) of (S)-pyrrolidine-2-carboxylic acid (3 g, 26.1 mmol) in THF (50 ml) and aqueous 1M $Na_2CO_3$ (60 ml, 60.0 mmol), and the reaction was stirred at 0° C. for 1 hour. The mixture was extracted twice with $Et_2O$, and the organic layers were discarded. The aqueous phase was cautiously acidified by addition of solid $KHSO_4$ to pH=3 and extracted twice with EtOAc. The combined organic layers were dried over $Na_2SO_4$ and evaporated to dryness to afford (S)-1-(phenylsulfonyl)pyrrolidine-2-carboxylic acid (6.1 g, 23.89 mmol, 92% yield). MS/ESI$^+$ 256.10 [MH]$^+$ Step 2: 3,5-dichloro-4-((S)-2-(4-(difluoromethoxy)-3-methoxyphenyl)-2-((S)-1-(phenylsulfonyl)pyrrolidine-2-carbonyloxy)ethyl)pyridine 1-oxide (305)

A mixture of (S)-3,5-dichloro-4-(2-(4-(difluoromethoxy)-3-methoxyphenyl)-2-hydroxyethyl)pyridine 1-oxide (164) (55 mg, 0.145 mmol), (S)-1-(phenylsulfonyl)pyrrolidine-2-carboxylic acid (111 mg, 0.434 mmol), EDC (83 mg, 0.434 mmol), and DMAP (53.0 mg, 0.434 mmol) in DCM (20 ml) was stirred at RT for 3 hours. The reaction mixture was washed twice with aqueous 1N HCl and then with aqueous 1M $K_2CO_3$; the organic layer was dried over $Na_2SO_4$ and the solvent was removed under reduced pressure. The residue was purified by preparative HPLC (Method 2) to afford 3,5-dichloro-4-((S)-2-(4-(difluoromethoxy)-3-methoxyphenyl)-2-((S)-1-(phenylsulfonyl)pyrrolidine-2-carbonyloxy) ethyl)pyridine 1-oxide (45 mg, 0.073 mmol, 50.4% yield); MS/ESI$^+$ 617.15 [MH]$^+$, $t_R$=3.71 min (Method 3); Diastereomeric Ratio >95:5 ($^1$H NMR); [$\alpha_D$]=−60.3 (c=0.39, DCM);

$^1$H NMR (B) (300 MHz, DMSO-$d_6$) δ ppm 8.61 (s, 2H), 7.75-7.85 (m, 2H), 7.69-7.76 (m, 1H), 7.56-7.69 (m, 2H), 7.19 (d, 1H), 7.18 (d, 1H), 7.00 (dd, 1H), 7.07 (t, 1H), 6.05 (dd, 1H), 4.16 (dd, 1H), 3.86 (s, 3H), 3.49 (dd, 1H), 3.39-3.44 (m, 1H), 3.29 (dd, 1H), 3.09-3.23 (m, 1H), 1.83-2.10 (m, 1H), 1.59-1.82 (m, 2H), 1.44-1.59 (m, 1H)

The compounds listed in Table 25 were prepared according to analogous procedures as those described for Scheme 40 using commercial suitable reagents and by reacting the appropriate alcohol listed, followed by appropriate purification step as below reported. Compound 315 was obtained as second eluted diastereoisomer from a mixture of diastereoisomers

TABLE 25

| Entry | Structure | SALT NAME | HPLC-MS characterization MS/ESI+ [MH]+ | tR/min Method 1, 2 or 3 | Diastereomeric ratio | 1H NMR | [α]D | Alcohol Precursor | Purification Method |
|---|---|---|---|---|---|---|---|---|---|
| 306 | 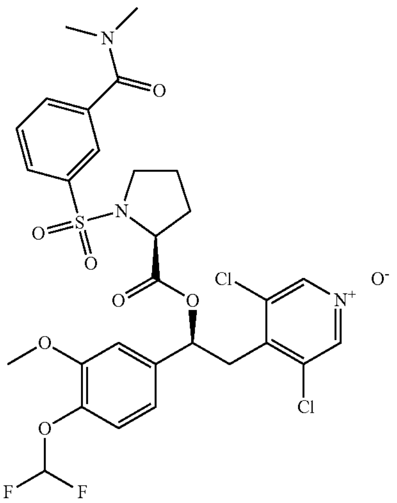 | Free Base | 688.22 | 3.24 (3) | >95:5 (1H NMR) | 1H NMR (300 MHz, DMSO-d6) δ ppm 8.58 (s, 2 H), 7.84 (dt, 1 H), 7.64-7.80 (m, 3 H), 7.13-7.26 (m, 2 H), 7.00 (dd, 1 H), 7.07 (t, 1 H), 6.05 (dd, 1 H), 4.21 (dd, 1 H), 3.86 (s, 3 H), 3.50 (dd, 1 H), 3.34-3.44 (m, 1 H), 3.29 (dd, 1 H), 3.20 (dt, 1 H), 3.02 (br. S., 3 H), 2.90 (br. S., 3 H), 1.89-2.13 (m, 1 H), 1.50-1.77 (m, 3 H) | −56.63 c = 0.47, DCM | 164 | Preparative HPLC (Method 2) |
| 307 | 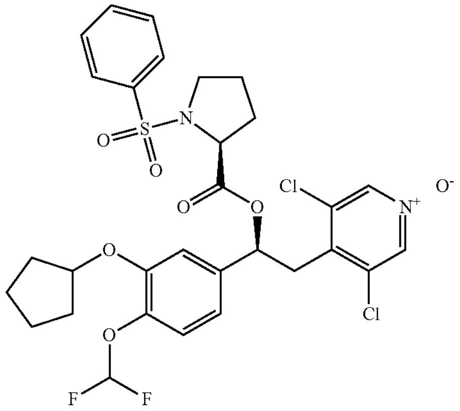 | Free Base | 671.24 | 4.32 (3) | 80:20 (1H NMR) | 1H NMR (300 MHz, DMSO-d6) δ ppm 8.60 (s, 2 H), 7.58-7.81 (m, 5 H), 7.17 (d, 1 H), 7.11 (d, 1 H), 6.97 (dd, 1 H), 7.00 (t, 1 H), 6.02 (dd, 1 H), 4.75-5.06 (m, 1 H), 3.99-4.31 (m, 1 H), 3.36-3.55 (m, 2 H), 3.06-3.27 (m, 2 H), 1.81-1.97 (m, 3 H), 1.47-1.79 (m, 9 H) | −56.4 c = 0.53, DCM | 165 | Preparative HPLC (Method 2) |
| 308 | 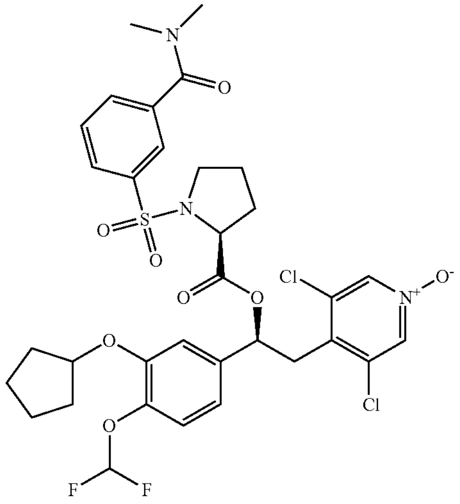 [SMILES: CN(C)C(=O)c1cccc(S(=O)(=O)N2CCC[C@H]2C(=O)O[C@@H](Cc2c(Cl)c[n+]([O-])cc2Cl)c2ccc(OC(F)F)c(OC3CCCC3)c2)c1] | Free Base | 741.12 | 3.86 (3) | >95:5 (1H NMR) | 1H NMR (300 MHz, DMSO-d6) δ ppm 8.57 (s, 2 H), 7.84 (dt, 1 H), 7.72-7.80 (m, 2 H), 7.71 (t, 1 H), 7.17 (d, 1 H), 7.11 (d, 1 H), 6.97 (dd, 1 H), 6.99 (t, 1 H), 6.02 (dd, 1 H), 4.93 (tt, 1 H), 4.22 (dd, 1 H), 3.48 (dd, 1 H), 3.15-3.38 (m, 3 H), 3.02 (br. S., 3 H), 2.90 (br. S., 3 H), 1.42- 2.10 (m, 12 H) | −55.6 (c = 0.49, DCM) | 165 | Preparative HPLC (Method 2) |

TABLE 25-continued

| Entry | Structure | SALT NAME | HPLC-MS characterization MS/ESI+ [MH]+ | $t_R$/min Method 1, 2 or 3 | Diastereomeric ratio | $^1$H NMR | $[\alpha]_D$ | Alcohol Precursor | Purification Method |
|---|---|---|---|---|---|---|---|---|---|
| 309 | 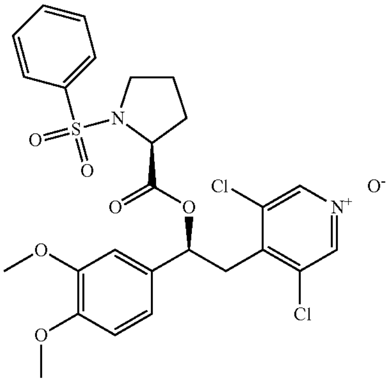 | Free Base | 581.15 | 3.14 (3) | >95:5 ($^1$H NMR) | $^1$H NMR (300 MHz, DMSO-d6) δ ppm 8.60 (s, 2 H), 7.74-7.83 (m, 2 H), 7.69-7.74 (m, 1 H), 7.56-7.69 (m, 2 H), 6.98 (d, 1 H), 6.95 (d, 1 H), 6.91 (dd, 1 H), 6.02 (dd, 1 H), 4.14 (dd, 1 H), 3.77 (s, 3 H), 3.76 (s, 3 H), 3.50 (dd, 1 H), 3.33-3.42 (m, 1 H), 3.26 (dd, 1 H), 3.17 (dt, 1 H), 1.77-2.03 (m, 1 H), 1.59-1.77 (m, 2 H), 1.36-1.59 (m, 1 H) | −71.5 (c = 0.46, DCM) | 170 | Preparative HPLC (Method 2) |
| 310 | 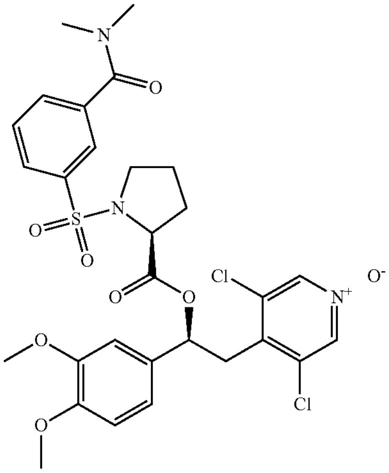 | Free Base | 652.25 | 2.74 (3) | >95:5 ($^1$H NMR) | $^1$H NMR (300 MHz, DMSO-d6) δ ppm 8.57 (s, 2 H), 7.83 (dt, 1 H), 7.60-7.80 (m, 3 H), 6.98 (d, 1 H), 6.95 (d, 1 H), 6.91 (dd, 1 H), 6.02 (dd, 1 H), 4.18 (dd, 1 H), 3.77 (s, 3 H), 3.76 (s, 3 H), 3.50 (dd, 1 H), 3.31-3.42 (m, 1 H), 3.26 (dd, 1 H), 3.12-3.22 (m, 1 H), 3.02 (br. S., 3 H), 2.90 (br. S., 3 H), 1.80-2.06 (m, 1 H), 1.41-1.80 (m, 3 H) | −70.4 (c = 0.85, DCM) | 170 | Preparative HPLC (Method 2) |
| 311 | 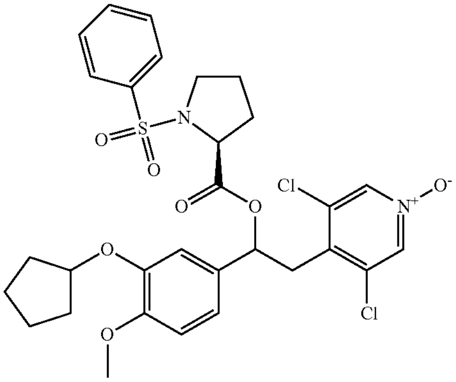 [SMILES: COc1ccc(C(Cc2c(Cl)c[n+]([O-])cc2Cl)OC(=O)[C@@H]2CCCN2S(=O)(=O)c2ccccc2)cc1OC1CCCC1] | Free Base | 635.23 | 3.84, 3.88 (3) | 1:1 ($^1$H NMR) | | | 157 | Preparative HPLC (Method 2) |

TABLE 25-continued
| Entry | Structure | SALT NAME | HPLC-MS characterization MS/ESI+ [MH]+ | $t_R$/min Method 1, 2 or 3 | Diastereomeric ratio | $^1$H NMR | $[\alpha]_D$ | Alcohol Precursor | Purification Method |
|---|---|---|---|---|---|---|---|---|---|
| 312 | 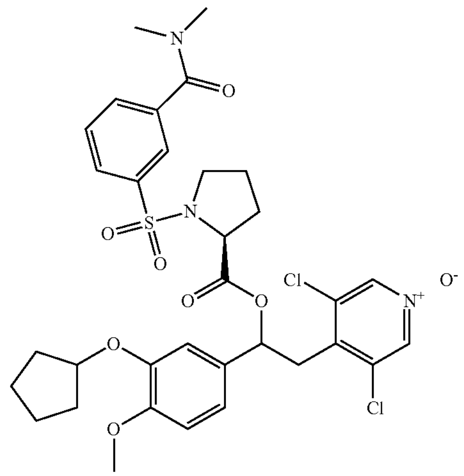 | Free Base | 706.16 | 3.41, 3.45 (3) | 1:1 ($^1$H NMR) | | | 157 | Preparative HPLC (Method 2) |
| 313 | 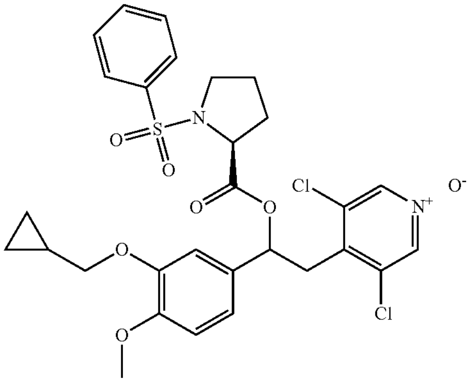 | Free Base | 621.2 | 3.63 (3) | 6:4 ($^1$H NMR) | | | 156 | Preparative HPLC (Method 2) |
| 314 | 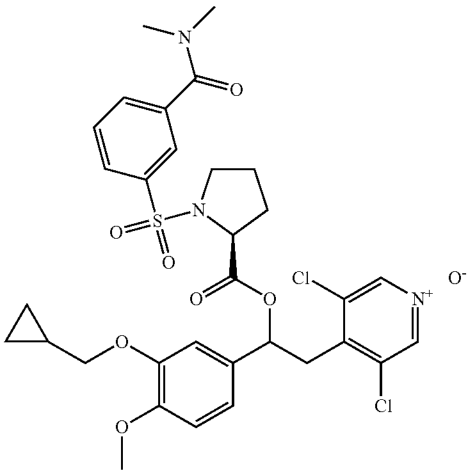 | Free Base | 692.28 | 3.23 (3) | 6:4 ($^1$H NMR) | | | 156 | Preparative HPLC (Method 2) |

TABLE 25-continued

| Entry | Structure | SALT NAME | HPLC-MS characterization MS/ ESI+ [MH]+ | tR/min Method 1, 2 or 3 | Dia-stereo-meric ratio | 1H NMR | [α]D | Alcohol Pre-cursor | Purification Method |
|---|---|---|---|---|---|---|---|---|---|
| 315 | 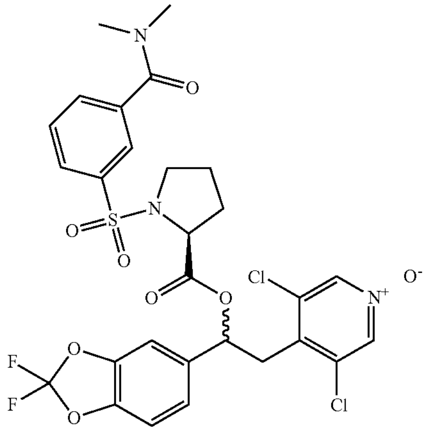 | Free Base | 672.13 | 3.42; 3.47 (3) | 5:95 (1H NMR) | 1H NMR (300 MHz, DMSO-d6) δ ppm 8.57 (s, 2 H), 7.83 (dt, 1 H), 7.72-7.79 (m, 2 H), 7.70 (td, 1 H), 7.54 (d, 1 H), 7.43 (d, 1 H), 7.26 (dd, 1 H), 6.04 (dd, 1 H), 4.19 (dd, 1 H), 3.49 (dd, 1 H), 3.32-3.44 (m, 1 H), 3.28 (dd, 1 H), 3.19 (dt, 1 H), 3.02 (br. S., 3 H), 2.90 (br. S., 3 H), 1.90-2.07 (m, 1 H), 1.46-1.81 (m, 3 H) | −67.58 (c = 0.47, DCM) | 172 | Preparative HPLC (Method 2) |
| 316 | 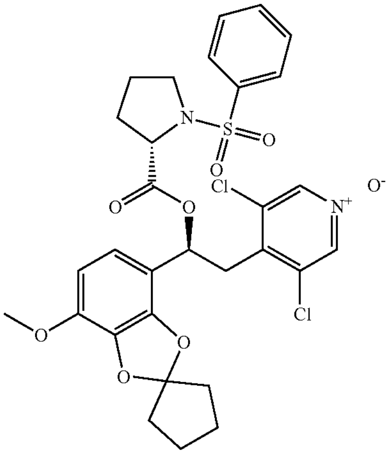 | Free Base | 649.35 | 3.97 (3) | 1:1 (1H NMR) | | | 173 | SCX cartridge followed by preparatibe HPLC (Method 2) |
| 317 | 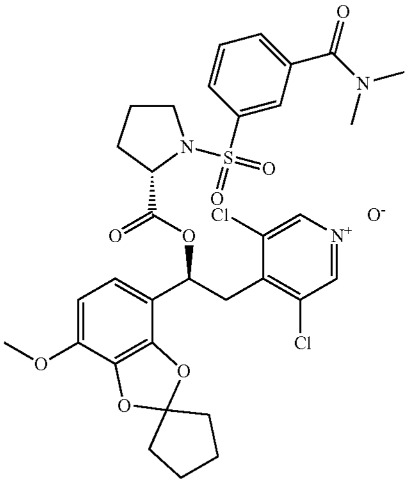 | Free Base | 720.43 | 3.56 (3) | 1:1 (1H NMR) | | | 173 | SCX cartridge followed by preparatibe HPLC (Method 2) |

Example 35. 3,5-dichloro-4-(2-(3-(cyclopropylmethoxy)-4-methoxyphenyl)-2-((S)-3-(3-(dimethylcarbamoyl)phenylsulfonyl)thiazolidine-2-carbonyloxy)ethyl)pyridine 1-oxide (320)

Scheme 41

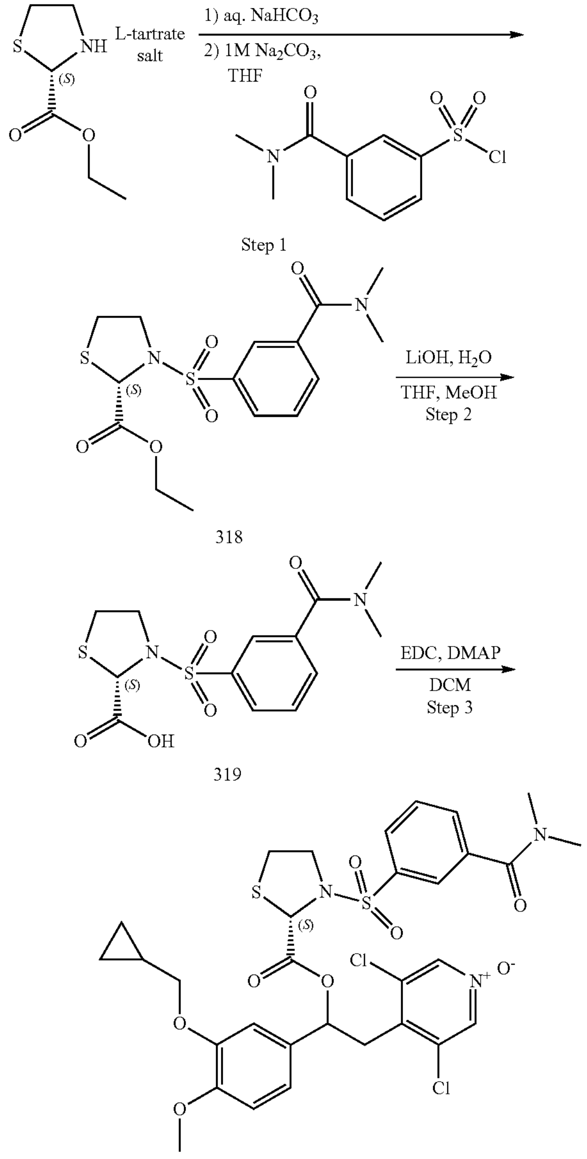

318

319

320

Step 1: (S)-ethyl 3-(3-(dimethylcarbamoyl)phenylsulfonyl)thiazolidine-2-carboxylate (318)

(S)-ethyl thiazolidine-2-carboxylate (2R,3R)-2,3-dihydroxysuccinate (prepared as described in Bull. Korean Chem. Soc., 2010, 31, 2709, which is incorporated herein by reference in its entirety), (4 g, 12.85 mmol) was poured into a separation funnel containing aqueous sat. $NaHCO_3$ (50 ml, 55.0 mmol) and $Et_2O$ (100.0 ml), previously cooled to 0° C. in an ice bath. The mixture was shaken to dissolution of the solid; the phases were separated, and the aqueous layer was extracted again with $Et_2O$ (100 ml). The combined organic layers were dried over $Na_2SO_4$ and evaporated to dryness without heating. The residue was dissolved in THF (50 ml), the solution was cooled to 0° C., and aqueous sat. $NaHCO_3$ (50 ml, 55.0 mmol) was added. A solution of 3-(dimethylcarbamoyl)benzene-1-sulfonyl chloride (3.18 g, 12.85 mmol) in THF (50 ml) was added to the biphasic mixture at 0° C. under vigorous stirring, and the reaction was left at RT for 4 hours. The mixture was partitioned between EtOAc and water, and the aqueous layer was extracted with EtOAc. The combined organic layers were washed with aqueous 1N HCl and brine, dried over $Na_2SO_4$ and evaporated to dryness to afford (S)-ethyl 3-(3-(dimethylcarbamoyl)phenylsulfonyl)thiazolidine-2-carboxylate (3.79 g, 10.18 mmol, 79% yield); MS/ESI$^+$ 373.04 [MH]$^+$ Step 2: (S)-3-(3-(dimethylcarbamoyl)phenylsulfonyl)thiazolidine-2-carboxylic acid (319)

(S)-ethyl 3-(3-(dimethylcarbamoyl)phenylsulfonyl)thiazolidine-2-carboxylate (3.79 g, 10.18 mmol) was dissolved in mixture of MeOH (30 ml), THF (30.0 ml), and water (30.0 ml). LiOH (0.487 g, 20.35 mmol) was added, and the reaction was stirred at RT for 30 minutes. The mixture was acidified with aqueous 1N HCl (pH=1), diluted with water, and extracted twice with EtOAc. The combined organic layers were dried over $Na_2SO_4$ and evaporated to dryness. The residue was triturated with a mixture of $Et_2O$ (15 ml) and petroleum ether (25 ml) yielding after filtration (S)-3-(3-(dimethylcarbamoyl)phenylsulfonyl)thiazolidine-2-carboxylic acid (1.86 g, 5.40 mmol, 53.1% yield); MS/ESI$^+$ 344.94 [MH]$^+$; [$\alpha_D$]=−36.1 (c=1.67, MeOH). To determine the enantiomeric purity, this intermediate was coupled with alcohol 1 (EDC, DMAP, DCM) to afford compound 52: Diastereomeric Ratio=95:5.

Step 3: 3,5-dichloro-4-(2-(3-(cyclopropylmethoxy)-4-methoxyphenyl)-2-((S)-3-(3-(dimethylcarbamoyl)phenylsulfonyl)thiazolidine-2-carbonyloxy)ethyl)pyridine 1-oxide (320)

To a solution of 3,5-dichloro-4-(2-(3-(cyclopropylmethoxy)-4-methoxyphenyl)-2-hydroxyethyl)pyridine 1-oxide (156) (160 mg, 0.416 mmol), EDC (160 mg, 0.833 mmol), and DMAP (102 mg, 0.833 mmol) in DCM (50 ml), (S)-3-(3-(dimethylcarbamoyl)phenylsulfonyl)thiazolidine-2-carboxylic acid (172 mg, 0.500 mmol) was added, and the resulting mixture was stirred at RT for 24 hours. The reaction mixture was washed twice with aqueous 1N HCl, and the organic layer was dried over $Na_2SO_4$. The solvent was removed under vacuum, and the residue was purified by preparative HPLC (Method 2) to afford 3,5-dichloro-4-(2-(3-(cyclopropylmethoxy)-4-methoxyphenyl)-2-((S)-3-(3-(dimethylcarbamoyl)phenylsulfonyl)thiazolidine-2-carbonyloxy)ethyl)pyridine 1-oxide (122 mg, 0.172 mmol, 41% yield); MS/ESI$^+$ 710.25 [MH]$^+$, $t_R$=3.25 min (Method 3); Diastereomeric Ratio 1:1 ($^1$H NMR).

The compounds listed in Table 26 were prepared according to Scheme 41 using commercial suitable reagents and by reacting the appropriate alcohol listed, followed by appropriate purification step as below reported. The enantiomeric purity of intermediate obtained using benzenesulfonylchloride was determined as described above in Step 2 (reference compound: 89; Diastereomeric Ratio=92:8)

TABLE 26
| Entry | Structure | SALT NAME | HPLC-MS characterization MS/ESI+ [MH]+ | $t_R$/min Method 1, 2 or 3 | Diastereomeric ratio | $^1$H NMR | $[\alpha]_D$ | Alcohol Precursor | Purification Method |
|---|---|---|---|---|---|---|---|---|---|
| 321 | 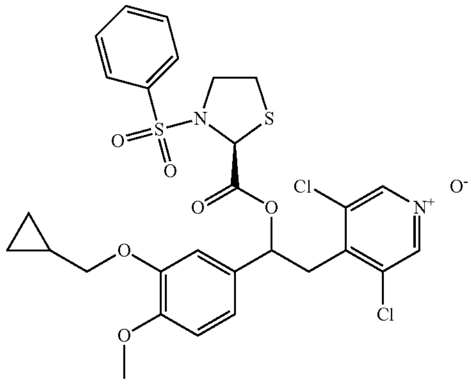 | Free Base | 639.08 | 3.66, 3.69 (3) | 1:1 ($^1$H NMR) | | | 156 | Preparative HPLC (Method 2) |
| 322 | 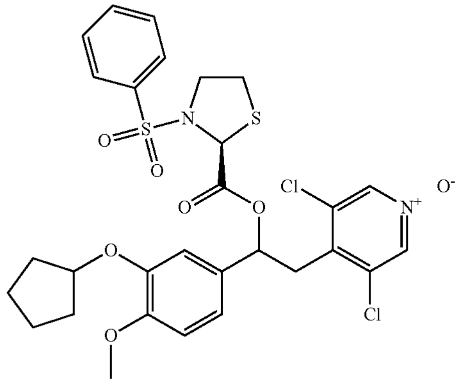 | Free Base | 653.08 | 3.91, 3.96 (3) | 1:1 ($^1$H NMR) | | | 157 | Preparative HPLC (Method 2) |
| 323 | 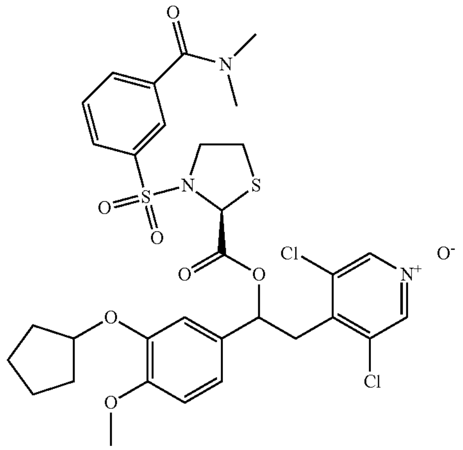 | Free Base | 724.26 | 3.48, 3.52 (3) | 1:1 ($^1$H NMR) | | | 157 | Preparative HPLC (Method 2) |

TABLE 26-continued

| Entry | Structure | SALT NAME | HPLC-MS characterization MS/ ESI+ [MH]+ | tR/ min Method 1, 2 or 3 | Diastereomeric ratio | $^1$H NMR | $[\alpha]_D$ | Alcohol Precursor | Purification Method |
|---|---|---|---|---|---|---|---|---|---|
| 324 | 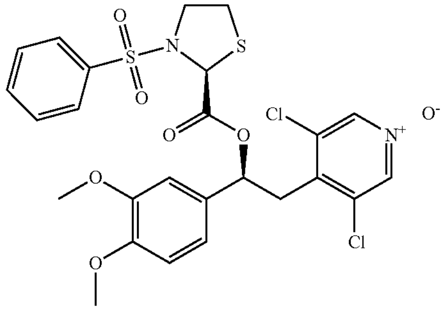 | Free Base | 599.22 | 3.23 (3) | >95:5 ($^1$H NMR) | 1H NMR (300 MHz, DMSO-d6) δ ppm 8.58 (s, 2 H), 7.83-7.92 (m, 2 H), 7.72-7.81 (m, 1 H), 7.60-7.71 (m, 2 H), 6.95 (d, 1 H), 6.95 (d, 1 H), 6.88 (dd, 1 H), 6.00 (dd, 1 H), 5.41 (s, 1 H), 3.78-3.86 (m, 1H), 3.77 (s, 3 H), 3.75 (s, 3H), 3.57-3.71 (m, 1 H), 3.48 (dd, 1 H), 3.30 (d, 1 H), 2.88-3.14 (m, 1 H), 2.64 (dt, 1 H) | −60.50 (c = 0.4, DCM) | 170 | Preparative HPLC (Method 2) |
| 325 | 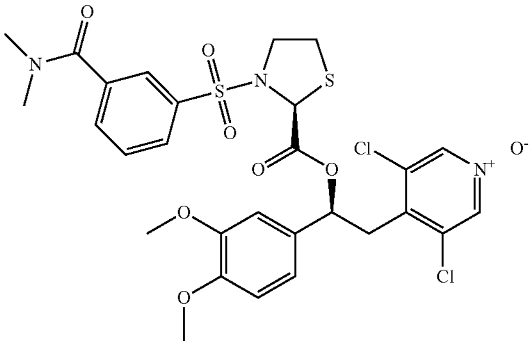 | Free Base | 670.17 | 2.83 (3) | 95:5 ($^1$H NMR) | $^1$H NMR (300 MHz, DMSO-$d_6$) δ ppm 8.56 (s, 2 H), 7.93 (dt, 1 H), 7.90 (t, 1 H), 7.77 (dt, 1 H), 7.71 (t, 1 H), 6.95 (d, 1 H), 6.94 (d, 1 H), 6.88 (dd, 1 H), 6.00 (dd, 1 H), 5.51 (s, 1 H), 3.81-3.96 (m, 1 H), 3.76 (s, 3 H), 3.75 (s, 3 H), 3.58-3.70 (m, 1 H), 3.48 (dd, 1 H), 3.31 (dd, 1 H), 3.02 (br.S., 3 H), 2.92-3.02 (m, 1 H), 2.89 (br. S., 3 H), 2.64 (dt, 1 H) | −50.25 (c = 0.40, DCM) | 170 | Preparative HPLC (Method 2) |

TABLE 26-continued

| Entry | Structure | SALT NAME | HPLC-MS characterization MS/ESI+ [MH]+ | tR/min Method 1, 2 or 3 | Diastereomeric ratio | $^1H$ NMR | $[\alpha]_D$ | Alcohol Precursor | Purification Method |
|---|---|---|---|---|---|---|---|---|---|
| 326 | 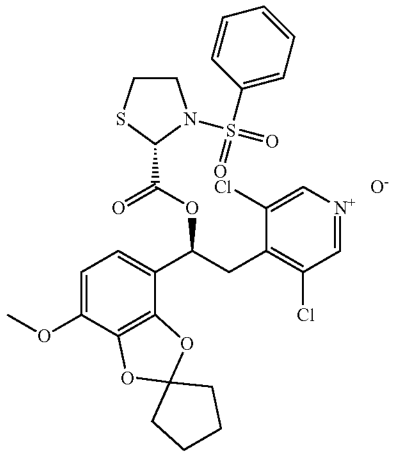 | Free Base | 667.31 | 4.05 (3) | 1:1 ($^1H$ NMR) | | | 174 | SCX cartridge followed by preparative HPLC (Method 2) |
| 327 | 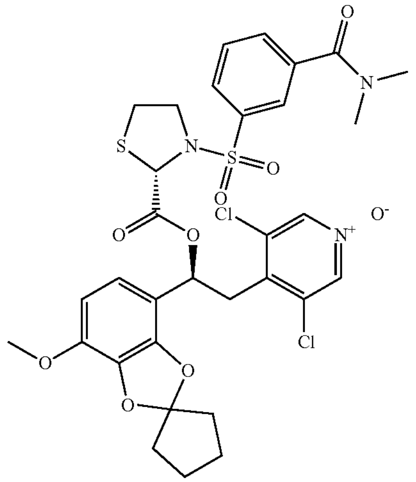 | Free Base | 738.39 | 3.63 | 1:1 ($^1H$ NMR) | | | 174 | SCX cartridge followed by preparative HPLC (Method 2) |

Pharmacological Activity of the Compounds of the Invention

Example 15. In Vitro Determination of PDE4 Inhibitory Activity in the Cell Free Assay PDE4 activity was determined in U937 human monocytic supernatants cells lysate. Cells were cultured, harvested and supernatant fraction prepared essentially as described in Torphy T J, et al., J. Pharmacol. Exp. Ther., 1992; 263:1195-1205, which is incorporated herein by reference in its entirety. U937 cells (Cell Bank, Interlab Cell Line Collection, ICLC HTL94002) were grown at 37° C., 5% $CO_2$ in RPMI 1640 with GlutaMAX™-I medium supplemented with 10% fetal bovine serum and 100 μg/ml Pen-strep (Gibco). Cells were harvested and washed twice by centrifugation (150×g, 8 minutes) in cold PBS. Washed cells were resuspended in cold Krebs-Ringer-Henseleit buffer at a final concentration $20\times10^6$ cells/ml and sonicated. After centrifugation at 15000×g for 20 min, the supernatants were pooled, divided in aliquots and stored at −80° C.

PDE4 activity was determined in cells supernatants by assaying cAMP disappearance from the incubation mixtures. The concentration of the test compounds ranged between $10^{-12}$ M and $10^{-6}$ M. Reactions were stopped by enzyme heat inactivation (2.5 minutes at 100° C.), and residual cAMP content was determined using the 'LANCE cAMP Assay' from PerkinElmer following the providers instructions. The results of the tested compounds, representatives of the invention, expressed as mean±standard deviation of the nM concentration of the test compound producing 50% inhibition of cAMP disappearance ($IC_{50}$) are shown in the following Table:

| Compound No. | PDE4 inhibition |
|---|---|
| 209, 234, 238, 239, 240, 241, 242, 227, 228, 206, 207, 269, 198, 271, 295, 210, 186, 244, 185, 281, 232, 218, 219, 220, 309, 310, 287, 288, 305, 283, 250, 314, 301, 302, 224, 300, 287, 288, 226, 299, 312, 285, 308, 189, 264, 278, 225, 191, 256, 274, 266, 275, 291, 195, 190, 237, 15, 17, 30, 31, 32, 33, 34, 38, 42, 52, 53, 54, 55, 56, 58, 64, 65, 66, 73, 75, 77, 78, 82, 84, 85, 88, 90, 91, 93, 94, 97, 100, 101, 102, 106, 107, 109, 110, 114, 118, 119, 121, 123, 124, 125, 126, 127, 128, 129, 130, 131, 132, 135, 137, 138, 139, 141, 143, 150, 151 | ++++ |
| 200, 201, 202, 203, 204, 205, 208, 229, 263, 284, 307, 311, 257, 292, 258, 199, 281, 19, 49, 57, 59, 62, 63, 67, 68, 69, 70, 71, 72, 74, 76, 79, 80, 81, 83, 86, 89, 103, 104, 105, 108, 136, 144 | +++ |
| 245, 246, 248, 249, 315, 303, 26 | ++ |

In the table above, PDE4 binding potencies ($IC_{50}$ values) are indicated as follows:
>10 nM "+";
10-1 nM "++";
1-0.1 nM "+++";
<0.1 nM "++++".

Percentage of inhibition of PDE4 activity was calculated, assuming cAMP disappearance in the absence of inhibitors as 100% and cAMP disappearance in heat inactivated samples as 0%.

Analogously, results for tested compounds of formula (II) (expressed as mean±standard deviation of the nM concentration of the test compound producing 50% inhibition of cAMP disappearance) ($IC_{50}$) are shown in the following Table:

| Compound No. | PDE4 inhibition |
|---|---|
| 8, 11, | +++ |
| 3, 9, 10, 14 | ++ |

In the table above, PDE4 binding potencies ($IC_{50}$ values) are indicated as follows:
>10 nM "+";
10-1 nM "++";
1-0.1 nM "+++";
<0.1 nM "++++'.

Example 16. In Vitro Determination of PDE4 Inhibitory Activity in the Peripheral Blood Mononuclear Cells (PBMCs) Assay The assay, which is based on the known inhibitory activity exerted by PDE4 inhibitors on the lipopolyshaccarides (LPS)-induced tumour necrosis factor-alpha (TNF-α release in peripheral blood mononuclear cells (PBMCs), was performed according to a method previously described (Hatzelmann A et al., J. Pharmacol. Exp. Ther., 2001; 297:267-279; and Draheim R et al., J. Pharmacol. Exp. Ther., 2004; 308:555-563, which are incorporated herein by reference in their entireties). Cryopreserved human PBMCs, (100 l/well) were incubated in 96-well plates ($10^5$ cells/well), for 30 minutes, in the presence or absence (50 microl) of the test compounds whose concentrations ranged from $10^{-12}$ M to $10^{-6}$ M or from $10^{-3}$ M to $10^{-7}$ M. Subsequently, LPS (3 ng/ml) was added.

After 18 hours of incubation at 37° C. in a humidified incubator under an atmosphere of 95% air and 5% $CO_2$, culture medium was collected and TNF-α measured by ELISA. The results of the tested compounds, representatives of the invention, expressed as mean±95% confidence limits of the molar concentration of the test compound producing 50% inhibition of LPS-induced TNF-α release ($IC_{50}$) are shown in the following Table:

| Compound No. | PDE4 inhibition |
|---|---|
| 239, 240, 241, 242, 206, 271, 210, 310, 250, 251, 252, 269, 287, 299, 35, 37, 38, 52, 54, 56, 59, 64, 66, 73, 74, 82, 83, 84, 85, 88, 90, 91, 92, 93, 94, 95, 96, 97, 101, 106, 107, 109, 113, 115, 116, 118, 119, 123, 124, 128, 129, 130, 131, 132, 133, 139, 140, 150, 155 | ++++ |
| 238, 201, 203, 228, 207, 198, 209, 295, 243, 186, 187, 185, 281, 253, 288, 200, 16, 17, 20, 22, 26, 31, 32, 34, 36, 39, 40, 41, 49, 51, 53, 55, 57, 58, 60, 61, 62, 63, 65, 67, 68, 69, 70, 75, 76, 77, 78, 79, 80, 81, 86, 87, 89, 98, 103, 104, 105, 108, 110, 111, 114, 117, 121, 125, 126, 127, 135, 136, 137, 138, 141, 142, 143, 144, 151 | +++ |
| 244, 263, 15, 19, 21, 30, 71, 99, 100 | ++ |

In the table above, PDE4 binding potencies ($IC_{50}$ values) are indicated as follows:
>10 nM "+";
10-1 nM "++";
1-0.1 nM "+++";
<0.1 nM "++++".

The effects of the tested compounds were calculated as percentage of inhibition of TNF-α release, assuming LPS-induced TNF-α production in the absence of inhibitor compound as 100% and basal TNF-α production of PBMCs in the absence of LPS as 0%.

Analogously, results of tested compounds for compounds of formula (II) expressed as mean±95% confidence limits of the molar concentration of the test compound producing 50% inhibition of LPS-induced TNF-α release ($IC_{50}$) are shown in the following Table:

| Compound No. | PDE4 inhibition |
|---|---|
| 6, 11 | +++ |
| 8, 9, | ++ |

In the table above, PDE4 binding potencies ($IC_{50}$ values) are indicated as follows:
>10 nM "+";
10-1 nM "++";
1-0.1 nM "+++";
<0.1 nM "++++".

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound of formula (I):

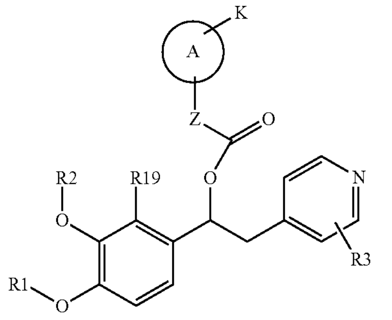

(I)

wherein:

$R_1$ is;
- H;
- ($C_3$-$C_7$) cycloalkylcarbonyl;
- ($C_1$-$C_6$) alkyl, optionally substituted by one or more substituents selected from ($C_3$-$C_7$) cycloalkyl or ($C_5$-$C_7$) cycloalkenyl;
- ($C_1$-$C_6$) haloalkyl;
- ($C_3$-$C_7$) cycloalkyl;
- ($C_5$-$C_7$) cycloalkenyl;
- ($C_2$-$C_6$) alkenyl; or
- ($C_2$-$C_6$) alkynyl;

$R_2$ is:
- H;
- ($C_3$-$C_7$) cycloalkylcarbonyl;
- ($C_1$-$C_6$) alkyl, optionally substituted by one or more substituents selected from ($C_3$-$C_7$) cycloalkyl or ($C_5$-$C_7$) cycloalkenyl;
- ($C_1$-$C_6$) haloalkyl;
- ($C_3$-$C_7$) cycloalkyl;
- ($C_5$-$C_7$) cycloalkenyl;
- ($C_2$-$C_6$) alkenyl; or
- ($C_2$-$C_6$) alkynyl;
- or, when $R_{19}$ is different from hydrogen, $R_2$ forms together with $R_{19}$ a group of formula (x) as defined below;
- or $R_1$ and $R_2$, together with the interconnecting atoms, form a 2,2-difluoro-1,3-dioxolane ring of formula (q) fused to the phenyl moiety which bears groups —$OR_1$ and —$OR_2$, wherein asterisks indicate carbon atoms shared with said phenyl ring:

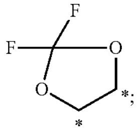

(q)

$R_{19}$ is hydrogen or, if different from hydrogen, it forms together with $R_2$ a group of formula (x) wherein bonds labeled with (1) and (2) indicate the points of attachment for group (x) to atoms bearing groups $R_{19}$ and $R_2$ respectively

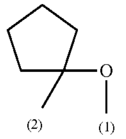

(x)

in such a way that $R_2$ and $R_{19}$ together with the interconnecting atoms form a ring of formula (w) which is fused to phenyl ring which bears groups —$OR_2$ and $R_{19}$, wherein asterisks indicate carbon atoms shared with said phenyl ring:

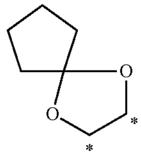

(w)

;

$R_3$ is one or more substituents independently selected from the group consisting of H, CN, $NO_2$, $CF_3$ and a halogen atom;

Z is a group —$(CH_2)_n$— wherein n is 0 or 1;

A is a group shown below:

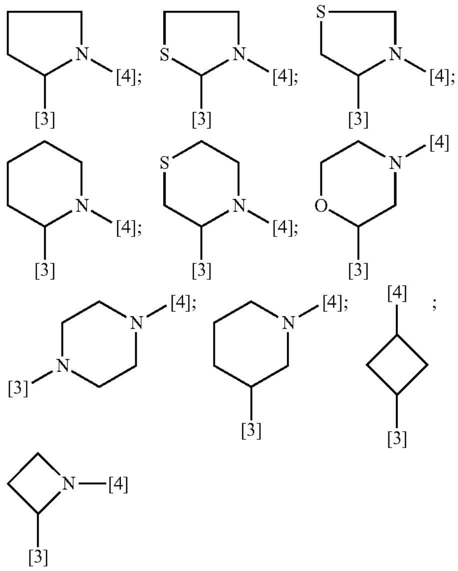

wherein the symbols [3] and [4] indicate the points of connection for group A with, respectively, groups Z and K;

K is:
- —$(CH_2)_m$C(O)$R_4$ wherein m may be 0 or 1;
- —C(O)$(CH_2)_j$$R_4$, wherein j may be 1 or 2;
- —$SO_2$ $(CH_2)_p$$R_4$ wherein p may be zero, 1 or 2;
- —$(CH_2)_y$$SO_2$$R_4$ wherein y may be 1 or 2;
- —$(CH_2)_z$$R_4$ wherein z may be 1 or 2; or
- —C(O)$(CH_2)_2$$SO_2$$R_4$;

$R_4$ is a ring system, that is a mono- or bicyclic ring which may be saturated, partially unsaturated or fully unsaturated, said ring system being optionally substituted by one or more groups $R_5$ which may be the same or different, and which are independently selected from the group consisting of (a), (b), (c), (d), (e), (f), (g), (h), (i), (j), (k), (l), (m), (n), (o), (p), and (q):

(a) ($C_1$-$C_6$) alkyl optionally substituted by one or more groups independently selected from the group consisting of: ($C_3$-$C_7$) cycloalkyl, —OH and a group —$NR_{18}C(O)(C_1$-$C_4$) alkyl, wherein $R_{18}$ is hydrogen or ($C_1$-$C_4$) alkyl;

(b) ($C_3$-$C_7$) heterocycloalkyl;

(c) 5 or 6-membered heteroaryl which is optionally substituted by one or two ($C_1$-$C_4$) alkyl groups;

(d) ($C_1$-$C_6$) haloalkyl;

(e) ($C_3$-$C_7$) heterocycloalkyl($C_1$-$C_4$) alkyl;

(f) a group —$OR_6$ wherein $R_6$ is

H;

($C_1$-$C_6$) haloalkyl;

a group —$SO_2R_7$, wherein $R_7$ is ($C_1$-$C_4$) alkyl;

a group —$C(O)R_7$ wherein $R_7$ is ($C_1$-$C_4$) alkyl;

($C_1$-$C_{10}$) alkyl optionally substituted by one or more ($C_3$-$C_7$) cycloalkyl groups or by a group !$NR_8R_9$ as below defined; or ($C_3$-$C_7$) cycloalkyl;

(g) a group —$SR_{20}$ wherein $R_{20}$ is

H;

($C_1$-$C_6$) haloalkyl;

a group $C(O)R_7$ wherein $R_7$ is ($C_1$-$C_4$) alkyl;

($C_1$-$C_{10}$) alkyl optionally substituted by one or more ($C_3$-$C_7$) cycloalkyl groups or by a group —$NR_8R_9$; or ($C_3$-$C_7$) cycloalkyl;

(h) a halogen atom;

(i) CN;

(j) $NO_2$;

(k) $NR_8R_9$ wherein $R_8$ and $R_9$ are different or the same and are independently selected from the group consisting of (1), (2), (3), (4), (5), and (6):

(1) H;

(2) ($C_1$-$C_4$) alkylene-$NR_{13}R_{14}$ wherein $R_{13}$ and $R_{14}$ are different or the same and are independently selected from the group consisting of: (i) H and (ii) ($C_1$-$C_6$) alkyl, which is optionally substituted with ($C_3$-$C_7$) cycloalkyl or ($C_3$-$C_7$) heterocycloalkyl; or they form with the nitrogen atom to which they are linked a saturated or partially saturated ($C_3$-$C_7$) heterocyclic ring;

(3) ($C_1$-$C_6$) alkyl, optionally substituted with ($C_3$-$C_7$) cycloalkyl, ($C_3$-$C_7$) heterocycloalkyl, a group —OH or ($C_1$-$C_6$) alkoxyl;

(4) a group —$SO_2R_{15}$, wherein $R_{15}$ is selected from the group consisting of: (i) ($C_1$-$C_4$) alkyl optionally substituted by ($C_3$-$C_7$) cycloalkyl or ($C_3$-$C_7$) heterocycloalkyl; (ii) ($C_3$-$C_7$) heterocycloalkyl; and (iii) phenyl optionally substituted by one or more ($C_1$-$C_6$) alkyl, halogen or a group !OH;

(5) a group —$C(O)R_{16}$, wherein $R_{16}$ is selected in the group consisting of: (i) ($C_1$-$C_{10}$) alkyl optionally substituted by ($C_3$-$C_7$) cycloalkyl or ($C_3$-$C_7$) heterocycloalkyl; (ii) ($C_3$-$C_7$) heterocycloalkyl; (iii) phenyl optionally substituted by one or more ($C_1$-$C_{10}$) alkyl, halogen or —OH; and (iv) a group —$NH_2$;

(6) a group —$C(O)OR_{17}$, wherein $R_{17}$ is selected in the group consisting of: (i) ($C_1$-$C_6$) alkyl optionally substituted by ($C_3$-$C_7$) cycloalkyl or ($C_3$-$C_7$) heterocycloalkyl; (ii) ($C_3$-$C_7$) heterocycloalkyl; (iii) phenyl optionally substituted by one or more ($C_1$-$C_6$) alkyl, halogen or —OH; and (iv) a group —$NH_2$;

or they form with the nitrogen atom to which they are linked a saturated or partially saturated heterocyclic ring, which is optionally substituted by one or more ($C_1$-$C_6$) alkyl or oxo groups;

(l) ($C_1$-$C_4$) alkylene-$NR_8R_9$ as above defined;

(m) $COR_{10}$ wherein $R_{10}$ is phenyl or ($C_1$-$C_{10}$) alkyl;

(n) oxo;

(o) —$SO_2R_{11}$ wherein $R_{11}$ is ($C_1$-$C_4$) alkyl, —OH or —$NR_8R_9$ wherein $R_8$ and $R_9$ are as defined above;

(p) —$COOR_{12}$ wherein $R_{12}$ is H, ($C_1$-$C_4$) alkyl or ($C_1$-$C_4$) alkylene-$NR_8R_9$ wherein $R_8$ and $R_9$ are as defined above; and (q) —$CONR_8R_9$ wherein $R_8$ and $R_9$ are as defined above;

wherein groups $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, and $R_{20}$ may be the same or different at each occurrence, if present in more than one group;

an N-oxide derivative on the pyridine ring, or a pharmaceutically acceptable salt thereof.

2. A compound according to claim 1, which is represented by formula (IC):

(IC)

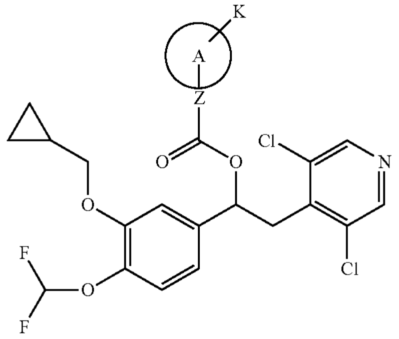

an N-oxide derivative on the pyridine ring, or a pharmaceutically acceptable salt thereof.

3. A compound according to claim 1, which is represented by formula (IF):

(IF)

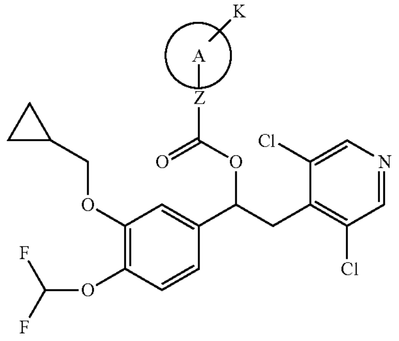

wherein:

Z is a bond,

A is a ($C_3$-$C_7$) heterocycloalkyl-ene group comprising a nitrogen atom which represents the connecting point to group K, K is a group selected from the group consisting of:

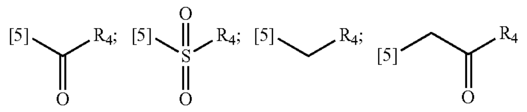

$R_4$ is a phenyl group or a 5 or 6-membered heteroaryl group, each $R_4$ being optionally substituted by one or more groups $R_5$;

An N-oxide derivative on the pyridine ring, or a pharmaceutically acceptable salt thereof.

4. A pyridine N-oxide according to claim 1, which is represented by formula (IH):

(IH)

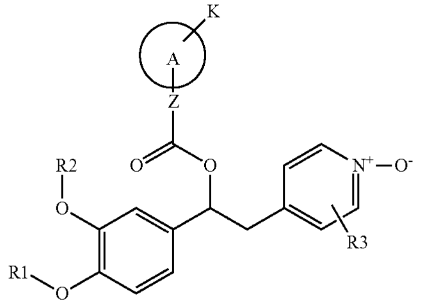

or a pharmaceutically acceptable salt thereof.

5. A compound according to claim 1, which is represented by formula (I)':

(I)'

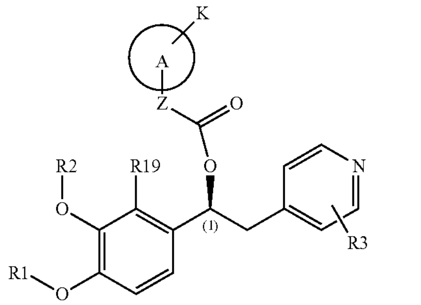

an N-oxide derivative on the pyridine ring, or a pharmaceutically acceptable salt thereof.

6. A pyridine N-oxide according to claim 1, which is represented by formula (IDa):

(IDa)

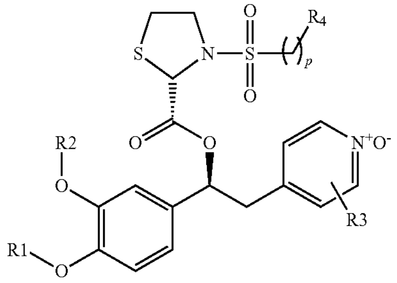

or a pharmaceutically acceptable salt thereof.

7. A compound according to claim 1, which is selected from the group consisting of:

3,5-dichloro-4-((S)-2-(3-(cyclopropylmethoxy)-4-(difluoromethoxy)phenyl)-2-((S)-1-(3-(cyclopropylmethoxy)-4-(methylsulfonamido)benzoyl)pyrrolidine-2-carbonyloxy)ethyl)pyridine 1-oxide;

3,5-dichloro-4-((S)-2-(3-(cyclopropylmethoxy)-4-(difluoromethoxy)phenyl)-2-((S)-1-(4-methoxy-3-(methylsulfonyloxy)benzoyl)pyrrolidine-2-carbonyloxy)ethyl)pyridine 1-oxide;

3,5-dichloro-4-((S)-2-(3-(cyclopropylmethoxy)-4-(difluoromethoxy)phenyl)-2-((S)-1-(3,4-dimethoxyphenylsulfonyl)pyrrolidine-2-carbonyloxy)ethyl)pyridine 1-oxide;

4-((2S)-2-(3-(4-aminophenylsulfonyl)thiazolidine-2-carbonyloxy)-2-(3-(cyclopropylmethoxy)-4-(difluoromethoxy)phenyl)ethyl)-3,5-dichloropyridine 1-oxide;

3,5-dichloro-4-((2S)-2-(3-(cyclopropylmethoxy)-4-(difluoromethoxy)phenyl)-2-(3-(4-(methylsulfonamido)phenylsulfonyl)thiazolidine-2-carbonyloxy)ethyl)pyridine 1-oxide;

3,5-dichloro-4-((2S)-2-(3-(cyclopropylmethoxy)-4-(difluoromethoxy)phenyl)-2-(3-(4-(N-(2-morpholinoethyl)methylsulfonamido)phenylsulfonyl)thiazolidine-2-carbonyloxy)ethyl)pyridine 1-oxide;

4-((S)-2-((R)-3-(4-aminophenylsulfonyl)thiazolidine-2-carbonyloxy)-2-(3-(cyclopropylmethoxy)-4-(difluoromethoxy)phenyl)ethyl)-3,5-dichloropyridine 1-oxide;

4-((S)-2-((S)-3-(4-aminophenylsulfonyl)thiazolidine-2-carbonyloxy)-2-(3-(cyclopropylmethoxy)-4-(difluoromethoxy)phenyl)ethyl)-3,5-dichloropyridine 1-oxide;

4-((S)-2-((S)-1-(4-aminophenylsulfonyl)pyrrolidine-2-carbonyloxy)-2-(3-(cyclopropylmethoxy)-4-(difluoromethoxy)phenyl)ethyl)-3,5-dichloropyridine 1-oxide;

3,5-dichloro-4-((2S)-2-(3-(cyclopropylmethoxy)-4-(difluoromethoxy)phenyl)-2-(1-((4-(methoxycarbonyl)-5-methylfuran-2-yl)methyl)pyrrolidine-2-carbonyloxy)ethyl)pyridine 1-oxide;

3,5-dichloro-4-((S)-2-(3-(cyclopropylmethoxy)-4-(difluoromethoxy)phenyl)-2-((S)-1-(3-(dimethylcarbamoyl)-4-methoxyphenylsulfonyl)pyrrolidine-2-carbonyloxy)ethyl)pyridine 1-oxide;

3,5-dichloro-4-((S)-2-(3-(cyclopropylmethoxy)-4-(difluoromethoxy)phenyl)-2-((R or S)-4-(3-sulfamoylphenylsulfonyl)morpholine-2-carbonyloxy)ethyl)pyridine 1-oxide;

3,5-dichloro-4-((2S)-2-(3-(cyclopropylmethoxy)-4-(difluoromethoxy)phenyl)-2-(3-(2-oxo-2-(thiophen-2-yl)ethyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S or R)-3-(4-(dimethylcarbamoyl)benzyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S or R)-3-(4-(dimethylcarbamoyl)benzyl)thiazolidine-2-carbonyloxy)ethyl)pyridine 1-oxide;

4-((2S)-2-(3-(4-aminobenzoyl)thiazolidine-2-carbonyloxy)-2-(3-(cyclopropylmethoxy)-4-(difluoromethoxy)phenyl)ethyl)-3,5-dichloropyridine 1-oxide;

3,5-dichloro-4-((2S)-2-(3-(cyclopropylmethoxy)-4-(difluoromethoxy)phenyl)-2-(3-(3-(dimethylcarbamoyl)phenylsulfonyl)thiazolidine-2-carbonyloxy)ethyl)pyridine 1-oxide;

3,5-dichloro-4-((2S)-2-(3-(cyclopropylmethoxy)-4-(difluoromethoxy)phenyl)-2-(4-(3-(dimethylcarbamoyl)phenylsulfonyl)thiomorpholine-3-carbonyloxy)ethyl)pyridine 1-oxide;

3,5-dichloro-4-((2S)-2-(3-(cyclopropylmethoxy)-4-(difluoromethoxy)phenyl)-2-(4-(4-(N-methylsulfamoyl)phenylsulfonyl)thiomorpholine-3-carbonyloxy)ethyl)pyridine 1-oxide;

4-((2S)-2-(3-(3-amino-4-methoxyphenylsulfonyl)thiazolidine-2-carbonyloxy)-2-(3-(cyclopropylmethoxy)-4-(difluoromethoxy)phenyl)ethyl)-3,5-dichloropyridine 1-oxide;

3,5-dichloro-4-((2S)-2-(3-(cyclopropylmethoxy)-4-(difluoromethoxy)phenyl)-2-(3-(phenylsulfonyl)thiazolidine-2-carbonyloxy)ethyl)pyridine 1-oxide;

4-((S)-2-((R)-3-(4-aminophenylsulfonyl)thiazolidine-4-carbonyloxy)-2-(3-(cyclopropylmethoxy)-4-(difluoromethoxy)phenyl)ethyl)-3,5-dichloropyridine 1-oxide;

4-((2S)-2-(4-(4-aminophenylsulfonyl)morpholine-2-carbonyloxy)-2-(3-(cyclopropylmethoxy)-4-(difluoromethoxy)phenyl)ethyl)-3,5-dichloropyridine 1-oxide;

3,5-dichloro-4-((S)-2-(3-(cyclopropylmethoxy)-4-(difluoromethoxy)phenyl)-2-((S)-1-(3-(dimethylcarbamoyl)phenylsulfonyl)pyrrolidine-2-carbonyloxy)ethyl)pyridine 1-oxide;

3,5-dichloro-4-((2S)-2-(3-(cyclopropylmethoxy)-4-(difluoromethoxy)phenyl)-2-(4-(3-(dimethylcarbamoyl)phenylsulfonyl)morpholine-2-carbonyloxy)ethyl)pyridine 1-oxide;

3,5-dichloro-4-((S)-2-(3-(cyclopropylmethoxy)-4-(difluoromethoxy)phenyl)-2-((R)-3-(3-(dimethylcarbamoyl)phenylsulfonyl)thiazolidine-4-carbonyloxy)ethyl)pyridine 1-oxide;

3,5-dichloro-4-((2S)-2-(3-(cyclopropylmethoxy)-4-(difluoromethoxy)phenyl)-2-(3-(1,3-dioxoisoindolin-5-ylsulfonyl)thiazolidine-2-carbonyloxy)ethyl)pyridine 1-oxide;

3,5-dichloro-4-((2S)-2-(3-(cyclopropylmethoxy)-4-(difluoromethoxy)phenyl)-2-(3-(4-(dimethylcarbamoyl)phenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((R)-1-(3-(dimethylcarbamoyl)phenylsulfonyl)pyrrolidine-2-carbonyloxy)ethyl)pyridine 1-oxide;

3,5-dichloro-4-((2S)-2-(3-(cyclopropylmethoxy)-4-(difluoromethoxy)phenyl)-2-(3-(3-sulfamoylphenylsulfonyl)thiazolidine-2-carbonyloxy)ethyl)pyridine 1-oxide;

4-((2S)-2-(3-(3-carboxy-4-methoxyphenylsulfonyl)thiazolidine-2-carbonyloxy)-2-(3-(cyclopropylmethoxy)-4-(difluoromethoxy)phenyl)ethyl)-3,5-dichloropyridine 1-oxide;

3,5-dichloro-4-((2S)-2-(3-(cyclopropylmethoxy)-4-(difluoromethoxy)phenyl)-2-(3-(3-fluorophenylsulfonyl)thiazolidine-2-carbonyloxy)ethyl)pyridine 1-oxide;

3,5-dichloro-4-((2S)-2-(3-(cyclopropylmethoxy)-4-(difluoromethoxy)phenyl)-2-(3-(2,4-dimethylphenylsulfonyl)thiazolidine-2-carbonyloxy)ethyl)pyridine 1-oxide;

3,5-dichloro-4-((2S)-2-(3-(cyclopropylmethoxy)-4-(difluoromethoxy)phenyl)-2-(3-(thiophen-2-ylsulfonyl)thiazolidine-2-carbonyloxy)ethyl)pyridine 1-oxide;

3,5-dichloro-4-((2S)-2-(3-(cyclopropylmethoxy)-4-(difluoromethoxy)phenyl)-2-(3-(3-(dimethylcarbamoyl)-4-methoxyphenylsulfonyl)thiazolidine-2-carbonyloxy)ethyl)pyridine 1-oxide;

(S)-3,5-dichloro-4-(2-(3-(cyclopropylmethoxy)-4-(difluoromethoxy)phenyl)-2-(2-(4-(3-(dimethylcarbamoyl)phenylsulfonyl)piperazin-1-yl)acetoxy)ethyl)pyridine 1-oxide;

3,5-dichloro-4-((2S)-2-(3-(cyclopropylmethoxy)-4-(difluoromethoxy)phenyl)-2-(3-(4-(4-methylpiperazine-1-carbonyl)phenylsulfonyl)thiazolidine-2-carbonyloxy)ethyl)pyridine 1-oxide;

3,5-dichloro-4-((2S)-2-(3-(3-chlorophenylsulfonyl)thiazolidine-2-carbonyloxy)-2-(3-(cyclopropylmethoxy)-4-(difluoromethoxy)phenyl)ethyl)pyridine 1-oxide;

3,5-dichloro-4-((2S)-2-(3-(cyclopropylmethoxy)-4-(difluoromethoxy)phenyl)-2-(3-(1-methyl-1H-imidazol-2-ylsulfonyl)thiazolidine-2-carbonyloxy)ethyl)pyridine 1-oxide;

3,5-dichloro-4-((2S)-2-(3-(cyclopropylmethoxy)-4-(difluoromethoxy)phenyl)-2-(3-(cyclopropylmethylsulfonyl)thiazolidine-2-carbonyloxy)ethyl)pyridine 1-oxide;

3,5-dichloro-4-((2S)-2-(3-(cyclopropylmethoxy)-4-(difluoromethoxy)phenyl)-2-(3-(pyridin-3-ylsulfonyl)thiazolidine-2-carbonyloxy)ethyl)pyridine 1-oxide;

3,5-dichloro-4-((2S)-2-(3-(cyclopropylmethoxy)-4-(difluoromethoxy)phenyl)-2-(3-(2,4-difluorophenylsulfonyl)thiazolidine-2-carbonyloxy)ethyl)pyridine 1-oxide;

3,5-dichloro-4-((2S)-2-(3-(2-chloro-4-fluorophenylsulfonyl)thiazolidine-2-carbonyloxy)-2-(3-(cyclopropylmethoxy)-4-(difluoromethoxy)phenyl)ethyl)pyridine 1-oxide;

3,5-dichloro-4-((2S)-2-(3-(cyclopropylmethoxy)-4-(difluoromethoxy)phenyl)-2-(3-(4-fluoro-2-methylphenylsulfonyl)thiazolidine-2-carbonyloxy)ethyl)pyridine 1-oxide;

3,5-dichloro-4-((2S)-2-(3-(2-chlorophenylsulfonyl)thiazolidine-2-carbonyloxy)-2-(3-(cyclopropylmethoxy)-4-(difluoromethoxy)phenyl)ethyl)pyridine 1-oxide;

3,5-dichloro-4-((2S)-2-(3-(cyclohexylsulfonyl)thiazolidine-2-carbonyloxy)-2-(3-(cyclopropylmethoxy)-4-(difluoromethoxy)phenyl)ethyl)pyridine 1-oxide;

3,5-dichloro-4-((2S)-2-(3-(cyclopropylmethoxy)-4-(difluoromethoxy)phenyl)-2-(3-(2,4-dioxo-1,2,3,4-tetrahydroquinazolin-6-ylsulfonyl)thiazolidine-2-carbonyloxy)ethyl)pyridine 1-oxide;

3,5-dichloro-4-((2S)-2-(3-(cyclopropylmethoxy)-4-(difluoromethoxy)phenyl)-2-(3-(thiophen-3-ylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(3-(dimethylcarbamoyl)phenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-1-(3-(dimethylcarbamoyl)phenylsulfonyl)piperidine-2-carbonyloxy)ethyl)pyridine 1-oxide;

3,5-dichloro-4-((S)-2-(3-(cyclopropylmethoxy)-4-(difluoromethoxy)phenyl)-2-((R)-1-(3-(dimethylcarbamoyl)phenylsulfonyl)piperidine-2-carbonyloxy)ethyl)pyridine 1-oxide;

3,5-dichloro-4-((2S)-2-(3-(cyclopropylmethoxy)-4-(difluoromethoxy)phenyl)-2-(3-(3-(cyclopropylmethoxy)-5-(N-(2-morpholinoethyl)methylsulfonamido)benzoyl)thiazolidine-2-carbonyloxy)ethyl)pyridine 1-oxide;

3,5-dichloro-4-((2S)-2-(3-(cyclopropylmethoxy)-4-(difluoromethoxy)phenyl)-2-(3-(3,4-dimethoxyphenylsulfonyl)thiazolidine-2-carbonyloxy)ethyl)pyridine 1-oxide;

(S)-4-(2-(2-(4-(4-aminophenylsulfonyl)piperazin-1-yl)acetoxy)-2-(3-(cyclopropylmethoxy)-4-(difluoromethoxy)phenyl)ethyl)-3,5-dichloropyridine 1-oxide;

3,5-dichloro-4-((S)-2-(3-(cyclopropylmethoxy)-4-(difluoromethoxy)phenyl)-2-((S)-1-(3-(dimethylcarbamoyl)-4-methoxyphenylsulfonyl)piperidine-2-carbonyloxy)ethyl)pyridine 1-oxide;

3,5-dichloro-4-((2S)-2-(3-(cyclopropylmethoxy)-4-(difluoromethoxy)phenyl)-2-(3-(6-morpholinopyridin-3-ylsulfonyl)thiazolidine-2-carbonyloxy)ethyl)pyridine 1-oxide;

3,5-dichloro-4-((2S)-2-(3-(cyclopropylmethoxy)-4-(difluoromethoxy)phenyl)-2-(3-(4-methoxy-3-(4-methylpiperazine-1-carbonyl)phenylsulfonyl)thiazolidine-2-carbonyloxy)ethyl)pyridine 1-oxide;

3,5-dichloro-4-((2S)-2-(3-(cyclopropylmethoxy)-4-(difluoromethoxy)phenyl)-2-(3-(4-methoxy-3-(morpholine-4-carbonyl)phenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S or R)-3-(4-methoxy-3-(morpholinomethyl)benzoyl)thiazolidine-2-carbonyloxy)ethyl)pyridine 1-oxide;

3,5-dichloro-4-((2S)-2-(3-(cyclopropylmethoxy)-4-(difluoromethoxy)phenyl)-2-(3-(3-(N,N-dimethylsulfamoyl)-4-methoxybenzoyl)thiazolidine-2-carbonyloxy)ethyl)pyridine 1-oxide;

4-((S)-2-((S or R)-3-(3-carboxyphenylsulfonyl)thiazolidine-2-carbonyloxy)-2-(3-(cyclopropylmethoxy)-4-(difluoromethoxy)phenyl)ethyl)-3,5-dichloropyridine 1-oxide;

3,5-dichloro-4-((2S)-2-(3-(cyclopropylmethoxy)-4-(difluoromethoxy)phenyl)-2-(3-(4-(morpholinomethyl)benzoyl)thiazolidine-2-carbonyloxy)ethyl)pyridine 1-oxide;

3,5-dichloro-4-((2S)-2-(3-(cyclopropylmethoxy)-4-(difluoromethoxy)phenyl)-2-(4-(phenylsulfonyl)morpholine-2-carbonyloxy)ethyl)pyridine 1-oxide;

3,5-dichloro-4-((2S)-2-(3-(cyclopropylmethoxy)-4-(difluoromethoxy)phenyl)-2-(3-(3,5-dimethylisoxazol-4-ylsulfonyl)thiazolidine-2-carbonyloxy)ethyl)pyridine 1-oxide;

3,5-dichloro-4-((2S)-2-(3-(cyclopropylmethoxy)-4-(difluoromethoxy)phenyl)-2-(3-(thiazole-5-carbonyl)thiazolidine-2-carbonyloxy)ethyl)pyridine 1-oxide;

3,5-dichloro-4-((2S)-2-(3-(cyclopropylmethoxy)-4-(difluoromethoxy)phenyl)-2-(3-(3-((dimethylamino)methyl)benzoyl)thiazolidine-2-carbonyloxy)ethyl)pyridine 1-oxide;

3,5-dichloro-4-((2S)-2-(3-(cyclopropylmethoxy)-4-(difluoromethoxy)phenyl)-2-(3-(oxazole-5-carbonyl)thiazolidine-2-carbonyloxy)ethyl)pyridine 1-oxide;

3,5-dichloro-4-((2S)-2-(3-(cyclopropylmethoxy)-4-(difluoromethoxy)phenyl)-2-(3-(3-(4-methylpiperazine-1-carbonyl)phenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-1-(1-methyl-1H-imidazol-2-ylsulfonyl)pyrrolidine-2-carbonyloxy)ethyl)pyridine 1-oxide;

3,5-dichloro-4-((S)-2-(3-(cyclopropylmethoxy)-4-(difluoromethoxy)phenyl)-2-((S)-1-(phenylsulfonyl)pyrrolidine-2-carbonyloxy)ethyl)pyridine 1-oxide;

3,5-dichloro-4-((2S)-2-(3-(cyclopropylmethoxy)-4-(difluoromethoxy)phenyl)-2-(3-(5-(methoxycarbonyl)thiophen-2-ylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(pyridin-3-ylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(3-(dimethylcarbamoyl)-4-methoxyphenylsulfonyl)thiazodine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(phenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(1-methyl-1H-imidazol-2-ylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(3-sulfamoylphenylsulfonyl)thiazolidine-2-carbonyloxy)ethyl)pyridine 1-oxide;

3,5-dichloro-4-((2S)-2-(3-(cyclopropylmethoxy)-4-(difluoromethoxy)phenyl)-2-(3-(4-(methylsulfonyl)phenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(3,4-dimethoxyphenylsulfonyl)thiazolidine-2-carbonyloxy)ethyl)pyridine 1-oxide;

3,5-dichloro-4-((2S)-2-(3-(cyclopropylmethoxy)-4-(difluoromethoxy)phenyl)-2-(3-(5-((dimethylamino)methyl)thiophene-2-carbonyl)thiazolidine-2-carbonyloxy)ethyl)pyridine 1-oxide;

4-((2S)-2-(3-(4-(2-aminoethyl)benzoypthiazolidine-2-carbonyloxy)-2-(3-(cyclopropylmethoxy)-4-(difluoromethoxy)phenyl)ethyl)-3,5-dichloropyridine 1-oxide;

3,5-dichloro-4-((S)-2-(3-(cyclopropylmethoxy)-4-(difluoromethoxy)phenyl)-2-((S)-3-(4-(N-methylsulfamoyl)phenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(furan-2-ylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(furan-3-ylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(3-(N,N-dimethylsulfamoyl)phenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-1-(3,4-dimethoxyphenylsulfonyl)piperidine-2-carbonyloxy)ethyl)pyridine 1-oxide;

3,5-dichloro-4-((S)-2-(3-(cyclopropylmethoxy)-4-(difluoromethoxy)phenyl)-2-((S)-1-(pyridin-3-ylsulfonyl)piperidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(4-(methoxycarbonyl)phenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(2-(methoxycarbonyl)phenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(3-(dimethylcarbamoyl)phenylsulfonyl)thiazolidine-4-carbonyloxy)ethyl)pyridine 1-oxide;

3,5-dichloro-4-((S)-2-(3-(cyclopropylmethoxy)-4-(difluoromethoxy)phenyl)-2-((S)-3-(3-methoxyphenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(3-(trifluoromethoxy)phenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(4-(1,1-dioxothiomorpholinobenzoyl)thiazolidine-2-carbonyloxy)ethyl)pyridine 1-oxide;

4-((S)-2-((S)-3-(4-carbamoylbenzoyl)thiazolidine-2-carbonyloxy)-2-(3-(cyclopropylmethoxy)-4-(difluoromethoxy)phenyl)ethyl)-3,5-dichloropyridine 1-oxide;

3,5-dichloro-4-((S)-2-(3-(cyclopropylmethoxy)-4-(difluoromethoxy)phenyl)-2-((S)-3-(6-morpholinopyridin-3-ylsulfonyl)thiazolidine-2-carbonyloxy)ethyl)pyridine 1-oxide;

4-((S)-2-((S or R)-3-(4-(aminomethyl)picolinoyl)thiazolidine-2-carbonyloxy)-2-(3-(cyclopropylmethoxy)-4-(difluoromethoxy)phenyl)ethyl)-3,5-dichloropyridine 1-oxide;

3,5-dichloro-4-((S)-2-(3-(cyclopropylmethoxy)-4-(difluoromethoxy)phenyl)-2-((S)-3-(2-methoxy-4-methylphenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(2,4-dimethylthiazol-5-ylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(4-methyl-3,4-dihydro-2H-benzo[b][1,4]oxazin-6-ylsulfonyl)thiazolidine-2-carbonyloxy)ethyl)pyridine 1-oxide;

3,5-dichloro-4-((2S)-2-(3-(cyclopropylmethoxy)-4-(difluoromethoxy)phenyl)-2-(3-picolinoylthiazolidine-2-carbonyloxy)ethyl)pyridine 1-oxide;

3,5-dichloro-4-((S)-2-(3-(cyclopropylmethoxy)-4-(difluoromethoxy)phenyl)-2-((S or R)-3-(3-((2-morpholinoethoxy)carbonyl)phenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(4-methoxyphenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-1-(6-morpholinopyridin-3-ylsulfonyl)piperidine-2-carbonyloxy)ethyl)pyridine 1-oxide;

3,5-dichloro-4-((S)-2-(3-(cyclopropylmethoxy)-4-(difluoromethoxy)phenyl)-2-((S)-1-(4-nitrophenylsulfonyl)piperidine-2-carbonyloxy)ethyl)pyridine 1-oxide;

3,5-dichloro-4-((S)-2-(3-(cyclopropylmethoxy)-4-(difluoromethoxy)phenyl)-2-((S)-1-(3-(N,N-dimethylsulfamoyl)phenylsulfonyl)piperidine-2-carbonyloxy)ethyl)pyridine 1-oxide;

3,5-dichloro-4-((S)-2-(3-(cyclopropylmethoxy)-4-(difluoromethoxy)phenyl)-2-((S)-1-(phenylsulfonyl)piperidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(2,5-dimethoxyphenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-1-(1-methyl-1H-imidazol-2-ylsulfonyl)piperidine-2-carbonyloxy)ethyl)pyridine 1-oxide;

4-((S)-2-((S)-3-(3-acetylphenylsulfonyl)thiazolidine-2-carbonyloxy)-2-(3-(cyclopropylmethoxy)-4-(difluoromethoxy)phenyl)ethyl)-3,5-dichloropyridine 1-oxide;

3,5-dichloro-4-((S)-2-(3-(cyclopropylmethoxy)-4-(difluoromethoxy)phenyl)-2-((S)-3-(4-(morpholinomethyl)benzoyl)thiazolidine-2-carbonyloxy)ethyl)pyridine 1-oxide:

3,5-dichloro-4-((S)-2-(3-(cyclopropylmethoxy)-4-(difluoromethoxy)phenyl)-2-((S)-3-(4-(1,1-dioxo thiomorpholinomethyl)benzoyl)thiazolidine-2-carbonyloxy)ethyl)pyridine 1-oxide;

4-((S)-2-((S)-3-(3-(aminomethyl)benzoyl)thiazolidine-2-carbonyloxy)-2-(3-(cyclopropylmethoxy)-4-(difluoromethoxy)phenyl)ethyl)-3,5-dichloropyridine 1-oxide;

3,5-dichloro-4-((S)-2-(3-(cyclopropylmethoxy)-4-(difluoromethoxy)phenyl)-2-((S)-3-(3-(oxazol-5-yl)benzoyl)thiazolidine-2-carbonyloxy)ethyl)pyridine 1-oxide;

4-((S)-2-((S)-3-(3-aminophenylsulfonyl)thiazolidine-2-carbonyloxy)-2-(3-(cyclopropylmethoxy)-4-(difluoromethoxy)phenyl)ethyl)-3,5-dichloropyridine 1-oxide;

3,5-dichloro-4-((S)-2-(3-(cyclopropylmethoxy)-4-(difluoromethoxy)phenyl)-2-((S)-3-(4-(methylsulfonyl)phenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(3-(4-methylpiperazine-1-carbonyl)phenylsulfonyl)thiazolidine-2-carbonyloxy)ethyl)pyridine 1-oxide;

3,5-dichloro-4-((2S)-2-(3-(cyclopropylmethoxy)-4-(difluoromethoxy)phenyl)-2-(3-(3-(N-methylsulfamoyl)phenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(1-methyl-1H-imidazol-4-ylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(2-phenylacetyl)thiazolidine-2-carbonyloxy)ethyl)pyridine 1-oxide;

3,5-dichloro-4-((S)-2-((S)-3-(2-cyclopropylacetyl)thiazolidine-2-carbonyloxy)-2-(3-(cyclopropylmethoxy)-4-(difluoromethoxy)phenyl)ethyl)pyridine 1-oxide;

3,5-dichloro-4-((S)-2-(3-(cyclopropylmethoxy)-4-(difluoromethoxy)phenyl)-2-((S)-3-(3-(phenylsulfonyl)propanoyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(3-morpholinopropanoyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(3-(4-methylpiperazin-1-yl)propanoyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-1-(3-(dimethylcarbamoyl)benzoyl)pyrrolidine-2-carbonyloxy)ethyl)pyridine 1-oxide;

4-((S)-2-(2-((S)-1-benzoylpyrrolidin-2-yl)acetoxy)-2-(3-(cyclopropylmethoxy)-4-(difluoromethoxy)phenyl)ethyl)-3,5-dichloropyridine 1-oxide;

3,5-dichloro-4-((S)-2-(3-(cyclopropylmethoxy)-4-(difluoromethoxy)phenyl)-2-(2-((S)-1-(3-(dimethylcarbamoyl)benzoyl)pyrrolidin-2-yl)acetoxy)ethyl)pyridine 1-oxide;

3,5-dichloro-4-((S)-2-(3-(cyclopropylmethoxy)-4-(difluoromethoxy)phenyl)-2-((S)-3-(2-(3-(dimethylcarbamoyl)phenyl)acetyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-1-(2-(3-(dimethylcarbamoyl)phenyl)acetyl)pyrrolidine-2-carbonyloxy)ethyl)pyridine 1-oxide;

3,5-dichloro-4-((S)-2-((S)-3-(2-cyanophenylsulfonyl)thiazolidine-2-carbonyloxy)-2-(3-(cyclopropylmethoxy)-4-(difluoromethoxy)phenyl)ethyl)pyridine 1-oxide;

3,5-dichloro-4-((S)-2-(3-(cyclopropylmethoxy)-4-(difluoromethoxy)phenyl)-2-((S)-3-(2,3-dihydrobenzo[b][1,4]dioxin-6-ylsulfonyl)thiazolidine-2-carbonyloxy)ethyl)pyridine 1-oxide;

3,5-dichloro-4-((S)-2-((S)-3-(2-cyano-5-methylphenylsulfonyl)thiazolidine-2-carbonyloxy)-2-(3-(cyclopropylmethoxy)-4-(difluoromethoxy)phenyl)ethyl)pyridine 1-oxide;

3,5-dichloro-4-((S)-2-(3-(cyclopropylmethoxy)-4-(difluoromethoxy)phenyl)-2-((S)-3-(2,5-dimethylthiophen-3-ylsulfonyl)thiazolidine-2-carbonyloxy)ethyl)pyridine 1-oxide;

4-((S)-2-((S)-3-(4-bromo-2-fluoro-5-methylphenylsulfonyl)thiazolidine-2-carbonyloxy)-2-(3-(cyclopropylmethoxy)-4-(difluoromethoxy)phenyl)ethyl)-3,5-dichloropyridine 1-oxide;

4-((S)-2-((S)-3-(3-bromo-4-methylphenylsulfonyl)thiazolidine-2-carbonyloxy)-2-(3-(cyclopropylmethoxy)-4-(difluoromethoxy)phenyl)ethyl)-3,5-dichloropyridine 1-oxide;

3,5-dichloro-4-((S)-2-((S)-3-(4-cyanophenylsulfonyl)thiazolidine-2-carbonyloxy)-2-(3-(cyclopropylmethoxy)-4-(difluoromethoxy)phenyl)ethyl)pyridine 1-oxide;

3,5-dichloro-4-((S)-2-((S)-3-(3-cyanophenylsulfonyl)thiazolidine-2-carbonyloxy)-2-(3-(cyclopropylmethoxy)-4-(difluoromethoxy)phenyl)ethyl)pyridine 1-oxide;

4-((S)-2-((S)-3-(4-(1H-pyrazol-1-yl)phenylsulfonyl)thiazolidine-2-carbonyloxy)-2-(3-(cyclopropylmethoxy)-4-(difluoromethoxy)phenyl)ethyl)-3,5-dichloropyridine 1-oxide;

3,5-dichloro-4-((S)-2-((S)-3-(3-cyano-4-fluorophenylsulfonyl)thiazolidine-2-carbonyloxy)-2-(3-(cyclopropylmethoxy)-4-(difluoromethoxy)phenyl)ethyl)pyridine 1-oxide;

3,5-dichloro-4-((S)-2-(3-(cyclopropylmethoxy)-4-(difluoromethoxy)phenyl)-2-((S)-3-(1-methyl-2-oxoindolin-5-ylsulfonyl)thiazolidine-2-carbonyloxy)ethyl)pyridine 1-oxide;

3,5-dichloro-4-((S)-2-((S)-3-(2-chloro-5-cyanophenylsulfonyl)thiazolidine-2-carbonyloxy)-2-(3-(cyclopropylmethoxy)-4-(difluoromethoxy)phenyl)ethyl)pyridine 1-oxide;

3,5-dichloro-4-((S)-2-(3-(cyclopropylmethoxy)-4-(difluoromethoxy)phenyl)-2-((S)-3-(5-methylbenzo[b]thiophen-2-ylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(4-(1-methyl-1H-pyrazol-3-yl)phenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(4-(difluoromethoxy)phenylsulfonyl)thiazolidine-2-carbonyloxy)ethyl)pyridine 1-oxide;

3,5-dichloro-4-((S)-2-((S)-3-(4-chloro-2-(trifluoromethyl)phenylsulfonyl)thiazolidine-2-carbonyloxy)-2-(3-(cyclopropylmethoxy)-4-(difluoromethoxy)phenyl)ethyl)pyridine 1-oxide;

3,5-dichloro-4-((S)-2-(3-(cyclopropylmethoxy)-4-(difluoromethoxy)phenyl)-2-((S)-3-(5-fluoro-2-methoxyphenylsulfonyl)thiazolidine-2-carbonyloxy)ethyl)pyridine 1-oxide;

4-((S)-2-((S)-3-(benzo[b]thiophen-2-ylsulfonyl)thiazolidine-2-carbonyloxy)-2-(3-(cyclopropylmethoxy)-4-(difluoromethoxy)phenyl)ethyl)-3,5-dichloropyridine 1-oxide;

3,5-dichloro-4-((S)-2-(3-(cyclopropylmethoxy)-4-(difluoromethoxy)phenyl)-2-((S)-3-(2-oxo-2,3-dihydrobenzo[d]oxazol-6-ylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(4-(2-oxopyrrolidin-1-yl)phenylsulfonyl)thiazolidine-2-carbonyloxy)ethyl)pyridine 1-oxide;

4-((S)-2-((S)-3-(1-acetyl-1,2,3,4-tetrahydroquinolin-6-ylsulfonyl)thiazolidine-2-carbonyloxy)-2-(3-(cyclopropylmethoxy)-4-(difluoromethoxy)phenyl)ethyl)-3,5-dichloropyridine 1-oxide;

4-((S)-2-((S)-3-(4-(2-acetamidoethyl)phenylsulfonyl)thiazolidine-2-carbonyloxy)-2-(3-(cyclopropylmethoxy)-4-(difluoromethoxy)phenyl)ethyl)-3,5-dichloropyridine 1-oxide;

3,5-dichloro-4-((S)-2-(3-(cyclopropylmethoxy)-4-(difluoromethoxy)phenyl)-2-((S)-3-(4-(2,2,2-trifluoroethoxy)phenylsulfonyl)thiazolidine-2-carbonyloxy)ethyl)pyridine 1-oxide;

4-(2-((S)-3-(benzylsulfonyl)thiazolidine-2-carbonyloxy)-2-(3-(cyclopropylmethoxy)-4-(difluoromethoxy)phenyl)ethyl)-3,5-dichloropyridine 1-oxide;

3,5-dichloro-4-((S)-2-(3-(cyclopropylmethoxy)-4-(difluoromethoxy)phenyl)-2-((S)-3-(phenethylsulfonyl)thiazolidine-2-carbonyloxy)ethyl)pyridine 1-oxide;

4-((S)-2-((S)-1-(benzylsulfonyl)pyrrolidine-2-carbonyloxy)-2-(3-(cyclopropylmethoxy)-4-(difluoromethoxy)phenyl)ethyl)-3,5-dichloropyridine 1-oxide;

3,5-dichloro-4-((S)-2-(3-(cyclopropylmethoxy)-4-(difluoromethoxy)phenyl)-2-((R)-3-(1-methyl-2-oxoindolin-5-ylsulfonyl)thiazolidine-4-carbonyloxy)ethyl)pyridine 1-oxide;

3,5-dichloro-4-((S)-2-(3-(cyclopropylmethoxy)-4-(difluoromethoxy)phenyl)-2-((R)-1-(phenylsulfonyl)piperidine-3-carbonyloxy)ethyl)pyridine 1-oxide;

3,5-dichloro-4-((S)-2-(3-(cyclopropylmethoxy)-4-(difluoromethoxy)phenyl)-2-(R)-1-(3-(dimethylcarbamoyl)phenylsulfonyl)piperidine-3-carbonyloxy)ethyl)pyridine 1-oxide;

3,5-dichloro-4-((S)-2-(3-(cyclopropylmethoxy)-4-(difluoromethoxy)phenyl)-2-((S)-1-(phenylsulfonyl)piperidine-3-carbonyloxy)ethyl)pyridine 1-oxide;

3,5-dichloro-4-((S)-2-(3-(cyclopropylmethoxy)-4-(difluoromethoxy)phenyl)-2-((S)-1-(3-(dimethylcarbamoyl)phenylsulfonyl)piperidine-3-carbonyloxy)ethyl)pyridine 1-oxide;

3,5-dichloro-4-((S)-2-(3-(cyclopropylmethoxy)-4-(difluoromethoxy)phenyl)-2-(R)-4-(phenylsulfonyl)morpholine-2-carbonyloxy)ethyl)pyridine 1-oxide;

3,5-dichloro-4-((S)-2-(3-(cyclopropylmethoxy)-4-(difluoromethoxy)phenyl)-2-(R)-4-(3-(dimethylcarbamoyl)phenylsulfonyl)morpholine-2-carbonyloxy)ethyl)pyridine 1-oxide;

3,5-dichloro-4-((S)-2-(3-(cyclopropylmethoxy)-4-(difluoromethoxy)phenyl)-2-((S)-4-(phenylsulfonyl)morpholine-2-carbonyloxy)ethyl)pyridine 1-oxide;

3,5-dichloro-4-((S)-2-(3-(cyclopropylmethoxy)-4-(difluoromethoxy)phenyl)-2-((S)-4-(3-(dimethylcarbamoyl)phenylsulfonyl)morpholine-2-carbonyloxy)ethyl)pyridine 1-oxide;

3,5-dichloro-4-((S)-2-(3-(cyclopropylmethoxy)-4-(difluoromethoxy)phenyl)-2-(2-((S)-1-(phenylsulfonyl)pyrrolidin-2-yl)acetoxy)ethyl)pyridine 1-oxide;

3,5-dichloro-4-((S)-2-(3-(cyclopropylmethoxy)-4-(difluoromethoxy)phenyl)-2-(2-((S)-1-(3-(dimethylcarbamoyl)phenylsulfonyl)pyrrolidin-2-yl)acetoxy)ethyl)pyridine 1-oxide;

4-((S)-2-(2-((S)-1-(benzylsulfonyl)pyrrolidin-2-yl)acetoxy)-2-(3-(cyclopropylmethoxy)-4-(difluoromethoxy)phenyl)ethyl)-3,5-dichloropyridine 1-oxide;

3,5-dichloro-4-((S)-2-(3-(cyclopropylmethoxy)-4-(difluoromethoxy)phenyl)-2-((S)-3-(2-oxo-2-phenylethyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-1-(2-oxo-2-phenylethyl)pyrrolidine-2-carbonyloxy)ethyl)pyridine 1-oxide;

4-((S)-2-((S)-1-benzylpyrrolidine-2-carbonyloxy)-2-(3-(cyclopropylmethoxy)-4-(difluoromethoxy)phenyl)ethyl)-3,5-dichloropyridine 1-oxide;

3,5-dichloro-4-((S)-2-(3-(cyclopropylmethoxy)-4-(difluoromethoxy)phenyl)-2-((S)-1-(3-(dimethylcarbamoyl)benzyl)pyrrolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(2-(3-(dimethylcarbamoyl)phenyl)-2-oxoethyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-1-(2-(3-(dimethylcarbamoyl)phenyl)-2-oxoethyl)pyrrolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(cyclopropylmethyl)thiazolidine-2-carbonyloxy)ethyl)pyridine 1-oxide;

4-((S)-2-((S)-3-benzylthiazolidine-2-carbonyloxy)-2-(3-(cyclopropylmethoxy)-4-(difluoromethoxy)phenyl)ethyl)-3,5-dichloropyridine 1-oxide;

3,5-dichloro-4-((S)-2-(3-(cyclopropylmethoxy)-4-(difluoromethoxy)phenyl)-2-((S)-3-(3-(dimethylcarbamoyl)benzyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-phenethylthiazolidine-2-carbonyloxy)ethyl)pyridine 1-oxide;

3,5-dichloro-4-((S)-2-(3-(cyclopropylmethoxy)-4-(difluoromethoxy)phenyl)-2-(2-((S)-1-(3-(dimethylcarbamoyl)benzyl)pyrrolidin-2-yl)acetoxy)ethyl)pyridine 1-oxide;

3,5-dichloro-4-((S)-2-(3-(cyclopropylmethoxy)-4-(difluoromethoxy)phenyl)-2-((S)-3-(3-ureidophenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(3-(hydroxymethyl)phenylsulfonyl)thiazolidine-2-carbonyloxy)ethyl)pyridine 1-oxide;

4-((2S)-2-(2-(3-benzoylthiazolidin-2-yl)acetoxy)-2-(3-(cyclopropylmethoxy)-4-(difluoromethoxy)phenyl)ethyl)-3,5-dichloropyridine 1-oxide;

3,5-dichloro-4-((2S)-2-(3-(cyclopropylmethoxy)-4-(difluoromethoxy)phenyl)-2-(2-(3-(3-(dimethylcarbamoyl)benzoyl)thiazolidin-2-yl)acetoxy)ethyl)pyridine 1-oxide;

3,5-dichloro-4-((2S)-2-(3-(cyclopropylmethoxy)-4-(difluoromethoxy)phenyl)-2-(2-(3-(phenylsulfonyl)thiazolidin-2-yl)acetoxy)ethyl)pyridine 1-oxide;

3,5-dichloro-4-((2S)-2-(3-(cyclopropylmethoxy)-4-(difluoromethoxy)phenyl)-2-(2-(3-(3-(dimethylcarbamoyl)phenylsulfonyl)thiazolidin-2-yl)acetoxy)ethyl)pyridine 1-oxide;

(S)-3,5-dichloro-4-(2-(3-(cyclopropylmethoxy)-4-(difluoromethoxy)phenyl)-2-(1-(3-(dimethylcarbamoyl)phenylsulfonyl)azetidine-3-carbonyloxy)ethyl)pyridine 1-oxide;

(S)-3,5-dichloro-4-(2-(3-(cyclopropylmethoxy)-4-(difluoromethoxy)phenyl)-2-(1-(phenylsulfonyl)azetidine-3-carbonyloxy)ethyl)pyridine 1-oxide;

3,5-dichloro-4-((S)-2-(3-(cyclopropylmethoxy)-4-(difluoromethoxy)phenyl)-2-((S)-1-(3-(dimethylcarbamoyl)phenylsulfonyl)azetidine-2-carbonyloxy)ethyl)pyridine 1-oxide;

3,5-dichloro-4-((S)-2-(3-(cyclopropylmethoxy)-4-(difluoromethoxy)phenyl)-2-((S)-1-(phenylsulfonyl)azetidine-2-carbonyloxy)ethyl)pyridine 1-oxide;

3,5-dichloro-4-((S)-2-(3-(cyclopropylmethoxy)-4-(difluoromethoxy)phenyl)-2-((S)-1-(1-methyl-2-oxoindolin-5-ylsulfonyl)pyrrolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(2-morpholinoethylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(2-(4-methylpiperazin-1-yl)ethylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-1-(2-(phenylsulfonyl)ethyl)pyrrolidine-2-carbonyloxy)ethyl)pyridine 1-oxide;

3,5-dichloro-4-((S)-2-(3-(cyclopropylmethoxy)-4-(difluoromethoxy)phenyl)-2-((S)-1-(2-phenylacetyl)pyrrolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(3-(dimethylcarbamoyl)benzylsulfonyl)thiazolidine-2-carbonyloxy)ethyl)pyridine 1-oxide;

3,5-dichloro-4-((S)-2-(4-(difluoromethoxy)-3-methoxyphenyl)-2-((S)-3-(3-(dimethylcarbamoyl)phenylsulfonyl)thiazolidine-2-carbonyloxy)ethyl)pyridine 1-oxide;

3,5-dichloro-4-((S)-2-(4-(difluoromethoxy)-3-methoxyphenyl)-2-((S)-3-(phenylsulfonyl)thiazolidine-2-carbonyloxy)ethyl)pyridine 1-oxide;

3,5-dichloro-4-((S)-2-(3-(cyclopentyloxy)-4-(difluoromethoxy)phenyl)-2-((S)-3-(phenylsulfonyl)thiazolidine-2-carbonyloxy)ethyl)pyridine 1-oxide;

3,5-dichloro-4-((S)-2-(3-(cyclopentyloxy)-4-(difluoromethoxy)phenyl)-2-((S)-3-(3-(dimethylcarbamoyl)phenylsulfonyl)thiazolidine-2-carbonyloxy)ethyl)pyridine 1-oxide;

3,5-dichloro-4-((S or R)-2-(2,2-difluorobenzo[d][1,3]dioxol-5-yl)-2-((S)-3-(3-(dimethylcarbamoyl)phenylsulfonyl)thiazolidine-2-carbonyloxy)ethyl)pyridine 1-oxide;

3,5-dichloro-4-((S)-2-(4-(difluoromethoxy)-3-methoxyphenyl)-2-((S)-1-(phenylsulfonyl)pyrrolidine-2-carbonyloxy)ethyl)pyridine 1-oxide;

3,5-dichloro-4-((S)-2-(4-(difluoromethoxy)-3-methoxyphenyl)-2-((S)-1-(3-(dimethylcarbamoyl)phenylsulfonyl)pyrrolidine-2-carbonyloxy)ethyl)pyridine 1-oxide;

3,5-dichloro-4-((S)-2-(3-(cyclopentyloxy)-4-(difluoromethoxy)phenyl)-2-((S)-1-(phenylsulfonyl)pyrrolidine-2-carbonyloxy)ethyl)pyridine 1-oxide;

3,5-dichloro-4-((S)-2-(3-(cyclopentyloxy)-4-(difluoromethoxy)phenyl)-2-((S)-1-(3-(dimethylcarbamoyl)phenylsulfonyl)pyrrolidine-2-carbonyloxy)ethyl)pyridine 1-oxide;

3,5-dichloro-4-((S)-2-(3,4-dimethoxyphenyl)-2-((S)-1-(phenylsulfonyl)pyrrolidine-2-carbonyloxy)ethyl)pyridine 1-oxide;

3,5-dichloro-4-((S)-2-(3,4-dimethoxyphenyl)-2-((S)-1-(3-(dimethylcarbamoyl)phenylsulfonyl)pyrrolidine-2-carbonyloxy)ethyl)pyridine 1-oxide;

3,5-dichloro-4-(2-(3-(cyclopentyloxy)-4-methoxyphenyl)-2-((S)-1-(phenylsulfonyl)pyrrolidine-2-carbonyloxy)ethyl)pyridine 1-oxide;

3,5-dichloro-4-(2-(3-(cyclopentyloxy)-4-methoxyphenyl)-2-((S)-1-(3-(dimethylcarbamoyl)phenylsulfonyl)pyrrolidine-2-carbonyloxy)ethyl)pyridine 1-oxide;

(S)-3,5-dichloro-4-(2-(3-(cyclopropylmethoxy)-4-methoxyphenyl)-2-(1-(phenylsulfonyl)pyrrolidine-2-carbonyloxy)ethyl)pyridine 1-oxide;

(S)-3,5-dichloro-4-(2-(3-(cyclopropylmethoxy)-4-methoxyphenyl)-2-(1-(3-(dimethylcarbamoyl)phenylsulfonyl)pyrrolidine-2-carbonyloxy)ethyl)pyridine 1-oxide;

3,5-dichloro-4-((S or R)-2-(2,2-difluorobenzo[d][1,3]dioxol-5-yl)-2-((S)-1-(3-(dimethylcarbamoyl)phenylsulfonyl)pyrrolidine-2-carbonyloxy)ethyl)pyridine 1-oxide;

3,5-dichloro-4-(2-(4-methoxyspiro[benzo[d][1,3]dioxole-2,1'-cyclopentane]-7-yl)-2-((S)-1-(phenylsulfonyl)pyrrolidine-2-carbonyloxy)ethyl)pyridine 1-oxide;

3,5-dichloro-4-(2-((S)-1-(3-(dimethylcarbamoyl)phenylsulfonyl)pyrrolidine-2-carbonyloxy)-2-(4-methoxyspiro[benzo[d][1,3]dioxole-2,1'-cyclopentane]-7-yl)ethyl)pyridine 1-oxide;

3,5-dichloro-4-(2-(3-(cyclopropylmethoxy)-4-methoxyphenyl)-2-((S)-3-(3-(dimethylcarbamoyl)phenylsulfonyl)thiazolidine-2-carbonyloxy)ethyl)pyridine 1-oxide;

3,5-dichloro-4-(2-(3-(cyclopropylmethoxy)-4-methoxyphenyl)-2-((S)-3-(phenylsulfonyl)thiazolidine-2-carbonyloxy)ethyl)pyridine 1-oxide;

3,5-dichloro-4-(2-(3-(cyclopentyloxy)-4-methoxyphenyl)-2-((S)-3-(phenylsulfonyl)thiazolidine-2-carbonyloxy)ethyl)pyridine 1-oxide;

3,5-dichloro-4-(2-(3-(cyclopentyloxy)-4-methoxyphenyl)-2-((S)-3-(3-(dimethylcarbamoyl)phenylsulfonyl)thiazolidine-2-carbonyloxy)ethyl)pyridine 1-oxide;

3,5-dichloro-4-((S)-2-(3,4-dimethoxyphenyl)-2-((S)-3-(phenylsulfonyl)thiazolidine-2-carbonyloxy)ethyl)pyridine 1-oxide;

3,5-dichloro-4-((S)-2-(3,4-dimethoxyphenyl)-2-((S)-3-(3-(dimethylcarbamoyl)phenylsulfonyl)thiazolidine-2-carbonyloxy)ethyl)pyridine 1-oxide;

3,5-dichloro-4-(2-(4-methoxyspiro[benzo[d][1,3]dioxole-2,1'-cyclopentane]-7-yl)-2-((S)-3-(phenylsulfonyl)thiazolidine-2-carbonyloxy)ethyl)pyridine 1-oxide;

3,5-dichloro-4-(2-((S)-3-(3-(dimethylcarbamoyl)phenylsulfonyl)thiazolidine-2-carbonyloxy)-2-(4-methoxyspiro[benzo[d][1,3]dioxole-2,1'-cyclopentane]-7-yl)ethyl)pyridine 1-oxide;

3,5-dichloro-4-((S)-2-(3-(cyclopropylmethoxy)-4-(difluoromethoxy)phenyl)-2-((S)-1-(3-(N,N-dimethylsulfamoyl)phenylsulfonyl)pyrrolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(3-methylisoxazolo[5,4-b]pyridin-5-ylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(1,3-dimethyl-1H-pyrazolo[3,4-b]pyridin-5-ylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(1-methyl-5-(methylcarbamoyl)-1H-pyrrol-3-ylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-3-(5-(pyrrolidine-1-carbonyl)-1H-pyrrol-3-ylsulfonyl)thiazolidine-2-carbonyloxy)ethyl)pyridine 1-oxide;

(S)—((S)-1-(3-(cyclopropylmethoxy)-4-(difluoromethoxy)phenyl)-2-(3,5-dichloropyridin-4-yl)ethyl) 3-(1-methyl-1H-imidazol-2-ylsulfonyl)thiazolidine-2-carboxylate;

4-((S)-2-((S)-3-(1H-1,2,4-triazol-5-ylsulfonyl)thiazolidine-2-carbonyloxy)-2-(3-(cyclopropylmethoxy)-4-(difluoromethoxy)phenyl)ethyl)-3,5-dichloropyridine 1-oxide;

4-((S)-2-((S)-3-benzoylthiazolidine-2-carbonyloxy)-2-(3-(cyclopropylmethoxy)-4-(difluoromethoxy)phenyl) ethyl)-3,5-dichloropyridine 1-oxide;

3,5-dichloro-4-((S)-2-(3-(cyclopropylmethoxy)-4-(difluoromethoxy)phenyl)-2-((S)-3-(3-(dimethylcarbamoyl)benzoyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((R)-1-(phenylsulfonyl)pyrrolidine-2-carbonyloxy)ethyl)pyridine 1-oxide;

4-((S)-2-((R)-1-benzoylpyrrolidine-2-carbonyloxy)-2-(3-(cyclopropylmethoxy)-4-(difluoromethoxy)phenyl) ethyl)-3,5-dichloropyridine 1-oxide;

3,5-dichloro-4-((S)-2-(3-(cyclopropylmethoxy)-4-(difluoromethoxy)phenyl)-2-((R)-1-(3-(dimethylcarbamoyl)benzoyl)pyrrolidine-2-carbonyloxy)ethyl)pyridine 1-oxide;

3,5-dichloro-4-((R)-2-(3-(cyclopropylmethoxy)-4-(difluoromethoxy)phenyl)-2-((R)-1-(3-(dimethylcarbamoyl)phenylsulfonyl)pyrrolidine-2-carbonyloxy)ethyl) pyridine 1-oxide;

3,5-dichloro-4-((R)-2-(3-(cyclopropylmethoxy)-4-(difluoromethoxy)phenyl)-2-((S)-1-(3-(dimethylcarbamoyl)phenylsulfonyl)pyrrolidine-2-carbonyloxy)ethyl) pyridine 1-oxide;

(S)—((S)-1-(3-(cyclopropylmethoxy)-4-(difluoromethoxy)phenyl)-2-(3,5-dichloropyridin-4-yl)ethyl) 3-(3-(dimethylcarbamoyl)phenylsulfonyl)thiazolidine-2-carboxylate;

3,5-dichloro-4-((R)-2-(3-(cyclopropylmethoxy)-4-(difluoromethoxy)phenyl)-2-((R)-3-(3-(dimethylcarbamoyl)phenylsulfonyl)thiazolidine-2-carbonyloxy)ethyl) pyridine 1-oxide;

3,5-dichloro-4-((R)-2-(3-(cyclopropylmethoxy)-4-(difluoromethoxy)phenyl)-2-((S)-3-(3-(dimethylcarbamoyl)phenylsulfonyl)thiazolidine-2-carbonyloxy)ethyl) pyridine 1-oxide;

3,5-dichloro-4-((S)-2-(4-(difluoromethoxy)-3-hydroxyphenyl)-2-((S)-3-(3-(dimethylcarbamoyl)phenylsulfonyl)thiazolidine-2-carbonyloxy)ethyl)pyridine 1-oxide;

3,5-dichloro-4-((S)-2-(3-(cyclopropylmethoxy)-4-(difluoromethoxy)phenyl)-2-((S)-1-(4-methyl-3,4-dihydro-2H-benzo[b][1,4]oxazin-6-ylsulfonyl)pyrrolidine-2-carbonyloxy)ethyl)pyridine 1-oxide;

3,5-dichloro-4-((S)-2-(3-(cyclopropylmethoxy)-4-(difluoromethoxy)phenyl)-2-((S)-1-(3-methylisoxazolo[5,4-b]pyridin-5-ylsulfonyl)pyrrolidine-2-carbonyloxy) ethyl)pyridine 1-oxide;

3,5-dichloro-4-((S)-2-(3-(cyclopropylmethoxy)-4-(difluoromethoxy)phenyl)-2-((R)-3-(4-methyl-3,4-dihydro-2H-benzo[b][1,4]oxazin-6-ylsulfonyl)thiazolidine-4-carbonyloxy)ethyl)pyridine 1-oxide;

3,5-dichloro-4-((S)-2-(3-(cyclopropylmethoxy)-4-(difluoromethoxy)phenyl)-2-((R)-3-(3-methylisoxazolo[5,4-b]pyridin-5-ylsulfonyl)thiazolidine-4-carbonyloxy) ethyl)pyridine 1-oxide; and 3,5-dichloro-4-((S)-2-(3-(cyclopropylmethoxy)-4-(difluoromethoxy)phenyl)-2-((S)-3-(3-(methylcarbamoyl) phenylsulfonyl)thiazolidine-2-carbonyloxy)ethyl)pyridine 1-oxide;

or a pharmaceutically acceptable salt thereof.

8. A process for preparing a compound of formula (IDa) according to claim 6, comprising:

(1) reacting a compound of formula (XV) with a compound of formula (XIV), to obtain a compound of formula (XII):

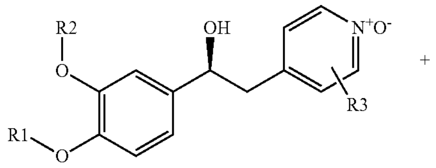

(XV)

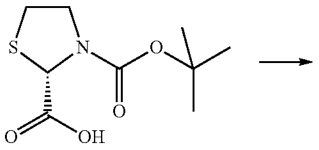

(XIV)

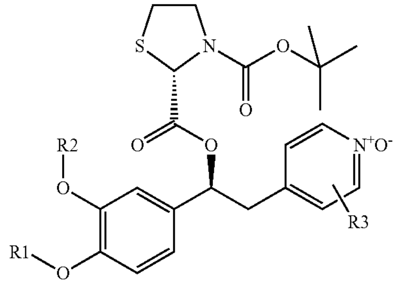

(XII)

by: a) adding a compound of formula (XIV), 4-dimethylaminopyridine, and 1-ethyl-3-(3-dimethylaminopropyl) carbodiimide) hydrochloride to a solution of a compound of formula (XV) in dimethylformamide, to obtain a mixture; b) stirring said mixture; c) pouring the mixture into cold water, to obtain a precipitate; and d) filtering the precipitate;

(2) converting said compound of formula (XII) to a compound of formula (XI):

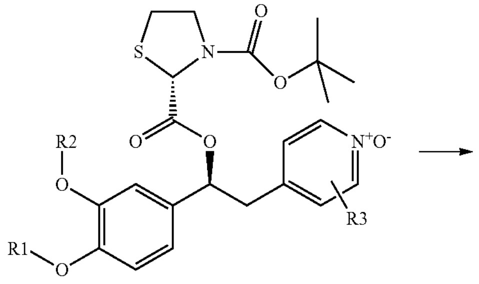

(XII)

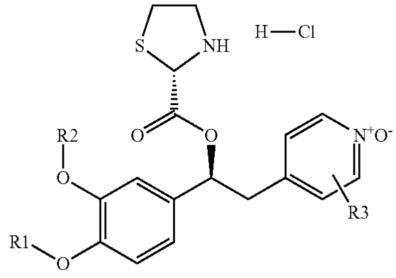

(XI)

by: a) adding, with stirring, a solution of concentrated HCl in dry ethyl acetate (9 vol.) to a solution of said compound of formula (XII) in ethyl acetate at room temperature; b) stirring, to obtain a precipitated solid; c) filtering said precipitated solid; and optionally d) washing said precipitated solid with ethyl acetate; and (3) reacting said compound of formula (XI) with a compound of formula (VII), to obtain said compound of formula (IDa):

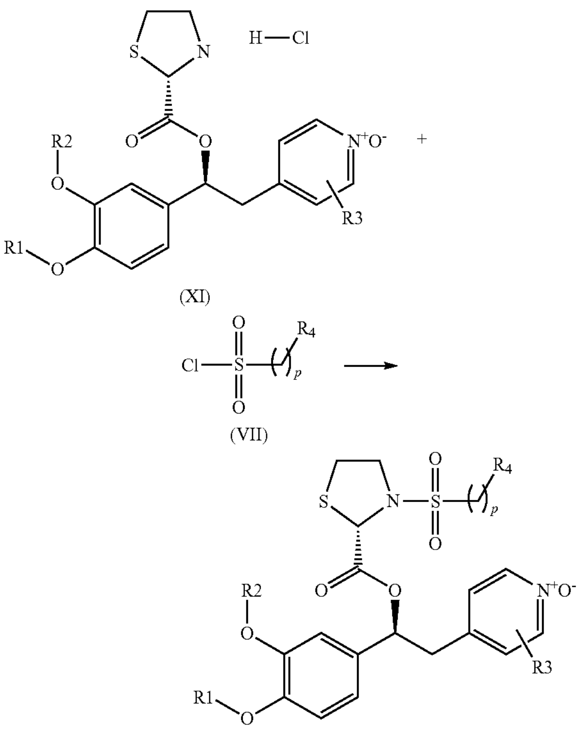

(XI)

(VII)

(IDa)

by: a) adding a solution of a compound of formula (VII) in pyridine to a refrigerated solution of said compound of formula (XI), in pyridine; b) stirring the resulting solution at room temperature; c) pouring the solution into aqueous HCl in excess, to obtain a precipitate; d) filtering said precipitated material and washing it with water or d') extracting the aqueous phase with ethyl acetate, washing with HCl 1M, brine and evaporating the resulting organic phase; f) dissolving the compounds in ethanol (8 vol); g) vigorously stirring overnight at room temperature; and h) filtering the solid formed;

wherein $R_1$, $R_2$, $R_3$, $R_4$ and p in compounds of formulas (XV), (XIV), (XII), (XI), (VII) and (IDa) have meanings as per compounds of formula (I).

9. A combination of a compound, N-oxide, or pharmaceutically acceptable salt according to claim 1 with a second pharmaceutical active component selected from the group consisting of a beta2-agonist, a corticosteroid, and an antimuscarinic agent.

10. A pharmaceutical composition, comprising a compound, N-oxide, or pharmaceutically acceptable salt according to claim 1 and one or more pharmaceutically acceptable carriers and/or excipients.

11. A pharmaceutical composition, comprising a combination according to claim 9 and one or more pharmaceutically acceptable carriers and/or excipients.

12. A method for treatment of a disease of the respiratory tract characterized by airway obstruction, said method comprising administering to a patient in need thereof a therapeutically effective amount of a compound, N-oxide, or pharmaceutically acceptable salt according to claim 1.

13. A method for treatment of allergic rhinitis, said method comprising administering to a patient in need thereof a therapeutically effective amount of a compound, N-oxide, or pharmaceutically acceptable salt according to claim 1.

14. A method for treatment of atopic dermatisis, said method comprising administering to a patient in need thereof a therapeutically effective amount of a compound, N-oxide, or pharmaceutically acceptable salt according to claim 1.

15. A device comprising a pharmaceutical composition according to claim 10.

16. A device comprising a pharmaceutical composition according to claim 11.

17. A kit comprising a pharmaceutical composition according to claim 10 and a device which is a single- or multi-dose dry powder inhaler, a metered dose inhaler, or a soft mist nebulizer.

18. A kit comprising a pharmaceutical composition according to claim 11 and a device which is a single- or multi-dose dry powder inhaler, a metered dose inhaler, or a soft mist nebulizer.

19. A method according to claim 12, wherein said disease of the respiratory tract characterized by airway obstruction is asthma or COPD.

* * * * *